United States Patent
Senokuchi et al.

(10) Patent No.: US 6,358,960 B1
(45) Date of Patent: Mar. 19, 2002

(54) AMIDINO DERIVATIVES AND DRUGS CONTAINING THE SAME AS THE ACTIVE INGREDIENT

(75) Inventors: Kazuhiko Senokuchi; Koji Ogawa, both of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/601,998

(22) PCT Filed: Feb. 12, 1999

(86) PCT No.: PCT/JP99/00622

§ 371 Date: Aug. 11, 2000

§ 102(e) Date: Aug. 11, 2000

(87) PCT Pub. No.: WO99/41231

PCT Pub. Date: Aug. 19, 1999

(30) Foreign Application Priority Data

Feb. 17, 1998 (JP) .............................................. 10-76815

(51) Int. Cl.[7] ..................... C07D 235/08; C07D 211/28; A61K 31/445; A61K 31/415
(52) U.S. Cl. ...................... 514/256; 514/330; 514/352; 514/354; 514/408; 514/436; 514/461; 544/242; 546/309; 546/184; 546/336; 548/400; 549/29; 549/429
(58) Field of Search ................................. 546/309, 336, 546/184; 514/352, 256, 330, 354, 408, 438, 461; 544/242; 548/400; 549/29, 429

(56) References Cited

U.S. PATENT DOCUMENTS

| | | | |
|---|---|---|---|
| 5,342,851 A | 8/1994 | Sanfilippo et al. | 514/370 |
| 5,563,127 A | 10/1996 | Amparo et al. | 514/64 |
| 5,602,145 A | 2/1997 | Samanen | 514/309 |
| 5,693,636 A | 12/1997 | Bondinell et al. | 514/221 |
| 5,698,538 A | 12/1997 | Amparo et al. | 514/64 |
| 5,741,804 A | 4/1998 | Keenan et al. | 514/394 |
| 5,939,412 A | 8/1999 | Bondinell et al. | 514/213 |
| 5,942,544 A | 8/1999 | Maduskuie, Jr. et al. | 514/341 |
| 6,127,390 A | 10/2000 | deSolms et al. | 514/341 |

FOREIGN PATENT DOCUMENTS

| | | |
|---|---|---|
| DE | 1902475 | 4/1970 |
| WO | 9723212 | 7/1997 |
| WO | 9857934 | 12/1998 |
| WO | 9857937 | 12/1998 |

*Primary Examiner*—Zinna Northington Davis
(74) *Attorney, Agent, or Firm*—Stevens, Davis, Miller & Mosher, L.L.P.

(57) ABSTRACT

The novel amidino derivatives of the formula (I):

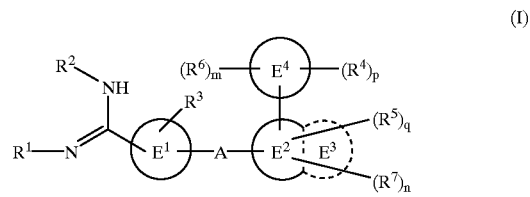

wherein all the symbols are as in specification defined; have an inhibitory activity of a blood coagulation factor VIIa and are useful for treatment and/or prevention of several angiopathy caused by enhancing a coagulation activity, such as disseminated intravascular coagulation, coronary thrombosis, cerebral infarction, cerebral embolism, transient ischemic attack, cerebrovascular disorders, pulmonary vascular diseases, deep venous thrombosis, peripheral arterial obstruction, thrombosis after artificial vascular transplantation and artificial valve transplantation, post-operative thrombosis, reobstruction and restenosis after coronary artery bypass operation, reobstruction and restenosis after PTCA or PTCR, thrombosis by extracorporeal circulation and procoagulative diseases such as glomerlonephriitis.

15 Claims, No Drawings

AMIDINO DERIVATIVES AND DRUGS CONTAINING THE SAME AS THE ACTIVE INGREDIENT

This application is a 371 of PCT/JP99/0062 filed Feb. 12, 1999.

TECHNICAL FIELD

This invention is related to amidino derivatives of the formula (I), non-toxic salts thereof, hydrates thereof, processes for the preparation thereof, and the blood coagulation factor VIIa inhibitors containing the derivatives as active ingredient.

More particularly, this invention is related to amidino derivatives of the formula (I)

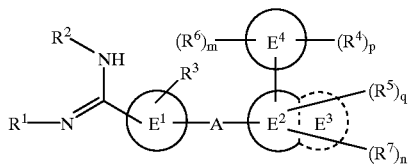

(I)

wherein all the symbols are as hereinafter defined, non-toxic salts thereof, hydrates thereof, processes for the preparation thereof, and the blood coagulation factor VIIa inhibitors containing the derivatives as active ingredient.

BACKGROUND ART

The blood coagulation is a protective reaction which is caused by vascular injury or irritate stimulus with endotoxin or the other foreign bodies. This reaction proceeds on the membrane of platelets which aggregate at the injured site or on the membrane of injured endothelial cells and it requires Ca ion. The blood coagulation system contains eight kinds of serine proenzymes (e.g. plasma prekallikrein factor XII, factor XI, factor VII, factor IX, factor X, prothrombin, protein C), five protein co-factor (e.g. macromolecule kininogen, tissue factor, factor VIII, factor V, protein S), and a fibrillar protein, fibrinogen. α-Thrombin produced by the coagulation cascade give information to endothelial cells and form insoluble fibrin gel. The scheme of the blood coagulation cascade is shown below.

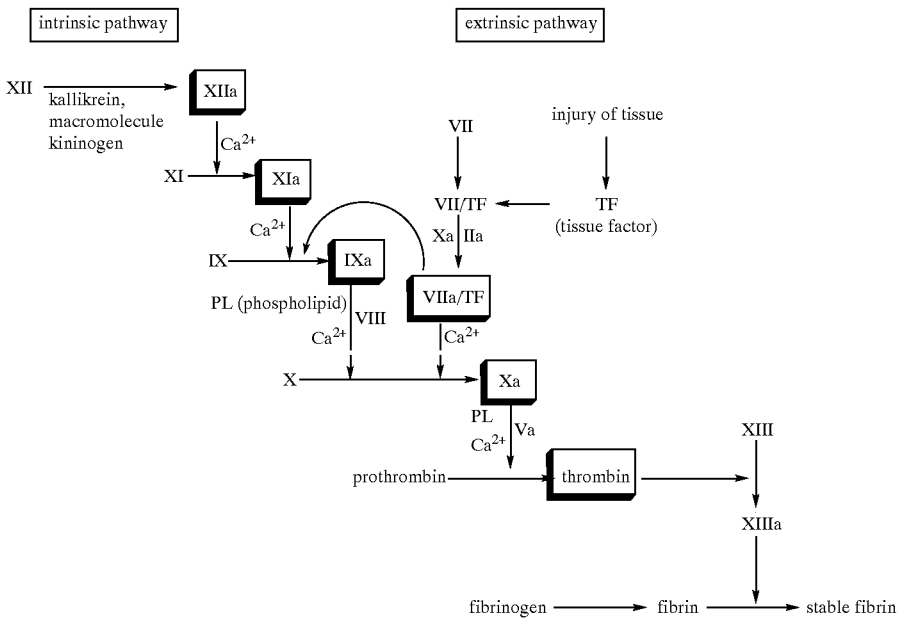

The blood coagulation cascade consists of the intrinsic pathway and the extrinsic pathway. The intrinsic pathway acts on foreign surface charged negatively. However, foreign surface in the body is uncertain, so the significance of the intrinsic pathway in hemostasis is not established. On the other hand, the extrinsic pathway is triggered by the complex formation of the blood coagulation factor VIIa (FVIIa) and tissue factor which is expressed by a vascular damage or the presence of endotoxin. This pathway confluents with the intrinsic pathway at a point of factor X and factor IX activation.

The extrinsic pathway seems to be more important than the intrinsic pathway in the physiologic condition (hemostasis) or pathological condition (thrombosis). The reasons are as follows.

1) The presence of tissue factor (TF) is recognized in physiological condition.
2) The expression of TF is induced by endotoxin on the membrane of vascular endothelial cells or/and monocytes.
3) Since TF is observed on foam cells in the plaque of arteriosclerosis, the extrinsic pathway is considered to contribute the topical coagulation activity.

Warfarin, an anticoagulant agent, inhibits the production of various factors, including protein C and S. Thrombin inhibitors such as heparin, which act at the downstream of a coagulation cascade, may inhibit blood coagulation excessively and do not inhibit the consumption of coagulation factors. Because of these reasons, bleeding tendency is the main problem in clinic.

On the other hand, FVIIa is located at the top site of the cascade in the extrinsic pathway. Therefore, FVIIa inhibitors inhibit the extrinsic pathway, leaving intact the activity of the intrinsic pathway.

Consequently, FVIIa inhibitors are different from thrombin inhibitors leaving a function of the intrinsic pathway. It is considered that FVIIa inhibitors have a resistance to bleeding, then it is expected to be able to reduce a bleeding tendency as a side effect.

FVIIa inhibitors suppress a coagulation activity of the extrinsic pathway, and then they are useful for treatment and/or prevention for several thormbotic diseases triggered by the extrinsic pathway. For example, several angiopathy caused by enhancing a coagulation activity, such as disseminated intravascular coagulation, coronary thrombosis (e.g. acute myocardial infarction, unstable angina), cerebral infarction, cerebral embolism, transient ischemic attack, cerebrovascular disorders, pulmonary vascular diseases (e.g. pulmonary infarction, pulmonary embolism), deep venous thrombosis, peripheral arterial obstruction, thrombosis after artificial vascular transplantation and artificial valve transplantation, post-operative thrombosis, reobstruction and restenosis after coronary artery bypass operation, reobstruction and restenosis after PTCA (percutaneous transluminal coronary angioplasty) or PTCR (percutaneous transluminal coronary recanalization), thrombosis by extracorporeal circulation and procoagulative diseases such as glomerlonephriitis.

(1) In the specification of WO 9620689, boric acid derivatives of the formula (A):

wherein $A^A$ is $-BY^{1A}Y^{2A}$, in which $Y^{A1}$ and $y^{2A}$ each independently, is $-OH$, C1–8 alkoxy; $-COOR^{3A}$, in which $R^{3A}$ is hydrogen, C1–8 alkyl; $R^{2A}$ is

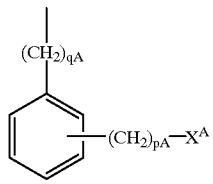

in which pA is 0–2, qA is 0–4, $X^A$ is $C(NH)NHR^{14A}$, in which $R^{14A}$ is hydrogen, C1–4 alkyl; $Z^A$ is $(CH_2)_{mA}CONR^{8A}$, $(CH_2)_{mA}CSNR^{8A}$, $(CH_2)_{mA}SO_2NR^{8A}$, $(CH_2)_{mA}CO_2$, $(CH_2)_{mA}CSO$, $(CH_2)_{mA}SO_2O$, $R^{8A}$ is hydrogen, C1–8 alkyl, mA is 0–6, $R^{1A}$ is $(CH_2)_{pA}$aryl, in which pA is 0–2, aryl is phenyl, naphthyl, biphenyl, and they may be substituted by 1–3 of $(CH_2)_{WA}CO_2R^{8A}$, $(CH_2)_{WA}CNR^{8A}R^{9A}$; WA is 0–5, $R^{8A}$ and $R^{9A}$ is hydrogen, C1–8 alkyl; with the proviso that explanations of each inhibitory activity of thrombin, Fxa, FVIIa.

(2) In the specification of WO 9429273, the compound of the formula (B):

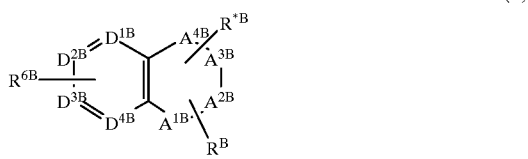

wherein $A^{1B}$ to $A^{4B}$ form a substituted 6 membered ring optionally unsaturated, and optionally containing up to two hetero atoms selected from O, S and N;

$D^{1B}$ to $D^{4B}$ form a substituted 6 membered aromatic ring optionally containing up to two nitrogens, $D^{1B}-D^{4B}$ is $CR^{11B}$ or N; $R^B$ is at least one substituent selected from $R^7$, $Q^B$—C1–4 alkyl, $Q^B$—C2–4 alkenyl and $Q^B$—C2–4 alkynyl;

$R^{*B}$ is hydrogen, $Q^B$—C1–6 alkyl, $Ar^B$ or $Het^B$;

$Q^B$ is hydrogen, C3–6 cycloalkylHet$^B$ or $Ar^B$;

$R^{6B}$ is $W^B-(CR^{'B2})q^B-Z^B-(CR^{'B}R^{10B})r^B-U^B-(CR^{'B2})s^B-V^B-$;

$R^{7B}$ is $-COR^{8B}$, $-PO(OR^{'B})_2$ and $Tet^B$;

$R^{8B}$ is $-OR^{'B}$, $-NR^{'B}R^{''B}$, $-NR^{'B}OR^{'B}$;

$R^{10B}$ is hydrogen, C1–4 alkyl or $-NR^{'B}R^{''B}$;

$R^{11B}$ is $Q^B$—C0–6 alkyl;

$R^{'B}$, $R^{''B}$ are hydrogen, C1–6 alkyl, C3–7 cycloalkyl-C0–4 alkyl, or $Ar^B$—C0–4 alkyl;

UB and VB is absent or $CONR^{'B}$, $NR^{'B}CO$, $S(O)_{nB}NR^{'B}$, $NR^{'B}S(O)_{nB}$, $NR^{'B}CR^{'B}_2$, $CR^{'B}_2NR^{'B}$, $CR^{'B}_2O$, $OCR^{'B}_2$, $C\equiv C$, $CR^{'B}=CR^{'B}$;

$W^B$ is

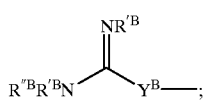

$Y^B$ is absent, S or O;

$Z^B$ is $(CH_2)_{tB}$, Het$^B$, $Ar^B$ or C3–7 cycloalkyl;

nB is 0–3; qB is 0–3; rB is 0–2; sB is 0–2; tB is 0–2; with the proviso that explanations of each groups were disclosed only necessary parts; or salts thereof are described to possible an inhibitory activity of fibrinogen receptor GPIIb/IIIa.

In the specification of WO 9300095 and WO 9412478, similarity compounds are described to possible an inhibitory activity of fibrinogen receptor GPIIb/IIIa.

(3) In the specification of WO 9730971, the compound of the formula (C):

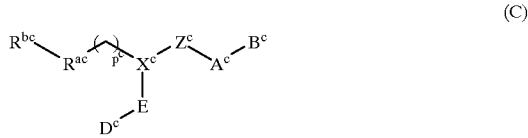

wherein $D^C$ is CN, $C(=NR^{7C})NR^{8C}R^{9C}$, $NHC(=NR^{7C})N^{R8}CR^{9C}$, $NR^{8C}CH(=NR^{7C})$ etc.; $E^C$ is phenyl, 2-pyridyl, 4-pyridyl, etc.; $R^{aC}$ is a single bond or $CH=CH$; $R^{bC}$ is $C(O)R^C$ or $G^C$; $G^C$ is hydrogen, $OG^{1C}$, $SG^{1C}$, $NG^{1C}G^{2C}$, etc.; $G^{1C}$ is hydrogen, C1–6 alkyl; $G^{2C}$ is hydrogen, C1–6 alkyl; $R^C$ is hydrogen, OH, C1–6 alkoxy, etc.; $R^{7C}$ is hydrogen, OH, C1–6 alkyl, C1–6 alkylcarbonyl, C1–6 alkoxy, C1–4 alkoxycarbonyl, etc.; $R^{8C}$ and $R^{9C}$ are hydrogen, C1–6 alkyl, $(CH_2)_n$-phenyl; $X^C$ is $CHCH(R^{1C})$, N, etc.; $Z^C$ is $(CH_2)_n$, $C(=O)$, etc.; $p^C$ is 1–4; $A^C$ is benzyl, C3–10 carbocyclic ring, 5–10 membered heterocyclic ring; $B^C$ is hydrogen, C1–6 alkyl, benzyl, C3–10 carbocyclic ring, 5–10 membered heterocyclic ring; are described to possible an inhibitory activity of FXa.

DISCLOSURE OF INVENTION

Energetic investigations have been carried out in order to make the blood coagulation factor VIIa inhibitors. The present inventors have found that the present compound of the formula (I) accomplished the present purpose.

The present invention is related to amidino derivatives of the formula (I):

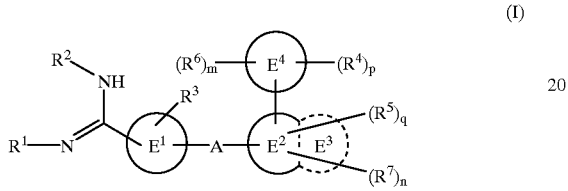

(I)

wherein $R^1$ and $R^2$ each independently, is
1) hydrogen,
2) hydroxy,
3) C1–4 alkoxycarbonyl,
4) C2–4 alkenyloxycarbonyl,
5) C1–4 alkoxycarbonyloxy or
6) —COO—(C1–4 alkyl)-phenyl,
when $R^2$ is group excepting hydrogen, $R^2$ is hydrogen, or when $R^2$ is group excepting hydrogen, $R^1$ is hydrogen;

$R^3$ is
1) hydrogen,
2) C1–4 alkyl,
3) hydroxy,
4) —O—(C1–4 alkyl)-phenyl, or
5) halogen atom;

$E^1$ ring is
1) 5–7 membered unsaturated carbocyclic ring or
2) 5–7 membered unsaturated heterocyclic ring;

$E^2$ ring is
1) 5–7 membered unsaturated carbocyclic ring or
2) 5–7 membered unsaturated heterocyclic ring;

$E^3$ ring is
1) absent,
2) 5–7 membered unsaturated or saturated carbocyclic ring or
3) 5–7 membered unsaturated or saturated heterocyclic ring;

$E^4$ ring is
1) 5–6 membered unsaturated carbocyclic ring or
2) 5–6 membered unsaturated heterocyclic ring;

$R^4$ and $R^5$ each independently is
1) —COOR$^8$, in which $R^8$ is hydrogen, C1–8 alkyl, —(C1–4 alkyl)-phenyl or —(C1–4 alkyl)—O—(C1–4 alkyl);
2) —(C1–4 alkyl)—COOR$^9$, in which $R^9$ is hydrogen, C1–8 alkyl, —(C1–4 alkyl)-phenyl or —(C1–4 alkyl)—O—(C1–4 alkyl);
3) —(C2–4 alkenyl)-COOR$^{10}$, in which $R^{10}$ is hydrogen, C1–8 alkyl, —(C1–4 alkyl)-phenyl or —(C1–4 alkyl)—O—(C1–4 alkyl);
4) —O—(C1–4 alkyl)-COOR$^{11}$, in which $R^{11}$ is hydrogen, C1–8 alkyl, —(C1–4 alkyl)-phenyl or —(C1–4 alkyl)—O—(C1–4 alkyl);
5) —CONR$^{12}$R$^{13}$, in which $R^{12}$ is hydrogen, C1–4 alkyl, $R^{13}$ is hydroxy, —O—(C1–4 alkyl)-phenyl or cyano;
6) —P(O)(OR$^{14}$)$_2$, in which $R^{14}$ is hydrogen, C1–4 alkyl or —(C1–4 alkyl)-phenyl; or
7) tetrazol-5-yl which is optionally substituted by C1–8 alkyl; p and q each independently, is 0 or 1–2, with the proviso that p+q is 1 or 2;

$R^6$ and $R^7$ each independently, is
1) hydrogen,
2) C1–8 alkyl,
3) nitro,
4) cyano,
5) halogen atom,
6) —(C1–4 alkyl)—O—(C1–4 alkyl)-phenyl,
7) —NR$^{15}$R$^{16}$, in which $R^{15}$ and $R^{16}$ each independently, is hydrogen or C1–8 alkyl;
8) —OR$^{17}$, in which $R^{17}$ is hydrogen, C1–8 alkyl, CF$_3$, C2–5 acyl, —(C1–4 alkyl)-phenyl, —(C1–4 alkyl)—OH, —(C1–4 alkyl)—O—(C1–4 alkyl), or —(C1–4 alkyl)—O—(C1–4 alkyl)—O—(C1–4 alkyl);
9) —(C1–4 alkyl)—OR$^{17}$, in which $R^{17}$ is as hereinbefore defined
10) —J$^1$—J$^2$, in which J$^1$ is
(1) —CONR$^{18}$—, in which $R^{18}$ is hydrogen or C1–4 alkyl;
(2) —NR$^{19}$CO—, in which $R^{19}$ is hydrogen or C1–4 alkyl;
(3) —SO$_2$NR$^{20}$—, in which $R^{20}$ is hydrogen or C1–4 alkyl;
(4) —NR$^{21}$SO$_2$—, in which $R^{21}$ is hydrogen or C1–4 alkyl;
(5) —(C1–4 alkyl)—NR$^{22}$—, in which $R^{22}$ is hydrogen or C1–4 alkyl;
(6) —CO—,
(7) —(C1–4 alkyl)—NR$^{23}$CO—, in which $R^{23}$ is hydrogen or C1–4 alkyl;
J$^2$ is
(1) C1–15 alkyl optionally substituted by 1–3 of following groups (i)–(x):
(i) C3–7 cycloalkyl optionally substituted by —(C1–4 alkyl)—OR$^{24}$;
(ii) phenyl,
(iii) 5–7 saturated heterocyclic ring optionally substituted by carboxyl or C1–4 alkoxycarbonyl;
(iv) OR$^{24}$, in which $R^{24}$ is hydrogen, C1–4 alkyl, —COO—(C1–4 alkyl)-phenyl, C2–5 acyl, or —(C1–4 alkyl)-phenyl;
(v) NR$^{25}$R$^{26}$, in which $R^{25}$ is hydrogen or C1–4 alkyl, $R^{26}$ is hydrogen, C1–4 alkyl, —COO (C1–4 alkyl)-phenyl, imino(C1–4 alkyl) or C1–4 alkoxycarbonyl;
(vi) —S(O)$_r$—(C1–4 alkyl), in which r is 0–2;
(vii) —COOR$^{27}$, in which $R^{27}$ is hydrogen, C1–4 alkyl or —(C1–4 alkyl)-phenyl;
(viii) —CONR$^{28}$R$^{29}$, in which $R^{28}$ and $R^{29}$ each independently, is
(i) hydrogen, (ii) C1–4 alkyl, (iii) hydroxy, or (iv) C1–4 alkyl substituted by one of hydroxy, phenyl or NR$^{25}$R$^{26}$, or $R^{28}$ and $R^{29}$ taken together with the nitrogen atom to which they are attached form 5–6 membered saturated heterocyclic ring containing nitrogen atom;

(ix) halogen atom,
(x) trihalomethyl;
(2) C2–8 alkenyl,
(3) C5–7 cycloalkyl optionally substituted by 1–3 of C1–4 alkyl, —COOR$^{27}$, in which R$^{27}$ is as hereinbefore defined; —(C1–4 alkyl)—OR$^{24}$, in which R$^{24}$ is as hereinbefore defined;
(4) —NR$^{25}$R$^{26}$, in which R$^{25}$ and R$^{26}$ is as hereinbefore defined;
(5) 5–6 membered saturated heterocyclic ring optionally substituted by 1–3 of C1–4 alkyl, oxo, imino(C1–4 alkyl); or R$^{18}$ and J$^2$ taken together with the nitrogen atom to which they are attached form saturated heterocyclic ring optionally substituted by 1–3 of C1–8 alkyl, C2–8 alkenyl or —COOR$^{27}$, in which R$^{27}$ is hereinbefore defined;

m is 1–3;
n is 1–3;
two R$^6$ taken together with the neighboring two carbon of E$^4$ ring to which they are attached form 5–6 membered unsaturated carbocyclic ring or 5–6 membered saturated heterocyclic ring, that rings may be substituted by 1–3 of R$^4$ or R$^6$;

A is
1) ethylene,
2) vinylene,
3) ethynylene,
4) —O—CH$_2$—,
5) —CH$_2$—O—,
6) —NR$^{30}$CO—, in which R$^{30}$ is hydrogen or C1–4 alkyl;
7) —NR$^{31}$CHR$^{32}$—, in which R$^{31}$ is hydrogen or C1–4 alkyl, R$^{32}$ is hydrogen, cyano, COOR$^{36}$, in which R$^{36}$ is hydrogen or C1–4 alkyl; or CONR$^{37}$R$^{38}$, in which R$^{37}$ and R$^{38}$ each independently, is hydrogen or C1–4 alkyl;
8) —CH$_2$—NR$^{33}$—, in which R$^{33}$ is hydrogen or C1–4 alkyl;
9) —S—CH$_2$—;
10) —CH$_2$—S—,
11) —SO$_2$NR$^{34}$—, in which R$^{34}$ is hydrogen or C1–4 alkyl;
12) —NR$^{35}$SO$_2$—, in which R$^{35}$ is hydrogen or C1–4 alkyl; non-toxic salts thereof, or hydrates thereof,
(2) the blood coagulation factor VIIa inhibitors containing the compound of formula (I) as active ingredient,
(3) processes for the preparation of the compound of formula (I).

DETAILED DESCRIPTION OF INVENTION

Unless otherwise specified, all isomers are included in the present invention. For example, alkyl, alkoxy and alkylene include straight and branched isomers. Isomers based on double bond, ring, fused ring (E, Z, cis, trans), isomers resulting from the presence of asymmetric carbon(s) (R-configuration, S-configuration, α-configuration, β-configuration, enantiomers, diastereoisomers), optically active compound having optical rotation (D, L, d, l-configuration), polar compounds obtained by chromatographic separations (high polar compound, low polar compound), equilibrium compounds, the mixtures are existed by free ratio, racemic mixtures are included in the present invention.

In the compound of the formula (I),
C1–4 alkyl represented by R$^3$, R$^{12}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{33}$, R$^{34}$, R$^{35}$, R$^{36}$, R$^{37}$, R$^{38}$, C1–4 alkyl in —COO—(C1–4 alkyl)-phenyl represented by R$^1$, R$^2$, R$^{24}$, R$^{26}$,
C1–4 alkyl in —O—(C1–4 alkyl)-phenyl represented by R$^3$, R$^{13}$,
C1–4 alkyl in —(C1–4 alkyl)-phenyl represented by R$^8$, R$^9$, R$^{10}$, R$^{11}$, R$^{14}$, R$^{17}$, R$^{27}$, R$^{28}$, R$^{29}$,
C1–4 alkyl in —(C14 alkyl)—O—(C1–4 alkyl) represented by R$^8$, R$^9$, R$^{10}$, R$^{11}$, R$^{17}$,
C1–4 alkyl in —(C1–4 alkyl)—COOR$^9$ represented by R$^4$, R$^5$,
C1–4 alkyl in —O—(C1–4 alkyl)—COOR$^{11}$ represented by R$^4$, R$^5$,
C1–4 alkyl in —(C1–4 alkyl)—O—(C1–4 alkyl)-phenyl represented by R$^6$, R$^7$,
C1–4 alkyl in —(C1–4 alkyl)—OH represented by R$^{17}$, R$^{28}$, R$^{29}$,
C1–4 alkyl in —(C1–4 alkyl)—O—(C1–4 alkyl)—O—(C1–4 alkyl) represented by R$^{17}$,
C1–4 alkyl in —(C1–4 alkyl)—NR$^{22}$—represented by J$^1$,
C1–4 alkyl in —(C1–4 alkyl)—NR$^{23}$CO— represented by J$^1$,
C1–4 alkyl in —S(O)$_r$—(C1–4 alkyl) represented in J$^2$,
C1–4 alkyl in J$^2$,
C1–4 alkyl in —(C1–4 alkyl)—R$^{24}$ represented in J$^2$,
C1–4 alkyl in —imino(C1–4 alkyl) represented in J$^2$ and by R$^{26}$,
C1–4 alkyl in —(C1–4 alkyl)—OR$^{17}$ represented by R$^6$, R$^7$,
C1–4 alkyl in —(C1–4 alkyl)—NR$^{25}$, R$^{26}$ represented by R$^{28}$, R$^{29}$ is methyl, ethyl, propyl, butyl and isomeric groups thereof.
C1–8 alkyl represented by R$^6$, R$^7$, R$^8$, R$^9$, R$^{10}$, R$^{11}$, R$^{15}$, R$^{16}$, J$^2$, C1–8 alkyl as substituents of heterocyclic ring containing nitrogen atom and tetrazol ring represented by R$^4$, R$^5$ is methyl, ethyl, propyl, butyl, pentyl, hexyl, heptyl, octyl and isomeric groups thereof.
C1–4 alkoxy in C1–4 alkoxycarbonyl represented by R$^1$, R$^2$, C1–4 alkoxy in C1–4 alkoxycarbonyloxy represented by R$^1$, R$^2$, C1–4 alkoxy in C1–4 alkoxycarbonyl as substituents of 5–7 membered saturated hetercyclic ring represented by J$^2$ is methoxy, ethoxy, propoxy, butoxy and isomeric groups thereof.
C2–4 alkenyl in C2–4 alkenyloxycarbonyl represented by R$^1$, R$^2$, C2–4 alkenyl in —(C2–4 alkenyl)—COOR$^{10}$ represented by R$^4$, R$^5$ is ethenyl, propenyl, butenyl and isomeric groups thereof.
Halogen atom represented by R$^6$, R$^7$ is fluorine, chlorine, bromine or iodine.
Trihalomethyl in J$^2$ is methyl substituted by 3 of halogen atoms that is fluorine, chlorine, bromine or iodine.
C3–7 cycloalkyl as substituents in J$^2$ is cyclopropyl, cyclobutyl, cyclopentyl, cyclohexyl or cycloheptyl.
C5–7 cycloalkyl as substituents in J$^2$ is cyclopentyl, cyclohexyl or cycloheptyl.
C2–5 acyl represented by R$^{17}$, R$^{24}$ is acetyl, propionyl, butyryl, valeryl and isomeric groups thereof.
5–7 membered unsaturated carbocyclic ring represented by E$^1$, E$^2$, E$^3$ is cyclopentadiene, benzene, cycloheptatriene, etc. 5–7 membered saturated carbocyclic ring represented by E$^3$ is cyclopentadane, cyclohexane, cycloheptane. 5–6 membered unsaturated carbocyclic ring represented by E$^4$, and 5–6 membered unsaturated carbocyclic ring formed by two R$^6$ is cyclopentadiene, benzene.
5–7 membered unsaturated or saturated heterocyclic ring represented by E$^1$, E$^2$, E$^3$, 5–7 membered saturated heterocyclic ring in $J^2$, means 5–7 membered unsaturated or saturated heterocyclic ring containing 1–2 of hetero atom(s) selected by oxygen, sulfur and/or nitrogen.

For example, 5–7 membered unsaturated or saturated heterocyclic ring containing 1–2 of hetero atom(s) selected by oxygen, sulfur and/or nitrogen is piperidine, piperazine, tetrahydropyrimidine, hexahydropyrimidine, tetrahydropyridazine, hexahydropyridazine, hexahydroazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, pyrrole, imidazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine.

5–6 membered unsaturated heterocyclic ring represented by $E^4$ means 5–6 membered saturated heterocyclic ring containing one of oxygen, sulfur or nitrogen, for example, furan, thiophene, pyrrole, pyridine.

5–6 membered saturated heterocyclic ring represented by $J^2$ means 5–6 membered saturated heterocyclic ring containing 1–2 of hetero atom(s) selected by oxygen atom, sulfur atom and/or nitrogen atom, for example, oxolane, oxane, pyrrolidine, piperidiene, dioxolane, dioxane, imidazolidine, pyrazolidine, piperazine, morpholine.

A saturated heterocyclic ring containing nitrogen formed by $R^{18}$ and $J^2$ taken together with the nitrogen atom to which they are attached, or $R^{28}$ and $R^{29}$ taken together with the nitrogen atom to which they are attached means 5–6 membered saturated heterocyclic ring containing one nitrogen, two nitrogens, one nitrogen and one oxygen, or one nitrogen and one sulfur, for example, pyrrolidine, piperidine, imidazolidine, pyrazolidine, piperazine, morpholine, thiomorpholine.

5–6 membered saturated heterocyclic ring formed by two $R^6$ taken together with the neighboring two carbon of $E^4$ ring to which they are attached means 5–6 membered saturated heterocyclic ring containing 1–2 of hetero atom(s) of oxygen, sulfur and/or nitrogen, for example, oxolane, oxane, pyrrolidine, piperidiene, thiolane, thiane, dioxolane, dioxane, imidazolidine, pyrazolidine, dithiolane, dithiane, piperazine, oxathiane, morpholine, thiomorpholine.

In the formula (I), the ring represented by

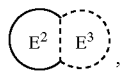

means $E^3$ ring is absent, that is only $E^2$ ring represents ring, and both of $E^2$ ring and $E^3$ ring represent ring, for example, benzene, naphthalene, 1,2,3,4-tetrahydronaphthalene, indan, benzofuran, 2,3-dihydrobenzofuran, benzoimidazole, 1,3-dioxaindan, benzothiophene, pyridine, pyrimidine, isoquinoline, thiophene, furan. Especially preferable group is benzene, pyridine, thiophene, furan.

In the formula (I), as ring represented by

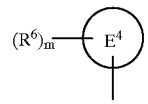

benzene, naphthalene, 2,3-dihydrobenzofuran, 1,3-dioxaindan, pyridine, furan, thiophen are preferable. Especially preferable group is benzene, pyridien, furan, thiophene.

In the formula (I), all groups represented by $R^4$ and $R^5$ are preferable. Especially preferable group is $COOR^8$.

Besides, especially preferable attachment point on $E^4$ ring of one $R^4$ is ortho position.

In the formula (I), all groups represented by $R^6$ are preferable. Especially preferably, at least one of $R^6$ is $—J^1—J^2$.

In the formula (I), all groups represented by $R^7$ are preferred. Especially preferably, at least one of $R^7$ is hydrogen, C1–4 alkyl, nitro, $NR^{15}R^{16}$, $OR^{17}$, $—(C1–4\ alkyl)—OR^{17}$.

In the formula (I), all groups represented by A are preferable. Especially preferable groups are $—CH_2—O—$, $NR^{30}CO—$, $—NR^{31}CHR^{32}—$.

In the compound of the formula (I), the compound of the formula

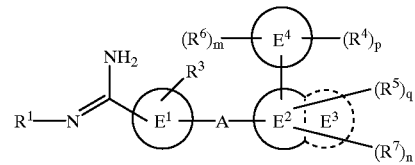

and the compound of the formula

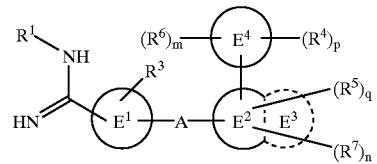

are equivalence, and the compound of the formula

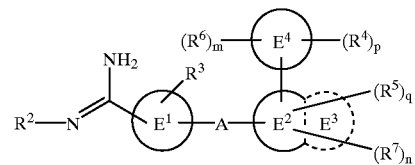

and the compound of the formula

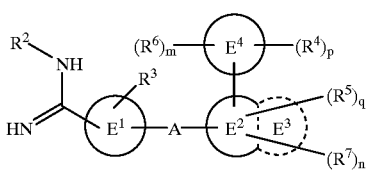

are equivalence.

In the compounds of the present invention of formulae (I), the compounds of the formula (I-1):

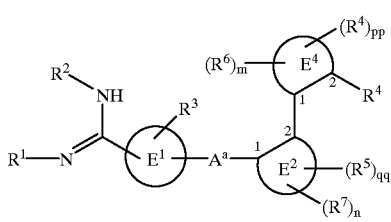

(I-1)

wherein $A^a$ is —CH$_2$—O—, —N$^{30}$CO— in which R$^{30}$ is as hereinbefore defined; —NR$^{31}$CHR$^{32}$— in which R$^{31}$ and R$^{32}$ are as hereinbefore defined; pp and qq each independently, is 0–1, with the proviso that pp+qq is 0 or 1, the other symbols are as hereinbefore defined, with the provisio that $A^a$ and E$^4$ ring attach to E$^2$ ring at ortho position, E$^2$ ring and essential one R$^4$ attach to E$^4$ ring at ortho position; are preferable.

The following compounds of the formulae are especially preferable: the formula (Ia):

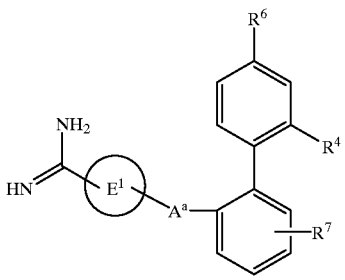

(Ia)

wherein all the symbols are as hereinbefore defined;
the formula (Ib):

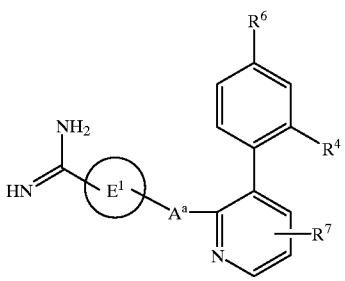

(Ib)

wherein all the symbols are as hereinbefore defined;
the formula (Ic):

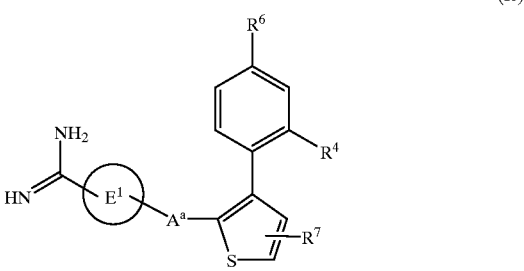

(Ic)

wherein all the symbols are as hereinbefore defined;
the formula (Id):

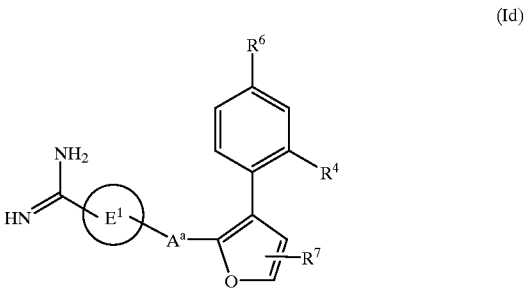

(Id)

wherein all the symbols are as hereinbefore defined;
the formula (Ie):

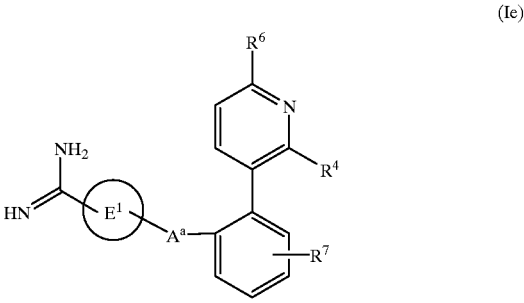

(Ie)

wherein all the symbols are as hereinbefore defined;
the formula (If):

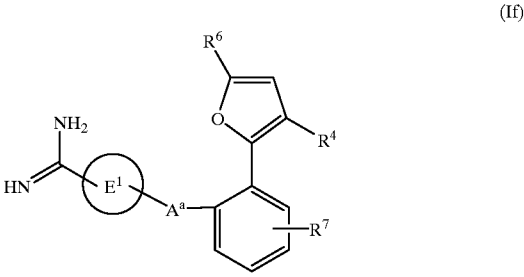

(If)

wherein all the symbols are as hereinbefore defined;
the formula (Ig):

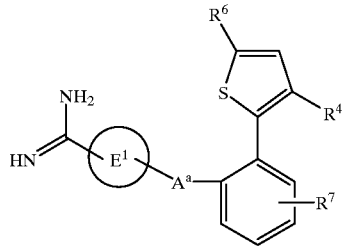

wherein all the symbols are as hereinbefore defined;
the formula (Ih):

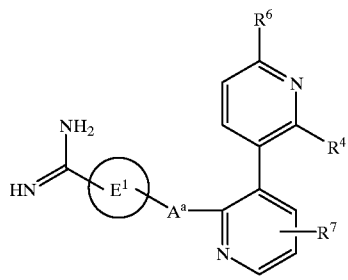

wherein all the symbols are as hereinbefore defined;
the formula (Ii):

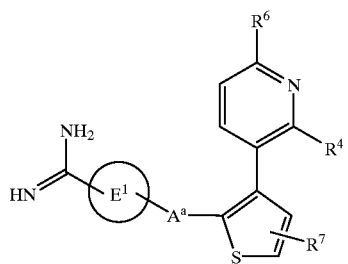

wherein all the symbols are as hereinbefore defined;
non-toxic salts thereof, or hydrates thereof.

As the specific compounds described in Table 1–Table 27, non-toxic salts thereof and hydrates thereof, and the compounds described in the Examples are preferable.

The following compounds include isomers resulting from the presence of asymmetric carbon(s), that is R-configuration, S-configuration and RS-configuration are also included.

TABLE 1

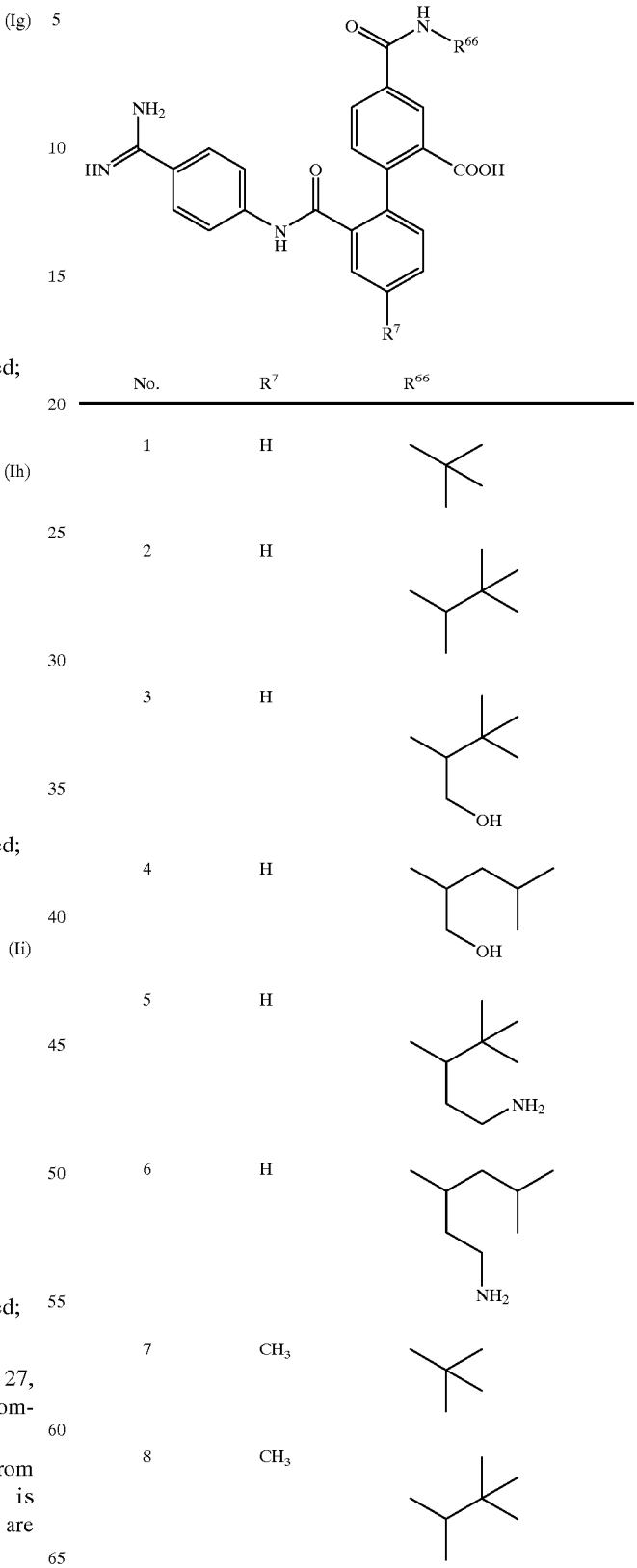

TABLE 1-continued
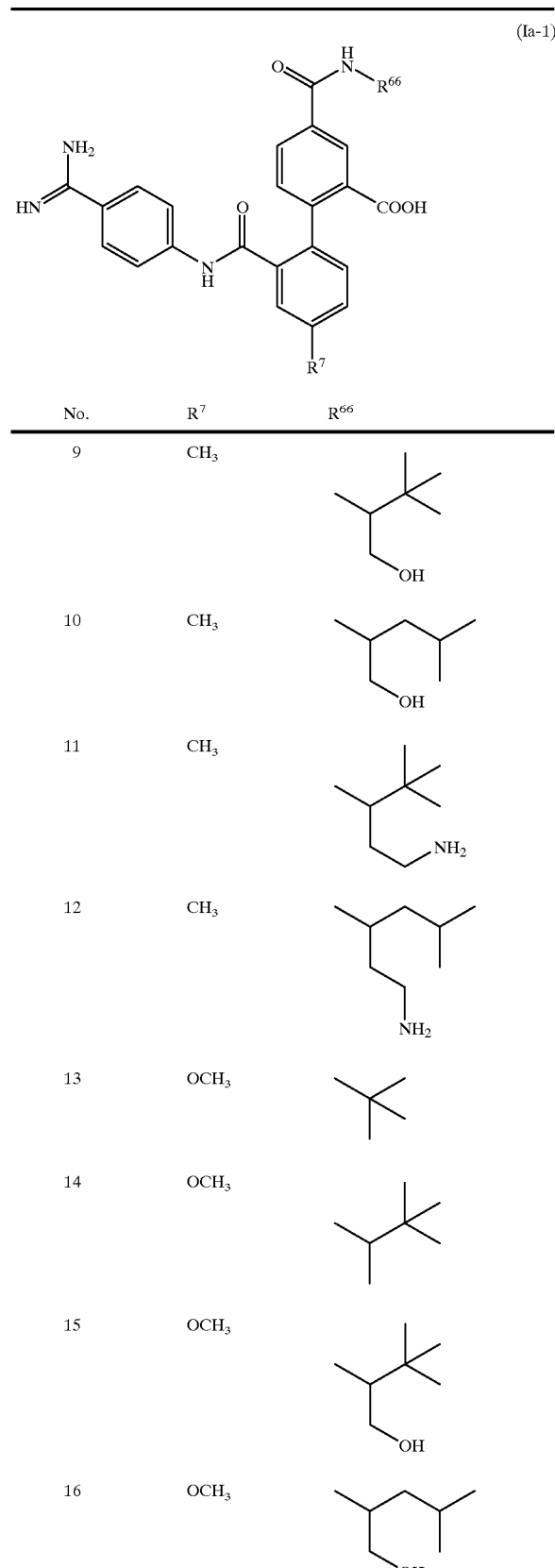
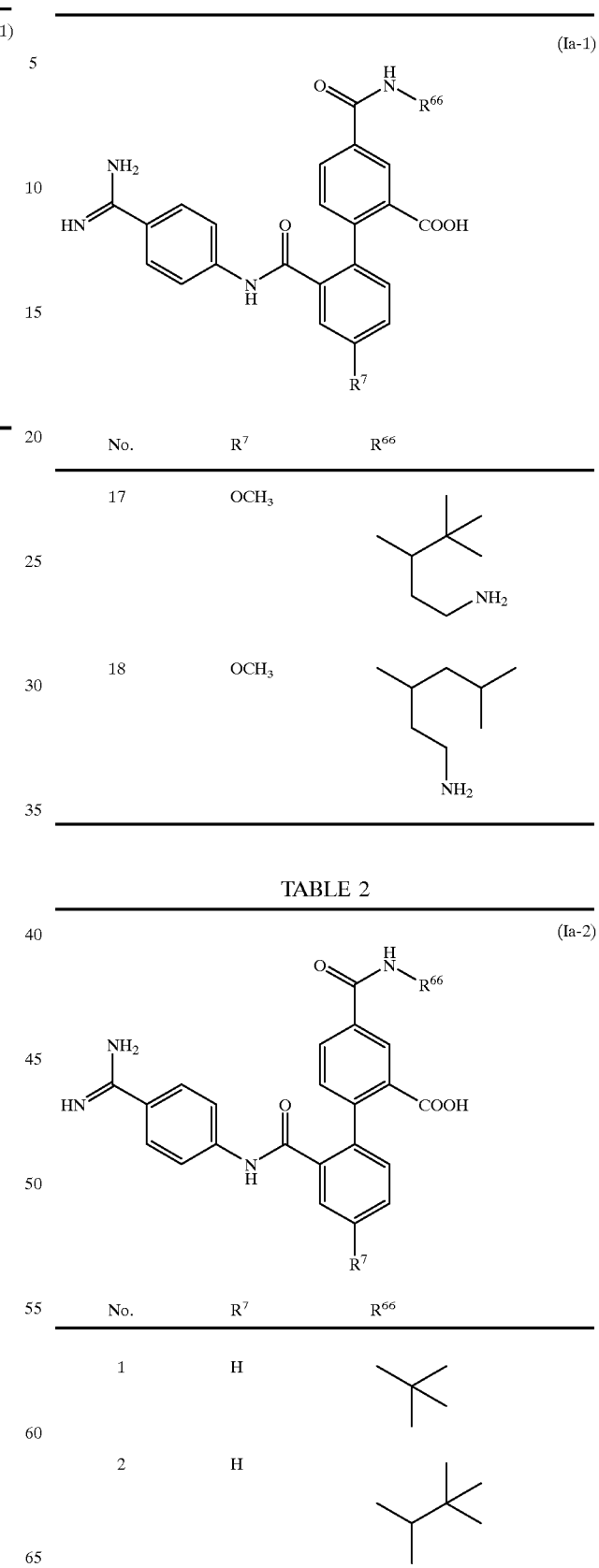

TABLE 2-continued (Ia-2)

| No. | R⁷ | R⁶⁶ |
|---|---|---|
| 3 | H | 2,2-dimethyl-3-hydroxypropyl-methyl (neopentyl-CH(CH₃)-CH₂OH) |
| 4 | H | isohexyl-OH |
| 5 | H | neopentyl-CH(CH₃)-CH₂NH₂ |
| 6 | H | isohexyl-NH₂ |
| 7 | CH₃ | tert-butyl |
| 8 | CH₃ | neopentyl-CH(CH₃) |
| 9 | CH₃ | neopentyl-CH(CH₃)-CH₂OH |
| 10 | CH₃ | isohexyl-OH |
| 11 | CH₃ | neopentyl-CH(CH₃)-CH₂NH₂ |
| 12 | CH₃ | isohexyl-NH₂ |
| 13 | OCH₃ | tert-butyl |
| 14 | OCH₃ | neopentyl-CH(CH₃) |
| 15 | OCH₃ | neopentyl-CH(CH₃)-CH₂OH |
| 16 | OCH₃ | isohexyl-OH |
| 17 | OCH₃ | neopentyl-CH(CH₃)-CH₂NH₂ |

TABLE 2-continued
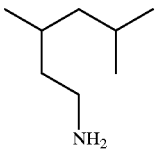
(Ia-2)
| No. | R⁷ | R⁶⁶ |
|---|---|---|
| 18 | OCH₃ |  |
TABLE 3
(Ia-3)
| No. | R⁷ | R⁶⁶ |
|---|---|---|
| 1 | H | 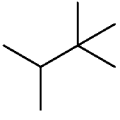 |
| 2 | H | 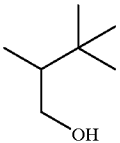 |
| 3 | H |  |
TABLE 3-continued
(Ia-3)
| No. | R⁷ | R⁶⁶ |
|---|---|---|
| 4 | H | (2-hydroxy-branched alkyl) |
| 5 | H | (amino-branched alkyl) |
| 6 | H | (amino-branched alkyl) |
| 7 | CH₃ | (tert-butyl) |
| 8 | CH₃ | (branched alkyl) |
| 9 | CH₃ | (hydroxy-branched alkyl) |
| 10 | CH₃ | (hydroxy-branched alkyl) |
| 11 | CH₃ | (amino-branched alkyl) |

TABLE 3-continued
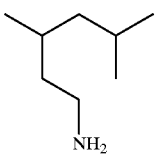
(Ia-3)
| No. | R⁷ | R⁶⁶ |
|---|---|---|
| 12 | CH₃ |  |
| 13 | OCH₃ | 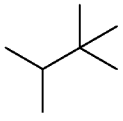 |
| 14 | OCH₃ | 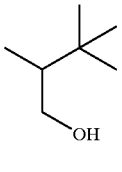 |
| 15 | OCH₃ | 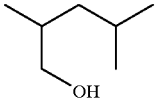 |
| 16 | OCH₃ | 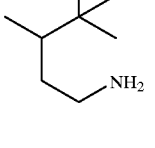 |
| 17 | OCH₃ | 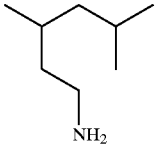 |
| 18 | OCH₃ |  |
TABLE 4
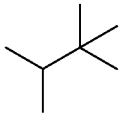
(Ib-1)
| No. | R⁷ | R⁶⁶ |
|---|---|---|
| 1 | H | 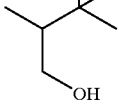 |
| 2 | H | 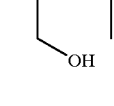 |
| 3 | H | 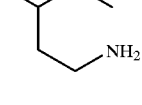 |
| 4 | H | 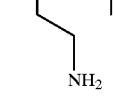 |
| 5 | H | 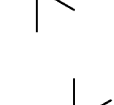 |
| 6 | H |  |
| 7 | CH₃ | |
| 8 | CH₃ | |

TABLE 4-continued (Ib-1)

| No. | R⁷ | R⁶⁶ |
|---|---|---|
| 9 | CH₃ | 2,2-dimethyl-3-hydroxy group (neopentyl-type with OH) |
| 10 | CH₃ | isohexyl with OH |
| 11 | CH₃ | branched alkyl with NH₂ |
| 12 | CH₃ | branched alkyl with NH₂ |
| 13 | OCH₃ | tert-butyl |
| 14 | OCH₃ | branched alkyl |
| 15 | OCH₃ | branched alkyl with OH |
| 16 | OCH₃ | branched alkyl with OH |
| 17 | OCH₃ | branched alkyl with NH₂ |
| 18 | OCH₃ | branched alkyl with NH₂ |

TABLE 5

(Ib-2)

| No. | R⁷ | R⁶⁶ |
|---|---|---|
| 1 | H | tert-butyl |
| 2 | H | branched alkyl |

TABLE 5-continued (Ib-2)

[Structure: 4-amidinophenyl-NH-C(O)- attached to pyridine (with R⁷ substituent) connected to benzene ring bearing COOH and C(O)NH-R⁶⁶]

| No. | R⁷ | R⁶⁶ |
|---|---|---|
| 3 | H | -CH(CH₃)CH(C(CH₃)₃)CH₂OH (neopentyl-type with OH) |
| 4 | H | -CH(CH₃)CH₂CH(CH₃)CH₂OH (isohexyl with OH) |
| 5 | H | -CH(CH₃)CH(C(CH₃)₃)CH₂CH₂NH₂ |
| 6 | H | -CH(CH₃)CH₂CH(CH₃)CH₂CH₂NH₂ |
| 7 | CH₃ | -C(CH₃)₃ (tert-butyl) |
| 8 | CH₃ | -CH(CH₃)C(CH₃)₃ |
| 9 | CH₃ | -CH(CH₃)CH(C(CH₃)₃)CH₂OH |
| 10 | CH₃ | -CH(CH₃)CH₂CH(CH₃)CH₂OH |
| 11 | CH₃ | -CH(CH₃)CH(C(CH₃)₃)CH₂CH₂NH₂ |
| 12 | CH₃ | -CH(CH₃)CH₂CH(CH₃)CH₂CH₂NH₂ |
| 13 | OCH₃ | -C(CH₃)₃ |
| 14 | OCH₃ | -CH(CH₃)C(CH₃)₃ |
| 15 | OCH₃ | -CH(CH₃)CH(C(CH₃)₃)CH₂OH |
| 16 | OCH₃ | -CH(CH₃)CH₂CH(CH₃)CH₂OH |
| 17 | OCH₃ | -CH(CH₃)CH(C(CH₃)₃)CH₂CH₂NH₂ |

TABLE 5-continued (Ib-2)

| No. | R⁷ | R⁶⁶ |
|---|---|---|
| 18 | OCH₃ | (3,5-dimethylhexyl)amine chain |

TABLE 6

(Ib-3)

| No. | R⁷ | R⁶⁶ |
|---|---|---|
| 1 | H | tert-butyl |
| 2 | H | 2,3,3-trimethylbutyl |
| 3 | H | 2,3,3-trimethyl-4-hydroxybutyl |
| 4 | H | 2,4-dimethyl-1-hydroxypentyl |
| 5 | H | 3,4,4-trimethyl-1-aminopentyl |
| 6 | H | 3,5-dimethyl-1-aminohexyl |
| 7 | CH₃ | tert-butyl |
| 8 | CH₃ | 2,3,3-trimethylbutyl |
| 9 | CH₃ | 2,3,3-trimethyl-4-hydroxybutyl |
| 10 | CH₃ | 2,4-dimethyl-1-hydroxypentyl |
| 11 | CH₃ | 3,3,4-trimethyl-1-aminopentyl |

TABLE 6-continued (Ib-3)

| No. | R⁷ | R⁶⁶ |
|---|---|---|
| 12 | CH₃ | 3,5-dimethyl-hexyl-NH₂ |
| 13 | OCH₃ | tert-butyl |
| 14 | OCH₃ | 2,3,3-trimethyl-butyl |
| 15 | OCH₃ | 2-(hydroxymethyl)-3,3-dimethyl-butyl |
| 16 | OCH₃ | 2,4-dimethyl-pentyl-OH |
| 17 | OCH₃ | 2-methyl-3,3-dimethyl-butyl-NH₂ |
| 18 | OCH₃ | 3,5-dimethyl-hexyl-NH₂ |

TABLE 7

(Ic-1)

| No. | R⁷ | R⁶⁶ |
|---|---|---|
| 1 | H | tert-butyl |
| 2 | H | 2,3,3-trimethyl-butyl |
| 3 | H | 2,2-dimethyl-propyl-OH |
| 4 | H | 2,4-dimethyl-pentyl-OH |
| 5 | H | 2-methyl-3,3-dimethyl-butyl-NH₂ |
| 6 | H | 3,5-dimethyl-hexyl-NH₂ |
| 7 | CH₃ | tert-butyl |
| 8 | CH₃ | 2,3,3-trimethyl-butyl |

TABLE 7-continued
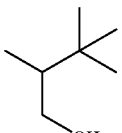
(Ic-1)
| No. | R⁷ | R⁶⁶ |
|---|---|---|
| 9 | CH₃ | 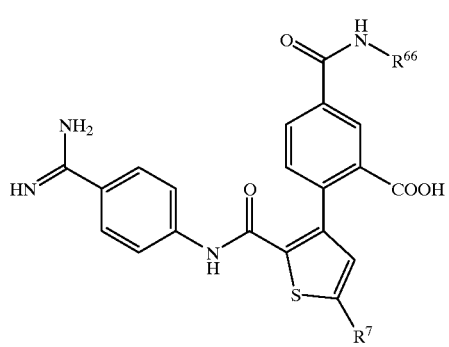 |
| 10 | CH₃ | 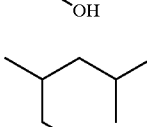 |
| 11 | CH₃ | 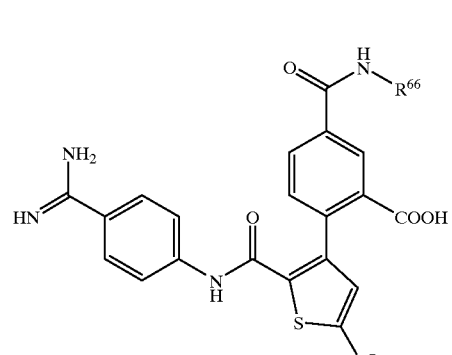 |
| 12 | CH₃ | 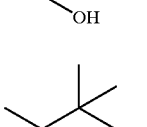 |
| 13 | OCH₃ | 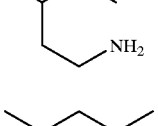 |
| 14 | OCH₃ | 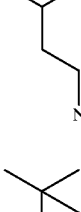 |
| 15 | OCH₃ | 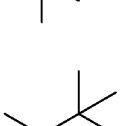 |
| 16 | OCH₃ | 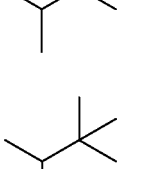 |
TABLE 7-continued
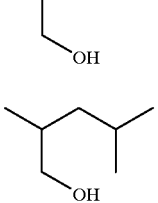
(Ic-1)
| No. | R⁷ | R⁶⁶ |
|---|---|---|
| 17 | OCH₃ | 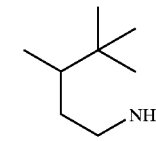 |
| 18 | OCH₃ | 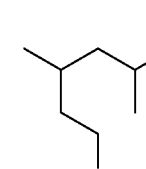 |
TABLE 8
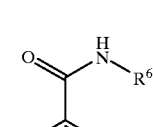
(Ic-2)
| No. | R⁷ | R⁶⁶ |
|---|---|---|
| 1 | H | 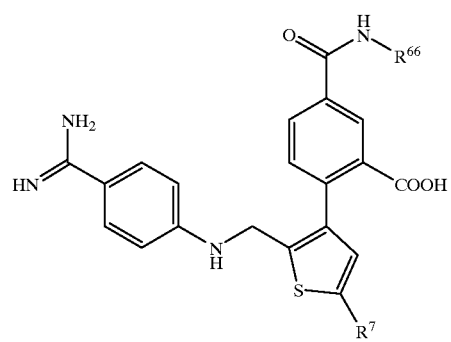 |
| 2 | H | 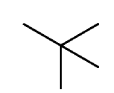 |

TABLE 8-continued (Ic-2)

| No. | R⁷ | R⁶⁶ |
|---|---|---|
| 3 | H | 2,2-dimethyl-propyl with OH (neopentyl-type, CH(CH3)C(CH3)3 with CH2OH) |
| 4 | H | 2,4-dimethylpentyl-1-ol |
| 5 | H | 3,3-dimethyl-butyl with NH2 |
| 6 | H | 2,4-dimethyl with NH2 |
| 7 | CH₃ | tert-butyl |
| 8 | CH₃ | 3,3-dimethylbutan-2-yl |
| 9 | CH₃ | 2-(tert-butyl) with OH |
| 10 | CH₃ | 2,4-dimethylpentyl-1-ol |
| 11 | CH₃ | with NH2 |
| 12 | CH₃ | with NH2 |
| 13 | OCH₃ | tert-butyl |
| 14 | OCH₃ | 3,3-dimethylbutan-2-yl |
| 15 | OCH₃ | with OH |
| 16 | OCH₃ | with OH |
| 17 | OCH₃ | with NH2 |
| 18 | OCH₃ | with NH2 |

TABLE 9

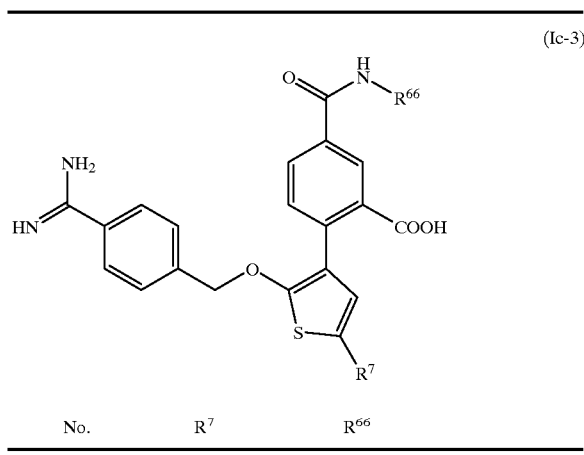

| No. | R⁷ | R⁶⁶ |
|---|---|---|
| 1 | H | *tert*-butyl |
| 2 | H | 2,3,3-trimethylbutyl |
| 3 | H | 2,3,3-trimethyl-1-hydroxybutyl |
| 4 | H | 2,4-dimethyl-1-hydroxypentyl |
| 5 | H | 3,4,4-trimethyl-1-amino group |
| 6 | H | 3,5-dimethyl-1-amino group |
| 7 | CH₃ | *tert*-butyl |
| 8 | CH₃ | 2,3,3-trimethylbutyl |

TABLE 9-continued

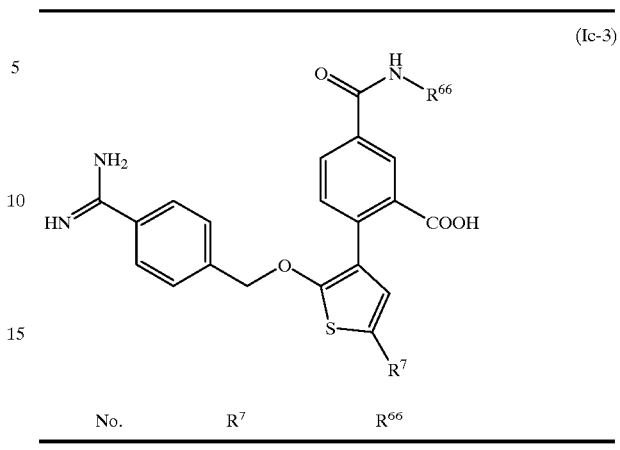

| No. | R⁷ | R⁶⁶ |
|---|---|---|
| 9 | CH₃ | 2,3,3-trimethyl-1-hydroxybutyl |
| 10 | CH₃ | 2,4-dimethyl-1-hydroxypentyl |
| 11 | CH₃ | 3,4,4-trimethyl-1-amino group |
| 12 | CH₃ | 3,5-dimethyl-1-amino group |
| 13 | OCH₃ | *tert*-butyl |
| 14 | OCH₃ | 2,3,3-trimethylbutyl |
| 15 | OCH₃ | 2,3,3-trimethyl-1-hydroxybutyl |
| 16 | OCH₃ | 2,4-dimethyl-1-hydroxypentyl |

TABLE 9-continued (Ic-3)

| No. | R⁷ | R⁶⁶ |
|---|---|---|
| 17 | OCH₃ | (branched alkyl with NH₂) |
| 18 | OCH₃ | (branched alkyl with NH₂) |

TABLE 10

(Id-1)

| No. | R⁷ | R⁶⁶ |
|---|---|---|
| 1 | H | tert-butyl |
| 2 | H | (branched alkyl) |
| 3 | H | (branched alkyl with OH) |
| 4 | H | (branched alkyl with OH) |
| 5 | H | (branched alkyl with NH₂) |
| 6 | H | (branched alkyl with NH₂) |
| 7 | CH₃ | tert-butyl |
| 8 | CH₃ | (branched alkyl) |
| 9 | CH₃ | (branched alkyl with OH) |
| 10 | CH₃ | (branched alkyl with OH) |

TABLE 10-continued (Id-1)

[Structure: phenyl group with NH₂ and HN=C(NH₂)– (amidine) substituent, connected via NH to C(=O) of a furan ring (with R⁷ at 5-position); furan 3-position connected to a benzene ring bearing COOH and C(=O)NH-R⁶⁶]

| No. | R⁷ | R⁶⁶ |
|---|---|---|
| 11 | CH₃ | –CH(CH₃)CH(C(CH₃)₃)CH₂CH₂NH₂ (3-methyl-4,4-dimethyl... with CH₂NH₂) |
| 12 | CH₃ | –CH(CH₃)CH₂CH(CH₃)CH₂CH₂NH₂ |
| 13 | OCH₃ | –C(CH₃)₃ |
| 14 | OCH₃ | –CH(CH₃)C(CH₃)₃ |
| 15 | OCH₃ | –CH(CH₂OH)C(CH₃)₃ |
| 16 | OCH₃ | –CH(CH₃)CH₂CH(CH₃)CH₂OH |
| 17 | OCH₃ | –CH(CH₃)CH(C(CH₃)₃)CH₂NH₂ |
| 18 | OCH₃ | –CH(CH₃)CH₂CH(CH₃)CH₂CH₂NH₂ |

TABLE 11

(Id-2)

[Structure: phenyl group with NH₂ and HN=C(NH₂)– (amidine) substituent, connected via NH-CH₂ to a furan ring (with R⁷ at 5-position); furan 3-position connected to a benzene ring bearing COOH and C(=O)NH-R⁶⁶]

| No. | R⁷ | R⁶⁶ |
|---|---|---|
| 1 | H | –C(CH₃)₃ |
| 2 | H | –CH(CH₃)C(CH₃)₃ |
| 3 | H | –CH(CH₂OH)C(CH₃)₃ |
| 4 | H | –CH(CH₃)CH₂CH(CH₃)CH₂OH |
| 5 | H | –CH(CH₃)CH(C(CH₃)₃)CH₂NH₂ |
| 6 | H | –CH(CH₃)CH₂CH(CH₃)CH₂CH₂NH₂ |
| 7 | CH₃ | –C(CH₃)₃ |
| 8 | CH₃ | –CH(CH₃)C(CH₃)₃ |

TABLE 11-continued (Id-2)

| No. | R⁷ | R⁶⁶ |
|---|---|---|
| 9 | CH₃ | 2,2-dimethylpropyl with OH (neopentyl-OH type) |
| 10 | CH₃ | 2,4-dimethylpentyl-OH |
| 11 | CH₃ | 3,4,4-trimethylpentyl-NH₂ |
| 12 | CH₃ | 3,5-dimethylhexyl-NH₂ |
| 13 | OCH₃ | tert-butyl |
| 14 | OCH₃ | 3,3-dimethylbutyl branched |
| 15 | OCH₃ | neopentyl-OH type |
| 16 | OCH₃ | 2,4-dimethylpentyl-OH |

TABLE 11-continued (Id-2)

| No. | R⁷ | R⁶⁶ |
|---|---|---|
| 17 | OCH₃ | 3,4,4-trimethylpentyl-NH₂ |
| 18 | OCH₃ | 3,5-dimethylhexyl-NH₂ |

TABLE 12

(Id-3)

| No. | R⁷ | R⁶⁶ |
|---|---|---|
| 1 | H | tert-butyl |
| 2 | H | 3,3-dimethylbutyl branched |

TABLE 12-continued
(Id-3)
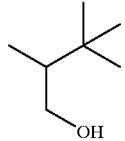
| No. | R7 | R66 |
|---|---|---|
| 3 | H | 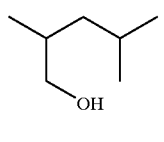 |
| 4 | H | 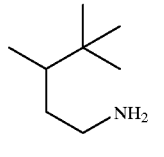 |
| 5 | H | 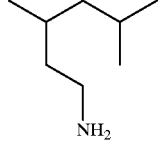 |
| 6 | H |  |
| 7 | CH3 | 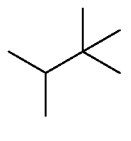 |
| 8 | CH3 | 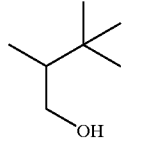 |
| 9 | CH3 | 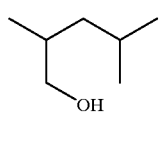 |
| 10 | CH3 | 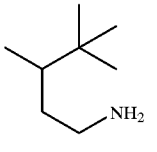 |
| 11 | CH3 | 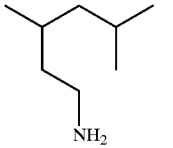 |
| 12 | CH3 |  |
| 13 | OCH3 | 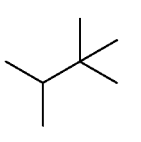 |
| 14 | OCH3 | 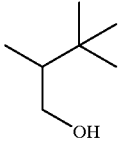 |
| 15 | OCH3 | 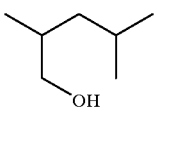 |
| 16 | OCH3 | 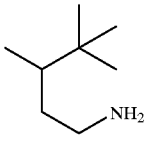 |
| 17 | OCH3 | 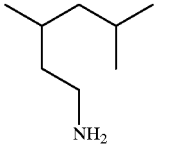 |
| 18 | OCH3 | |

TABLE 13
(Ie-1)
| No. | R⁷ | R⁶⁶ |
|---|---|---|
| 1 | H |  |
| 2 | H | 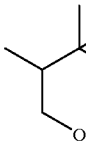 |
| 3 | H |  |
| 4 | H | 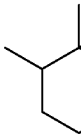 |
| 5 | H | 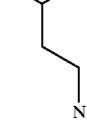 |
| 6 | H |  |
| 7 | CH₃ |  |
| 8 | CH₃ | 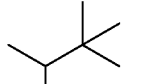 |
| 9 | CH₃ | 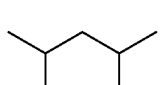 |
| 10 | CH₃ | 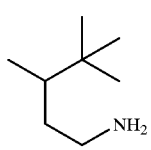 |
| 11 | CH₃ | 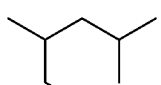 |
| 12 | CH₃ |  |
| 13 | OCH₃ | 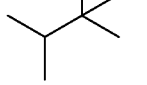 |
| 14 | OCH₃ | 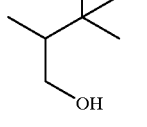 |
| 15 | OCH₃ | 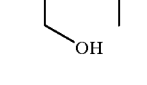 |
| 16 | OCH₃ | |

TABLE 13-continued (Ie-1)

| No. | R⁷ | R⁶⁶ |
|---|---|---|
| 17 | OCH₃ | (3,3-dimethyl-2-methylbutyl)methylamine group with NH₂ |
| 18 | OCH₃ | (2,4-dimethylpentyl) group with NH₂ |

TABLE 14

(Ie-2)

| No. | R⁷ | R⁶⁶ |
|---|---|---|
| 1 | H | tert-butyl |
| 2 | H | 2,3,3-trimethylbutyl |

TABLE 14-continued (Ie-2)

| No. | R⁷ | R⁶⁶ |
|---|---|---|
| 3 | H | 2,3,3-trimethyl-1-hydroxybutyl |
| 4 | H | 2,4-dimethyl-1-hydroxypentyl |
| 5 | H | 3,3-dimethyl-2-methyl-aminobutyl |
| 6 | H | 2,4-dimethyl-aminopentyl |
| 7 | CH₃ | tert-butyl |
| 8 | CH₃ | 2,3,3-trimethylbutyl |
| 9 | CH₃ | 2,3,3-trimethyl-1-hydroxybutyl |
| 10 | CH₃ | 2,4-dimethyl-1-hydroxypentyl |

TABLE 14-continued
(Ie-2)
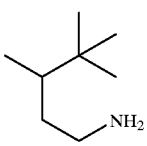
| No. | R⁷ | R⁶⁶ |
|---|---|---|
| 11 | CH₃ | 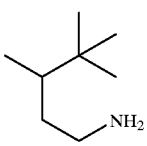 |
| 12 | CH₃ | 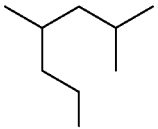 |
| 13 | OCH₃ | 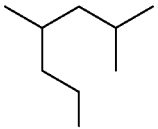 |
| 14 | OCH₃ |  |
| 15 | OCH₃ | 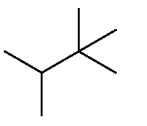 |
| 16 | OCH₃ | 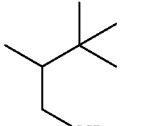 |
| 17 | OCH₃ | 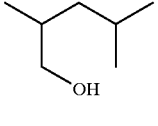 |
TABLE 14-continued
(Ie-2)
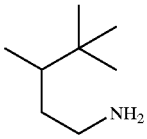
| No. | R⁷ | R⁶⁶ |
|---|---|---|
| 18 | OCH₃ | 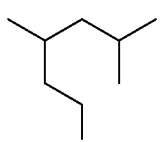 |
TABLE 15
(Ie-3)
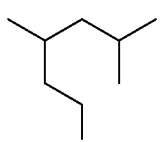
| No. | R⁷ | R⁶⁶ |
|---|---|---|
| 1 | H | 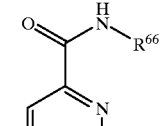 |
| 2 | H | 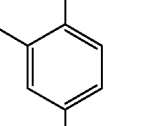 |
| 3 | H | 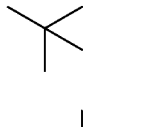 |

TABLE 15-continued (Ie-3)

| No. | R⁷ | R⁶⁶ |
|---|---|---|
| 4 | H | isohexyl-OH |
| 5 | H | neohexyl-NH₂ |
| 6 | H | isohexyl-NH₂ |
| 7 | CH₃ | tert-butyl |
| 8 | CH₃ | neopentyl-methyl |
| 9 | CH₃ | neohexyl-OH |
| 10 | CH₃ | isohexyl-OH |
| 11 | CH₃ | neohexyl-NH₂ |
| 12 | CH₃ | isohexyl-NH₂ |
| 13 | OCH₃ | tert-butyl |
| 14 | OCH₃ | neopentyl-methyl |
| 15 | OCH₃ | neohexyl-OH |
| 16 | OCH₃ | isohexyl-OH |
| 17 | OCH₃ | neohexyl-NH₂ |
| 18 | OCH₃ | isohexyl-NH₂ |

TABLE 16

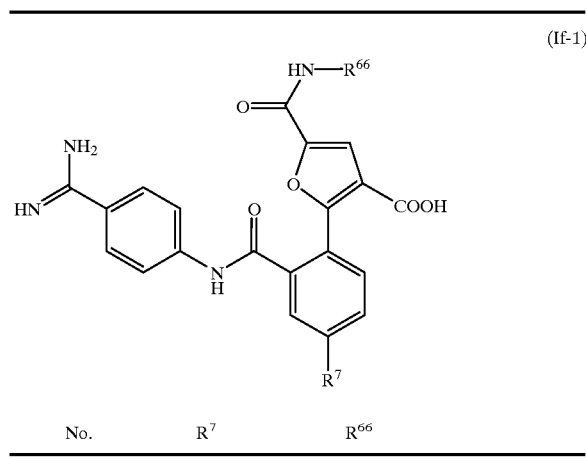

(If-1)

| No. | R[7] | R[66] |
|---|---|---|
| 1 | H | tert-butyl |
| 2 | H | 2,3,3-trimethylbutyl |
| 3 | H | 2,2-dimethyl-3-hydroxypropyl (neopentyl-OH) |
| 4 | H | 2,4-dimethyl-1-hydroxypentyl |
| 5 | H | 2,3,3-trimethyl-aminobutyl |
| 6 | H | 3,5-dimethyl-aminohexyl |
| 7 | CH₃ | tert-butyl |
| 8 | CH₃ | 2,3,3-trimethylbutyl |

TABLE 16-continued

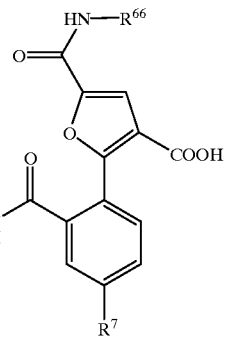

(If-1)

| No. | R[7] | R[66] |
|---|---|---|
| 9 | CH₃ | 2,2-dimethyl-3-hydroxypropyl |
| 10 | CH₃ | 2,4-dimethyl-1-hydroxypentyl |
| 11 | CH₃ | 2,3,3-trimethyl-aminobutyl |
| 12 | CH₃ | 3,5-dimethyl-aminohexyl |
| 13 | OCH₃ | tert-butyl |
| 14 | OCH₃ | 2,3,3-trimethylbutyl |
| 15 | OCH₃ | 2,2-dimethyl-3-hydroxypropyl |
| 16 | OCH₃ | 2,4-dimethyl-1-hydroxypentyl |

TABLE 16-continued (If-1)

| No. | R⁷ | R⁶⁶ |
|---|---|---|
| 17 | OCH₃ | (3,3-dimethyl-2-methylbutyl)methylamine group |
| 18 | OCH₃ | (3,5-dimethylhexyl)amine group |

TABLE 17

(If-2)

| No. | R⁷ | R⁶⁶ |
|---|---|---|
| 1 | H | tert-butyl |
| 2 | H | 2,3,3-trimethylbutyl |

TABLE 17-continued (If-2)

| No. | R⁷ | R⁶⁶ |
|---|---|---|
| 3 | H | 2,3,3-trimethyl-1-hydroxybutyl group |
| 4 | H | 2,4-dimethyl-1-hydroxypentyl group |
| 5 | H | (3,3-dimethyl-2-methylbutyl)methylamine group |
| 6 | H | (3,5-dimethylhexyl)amine group |
| 7 | CH₃ | tert-butyl |
| 8 | CH₃ | 2,3,3-trimethylbutyl |
| 9 | CH₃ | 2,3,3-trimethyl-1-hydroxybutyl group |
| 10 | CH₃ | 2,4-dimethyl-1-hydroxypentyl group |

TABLE 17-continued
(If-2)
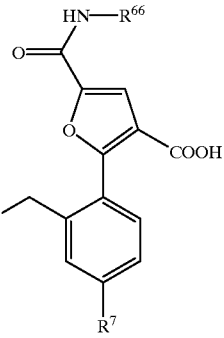
| No. | R⁷ | R⁶⁶ |
|---|---|---|
| 11 | CH₃ |  |
| 12 | CH₃ | 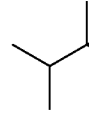 |
| 13 | OCH₃ | 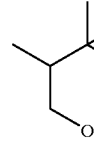 |
| 14 | OCH₃ | 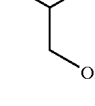 |
| 15 | OCH₃ | 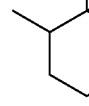 |
| 16 | OCH₃ | 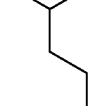 |
| 17 | OCH₃ | 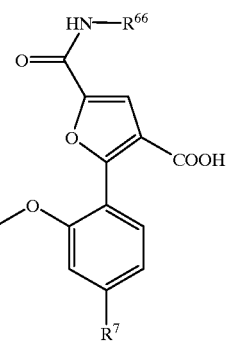 |
| 18 | OCH₃ | 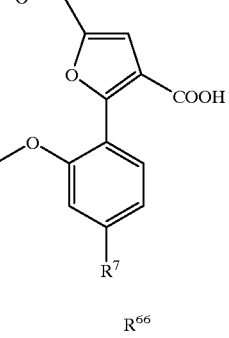 |
TABLE 18
(If-3)
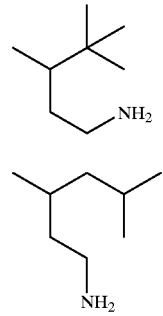
| No. | R⁷ | R⁶⁶ |
|---|---|---|
| 1 | H | 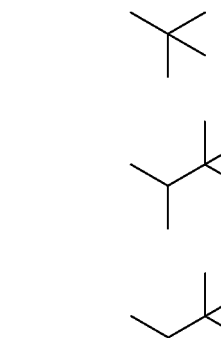 |
| 2 | H | 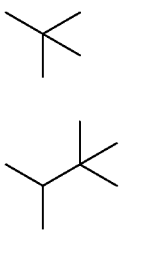 |
| 3 | H | 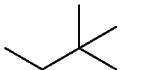 |
| 4 | H | 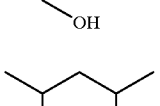 |
| 5 | H | 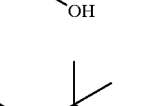 |
| 6 | H | 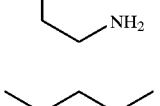 |
| 7 | CH₃ | 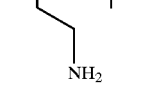 |
| 8 | CH₃ |  |

TABLE 18-continued (If-3)

| No. | R⁷ | R⁶⁶ |
|---|---|---|
| 9 | CH₃ | (2,3,3-trimethylbutyl with OH) |
| 10 | CH₃ | (2,4-dimethylpentyl with OH) |
| 11 | CH₃ | (3,4,4-trimethylpentyl with NH₂) |
| 12 | CH₃ | (3,5-dimethylhexyl with NH₂) |
| 13 | OCH₃ | (tert-butyl) |
| 14 | OCH₃ | (3,3-dimethylbutan-2-yl) |
| 15 | OCH₃ | (2,3,3-trimethylbutyl with OH) |
| 16 | OCH₃ | (2,4-dimethylpentyl with OH) |

TABLE 18-continued (If-3)

| No. | R⁷ | R⁶⁶ |
|---|---|---|
| 17 | OCH₃ | (3,4,4-trimethylpentyl with NH₂) |
| 18 | OCH₃ | (3,5-dimethylhexyl with NH₂) |

TABLE 19

(Ig-1)

| No. | R⁷ | R⁶⁶ |
|---|---|---|
| 1 | H | (tert-butyl) |
| 2 | H | (3,3-dimethylbutan-2-yl) |

TABLE 19-continued (Ig-1)

| No. | R⁷ | R⁶⁶ |
|---|---|---|
| 3 | H | 2,2-dimethyl-propyl with OH (neopentyl-type with OH) |
| 4 | H | 2,4-dimethylpentyl-OH |
| 5 | H | 3,3-dimethyl-butyl-NH₂ branched |
| 6 | H | 2,4-dimethylpentyl-NH₂ |
| 7 | CH₃ | tert-butyl |
| 8 | CH₃ | 3,3-dimethyl-2-methylbutyl |
| 9 | CH₃ | 2,2-dimethyl-propyl-OH branched |
| 10 | CH₃ | 2,4-dimethylpentyl-OH |
| 11 | CH₃ | branched alkyl-NH₂ |
| 12 | CH₃ | 2,4-dimethylpentyl-NH₂ |
| 13 | OCH₃ | tert-butyl |
| 14 | OCH₃ | 3,3-dimethyl-2-methylbutyl |
| 15 | OCH₃ | branched alkyl-OH |
| 16 | OCH₃ | 2,4-dimethylpentyl-OH |
| 17 | OCH₃ | branched alkyl-NH₂ |
| 18 | OCH₃ | 2,4-dimethylpentyl-NH₂ |

TABLE 20

(Ig-2)

| No. | R⁷ | R⁶⁶ |
|---|---|---|
| 1 | H | tert-butyl |
| 2 | H | 3,3-dimethylbut-2-yl |
| 3 | H | 2-(hydroxymethyl)-3,3-dimethylbutyl |
| 4 | H | 4-methyl-2-methylpentan-1-ol |
| 5 | H | 4,4-dimethyl-3-methylpentylamine |
| 6 | H | 5-methyl-3-methylhexylamine |
| 7 | CH₃ | tert-butyl |
| 8 | CH₃ | 3,3,4-trimethylpentan-2-yl |
| 9 | CH₃ | 2-(hydroxymethyl)-3,3-dimethylbutyl |
| 10 | CH₃ | 4-methyl-2-methylpentan-1-ol |
| 11 | CH₃ | 4,4-dimethyl-3-methylpentylamine |
| 12 | CH₃ | 5-methyl-3-methylhexylamine |
| 13 | OCH₃ | tert-butyl |
| 14 | OCH₃ | 3,3-dimethylbut-2-yl |
| 15 | OCH₃ | 2-(hydroxymethyl)-3,3-dimethylbutyl |
| 16 | OCH₃ | 4-methyl-2-methylpentan-1-ol |

TABLE 20-continued (Ig-2)

| No. | R⁷ | R⁶⁶ |
|---|---|---|
| 17 | OCH₃ | (3,3-dimethylbutyl with methyl branch)-CH₂NH₂ |
| 18 | OCH₃ | (3,5-dimethylhexyl)-NH₂ |

TABLE 21

(Ig-3)

| No. | R⁷ | R⁶⁶ |
|---|---|---|
| 1 | H | tert-butyl |
| 2 | H | 2,3,3-trimethylbutyl |

TABLE 21-continued (Ig-3)

| No. | R⁷ | R⁶⁶ |
|---|---|---|
| 3 | H | (2,3,3-trimethylbutyl)-OH |
| 4 | H | (3-methylbutyl)-OH |
| 5 | H | (2,3,3-trimethylbutyl)-NH₂ |
| 6 | H | (3,5-dimethylhexyl)-NH₂ |
| 7 | CH₃ | tert-butyl |
| 8 | CH₃ | 2,3,3-trimethylbutyl |
| 9 | CH₃ | (2,3,3-trimethylbutyl)-OH |
| 10 | CH₃ | (3-methylbutyl)-OH |

TABLE 21-continued (Ig-3)

| No. | R⁷ | R⁶⁶ |
|---|---|---|
| 11 | CH₃ | (3,3-dimethylbutyl with methyl branch, terminal NH₂) |
| 12 | CH₃ | (dimethyl-branched alkyl, terminal NH₂) |
| 13 | OCH₃ | tert-butyl |
| 14 | OCH₃ | (isopropyl-tert-butyl alkyl) |
| 15 | OCH₃ | (branched alkyl with terminal OH) |
| 16 | OCH₃ | (branched alkyl with terminal OH) |
| 17 | OCH₃ | (branched alkyl with terminal NH₂) |
| 18 | OCH₃ | (branched alkyl with terminal NH₂) |

TABLE 22

(Ih-1)

| No. | R⁷ | R⁶⁶ |
|---|---|---|
| 1 | H | tert-butyl |
| 2 | H | (isopropyl-tert-butyl alkyl) |
| 3 | H | (branched alkyl with terminal OH) |
| 4 | H | (branched alkyl with terminal OH) |
| 5 | H | (branched alkyl with terminal NH₂) |
| 6 | H | (branched alkyl with terminal NH₂) |
| 7 | CH₃ | tert-butyl |
| 8 | CH₃ | (isopropyl-tert-butyl alkyl) |

TABLE 22-continued (Ih-1)

| No. | R⁷ | R⁶⁶ |
|---|---|---|
| 9 | CH₃ | 2,2-dimethyl-3-hydroxymethylpropyl (neopentyl with CH₂OH) |
| 10 | CH₃ | 4-methyl-2-methylpentan-1-ol substituent |
| 11 | CH₃ | 2-tert-butyl-4-aminobutyl |
| 12 | CH₃ | 2,4-dimethyl-6-aminohexyl |
| 13 | OCH₃ | tert-butyl |
| 14 | OCH₃ | 2,3,3-trimethylbutyl |
| 15 | OCH₃ | 2,2-dimethyl-3-hydroxymethylpropyl |
| 16 | OCH₃ | 4-methyl-2-methylpentan-1-ol substituent |

TABLE 22-continued (Ih-1)

| No. | R⁷ | R⁶⁶ |
|---|---|---|
| 17 | OCH₃ | 2-tert-butyl-4-aminobutyl |
| 18 | OCH₃ | 2,4-dimethyl-6-aminohexyl |

TABLE 23

(Ih-2)

| No. | R⁷ | R⁶⁶ |
|---|---|---|
| 1 | H | tert-butyl |
| 2 | H | 2,3,3-trimethylbutyl |

TABLE 23-continued (Ih-2)

| No. | R⁷ | R⁶⁶ |
|---|---|---|
| 3 | H | 2,2-dimethyl-3-hydroxymethylbutyl (neopentyl-CH(CH₃)CH₂OH) |
| 4 | H | 2,4-dimethyl-1-hydroxypentyl chain |
| 5 | H | 3,3-dimethyl-2-methyl-4-aminobutyl |
| 6 | H | 3,5-dimethyl-1-aminohexyl |
| 7 | CH₃ | tert-butyl |
| 8 | CH₃ | 3,3-dimethyl-2-methylbutyl |
| 9 | CH₃ | 2,2-dimethyl-3-hydroxymethylbutyl |
| 10 | CH₃ | 2,4-dimethyl-1-hydroxypentyl |
| 11 | CH₃ | 3,3-dimethyl-2-methyl-4-aminobutyl |
| 12 | CH₃ | 3,5-dimethyl-1-aminohexyl |
| 13 | OCH₃ | tert-butyl |
| 14 | OCH₃ | 3,3-dimethyl-2-methylbutyl |
| 15 | OCH₃ | 2,2-dimethyl-3-hydroxymethylbutyl |
| 16 | OCH₃ | 2,4-dimethyl-1-hydroxypentyl |
| 17 | OCH₃ | 3,3-dimethyl-2-methyl-4-aminobutyl |

TABLE 23-continued
(Ih-2)
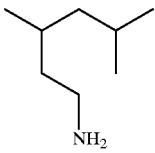
| No. | R⁷ | R⁶⁶ |
|---|---|---|
| 18 | OCH₃ | 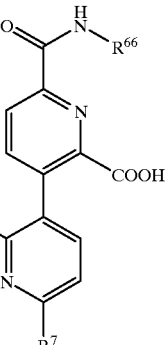 |
TABLE 24
(Ih-3)
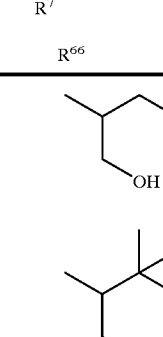
| No. | R⁷ | R⁶⁶ |
|---|---|---|
| 1 | H | 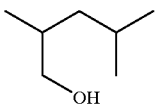 |
| 2 | H | 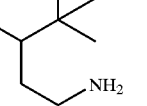 |
| 3 | H | 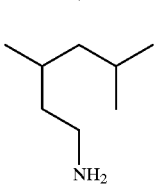 |
TABLE 24-continued
(Ih-3)
| No. | R⁷ | R⁶⁶ |
|---|---|---|
| 4 | H | 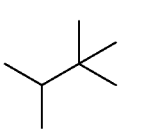 |
| 5 | H | 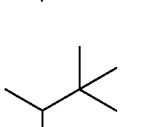 |
| 6 | H | 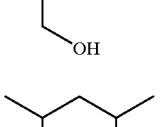 |
| 7 | CH₃ | 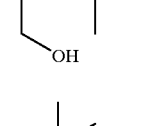 |
| 8 | CH₃ | 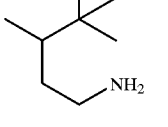 |
| 9 | CH₃ |  |
| 10 | CH₃ |  |
| 11 | CH₃ | 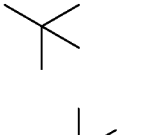 |

TABLE 24-continued (Ih-3)

| No. | R⁷ | R⁶⁶ |
|---|---|---|
| 12 | CH₃ | 3,5-dimethylhexyl-1-amine (2,4-dimethyl-6-aminohexyl) |
| 13 | OCH₃ | tert-butyl |
| 14 | OCH₃ | 2,3,3-trimethylbutyl |
| 15 | OCH₃ | 2,3,3-trimethyl-4-hydroxybutyl |
| 16 | OCH₃ | 2,4-dimethyl-5-hydroxypentyl |
| 17 | OCH₃ | 2,3,3-trimethyl-5-aminopentyl |
| 18 | OCH₃ | 2,4-dimethyl-6-aminohexyl |

TABLE 25

(Ii-1)

| No. | R⁷ | R⁶⁶ |
|---|---|---|
| 1 | H | tert-butyl |
| 2 | H | 2,3,3-trimethylbutyl |
| 3 | H | 2,3,3-trimethyl-4-hydroxybutyl |
| 4 | H | 2,4-dimethyl-5-hydroxypentyl |
| 5 | H | 2,3,3-trimethyl-5-aminopentyl |
| 6 | H | 2,4-dimethyl-6-aminohexyl |
| 7 | CH₃ | tert-butyl |
| 8 | CH₃ | 2,3,3-trimethylbutyl |

TABLE 25-continued (Ii-1)

| No. | R⁷ | R⁶⁶ |
|---|---|---|
| 9 | CH₃ | 2,2-dimethyl-hydroxybutyl group |
| 10 | CH₃ | 2,4-dimethyl-hydroxypentyl group |
| 11 | CH₃ | 3,4,4-trimethyl-aminopentyl group |
| 12 | CH₃ | 3,5-dimethyl-aminohexyl group |
| 13 | OCH₃ | tert-butyl |
| 14 | OCH₃ | 3,3-dimethyl-2-methylbutyl |
| 15 | OCH₃ | 2,2-dimethyl-hydroxybutyl group |
| 16 | OCH₃ | 2,4-dimethyl-hydroxypentyl |

TABLE 25-continued (Ii-1)

| No. | R⁷ | R⁶⁶ |
|---|---|---|
| 17 | OCH₃ | 3,4,4-trimethyl-aminopentyl |
| 18 | OCH₃ | 3,5-dimethyl-aminohexyl |

TABLE 26

(Ii-2)

| No. | R⁷ | R⁶⁶ |
|---|---|---|
| 1 | H | tert-butyl |
| 2 | H | 3,3-dimethyl-2-methylbutyl |

TABLE 26-continued
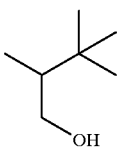
(Ii-2)
| No. | R⁷ | R⁶⁶ |
|---|---|---|
| 3 | H | 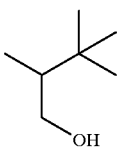 |
| 4 | H | 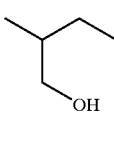 |
| 5 | H | 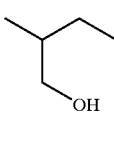 |
| 6 | H | 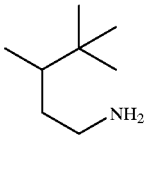 |
| 7 | CH₃ | 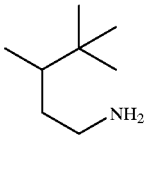 |
| 8 | CH₃ | 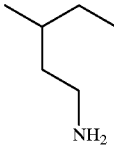 |
| 9 | CH₃ | 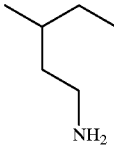 |
| 10 | CH₃ |  |
TABLE 26-continued
(Ii-2)
| No. | R⁷ | R⁶⁶ |
|---|---|---|
| 11 | CH₃ | 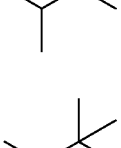 |
| 12 | CH₃ | 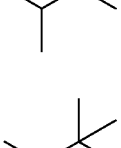 |
| 13 | OCH₃ | 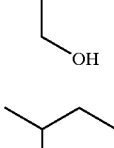 |
| 14 | OCH₃ | 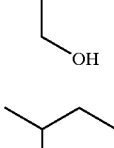 |
| 15 | OCH₃ | 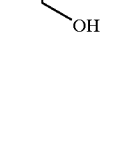 |
| 16 | OCH₃ | 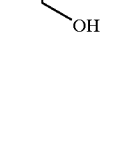 |
| 17 | OCH₃ | 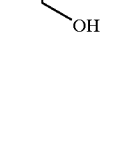 |
| 18 | OCH₃ | 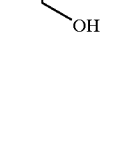 |

TABLE 27
(Ii-3)
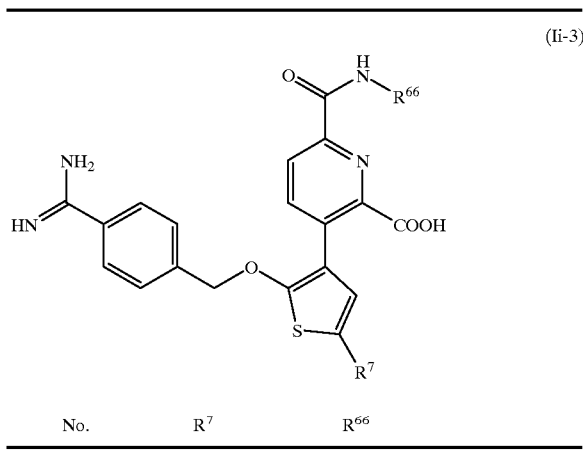
| No. | R⁷ | R⁶⁶ |
|---|---|---|
| 1 | H | *tert*-butyl |
| 2 | H | 2,3,3-trimethylbutyl-like |
| 3 | H | 2,3,3-trimethyl-1-ol |
| 4 | H | 2,4-dimethyl-1-ol |
| 5 | H | 3,4,4-trimethyl-amine |
| 6 | H | 3,5-dimethyl-hexyl-amine |
| 7 | CH₃ | *tert*-butyl |
| 8 | CH₃ | 2,3,3-trimethylbutyl-like |
TABLE 27-continued
(Ii-3)
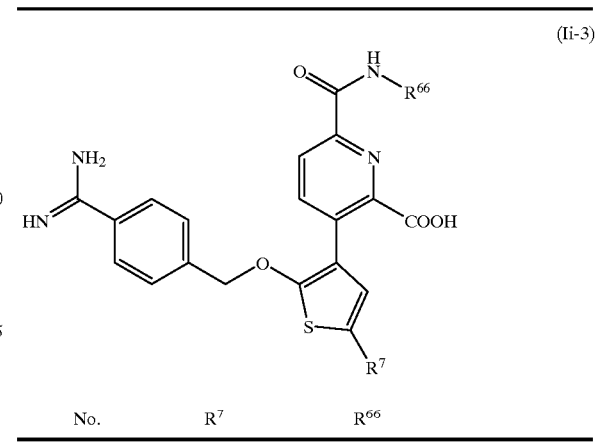
| No. | R⁷ | R⁶⁶ |
|---|---|---|
| 9 | CH₃ | 2,3,3-trimethyl-1-ol |
| 10 | CH₃ | 2,4-dimethyl-1-ol |
| 11 | CH₃ | 3,4,4-trimethyl-amine |
| 12 | CH₃ | 3,5-dimethyl-hexyl-amine |
| 13 | OCH₃ | *tert*-butyl |
| 14 | OCH₃ | 2,3,3-trimethylbutyl-like |
| 15 | OCH₃ | 2,3,3-trimethyl-1-ol |
| 16 | OCH₃ | 2,4-dimethyl-1-ol |

TABLE 27-continued

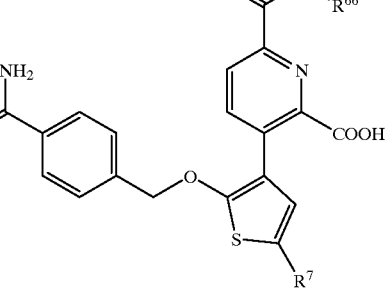

(Ii-3)

| No. | R⁷ | R⁶⁶ |
|---|---|---|
| 17 | OCH₃ | 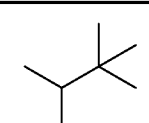 |
| 18 | OCH₃ | 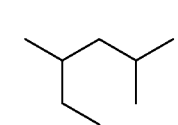 |

Salts

Non-toxic salts of the present invention include all pharmaceutically acceptable salts.

The compounds of formulae (I) of the present invention may be converted into the corresponding salts. Non-toxic salts and water-soluble salts are preferred. Suitable salts, for example, include: salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, dicyclohexylamine, benzylamine, phenethylamine, piperidine, monoethanolamine, diethanolamine, tris(hydroxymethyl)amine, lysine, arginine, N-methyl-D-glucamine).

The compounds of formulae (I) may be converted into the corresponding acid addition salts. Non-toxic acid addition salts and water-soluble acid addition salts are preferred. Suitable salts, for example, include: salts of inorganic acids e.g. hydrochloride, hydrobromide, sulfate, phosphate, nitrate; salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of formulae (I) and salts thereof may be converted into the corresponding hydrates by conventional manner.

Process for the Preparation of the Present Compound (a-1) In the compound of the present invention of the formula (I), the compound in which A is —NR³⁰CO—, and R¹, R² and R³ are not groups including hydroxy, and R⁴ and R⁵ are groups excepting CONR¹²R¹³ and are not groups including —COOH, P(O)(OH)₂ and tetrazol-5-yl, and R⁶ and R⁷ are not groups including amino and are optionally protected hydroxy, E⁴ ring is not pyrrole, furan and thiophene, that is the compound of the formula (I-A-1):

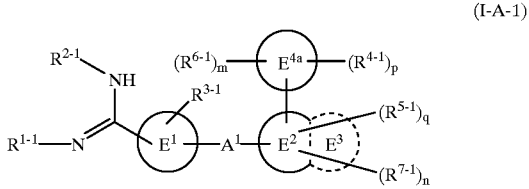

(I-A-1)

wherein

R$^{1-1}$, R$^{2-1}$ and R$^{3-1}$ each independently, is a same meaning as R¹, R² and R³, with the proviso that in the case of R¹, R² and R³ are groups including hydroxy, then the hydroxy represented by corresponding R$^{1-1}$, R$^{2-1}$ and R$^{3-1}$ is protected hydroxy, R$^{4-1}$ is a same meaning as R⁴ excepting CONR¹²R¹³, with the proviso that in the case of R⁴ is groups including —COOH, P(O)(OH)₂ and tetrazol-5yl, then —COOH, P(O)(OH)₂ and tetrazol-5yl represented by corresponding R$^{4-1}$ are protected —COOH, P(O)(OH)₂ and tetrazol-5yl, R$^{5-1}$ is a same meaning as R⁵ excepting CONR¹²R¹³, with the proviso that in the case of R⁵ is groups including —COOH, P(O)(OH)₂ and tetrazol-5yl, then —COOH, P(O)(OH)₂ and tetrazol-5yl represented by corresponding R$^{5-1}$ are protected —COOH, P(O)(OH)₂ and tetrazol-5yl, R$^{6-1}$ and R$^{7-1}$ are a same meaning as R⁶ and R⁷, with the proviso that in the case of R⁶ and R⁷ are groups including hydroxy and amino, then the hydroxy and amino represented by corresponding R$^{6-1}$ and R$^{7-1}$ are hydroxy or protected hydroxy and protected amino, A¹ is —NR³⁰CHO—, E$^{4a}$ ring is a same meaning as E⁴, with the proviso that it is not pyrrole, furan and thiophene, the other symbols are as hereinbefore defined;

may be prepared by amidation the compound of the formula (II):

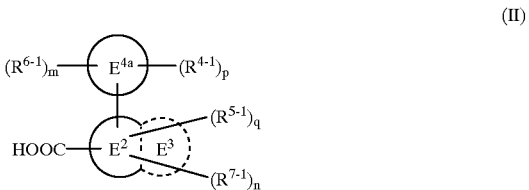

(II)

wherein all the symbols are as hereinbefore defined; with the compound of the formula (III):

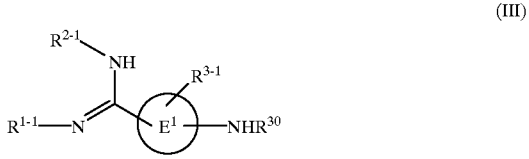

(III)

wherein all the symbols are as hereinbefore defined; or in the case of the compound in which R$^{6-1}$ and R$^{7-1}$ are the group containing protected hydroxy, continually, may be prepared by deprotection.

The method of amidation is known. It includes the method
(1) via an acyl halide,
(2) via a mixed acid anhydride,
(3) using a condensing agent.

These methods are explained as follows.

(1) The method via an acyl halide, for example, may be carried out in an organic solvent (e.g. chloroform, methylene chloride, diethyl ether or tetrahydrofuran, ethyl acetate) or without a solvent, using an acyl halide (e.g. oxalyl chloride or thionyl chloride) at −20° C. to reflux temperature, and the obtained acyl halide derivative may be reacted with an amine in an organic solvent (e.g. chloroform, methylene chloride, diethyl ether or tetrahydrofuran) in the presence of a tertiary amine (e.g. pyridine, triethyl amine, dimethyl aniline or dimethylaminopyridine) at 0–40° C.

(2) The method via a mixed acid anhydride may be carried out, for example, by reacting a carboxylic acid with an acyl halide (e.g. pivaloyl chloride, tosyl chloride, mesyl chloride, ethyl chloroformate or isobutyl chloroformate) in an organic solvent (e.g. chloroform, methylene chloride, diethyl ether or tetrahydrofuran) or without a solvent, in the presence of a tertiary amine (e.g. pyridine, triethylamine, dimethylaniline or dimethylaminopyridine, N-methylmorpholine) at −20° C.–40° C., and the obtained mixed acid anhydride derivative may be reacted with a corresponding amine in an organic solvent (e.g. chloroform, methylene chloride, diethyl ether or tetrahydrofuran) at 0–40° C.

(3) The method using a condensing agent (e.g. 1,3-dicyclohexyl carbodiimide (DCC), 1-ethyl-3-[3-(dimethylamino)propyl]carbodiimide (EDC) or 2-chloro-1-methylpyridinium iodide, 1,1'-carbonyldiimidazole (CDI)) may be carried out, for example, by reacting a carboxylic acid with an amine in an organic solvent (e.g. chloroform, methylene chloride, dimethylformamide, diethyl ether, tetrahydrofuran) or without a solvent, optionally in the presence of a tertiary amine (e.g. pyridine, triethylamine, dimethylaniline or dimethylaminopyridine) using a condensing agent, using 1-hydroxybenzotriazole (HoBt) or without HoBt at 0–40° C.

The reaction described in (1), (2) and (3) may be carried out under an inert gas (e.g. argon, nitrogen) to avoid water in order to obtain a preferable result.

The deprotection of hydroxy is known, for example, it includes the method deprotection under acidic conditions or hydrogenolysis.

Deprotection under acidic conditions, for example, may be carried out in a solvent (e.g. methylene chloride, chloroform, dioxane, ethyl acetate, anisole) or without solvent, using an organic acid (e.g. acetic acid, trifluoroacetic acid, methansulfonic acid, trimethylsilyl iodide), or an inorganic acid (e.g. hydrogen chloride) or a mixture thereof (e.g. hydrogen bromide acetic acid) at 0–90°C.

Hydrogenolysis, for example, may be carried out in a solvent (e.g. tetrahydrofuran, dioxane, diethyl ether, ethyl acetate, methanol, ethanol), in the presence of a catalyst (e.g. palladium on carbon, palladium, palladium hydroxide, palladium acetate, palladium black, platinum black, nickel or Raney-nickel), at ordinary or elevated pressure of hydrogen gas at 0–80° C.

(a-2) In the compound of the present invention of the formula (I), the compound in which A is —NR$^{30}$CHO—, and R$^1$, R$^2$ and R$^3$ are not groups including hydroxy, and R$^4$ and R$^5$ are groups excepting CONR$^{12}$R$^{13}$ and are not groups including —COOH, P(O)(OH)$_2$ and tetrazol-5-yl, and R$^6$ and R$^7$ are not groups including hydroxy and amino, E$^4$ ring is pyrrole, furan or thiophene, that is the compound of the formula (I-A-2):

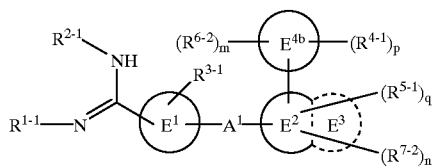

(I-A-2)

wherein

E$^{4b}$ is pyrrole, furan or thiophene,

R$^{6-2}$ and R$^{7-2}$ are a same meaning as R$^6$ and R$^7$, with the proviso that in the case of R$^6$ and R$^7$ are groups including hydroxy and amino, then the hydroxy and amino represented by corresponding R$^{6-2}$ and R$^{7-2}$ are protected hydroxy and protected amino, the other symbols are as hereinbefore defined;

may be prepared by subjecting to condensation reaction, the compound of the formula (XI-a):

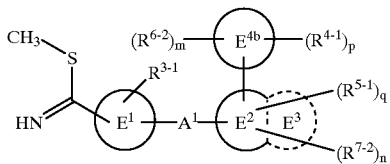

(XI-a)

wherein all the symbols are as hereinbefore defined;

with the compound of the formula (IX):

$$H_2N\text{—}R^1 \qquad (IX)$$

wherein R$^1$ is as hereinbefore defined.

The condensation reaction is known, for example, it may be carried out by reacting with the compound of the formula (IX) or salt thereof in organic solvent (e.g. methanol, ethanol, acetonitrile, methylene chloride, diethyl ether, tetrahydrofuran, toluene, dimethylformamide) without a solvent, optionally in the presence of an base (e.g. triethylamine, sodium hydride, sodium methoxide, sodium ethoxide) at 0° C. to reflux temperature.

(b) In the compound of the present invention of the formula (I), the compound in which A is —SO$_2$NR$^{34}$— or —NR$^{35}$SO$_2$—, and R$^1$, R$^2$ and R$^3$ are not groups including hydroxy, and R$^4$ and R$^5$ are groups excepting CONR$^{12}$R$^{13}$ and are not groups including —COOH, P(O)(OH)$_2$ and tetrazol-5-yl, and R$^6$ and R$^7$ are not groups including amino and optionally protected hydroxy, that is the compound of the formula (I-B):

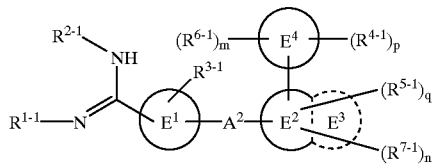

(I-B)

wherein A$^2$ is —SO$_2$NR$^{34}$— or —NR$^{35}$SO$_2$—, the other symbols are as hereinbefore defined;

may be prepared by reacting the compound of the formula (IV-1):

(IV-1)

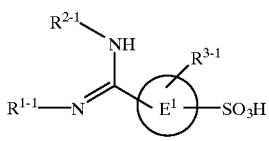

wherein all the symbols are as hereinbefore defined;
with the compound of the formula (V-1):

(V-1)

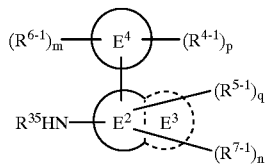

wherein all the symbols are as hereinbefore defined;
or by reacting the compound of the formula (IV-2):

(IV-2)

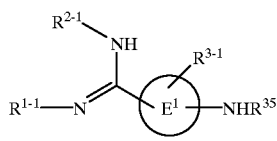

wherein all the symbols are as hereinbefore defined;
with the compound of the formula (V-2):

(V-2)

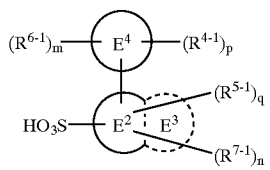

wherein all the symbols are as hereinbefore defined;
or in the case of the compound in which $R^{6-1}$ and $R^{7-1}$ are the group containing protected hydroxy, continually, may be prepared by deprotection.

The above reaction is known, for example, may be carried out by reacting sulfonic acid and acyl halide (e.g. oxalyl chloride or thionyl chloride) in an organic solvent (e.g. chloroform, methylene chloride, diethyl ether, tetrahydrofuran, ethyl acetate) or without a solvent at −20° C. to reflux temperature, and the obtained acyl halide derivative may be reacted with an amine in an organic solvent (e.g. chloroform, methylene chloride, diethyl ether or tetrahydrofuran) in the presence of a tertiary amine (e.g. pyridine, triethyl amine, dimethyl aniline or dimethylaminopyridine) at 0–40° C.

The deprotection reaction is known, for example, may be carried out as method hereinbefore defined.

(c-1) In the compound of the present invention of the formula (I), the compound in which A is —O—CH$_2$—, —S—CH$_2$—, —NR$^{31}$CHR$^{32-1}$—, and R$^1$, R$^2$ and R$^3$ are not groups including hydroxy, and R$^4$ and R$^5$ are groups excepting CONR$^{12}$R$^{13}$ and are not groups including —COOH, P(O)(OH)$_2$ and tetrazol-5-yl, and R$^6$ and R$^7$ are not groups including hydroxy and amino, E$^4$ ring is not pyrrole, furan and thiophene, that is the compound of the formula (I-C-1):

(I-C-1)

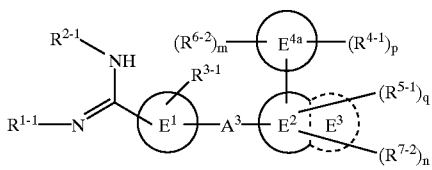

wherein $A^3$ is —O—CH$_2$—, —S—CH$_2$— or —NR$^{31}$CHR$^{32-1}$—, in which $R^{32-1}$ is hydrogen, cyano, COO$^{36-1}$, in which $R^{36-1}$ is C1–4 alkyl; or CONR$^{37-1}$R$^{38-1}$, in which $R^{37-1}$ and $R^{38-1}$ each independently, is hydrogen, C1–4 alkyl, but both are not hydrogen at the same time; the other symbols are as hereinbefore defined;

may be prepared by alkylation the compound of the formula (VI):

(VI)

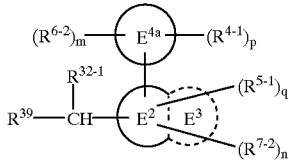

wherein $R^{39}$ is halogen atom, methansulfonyloxy or p-toluenesulfonyloxy, the other symbols are as hereinbefore defined;

with the compound of the formula (VII):

(VII)

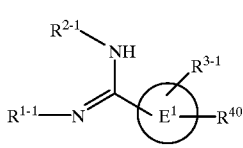

wherein $R^{40}$ is —OHSH or —NHR$^{31}$, the other symbols are as hereinbefore defined.

The above alkylation is known, for example, may be carried out in an inert organic solvent (e.g. tetrahydrofuran (THF), diethyl ether, methylene chloride, chloroform, carbon tetrachloride, pentane, hexane, benzene, toluene, dimethylformamide (DMF), dimethylsulfoxide (DMSO), hexamethylphosphric triamide (HMPA)), in the presence of an base (e.g. sodium hydride, potassium carbonate, triethylamine, pyridine, sodium iodide, cesium carbonate) at 0–80° C.

In the case of the compound in which A$^3$ or —NR$^{31}$CH$_2$—, it may be also prepared by subjecting the compound of the formula (XII):

(XII)

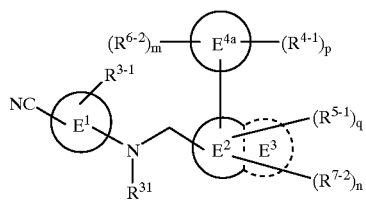

wherein all the symbols are as hereinbefore defined;
to pinner method.

The pinner method is known, for example, it may be carried out in an organic solvent (e.g. ethanol, methylene chloride) using hydrochloride at 0–50° C., continually, in an organic solvent (e.g. methanol, ethanol) using ammonium gas at 0–50° C.

(c-2) In the compound of the present invention of the formula (I), the compound in which A is —O—CH$_2$—, —S—CH$_2$— or —NR$^{31}$CHR$^{32-1}$, and R$^1$, R$^2$ and R$^3$ are not groups including hydroxy, and R$^4$ and R$^5$ are groups excepting CONR$^{12}$R$^{13}$ and are not groups including —COOH, P(O)(OH)$_2$ and tetrazol-5-yl, and R$^6$ and R$^7$ are not groups including hydroxy and amino, E$^4$ ring is pyrrole, furan or thiophene, that is the compound of the formula (I-C-2):

(I-C-2)

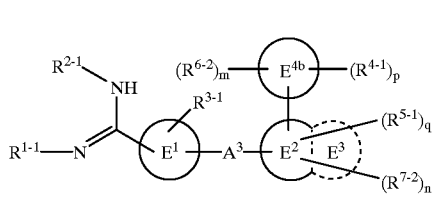

wherein
A$^3$ is —O—CH$_2$—, —S—CH$_2$— or —NR$^{31}$CHR$^{32-1}$—, the other symbols are as hereinbefore defined;
may be prepared by subjecting to condensation reaction, the compound of the formula (XI-b):

(XI-b)

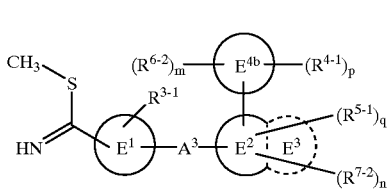

wherein all the symbols are as hereinbefore defined;
with the compound of the formula (IX):

H$_2$N—R$^1$ (IX)

wherein R$^1$ is as hereinbefore defined.

The condensation reaction is known, for example, it may be carried out as method hereinbefore defined.

(d-1) In the compound of the present invention of the formula (I), the compound in which A is vinylene, ethynylene, —CH$_2$—O—, —CH$_2$—NR$^{33}$—, —CH$_2$—S—, and R$^3$ are not groups including hydroxy, and R$^4$ and R$^5$ are groups excepting CONR$^{12}$R$^{13}$ and are not groups including —COOH, P(O)(OH)$_2$ and tetrazol-5-yl, and R$^6$ and R$^7$ are not groups including hydroxy and amino, when A is vinylene or ethynylene, then E$^4$ ring is not pyrrole, furan and thiophene, that is the compound of the formula (I-D-1):

(I-D-1)

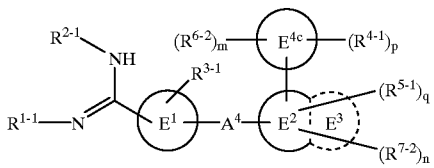

wherein

A$^4$ is vinylene, ethynylene, —CH$_2$—O—, —CH$_2$—NR$^{33}$—, —CH$_2$—S—,

E$^{4c}$ ring is a same meaning as E$^4$ ring, with the proviso that it is not pyrrole, furan and thiophene, when A is vinylene or ethynylene, the other symbols are as hereinbefore defined;

may be prepared by subjecting to condensation reaction, the compound of the formula (VIII):

(VIII)

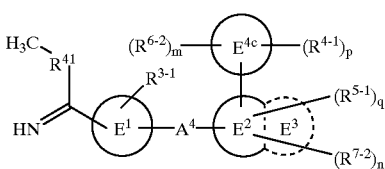

wherein

R$^{41}$ is —O— or —S—, and the other symbols are as hereinbefore defined;

with the compound of the formula (IX):

H$_2$N—R$^1$ (IX)

wherein R$^1$ is as hereinbefore defined.

The above reaction is known, for example, the compound of the formula (VIII) may be carried out by reacting with the compound of the formula (IX) or salts thereof in an organic solvent (e.g. methanol, ethanol, acetonitrile, methylene chloride, diethyl ether, tetrahydrofuran, toluene, dimethylformamide) or without a solvent, optionally in the presence of an base (e.g. triethylamine, sodium hydride, sodium methoxide, sodium ethoxide) at 0° C. to reflux temperature.

(d-2) In the compound of the present invention of the formula (I), the compound in which A is vinylene, ethynylene, and R$^3$ are not groups including hydroxy, and R$^4$ and R$^5$ are groups excepting CONR$^{12}$R$^{13}$ and are not groups including —COOH, P(O)(OH)$_2$ and tetrazol-5-yl, and R$^6$ and R$^7$ are not groups including hydroxy and amino, E$^4$ ring is pyrrole, furan or thiophene, that is the compound of the formula (I-D-2):

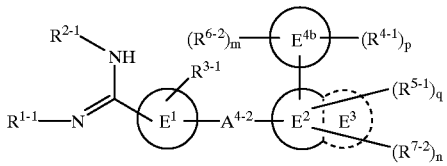

(I-D-2)

wherein $A^{4-2}$ is vinylene, ethynylene, and the other symbols are as hereinbefore defined;

may be prepared by subjecting to condensation reaction, the compound of the formula (XI-c):

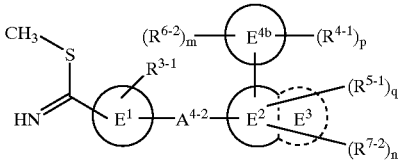

(XI-c)

wherein all the symbols are as hereinbefore defined; with the compound of the formula (IX):

$$H_2N\text{—}R^1 \qquad (IX)$$

wherein $R^1$ is as hereinbefore defined.

The condensation reaction is known, for example, it may be carried out as method hereinbefore defined.

(e) In the compound of the present invention of the formula (I), the compound in which A is ethylene, and $R^1$, $R^2$ and $R^3$ are not groups including hydroxy; and $R^4$ and $R^5$ are groups excepting $CONR^{12}R^{13}$ and are not groups including —COOH, $P(O)(OH)_2$ and tetrazol-5-yl, and $R^6$ and $R^7$ are not groups including hydroxy and amino, that is the compound of the formula (I-E):

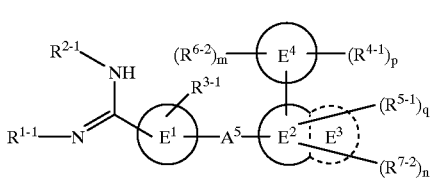

(I-E)

wherein $A^5$ is ethylene, and the other symbols are as hereinbefore defined;

may be prepared by subjecting to reduction the compound in which $A^4$ is vinylene or ethynylene in the compound of the formula (I-D-1), or the compound of the formula (I-D-2).

The above reduction reaction is known, for example, in an organic solvent (e.g. tetrahydrofuran, dioxane, diethyl ether, ethyl acetate, methanol, ethanol), using a catalyst (e.g. palladium on carbon, palladium, palladium hydroxide, palladium acetate, palladium black, platinum black, nickel or Raney-nickel), at ordinary or elevated pressure of hydrogen gas at 0–80° C.

(f) In the compound of the present invention of the formula (I), $R^4$ and $R^5$ are groups excepting $CONR^{12}R^{13}$, $R^1$, $R^2$ and $R^3$ are groups including hydroxy, or $R^4$ and $R^5$ are groups including —COOH, $P(O)(OH)_2$ and tetrazol-5-yl, or $R^6$ and $R^7$ are groups including hydroxy and amino, that is the compound of the formula (I-F):

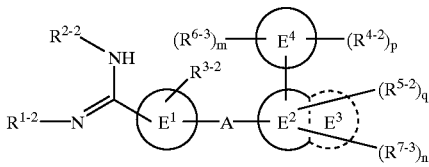

(I-F)

wherein $R^{1-2}$, $R^{2-2}$, $R^{3-2}$, $R^{6-3}$ and $R^{7-3}$ each is the same meaning as $R^1$, $R^2$, $R^3$, $R^6$ and $R^7$, $R^{4-2}$ and $R^{5-2}$ each is the same meaning as $R^4$ and $R^5$ excepting $CONR^{12}R^{13}$, with the proviso that at least one of $R^{1-2}$, $R^{2-2}$, $R^{3-2}$, $R^{4-2}$, $R^{5-2}$, $R^{6-3}$, and $R^{7-3}$ is hydroxy, —COOH, amino, $P(O)(OH)_2$, tetrazol-5-yl, or a group including them, the other symbols are as hereinbefore defined;

may be prepared by deprotection under an alkaline condition, deprotection under an acidic conditions and/or hydrogenolysis, the compound of the formula (I-A-1), (I-A-2), (I-B),(I-C-1), (I-C-2), (I-D-1), (I-D-2) or (I-E).

Deprotection under an alkaline condition is known, for example, may be carried out in an organic solvent (e.g. methanol, tetrahydrofuran, dioxane), using an alkali metal hydroxide (e.g. sodium hydroxide, potassium hydroxide, lithium hydroxide), an alkaline earth metal hydroxide (e.g. calcium hydroxide) or a carbonate (e.g. sodium carbonate, potassium carbonate), or an aqueous solution thereof or mixture thereof at 0–40° C.

Deprotection under acidic conditions, for example, may be carried out in a solvent (e.g. methylene chloride, chloroform, dioxane, ethyl acetate, anisole) or without a solvent, using an organic acid (e.g. acetic acid, trifluoroacetic acid, methansulfonic acid, trimethylsilyl iodide), or an inorganic acid (e.g. hydrogen chloride) or a mixture thereof (e.g. hydrogen bromide acetic acid) at 0–90° C.

Hydrogenolysis, for example, may be carried out in a solvent (e.g. tetrahydrofuran, dioxane, diethyl ether, methanol, ethanol), in the presence of a catalyst (e.g. palladium on carbon, palladium, palladium hydroxide, palladium acetate, palladium black, platinum black, nickel or Raney-nickel), at ordinary or elevated pressure of hydrogen gas at 0–80° C.

(g) In the compound of the present invention of the formula (I), $R^4$ and $R^5$ are $CONR^{12}R^{13}$, that is the compound of the formula (I-G):

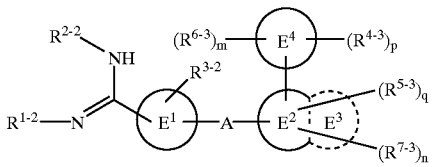

(I-G)

wherein $R^{4-3}$ and $R^{5-3}$ each independently, is $CONR^{12}R^{13}$, and $R^{1-2}$, $R^{2-2}$, $R^{3-2}$, $R^{6-3}$ and $R^{7-3}$ each is the same meaning as $R^1$, $R^2$, $R^3$, $R^6$ and $R^7$, with the proviso that at least one of $R^{1-2}$, $R^{2-2}$, $R^{3-2}$, $R^{6-3}$ and $R^{7-3}$ is hydroxy, —COOH, amino or a group including them, the other symbols are as hereinbefore defined;

may be prepared by amidation the compound in which at least one of $R^4$ and $R^5$ is —COOH or a group including it in the compound of the formula (I-F), with the compound of the formula (X):

$$NHR^{12}R^{13} \qquad (X)$$

wherein all the symbols are as hereinbefore defined.

Amidation is known, for example, it may be carried out by the same method as hereinbefore described.

As will be apparent to those skilled in the art, t-butyl or benzyl may be used as protecting groups for carboxyl, and t-butyl, benzyl, t-butyldimethylsilyl, trimethylsilyl may be used as protecting groups for hydroxy, but other groups which may be removed easily and selectively are also preferred. For example, the groups described in T. W. Greene, Protective Groups in Organic Synthesis, Wiley, New York, 1991, may be used.

Benzyloxycarbonyl, t-butoxycarbonyl may be used as protecting groups for amino, but other groups which may be removed easily and selectively are also preferred.

t-Butyl or benzyl may be used as protecting groups for hydroxylamine, but other groups which may be removed easily and selectively are also preferred. For example —$C(CH_3)_2$—$OCH_3$ may be used.

The desired compound of the present invention may be easily prepared using these protecting groups.

The compound of the formula (II), (III), (IV-1), (IV-2), (V-1), (V-2), (VI), (VII), (VIII), (IX), (X), (XI-a), (XI-b), (XI-c) and (XII) are known per se or may be prepared by known methods, or methods in the Examples.

For example, the compound of the formula (II), (V-1), (V-2), (VI), (VIII), (XI), and (XII) may be prepared by using a reaction depicted in following schemes.

Symbols in each schemes mean as follows, the other symbols are as hereinbefore defined.

L: OTf, halogen atom,
Tf: trifluoromethansulfonyl,
M: —$B(OH)_2$, —$Sn(C1-4\ alkyl)_3$,
$R^{42}$: a general protecting groups of amine,
$R^{43}$: a general protecting groups of hydroxy,
$Tf_2O$: trifluoromethansulfonic acid anhydrous,
$HC(SMe)_3$: tris(methylthio)methane,
NBS: N-bromosuccinimide,
TMSCN: trimethylsilylcyanide,
HClaq: an aqueous solution of hydrochloric acid,
MsCl: methanesulfonyl chloride,
TsCl: p-toluenesulfonyl chloride,
$A^{4-1}$: —$CH_2$—O—, —$CH_2$—$NR^{33}$—, —$CH_2$—S—,
$A^6$: —$NR^{30}CO$—, —O—$CH_2$—, —S—$CH_2$—, —$NR^{31}CHR^{32-1}$—, vinylene, ethylene,
NaSH: sodium bisulfate,
MeI: methyl iodide,
MeOH: methanol.

Scheme 1

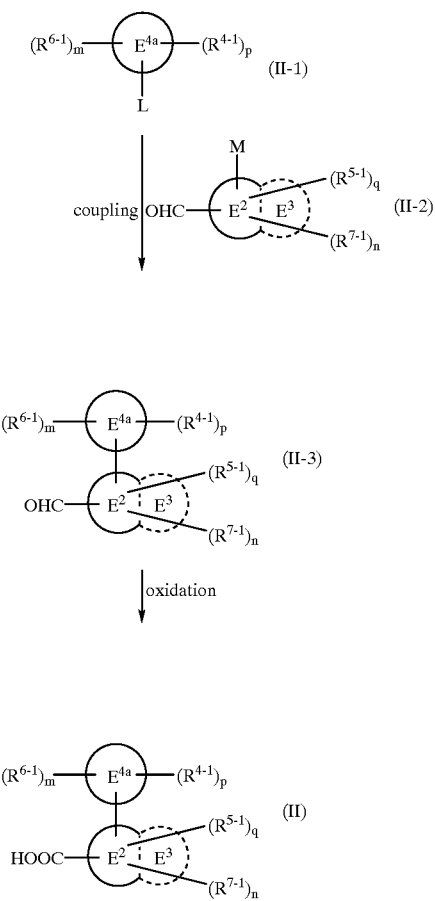

Scheme 2

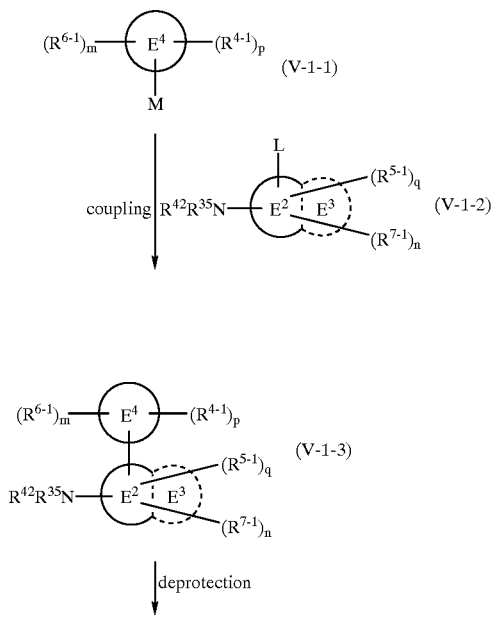

Scheme 3
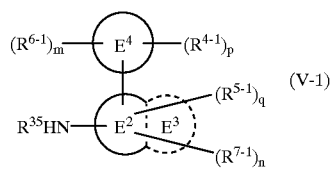
(V-1)
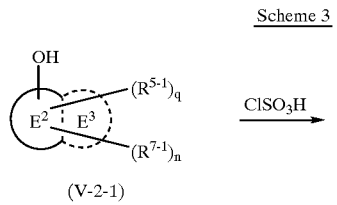
(V-2-1)
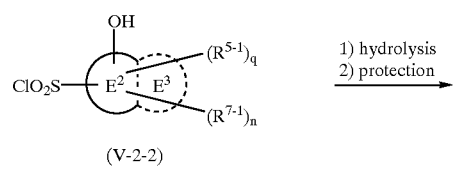
(V-2-2)
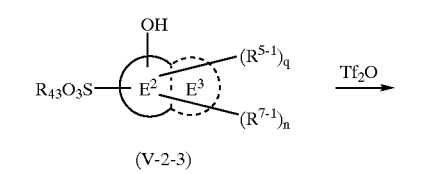
(V-2-3)
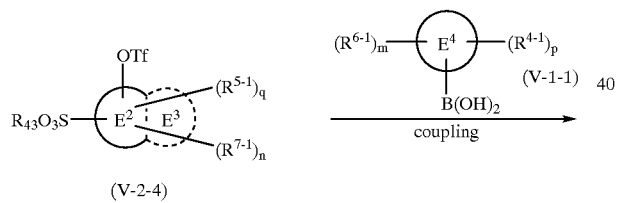
(V-2-4)
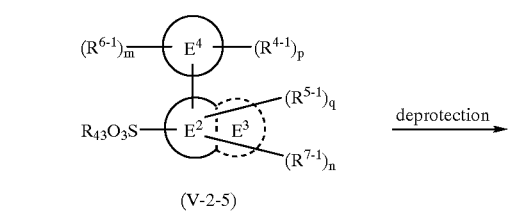
(V-2-5)
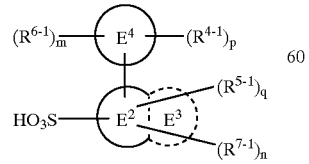
(V-2)
Scheme 4-1
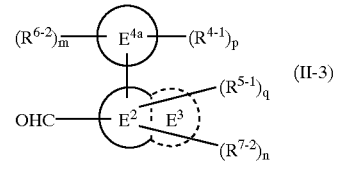
(II-3)
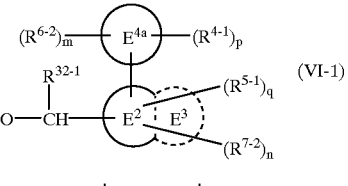
(VI-1)
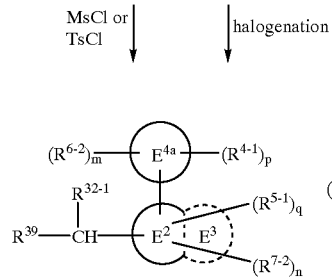
(VI)
Scheme 4-2
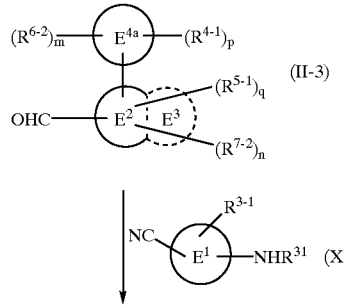
(II-3)
(XII-1)
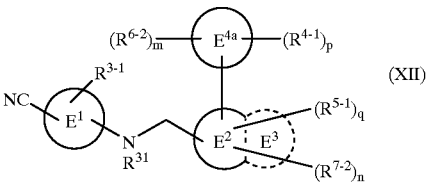
(XII)

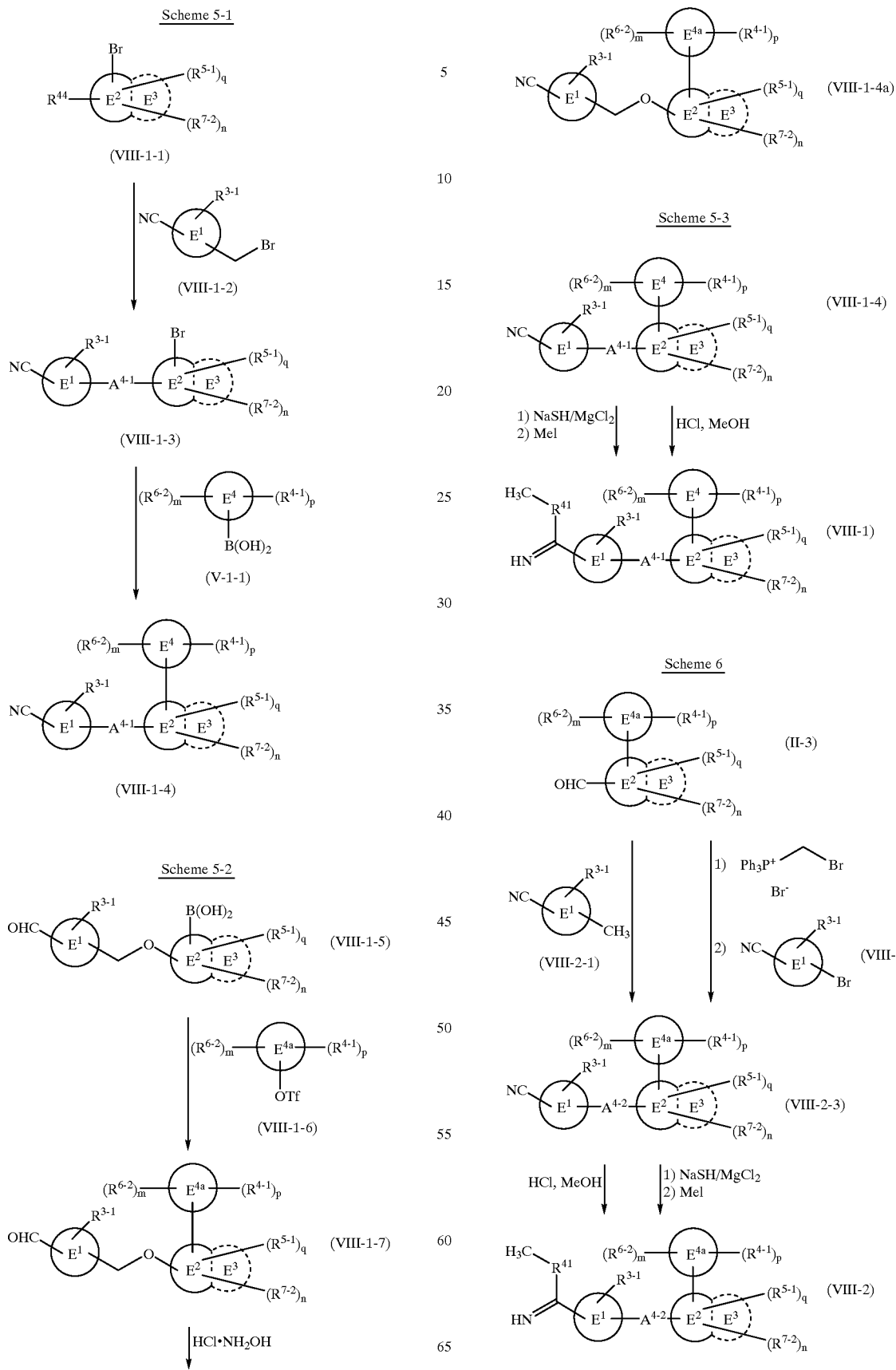

Scheme 7-1
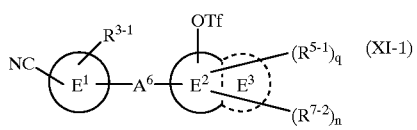
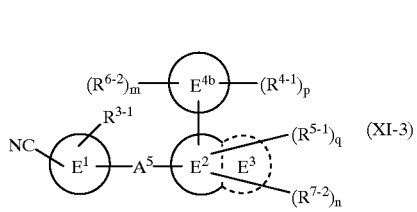
Scheme 7-2
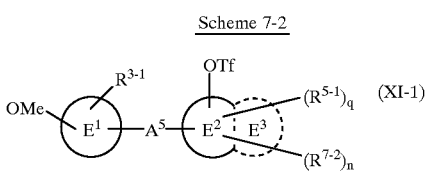
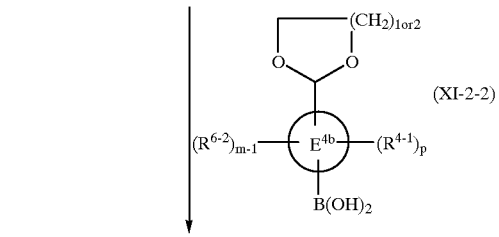
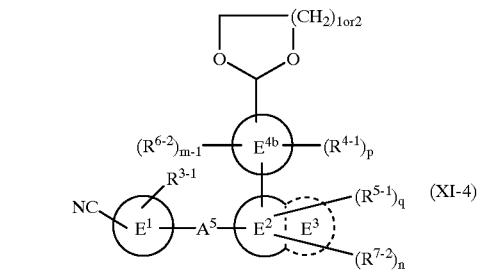
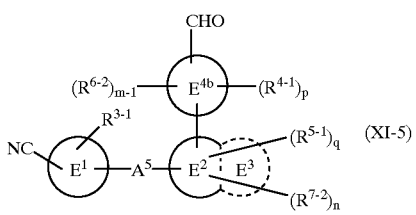
Scheme 7-3

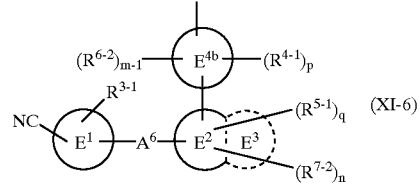
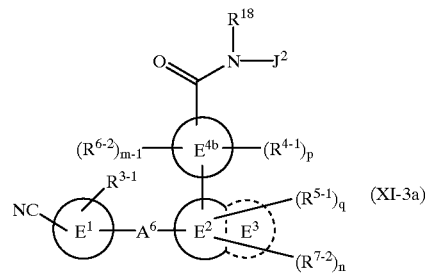
Scheme 7-4
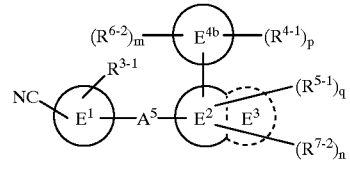
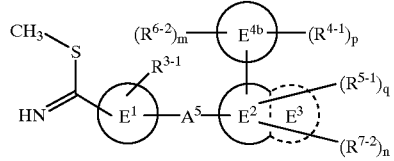
The starting materials in each scheme are known per se or may be prepared by known methods.
The reaction in each scheme are carried out by known methods.

The other starting materials and reagents in the present invention are known per se or may be prepared by known methods.

Pharmacological Activities (1) FVIIa inhibitory activity

10 μl of the compound of the present invention in 10% DMSO were added to 65 μl of the buffer solution including FVIIa (ADI#407, final 10 nM), tissue factor (ADI#4500, final 10 nM) and calcium chloride. The mixture was incubated for 10 minutes at 37° C., then 25 μl of 2 mM H-D-Ile-Pro-Arg-pNA (Chromogenix S-2288) was added (total volume 100 μl). The absorbance was measured at 405 nm at regular time intervals, and an initial velocity was calculated. The control value was measured with 10% of DMSO. Inhibitory activity was expressed as a 50% inhibition of control (IC50).

The final concentration of calcium chloride and S-2288 were 2 mM and 0.5 mM respectively. The buffer solution consisted of 50 mM tris-hydrochloric acid buffer (pH 7.5) containing 0.2% PEG6000 and 150 mM sodium chloride.

These results are shown in Table 28.

TABLE 28

| Compound | IC50 (μM) |
| --- | --- |
| Example 19(47) | 0.012 |
| Example 46 | 0.013 |

(2) Anticoagulant effect on the prothrombin time (PT) and the activated partial thromboplastin time (APTT)

PT is assayed by addition of tissue factor and indicates the coagulant activity of the extrinsic pathway, and APTT is assayed by addition of negative charged substances and indicates the coagulant activity of the intrinsic pathway.

The assay method was as follows.

Purified human plasma (verify reference plasma, organon technica) and the compound of the present invention in 10% DMSO solution were mixed at the rate of 9:1.

(a) PT determination

An automatic coagulation determination device (Sysmex CA5000) was used for the measurement of blood coagulation time, using the plasma described above and thromboplastin C (Dade).

The control value was determined by adding solvent without the compound of the present invention. The concentration of the compound of the present invention at which the coagulation time prolonged two time of the control (PTCT2), was calculated.

(b) APTT determination

An automatic coagulation determination device (Sysmex CA5000) was used for the measurement of blood coagulation time, using the plasma described above, datefy APTT (Dade) and 20 mM calcium chloride.

The control value was determined by adding solvent without the compound of the present invention. The concentration of the compound of the present invention at which the coagulation time prolonged two time of the control (APTTCT2), was calculated, and an extension rate (%) of APTT on PTCT2 were estimated.

An extension rate of APTT on PTCT2 of the compound of the present invention was not effective.

INDUSTRIAL APPLICABILITY

Toxicity

The toxicity of the compounds of the present invention is very low and therefore the compounds may be considered safe for pharmaceutical use.

Utility

The formula (I) of amidino derivatives, their non-toxic salts and hydrates have an inhibitory activity for a blood coagulation factor VIIa and are useful for treatment and/or prevention of several angiopathologic diseases due to the hypercoagulability, such as disseminated intravascular coagulation, coronary thrombosis (e.g. acute myocardial infarction, unstable angina), cerebral infarction, cerebral embolism, transient ischemic attack, diseases caused by cerebrovascular disorders, pulmonary vascular diseases (e.g. pulmonary infarction, pulmonary embolism), deep venous thrombosis, peripheral arterial obstruction, thrombosis after artificial vascular transplantation and artificial valve transplantation, post-operative thrombosis, reobstruction and restenosis after coronary artery bypass operation, reobstruction and restenosis after PTCA (percutaneous transluminal coronary angioplasty) or PTCR (percutaneous transluminal coronary recanalization), thrombosis by extracorporeal circulation and procoagulative diseases such as glomerlonephriitis.

Application for Pharmaceuticals

For the purpose above described, the compounds of formulae (I) of the present invention, non-toxic salts, acid addition salts or hydrates thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 0.1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof. Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof.

Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se. Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. No. 2,868,691 or 3,095,355 may be used.

BEST MODE FOR CARRYING OUT THE INVENTION

The following Reference Examples and Examples illustrate the present invention, but do not limit the present invention.

The solvents in the parentheses show the developing or eluting solvents and the ratios of the solvents used are by volume in chromatographic separations or TLC.

The solvents in the parentheses in NMR show the solvents used in measurement.

REFERENCE EXAMPLE 1

Benzyl 2-trifluoromethylsulfonyloxy-5-formylbenzate

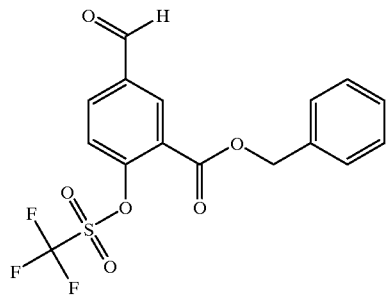

Potassium bicarbonate (3.3 g) and benzyl bromide (3.9 ml), successively, were added to a solution of 2-hydroxy-5-formylbenzoic acid (5 g) in dimethylformamide (80 ml) under an atmosphere of argon at room temperature. The mixture was stirred for 14 hours at room temperature. The reaction mixture was poured into water (150 ml). The solution was extracted with ethyl acetate. The extract was washed with a saturated aqueous solution of sodium chloride, dried over anhydrous magnesium sulfate and concentrated. To a solution of the residue (5.9 g) in methylene chloride (25 ml), pyridine (9.3 ml) and trifluoromethanesulfonic acid anhydrous (7.7 ml), successively, were added under an atmosphere of argon at 0° C. The mixture was stirred for 30 minutes. The reaction mixture was poured into water (60 ml). The solution was extracted with ethyl acetate (150 ml). The extract was washed with a saturated aqueous solution of sodium chloride, dried over anhydrous magnesium sulfate and concentrated. The residue was purified by column chromatography on silica gel (hexane:ethyl acetate= 5:1) to give the present compound (6.23 g) having the following physical data.

TLC: Rf 0.33 (Hexane:Ethyl acetate=5:1); NMR (CDCl$_3$): δ 10.1 (1H, s), 8.57 (1H, d, J=2.2 Hz), 8.16 (1H, dd, J=2.2, 8.4 Hz), 7.52–7.38 (6H, m), 5.45 (2H, s).

REFERENCE EXAMPLE 2

3-benzyloxycarbonyl-4-trifluoromethylsulfonyloxy-benzoic acid

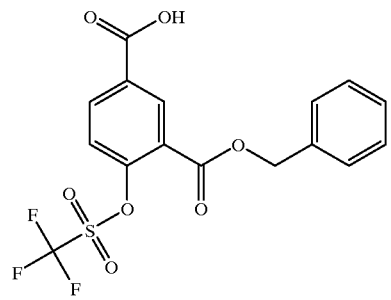

To the mixed solution of the compound prepared in Reference Example 1 (1.86 g)in t-butanol—acetonitrile—water (27 ml; 6:1:2), 2-methyl-2-butene (2.3 ml), sodium dihydrogenphosphate (690 mg) and sodium chloride (1.9 g), successively, were added. The mixture was stirred for 20 minutes at room temperature. The reaction mixture was poured into ice-water. The solution was extracted with ethyl acetate (60 ml, 2 times). The extract was washed with a saturated aqueous solution of sodium chloride, dried over anhydrous magnesium sulfate and concentrated. The residue (1.94 g) was used to the next reaction without being purified.

TLC: Rf 0.23 (Chloroform:Methanol:Water=9:1:0.1).

REFERENCE EXAMPLE 3

Benzyl 2-trifluoromethylsulfonyloxy-5-((2,2-dimethylpropyl)carbamoyl) benzoate

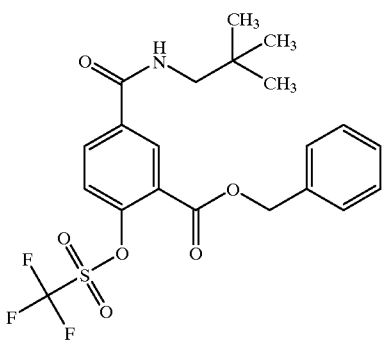

Oxalyl chloride (0.21 ml) and dimethylformamide (1 drop) were added to a solution of the compound (808 mg) prepared in Reference Example 2 in methylene chloride (8 ml) under an atmosphere of argon at 0° C. The mixture was stirred for 3 minutes at 0° C., and stirred for 1 hour at room temperature. The reaction mixture was concentrated. The residue was distilled off an azeotropic mixture with toluene (5 ml, 2 times). The residue was dissolved into methylene chloride (8 ml), and cooled to 0° C. Triethylamine (0.5 ml) and 2,2-dimethylpropylamine (0.24 ml) were added to the solution. The mixture was stirred for 5 minutes at 0° C., stirred for 10 minutes at room temperature. The reaction mixture was poured into ice-water (30 ml). The solution was extracted with ethyl acetate (30 ml, 2 times). The extract was washed with a saturated aqueous solution of sodium chloride, dried over anhydrous magnesium sulfate and concentrated. The residue was purified by column chromatography on silica gel (hexane:ethyl acetate=5:1) to give the present compound (857 mg) having the following physical data. NMR (CDCl$_3$): δ 8.39 (1H, d, J=2.6 Hz), 8.08 (1H, dd, J=2.6, 8.4 Hz), 7.50–7.37 (6H, m), 6.16 (1H, brs), 5.44 (2H, s), 3.28 (2H, d, J=6.4 Hz), 0.98 (9H, s).

REFERENCE EXAMPLE 4

Benzyl 2'-formyl-4-((2,2-dimethylpropyl)carbamoyl)-2-biphenylcarboxylate

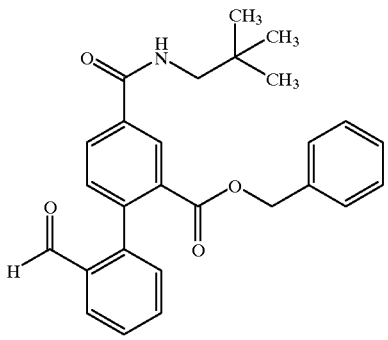

2-formylphenylboric acid (269 mg) tripotassium phosphate (569 mg) added to a solution of the compound prepared in Reference Example 3 (847 mg) in dimethylformamide (7 ml). The mixture was stirred for 30 minutes at 100° C. The reaction mixture was poured into ice-water (30 ml). The solution was extracted with ethyl acetate (30 ml, 2 times). The extract was washed with a saturated aqueous solution of sodium chloride, dried over anhydrous magnesium sulfate and concentrated. The residue was purified by column chromatography on silica gel (hexane:ethyl acetate= 3:1) to give the present compound (770 mg) having the following physical data.

TLC: Rf 0.27 (Hexane:Ethyl acetate=3:1); NMR (CDCl$_3$): δ 9.76 (1H, s), 8.41 (1H, d, J=1.8 Hz), 8.02 (1H, dd, J=1.8, 8.0 Hz), 7.87 (1H, dd, J=1.6, 7.8 Hz), 7.57–7.25 (6H, m), 7.20–7.16 (1H, m), 7.10–7.05 (2H, m), 6.27 (1H, brs), 5.04 (2H, s), 3.32 (2H, d, J=6.2 Hz), 1.01 (9H, s).

REFERENCE EXAMPLE 5

2'-benzyloxycarbonyl-4'-((2,2-dimethylpropyl)carbamoyl)-2-biphenylcarboxylic acid

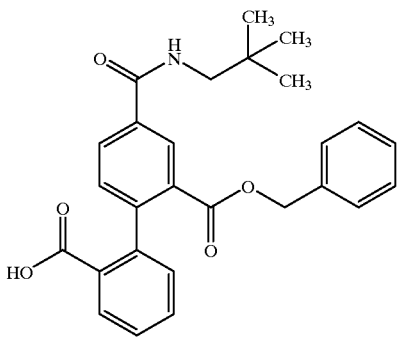

The title compound having the following physical data was obtained by the same procedure as a series of reaction of Reference Example 2, using a compound prepared in Reference Example 4.

TLC: Rf 0.38 (Chloroform:Methanol:Water=9:1:0.1).

EXAMPLE 1

Benzyl 2'-(4amidinophenylcarbamoyl)-4-((2,2-dimethylpropyl)carbamoyl)-2-biphenylcarboxylic acid

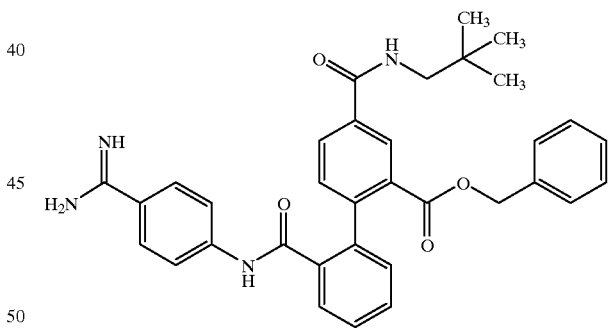

Dicyclohexylcarbodiimide (513 mg), pyridine (7 ml) and 4-amidinoaniline (345 mg), successively, were added to a solution of the compound prepared in Reference Example 5 (740 mg) in dimethylformamide (7 ml). The mixture was stirred over night. The reaction mixture was filtered, and the filtrate was concentrated. The residue was purified by column chromatography on silica gel (Chloroform:Methanol:Water=9:1:0.1→8:2:0.1) to give the present compound (835 mg) having the following physical data.

TLC: Rf 0.38 (Chloroform:Methanol:Water=8:2:0.1); NMR (CD$_3$OD): δ 8.32 (1H, d, J=2.0 Hz), 7.97 (1H, dd, J=2.0, 7.6 Hz), 7.70–7.52 (7H, m), 7.43 (1H, d, J=7.6 Hz), 7.30–7.26 (4H, m), 7.18–7.13 (2H, m), 5.13 (2H, s), 3.20 (2H, s), 0.95 (9H, s).

EXAMPLE 2

2'-(4-amidinophenylcarbamoyl)-4-((2,2-dimethylpropyl)carbamoyl)-2-biphenylcarboxylic acid methanesulfonate

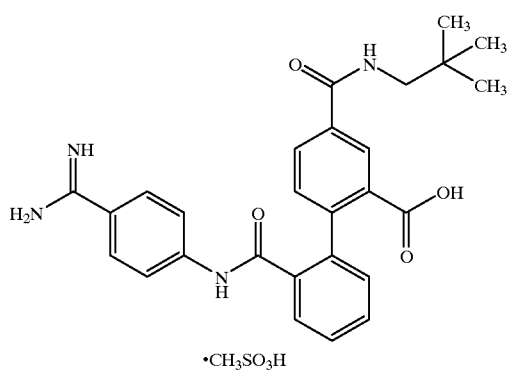

10% palladium carbon (80 mg) was added to a solution of the compound prepared in Example 1 (814 mg) in methanol (15 ml) under an atmosphere of argon at room temperature. Hydrogen substitution was done, and the mixture was stirred for 20 minutes at room temperature. The reaction mixture was filtered through celite (registered trade mark). 1N methanesulfonic acid in methanol (1.45 ml) was added to the filtrate, and the mixture was concentrated. The residue was crystallized with ether to give the present compound (820 mg) having the following physical data.

TLC: Rf 0.19 (Chloroform:Methanol:Water=8:2:0.1); NMR (d$_6$-DMSO): δ 10.6 (1H, s), 9.18 (2H, br s), 8.91 (2H, br s), 8.56 (1H, t, J=6.6 Hz), 8.31 (1H, d, J=1.8 Hz), 7.99 (1H, dd, J=1.8, 8.2 Hz), 7.74–7.69 (5H, m), 7.59–7.53 (2H, m), 7.33 (1H, d, J=8.0 Hz), 7.31–7.26 (1H, m), 3.12 (2H, d, J=6.6 Hz), 2.38 (3H, s), 0.90 (9H, s).

REFERENCE EXAMPLE 6

Methoxymethyl 2'-benzyloxycarbonyl-4'-methyl-2-biphenylcarboxylate

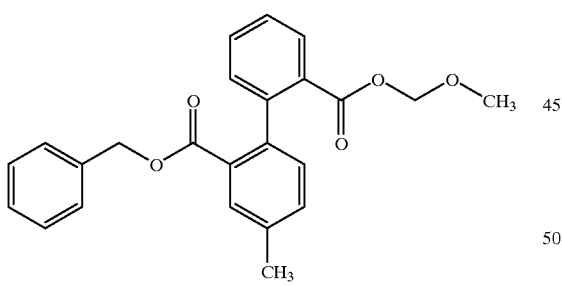

Isopropylethylamine (488 μl) was added to a solution of 2'-benzyloxycarbonyl-4'-methyl-2-biphenylcarboxylic acid (880 mg) in methylene chloride (8 ml) which was prepared by the same procedure as a series of reaction of Reference Example 4→Reference Example 5, using benzyl 2-trifluoromethylsulfonyloxy-5-methylbenzoate. The mixture was cooled to 0° C., and methoxy chloride (212 μl) was added to a solution. The mixture was stirred for 30 minutes. Water was added to the reaction mixture, and the solution was extracted with chloroform. The extract was washed with 1N hydrochloric acid and a saturated aqueous solution of sodium chloride, successively, dried over anhydrous sodium sulfate and concentrated to give the present compound (993 mg) having the following physical data.

TLC: Rf 0.41 (Hexane:Ethyl acetate=8:2); NMR (CDC$_3$): δ 7.98 (1H, dd, J=8.0, 1.5 Hz), 7.86 (1H, s), 7.52–7.05 (10H, m), 5.18 (1H, d, J=6.0 Hz), 5.12 (1H, d, J=6.0 Hz), 5.04 (2H, s), 3.22 (3H, s), 2.43 (3H, s).

EXAMPLE 3

Methoxymethyl 2'-(4-amidinophenylcarbamoyl)-4'-methyl-2-biphenylcarboxylate

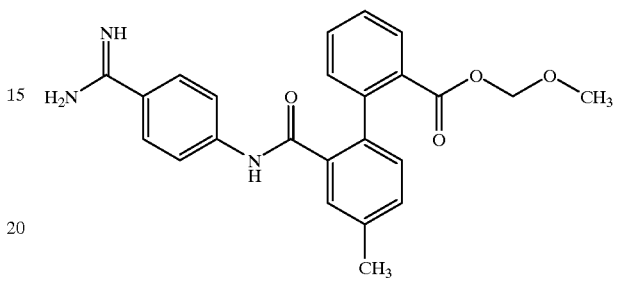

The present compound having the following physical data was obtained by the same procedure as a series of reaction of Example 2 (without a procedure of conversion to salt thereof)→Example 1, using the compound prepared in Reference Example 6.

TLC: Rf 0.51 (Chloroform:Methanol:Acetic acid= 10:2:1).

EXAMPLE 4

2'-(4-amidinophenylcarbamoyl)-4'-methyl-2-biphenylcarboxylic acid methanesulfonate

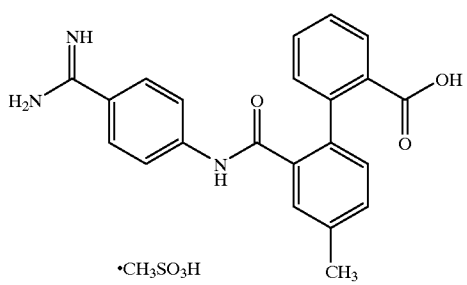

A solution of the compound prepared in Example 3 (340 mg) in 90% aqueous solution of trifluoroacetic acid (3 ml) was stirred for 2 hours at room temperature. The reaction mixture was concentrated. The residue was distilled off an azeotropic mixture with toluene, and was crystallized with a mixed solution of methanol and ether. The crystals was dissolved with a little of methanol. Methanesulfonic acid (53 μl), and ethyl acetate was added to the solution. The mixture was stirred for 14 hours. The reaction mixture was filtered to give the present compound (182 mg) having the following physical data.

TLC: Rf 0.16 (Chloroform:Methanol:Acetic acid= 10:2:1); NMR (d$_6$-DMSO): δ 13.2–12.2 (1H, broad), 10.40 (1H, s), 9.14 (2H, brs), 8.87 (2H, brs), 7.80 (1H, d, J=8 Hz), 7.74 (2H, d, J=9 Hz), 7.67 (2H, d, J=9Hz), 7.49 (1H, td, J=8 Hz, 2 Hz), 7.47 (1H, s), 7.43–7.33 (2H, m), 7.20 (1H, d, J=8 Hz, 2 Hz), 7.13 (1H, d, J=8 Hz), 2.43 (3H, s), 2.35 (3H, s).

REFERENCE EXAMPLE 7

Benzyl 2-(3-methoxymethoxycarbonylnaphthalen-2-yl)benzoate

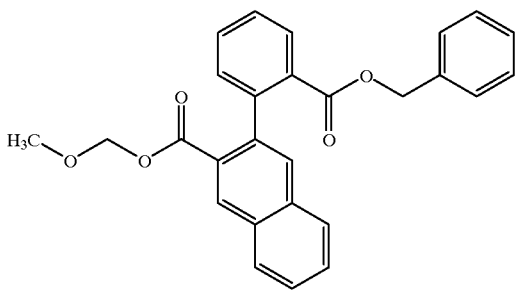

Benzyl bromide (160 μl) and potassium carbonate (202 mg) were added to a solution of 2-(3-(methoxymethoxycarbonyl)naphthalen-2-yl)benzoic acid (410 mg) which was prepared by the same procedure as a series of reaction of Reference Example 4→Reference Example 5 using methoxymethyl 2-trifluoromethylsulfonyloxy-3-naphthalenecarboxylate, in dimethylformamid (5 ml). The mixture was stirred for 22 hours at room temperature. Water was added to the reaction mixture, and the solution was extracted with ethyl acetate. The extract was washed with water and a saturated aqueous solution of sodium chloride, successively, dried over anhydrous sodium sulfate and concentrated. The residue was purified by column chromatography on silica gel (hexane:ethyl acetate=8:2) to give the title compound (498 mg) having the following physical data.

TLC: Rf 0.53 (Hexane:Ethyl acetate=7:3); NMR (CDCl$_3$): δ 8.54 (1H, s), 8.10 (1H, dd, J=8.0, 1.5 Hz), 7.94 (1H, d, J=8.0 Hz), 7.80 (1H, d, J=8.0 Hz), 7.64–7.53 (4H, m), 7.46 (1H, td, J=8.0, 1.5 Hz), 7.32 (1H, dd, J=8.0, 1.5 Hz), 7.17–7.01 (3H, m), 6.95–6.90 (2H, m), 5.24 (1H, d, J=6.0 Hz), 5.18 (1H, d, J=6.0 Hz), 5.05 (1H, d, J=12 Hz), 4.95 (1H, d, J=12 Hz), 3.26 (3H, s).

REFERENCE EXAMPLE 8

3-(2-benzyloxycarbonylphenyl)-2-naphthalenecarboxylic acid

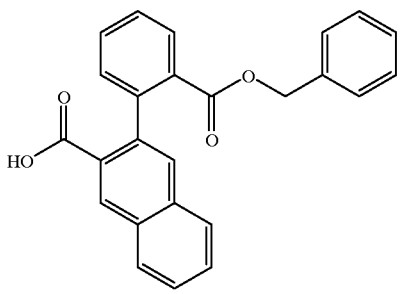

1N Hydrochloric acid (2.3 ml) was added to a solution of the compound prepared in Reference Example 7 (490 mg) in dioxane (7 ml). The mixture was stirred for 5.5 hours at 50° C. Water was added to the reaction mixture, and the solution was extracted with ethyl acetate. The extract was washed with a saturated aqueous solution of sodium chloride, dried over anhydrous sodium sulfate and concentrated. The residue was crystallized with hexane to give the title compound (423 mg) having the following physical data.

TLC: Rf 0.16 (Hexane:Ethyl acetate=1:1); NMR (CDCl$_3$): δ 8.51 (1H, s), 8.08 (1H, dd, J=8.0, 1.5 Hz), 7.91 (1H, d, J=8.0 Hz), 7.78 (1H, d, J=8.0 Hz), 7.65–7.42 (5H, m), 7.28 (1H, dd, J=8.0, 1.5 Hz), 7.16–6.90 (5H, m), 5.05 (1H, d, J=12 Hz), 4.95 (1H, d, J=12 Hz).

EXAMPLE 5

Benzyl 2-(3-(4-amidinophenylcarbamoyl)naphthalen-2-yl)benzoate

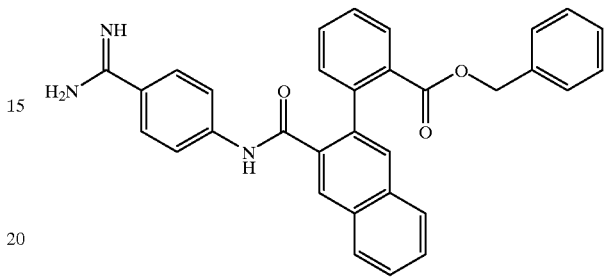

The present compound having the following physical data was obtained by the same procedure as a series of reaction of Example 1, using the compound prepared in Reference Example 8.

TLC: Rf 0.62 (Chloroform:Methanol:Acetic acid=10:2:1); NMR (CD$_3$OD): δ 8.18 (1H, s), 8.10–7.82 (3H, m), 7.78–7.52 (8H, m), 7.46 (1H, dd, J=8 Hz, 2 Hz), 7.41 (1H, d, J=8 Hz), 7.18–6.90 (5H, m), 5.06 (2H, s).

EXAMPLE 6

2-(3-(4-amidinophenylcarbamoyl)naphthalen-2-yl)benzoic acid methanesulfonate

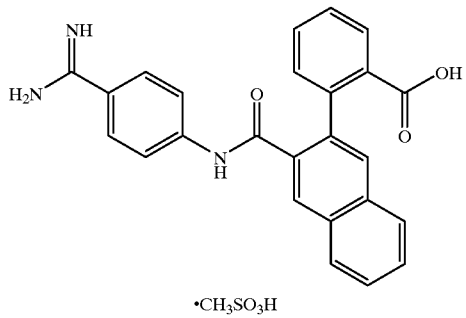

·CH$_3$SO$_3$H

The present compound having the following physical data was obtained by the same procedure as a series of reaction of Example 2, using the compound prepared in Example 5.

TLC: Rf 0.64 (Chloroform:Methanol:Water=7:3:0.3); NMR (d$_6$-DMSO): δ 12.4–12.9 (1H, broad), 10.67 (1H, s), 9.20 (2H, s), 8.98 (2H, s), 8.28 (1H, s), 8.16–7.92 (2H, m), 7.87 (1H, d, J=8 Hz), 7.79 (1H, s), 7.77 (4H, s), 7.70–7.50 (3H, m), 7.44 (1H, t, J=8 Hz), 7.34 (1H, d, J=8 Hz), 2.36 (3H, s).

EXAMPLE 7—7(115)

The following compounds were obtained by the same procedure as a series of reaction of Reference Example 4 (using 2-formylphenylboric acid or a corresponding derivatives)→Reference Example 5→Example 1 (using 4-amidinoaniline or a corresponding derivatives), using the compound prepared in Reference Example 3 or a corresponding derivatives.

EXAMPLE 7 t-Butyl 2'-(4-amidinophenylcarbamoyl)-2-biphenylcarboxylate

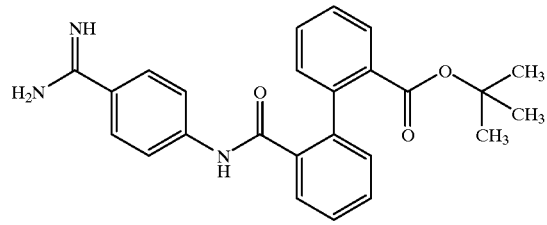

TLC: Rf 0.27 (Chloroform:Methanol:Water=8:2:0.2); NMR (CD₃OD): δ 7.66–7.81 (2H, m), 7.69 (2H, d, J=9.2 Hz), 7.50–7.60 (2H, m), 7.57 (2H, d, J=9.2 Hz), 7.48 (1H, dt, J=1.8,7.6 Hz), 7.39 (1H, dt, J=1.8,7.6 Hz), 7.22–7.27 (2H, m), 1.34 (9H, s).

EXAMPLE 7(1)

Benzyl 2'-(4-amidinophenylcarbamoyl)-2-biphenylcarboxylate

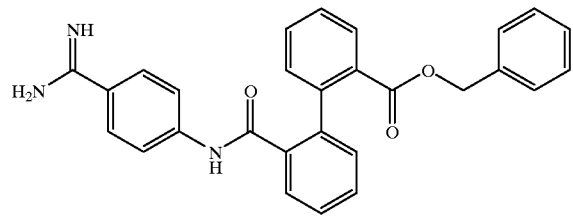

TLC: Rf 0.57 (Chloroform:Methanol:Acetic acid= 10:2:1); NMR (CD₃OD): δ 7.85 (1H, dd, J=8 Hz, 2 Hz), 7.68–7.62 (3H, m), 7.57–7.13 (13H, m), 5.13 (2H, s).

EXAMPLE 7(2)

Benzyl 3-(4-amidinophenylcarbamoyl)-4-biphenylcarboxylate

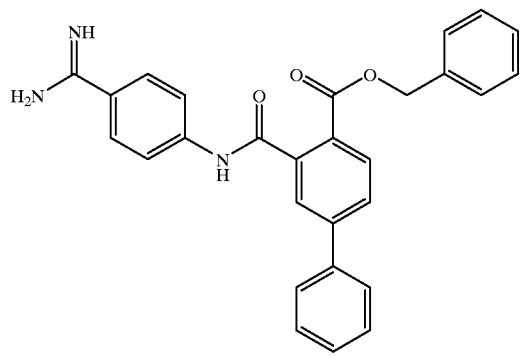

TLC: Rf 0.54 (Chloroform:Methanol:Acetic acid= 10:2:1); NMR (CD₃OD): δ 8.12 (1H, d, J=8 Hz), 7.91–7.68 (8H, m), 7.55–7.40 (3H, m), 7.38–7.28 (2H, m), 7.26–7.16 (3H, m), 5.28 (2H, s).

EXAMPLE 7(3)

Benzyl 4-(4-amidinophenylcarbamoyl)-3-biphenylcarboxylate

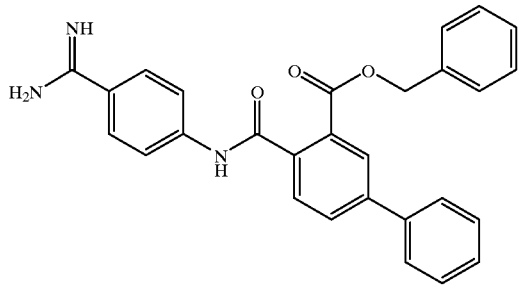

TLC: Rf 0.51 (Chloroform:Methanol:Acetic acid= 10:2:1); NMR (CD₃OD): δ 8.24 (1H, d, J=2 Hz), 7.96 (1H, dt, J=8 Hz, 2 Hz), 7.91–7.64 (7H, m), 7.56–7.41 (3H, m), 7.36–7.29 (2H, m), 7.24–7.16 (3H, m), 5.29 (2H, s).

EXAMPLE 7(4)

Benzyl 3'-(4-amidinophenylcarbamoyl)-2-biphenylcarboxylate

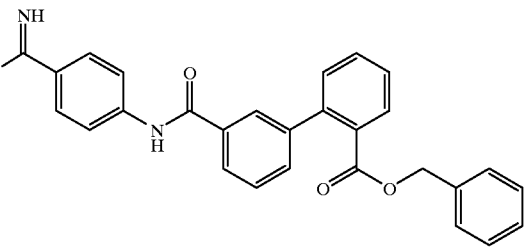

TLC: Rf 0.57 (Chloroform:Methanol:Acetic acid= 10:2:1); NMR (CD₃OD): δ 8.04 (2H, d, J=9 Hz), 7.97–7.80 (3H, m), 7.85 (2H, d, J=9 Hz), Hz), 7.64 (1H, td, J=8 Hz, 2 Hz), 7.55–7.43 (4H, m), 7.24–7.18 (3H, m), 7.11–7.06 (2H, m), 5.09 (2H, s).

EXAMPLE 7(5)

Benzyl 2,3-dihydro-2,2-dimethyl-5-(2-(4-amidinophenylcarbamoyl)phenyl)-6-benzofurancarboxylate

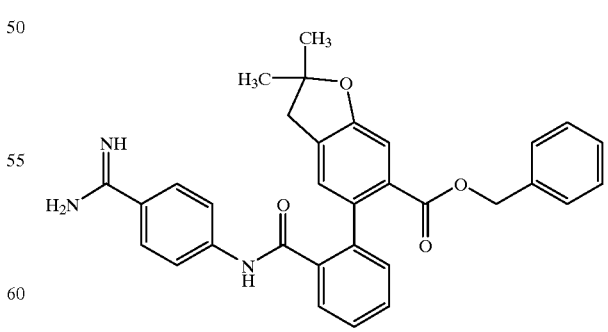

TLC: Rf 0.44 (Chloroform:Methanol:Acetic acid= 20:2:1); NMR (CD₃OD): δ 7.72–7.39 (7H, m), 7.35–7.12 (6H, m), 7.08 (1H, s), 7.07 (1H, s), 5.12 (2H, s), 1.43 (3H, brs), 1.38 (3H, brs).

EXAMPLE 7(6)

Benzyl 2'-(4-amidinophenylcarbamoyl)-3-biphenylcarboxylate

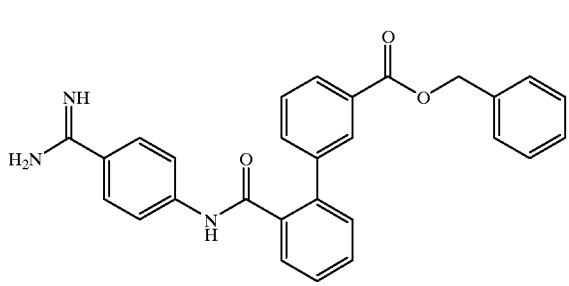

TLC: Rf 0.61 (Chloroform:Methanol:Acetic acid=10:2:1); NMR (CD$_3$OD): δ 8.17 (1H, s), 7.95 (1H, d, J=8 Hz), 7.76–7.46(10H, m), 7.45–7.30 (5H, m), 5.30 (2H, s).

EXAMPLE 7(7)

Dibenzyl 2'-(4-amidinophenylcarbamoyl)-2,3-biphenyldicarboxylate

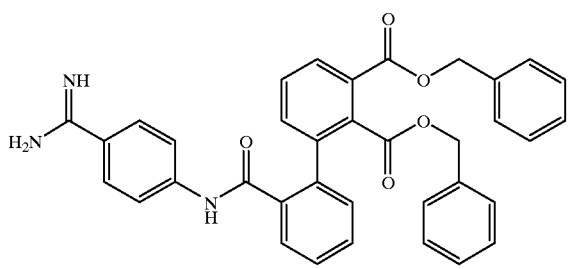

TLC: Rf 0.65 (Chloroform:Methanol:Acetic acid=10:2:1); NMR (d$_6$-DMSO): δ 10.67 (1H, s), 9.50–8.95 (3H, broad), 7.91 (1H, dd, J=8 Hz, 2 Hz), 7.82–7.68 (5H, m), 7.68–7.46 (4H, m), 7.45–7.30 (5H, m), 7.30–7.16 (4H, m), 7.02–6.90 (2H, m), 5.24 (2H, s), 5.00–4.65 (2H, broad).

EXAMPLE 7(8)

Benzyl 2'-(4-amidinophenylcarbamoyl)-6-m ethyl-2-biphenylcarboxylate

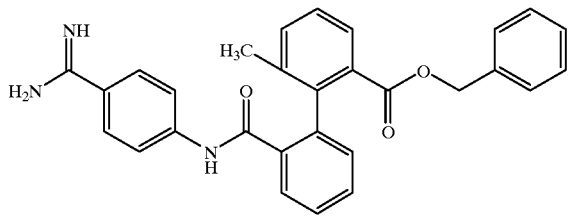

TLC: Rf 0.61 (Chloroform:Methanol:Acetic acid=10:2:1); NMR (CD$_3$OD): δ 7.72–7.62 (4H, m), 7.58–7.45 (4H, m), 7.42–7.22 (7H, m), 7.11–7.02 (1H, m), 5.22 (1H, d, J=11 Hz), 5.15 (1H, d, J=11 Hz), 1.98 (3H, s).

EXAMPLE 7(9)

Benzyl 2'-(4-amidinophenylcarbamoyl)-5-methoxy-2-biphenylcarboxylate

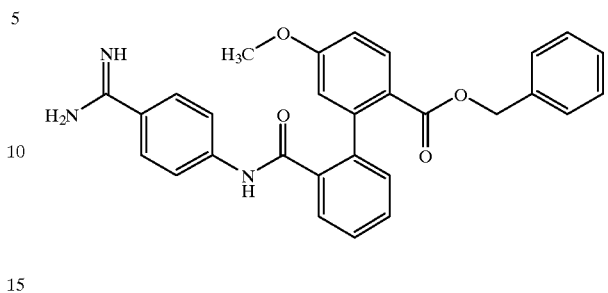

TLC: Rf 0.32(Chloroform:Methanol:Water=8:2:0.2); NMR (d$_6$-DMSO): δ 10.74 (1H, s), 9.07 (3H, br.s), 7.80 (1H, d, J=8.8 Hz), 7.74 (2H, d, J=9.4 Hz), 7.70 (2H, d, J=9.4 Hz), 7.62 (1H, dd, J=2.2,7.0 Hz), 7.47–7.54 (2H, m), 7.23–7.32 (4H, m), 7.03–7.07 (2H, m), 6.96 (1H, dd, J=2.6,8.8 Hz), 6.82 (1H, d, J=2.6 Hz), 4.99 (2H, s), 3.80 (3H, s).

EXAMPLE 7(10)

Benzyl 2'-(4-amidinophenylcarbamoyl)-4-methoxy-2-biphenylcarboxylate

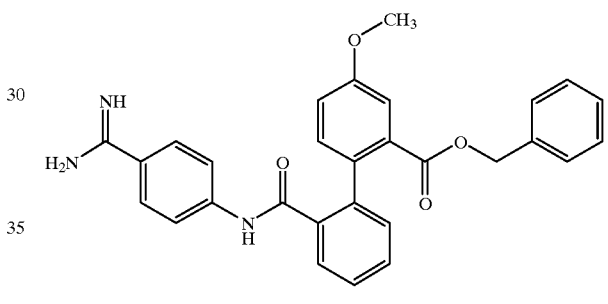

TLC: Rf 0.30 (Chloroform:Methanol:Water=8:2:0.2); NMR (OD$_3$OD): δ 7.67 (2H, d, J=8.8 Hz), 7.63 (1H, m), 7.54 (2H, d, J=8.8 Hz), 7.45–7.49 (2H, m), 7.36 (1H, d, J=2.6 Hz), 7.25–7.30 (4H, m), 7.06–7.23 (4H, m), 5.14 (2H, s), 3.81 (3H, s).

EXAMPLE 7(11)

Benzyl 2'-(4-amidinophenylcarbamoyl)-4-biphenylcarboxylate

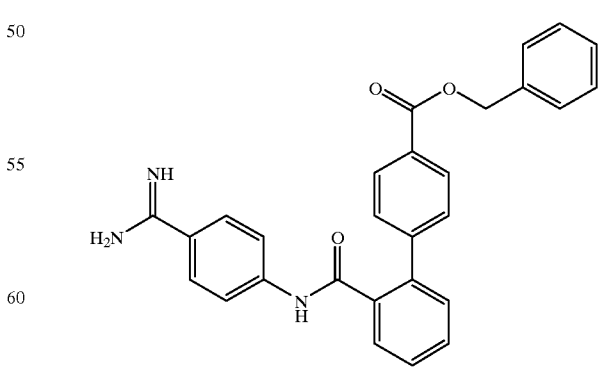

TLC: Rf 0.41 (Chloroform:Methanol:Acetic acid=10:2:1); NMR (CD$_3$OD): δ 8.01 (2H, d, J=8.5 Hz), 7.70 (4H, s), 7.68–7.50 (6H, m), 7.46–7.32 (5H, m), 5.33 (2H, s).

EXAMPLE 7(12)

Benzyl 2'-(4-amidinophenylcarbamoyl)-6-methoxy-2-biphenylcarboxylate

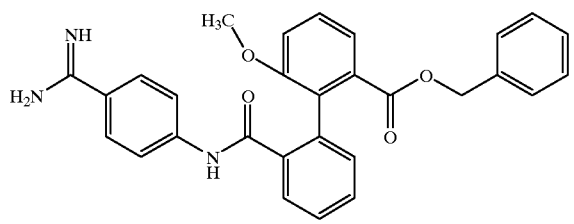

TLC: Rf 0.34 (Chloroform:Methanol:Water=8:2:0.2); NMR (CD$_3$OD): δ 7.67 (2H, d, J=8.8 Hz), 7.67(1H, m), 7.52 (2H, d, J=8.8 Hz), 7.38–7.50 (4H, m), 7.28–7.34 (3H, m), 7.04–7.20 (4H, m), 5.15 (1H, d, J=12.0 Hz), 5.08 (1H, d, J=12.0 Hz), 3.63 (3H, s).

EXAMPLE 7(13)

Benzyl 2'-(4-amidinophenylcarbamoyl)-4-benzyloxy-2-biphenylcarboxylate

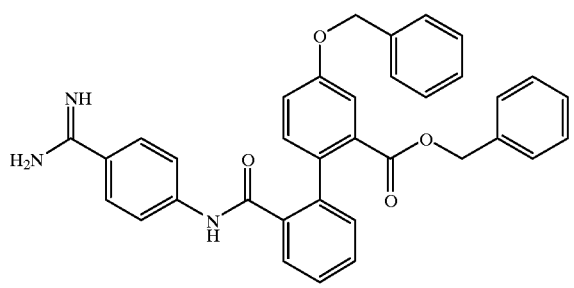

TLC: Rf 0.41 (Chloroform:Methanol:Water=8:2:0.2); NMR (CD$_3$OD): δ 7.67 (2H, d, J=8.8 Hz), 7.63 (1H, m), 7.54 (2H, d, J=8.8 Hz), 7.14–7.49 (16H, m), 5.12 (2H, s), 5.10 (2H, s).

EXAMPLE 7(14)

Benzyl 2'-(4-amidinophenylcarbamoyl)-5-benzyloxy-2-biphenylcarboxylate

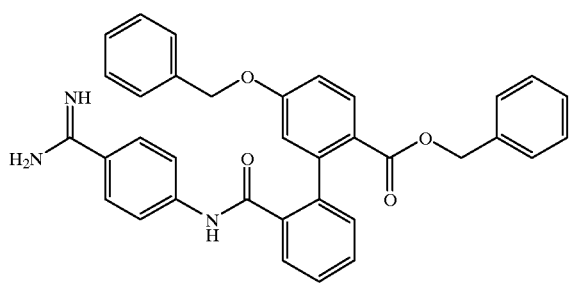

TLC: Rf 0.43 (Chloroform:Methanol:Water=8:2:0.2); NMR (d$_6$-DMSO): δ 10.50 (1H, s), 9.21 (1.5H, s), 8.96 (1.5H, s), 7.81 (1H, d, J=8.4 Hz), 7.76 (4H, s), 7.65 (1H, m), 7.48–7.55 (2H, m), 7.24–7.40 (9H, m), 7.03–7.08 (3H, m), 6.93 (1H, d, J=2.6 Hz), 5.15 (2H, s), 5.00 (2H, s).

EXAMPLE 7(15)

Benzyl 2'-(4-amidinophenylcarbamoyl)-5-methyl-2-biphenylcarboxylate

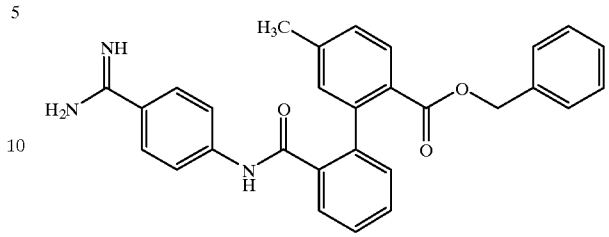

TLC: Rf 0.44 (Chloroform:Methanol:Acetic acid= 10:2:1); NMR (d$_6$-DMSO): δ 9.11 (2H, s), 8.87 (2H, s), 7.61 (4H, t, J=8.0 Hz), 7.52 (1H, dd, J=2.0, 8.0 Hz), 7.45 (1H, d, J=8.5 Hz), 7.42 (1H,t, J=8.0 Hz), 7.38 (1H, t, J=8.0 Hz), 7.20–7.03 (5H, m), 7.01 (1H, brs), 6.92 (1H, d, J=7.5 Hz), 6.91 (1H, d, J=8.0 Hz), 4.87 (2H, s), 2.22 (3H, s).

EXAMPLE 7(16)

Benzyl 2'-(4-amidinophenylcarbamoyl)-4-methyl-2-biphenylcarboxylate

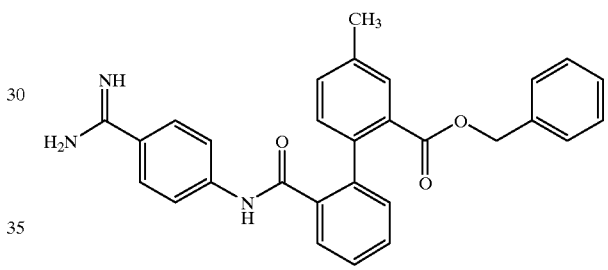

TLC: Rf 0.44 (Chloroform:Methanol:Acetic acid= 10:2:1); NMR (d$_6$-DMSO): δ 9.15 (2H, brs), 8.89 (2H, s), 7.66 (4H, brs), 7.60–7.47 (2H, m), 7.45 (1H, brt, J=8.0 Hz), 7.31 (1H, d, J=8.0 Hz), 7.26–7.02 (5H, m), 7.02–6.90 (2H, m), 4.93 (2H, s), 2.26 (3H, s).

EXAMPLE 7(17)

Benzyl 2'-(4-amidinophenylcarbamoyl)-3-benzyloxy-2-biphenylcarboxylate

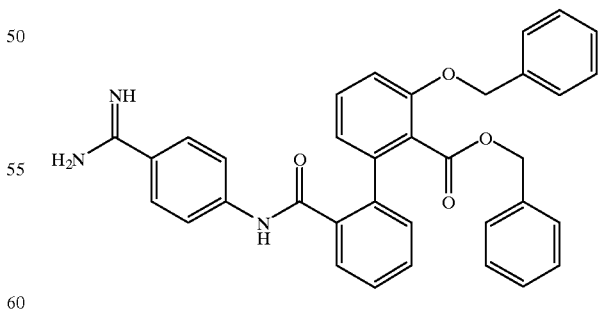

TLC: Rf 0.43 (Chloroform:Methanol:Water=8:2:0.2); NMR (CDCl$_3$): δ 7.67 (1H, m), 7.66 (2H, d, J=8.8 Hz), 7.45–7.56 (2H,m), 7.53 (2H, d, J=8.8 Hz), 7.13–7.39 (12H, m), 7.09 (1H, d, J=8.4 Hz), 6.82 (1H, d, J=6.8 Hz), 5.15 (2H, s), 4.86 (2H, s).

EXAMPLE 7(18)

Benzyl 2'-(4-amidinophenylcarbamoyl)-4'-methyl-5-chloro-2-biphenylcarboxylate

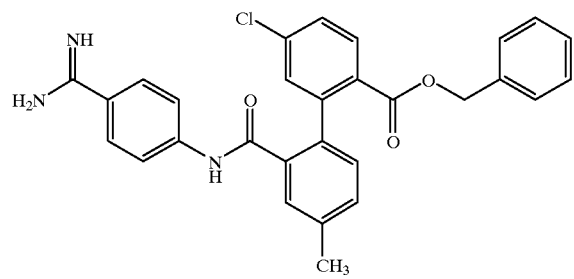

TLC: Rf 0.42 (Chloroform:Methanol=4:1); NMR (CDCl$_3$): δ 9.29 (1H, s), 8.80 (2H, s), 8.59 (2H, s), 7.72 (2H, d, J=8.2 Hz), 7.49 (1H, s), 7.40 (2H, d, J=8.2 Hz), 7.4–7.1 (9H, m), 6.94 (1H, d, J=8.2 Hz), 5.10 (2H, s), 2.36 (3H, s).

EXAMPLE 7(19)

Benzyl 2'-(4-amidinophenylcarbamoyl)-3-methoxy-2-biphenylcarboxylate

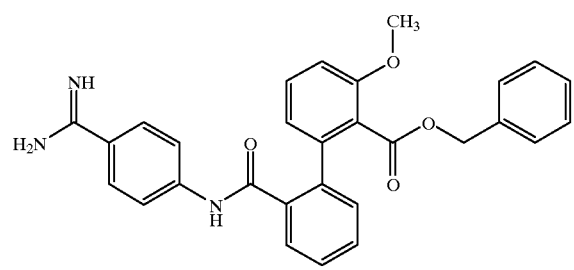

TLC: Rf 0.27 (Chloroform:Methanol:Water=8:2:0.2); NMR (CD$_3$OD): δ 7.67 (2H, d, J 8.8 Hz), 7.66 (1H, m), 7.43–7.55 (2H, m), 7.52 (2H, d, J=8.8 Hz), 7.27–7.40 (4H, m), 7.16–7.22 (3H, m), 7.03 (1H, d, J=8.4 Hz), 6.80 (1H, d, J=7.0 Hz), 5.15 (2H, s), 3.84 (3H, s).

EXAMPLE 7(20)

Benzyl 2'-(4-amidinophenylcarbamoyl)-4'-methyl-4-methoxy-2-biphenylcarboxylate

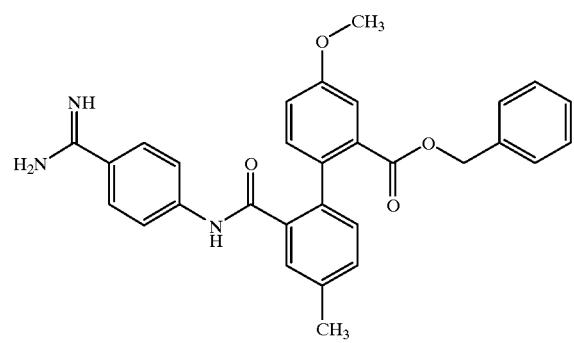

TLC: Rf 0.34 (Chloroform:Methanol=4:1); NMR (CDCl$_3$): δ 8.95 (2H, brs), 8.44 (1H, brs), 7.72 (2H, brs), 7.45 (1H, s), 7.4–7.3 (6H, m), 7.17 (2H, d, J=6.4 Hz), 7.07 (1H, d, J=8.4 Hz), 6.96 (1H, s), 6.60 (2H, d, J=8.8 Hz), 5.17 (2H, s), 3.74 (3H, s), 2.40 (3H, s).

EXAMPLE 7(21)

Benzyl 2-(2-(4-amidinophenylcarbamoyl)phenyl)-1-naphthalenecarboxylate

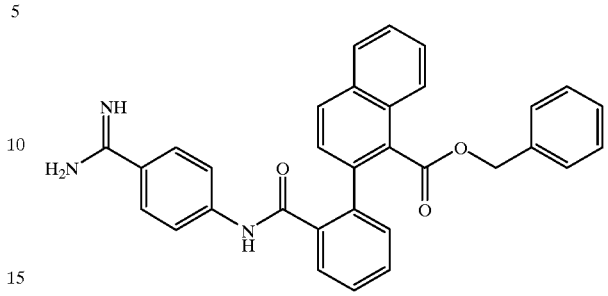

TLC: Rf 0.34 (Chloroform:Methanol:Water=8:2:0.2); NMR (d$_6$-DMSO): δ 10.62 (1H,s), 9.09 (3H, br.s), 7.98–8.05 (2H, m), 7.78–7.90 (2H, m), 7.73 (4H, s), 7.57–7.63 (4H, m), 7.46 (1H, d, J=8.4 Hz), 7.35 (1H, m), 7.26–7.29 (3H, m), 7.08–7.12 (2H, m), 5.16 (2H, br.s).

EXAMPLE 7(22)

Benzyl 2'-(4-amidinophenylcarbamoyl)-3-methyl-2-biphenylcarboxylate

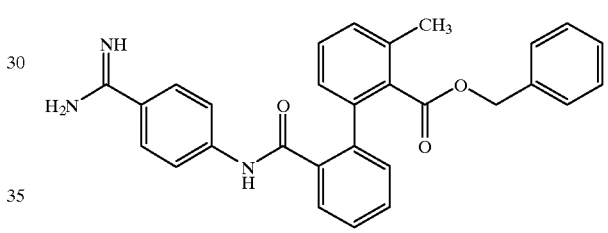

TLC: Rf 0.56 (Chloroform:Methanol:Acetic acid= 10:2:1); NMR (d$_6$-DMSO): δ 9.09 (2H, brs), 8.82 (1H, s), 8.33 (2H, brs), 7.82–7.60 (3H, m), 7.52–7.03 (12H, m), 6.98 (1H, dd, J=1.0, 8.5 Hz), 5.15 (1H, d, J=10 Hz), 5.03 (1H, d, J=10 Hz), 2.40 (3H, s).

EXAMPLE 7(23)

Benzyl 3-(2-(4-amidinophenylcarbamoyl)phenyl)-7-methoxy-2-naphthalenecarboxylate

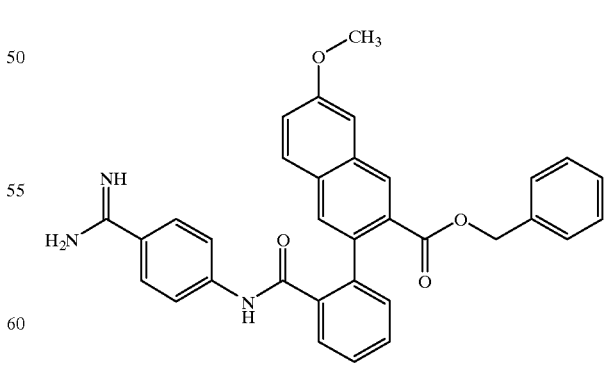

TLC: Rf 0.48 (Chloroform:Methanol:Water=10:3:0.2); NMR (d$_6$-DMSO): δ 10.53 (1H, br.s), 9.08 (3H, br.s), 8.33 (1H, s), 7.89 (1H, d, J=9.2 Hz), 7.7–7.4 (10H, m), 7.4–7.2 (4H, m), 7.2–7.0 (2H, m), 5.06 (2H, br.s), 3.87 (3H, s).

EXAMPLE 7(24)

Benzyl 3-(2-(4-amidinophenylcarbamoyl)phenyl)-5-methoxy-2-naphthalenecarboxylate

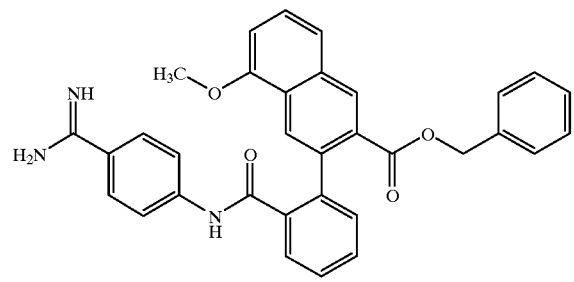

TLC: Rf 0.42 (Chloroform:Methanol:Water=10:3:0.2); NMR (d$_6$-DMSO): δ 10.56 (1H, s), 9.06 (3H, br.s), 8.38 (1H, s), 8.02 (1H, s), 7.8–7.4 (10H, m), 7.3–7.2 (3H, m), 7.2–7.0 (3H, m), 5.07 (2H, s), 3.94 (3H, s).

EXAMPLE 7(25)

Dibenzyl 2'-(4-amidinophenylcarbamoyl)-2,4-biphenyldicarboxylate

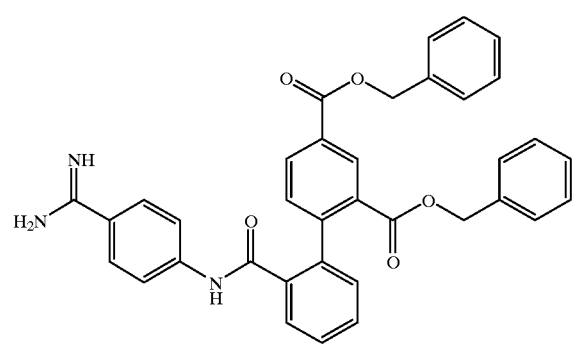

TLC: Rf 0.45 (Chloroform:Methanol:Water=8:2:0.2); NMR (CD$_3$OD): δ 8.50 (1H, d, J=1.8 Hz), 8.18 (1H, dd, J=1.8,8.0 Hz), 7.67 (2H, d, J=9.0 Hz), 7.61 (2H, d, J=9.0 Hz), 7.10–7.54 (15H, m), 5.37 (2H, s), 5.11 (2H, s).

EXAMPLE 7(26)

Benzyl 2'-(4-amidinophenylcarbamoyl)-4-dimethylcarbamoyl-2-biphenylcarboxylate

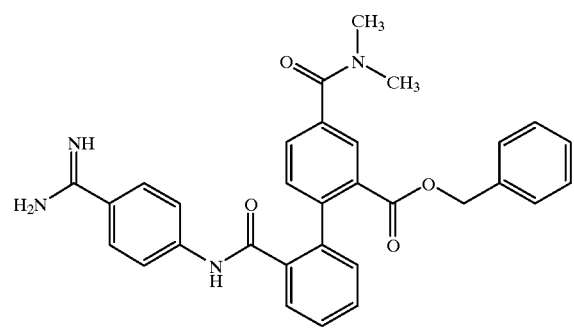

TLC: Rf 0.30 (Chloroform:Methanol:Water 8:2:0.2); NMR (CD$_3$OD): δ 7.90 (1H, d, J=1.8 Hz), 7.50–7.70 (8H, m), 7.42 (1H, d, J=8.0 Hz), 7.25–7.31 (4H, m), 7.12–7.16 (2H, m), 5.12 (2H, s), 3.09 (3H, s), 2.92 (3H, s).

EXAMPLE 7(27)

Benzyl 3-(2-(4-amidinophenylcarbamoyl)phenyl)-6-methoxy-2-naphthalenecarboxylate

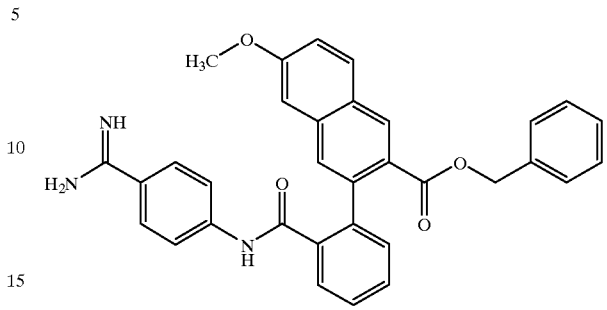

TLC: Rf 0.51 (Chloroform:Methanol:Water=10:3:0.2).

EXAMPLE 7(28)

Benzyl 2'-(4-amidinophenylcarbamoyl)-4-methylcarbamoyl-2-biphenylcarboxylate

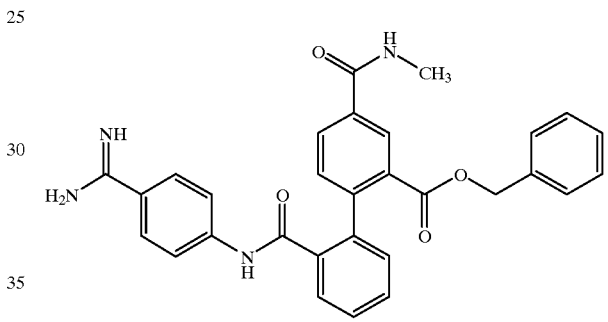

TLC: Rf 0.24 (Chloroform:Methanol:Water=8:2:0.2); NMR (CD$_3$OD): δ 8.32 (1H, d, J=1.8 Hz), 7.96 (1H, dd, J=1.8, 8.0 Hz), 7.67 (2H, d, J=8.8 Hz), 7.65 (1H, m), 7.58 (2H, d, J=8.8 Hz), 7.49–7.55 (2H, m), 7.42 (1H, d J=8.0 Hz), 7.24–7.30 (4H, m), 7.13–7.18 (2H, m), 5.16 (2H, s), 2.91 (3H, s).

EXAMPLE 7(29)

Benzyl 3-(2-(4-amidinophenylcarbamoyl)phenyl)-8-methoxy-3-naphthalenecarboxylate

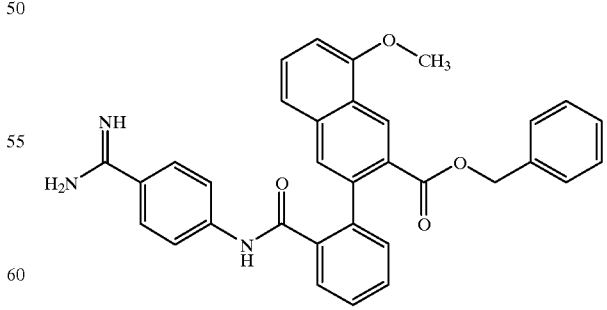

TLC: Rf 0.43 (Chloroform:Methanol:Water=10:3:0.2); NMR (d$_6$-DMSO): δ 10.57 (1H, s), 9.3–8.8 (3H, br), 8.62 (1H, s), 7.80 (1H, s), 7.8–7.4 (10H, m), 7.4–7.2 (3H, m), 7.2–7.0 (3H, m), 5.07 (2H, br.s), 3.98 (3H, s).

EXAMPLE 7(30)

Benzyl 2'-(4-amidinophenylcarbamoyl)-3,4-dimethoxy-2-biphenylcarboxylate

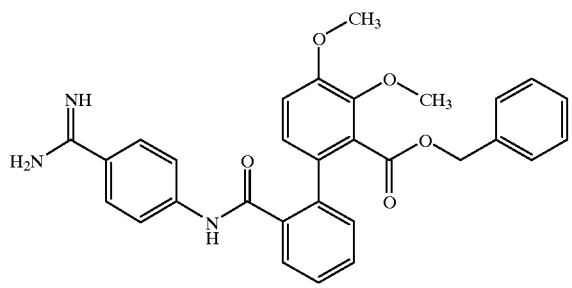

TLC: Rf 0.70 (Chloroform:Methanol:Acetic acid=10:2:1); NMR (CD$_3$OD): δ 7.71–7.62 (3H, m), 7.54 (2H, d, J=9.0 Hz), 7.50 (1H, td, J=7.5 Hz, 1.5 Hz), 7.43 (1H, td, J=7.5 Hz, 1.5 Hz), 7.33–7.16 (6H, m), 7.06 (1H, d, J=9.0 Hz), 6.94 (1H, d, J=9.0 Hz), 5.17 (2H, s), 3.80 (3H, s), 3.77 (3H, s).

EXAMPLE 7(31)

Benzyl 6-(2-(4-amidinophenylcarbamoyl)phenyl)-1,2-methylenedioxybenzene-5-carboxylate

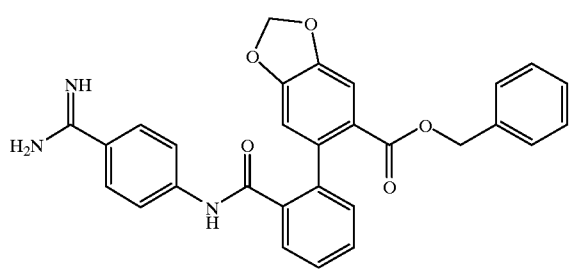

TLC: Rf 0.70 (Chloroform:Methanol:Acetic acid=10:2:1); NMR (CD$_3$OD): δ 7.69 (2H, d, J=9.0 Hz), 7.62–7.55 (3H, m), 7.51–7.41 (2H, m), 7.31–7.22 (4H, m), 7.22–7.10 (3H, m), 6.72 (1H, s), 6.03 and 6.00 (2H, brs), 5.08 (2H, s).

EXAMPLE 7(32)

Benzyl 2'-(4-amidinophenylcarbamoyl)-4'-nitro-2-biphenylcarboxylate

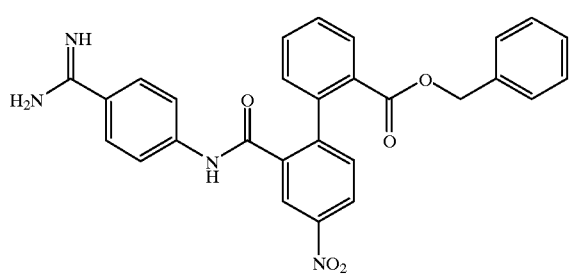

TLC: Rf 0.62 (Chloroform:Methanol:Acetic acid=10:2:1); NMR (CD$_3$OD): δ 8.32 (1H, d, J=2.5 Hz), 8.19 (1H, dd, J=8.5 Hz, 2.5 Hz), 8.01–7.96 (1H, m), 7.71 (2H, d, J=9.0 Hz), 7.63 (2H, d, J=9.0 Hz), 7.60 (1H, td, J=7.5 Hz, 1.5 Hz), 7.48 (1H, td, J=7.5 Hz, 1.5 Hz), 7.44 (1H, d, J=8.5 Hz), 7.33 (1H, dd, J=7.5 Hz, 1.5 Hz), 7.24–7.66 (5H, m), 5.06 and 5.04 (2H, s).

EXAMPLE 7(33)

Benzyl 2'-(4-amidinophenylcarbamoyl)-4-((benzyloxycarbonylmethyl) carbamoyl)-2-biphenylcarboxylate

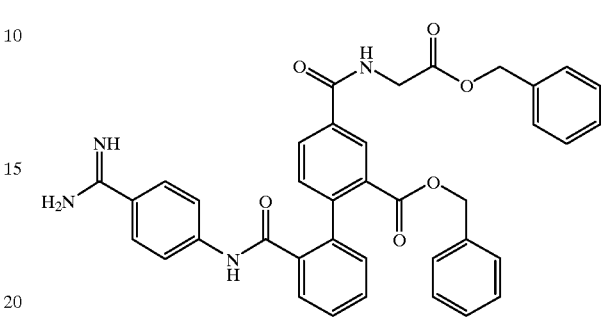

TLC: Rf 0.40 (Chloroform:Methanol:Water=8:2:0.2); NMR (CD$_3$OD): δ 8.37 (1H, d, J=1.8 Hz), 8.00 (1H, dd, J=1.8,8.0 Hz), 7.67 (2H, d, J=9.2 Hz), 7.66 (1H, m), 7.59 (2H, d, J=9.2 Hz), 7.50–7.55 (2H, m), 7.4 (1H, d, J=8.0 Hz), 7.25–7.37 (9H, m), 7.13–7.18 (2H, m), 5.20 (2H, s), 5.14 (2H, s), 4.16 (2H, s).

EXAMPLE 7(34)

Benzyl 2'-(4-amidinophenylcarbamoyl)-4-((1-benzyloxycarbonyl-2-phenylethyl)carbamoyl)-2-biphenylcarboxylate

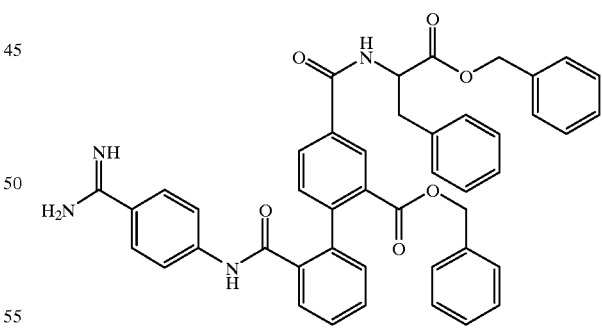

TLC: Rf 0.44 (Chloroform:Methanol:Water=8:2:0.2); NMR (CD$_3$OD): δ 8.23 (1H, d, J=1.8 Hz), 7.86 (1H, dd, J=1.8,7.8 Hz), 7.67 (2H, d, J=9.0 Hz), 7.66 (1H, m), 7.59 (2H, d, J=9.0 Hz), 7.49–7.54 (2H, m), 7.39 (1H, d, J=7.8 Hz), 7.27–7.29 (8H, m), 7.18–7.20 (8H, m), 5.15 (2H, s), 5.13 (2H, s), 4.83 (1H, dd, J=6.2,9.2 Hz), 3.27 (1H, dd, J=6.2,13.8 Hz), 3.10 (1H, dd, J=9.2,13.8 Hz).

EXAMPLE 7(35)

Dibenzyl 2'-(4-amidinophenylcarbamoyl)-2-biphenylphosphorate

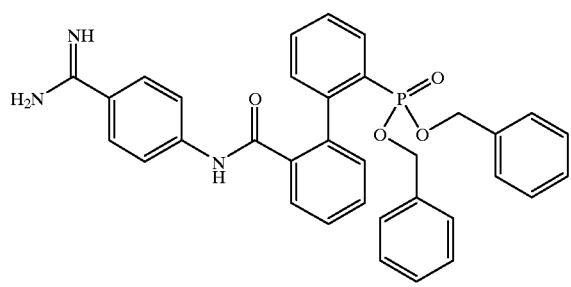

TLC: Rf 0.80 (Chloroform:Methanol:Acetic acid=10:2:1); NMR (CD$_3$OD): δ 7.96–7.84 (1H, m), 7.68–7.20 (21H, m), 4.90–4.82 (4H, m).

EXAMPLE 7(36)

Benzyl 2'-(4-amidinophenylcarbamoyl)-4-fluoro-2-biphenylcarboxylate

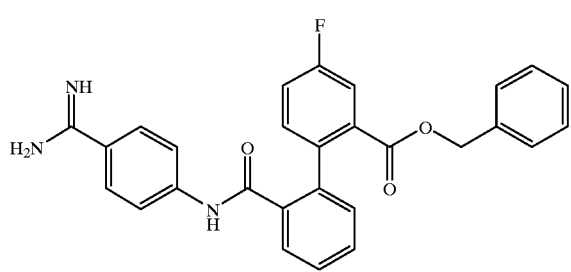

TLC: Rf 0.35 (Chloroform:Methanol:Water=8:2:0.2); NMR (CD$_3$OD): δ 7.58–7.72 (6H, m), 7.47–7.55 (2H, m), 7.22–7.34 (6H, m), 7.11–7.16 (2H, m), 5.12 (2H, s).

EXAMPLE 7(37)

Benzyl 2'-(4-amidinophenylcarbamoyl)-4-benzylcarbamoyl-2-biphenylcarboxylate

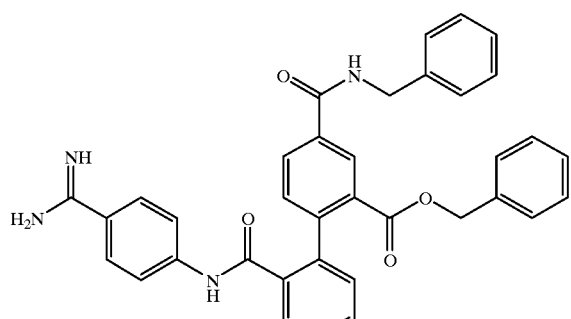

TLC: Rf 0.22 (Chloroform:Methanol:Water=8:2:0.2); NMR (CD$_3$OD): δ 8.37 (1H, d, J=1.8 Hz), 8.00 (1H, dd, J=1.8,8.0 Hz), 7.65–7.69 (3H, m), 7.59 (2H, d, J=9.2 Hz), 7.50–7.55 (2H, m), 7.42 (1H, d, J=8.0 Hz), 7.24–7.34 (9H, m), 7.13–7.17 (2m), 5.13 (2H, s), 4.56 (2H, s).

EXAMPLE 7(38)

Benzyl 2'-(4-amidinophenylcarbamoyl-4-phenylcarbamoyl-2-biphenylcarboxylate

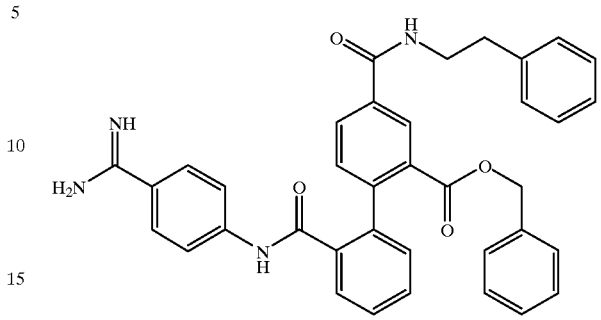

TLC: Rf 0.55 (Chloroform:Methanol:Water=7:3:0.3); NMR (CD$_3$OD): δ 8.28 (1H, d, J=2.0 Hz), 7.92 (1H, dd, J=2.0,8.0 Hz), 7.66–7.70 (3H, m), 7.59 (2H, d, J=9.2 Hz), 7.49 –7.54 (2H, m), 7.41 (1H, d, J=8.0 Hz), 7.13–7.30 (11H, m), 5.13 (2H, s), 3.58 (2H, t, J=7.0 Hz) 2.89 (2H, t, J=7.0 Hz).

EXAMPLE 7(39)

Benzyl 2'-(4-amidinophenylcarbamoyl)-4-((1 E)-2-methoxycarbonylethenyl)-2-biphenylcarboxylate

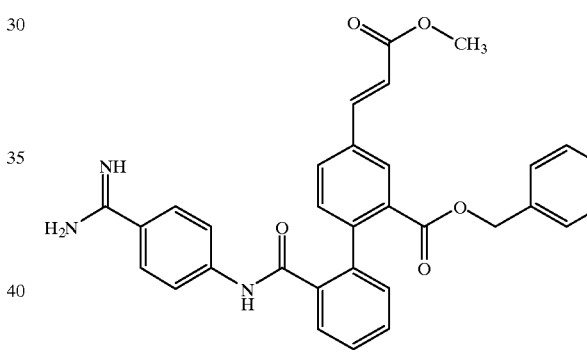

TLC: Rf 0.32 (Chloroform:Methanol=4:1); NMR (CDCl$_3$+CD$_3$OD): δ 7.97 (1H, s), 7.8–7.5 (6H, m) 7.6–7.4 (2H, m), 7.4–7.2 (7H, m), 7.11 (1H, d, J=6.6 Hz), 6.46 (1H d, J=16.2 Hz), 5.24 (2H, d, J=5.6 Hz), 3.80 (3H, s).

EXAMPLE 7(40)

Benzyl 2'-(4-amidinophenylcarbamoyl)-4-(2-methoxyethoxy)-2-biphenylcarboxylate

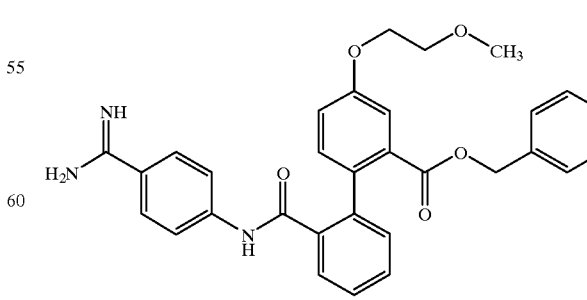

TLC: Rf 0.62 (Chloroform:Methanol:Water=10:3:0.2); NMR (d$_6$-DMSO): δ 10.47 (1H, br.s), 9.11 (3H, br.s), 7.8–7.4 (3H, m), 7.73 (4H, like s), 7.4–7.1 (7H, m), 7.1–7.0 (2H, m), 5.01 (2H, s), 4.12 (2H, t, J=4.4 Hz), 3.64 (2H, t, J=4.4 Hz), 3.33 (3H, s).

d, J=7.0 Hz), 3.90 (3H, s), 3.74 (3H, s), 2.25 (1H, m), 1.02 (3H, d, J=7.0 Hz), 1.00 (3H, d, J=7.0 Hz).

EXAMPLE 7(41)

Benzyl 2'-(4-amidinophenylcarbamoyl)-4-((2-methylpropyl)carbamoyl)-2-biphenylcarboxylate

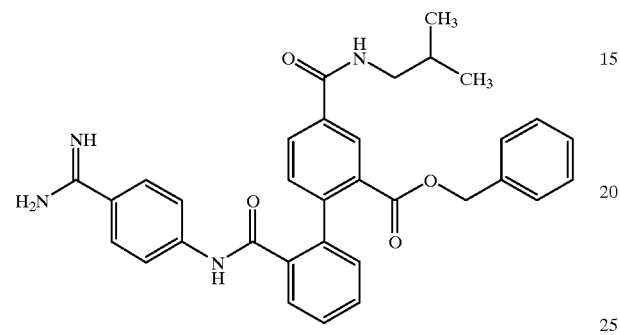

TLC: Rf 0.26 (Chloroform:Methanol:Water=8:2:0.2); NMR (CD₃OD): δ 8.33 (1H, d, J=1.6 Hz), 7.97 (1H, dd, J=1.6,8.0 Hz), 7.65–7.70 (3H, m), 7.59 (2H, d, J=8.8 Hz), 7.50–7.54 (2H, m), 7.42 (1H, d, J=8.0 Hz), 7.26–7.29 (4H, m), 7.15–7.18 (2H, m), 5.14 (2H, s), 3.18 (2H, d, J=6.8 Hz), 1.92 (1H, m), 0.95 (6H, d, J=6.8 Hz).

EXAMPLE 7(42)

Benzyl 2'-(4-amidinophenylcarbamoyl)-4'-methoxy-4-((1-methoxycarbonyl-2-methylpropyl)carbamoyl)-2-biphenylcarboxylate

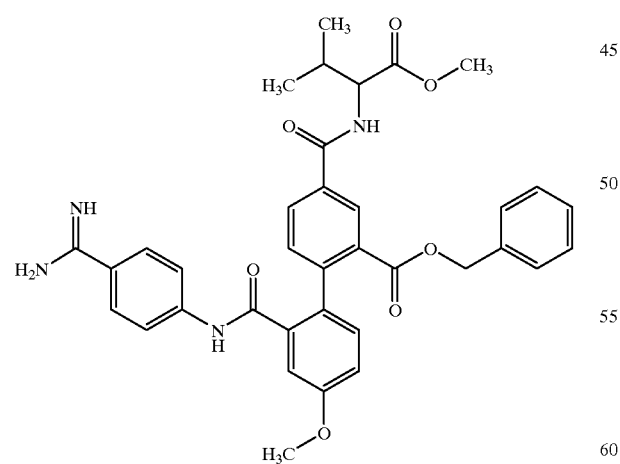

TLC: Rf 0.31 (Chloroform:Methanol:Water=8:2:0.2); NMR (CD₃OD): δ 8.30 (1H, d, J=1.8 Hz), 7.97 (1H, dd, J=1.8,8.0 Hz), 7.68 (2H, d, J=9.2 Hz), 7.59 (2H, d, J=9.2 Hz), 7.42 (1H, d, J=8.0 Hz), 7.25–7.30 (3H, m), 7.14–7.20 (4H, m), 7.06 (1H, dd, J=1.8,8.0 Hz), 5.14 (2H, s), 4.47 (1H,

EXAMPLE 7(43)

Benzyl 2'-(4-amidinophenylcarbamoyl)-4-trifluoromethyloxy-2-biphenylcarboxylate

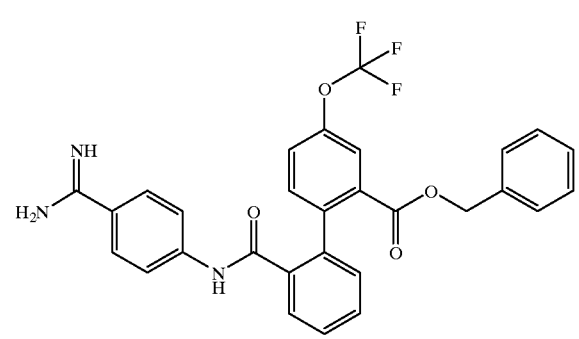

TLC: Rf 0.38 (Chloroform:Methanol:Water=8:2:0.1); NMR (CD₃OD): δ 7.73–7.11 (16H, m), 5.11 (2H, s).

EXAMPLE 7(44)

Benzyl 2-(3-(4-amidinophenylcarbamoyl)naphthalen-2-yl)-5-((1-methoxycarbonyl-2-methylpropyl)carbamoyl)benzoate

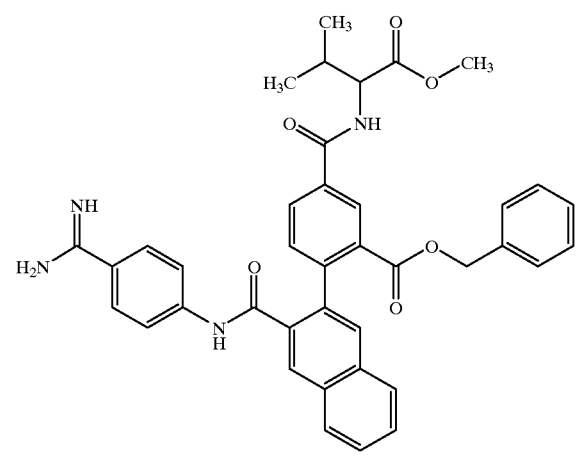

TLC: Rf 0.34 (Chloroform:Methanol:Water=8:2:0.2); NMR (CD₃OD): δ 8.39 (1H, d, J=1.8 Hz), 8.21 (1H, s), 8.00–8.07 (2H, m), 7.88 (1H, m), 7.75 (1H, s), 7.71 (4H, s), 7.62–7.66 (2H, m), 7.53 (1H, d, J=7.8 Hz), 6.92–7.13 (5H, m), 5.06 (2H, s), 4.50 (1H, d, J=7.0 Hz), 3.75 (3H, s), 2.27 (1H, m), 1.04 (3H, d, J=6.6 Hz), 1.02 (3H, d, J=6.6 Hz).

EXAMPLE 7(45)

Benzyl 3-(2-(4-amidinophenylcarbamoyl)phenyl)-8-(2-methoxyethoxy)-2-naphthalenecarboxylate

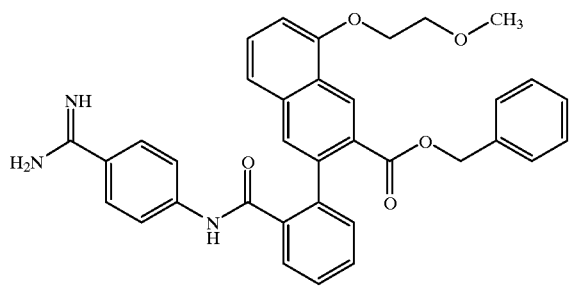

TLC: Rf 0.32 (Chloroform:Methanol:Water 10:3:0.2); NMR (d$_6$-DMSO): δ 10.58 (1H, s), 9.09 (3H, br.s), 8.65 (1H, s), 7.79 (1H, s), 7.75–7.65 (5H, m), 7.65–7.4 (5H, m), 7.3–7.2 (3H, m), 7.2–7.0 (3H, m), 5.04 (2H, br.s), 4.4–4.2 (2H, m), 3.8–3.7 (2H, m), 3.32 (3H, s).

EXAMPLE 7(46)

Benzyl 2'-(4-amidinophenylcarbamoyl)-4-((isopropylcarbonyl)aminomethyl)-2-biphenylcarboxylate

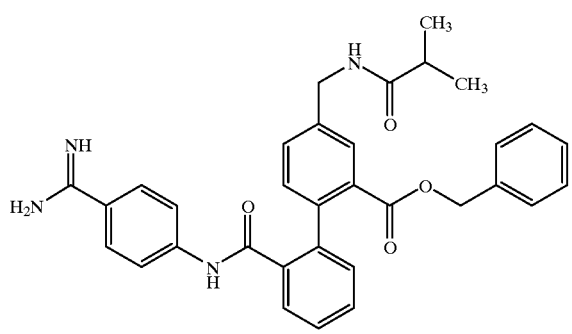

TLC: Rf 0.32 (Chloroform:Methanol:Water=8:2:0.1); NMR (CD$_3$OD): δ 7.76–7.42 (9H, m), 7.30–7.14 (7H, m), 5.12 (2H, s), 4.38 (2H, s), 2.53–2.40 (1H, m), 1.09 (6H, d, J=6.8 Hz).

EXAMPLE 7(47)

Benzyl 2-(3-(4-amidinophenylcarbamoyl)naphthalen-2-yl)-5-((2-methylpropyl)carbamoyl)benzoate

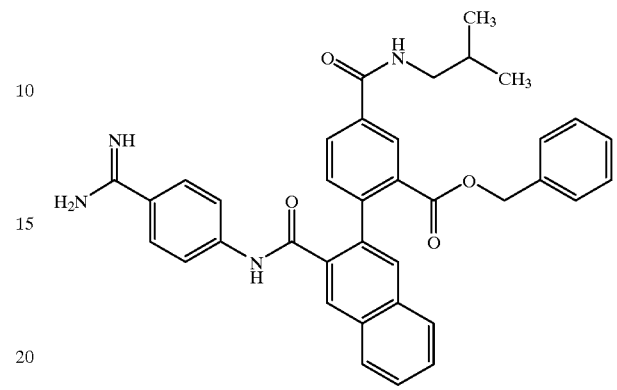

TLC: Rf 0.35 (Chloroform:Methanol:Water=8:2:0.2); NMR (CD$_3$OD): δ 8.38 (1H, d, J=2.0 Hz), 8.22 (1H, s), 8.00–8.06 (2H, m), 7.90 (1H, m), 7.76 (1H, s), 7.71 (4H, s), 7.62–7.69 (3H, m), 7.53 (1H, d, J=8.0 Hz), 6.91–7.13 (4H, m), 5.06 (2H, s), 3.21 (2H, d, J=7.0 Hz), 1.94 (1H, m), 0.97 (6H, d, J=6.6 Hz).

EXAMPLE 7(48)

Benzyl 2'-(4-amidinophenylcarbamoyl)-4'-methoxy-4-((2-methylpropyl)carbamoyl)-2-biphenylcarboxylate

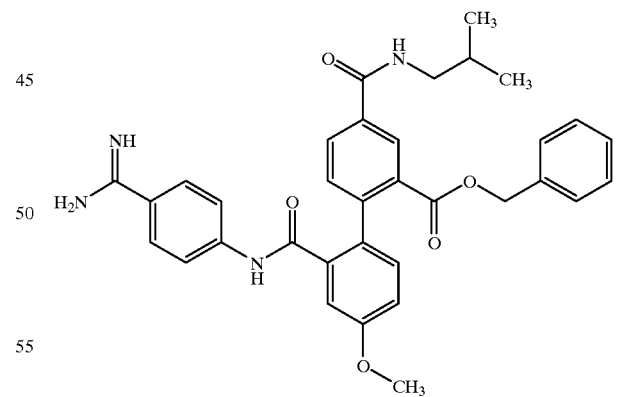

TLC: Rf 0.38 (Chloroform:Methanol:Water=8:2:0.2); NMR (CD$_3$OD): δ 8.29 (1H, d, J=2.0 Hz), 7.94 (1H, dd, J=2.0,8.0 Hz), 7.67 (2H, d, J=9.2 Hz), 7.58 (2H, d, J=9.2 Hz), 7.40 (1H, d, J=8.0 Hz), 7.25–7.30 (3H, m), 7.15–7.19 (4H, m), 7.05 (1H, dd, J=2.6, 8.8 Hz), 5.14 (2H, s), 3.89 (3H, s), 3.18 (2H, d, J=7.0 Hz), 1.91 (1H, m), 0.95 (6H, d, J=6.6 Hz).

EXAMPLE 7(49)

Benzyl 2'-(4-amidinophenylcarbamoyl)-4-isopropylcarbamoyl-2-biphenylcarboxylate

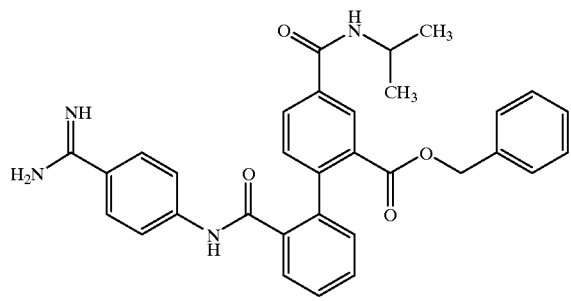

TLC: Rf 0.19 (Chloroform:Methanol:Water=8:2:0.1); NMR (CD$_3$OD): δ 8.30 (1H, d, J=1.8 Hz), 7.96 (1H, dd, J=1.8, 7.6 Hz), 7.70–7.50 (7H, m), 7.41 (1H, d, J=8.0 Hz), 7.29–7.26 (4H, m), 7.18–7.12 (2H, m), 5.14 (2H, s), 4.19 (1H, quintet, J=6.6 Hz), 1.24 (6H, d, J=6.6 Hz).

EXAMPLE 7(50)

Benzyl 2'-(4-amidinophenylcarbamoyl)-4-((3-methylbutyl)carbamoyl)-2-biphenylcarboxylate

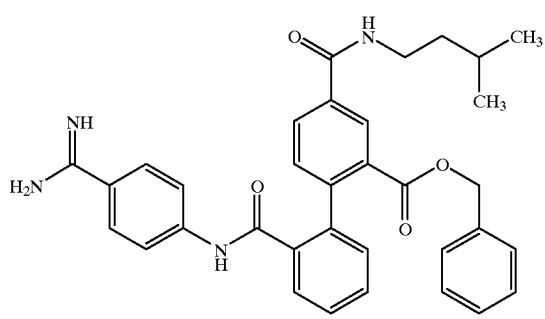

TLC: Rf 0.34 (Chloroform:Methanol:Water 8:2:0.1); NMR (CD$_3$OD): δ 8.31 (1H, d, J=1.8 Hz), 7.96 (1H, dd, J=1.8, 8.0 Hz), 7.69–7.50 (7H, m), 7.42 (1H, d, J=8.0 Hz), 7.29–7.26 (4H, m), 7.18–7.12 (2H, m), 5.13 (2H, s), 3.43–3.29 (2H, m), 1.75–1.60 (1H, m), 1.60–1.45 (2H, m), 0.95 (6H, d, J=6.6 Hz).

EXAMPLE 7(51)

Benzyl 2'-(4-amidinophenylcarbamoyl)-4-ethylcarbamoyl-2-biphenylcarboxylate

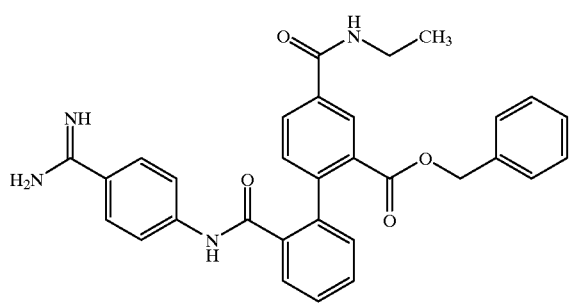

TLC: Rf 0.29 (Chloroform:Methanol:Water=8:2:0.1); NMR (CD$_3$OD): δ 8.32 (1H, d, J=1.8 Hz), 7.97 (1H, dd, J=1.8, 8.0 Hz), 7.69–7.50 (7H, m), 7.42 (1H, d, J=8.0 Hz), 7.29–7.26 (4H, m), 7.17–7.15 (2H, m), 5.13 (2H, s), 3.45–3.35 (2H, m), 1.21 (3H, t, J=7.4 Hz).

EXAMPLE 7(52)

Benzyl 2'-(4-amidinophenylcarbamoyl-2-biphenylcarboxylate

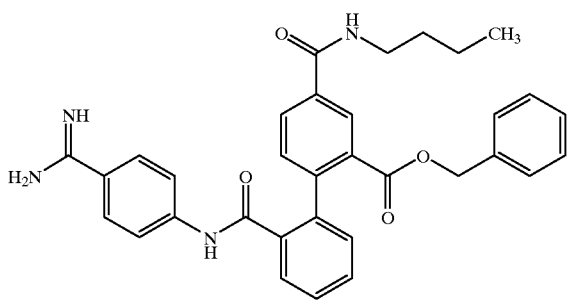

TLC: Rf 0.36 (Chloroform:Methanol:Water=8:2:0.1); NMR (CD$_3$OD): δ 8.31 (1H, d, J=1.8 Hz), 7.97 (1H, dd, J=1.8, 8.0 Hz), 7.70–7.50 (7H, m), 7.42 (1H, d, J=8.0 Hz), 7.29–7.25 (4H, m), 7.18–7.12 (2H, m), 5.13 (2H, s), 3.40–3.32 (2H, m), 1.65–1.30 (4H, m), 0.96 (3H, t, J=7.4 Hz).

EXAMPLE 7(53)

Benzyl 2'-(4-amidinophenylcarbamoyl)-4'-methyl-4-((2-methylpropyl)carbamoyl)-2-biphenylcarboxylate

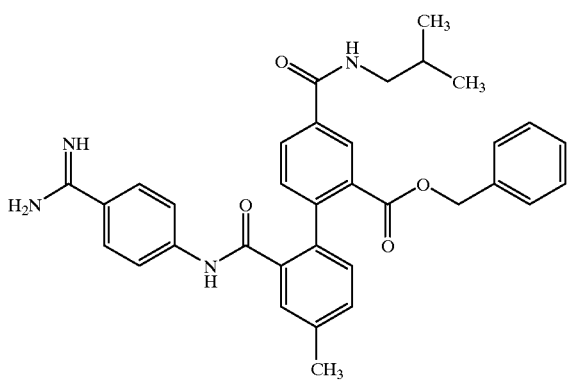

TLC: Rf 0.33 (Chloroform:Methanol:Water=8:2:0.2); NMR (CD$_3$OD): δ 8.31 (1H, d, J=1.8 Hz), 7.95 (1H, dd, J=1.8,8.0 Hz), 7.67 (2H, d, J=8.8 Hz), 7.59 (2H, d, J=8.8 Hz), 7.47 (1H, m), 7.39 (1H, d, J=8.0 Hz), 7.35 (1H, m), 7.25–7.31 (3H, m), 7.11–7.17 (3H, m), 5.13 (2H, s), 3.18 (2H, d, J=6.8 Hz), 2.46 (3H, s), 1.91 (1H, m), 0.95 (6H, d, J=6.6 Hz).

EXAMPLE 7(54)

Benzyl 2'-(4-amidinophenylcarbamoyl)-4-((cyclohexylmethyl)carbamoyl)-2-biphenylcarboxylate

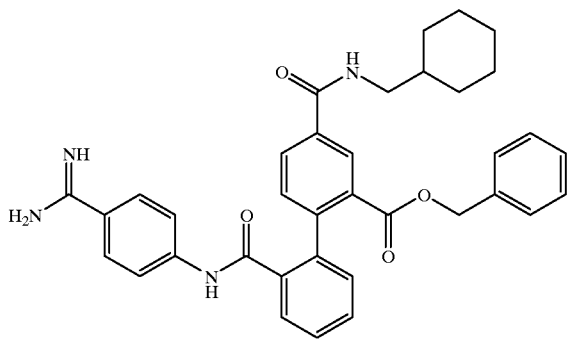

TLC: Rf 0.38 (Chloroform:Methanol:Water=8:2:0.1); NMR (CD$_3$OD): δ 8.31 (1H, d, J=1.8 Hz), 7.97 (1H, dd, J=1.8, 8.0 Hz), 7.69–7.50 (7H, m), 7.42 (1H, d, J=8.0 Hz), 7.29–7.26 (4H, m), 7.18–7.15 (2H, m), 5.13 (2H, s), 3.20 (2H, d, J=7.0 Hz), 1.85–1.40 (6H, m), 1.40–0.90 (5H, m).

EXAMPLE 7(55)

Benzyl 2'-(4-amidinophenylcarbamoyl)-4-(t-butoxycarbonylamino pentyl)carbamoyl)-2-biphenylcarboxylate

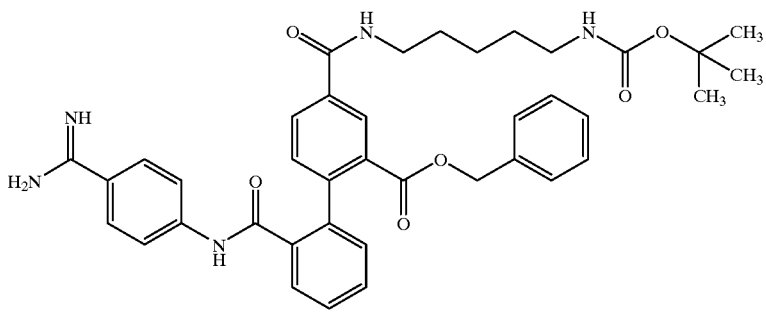

TLC: Rf 0.43 (Chloroform:Methanol:Water=8:2:0.1); NMR (CD$_3$OD): δ 8.32 (1H, d, J=1.8 Hz), 7.97 (1H, dd, J=1.8, 8.0 Hz), 7.70–7.50 (7H, m), 7.42 (1H, d, J=8.0 Hz), 7.29–7.25 (4H, m), 7.18–7.13 (2H, m), 5.13 (2H, s), 3.40–3.32 (2H, m), 3.03 (2H, t, J=6.6 Hz), 1.70–1.30 (6H, m), 1.41 (9H, s).

EXAMPLE 7(56)

Benzyl 2'-(4-amidinophenylcarbamoyl)-4-((1-methylpropyl)carbamoyl)-2-biphenylcarboxylate.

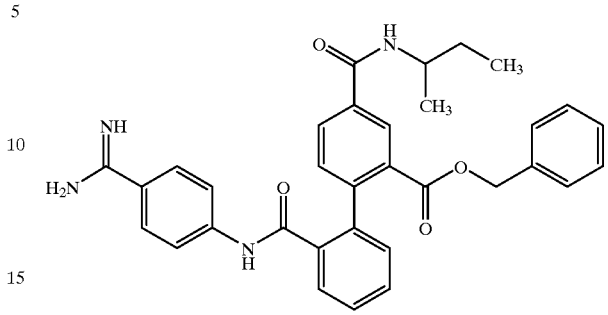

TLC: Rf 0.33 (Chloroform:Methanol:Water=8:2:0.1); NMR (CD$_3$OD): δ 8.31 (1H, d, J=2.0 Hz), 7.97 (1H, dd, J=2.0, 8.0 Hz), 7.70–7.50 (7H, m), 7.42 (1H, d, J=8.0 Hz), 7.29–7.25 (4H, m), 7.18–7.13 (2H, m), 4.01 (1H, sextet, J=6.6 Hz), 1.66–1.51 (2H, m), 1.21 (3H, d, J=6.6 Hz), 0.94 (3H, t, J=7.2 Hz).

EXAMPLE 7(57)

Benzyl 2'-(4-amidinophenylcarbamoyl)-4-((tetrahydropyran-4-methyl)carbamoyl)-2-biphenylcarboxylate

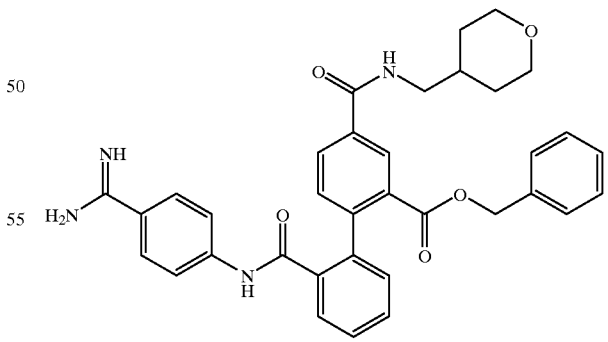

TLC: Rf 0.48 (Chloroform:Methanol:Acetic acid=10:2:1); NMR (CD$_3$OD): δ 8.31 (1H, d, J=2.0 Hz), 7.97 (1H, dd, J=8.0 Hz, 2.0 Hz), 7.69–7.65 (3H, m), 7.60 (2H, d, J=9.0 Hz), 7.57–7.47 (2H, m), 7.42 (1H, d, J=8.0 Hz), 7.29–7.23 (4H, m), 7.17–7.12 (2H, m), 5.12 (2h, brs), 3.93 (2H, dd, J=11 Hz, 2.5 Hz), 3.83 (2H, td, J=11 Hz, 2.0 Hz) 3.26 (2H, d, J=7.0 Hz), 1.96–1.80 (1H, m), 1.65 (2H, dd, J=13 Hz), 1.40–1.24 (2H, m).

EXAMPLE 7(58)

Benzyl 2'-(4-amidinophenylcarbamoyl)-4-((2-benzyloxycarbonyloxypropyl) carbamoyl)-2-buphenylcarboxylate

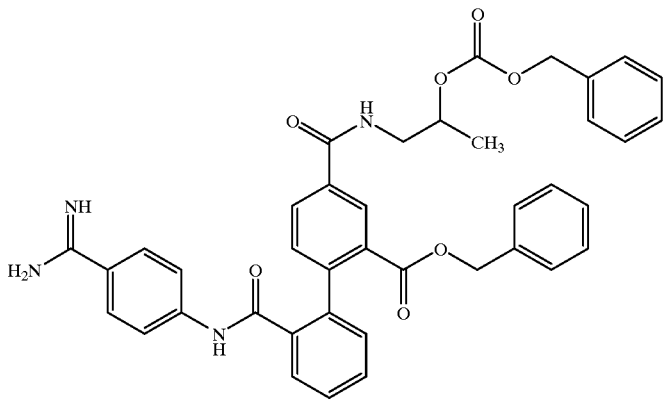

TLC: Rf 0.52 (Chloroform:Methanol:Water=8:2:0.1); NMR (CD$_3$OD): δ 8.31 (1H, d, J=1.8 Hz), 7.92 (1H, dd, J=1.8, 8.0 Hz), 7.68–7.51 (7H, m), 7.41 (1H, d, J=8.2 Hz), 7.28–7.25 (9H, m), 7.17–7.14 (2H, m), 5.12 (2H, s), 5.07 (2H, s), 5.07–4.90 (1H, m), 3.61 (1H , dd, J=4.0, 14.0 Hz), 3.47 (1H, dd, J=7.4, 14.0 Hz), 1.30 (3H, d, J=6.4 Hz).

EXAMPLE 7(59)

Benzyl 2'-(4-amidino-2-benzyloxyphenylcarbamoyl)-4-((2-methylpropyl) carbamoyl)-2-biphenylcarboxylate

EXAMPLE 7(60)

Benzyl 2'-(4-amidinophenylcarbamoyl)-4(N-methyl-N-(2-methylpropyl)carbamoyl)-2-biphenylcarboxylate

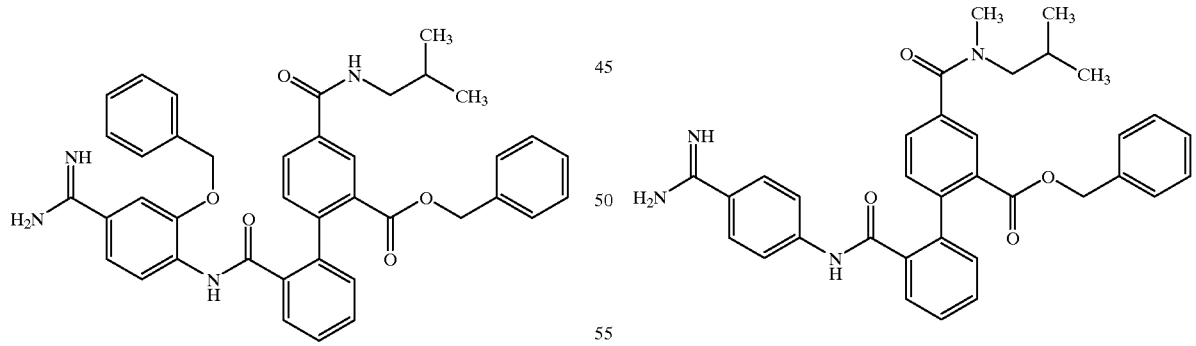

TLC: Rf 0.71 (Chloroform:Methanol:Acetic acid= 10:2:1); NMR (CD$_3$OD): δ 8.43 (1H, d, J=8.5 Hz), 8.24 (1H, d, J=2.0 Hz), 7.86 (1H, dd, J=8.0 Hz, 2.0 Hz), 7.69–7.65 (1H, m), 7.51–7.42 (2H, m), 7.38–7.29 (5H, m), 7.27 (1H, d, J=1.5 Hz), 7.25–7.16 (5H, m), 7.13–7.09 (1H, m), 7.02–6.98 (2H, m), 5.06 (1H, d, J=12 Hz), 5.01 (1H, d, J=12 Hz), 4.94 (1H, d, J=12 Hz), 4.86 (1H, d, J=12 Hz), 3.18 (2H, d, J 7.0 Hz), 1.98–1.84 (1H, m), 0.95 (6H, d, J=6.5 Hz).

TLC: Rf 0.43 (Chloroform:Methanol:Water=8:2:0.1); NMR (CD$_3$OD): δ 7.87 (1H, br s), 7.71–7.41 (9H, m), 7.31–7.26 (4H, m), 7.15–7.13 (2H, m), 5.13 (2H, s), 3.40–3.31 (2H, m, each of rotamers), 3.30–3.05 (2H, m, each of rotamers), 3.05 (3H, s, each of rotamers), 2.89 (3H, s, each of rotamers), 2.20–1.80 (1H, m), 0.98 (3H, d, J=6.6 Hz, each of rotamers), 0.65 (3H, d, J=6.6 Hz, each of rotamers).

EXAMPLE 7(61)

Benzyl 2'-(4-amidinophenylcarbamoyl)-4-((2-methyl-1-(N-methyl-N-benzyl oxycarbonylaminomethyl)propyl)carbamoyl)-2-biphenylcarboxylate

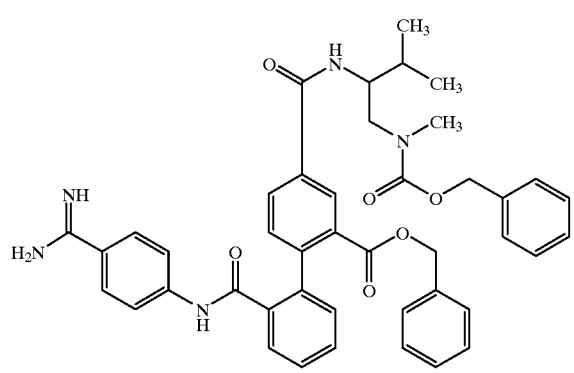

TLC: Rf 0.54 (Chloroform:Methanol:Water 10:3:0.2); NMR (d$_6$-DMSO): δ 10.68 (1H,br.s),9.4–8.8 (3H, br), '8.5–8.2 (1H, br), 8.24 (1H, br.s), 8.1–7.9 (1H, br), 7.8–7.6 (5H, m), 7.56 (2H, m), 7.40 (1H, d, J=8.2 Hz), 7.4–7.1 (9H, m), 7.1–7.0 (2H, m), 5.03 (2H, s), 4.97 (2H, s), 4.2–4.0 (1H, br), 3.7–3.2 (2H, m), 2.9–2.7 (3H, m), 1.75 (1H, m), 1.0–0.8 (6H, m).

EXAMPLE 7(62)

Benzyl 2'-(4-amidinophenylcarbamoyl)-4-((2-hydroxy-2-methylpropyl)carbamoyl)-2-biphenylcarboxylate

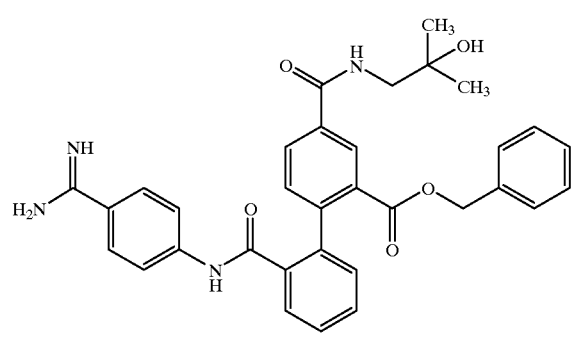

TLC: Rf 0.40 (Chloroform:Methanol:Water=8:2:0.1); NMR (CD$_3$OD): δ 8.35 (1H, d, J=2.2 Hz), 8.01 (1H, dd, J=2.2, 8.0 Hz), 7.70–7.61 (5H, m), 7.55–7.50 (2H, m), 7.44 (1H, d, J=8.0 Hz), 7.30–7.20 (4H, m), 7.18–7.13 (2H, m), 5.13 (2H, s), 3.40 (2H,, s), 1.22 (6H, s).

EXAMPLE 7(63)

Benzyl 2'-(4-amidino-2-methylphenylcarbamoyl)-4-((2-methylpropyl) carbamoyl)-2-biphenylcarboxylate

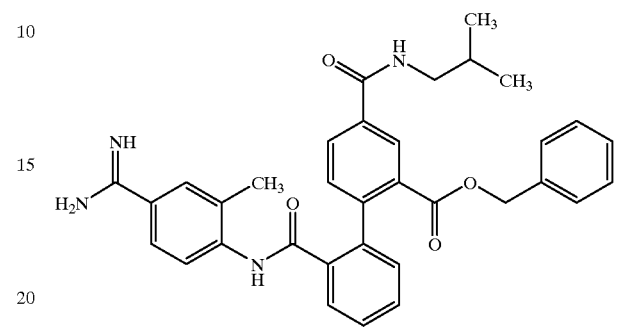

TLC: Rf 0.61 (Chloroform:Methanol:Acetic acid= 10:2:1); NMR (CD$_3$OD): δ 8.35 (1H, d, J=2.0 Hz), 7.99 (1H, dd, J=8.0 Hz, 2.0 Hz), 7.76–7.70 (1H, m), 7.69 (1H, d, J=8.0 Hz), 7.58–7.48 (4H, m), 7.45 (1H, d, J=8.0 Hz), 7.30–7.21 (4H, m), 7.21–7.10 (2H, m), 5.14 (2H,s), 3.19 (2H, d, J=7.0 Hz), 1.95 (3H, s), 2.02–1.81 (1H, m), 0.95 (6H, d, J=6.5 Hz).

EXAMPLE 7(64)

Benzyl 2'-(4-amidinophenylcarbamoyl)-4-((cyclopropylmethyl)carbamoyl)-2-biphenylcarboxylate

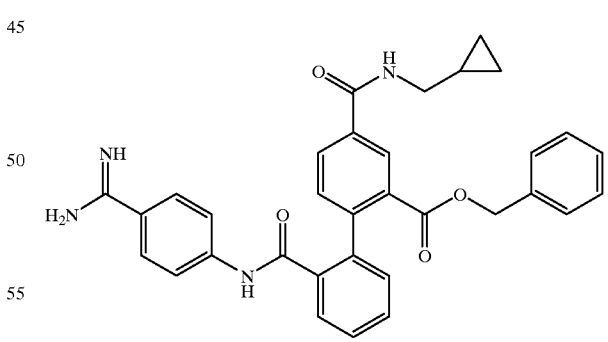

TLC: Rf 0.27 (Chloroform:Methanol:Water=8:2:0.2); NMR (CD$_3$OD): δ 8.34 (1H, d, J=2.0 Hz), 7.98 (1H, dd, J=2.0,8.0 Hz), 7.50–7.70 (7H, m), 7.42 (1H, d, J=8.0 Hz), 7.25–7.30 (4H, m), 7.14–7.19 (2H, m), 5.14 (2H, s), 3.23 (2H, d, J=7.0 Hz), 1.09 (1H, m), 0.47–0.56 (2H, m), 0.23–0.30 (2H, m). biphenylcarboxylate

EXAMPLE 7(65)

Benzyl 2'-(4-amidinophenylcarbamoyl)-4-((1-(methylcarbamoyl)-2-methylpropyl)carbamoyl)-2-

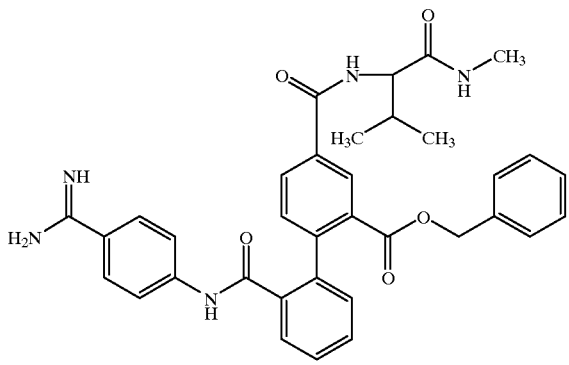

TLC: Rf 0.36 (Chloroform:Methanol:Water=8:2:0.1); NMR (CD₃OD): δ 8.33 (1H, d, J=1.5 Hz), 8.01 (1H, dd, J=1.5, 7.8 Hz), 7.68–7.65 (4H, m), 7.61–7.58 (2H, m), 7.53–7.50 (2H, m), 7.44 (1H, d, J=7.8 Hz), 7.28–7.26 (3H, m), 7.17–7.14 (2H, m), 5.13 (2H, s), 4.27 (1H, d, J=8.1 Hz), 2.75 (3H, s), 2.14 (1H, sextet, J=8.1 Hz), 1.01–0.97 (6H, m).

Benzyl 2'-(4-amidinophenylcarbamoyl)-4-((cyclopentylmethyl)carbamoyl)-2-biphenylcarboxylate

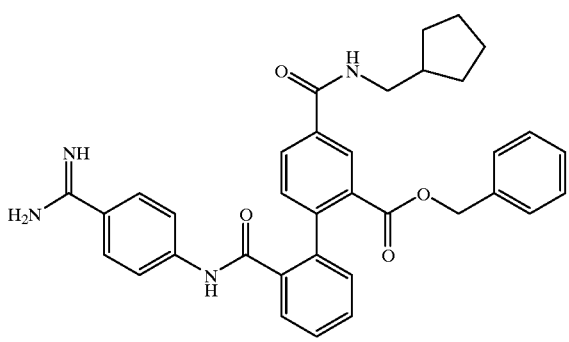

TLC: Rf 0.30 (Chloroform:Methanol:Water=8:2:0.2); NMR (CD₃OD): δ 8.32 (1H, d, J=2.0 Hz), 7.96 (1H, dd, J=2.0,8.0 Hz), 7.67 (2H, d, J=8.4 Hz), 7.59 (2H, d, J=8.4 Hz), 7.50–7.55 (2H, m), 7.41 (1H, d, J=8.0 Hz), 7.25–7.29 (4H, m), 7.13–7.18 (3H, m), 5.14 (2H, s), 3.29 (2H, d, J=6.8 Hz), 2.21 (1H, m), 1.56–1.79 (6H, m), 1.27–1.31 (2H, m).

EXAMPLE 7(67)

Benzyl 2'-(4-amidinophenylcarbamoyl)-4-((cyclobutylmethyl)carbamoyl)-2-biphenylcarboxylate

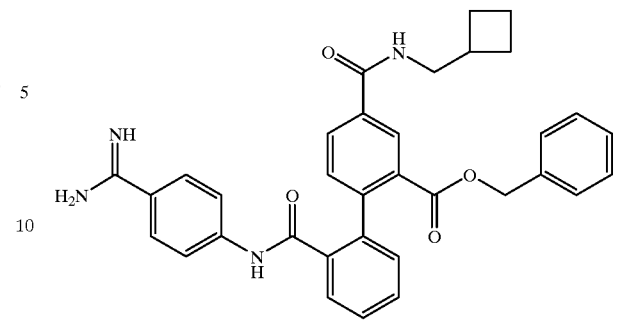

TLC: Rf 0.31 (Chloroform:Methanol:Water=8:2:0.2); NMR (CD₃OD): δ 8.31 (1H, d, J=2.0 Hz), 7.95 (1H, dd, J=2.0,8.0 Hz), 7.67 (2H, d, J=9.2 Hz), 7.59 (2H, d, J=9.2 Hz), 7.49–7.54 (2H, m), 7.41 (1H, d, J=8.0 Hz), 7.24–7.29 (4H, m), 7.13–7.17 (3H, m), 5.13 (2H, s), 3.39 (2H, d, J=7.0 Hz), 2.61 (1H, m), 1.76–2.11 (6H, m).

EXAMPLE 7(68)

Benzyl 2'-(4-amidinophenylcarbamoyl)-4-((2-methylpropyl)sulfamoyl)-2-biphenylcarboxylate

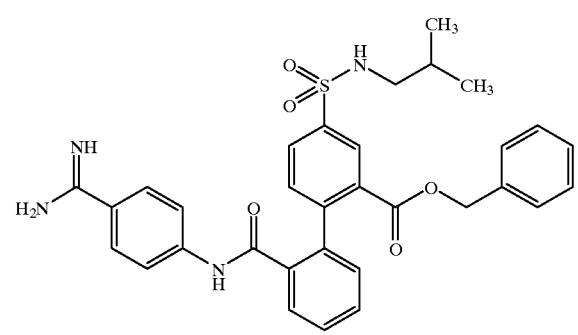

TLC: Rf 0.43 (Chloroform:Methanol:Water=8:2:0.1); NMR (CD₃OD): δ 8.30 (1H, d, J=1.5 Hz), 7.91 (1H, d, J=7.5 Hz), 7.65–7.60 (5H, m), 7.60–7.50 (3H, m), 7.30–7.20 (4H, m), 7.20–7.10 (2H, m), 5.12 (2H, s), 2.63 (2H, d, J=6.6 Hz), 1.70–1.60 (1H, m), 0.83 (6H, d, J=6.6 Hz).

EXAMPLE 7(69)

Methoxymethyl 2'-(4-amidinophenylcarbamoyl)-5-chloro-2-biphenylcarboxylate

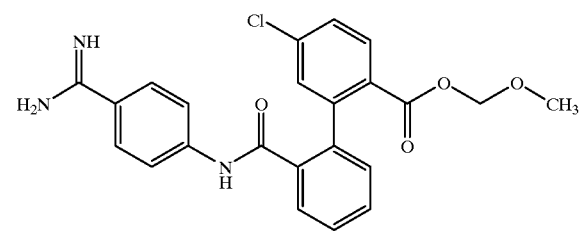

TLC: Rf 0.55 (Chloroform:Methanol:Acetic acid= 10:2:1).

EXAMPLE 7(70)

Methoxymethyl 3-(2-(4-amidinophenylcarbamoyl)phenyl)-2-naphthalene carboxylate

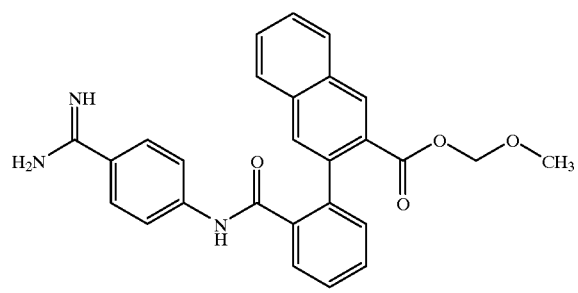

TLC: Rf 0.46 (Chloroform:Methanol:Acetic acid= 10:2:1); NMR ($d_6$-DMSO): δ 10.56 (1H, s), 9.2–8.9 (3H, s), 8.50 (1H, s), 8.12 (1H, d, J=7.0 Hz), 7.97 (1H, d, J=7.0 Hz), 7.83 (1H, s), 7.8–7.4 (10H, m), 5.16 (2H, br), 3.18 (3H, s).

EXAMPLE 7(71)

t-Butyl 2'-(3-amidinophenylcarbamoyl)-2-biphenylcarboxylate

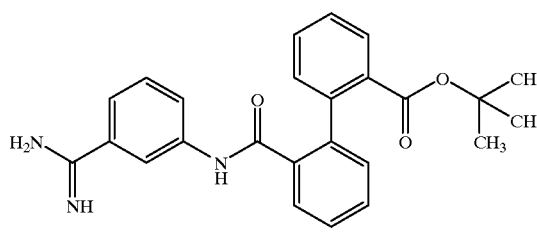

TLC: Rf 0.39 (Chloroform:Methanol:Water=8:2:0.2); NMR (CD$_3$OD): δ 8.07 (1H, s), 7.81 (1H, dd, J=1.6,7.8 Hz), 7.73 (1H, m), 7.50–7.58 (2H, m), 7.44–7.50 (3H, m), 7.36–7.41 (2H, m), 7.23–7.28 (2H, m), 1.32 (9H, s).

EXAMPLE 7(72)

t-Butyl 2-(2-(4-amidinophenylcarbamoyl)phenyl)cinnamate

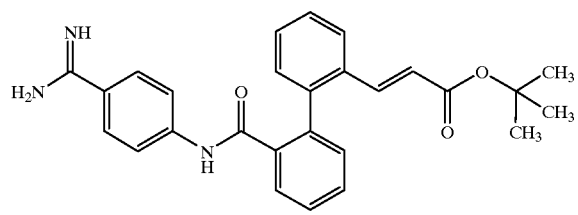

TLC: Rf 0.43 (Chloroform:Methanol:Acetic acid= 10:2:1); NMR (CD$_3$OD): δ 7.76–7.30 (13H, m), 6.28 (1H, d, J=16 Hz), 1.43 (9H, s).

EXAMPLE 7(73)

t-Butyl 2'-(4-amidinophenylcarbamoyl)biphenyl-2-yloxyacetate

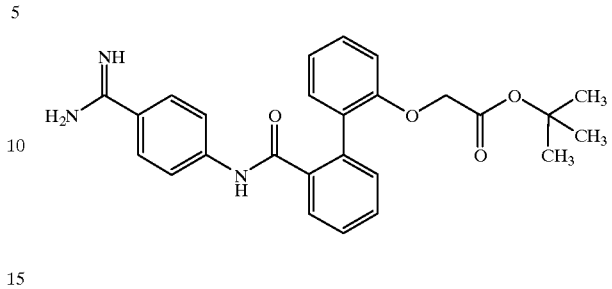

TLC: Rf 0.52 (Chloroform:Methanol:Acetic acid= 10:2:1); NMR (CD$_3$OD): δ 7.75–7.43 (8H, m), 7.33–7.21 (2H, m), 7.01 (1H, td, J=8.0 Hz, 1.0 Hz), 6.84 (1H, d, J=8.0 Hz), 4.47 (2H, s), 1.40 (9H, s).

EXAMPLE 7(74)

Methoxymethyl 3-(2-(4-amidinophenylcarbamoyl)-4-methylphenyl)-2-naphthalenecarboxylate

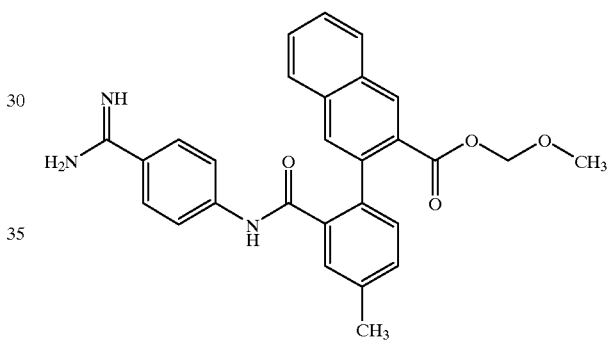

TLC: Rf 0.27 (Chloroform:Methanol=4:1); NMR (CDCl$_3$): δ 9.38 (1H, s), 8.68 (2H, brs), 8.35 (3H, s), 7.80 (1H, dd, J=7.0, 2.2 Hz), 7.7–7.6 (2H, m), 7.56 (2H, d, J=8.4 Hz), 7.5–7.4 (2H, m), 7.37 (2H, d, J=8.4 Hz), 7.22 (1H, dd, J=7.6, 2.0 Hz), 7.05 (1H, d, J=7.6 Hz), 5.37 (1H, d, J=6.0 Hz), 5.30 (1H, d, J=6.0 Hz), 3.35 (3H, s), 2.35 (3H, s).

EXAMPLE 7(75)

Methoxymethyl 1-(2-(4-amidinophenylcarbamoyl)phenyl)-2-naphthalenecarboxylate

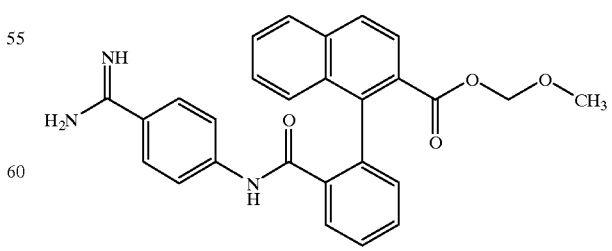

TLC: Rf 0.65 (Chloroform:Methanol:Acetic acid= 10:2:1).

EXAMPLE 7(76)

Methoxymethyl 2-(3-(4-amidinophenylcarbamoyl)-6-methoxynaphthalen-2-yl)benzoate

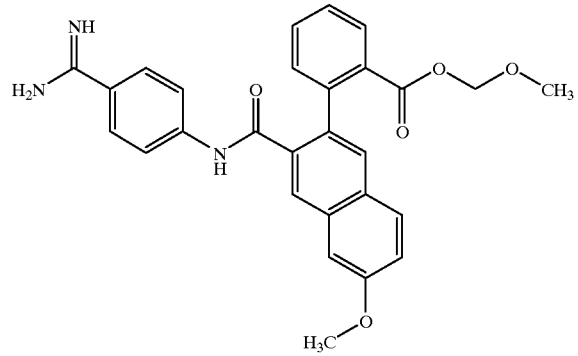

TLC: Rf 0.51 (Chloroform:Methanol:Water=10:3:0.2); NMR (d$_6$-DMSO): δ 10.74 (1H, br.s), 9.4–9.0 (3H, br), 8.16 (1H, s), 8.0–7.7 (3H, m), 7.79 (4H, like s), 7.63 (1H, m), 7.6–7.2 (4H, m), 5.07 (2H, br.s), 3.91 (3H, s), 3.03 (3H, s).

EXAMPLE 7(77)

Methoxymethyl 3-(2-(4-amidinophenylcarbamoyl)-4-methoxyphenyl)-2-naphthalenecarboxylate

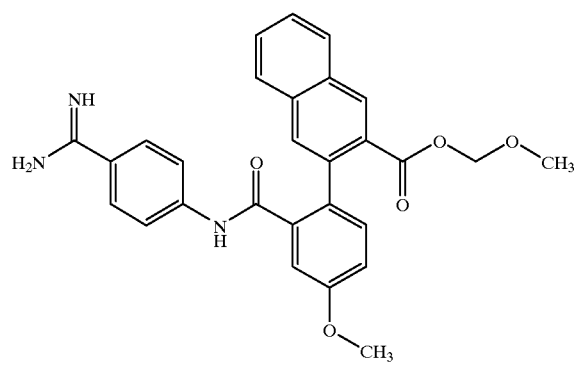

TLC: Rf 0.55 (Chloroform:Methanol:Acetic acid 10:2:1); NMR (CD$_3$OD): δ 8.44 (1H, s), 7.96 (1H, dd, J=7.0 Hz, 2.0 Hz), 7.87 (1H, dd, J=7.0 Hz, 2.0 Hz), 7.79 (1H, s), 7.65–7.50 (6H, m), 7.31 (1H, d, J=8.5 Hz), 7.25 (1H, d, J=2.5 Hz), 7.15 (1H, dd, J=8.5 Hz, 2.5 Hz), 5.32 (2H, s), 3.91 (3H, s), 3.36 (3H, s).

EXAMPLE 7(78)

Methoxymethyl 3-(2-(4-amidinophenylcarbamoyl)-4-propoxyphenyl)-2-naphthalenecarboxylate

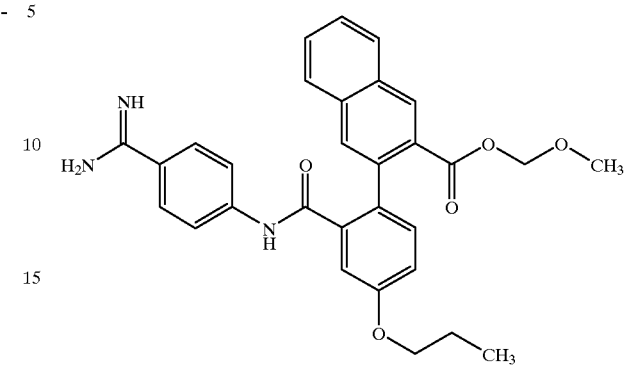

TLC: Rf 0.65 (Chloroform:Methanol:Acetic acid= 10:2:1); NMR (CD$_3$OD): δ 8.44(1H, s), 7.96(1H, dd, J=7.0 Hz, 2.0 Hz), 7.87(1H, dd, J=7.0 Hz, 2.0 Hz), 7.79 (1H, s), 7.65–7.50 (6H, m), 7.30 (1H, d, J=8.5 Hz), 7.24 (1H, d, J=2.5 Hz), 7.14 (1H, dd, J=8.5 Hz, 2.5 Hz), 5.32 (2H, s), 4.06 (2H, t, J=7.0 Hz), 3.36 (3H, s), 1.86 (2H, sextet, J=7.0 Hz), 1.09 (3H, t, J=7.0 Hz).

EXAMPLE 7(79)

Methoxymethyl 2-(3-(4-amidinophenylcarbamoyl)-7-methoxynaphthalen-2-yl)benzoate

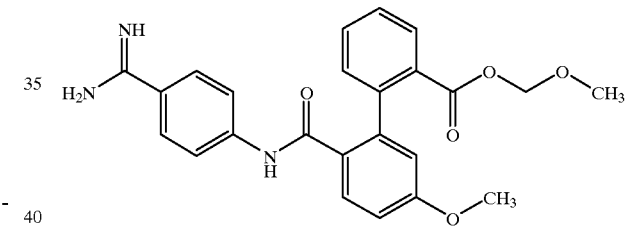

TLC: Rf 0.71 (Chloroform:Methanol:Water=10:3:0.2).

EXAMPLE 7(80)

Methoxymethyl 2-(3-(4-amidinophenylcarbamoyl)-5-methoxynaphthalen-2-yl)benzoate

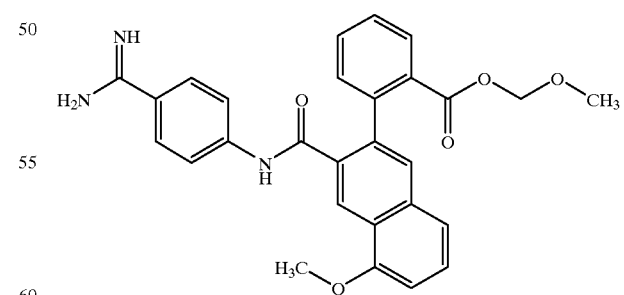

TLC: Rf 0.54 (Chloroform:Methanol:Water=10:3:0.2); NMR (d$_6$-DMSO): δ 10.80 (1H, s), 9.3–9.1 (3H, br), 8.44 (1H, s), 7.88 (1H, dd, J=1.4, 7.4 Hz), 7.79 (4H, s), 7.7–7.3 (6H, m), 7.10 (1H, m), 5.07 (2H, br.s), 4.03 (3H, s), 3.03 (3H, s).

EXAMPLE 7(81)

Methoxymethyl 2'-(4-amidinophenylcarbamoyl)-4-nitro-2-biphenylcarboxylate

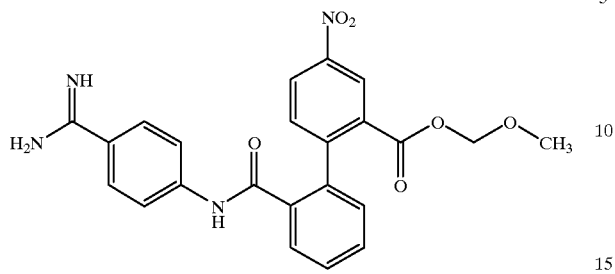

TLC: Rf 0.46 (Chloroform:Methanol:Acetic acid= 10:2:1); NMR (CD$_3$OD): δ 8.71 (1H, d, J=2.5 Hz), 8.41 (1H, dd, J=8.5 Hz, 2.5 Hz), 7.81–7.52 (8H, m), 7.37 (1H, dd, J=8.0 Hz, 1.5 Hz), 5.23 (2H, s), 3.22 (3H, s).

EXAMPLE 7(82)

Methoxymethyl 2'-(4-amidinophenylcarbamoyl)-4-methylsulfonylamino-2-biphenylcarboxylate

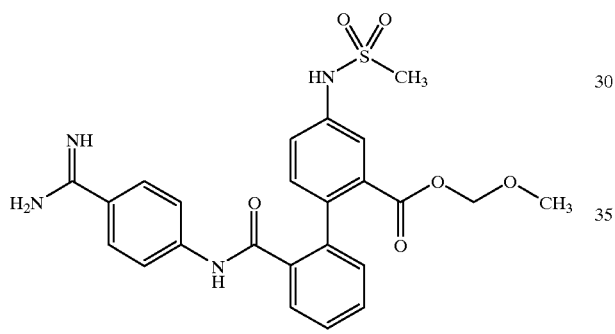

TLC: Rf 0.44 (Chloroform:Methanol:Water=7:3:0.3); NMR (d$_6$-DMSO): δ 10.49 (1H, brs), 10.2–9.8 (1H, broad), 9.3–8.9 (3H, broad), 7.80–7.22 (11H, m), 5.10 (2H, s), 3.12 (3H, s), 2.99 (3H, s).

EXAMPLE 7(83)

Methoxymethyl 2'-(4-amidinophenylcarbamoyl)-4-chloro-2-biphenylcarboxylate

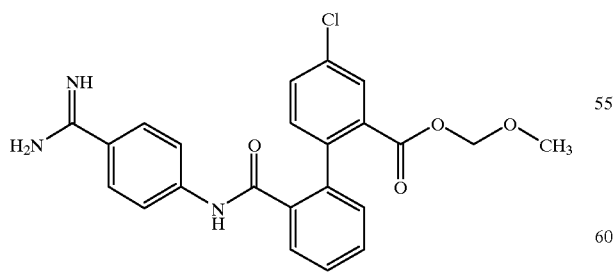

TLC: Rf 0.29 (Chloroform:Methanol:Water=8:2:0.2); NMR (CD$_3$OD): δ 7.88 (1H, d, J=2.0 Hz), 7.71 (4H, s), 7.68 (1H, m), 7.52–7.61 (3H, m), 7.30–7.35 (2H, m), 5.22 (2H, s), 3.24 (3H, s).

EXAMPLE 7(84)

Methyl 2'-(4-amidinophenylcarbamoyl)-2-biphenylcarboxylate hydrochloride

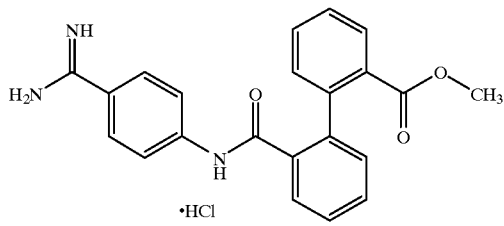

TLC: Rf 0.45 (Chloroform:Methanol:Acetic acid= 10:2:1); NMR (d$_6$-DMSO): δ 10.52 (1H, s), 9.29 (2H, brs), 9.12 (2H, brs), 7.82–7.25 (12H, m), 3.51 (3H, s).

EXAMPLE 7(85)

Ethyl 2'-(4-amidinophenylcarbamoyl)-4-((2-methylpropyl)carbamoyl)-2-biphenylcarboxylate methanesulfonate

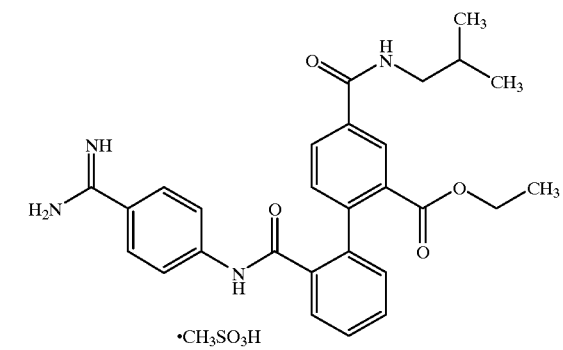

TLC: Rf 0.23 (Chloroform:Methanol:Water=8:2:0.2); NMR (d$_6$-DMSO): δ 10.56 (1H, s), 9.15 (2H, s), 8.85 (2H, s), 8.66 (1H, br.t, J=6.2 Hz), 8.24 (1H, d, J=2.0 Hz), 8.03 (1H, dd, J=2.0,8.0 Hz), 7.74 (4H, s), 7.70 (1H, dd, J=2.0,8.0 Hz), 7.61 (1H, dt, J=2.0,8.0 Hz), 7.55 (1H, dt, J=2.0,8.0 Hz), 7.41 (1H, d, J=8.0 Hz), 7.32 (1H, dd, J=2.0,8.0 Hz), 4.00 (2H, q, J=6.6 Hz), 3.10 (2H, t, J=6.2 Hz), 2.36 (3H, s), 1.86 (1H, m), 0.91 (3H, t, J=6.6 Hz), 0.89 (6H, d, J=6.4 Hz).

EXAMPLE 7(86)

Methyl 2'-(4-amidinophenylcarbamoyl)biphenyl-2-ylacetate

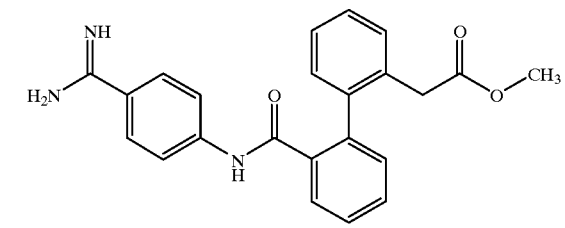

TLC: Rf 0.57 (Chloroform:Methanol:Acetic acid= 10:2:1); NMR (CD$_3$OD): δ 7.76–7.64 (3H, m), 7.59–7.51 (4H, m), 7.42–7.35 (2H, m), 7.29–7.16 (3H, m), 4.09 (1H, d, J=17 Hz), 3.74 (1H, d, J=17 Hz), 3.52 (3H, s).

EXAMPLE 7(87)

Ethyl 2'-(4-amidinophenylcarbamoyl)-5-nitro-2-biphenylcarboxylate

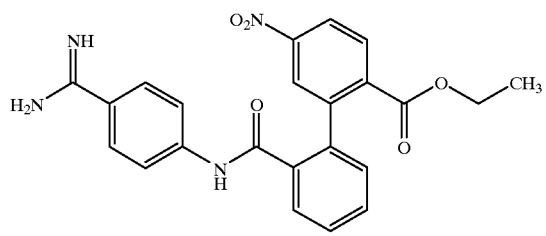

TLC: Rf 0.29 (Chloroform:Methanol:Water=8:2:0.1); NMR (CD$_3$OD): δ 8.27 (1H, dd, J=2.2, 8.4 Hz), 8.19 (1H, d, J=2.2 Hz), 7.78–7.59 (7H, m), 7.38 (1H, dd, J=1.8, 8.4 Hz), 4.11 (2H, q, J=7.4 Hz), 1.02 (3H, t, J=7.4 Hz).

EXAMPLE 7(88)

Benzyl 2'-(4-amidinophenylcarbamoyl)-4-(N-methyl-N-(t-butoxycarbonyl)aminomethyl)-2-biphenylcarboxylate

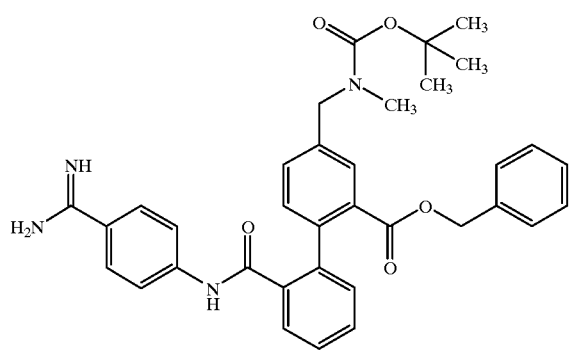

TLC: Rf 0.40 (Chloroform:Methanol:Water=8:2:0.2); NMR (CD$_3$OD): δ 7.76 (1H, br.s), 7.62–7.68 (3H, m), 7.40–7.56 (5H, m), 7.27–7.33 (5H, m), 7.14–7.19 (2H, m), 5.13 (2H, s), 4.44 (2H, br.s), 2.73 (3H, br.s), 1.36 (9H, br.s).

EXAMPLE 7(89)

Benzyl 2'-(4-amidinophenylcarbamoyl)-4-ethoxycarbonylmethoxy-2-biphenylcarboxylate

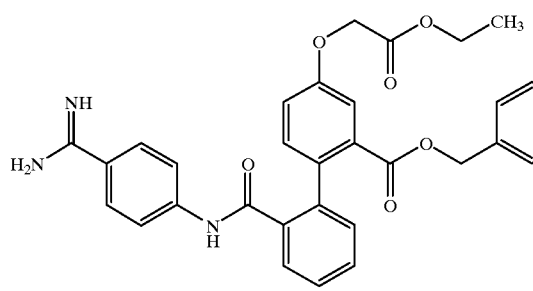

TLC: Rf 0.63 (Chloroform:Methanol:Water 10:3:0.2); NMR (d$_6$-DMSO): δ 10.51 (1H, s), 9.14 (3H, br.s), 7.9–7.6 (5H, m), 7.6–7.4 (2H, m), 7.4–7.1 (7H, m), 7.1–7.0 (2H, m), 5.01 (2H, s), 4.84 (2H, s), 4.13 (2H, q, J=7.0 Hz), 1.16 (3H, t, J=7.0 Hz).

EXAMPLE 7(90)

Benzyl 2'-(4-amidinophenylcarbamoyl)-4-((1-methoxycarbonyl-2-methylpropyl)carbamoyl)-2-biphenylcarboxylate

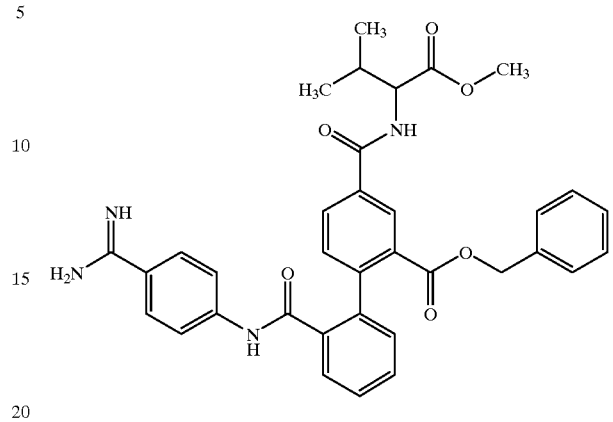

TLC: Rf 0.41 (Chloroform:Methanol:Water=8:2:0.2); NMR (CD$_3$OD): δ 8.34 (1H, d, J=1.8 Hz), 8.00 (1H, dd, J=1.8,8.0 Hz), 7.59–7.71 (5H, m), 7.50–7.55 (2H, m), 7.43 (1H, d, J=7.8 Hz), 7.26–7.29 (4H, m), 7.13–7.18 (2H, m), 5.13 (2H, s), 4.47 (1H, d, J=6.8 Hz), 3.74 (3H, s), 2.25 (1H, m), 1.02 (3H, d, J=7.0 Hz), 1.00 (3H, d, J=7.0 Hz).

EXAMPLE 7(91)

Benzyl 2'-(4-amidinophenylcarbamoyl)-4-(2-(methoxymethoxy)ethoxy)-2-biphenylcarboxylate

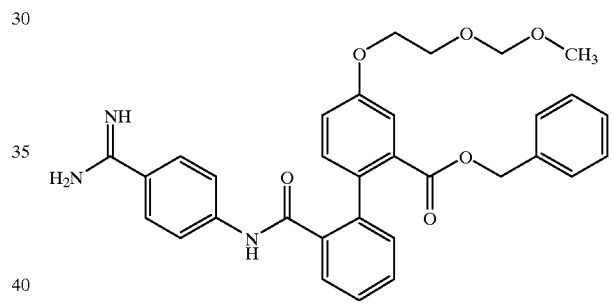

TLC: Rf 0.53 (Chloroform:Methanol:Water=10:3:0.2); NMR (d$_6$-DMSO): δ 10.47 (1H, s), 9.12 (3H, br.s), 7.8–7.6 (4H, m), 7.7–7.5 (1H, m), 7.6–7.4 (2H, m), 7.3–7.1 (7H, m), 7.1–6.9 (2H, m), 5.01 (2H, s), 4.59 (2H, s), 4.2–4.0 (2H, m), 3.8–3.7 (2H, m), 3.24 (3H, s).

EXAMPLE 7(92)

Benzyl 3-(2-(4-amidinophenylcarbamoyl)phenyl)-5-methoxymethoxy-2-naphthalenecarboxylate

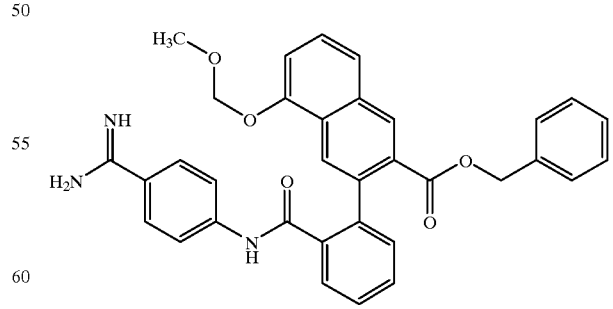

TLC: Rf 0.74 (Chloroform:Methanol:Water=10:3:0.2); NMR (d$_6$-DMSO): δ 10.64 (1H, s), 9.11 (3H, br.s), 8.42 (1H, s), 8.06 (1H, s), 7.8–7.6 (6H, m), 7.6–7.4 (4H, m), 7.3–7.1 (4H, m), 7.2–7.0 (2H, m), 5.38 (2H, s), 5.08 (2H, s), 3.33 (3H, s).

EXAMPLE 7(93)

Benzyl 3-(2-(4-amidinophenylcarbamoyl)phenyl)-8-methoxymethoxy-2-naphthalenecarboxylate

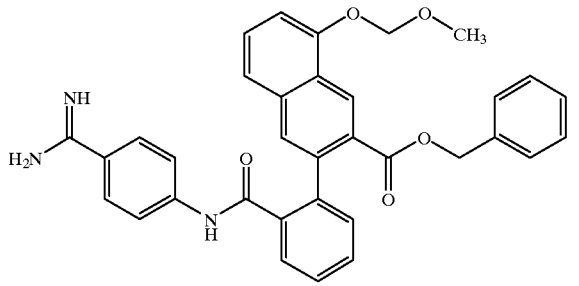

TLC: Rf 0.39 (Chloroform:Methanol:Water=10:2:0.1); NMR (d$_6$-DMSO): δ 10.59 (1H, s), 9.09 (3H, br.s), 8.66 (1H, s), 7.81 (1H, s), 7.71 (5H, like s), 7.7–7.5 (4H, m), 7.44 (1H, m), 7.3–7.1 (4H, m), 7.1–7.0 (2H, m), 5.44 (2H, s), 5.07 (2H, s), 3.43 (3H, s).

EXAMPLE 7(94)

Benzyl 2'-(4-amidinophenylcarbamoyl)-4-(N-(t-butoxycarbonyl)-N-(2-methylpropyl)aminomethyl)-2-biphenylcarboxylate

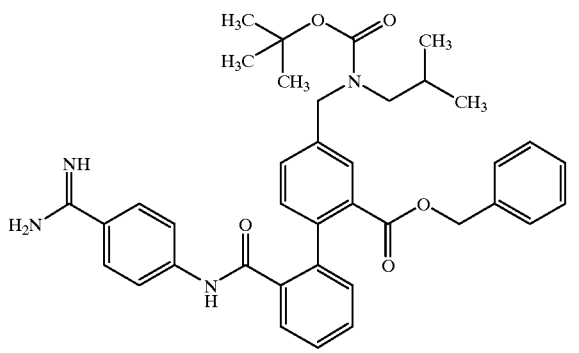

TLC: Rf 0.51 (Chloroform:Methanol:Water=8:2:0.1); NMR (CD$_3$OD): δ 7.76–7.39 (9H, m), 7.31–7.15 (7H, m), 5.13 (2H, s), 4.46 (2H, br s), 2.96 (2H, d, J=7.2 Hz), 1.95–1.80 (1H, m), 1.43–1.30 (9H, m), 0.82 (6H, d, J=6.6 Hz).

EXAMPLE 7(95)

Benzyl 2'-(4-amidinophenylcarbamoyl)-4-((2-methoxycarbonylethyl)carbamoyl)-2-biphenylcarboxylate

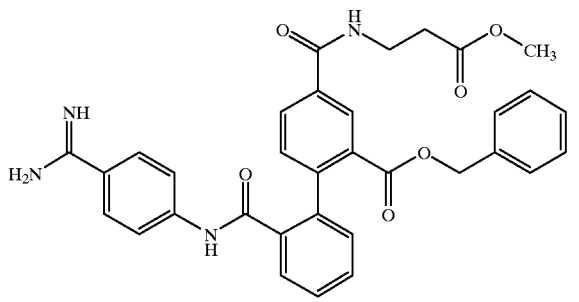

TLC: Rf 0.49 (Chloroform:Methanol:Acetic acid=10:2:1); NMR (CD$_3$OD): δ 8.30 (1H, d, J=2.0 Hz), 7.95 (1H, dd, J=8.0 Hz, 2.0 Hz), 7.68 (2H, d, J=9.0 Hz), 7.66 (1H, dd, J=7.5 Hz, 1.5 Hz), 7.59 (2H, d, J=9.0 Hz), 7.58–7.46 (2H, m), 7.42 (1H, d, J=8.0 Hz), 7.30–7.23 (4H, m), 7.18–7.10 (2H, m), 5.12 (2H, s), 3.66 (3H, s), 3.62 (2H, t, J=7.0 Hz), 2.64 (2H, t, J=7.0 Hz).

EXAMPLE 7(96)

Benzyl 2'-(4-amidinophenylcarbamoyl)-4-((3-ethoxycarbonylpropyl)carbamoyl)-2-biphenylcarboxylate

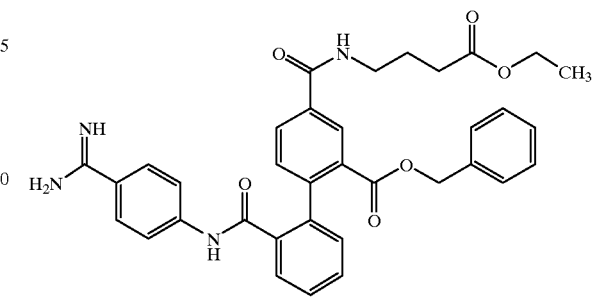

TLC: Rf 0.54 (Chloroform:Methanol:Acetic acid=10:2:1); NMR (CD$_3$OD): δ 8.32 (1H, d, J=2.0 Hz), 7.96 (1H, dd, J=8.0 Hz, 2.0 Hz), 7.68 (2H, d, J=9.0 Hz), 7.66 (1H, dd, J=7.5 Hz, 1.5 Hz), 7.58 (2H, d, J=9.0 Hz), 7.58–7.46 (2H, m), 7.42 (1H, d, J=8.0 Hz), 7.30–7.22 (4H, m), 7.18–7.12 (2H, m), 5.13 (2H, s), 4.07 (2H, q, J=7.0 Hz), 3.40 (2H, t, J=7.0 Hz), 2.38 (2H, t, J=7.0 Hz), 1.90 (2H, quint, J=7.0 Hz), 1.20 (3H, t, J=7.0 Hz).

EXAMPLE 7(97)

Benzyl 2'-(4-amidinophenylcarbamoyl)-4-((1-t-butoxycarbonylpyperidin-4-ylmethyl)carbamoyl)-2-biphenylcarboxylate

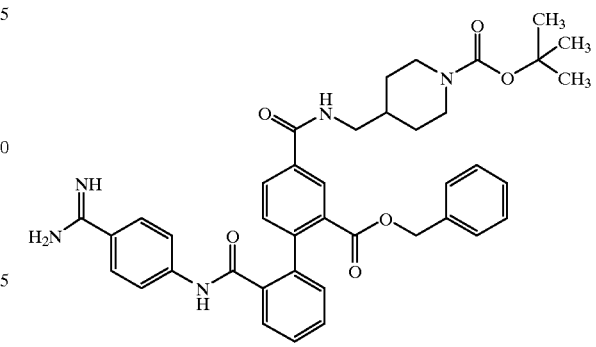

TLC: Rf 0.52 (Chloroform:Methanol:Water=8:2:0.1); NMR (CD$_3$OD): δ 8.31 (1H, d, J=1.5 Hz), 7.97 (1H, dd, J=1.5, 7.8 Hz), 7.69–7.59 (5H, m), 7.53–7.50 (2H, m), 7.43 (1H, d, J=8.1 Hz), 7.28–7.26 (4H, m), 7.16–7.14 (2H, m), 5.13 (2H, s), 4.07 (2H, d, J=12.9 Hz), 3.27–3.23 (2H, m), 2.74 (2H, m), 1.90–1.70 (3H, m), 1.45 (9H, s), 1.20–1.05 (2H, m).

EXAMPLE 7(98)

Benzyl 2'-(4-amidinophenylcarbamoyl)-4-((2-methylsulfinylethyl)carbamoyl)-2-biphenylcarboxylate

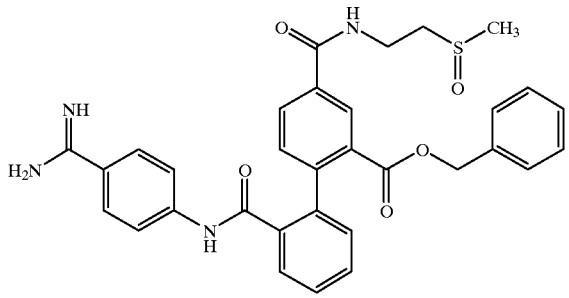

TLC: Rf 0.64 (Chloroform:Methanol:Acetic acid= 10:2:1); NMR (d$_6$-DMSO): δ 10.63 (1H, s), 9.4–9.0 (3H, br), 9.03 (1H, br.t), 8.26 (1H, d, J=2.0 Hz), 8.04 (1H, dd, J=2.0, 8.0 Hz), 7.8–7.6 (5H, m), 7.6–7.4 (2H, m), 7.42 (1H, d, J=8.0 Hz), 7.4–7.2 (4H, m), 7.1–7.0 (2H, m), 5.04 (2H, s), 3.62 (2H, m), 3.06 (1H, dt, J=13.0, 6.0 Hz), 2.87 (1H, dt, J=13.0, 6.0 Hz), 2.58 (3H, s).

EXAMPLE 7(99)

Benzyl 2-(4-(4-amidinophenylcarbamoyl)pyridin-3-yl)-5-((2-methylpropyl)carbamoyl)benzoate

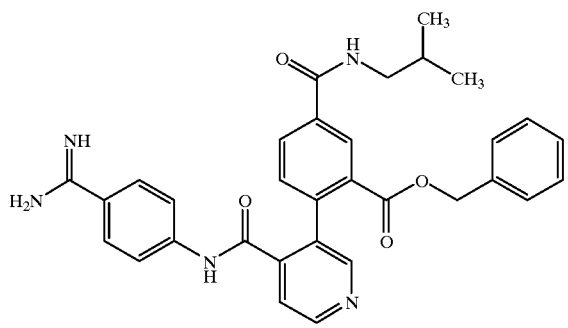

TLC: Rf 0.45 (Chloroform:Methanol:Acetic acid= 10:2:1); NMR (CD$_3$OD): δ 8.63 (1H, d, J=5.0 Hz), 8.50 (1H, s), 8.43 (1H, d, J=2.0 Hz), 8.04 (1H, dd, J=8.0 Hz, 2.0 Hz), 7.72 (2H, d, J=9.0 Hz, 7.65 (2H, d, J=9.0 Hz), 7.60 (1H, d, J=5.0 Hz), 7.48 (1H, d, J=8.0 Hz), 7.30–7.22 (3H, m), 7.22–7.13 (2H, m), 5.11 (2H, s), 3.19 (2H, d, J=7.5 Hz), 2.02–1.81 (1H, m), 0.95 (6H, d, J=6.5 Hz).

EXAMPLE 7(100)

Ethyl 2-(2-(4-amidinophenylcarbamoyl)pyridin-3-yl)benzoate

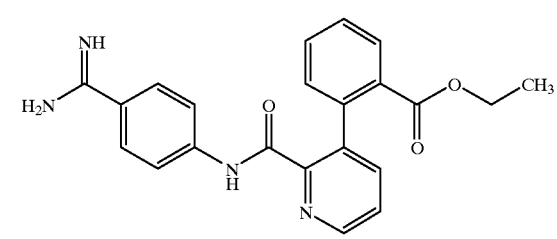

TLC: Rf 0.50 (Chloroform:Methanol:Water=10:3:0.2); NMR (d$_6$-DMSO): δ 10.96 (1H, br.s), 9.18 (3H, br.s), 8.73 (1H, d, J=4.4 Hz), 8.0–7.8 (1H, m), 7.92 (2H, d, J=8.8 Hz), 7.80 (2H, d, J=8.8 Hz), 7.8–7.6 (2H, m), 7.62 (1H, d, J=7.2 Hz), 7.50 (1H, t, J=7.2 Hz, 7.29 (1H, d, J=7.2 Hz), 3.93 (2H, q, J=7.4 Hz), 0.88 (3H, t, J=7.4 Hz).

EXAMPLE 7(101)

Benzyl 2'-(4-amidinophenylcarbamoyl)-4-propylcarbamoyl-2-biphenylcarboxylate

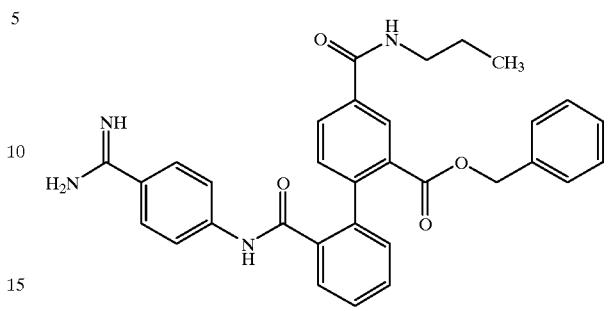

TLC: Rf 0.38 (Chloroform:Methanol:Water=8:2:0.1); NMR (CD$_3$OD): δ 8.32 (1H, d, J=1.8 Hz), 7.97 (1H, dd, J=1.8, 8.0 Hz), 7.69–7.50 (8H, m), 7.42 (1H, d, J=8.0 Hz), 7.29–7.26 (3H, m), 7.18–7.15 (2H, m), 5.13 (2H, s), 3.35–3.29 (2H, m), 1.62 (2H, sextet, J=7.2 Hz), 0.96 (3, t, J=7.2 Hz).

EXAMPLE 7(102)

Benzyl 2'-(4-amidinophenylcarbamoyl)-4-((3hydroxy-2,2-dimethylpropyl)carbamoyl)-2-biphenylcarboxylate

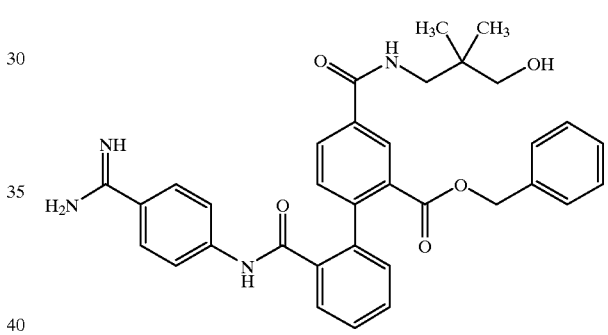

TLC: Rf 0.38 (Chloroform:Methanol:Water=8:2:0.1); NMR (CD$_3$OD): δ 8.33 (1H, d, J=2.0 Hz), 7.98 (1H, dd, J=2.0, 8.0 Hz), 7.70–7.58 (6H, m), 7.55–7.50 (2H, m), 7.43 (1H, d, J=8.0 Hz), 7.29–7.26 (3H, m), 7.17–7.10 (2H, m), 5.13 (2H, s), 3.29–3.24 (4H, m), 0.92 (6H, s).

EXAMPLE 7(103)

Benzyl 2'-(4-amidinophenylcarbamoyl)-4-((1,2,2-trimethylpropyl)carbamoyl)-2-biphenylcarboxylate

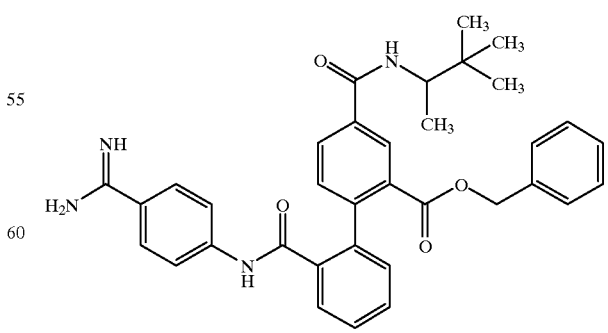

TLC: Rf 0.33 (Chloroform:Methanol:Water=8:2:0.2); NMR (CD$_3$OD): δ 8.28 (1H, d, J=1.8 Hz), 7.93 (1H, dd, J=1.8,8.0 Hz), 7.66–7.69 (3H, m), 7.61 (2H, d, J=9.0 Hz), 7.50–7.54 (2H, m), 7.41 (1H, d, J=8.0 Hz), 7.25–7.29 (4H, m), 7.14–7.17 (2H, m), 5.13 (2H, s), 4.05 (1H, q, J=7.0 Hz), 1.16 (3H, d, J=7.0 Hz), 0.96 (9H, s).

EXAMPLE 7(104)

Benzyl 2'-(4-amidinophenylcarbamoyl)-4-pentylcarbamoyl-2-biphenylcarboxylate

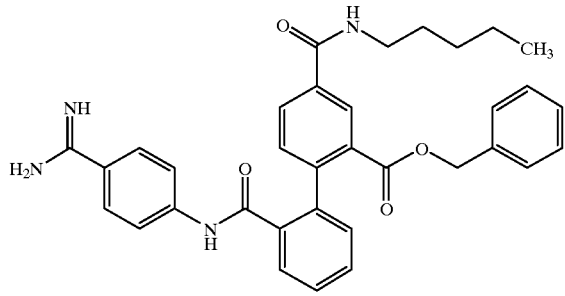

TLC: Rf 0.32 (Chloroform:Methanol:Water=8:2:0.2); NMR (CD$_3$OD): δ 8.31 (1H, d, J=2.0 Hz), 7.96 (1H, dd, J=2.0,8.0 Hz), 7.66–7.68 (3H, m), 7.61 (2H, d, J=9.0 Hz), 7.50–7.54 (2H, m), 7.42 (1H, d, J=8.0 Hz), 7.26–7.28 (4H, m), 7.14–7.17 (2H, m), 5.13 (2H, s), 3.35 (2H, t, J=7.0 Hz), 1.59–1.63 (2H, m), 1.33–1.38 (4H, m), 0.90–0.95 (3H, m).

EXAMPLE 7(105)

Benzyl 2'-(4-amidinophenylcarbamoyl)-4-hexylcarbamoyl-2-biphenylcarboxylate

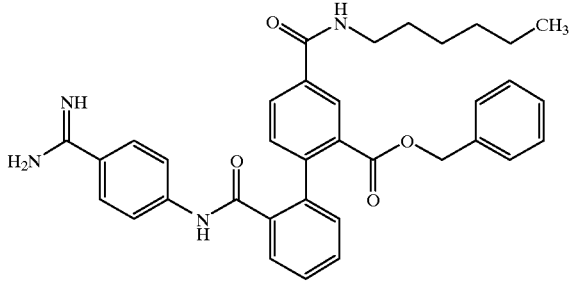

TLC: Rf 0.48 (Chloroform:Methanol:Water=8:2:0.1); NMR (CD$_3$OD): δ 8.32 (1H, d, J=1.8 Hz), 7.97 (1H, dd, J=1.8, 8.0 Hz), 7.70–7.49 (8H, m), 7.42 (1H, d, J=8.0 Hz), 7.29–7.26 (3H, m), 7.18–7.13 (2H, m), 5.13 (2H, s), 3.39–3.30 (2H, m), 1.70–1.50 (2H, m), 1.50–1.20 (6H, m), 0.90 (3H, t, J=6.6 Hz).

EXAMPLE 7(106)

Benzyl 2'-(4-amidinophenylcarbamoyl)-4-((1,2-dimethylpropyl)carbamoyl)-2-biphenylcarboxylate

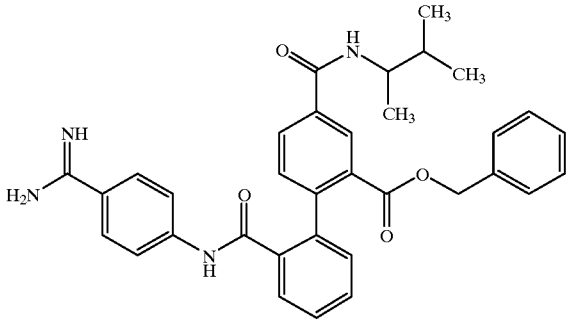

TLC: :Rf 0.45 (Chloroform:Methanol:Water=8:2:0.1); NMR (CD$_3$OD): δ 8.31 (1H, d, J=1.8 Hz), 7.96 (1H, dd, J=1.8, 8.0 Hz), 7.70–7.50 (8H, m), 7.41 (1H, d, J=8.0 Hz), 7.29–7.26 (3H, m), 7.18–7.13 (2H, m), 5.14 (2H, s), 3.91 (1H, m), 1.80 (1H, sextet, J=6.6 Hz), 1.18 (3H, d, J=6.6 Hz), 0.95 (6H, d, J=6.6 Hz).

EXAMPLE 7(107)

Methyl 2'-(4-amidinophenylcarbamoyl)-4-(((1S)-1-hydroxymethyl-2-methylpropyl)carbamoyl)-2-biphenylcarboxylate

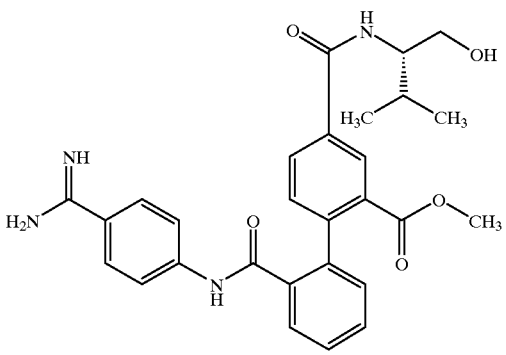

TLC: Rf 0.49 (Chloroform:Methanol:Acetic acid= 10:2:1); NMR (d$_6$-DMSO): δ 10.63 (1H, s), 9.3–8.8 (3H, br), 8.24 (1H, d, J=1.8 Hz), 8.22 (1H, br.d, J=9.3 Hz), 8.06 (1H, dd, J=1.8, 7.8 Hz), 7.75 (4H, like s), 7.68 (1H, dd, J=1.8, 7.8 Hz), 7.60 (1H, dt, J=1.8, 7.8 Hz), 7.54 (1H, dt, J=1.8, 7.8 Hz), 7.40 (1H, d, J=7.8 Hz), 7.31 (1H, dd, J=1.8, 7.8 Hz), 4.60 (1H, t, J=6.0 Hz), 3.81 (1H, m), 3.54 (3H, s), 3.6–3.4 (2H, m), 1.90 (1H, like sextet, J=6.9 Hz), 0.90 (3H, d, J=6.9 Hz), 0.87 (3H, d, J=6.9 Hz).

EXAMPLE 7(108)

Benzyl 2'-(4-amidinophenylcarbamoyl)-4-((3,3-dimethylbutyl)carbamoyl)-2-biphenylcarboxylate

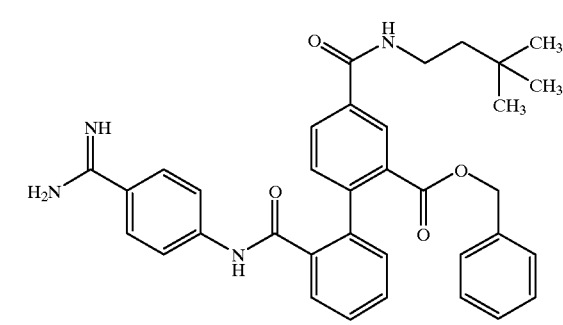

TLC: Rf 0.28 (Chloroform:Methanol:Water=8:2:0.2); NMR (CD₃D): δ 8.32 (1H, d, J=2.0 Hz), 7.95 (1H, dd, J=2.0,8.0 Hz), 7.65–7.69 (3H, m), 7.60 (2H, d, J=9.0 Hz), 7.49–7.53 (2H, m), 7.40 (1H, d, J=8.0 Hz), 7.24–7.28 (4H, m), 7.13–7.16 (2H, m), 5.12 (2H, s), 3.35–3.41 (2H, m), 1.50–1.55 (2H, m), 0.97 (9H, s).

EXAMPLE 7(109)

Methyl 2'-(4-amidinophenylcarbamoyl)-4-(((1R)-1-hydroxymethyl-2-methylpropyl)carbamoyl)-2-biphenylcarboxylate

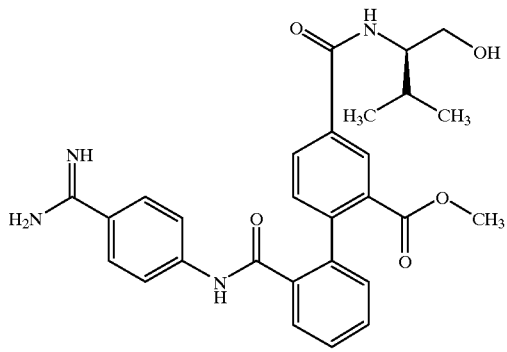

TLC: Rf 0.49 (Chloroform:Methanol:Acetic acid= 10:2:1); NMR (d₆-DMSO): δ 10.63 (1H, br.s), 9.3–8.8 (3H, br), 8.24 (1H, d, J=1.5 Hz), 8.22 (1H, d, J=8.0 Hz), 8.06 (1H, dd, J=1.5, 8.0 Hz), 7.75 (4H, like s), 7.68 (1H, dd, J=1.5, 8.0 Hz), 7.60 (1H, dt, J=1.5, 8.0 Hz), 7.54 (1H, dt, J=1.5, 8.0 Hz), 7.40 (1H, d, J=8.0 Hz), 7.32 (1H, dd, J=1.5, 8.0 Hz), 4.61 (1H, t, J=7.8 Hz), 3.81 (1H, m), 3.54 (3H, s), 3.6–3.4 (2H, m), 1.90 (1H, like sextet, J=6.8 Hz), 0.90 (3H, d, J=6.8 Hz), 0.86 (3H, d, J=6.8 Hz).

EXAMPLE 7(110)

Benzyl 2'-(4-amidinophenylcarbamoyl)-4-(((1S)-1-methoxycarbonyl-2-methylpropyl)carbamoyl)-2-biphenylcarboxylate

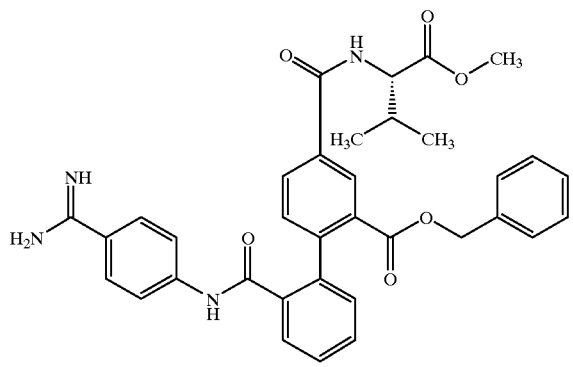

TLC: Rf 0.45 (Chloroform:Methanol:Water=8:2:0.1); NMR (CD₃OD): δ 8.32 (1H, d, J=1.4 Hz), 8.00 (1H, dd, J=1.4, 8.0 Hz), 7.70–7.58 (5H, m), 7.55–7.49 (2H, m), 7.43 (1H, d, J=8.0 Hz), 7.30–7.25 (4H, m), 7.17–7.12 (2H, m), 5.12 (2H, s), 4.46 (1H, d, J=7.0 Hz), 3.73 (3H, s), 2.24 (1H, sextet, J=7.0 Hz), 1.01 (6H, dd, J=3.6, 7.0 Hz).

EXAMPLE 7(111)

Benzyl 2'-(4-amidinophenylcarbamoyl)-4-(((1R)-1-methoxycarbonyl-2-methylpropyl)carbamoyl)-2biphenylcarboxylate -

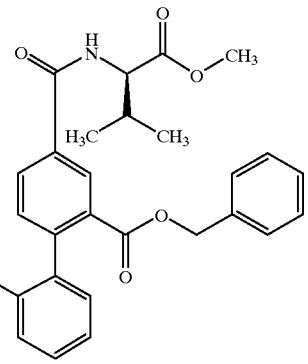

TLC: Rf 0.48 (Chloroform:Methanol:Water=8:2:0.1); NMR (CD₃OD): δ 8.32 (1H, d, J=2.1 Hz), 7.99 (1H, dd, J=2.1, 8.1 Hz), 7.69–7.50 (7H, m), 7.43 (1H, d, J=8.1 Hz), 7.29–7.25 (4H, m), 7.16–7.13 (2H, m), 5.12 (2H, s), 4.46 (1H, d, J=6.9 Hz), 3.73 (3H, s), 2.24 (1H, sextet, J=6.9 Hz), 1.10 (6H, dd, J=5.1, 6.9 Hz).

EXAMPLE 7(112)

Benzyl 2'-(4-amidinophenylcarbamoyl)-4-(3-methylbutoxy)-2-biphenylcarboxylate

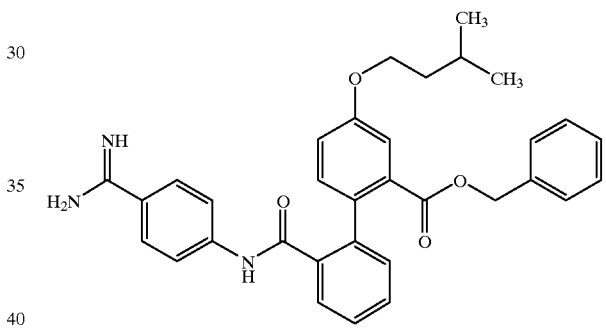

TLC: Rf 0.51 (Chloroform:Methanol:Water=8:2:0.1); NMR (CD₃OD): δ 7.69–7.41 (7H, m), 7.34–7.04 (9H, m), 5.12 (2H, s), 4.01 (2H, t, J=6.6 Hz), 1.88–1.59 (3H, m), 0.94 (6H, d, J=6.6 Hz).

EXAMPLE 7(113)

Benzyl 2-(3-(4-amidinophenylcarbamoyl)pyridin-4-yl)-5-((2-methylpropyl)carbamoyl)benzoate

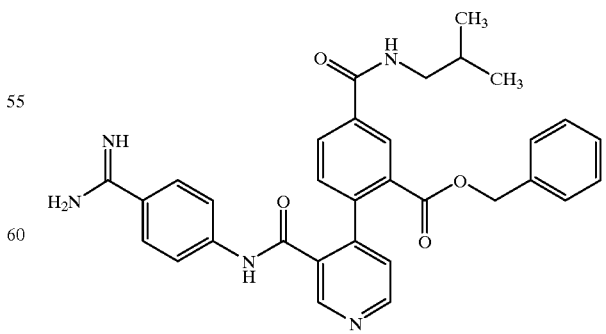

TLC: Rf 0.33 (Chloroform:Methanol:Acetic acid= 10:2:1); NMR (CD₃OD): δ 8.77 (1H, s), 8.63 (1H, dd, J=5.0

Hz), 8.43 (1H, d, J=2.0 Hz), 8.04 (1H, dd, J=8.0 Hz, 2.0 Hz), 7.70 (4H, s), 7.43 (1H, d, J=8.0 Hz), 7.38 (1H, d, J=5.0 Hz), 7.30–7.12 (5H, m), 5.11 (2H, s), 3.19 (2H, d, J=7.0 Hz), 2.02–1.81 (1H, m), 0.95 (6H, d, J=6.5 Hz).

EXAMPLE 7(114)

Benzyl 2'-(4-amidinophenylcarbamoyl)-4'-methoxy-4-((1,2,2-trimethylpropyl)carbamoyl)-2-biphenylcarboxylate

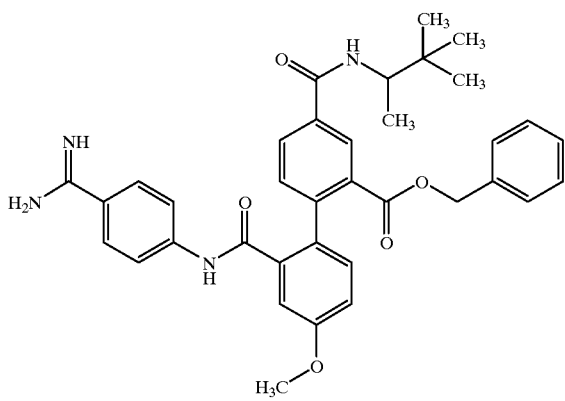

TLC: Rf 0.67 (Chloroform:Methanol:Acetic acid= 10:2:1); NMR (CD$_3$OD): δ 8.77 (1H, d, J=2.5 Hz), 8.25 (1H, d, J=2.0 Hz), 8.18 (1H, dd, J=8.5 Hz,2.5 Hz), 8.02 (1H, d, J=8.5 Hz), 7.93 (1H, dd, J=8.0 Hz, 2.0 Hz), 7.42 (1H, d, J=8.0 Hz), 7.27–7.17 (5H, m), 7.26–7.09 (2H, m), 7.08 (1H, dd, J=8.5 Hz, 2.5 Hz), 5.10 (2H, s), 4.05 (1H, q, J=7.0 Hz), 3.89 (3H, s), 1.15 (3H, d, J=7.0 Hz), 0.95 (9H, s).

EXAMPLE 7(115)

Benzyl 2'-(4-amidinophenylcarbamoyl)-4-(((1S)-1-hydroxymethyl-2,2-dimethylpropyl)carbamoyl)-2-biphenylcarboxylate

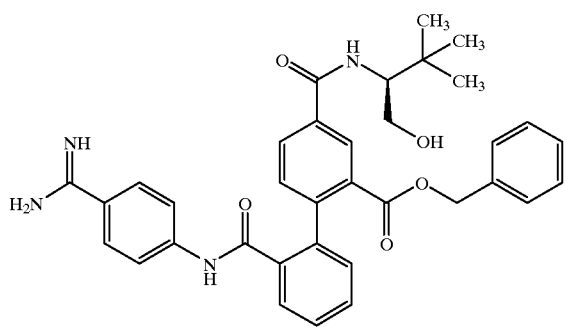

TLC: Rf 0.32 (Chloroform:Methanol:Water 8:2:0.1); NMR (CD$_3$OD): δ 8.33 (1H, d, J=1.8 Hz), 7.99 (1H, dd, J=1.8, 7.8 Hz), 7.70–7.49 (7H, m), 7.42 (1H, d, J=8.0 Hz), 7.29–7.25 (4H, m), 7.18–7.13 (2H, m), 5.13 (2H, s), 4.04 (1H, dd, J=3.6, 9.2 Hz), 3.87 (1H, dd, J=3.6, 11.8 Hz), 3.61 (1H, dd, J=9.0, 11.8 Hz), 0.98 (9H, s).

EXAMPLE 8–EXAMPLE 8(7)

The following compounds were obtained by the same procedure as a series of reaction of Reference Example 7→Reference Example 8→Example 1, using a compound prepared in Reference Example 5 or a corresponding compound, with the proviso that, the compound of Example 8(6) was obtained by the same procedure as a series of reaction of Reference Example 3 instead of Example 1.

EXAMPLE 8

Benzyl 2-(3-(4-amidinophenylcarbamoyl)naphthalen-2-yl)-5-methylbenzoate

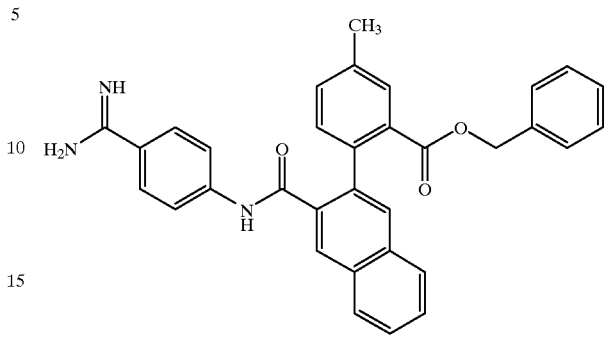

TLC: Rf 0.20 (Chloroform:Methanol=4:1); NMR (CD$_3$OD): δ 8.16 (1H, s), 8.1–8.0 (1H, m), 7.9–7.8 (1H, m), 7.7–7.6 (8H, m), 7.39 (1H, dd, J=6.6, 1.8 Hz), 7.29 (1H, d, J=7.6 Hz), 7.2–7.0 (3H, m), 6.94 (2H, dd, J=7.6, 1.0) 5.06 (2H, s), 2.39 (3H, s).

EXAMPLE 8(1)

Benzyl 2-(2-(4-amidinophenylcarbamoyl)naphthalen-1-yl)benzoate

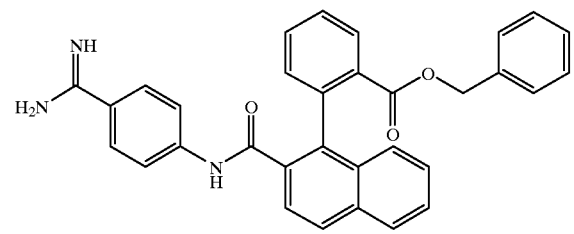

TLC: Rf 0.75 (Chloroform:Methanol:Acetic acid= 10:2:1); NMR (CD$_3$OD): δ 8.03–7.92 (3H, m), 7.69–7.46 (8H, m), 7.42–7.10 (6H, m), 6.93–6.89 (2H, m), 5.02 (1H, d, J=12 Hz), 4.95 (1H, d, J=12 Hz).

EXAMPLE 8(2)

Benzyl 2-(3-(4-amidinophenylcarbamoyl)naphthalen-2-yl)-5-benzoate

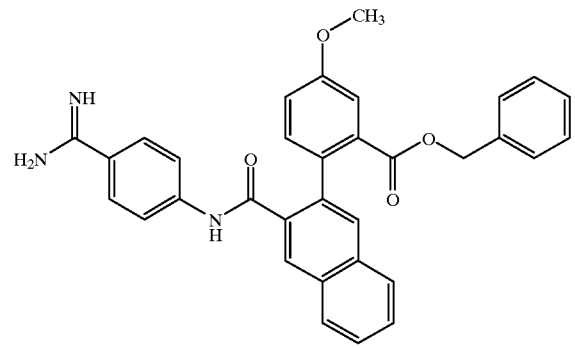

TLC: Rf 0.58 (Chloroform:Methanol:Acetic acid= 10:2:1); NMR (CD$_3$OD): δ 8.14 (1H, s), 8.02–7.97 (1H, m), 7.88–7.83 (1H, m), 7.73–7.58 (7H, m), 7.41 (1H, d, J=2.5 Hz), 7.33 (1H, d, J=8.0 Hz), 7.16–6.87 (6H, m), 5.05 (2H, s), 3.82 (3H, s).

EXAMPLE 8(3)

Benzyl 2-(3-(4-amidinophenylcarbamoyl)naphthalen-2-yl)-5-propoxybenzoate

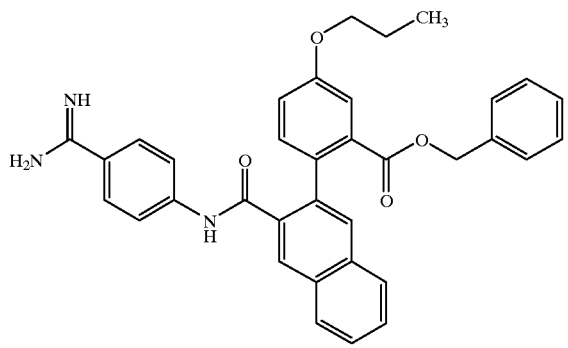

TLC: Rf 0.58 (Chloroform:Methanol:Acetic acid= 10:2:1); NMR (CD₃OD): δ 8.14 (1H, s), 8.03–7.97 (1H, m), 7.89–7.83 (1H, m), 7.73–7.58 (7H, m), 7.39 (1H, d, J=2.5 Hz), 7.32 (1H, d, J=8.0 Hz), 7.16–6.87 (6H, m), 5.05 (2H, s), 3.96 (2H, t, J=7.9 Hz), 1.79 (2H, sextet, J=7.0 Hz), 1.03 (3H, t, J=7.0 Hz).

EXAMPLE 8(4)

Benzyl 2'-(4-amidinophenylcarbamoyl)-4'-chloro-2-biphenylcarboxylate

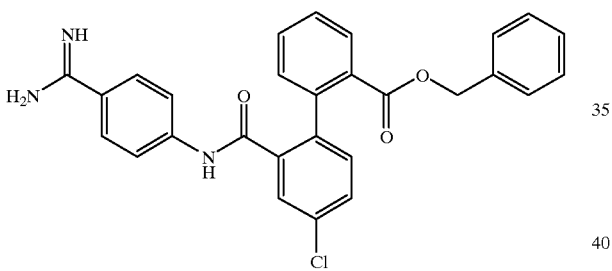

TLC: Rf 0.24 (Chloroform:Methanol:Water=8:2:0.2); NMR (CD₃OD): δ 7.90 (1H, dd, J=1.6,7.8 Hz), 7.67 (2H, d, J=9.2 Hz), 7.55–7.61 (3H, m), 7.39–7.52 (3H, m), 7.28–7.33 (4H, m), 7.20 (1H, d, J=7.8 Hz, 7,14–7.17 (2H, m), 5.13 (2H, s).

EXAMPLE 8(5)

Benzyl 2'-(4-amidinophenylcarbamoyl)-4'-((E)-2-methoxycarbonylethenyl)-2-biphenylcarboxylate

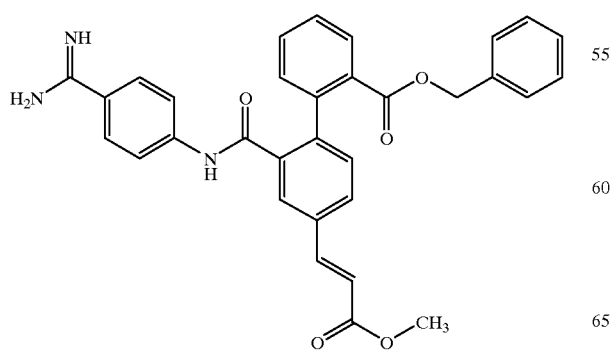

TLC: Rf 0.19 (Chloroform:Methanol=4:1); NMR (CDCl₃): δ 9.25 (1H, s), 8.82 (2H, br s), 8.56 (2H, br s), 7.81 (1H, s), 7.9–7.7 (1H, m), 7.69 (2H, d, J=7.8 Hz), 7.5–7.1 (13H, m), 7.07 (1H, d, J=8.0 Hz), 6.48 (1H, d, J=16.2 Hz), 5.11 (2H, s), 3.75 (3H, s).

EXAMPLE 8(6)

Benzyl 2'-(4-(N¹-t-butoxycarbonylamidino)phenylcarbamoyl)-3'-benzyloxy-2-biphenylcarboxylate

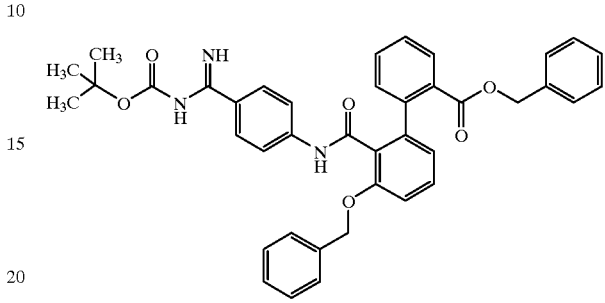

TLC: Rf 0.53 (Hexane:Ethyl acetate=1:1); NMR (CDCl₃) δ 9.80–9.00 (1H, broad), 8.37 (1H, s), 7.77 (1H, d, J=8.0 Hz), 7.62 (2H, d, J=9.0 Hz), 7.47–7.15 (15H, m), 7.09 (2H, d, J=9.0 Hz), 7.02 (1H, d, J=8.0 Hz), 6.72 (1H, d, J=8.0 Hz), 5.21 (1H, d, J=12 Hz), 5.20 (2H, s), 5.10 (1H, d, J=12 Hz), 1.53 (9H, s).

EXAMPLE 8(7)

Benzyl 2-(2-(4-amidinophenylcarbamoyl)benzothiophen-3-yl)benzoate

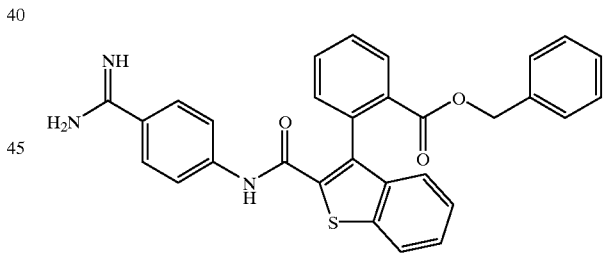

TLC: Rf 0.72 (Chloroform:Methanol:Acetic acid= 10:2:1); NMR (CD₃OD): δ 8.09 (1H, dd, J=8.0, 1.5 Hz), 7.93 (1H, d, J=8.0 Hz) 7.77–7.58 (4H, m), 7.56–7.41 (4H, m), 7.34 (1H, td, J=7.0 Hz, 1.5 Hz), 7.26–7.08 (3H, m), 6.97–6.90 (2H, m), 5.02 (1H, d, J=12 Hz), 4.95 (1H, d, J=12 Hz).

EXAMPLE 9–EXAMPLE 9(31)

The following compounds were obtained by the same procedure as a series of reaction of Reference Example 6→Example 2→Example 1, using a compound prepared in Reference Example 5 or a corresponding compound.

EXAMPLE 9

Methoxymethyl 2-(2,3-dihydro-2,2-dimethyl-6-(4-amidinophenylcarbamoyl) benzofuran-5-yl)benzoate

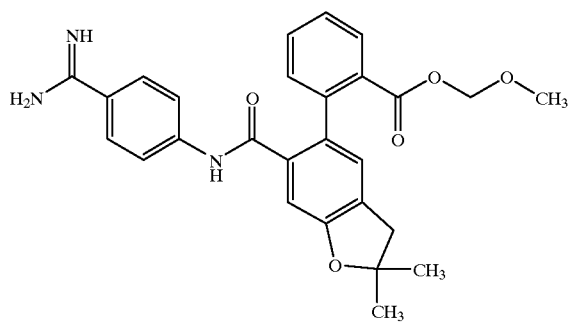

TLC: Rf 0.33 (Chloroform:Methanol:Acetic acid= 20:2:1); NMR (CD$_3$OD): δ 7.83 (1H, d, J=8 Hz), 7.69 (2H, d, J=9 Hz), 7.58 (2H, d, J=9 Hz), 7.51 (1H, t, J=8 Hz), 7.38 (1H, t, J=8 Hz), 7.31 (1H, d, J=8 Hz), 7.05 (1H, s), 6.95 (1H, s), 5.28 (2H, s), 3.30 (3H, s), 3.10 (2H, s), 1.50 (6H, s).

EXAMPLE 9(1)

Methoxymethyl 2'-(4-amidinophenylcarbamoyl)-6'-methyl-2-biphenylcarboxylate

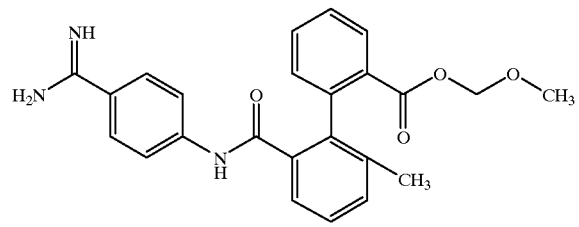

TLC: Rf 0.47 (Chloroform:Methanol:Acetic acid= 10:2:1).

EXAMPLE 9(2)

Methoxymethyl 2'-(4-amidinophenylcarbamoyl)-5'-methyl-2-biphenylcarboxylate

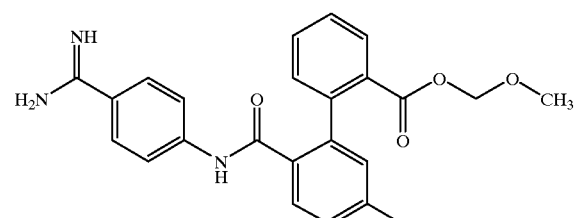

TLC: Rf 0.47 (Chloroform:Methanol:Acetic acid= 10:2:1).

EXAMPLE 9(3)

Methoxymethyl 2'-(4-amidinophenylcarbamoyl)-4'-isopropyl-2-biphenylcarboxylate

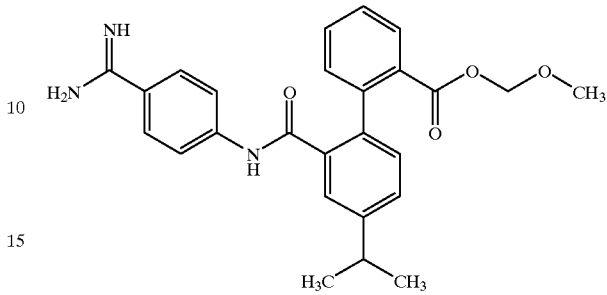

TLC: Rf 0.43 (Chloroform:Methanol:Acetic acid= 10:2:1).

EXAMPLE 9(4)

Methoxymethyl 2'-(4-amidinophenylcarbamoyl)-4'-t-butyl-2-biphenylcarboxylate

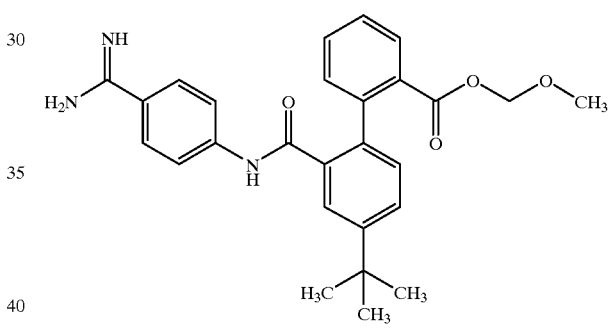

TLC: Rf 0.41 (Chloroform:Methanol:Acetic acid= 10:2:1).

EXAMPLE 9(5)

Methoxymethyl 2'-(4-amidinophenylcarbamoyl)-4'-ethyl-2-biphenylcarboxylate

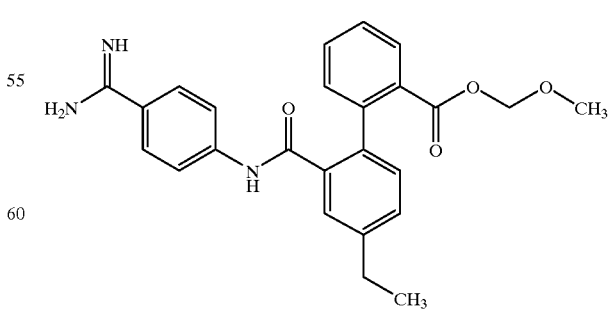

TLC: Rf 0.13 (Chloroform:Methanol:Water=9:1:0.1).

EXAMPLE 9(6)

Methoxymethyl 2'-(4-amidinophenylcarbamoyl)-4'-methoxy-2-biphenylcarboxylate

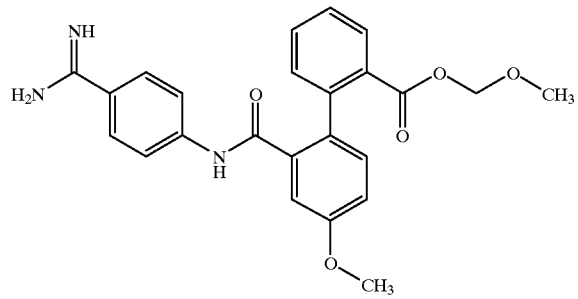

TLC: Rf 0.43 (Chloroform:Methanol:Acetic acid= 10:2:1).

EXAMPLE 9(7)

Methoxymethyl 2-(5,6,7,8-tetrahydro-3-(4-amidinophenylcarbamoyl) naphthalen-2-yl) benzoate

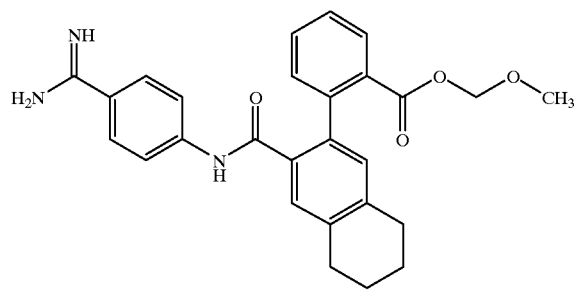

TLC: Rf 0.25 (Chloroform:Methanol:Acetic acid= 10:2:1).

EXAMPLE 9(8)

Methoxymethyl 2'-(4-amidinophenylcarbamoyl)-4'-cyano-2-biphenylcarboxylate

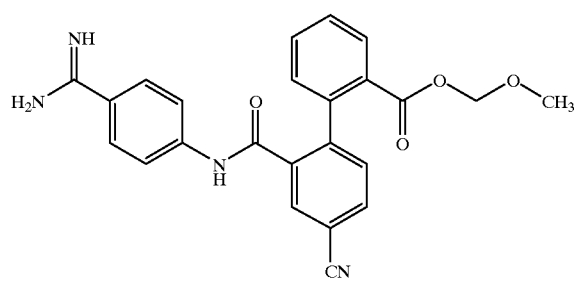

TLC: Rf 0.12 (Chloroform:Methanol:Acetic acid= 10:2:1).

EXAMPLE 9(9)

Methoxymethyl 2-(6-(4-amidinophenylcarbamoyl)indan-5-yl) benzoate

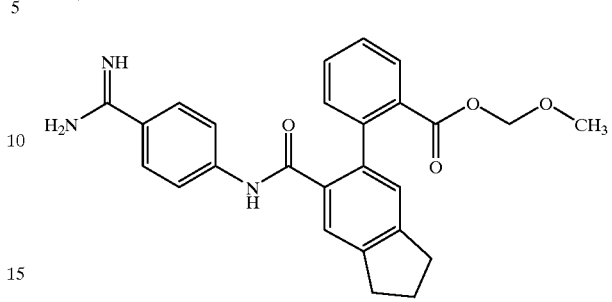

TLC: Rf 0.24 (Chloroform:Methanol:Acetic acid= 10:2:1).

EXAMPLE 9(10)

Methoxymethyl 2'-(4-amidinophenylcarbamoyl)-5'-methoxy-2-biphenylcarboxylate

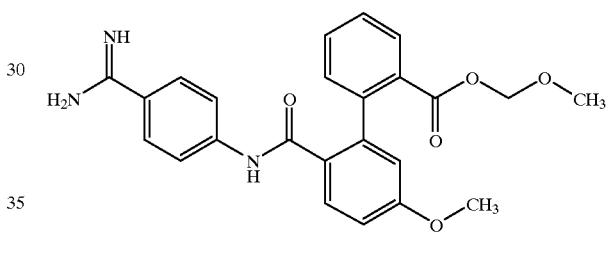

TLC: Rf 0.25 (Chloroform:Methanol:Water=8:2:0.2); NMR (CD$_3$OD): δ 7.89 (1H, dd, J=1.4,8.0 Hz), 7.69 (2H, d, J=9.0 Hz), 7.67 (1H, d, J=8.6 Hz), 7.60 (2H, d, J=9.0 Hz), 7.57 (1H, dt, J=1.4,8.0 Hz), 7.44 (1H, dt, J=1.4,8.0 Hz), 7.34 (1H, dd, J=1.4,8.0 Hz), 7.05 (1H, dd, J=2.6, 8.6 Hz), 6.80 (1H, d, J=2.6 Hz), 5.27 (2H, br.s), 3.87 (3H, s), 3.29 (3H, s).

EXAMPLE 9(11)

Methoxymethyl 2'-(4-amidinophenylcarbamoyl)-6'-methoxy-2-biphenylcarboxylate

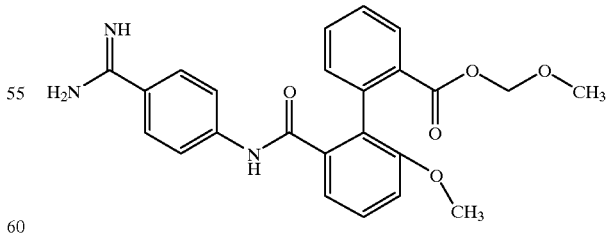

TLC: Rf 0.27 (Chloroform:Methanol:Water=8:2:0.2); NMR (CD$_3$OD): δ 7.91 (1H, dd, J=1.4,7.6 Hz), 7.68 (2H, d, J=9.2 Hz), 7.59 (2H, d, J=9.2 Hz), 7.51 (1H, dt, J=1.4,7.6 Hz), 7.47 (1H, d, J=7.6 Hz), 7.38 (1H, dt, J=1.4,7.6 Hz), 7.16–7.28 (3H, m), 5.32 (2H, s), 3.72 (3H, s), 3.35 (3H, s).

EXAMPLE 9(12)

Methoxymethyl 2'-(4-amidinophenylcarbamoyl)-5'-chloro-4-methyl-2-biphenylcarboxylate

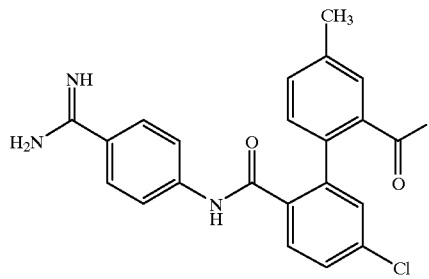

TLC: Rf 0.27 (Chloroform:Methanol=4:1); NMR (CDCl$_3$): δ 9.46 (1H, s), 8.70 (2H, s), 8.58 (2H, s), 7.72 (2H, d, J=8.4 Hz), 7.62 (2H, d, J=8.8 Hz), 7.44 (2H, d, J=8.4 Hz), 7.4–7.2 (2H, m), 7.12 (1H, s), 7.09 (1H, d, J=8.6 Hz), 5.27 (2H, d, J=3.6 Hz), 3.32 (3H, s), 2.30 (3H, s).

EXAMPLE 9(13)

Methoxymethyl 2'-(4-amidinophenylcarbamoyl)-4'-methoxy-4-methyl-2-biphenylcarboxylate

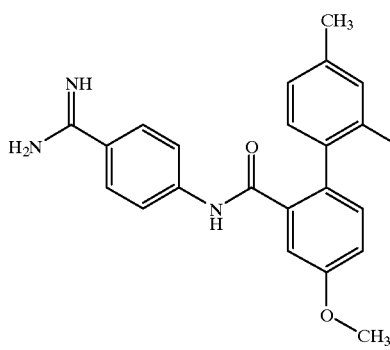

TLC: Rf 0.34 (Chloroform:Methanol=4:1); NMR (CDCl$_3$): δ 9.34 (1H, s), 8.76 (2H, brs), 8.55 (2H, brs), 7.75 (2H, d, J=8.4 Hz), 7.59 (1H, d, J=1.4 Hz), 7.43 (2H, d, J=8.4 Hz), 7.21 (1H, d, J=8.4 Hz), 7.20 (1H, dd, J=7.8, 1.4 Hz), 7.09 (1H, d, J=7.8 Hz), 7.02 (1H, d, J=8.4 Hz), 6.93 (1H, dd, J=8.4, 2.4 Hz), 5.29 (2H, d, J=6.2 Hz), 3.81 (3H, s), 3.33 (3H, s), 2.36 (3H, s).

EXAMPLE 9(14)

Methoxymethyl 2-(3-(4-amidinophenylcarbamoyl)-8-methoxynaphthalen-2-yl)benzoate

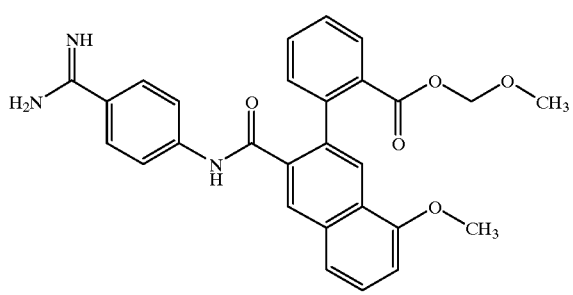

TLC: Rf 0.52 (Chloroform:Methanol:Water=10:3:0.2); NMR (d$_6$-DMSO): : δ 10.79 (1H, s), 9.4–8.9 (3H, br), 8.24 (1H, s), 7.97 (1H, s), 7.88 (1H, dd, J=1.0, 7.6 Hz), 7.79 (4H, likes), 7.7–7.3 (5H, m), 7.10 (1H, d, J=7.0 Hz), 5.08 (2H, br.s), 3.97 (3H, s), 3.05 (3H, s).

EXAMPLE 9(15)

Methoxymethyl 2'-(4-amidinophenylcarbamoyl)-4'-dimethylcarbamoyl-2-biphenylcarboxylate

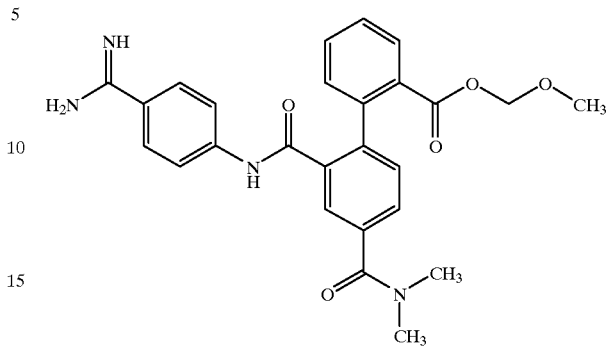

TLC: Rf 0.30 (Chloroform:Methanol:Water=8:2:0.2); NMR (CD$_3$OD): δ 7.96 (1H, dd, J=1.6,7.8 Hz), 7.56–7.74 (7H, m), 7.35–7.51 (3H, m), 5.25 (2H, s), 3.30 (3H, s), 3.16 (3H, br.s), 3.13 (3H, br.s).

EXAMPLE 9(16)

Bis(methoxymethyl) 2'-(4-amidinophenylcarbamoyl)-2,4'-biphenyldicarboxylate

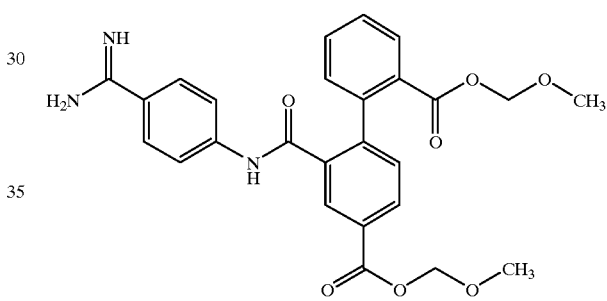

TLC: Rf 0.27 (Chloroform:Methanol:Water=8:2:0.2); NMR (CD$_3$OD): δ 8.33 (1H, d, J=1.8 Hz), 8.24 (1H, dd, J=1.8,7.8 Hz), 7.98 (1H, dd, J=1.4,7.8 Hz), 7.73 (2H, d, J=9.0 Hz), 7.67 (2H, d, J=9.0 Hz), 7.62 (1H, dt, J=1.4,7.8 Hz), 7.48 (1H, dt, J=1.4,7.8 Hz), 7.47 (1H, d, J=7.8 Hz), 7.37 (1H, dd, J=1.4,7.8 Hz), 5.53 (2H, s), 5.24 (2H, s), 3.57 (3H, s), 3.29 (3H, s).

EXAMPLE 9(17)

Methoxymethyl 2'-(4-amidinophenylcarbamoyl)-4'-methylcarbamoyl-2-biphenylcarboxylate

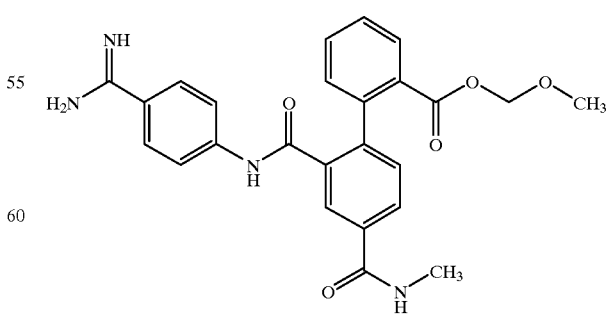

TLC: Rf 0.20 (Chloroform:Methanol:Water=8:2:0.2); NMR (CD$_3$OD): δ 8.15 (1H, d, J=1.8 Hz), 8.00 (1H, dd, J=1.4,8.0 Hz), 7.96 (1H, dd, J=1.4,8.0 Hz), 7.73 (2H, d, J=9.0 Hz), 7.67 (2H, d, J=9.0 Hz), 7.60 (1H, dt, J=1.4,8.0 Hz), 7.47 (1H, dt, J=1.4,8.0 Hz), 7.42 (1H, d, J=8.0 Hz), 7.36 (1H, dd, J=1.4,8.0 Hz), 5.23 (2H, s), 3.26 (3H, s), 2.98 (3H, s).

EXAMPLE 9(18)

Methoxymethyl 2'-(4-amidinophenylcarbamoyl)-4'-methylaminomethyl-2-biphenylcarboxylate

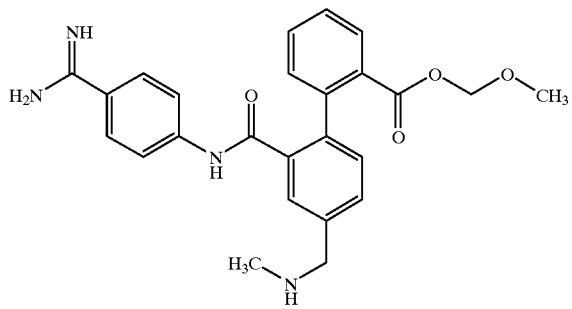

TLC: Rf 0.26 (Chloroform:Methanol:Water=8:2:0.2); NMR (CD$_3$OD): δ 7.90 (1H, dd, J=1.8,7.8 Hz), 7.53–7.73 (6H, m), 7.39–7.48 (2H, m), 7.33 (1H, dd, J=1.8,7.8 Hz), 7.29 (1H, d, J=7.8 Hz), 5.26 (2H, s), 4.56 (2H, s), 3.29 (3H, s), 2.92 (3H, s), 1.50 (9H, s).

EXAMPLE 9(19)

Methoxymethyl 2-(6-(4-amidinophenylcarbamoyl)-1,2-methylenedioxy benzen-5-yl)benzoate

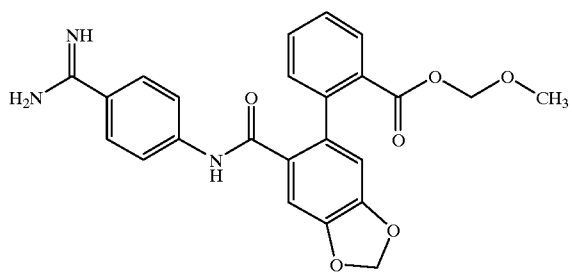

TLC: Rf 0.53 (Chloroform:Methanol:Acetic acid=10:2:1); NMR (CD$_3$OD): δ 7.86 (1H, dd, J=8.0 Hz, 1.5 Hz), 7.68 (2H, d, J=9.0 Hz), 7.56 (2H, d, J=9.0 Hz), 7.54 (1H, td, J=8.0 Hz, 1.5 Hz), 7.40 (1H, td, J=8.0 Hz, 1.5 Hz), 7.32 (1H, dd, J=8.0 Hz, 1.5 Hz), 7.15 (1H, s), 6.74 (1H, s), 6.09 (2H, s), 5.29 (2H, s), 3.36 (3H, s).

EXAMPLE 9(20)

Methoxymethyl 2'-(4-amidinophenylcarbamoyl)-4'-(2-methoxymethoxyethoxy)-2-biphenylcarboxylate

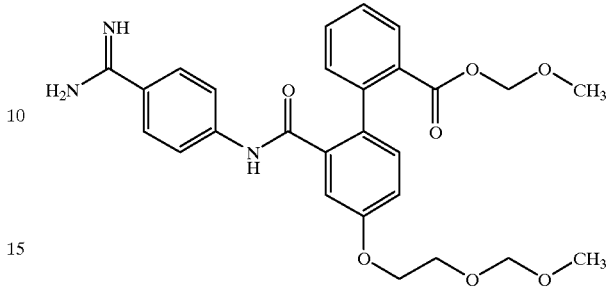

TLC: Rf 0.66 (Chloroform:Methanol:Water=10:2:0.1); NMR (d$_6$-DMSO): δ 10.51 (1H, s), 9.3–8.9 (3H, br.d), 7.9–7.6 (5H, m), 7.56 (1H, dt, J=1.6, 7.4 Hz), 7.42 (1H, dt, J=1.6, 7.4 Hz), 7.4–7.1 (4H, m), 5.11 (2H, br.s), 4.65 (2H, s), 4.24 (2H, t, J=5.0 Hz), 3.83 (2H, t, J=5.0 Hz), 3.29 (3H, s), 3.16 (3H, s).

EXAMPLE 9(21)

Methoxymethyl 2'-(4-amidinophenylcarbamoyl)-4'-fluoro-2-biphenylcarboxylate

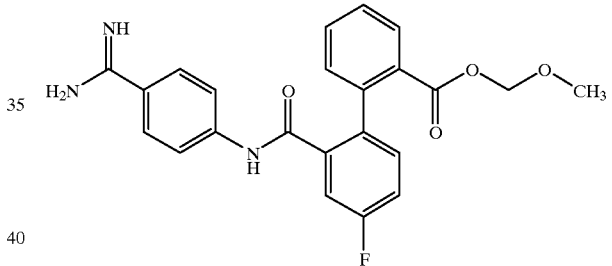

TLC: Rf 0.29 (Chloroform:Methanol:Water=8:2:0.2); NMR (CD$_3$OD): δ 7.92 (1H, dd, J=1.6,7.8 Hz), 7.71 (2H, d, J=9.2 Hz), 7.63 (2H, d, J=9.2 Hz), 7.56 (1H, m), 7.40–7.49 (2H, m), 7.30–7.37 (3H, m), 5.26 (2H, s), 3.31 (3H, s).

EXAMPLE 9(22)

Methoxymethyl 2-(3-(4-amidinophenylcarbamoyl)-8-methoxymethoxy naphthalen-2-yl)benzoate

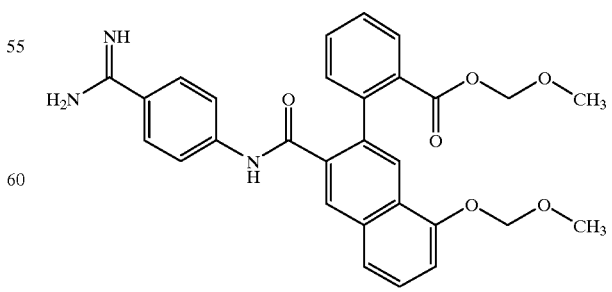

TLC: Rf 0.49 (Chloroform:Methanol:Water=10:3:0.2).

EXAMPLE 9(23)

Methoxymethyl 2'-(4-amidinophenylcarbamoyl)-4'-(2-methoxyethoxy)-2-biphenylcarboxylate

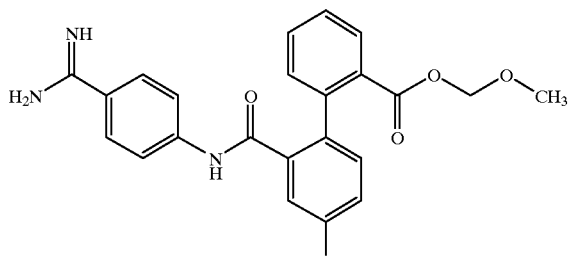

TLC: Rf 0.70 (Chloroform:Methanol:Acetic acid= 10:2:1); NMR (d$_6$-DMSO): δ 10.50 (1H, s), 9.3–8.9 (3H, br), 7.81 (1H, dd, J=1.4, 7.8 Hz), 7.74 (4H, like s), 7.56 (1H, dt, J=1.4, 7.4 Hz), 7.42 (1H, dt, J=1.4, 7.4 Hz), 7.35–7.10 (4H, m), 5.11 (2H, br.s), 4.21 (2H, t, J=4.4 Hz), 3.69 (2H, t, J=4.4 Hz), 3.32 (3H, s), 3.16 (3H, s).

EXAMPLE 9(24)

Methoxymethyl 2'-(4-amidinophenylcarbamoyl)-4'-trifluoromethoxy-2-biphenylcarboxylate

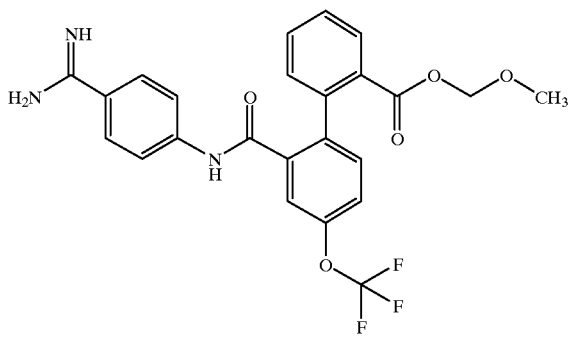

TLC: Rf 0.31 (Chloroform:Methanol:Water=8:2:0.1); NMR (CD$_3$OD): δ 7.95 (1H, dd, J=2.0, 7.4 Hz), 7.74–7.14 (10H, m), 5.25 (2H, s), 3.29 (3H, s).

EXAMPLE 9(25)

Methoxymethyl 2-(3-(4-amidinophenylcarbamoyl)-5-(2-methoxyethoxy) naphthalen-2-yl)benzoate

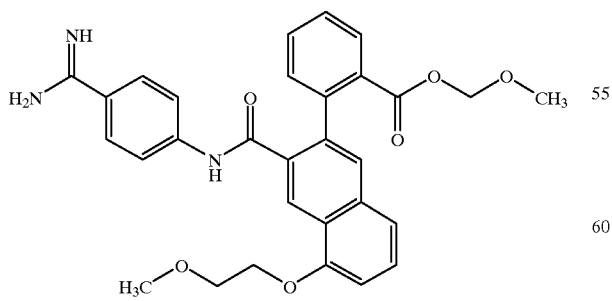

TLC: Rf 0.45 (Chloroform:Methanol:Water=10:3:0.2); NMR (d$_6$-DMSO): δ 10.77 (1H, s), 9.3–9.0 (3H, s), 8.40 (1H, s), 8.0–7.7 (6H, m), 7.7–7.4 (5H, m), 7.12 (1H, m), 5.09 (2H, br.s), 4.35 (2H, t, J=5.0 Hz), 3.83 (2H, t, J=5.0 Hz), 3.36 (3H, s), 3.06 (3H, s).

EXAMPLE 9(26)

Methoxymethyl 2-(3-(4-amidinophenylcarbamoyl)-5-methoxymethoxy naphthalen-2-yl)benzoate

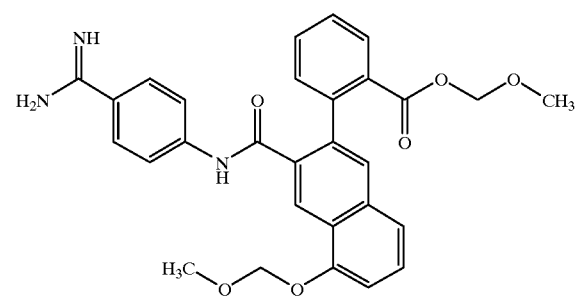

TLC: Rf 0.57 (Chloroform:Methanol:Water=10:3:0.2); NMR (d$_6$-DMSO): δ 10.81 (1H, s), 9.3–9.0 (3H, br), 8.44 (1H, s), 7.78 (4H, like s), 8.0–7.6 (3H, m), 7.7–7.4 (3H, m), 7.42 (1H, br.d, J=7.8 Hz), 7.22 (1H, br.d, J=6.4 Hz), 5.49 (2H, s), 5.09 (2H, br.s), 3.49 (3H, s), 3.05 (3H, s).

EXAMPLE 9(27)

Methoxymethyl 2'-(4-amidinophenylcarbamoyl)-4'-((methoxycarbonylmethyl) carbamoyl)-2-biphenylcarboxylate

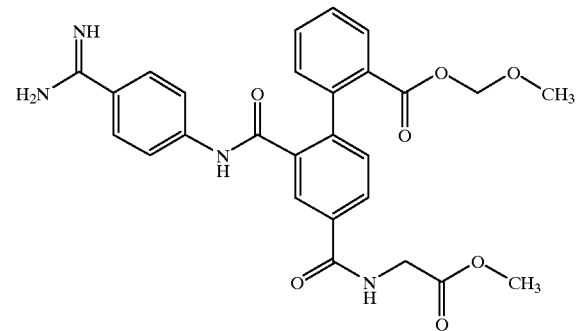

TLC: Rf 0.21 (Chloroform Methanol:Water=8:2:0.2); NMR (CD$_3$OD): δ 8.20 (1H, d, J=1.8 Hz), 8.06 (1H, dd, J=1.8,7.8 Hz), 7.97 (1H, dd, J=1.8,7.8 Hz), 7.72 (2H, d, J=9.2 Hz), 7.67 (2H, d, J=9.2 Hz), 7.61 (1H, dt, J=1.8,7.8 Hz), 7.48 (1H, dt, J=1.8,7.8 Hz), 7.44 (1H, d, J=7.8 Hz), 7.37 (1H, dd, J=1.8,7.8 Hz), 5.23 (2H, s), 4.18 (2H, s), 3.77 (3H, s), 3.27 (3H, s).

EXAMPLE 9(28)

Methoxymethyl 2'-(4-amidinophenylcarbamoyl)-4'-((1-methoxycarbonyl-2-phenylethyl)carbamoyl)-2-biphenylcarboxylate

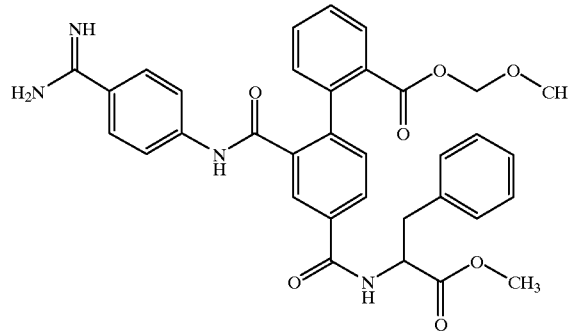

TLC: Rf 0.37 (Chloroform:Methanol:Water=8:2:0.2); NMR (CD$_3$OD): δ 8.06 (1H, d, J=1.6 Hz), 7.95 (1H, dd, J=1.6,7.6 Hz), 7.94 (1H, dd, J=1.6,7.6 Hz), 7.72 (2H, d, J=9.0 Hz), 7.66 (2H, d, J=9.0 Hz), 7.60 (1H, dt, J=1.6,7.6 Hz), 7.46 (1H, dt, J=1.6,7.6 Hz), 7.39 (1H, d, J=7.6 Hz), 7.35 (1H, dd, J=1.6,7.6 Hz), 7.20–7.29 (5H, m), 5.22 (2H, s), 4.92 (1H, m), 3.75 (3H, s), 3.23 (3H, s), 3.09–3.39 (2H, m).

EXAMPLE 9(29)

Methoxymethyl 2'-(4-amidinophenylcarbamoyl)-4'-ethoxycarbonylmethoxy-2-biphenylcarboxylate

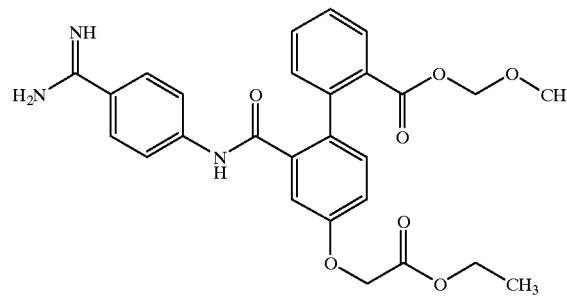

TLC: Rf 0.50 (Chloroform:Methanol:Water=10:3:0.2); NMR (d$_6$-DMSO): δ 10.51 (1H, s), 9.3–8.9 (3H, br), 7.9–7.6 (5H, m), 7.57 (1H, dt, J=1.4, 7.4 Hz), 7.42 (1H, dt, J=1.4, 7.4 Hz), 7.4–7.1 t3H, m), 7.12 (1H, dd, J=2.6, 8.4 Hz), 5.11 (2H, s), 4.91 (2H, s), 4.19 (2H, q, J=7.4 Hz), 3.14 (3H, s), 1.22 (3H, t, J=7.4 Hz).

EXAMPLE 9(30)

Methoxymethyl 2'-(4-amidinophenylcarbamoyl)-4'-((1-methoxycarbonyl-2-methylpropyl)carbamoyl)-2-biphenylcarboxylate

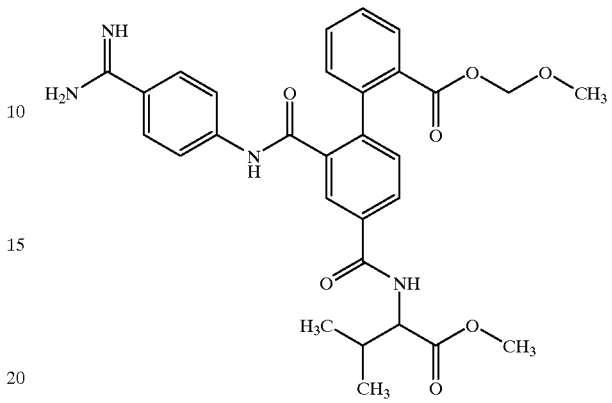

TLC: Rf 0.33 (Chloroform:Methanol:Water=8:2:0.2); NMR (CD$_3$OD): δ 8.18 (1H, d, J=1.8 Hz), 8.06 (1H, dd, J=1.8,7.8 Hz), 7.97 (1H, dd, J=1.8,7.8 Hz), 7.73 (2H, d, J=9.2 Hz), 7.67 (2H, d, J=9.2 Hz), 7.61 (1H, dt, J=1.8,7.8 Hz), 7.48 (1H, dt, J=1.8,7.8 Hz), 7.43 (1H, d, J=7.8 Hz), 7.36 (1H, dd, J=1.8,7.8 Hz), 5.25 (2H, s), 4.56 (1H, m), 3.78 (3H, s), 3.29 (3H, s), 2.30 (1H, m), 1.06 (3H, d, J=6.8 Hz), 1.04 (3H, d, J=6.8 Hz).

EXAMPLE 9(31)

A mixture of Methoxymethyl 2-(6-(4-amidinophenylcarbamoyl)-1-benzyloxymethylbenzoimidazol-5-yl)benzoate and Methoxymethyl 2-(5-(4-amidinophenylcarbomoyl-1-benzylmethylbenzoimidazol-6-yl)benzoate TLC: Rf 0.23 (Chloroform:Methanol:Water=8:2:0.2); NMR (CD$_3$OD): δ 8.46 (0.5H, s), 8.43 (0.5H, s), 8.03 (0.5H, s), 7.98 (0.5H, s), 7.93 (0.5H, dd, J=1.2,7.5 Hz), 7.90 (0.5H, dd, J=1.2,7.5 Hz), 7.71 (1H, d, J=9.0 Hz), 7.70 (1H, d, J=9.0 Hz), 7.66 (1H, d, J=9.0 Hz), 7.63 (1H, d, J=9.0 Hz), 7.59 (0.5H, dt, J=1.2,7.5 Hz), 7.58 (0.5H, dt, J=1.2,7.5 Hz), 7.57

(0.5H, s), 7.52 (0.5H, s), 7.46 (0.5H, dt, J=1.2,7.5 Hz), 7.44 (0.5H, dt, J=1.2,7.5 Hz), 7.41 (0.5H, dd, J=1.2,7.5 Hz), 7.40 (0.5H, dd, J=1.2,7.5 Hz), 7.30 (2.5H, s), 7.25 (2.5H, s), 5.85 (1H, s), 5.78 (1H, s), 5.24 (1H, br.s), 5.18 (1H, br.s), 4.60 (1H, s), 4.55 (1H, s), 3.22 (1.5H, s), 3.15 (1.5H, s).

EXAMPLE 10

2'-(4-amidinophenylcarbamoyl)-4'-((1-methoxycarbonyl-2-methylpropyl)carbamoyl)-2-biphenylcarboxylic acid methanesulfonate

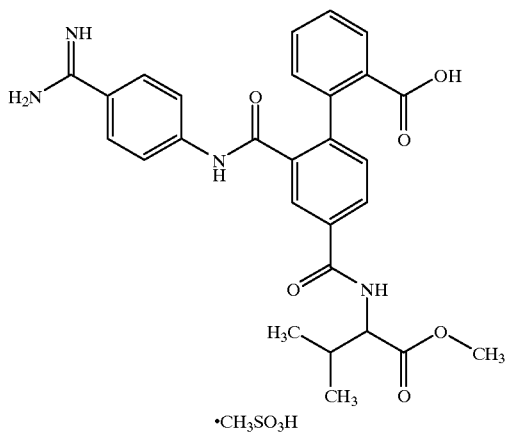

The present compound having the following physical data was obtained by the same procedure as a series of reaction of Example 4, using a compound prepared in Example 9(30).

TLC: Rf 0.42 (Chloroform:Methanol:Water=7:3:0.3); NMR (CD$_3$OD): δ 8.17 (1H, d, J=1.8 Hz), 8.02 (1H, dd, J=1.8,7.8 Hz), 7.92 (1H, dd, J=1.8,7.8 Hz), 7.71 (2H, d, J=9.2 Hz), 7.62 (2H, d, J=9.2 Hz), 7.54 (1H, dt, J=1.8,7.8 Hz), 7.44 (1H, dt, J=1.8,7.8 Hz), 7.36 (1H, d, J=7.8 Hz), 7.28 (1H, dd, J=1.8,7.8 Hz), 4.55 (1H, d, J=6.4 Hz), 3.77 (3H, s), 2.70 (3H, s), 2.29 (1H, m), 1.06 (3H, d, J=6.4 Hz), 1.04 (3H, d, J=6.4 Hz).

EXAMPLE 11

2'-(4-amidinophenylcarbamoyl)-4'-((1-carboxy-2-methylpropyl)carbamoyl)-2-biphenylcarboxylic acid methanesulfonate

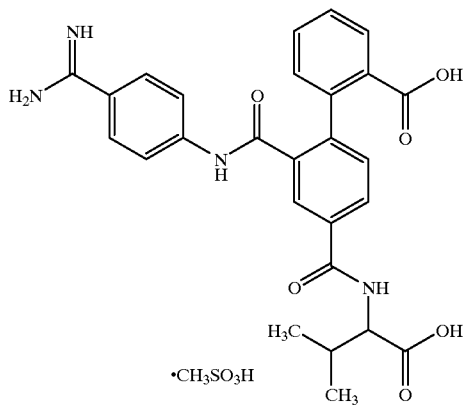

2N aqueous solution of sodium hydroxide (1.5 ml) was added to a solution of the compound prepared in Example 10 (710 mg) in methanol (10 ml). The mixture was stirred for 12 hours at room temperature. 2N hydrochloric acid was added to the reaction mixture, and the solution was concentrated. The residue was purified by column chromatography on silica gel (Chloroform:Methanol:Water= 7:3:0.3→Trifluoroacetic acid:dimethylformamide=1:99). 1N methanesulfonic acid (1.0 ml) was added to the purified compound to give the present compound (652 mg) having the following physical data.

TLC: Rf 0.11 (Chloroform:Methanol:Water=7:3:0.3); NMR (d$_6$-DMSO): δ 10.69 (1H, s), 9.26 (2H, s), 9.05 (2H, s), 8.67 (1H, d, J=8.2 Hz), 8.25 (1H, s), 8.05 (1H, dd, J=1.8,8.0 Hz), 7.88 (1H, dd, J=1.8,8.0 Hz), 7.79 (2H, d, J=9.2 Hz), 7.75 (2H, d, J=9.2 Hz), 7.55 (1H, dt, J=1.8,8.0 Hz), 7.44 (1H, dt, J=1.8,8.0 Hz), 7.35 (1H, d, J=8.0 Hz), 7.25 (1H, dd, J=1.8,8.0 Hz), 4.36 (1H, m), 2.37 (3H, s), 2.25 (1H, m), 1.02 (3H, d, J=6.8 Hz), 1.00 (3H, d, J=6.8 Hz).

REFERENCE EXAMPLE 9

2'-methoxymethoxycarbonyl-4-acetoxy-2-biphenylcarboxylic acid

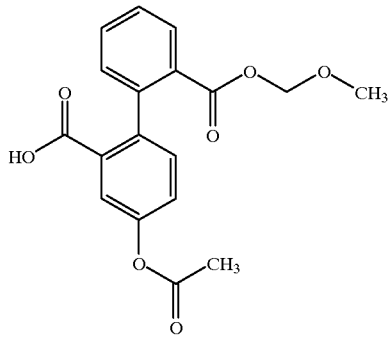

2'-methoxymethoxycarbonyl-4-hydroxy-2-biphenylcarboxylic acid (606 mg) which was prepared by the same procedure as a series of reaction of Reference Example 4→Reference Example 5→Reference Example 6→Example 2 (without a procedure of conversion to salt thereof), using benzyl 2-trifluoromethylsulfonyloxy-5-benzyloxybenzoate, was dissolved into acetic acid anhydrous (1 ml) and pyridine (2 ml). The solution was stirred for 12 hours at room temperature. Water (100 ml) was added to the reaction mixture, and the solution was extracted with ethyl acetate (2 times). The extract was washed with a saturated aqueous solution of ammonium chloride, a saturated aqueous solution of sodium chloride, dried over anhydrous magnesium sulfate and concentrated to give the title compound (700 mg) having the following physical data.

TLC: Rf 0.31 (Chloroform:Methanol:Water=9:1:0.1);

NMR (CDCl$_3$): δ 8.06 (1H, dd, J=1.4,7.6 Hz), 7.82 (1H, d, J=2.8 Hz), 7.55 (1H, dt, J=1.4,7.6 Hz), 7.44 (1H, dt, J=1.4,7.6 Hz), 7.19–7.36 (3H, m), 5.24 (1H, d, J=6.2 Hz), 5.14 (1H, d, J=6.2 Hz), 3.22 (3H, s), 2.33 (3H, s).

REFERENCE EXAMPLE 9(1)

2'-methoxymethoxycarbonyl-5-acetoxy-2-biphenylcarboxylic acid

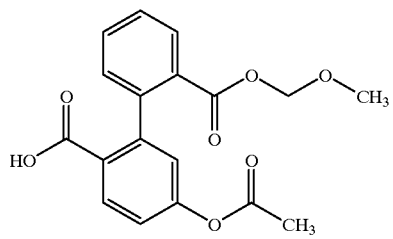

The title compound having the following physical data was prepared by the same procedure as a series of reaction of Reference Example 9, using 2'-methoxymethoxycarbonyl-5-hydroxy-2-biphenylcarboxylic acid which was prepared by the same procedure as a series of reaction of Reference Example 4→Reference Example 5→Reference Example 4→Example 2 (without a procedure of conversion to salt thereof), using benzyl 2-trifluoromethylsulfonyloxy-4-benzyloxybenzoate.

TLC: Rf 0.38 (Chloroform:Methanol=20:1); NMR (CDCl$_3$): δ 8.11 (1H, d, J=8.8 Hz), 8.06 (1H, dd, J=1.4,7.6 Hz), 7.54 (1H, dt, J=1.4,7.6 Hz), 7.44 (1H, dt, J=1.4,7.6 Hz), 7.23 (1H, dd, J=1.4,7.6 Hz), 7.19 (1H, dd, J=2.2,8.8 Hz), 6.98 (1H, d, J=2.2 Hz), 5.22 (1H, d, J=6.0 Hz), 5.18 (1H, d, J=6.0 Hz), 3.24 (3H, s), 2.29 (3H, s).

REFERENCE EXAMPLE 10

Methyl 2'-benzyloxycarbonyl-4'-nitro-2-biphenylcarboxylate

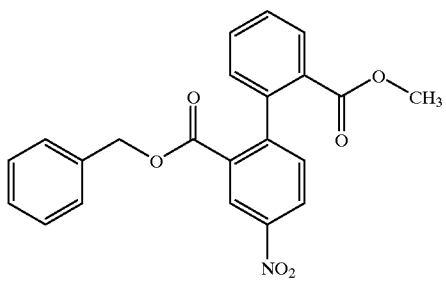

To a solution of 2'-benzyloxycarbonyl-4'-nitro-2-biphenylcarboxylic acid (2.8 g) which was prepared by the same procedure as a series of reaction of Reference Example 4→Reference Example 5, using Benzyl 2-trifluoromethylsulfonyloxy-5-nitrobenzoate, in ether-ethyl acetate (1:1, 40 ml), diazomethane (30 ml) was added. Acetic acid was added to the reaction mixture, and the solution was concentrated. The residue was purified by column chromatography on silica gel (hexane:ethyl acetate= 5:2) to give the title compound (2.57 g) having the following physical data.

TLC: Rf 0.51 (Hexane:Ethyl acetate=5:2); NMR (CDCl$_3$): δ 8.89 (1H, d, J=2.2 Hz), 8.37 (1H, dd, J=2.2,8.4 Hz), 8.00 (1H, dd, J=1.6,7.6 Hz), 7.53 (1H, dt, J=1.6,7.6 Hz), 7.43 (1H, dt, J=1.6,7.6 Hz), 7.37 (1H, d, J=8.4 Hz), 7.27–7.32 (3H, m), 7.12–7.16 (3H, m), 5.09 (2H, s), 3.60 (3H, s).

REFERENCE EXAMPLE 11

2'-benzyloxycarbonyl-4'-amino-2-biphenylcarboxylic acid

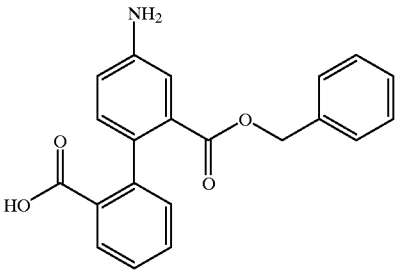

To a solution of 2'-benzyloxycarbonyl-4'-nitro-2-biphenylcarboxylic acid (2.08 g) which was prepared by the same procedure as a series of reaction of Reference Example 4→Reference Example 5, using Benzyl 2-trifluoromethylsulfonyloxy-5-nitrobenzoate, in concentration hydrochloric acid-ethanol (5:3, 8 ml), a solution of Tin (II) chloride dihydrate (3.7 g) in ethanol (5 ml) was added. The mixture was stirred for 1 hour at room temperature. 2N aqueous solution of sodium hydroxide was added to the reaction solution, the solution was extracted with ethyl acetate (2 times). The extract was washed with water, dried over anhydrous magnesium sulfate and concentrated. The residue was purified by column chromatography on silica gel (Chloroform:Methanol:Water=9:1:0.1→8:2:0.2) to give the title compound (1.07 g) having the following physical data.

TLC: Rf 0.57 (Chloroform:Methanol:Water=8:2:0.2); NMR (CDCl$_3$): δ 7.86 (1H, dd, J=1.8,7.8 Hz), 7.42 (1H, dt, J=1.8,7.8 Hz), 7.31 (1H, dt, J=1.8,7.8 Hz), 7.24–7.27 (4H, m), 7.06–7.15 (3H, m), 6.95 (1H, d, J=7.8 Hz), 6.77 (1H, dd, J=1.8,7.8 Hz), 5.03 (2H, s).

REFERENCE EXAMPLE 12

2'-methoxycarbonyl-4-amino-2-biphenylcarboxylic acid

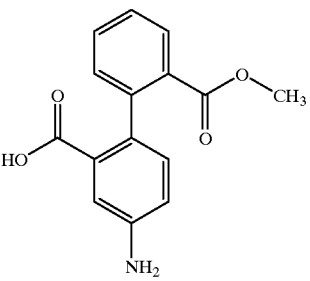

To a mixed solution of the compound prepared in Reference Example 10 (2.5 g) in methanol-ethyl acetate (4:1, 10 ml), 20% palladium hydroxide on carbon (160 mg) was added. The mixture was stirred for 1 hour under an atmosphere of hydrogen gas. The reaction mixture was filtered through celite (registered trade mark). The filtrate was concentrated. The residue was purified by column chromatography on silica gel (Chloroform:Methanol:Water= 9:1:0.1→7:3:0.3) to give the title compound (1.15 g) having the following physical data.

TLC: Rf 0.24 (Chloroform:Methanol:Water=9:1:0.1); NMR (CD$_3$OD): δ 7.82 (1H, dd, J=1.4,7.6 Hz), 7.49 (1H, dt, J=1.4,7.6 Hz), 7.34 (1H, dt, J=1.4,7.6 Hz), 7.27 (1H, d, J=2.0 Hz), 7.23 (1H, dd, J=1.4,7.6 Hz), 6.89 (1H, d, J=8.0 Hz), 6.85 (1H, dd, J=2.0,8.0 Hz), 3.59 (3H, s).

REFERENCE EXAMPLE 13

2'-methoxycarbonyl-4-bromo-2-biphenylcarboxylic acid

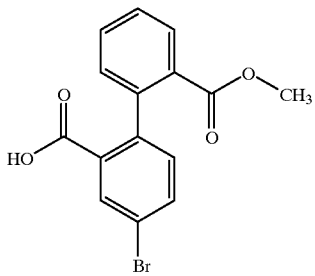

To a solution of the compound prepared in Reference Example 12 (550 mg) in 48% aqueous solution of hydrogen bromide (2.7 ml), an aqueous solution (1.4 ml) of sodium nitrate (140 mg) was added at 5–10° C. Copper bromide (160 mg) was added to the reaction mixture, and the mixture was stirred for 30 minutes at 50° C. Water (50 ml) was added to the reaction mixture, and the solution was extracted with ethyl acetate. The extract was washed with water, dried over anhydrous magnesium sulfate and concentrated. The residue was washed with hexane to give the title compound (585 mg) having the following physical data.

TLC: Rf 0.63 (Chloroform:Methanol:Water=9:1:0.1); NMR (CDCl$_3$): δ 8.16 (1H, d, J=2.2 Hz), 8.00 (1H, dd, J=1.8,7.4 Hz), 7.67 (1H, dd, J=2.2,8.4 Hz), 7.54 (1H, dt, J=1.8,7.4 Hz), 7.44 (1H, dt, J=1.8,7.4 Hz), 7.16 (1H, dd, J=1.8,7.4 Hz), 7.05 (1H, d, J=8.4 Hz), 3.67 (3H, s).

REFERENCE EXAMPLE 13(1)

2'-benzyloxycarbonyl-4'-bromo-2-biphenylcarboxylic acid

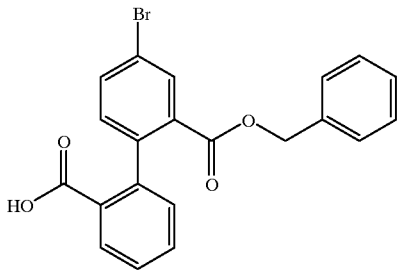

The title compound was obtained by the same procedure as a series of reaction of Reference Example 13, using the compound prepared in Reference Example 11.

TLC: Rf 0.48 (Chloroform:Methanol:Water=9:1:0.1); NMR (CDCl$_3$): δ 8.15 (1H, d, J=2.2 Hz), 7.96 (1H, dd, J=1.6,7.8 Hz), 7.61 (1H, dd, J=2.2,8.2 Hz), 7.48 (1H, dt, J=1.6, 7.8 Hz), 7.36 (1H, dt, J=1.6,7.8 Hz), 7.24–7.27 (3H, m), 7.08–7.13 (3H, m), 7.03 (1H, d, J=8.2 Hz), 5.02 (2H, s).

EXAMPLE 12–EXAMPLE 12(3)

The following compounds were obtained by the same procedure as a series of reaction of Example 1, using the compound prepared in Reference Example 9–Reference Example 9(1), and Reference Example 13–Reference Example 13(1).

EXAMPLE 12

Methoxymethyl 2'-(4-amidinophenylcarbamoyl)-4'-acetoxy-2-biphenyl carboxylate

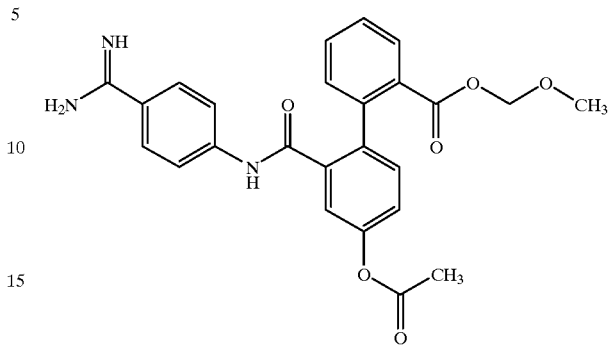

TLC: Rf 0.40 (Chloroform:Methanol:Water=8:2:0.2); NMR (CD$_3$OD): δ 7.92 (1H, dd, J=1.4,7.6 Hz), 7.71 (2H, d, J=9.0 Hz), 7.62 (2H, d, J=9.0 Hz), 7.57 (1H, dd, J=1.4,7.6 Hz), 7.34–7.49 (5H, m), 5.24 (2H, br.s), 3.26 (3H, s), 2.33 (3H, s).

EXAMPLE 12(1)

Methoxymethyl 2'-(4-amidinophenylcarbamoyl)-5'-acetoxy-2-biphenyl carboxylate

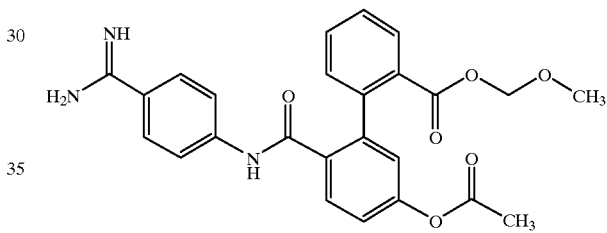

TLC: Rf 0.25 (Chloroform:Methanol:Water=8:2:0.2); NMR (CD$_3$OD): δ 7.92 (1H, dd, J=1.4,7.8 Hz), 7.61–7.74 (5H, m), 7.57 (1H, dt, J=1.4,7.8 Hz), 7.45 (1H, dt, J=1.4,7.8 Hz), 7.35 (1H, dd, J=1.4,7.8 Hz), 7.27 (1H, dd, J=2.4,8.4 Hz), 7.08 (1H, d, J=2.4 Hz), 5.25 (2H, s), 3.27 (3H, s), 2.30 (3H, s).

EXAMPLE 12(2)

Methoxymethyl 2'-(4-amidinophenylcarbamoyl)-4'-bromo-2-biphenyl)carboxylate

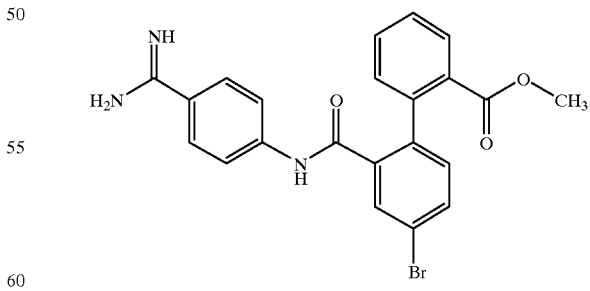

TLC: Rf 0.25 (Chloroform:Methanol:Water=8:2:0.2); NMR (CD$_3$OD): δ 7.85 (1H, dd, J=1.4,7.8 Hz), 7.82 (1H, d, J=2.2 Hz), 7.72 (1H, dd, J=2.2,8.4 Hz), 7.71 (2H, d, J=9.2 Hz), 7.63 (2H, d, J=9.2 Hz), 7.56 (1H, dt, J=1.4,7.8 Hz), 7.43 (1H, dt, J=1.4,7.8 Hz), 7.34 (1H, dd, J=1.4,7.8 Hz), 7.21 (1H, d, J=8.4 Hz),3.69 (3H, s).

EXAMPLE 12(3)

Benzyl 2'-(4-amidinophenylcarbamoyl)-4-bromo-2-biphenylcarboxylate

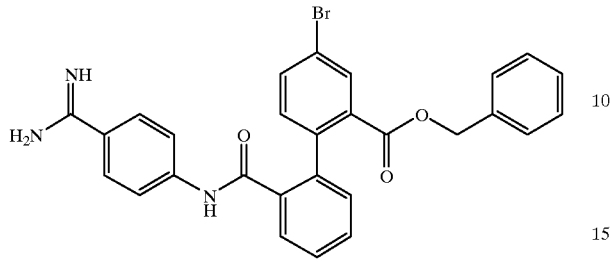

TLC: Rf 0.25 (Chloroform:Methanol:Water=8:2:0.2); NMR (CD$_3$OD): δ 7.97 (1H, d, J=2.2 Hz), 7.60–7.73 (6H, m), 7.48–7.53 (2H, m), 7.22–7.29 (5H, m), 7.10–7.15 (2H, m), 5.10 (2H, s).

EXAMPLE 13

Methyl 2'-(4-(N$^2$-t-butoxycarbonylamidino)phenylcarbamoyl)-3'-methoxy-2-biphenylcarboxylate

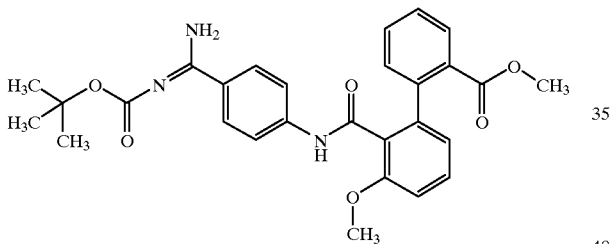

The present compound having the following physical data was obtained by the same procedure as a series of reaction of Reference Example 4→Reference Example 5→Reference Example 10→Reference Example 12→Reference Example 3, using benzyl 2-trifluoromethylsulfonyloxy-6-methoxybenzoate.

TLC: Rf 0.63 (Chloroform:Methanol:Water=9:1:0.1); NMR (CDCl$_3$): δ 8.81 (1H, s), 7.67–7.75 (1H, m), 7.68 (2H, d, J=8.6 Hz), 7.28–7.46 (4H, m), 7.33 (2H, d, J=8.6 Hz), 6.99 (1H, d, J=8.4 Hz), 6.69 (1H, d, J=7.6 Hz), 3.92 (3H, s), 3.84 (3H, s), 1.53 (9H, s).

EXAMPLE 14–EXAMPLE 14(2)

The following compounds having the following physical data were obtained by the same procedure as a series of reaction of Reference Example 4→Reference Example 5→Reference Example 7→Reference Example 8→Reference Example 5→Reference Example 3 (using a corresponding derivative instead of 2,2-dimethylpropylamine) →Example 2→Example 1, using methyl 5-(1,3-dioxoran-2-yl)-2-trifluoromethylsulfonyloxybenzoate.

EXAMPLE 14

Methyl 2'-(4-amidinophenylcarbamoyl)-4-((1-dimethylaminomethyl-2-methylpropyl)carbamoyl)-2-biphenylcarboxylate

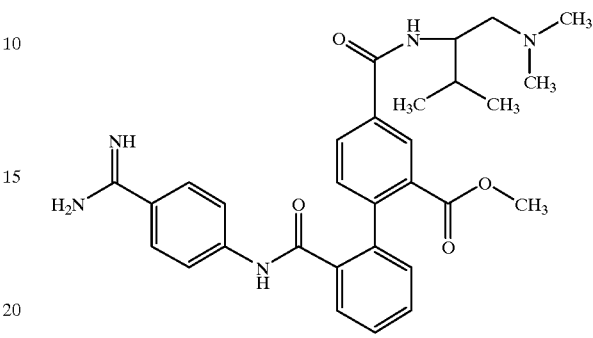

TLC: Rf 0.28 (Chloroform:Methanol:Acetic acid=10:2:1); NMR (d$_6$-DMSO): δ 10.72 (1H, s), 9.35–9.1 (3H, br), 8.73 (1H, d, J=9.4 Hz), 8.29 (1H, s), 8.19 (1H, d, J=7.8 Hz), 7.78 (4H, like s), 7.71 (1H, d, J=7.8 Hz), 7.7–7.5 (2H, m), 7.42 (1H, d, J=7.8 Hz), 7.29 (1H, d, J=7.8 Hz), 4.21 (1H, br), 3.54 (3H, s), 3.6–3.2 (2H, br), 2.78 (3H, s), 2.77 (3H, s), 1.84 (1H, m), 0.92 (3H, d, J=7.4 Hz), 0.88 (3H, d, J=7.4 Hz).

EXAMPLE 14(1)

Methyl 2'-(4-amidinophenylcarbamoyl)-4-((1-(pyrrolidin-1-ylmethyl)-2-methylpropyl)carbamoyl)-2-biphenylcarboxylate

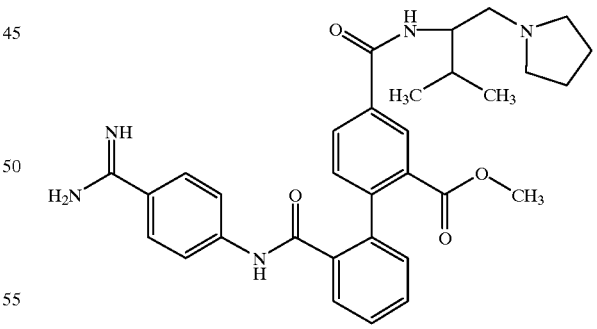

TLC: Rf 0.28 (Chloroform:Methanol:Acetic acid=10:2:1); NMR (d$_6$-DMSO): δ 10.73 (1H, s), 9.4–9.1 (3H, br), 8.73 (1H, d, J=7.4 Hz), 8.30 (1H, d, J=2.0 Hz), 8.20 (1H, dd, J=2.0, 8.0 Hz), 7.9–7.6 (5H, m), 7.7–7.5 (2H, m), 7.41 (1H, d, J=8.0 Hz), 7.29 (1H, dd, J=2.0, 8.0 Hz), 4.17 (1H, br), 3.54 (3H, s), 3.6–3.3 (4H, br), 3.2–3.0 (2H, br), 2.0–1.7 (5H, m), 0.92 (3H, d, J=8.0 Hz), 0.88 (3H, d, J=8.0 Hz).

EXAMPLE 14(2)

Methyl 2'-(4-amidinophenylcarbamoyl)-4-((1-hydroxymethyl-2-methylpropyl)carbamoyl)-2-biphenylcarboxylate

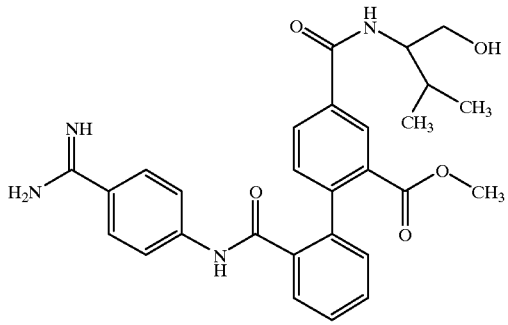

TLC: Rf 0.49 (Chloroform:Methanol:Acetic acid= 10:2:1); NMR (d$_6$-DMSO): δ 10.62 (1H, br.s), 9.11 (3H, s), 8.25 (1H, s), 8.21 (1H, br), 8.06 (1H, dd, J=1.5, 7.8 Hz), 7.75 (4H, like s), 7.69 (1H, br.d, J=7.2 Hz), 7.60 (1H, dt, J=1.5, 7.2 Hz), 7.54 (1H, dt, J=1.5, 7.2 Hz), 7.40 (1H, d, J=7.8 Hz), 7.31 (1H, br.d, J=7.2 Hz), 4.60 (1H, br), 4.09 (1H, br), 3.81 (1H, m), 3.54 (3H, s), 3.51 (1H, m), 1.91 (1H, like sextet, J=6.6 Hz), 0.90 (3H, d, J=7.0 Hz), 0.87 (3H, d, J=7.0 Hz).

REFERENCE EXAMPLE 14

Methyl 2-(6-benzyloxycarbonylbenzofuranr-5-yl)benzoate

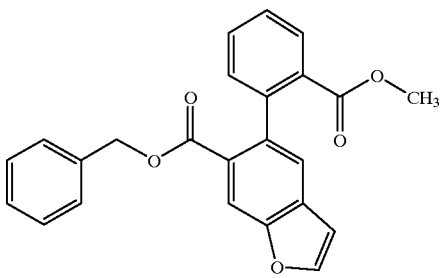

To a solution of 2-(6-benzyloxycarbonylbenzofuran-5-yl)benzoic acid (1.12 g) which was prepared by the same procedure as a series of reaction of Reference Example 4→Reference Example 5, using benzyl 5-trifluoromethylsulfonyloxy-6-benzofurancarboxylate, in dimethylformamide (12 ml), methyl iodide (205 μl) and potassium carbonate (455 mg) was added. The mixture was stirred for 14 hours at room temperature. Water was added to the reaction mixture, and the solution was extracted with ethyl acetate. The extract was washed with water and a saturated aqueous solution of sodium chloride, dried over anhydrous sodium sulfate and concentrated to give the title compound (1.16 g) having the following physical data.

TLC: Rf 0.49 (Hexane:Ethyl acetate=8:2); NMR (CDCl$_3$): δ 8.24 (1H, d, J=1.0 Hz), 7.93 (1H, dd, J=8.0, 1.5 Hz), 7.77 (1H, d, J=2.0 Hz), 7.49 (1H, td, J=8.0, 1.5 Hz), 7.38 (1H, s), 7.37 (1H, td, J=8.0, 1.5 Hz), 7.32–7.14 (6H, m), 6.79 (1H, dd, J=2.0, 1.0 Hz), 5.09 (2H, s), 3.55 (3H, s).

REFERENCE EXAMPLE 14(1)

Methyl 2-(5-benzyloxycarbonylbenzofuran-6-yl)benzoate

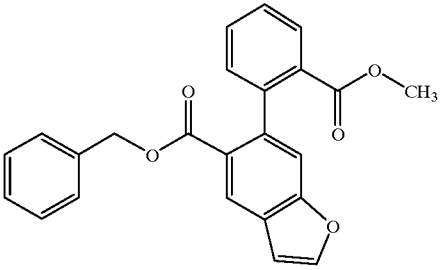

The title compound having the following physical data was obtained by the same procedure as a series of reaction of Reference Example 14, using 2-(5-benzyloxycarbonylbenzofuran-6-yl)benzoic acid.

TLC: Rf 0.50 (Hexane:Ethyl acetate=8:2); NMR (CDCl$_3$): δ 8.35 (1H, s), 7.94 (1H, dd, J=8.0, 1.5 Hz), 7.68 (1H, d, J=2.0 Hz), 7.50 (1H, td, J=8.0, 1.5 Hz), 7.37 (1H, td, J=8.0, 1.5 Hz), 7.33–7.13 (7H, m), 6.85 (1H, dd, J=2.0, 1.0 Hz), 5.07 (2H, s), 3.56 (3H, s).

EXAMPLE 15–EXAMPLE 15(1)

The following compounds were obtained by the same procedure as a series of reaction of Example 2→Example 1, using the compounds prepared in Reference Example 14→Reference Example 14(1).

EXAMPLE 15

Methyl 2-(6-(4-amidinophenylcarbamoyl)benzofuran-5-yl)benzoate

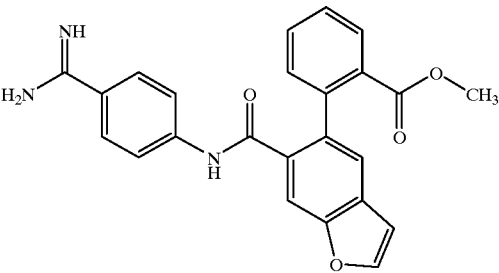

TLC: Rf 0.60 (Chloroform:Methanol:Acetic acid= 10:2:1); NMR (CD$_3$OD): δ 7.95(1H, d, J=2.0 Hz), 7.85(1H, d, J=1.0 Hz), 7.82 (1H, dd, J=8.0 Hz, 1.5 Hz), 7.70 (2H, d, J=9.0 Hz), 7.61 (2H, d, J=9.0 Hz), 7.54 (1H, td, J=8.0 Hz, 1.5 Hz), 7.50 (1H, s), 7.40 (1H, td, J=8.0 Hz, 1.5 Hz), 7.37 (1H, dd, J=8.0 Hz, 1.5 Hz), 6.94 (1H, dd, J=2.0 Hz, 1.0 Hz), 3.67 (3H, s).

EXAMPLE 15(1)

Methyl 2-(5-(4-amidinophenylcarbamoyl)benzofuran-6-yl)benzoate

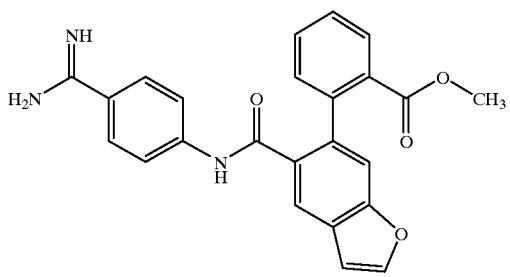

TLC: Rf 0.60 (Chloroform:Methanol:Acetic acid=10:2:1); NMR (CD$_3$OD): δ 7.96 (1H, s), 7.90 (1H, d, J=2.0 Hz), 7.83 (1H, dd, J=8.0 Hz, 1.5 Hz), 7.70 (2H, d, J=9.0 Hz), 7.61 (2H, d, J=9.0 Hz), 7.54 (1H, td, J=8.0 Hz, 1.5 Hz), 7.40 (1H, td, J=8.0 Hz, 1.5 Hz), 7.40 (1H, d, J=1.0 Hz), 7.38 (1H, dd, J=8.0 Hz, 1.5 Hz), 7.00 (1H, dd, J=2.0 Hz, 1.0 Hz), 3.67 (3H, s).

REFERENCE EXAMPLE 15

Benzyl 2'-hydroxymethyl-4-((2,2-dimethylpropyl)carbamoyl)-2-biphenylcarboxylate

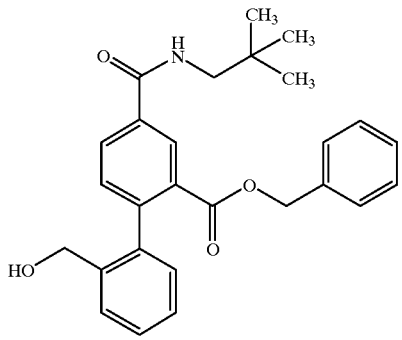

To a solution of the compound prepared in Reference Example 4 (1.65 g) in methanol (20 ml), sodium borohydride (174 mg) was added at −50° C. The mixture was stirred for 15 minutes at −50° C. Acetone was added to a reaction solution, and was diluted with ethyl acetate (80 ml). The solution was washed with a saturated aqueous solution of sodium chloride (40 ml, 2 times), dried over anhydrous sodium sulfate and concentrated to give the present compound (1.65 g) having the following physical data.

TLC: Rf 0.40 (Hexane:Ethyl acetate=1:1).

REFERENCE EXAMPLE 16

Benzyl 2'-bromomethyl-4-((2,2-dimethylpropyl)carbamoyl)-2-biphenylcarboxylate

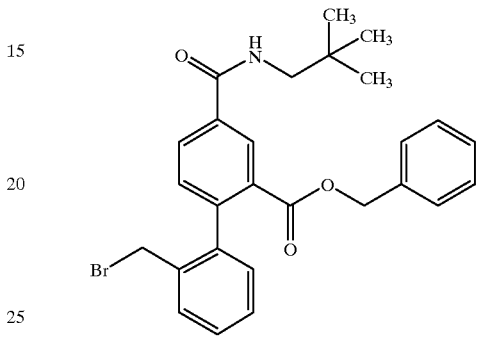

A solution of the compound prepared in Reference Example 15 (1.65 g) in methylene chloride (15 ml), carbon tetrabromide (2.55 g) and triphenylphosphine (1.51 g) were added at 0° C. The mixture was stirred for 15 minutes at room temperature. A saturated aqueous solution of sodium bicarbonate (50 ml) was added to the mixture, and the solution was extracted with ethyl acetate (50 ml, 2 times). The extract was washed with a saturated aqueous solution of sodium chloride (100 ml), dried over anhydrous sodium sulfate and concentrated. The residue was purified by column chromatography on silica gel (hexane:ethyl acetate=3:1) to give the title compound (1.45 g) having the following physical data.

TLC: Rf 0.56 (Hexane:Ethyl acetate=1:1).

EXAMPLE 16

Benzyl 2'-(4-(N$^2$-benzyloxycarbonylamidino)phenylaminomethyl)-4-((2,2-dimethylpropyl)carbamoyl)-2-biphenylcarboxylate

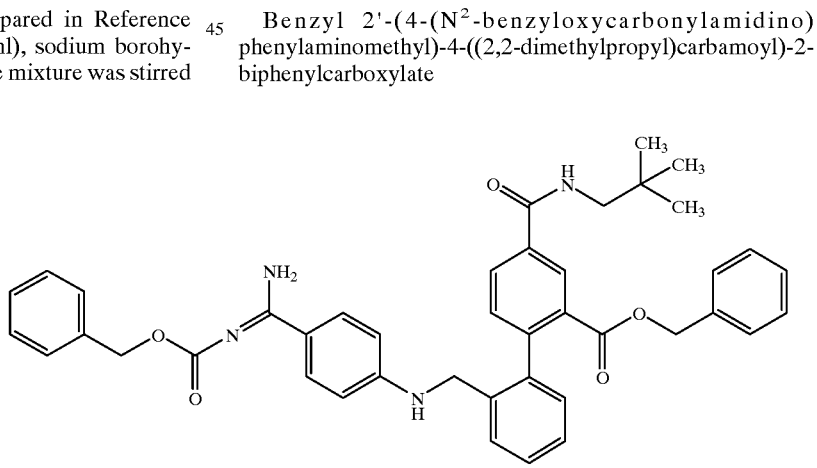

The compound prepared in Reference Example 16 (900 mg), potassium carbonate (301 mg), sodium iodide (273 mg) and 4-($N^2$-benzyloxycarbonyamidino)aniline (587 mg) were dissolved into dimethylformamide (20 ml). The mixture was stirred for 65 hours at room temperature. The reaction mixture was diluted with ethyl acetate (100 ml), and washed with a saturated aqueous solution of sodium chloride (150 ml; three times). The organic layer was dried over anhydrous sodium sulfate and concentrated. The residue was purified by column chromatography on silica gel (Chloroform:Ethyl acetate=3:1). The obtained solid was washed with ether to give the present compound (667 mg) having the following physical data.

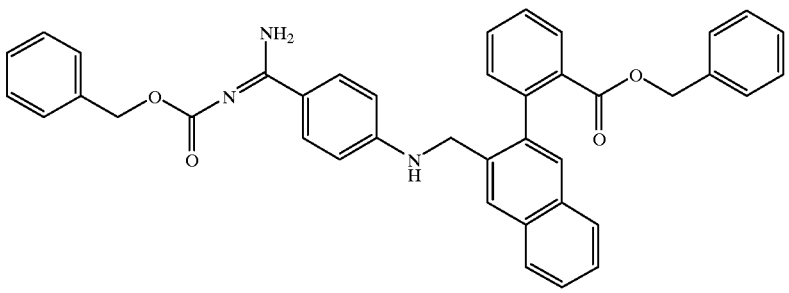

TLC: Rf 0.83 (Chloroform:Methanol=10:1); NMR ($d_6$-DMSO): δ 9.4–8.4 (2H, br), 8.57 (1H, br), 8.37 (1H, d, J=1.8 Hz), 8.09 (1H, dd, J=1.8, 8.0 Hz), 7.72 (2H, d, J=9.0 Hz), 7.49 (1H, d, J=8.0 Hz), 7.4–7.2 (11H, m), 7.2–7.1 (2H, m), 7.05 (1H, d, J=8.0 Hz), 6.57 (1H, br), 6.41 (2H, d, J=9.0 Hz), 5.12 (2H, s), 5.05 (2H, s), 3.98 (2H, br.s), 3.12 (2H, d, J=6.6 Hz), 0.90 (9H, s).

EXAMPLE 17–EXAMPLE 17(10)

The following compounds were obtained by the same procedure as a series of reaction of Reference Example 15→Reference Example 16→Example 16, using a corresponding derivatives instead of the starting compound in Reference Example 15.

EXAMPLE 17

Benzyl 2'-(4-($N^2$-benzyloxycarbonylamidino) phenylaminomethyl)-2-biphenylcarboxylate

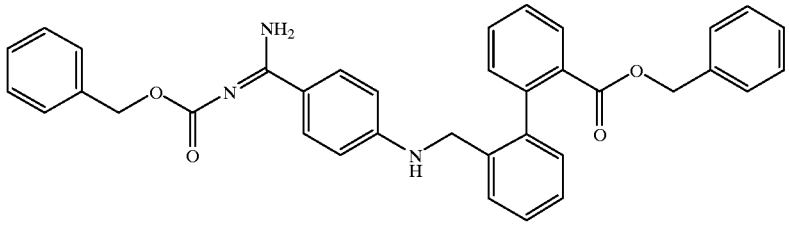

TLC Rf 0.68 (Chloroform:Ethyl acetate=8:2); NMR (CDCl$_3$): δ 9.7–9.2 (1H, broad), 7.95 (1H, dd, J=8.0 Hz, 1.5 Hz), 7.62–7.05 (19H, m), 6.25 (2H, d, J=9.0 Hz), 5.19 (2H, s), 5.13 (1H, d, J=12 Hz), 5.03 (1H, d, J=12 Hz), 4.37 (1H, t, J=5.0 Hz), 4.04 (2H, d, J=5.0 Hz).

EXAMPLE 17(1)

Benzyl 2-(3-(4-($N^2$-benzyloxycarbonylamidino) phenylaminomethyl) naphthalen-2-yl)benzoate TLC: Rf 0.18 (Toluene:Ethyl acetate=6:1); NMR ($d_6$-DMSO): δ 9.4–8.4 (2H, br), 8.0–6.8 (23H, m), 6.46 (2H, d, J=8.8 Hz), 5.12 (1H, d, J=12.8 Hz), 5.05 (2H, s), 5.03 (1H, d, J=12.8 Hz), 4.11 (2H, d, J=4.8 Hz).

EXAMPLE 17(2)

Benzyl 2'-(4-(N²-benzyloxycarbonylamidino)phenylaminomethyl)-4'-methoxy-2-biphenylcarboxylate

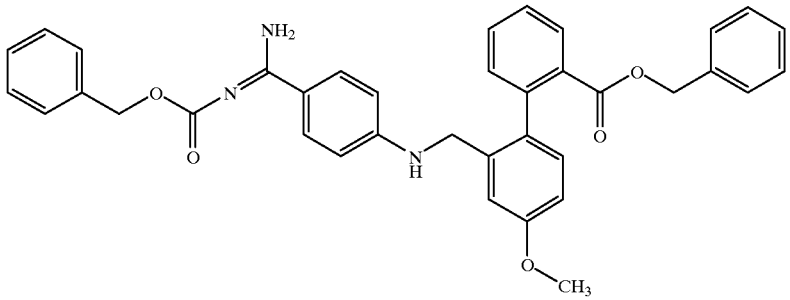

TLC:Rf 0.56 (Chloroform:Ethyl acetate=8:2); NMR (CDCl$_3$): δ 9.8–9.2 (1H, broad), 7.92 (1H, dd, J=8.0 Hz, 1.5 Hz), 7.60 (2H, d, J=9.0 Hz), 7.52–7.10 (13H, m), 7.01 (1H, d, J=8.0 Hz), 6.90 (1H, d, J=2.5 Hz), 6.81 (1H, dd, J=8.0 Hz, 2.5 Hz), 6.27 (2H, d, J=9.0 Hz), 5.19 (2H, s), 5.13 (1H, d, J=12 Hz), 5.06 (1H, d, J=12 Hz), 4.38 (1H, brt, J=7.0 Hz), 4.00 (2H, d, J=7.0 Hz), 3.81 (3H, s).

EXAMPLE 17(3)

Benzyl 2-(3-(4-(N²-benzyloxycarbonylamidino)phenylaminomethyl) naphthalen-2-yl)-5-((2-methylpropyl)carbamoyl)benzoate

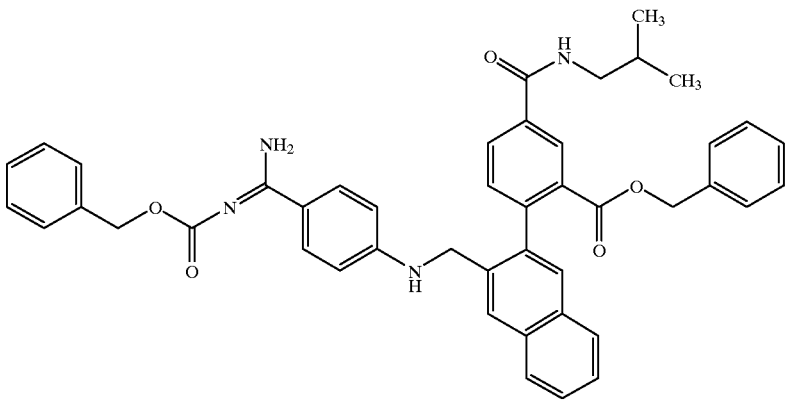

TLC: Rf 0.41 (Hexane:Ethyl acetate=2:3); NMR (CDCl$_3$): δ 8.22 (1H, d, J=2.0 Hz), 7.74–7.90 (4H, m), 7.42–7.58 (8H, m), 7.31–7.36 (3H, m), 7.08–7.23 (3H, m), 6.89–6.92 (2H, m), 6.21–6.25 (3H, m), 5.19 (2H, s), 5.05 (1H, d, J=12.0 Hz), 5.00 (1H, d, J=12.0 Hz), 4.31 (1H, br.t, J=5.2 Hz), 4.19 (2H, br.d, J=5.2 Hz), 3.28 (2H, t, J=6.6 Hz), 1.90 (1H, m), 0.97 (6H, d, J=6.6 Hz).

EXAMPLE 17(4)

Benzyl 2'-(4-(N²-benzyloxycarbonylamidino)phenylaminomethyl)-4'-methoxy-4-((2-methylpropyl)carbamoyl)-2-biphenylcarboxylate TLC: Rf 0.37(Hexane:Ethyl acetate=2:3); NMR (CDCl$_3$): δ 8.21 (1H, d, J=2.0 Hz), 7.84 (1H, dd, J=2.0,8.0 Hz), 7.52 (2H, d, J=8.8 Hz), 7.41–7.46 (2H, m), 7.24–7.36 (7H, m), 7.10–7.15 (2H, m), 6.97 (1H, d, J=8.4 Hz), 6.88 (1H, d, J=2.6 Hz), 6.80 (1H, dd, J=2.6,8.4 Hz), 6.39 (1H, br.t, J=6.6 Hz), 6.18 (2H, d, J=8.8 Hz), 5.18 (2H, s), 5.12 (1H, d, J=12.0 Hz), 5.06 (1H, d, J=12.0 Hz), 4.27 (1H, br.t, J=5.0 Hz), 3.98 (2H, br.t, J=5.0 Hz), 3.81 (3H, s), 3.24 (2H, t, J=6.6 Hz), 1.87 (1H, m), 0.94 (6H, d, J=6.6 Hz).

EXAMPLE 17(5)

Benzyl 2'-(4-(N²-benzyloxycarbonylamidino)phenylaminomethyl)-4-((2-methylpropyl)carbamoyl)-2-biphenylcarboxylate TLC: Rf 0.70 (Chloroform:Ethyl acetate=1:1); NMR (d$_6$-DMSO): δ 9.3–8.6 (2H, broad), 8.69 (1H, brt, J=5.5 Hz), 8.37 (1H, d, J=2.0 Hz), 8.08 (1H, dd, J=8.0 Hz, 2.0 Hz), 7.71 (2H, d, J=9.0 Hz), 7.48 (1H, d, J=8.0 Hz), 7.40–7.20 (11H, m), 7.18–7.09 (2H, m), 7.05 (1H, d, J=7.5 Hz), 6.76 (1H, brt, J=5.5 Hz), 6.40 (2H, d, J=9.0 Hz), 5.11 (2H, s), 5.05 (2H, s), 3.97 (2H, d, J=5.5 Hz), 3.10 (2H, t, J=6.0 Hz), 1.85 (1H, m), 0.88 (6H, d, J=6.5 Hz).

EXAMPLE 17(6)

Ethyl 2'-(4-(N²-ethoxycarbonylamidino)phenylaminomethyl)-4-((2-methyl propyl)carbamoyl)-2-biphenylcarboxylate methanesulfonate

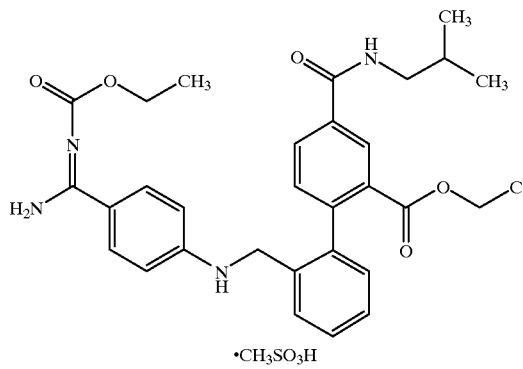

·CH₃SO₃H

TLC: Rf 0.42 (Chloroform:Ethyl acetate=1:1); NMR (d₆-DMSO): δ 11.80 (1H, brs), 10.61 (1H, brs), 9.99 (1H, brs), 8.70 (1H, brt, J=6.0 Hz), 8.34 (1H, d, J=2.0 Hz), 8.07 (1H, dd, J=8.0 Hz, 2.0 Hz), 7.60–7.46 (1H, broad), 7.57 (2H, d, J=8.5 Hz), 7.50 (1H, d, J=8.0 Hz), 7.38–7.26 (3H, m), 7.07 (1H, d, J=7.5 Hz), 6.53 (2H, d, J=8.5 Hz), 4.30 (2H, q, J=7.0 Hz), 4.20–3.96 (4H, m), 3.11 (2H, t, J=6.5 Hz), 2.30 (3H, s), 1.93–1.79 (1H, m), 1.30 (3H, t, J=7.0 Hz), 0.90 (3H, t, J=7.0 Hz), 0.90 (6H, d, J=7.0 Hz).

EXAMPLE 17(7)

Ethyl 2'-(4-(N²-benzyloxycarbonylamidino)phenylaminomethyl)-4-((2-methylpropyl)carbamoyl)-2-biphenylcarboxylate

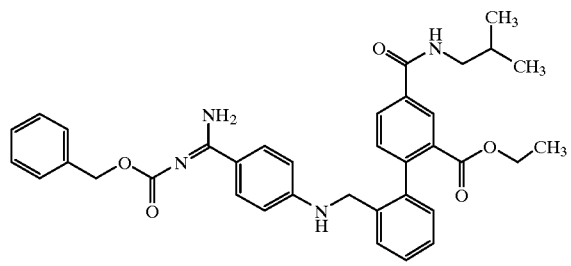

TLC: Rf 0.59 (Chloroform:Ethyl acetate=1:1); NMR (d₆-DMSO): δ 9.4–8.4 (2H, broad), 8.69 (1H, brt, J=6.0 Hz), 8.33 (1H, d, J=2.0 Hz), 8.07 (1H, dd, J=8.0 Hz, 2.0 Hz), 7.73 (2H, d, J=9.0 Hz), 7.50 (1H, d, J=8.0 Hz), 7.40–7.24 (8H, m), 7.04 (1H, d, J=7.0 Hz), 6.87 (1H, brt, J=6.0 Hz), 6.43 (2H, d, J=9.0 Hz), 5.05 (2H, s), 4.10–3.93 (2H, m), 4.02 (2H, q, J=7.0 Hz), 3.10 (2H, t, J=6.5 Hz), 1.92–1.78 (1H, m), 0.89 (6H, d, J=6.5 Hz), 0.89 (3H, t, J=7.0 Hz).

EXAMPLE 17(8)

Ethyl 2'-(4-(N²-t-butoxycarbonyloxyamidino)phenylaminomethyl)-4-((2-methylpropyl)carbamoyl)-2-biphenylcarboxylate

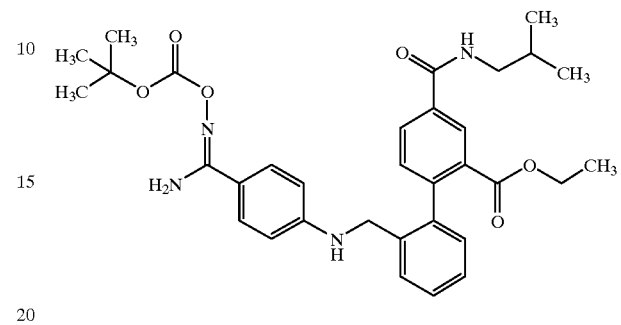

TLC: Rf 0.68 (Chloroform:Ethyl acetate=1:1); NMR (d₆-DMSO): δ 8.69 (1H, brt, J=6.0 Hz), 8.33 (1H, d, J=2.0 Hz), 8.07(1H, dd, J=8.0 Hz, 2.0 Hz), 7.50 (1H, d, J=8.0 Hz), 7.39–7.23 (5H, m), 7.04 (1H, dd, J=7.5 Hz, 1.5 Hz), 6.53 (1H, brt, J=6.0 Hz), 6.41 (2H, d, J=9.0 Hz), 6.34 (2H, brs), 4.10–3.85 (4H, m), 3.11 (2H, t, J=6.5 Hz), 1.92–1.79 (1H, m), 1.44 (9H, s), 0.89 (3H, t, J=7.0 Hz), 0.89 (6H, d, J=6.5 Hz).

EXAMPLE 17(9)

Ethyl 2'-(4-(N²-t-butoxycarbonylamidino)phenoxymethyl)-4-((2-methylpropyl)carbamoyl)-2-biphenylcarboxylate

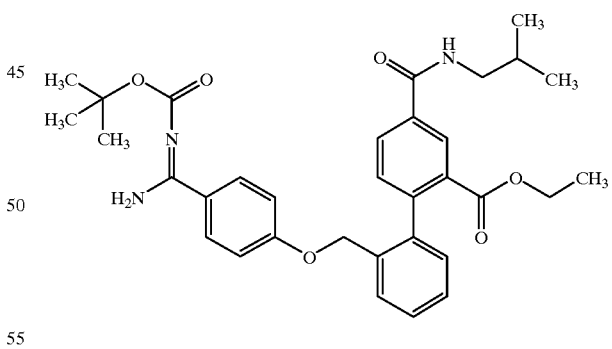

TLC: Rf 0.36 (Hexane:Ethyl acetate=1:1); NMR (CDCl₃): δ 9.8–8.8 (1H, broad), 8.28 (1H, d, J=2.0 Hz), 7.91 (1H, dd, J=8.0 Hz, 2.0 Hz), 7.71 (2H, d, J=9.0 Hz), 7.53 (1H, dd, J=7.5 Hz, 1.5 Hz), 7.41 (1H, td, J=7.5 Hz, 1.5 Hz), 7.37 (1H, d, J=8.0 Hz), 7.36 (1H, td, J=7.5 Hz, 1.5 Hz), 7.14 (1H, dd, J=7.5 Hz, 1.5 Hz), 6.77 (2H, d, J=9.0 Hz), 6.29 (1H, brt, J=6.5 Hz), 4.81 (2H, s), 4.06 (2H, q, J=7.0 Hz), 3.31 (2H, t, J=6.5 Hz), 1.99–1.87 (1H, m), 1.54 (9H, s), 0.99 (6H, d, J=7.0 Hz), 0.96 (3H, t, J=7.0 Hz).

EXAMPLE 17(10)

Ethyl 2'-(4-(N²-t-butoxycarbonylamidino) phenylthiomethyl)-4-((2-methylpropyl)carbamoyl)-2-biphenylcarboxylate

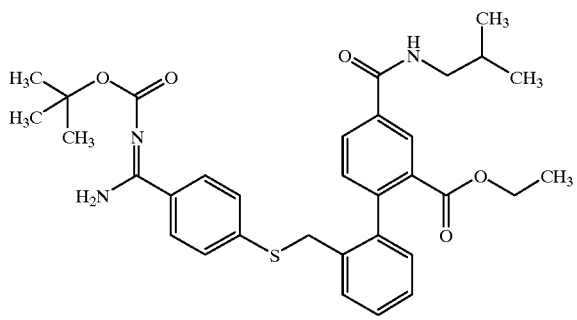

TLC: Rf 0.40 (Hexane:Ethyl acetate=1:1); NMR (CDCl$_3$): δ 8.26 (1H, d, J=1.8 Hz), 7.81 (1H, dd, J=1.8, 8.0 Hz), 7.56 (2H, d, J=9.0 Hz), 7.42 (1H, dd, J=1.8, 8.0 Hz), 7.32 (1H, dt, J=1.8, 8.0 Hz), 7.27 (1H, dt, J=1.8, 8.0 Hz), 7.23 (1H, d, J=8.0 Hz), 7.06 (1H, dd, J=1.8, 8.0 Hz), 7.02 (2H, d, J=9.0 Hz), 6.46 (1H, br.s), 4.06 (2H, q, J=7.4 Hz), 3.94 (1H, d, J=13.2 Hz), 3.86 (1H, d, J=13.2 Hz), 3.29 (2H, t, J=6.6 Hz), 1.91 (1H,m), 1.53 (9H, s), 0.97 (6H, d, J=6.6 Hz), 0.96 (3H, t, J=7.4 Hz).

EXAMPLE 18

Ethyl 2'-(4-(N²-t-butoxycarbonyloxyamidino) phenylcarbamoyl)-4-((2-methylpropyl)carbamoyl)-2-biphenylcarboxylate

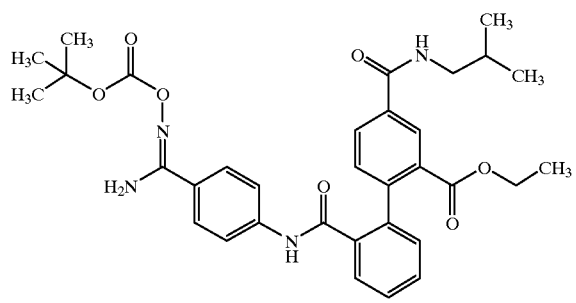

4'-((2-methylpropyl)carbamoyl)-2'-ethoxycarbonyl-2-biphenyl carboxylic acid (1.0 g) which was prepared by the same procedure as a series of reaction of Reference Example 4→Reference Example 5, using ethyl 2-trifluoromethylsulfonyloxy-5-((2-methylpropyl) carbamoyl)benzoate, was dissolved into ethyl acetate (20 ml). Thionyl chloride (0.22 ml) was dropped into the above solution. The mixture was stirred for 15 minutes at 50° C. The reaction mixture was cooled to room temperature, and concentrated. A solution of the prepared acyl chloride compound in methylene chloride (10 ml) and triethylamine (0.57 ml) were added to a solution of 4-(N²-t-butoxycarbonyloxyamidino)aniline in methylene chloride (10 ml) at 0° C. The mixture was stirred for 1 hour at room temperature. The reaction mixture was diluted with ethyl acetate (150 ml), and washed with a saturated aqueous solution of sodium chloride (75 ml, 2 times). The organic layer was dried over anhydrous magnesium sulfate and concentrated. The residue was purified by column chromatography on silica gel (methylene chloride:methanol=100:1) to give the present compound (1.56 g) having the following physical data.

TLC: Rf 0.62 (Chloroform:Methanol=10:1).

EXAMPLE 18(1)–EXAMPLE 18(10)

The following compounds were obtained by the same procedure as a series of reaction of Example 18, using a corresponding derivative instead of the starting compound in Example 18.

EXAMPLE 18(1)

Ethyl 2'-(4-(N²-ethoxycarbonylamidino) phenylcarbamoyl)-2-biphenylcarboxylate

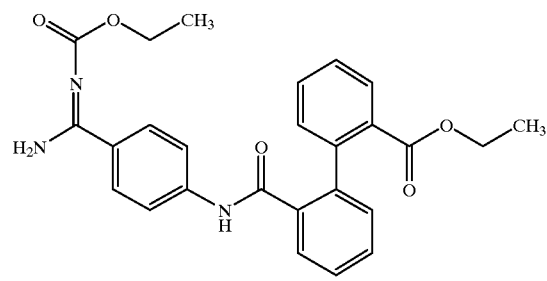

TLC: Rf 0.66 (Chloroform:Methanol:Water=9:1:0.1); NMR (d$_6$-DMSO): δ 10.27 (1H, s), 9.3–8.7 (2H, broad), 7.89 (2H, d, J=9.0 Hz), 7.77 (1H, dd, J=7.5 Hz, 1.5 Hz), 7.70–7.48 (6H, m), 7.42 (1H, td, J=7.5 Hz, 1.5 Hz), 7.34–7.24 (2H, m), 4.04 (2H, q, J=7.0 Hz), 3.96 (2H, q, J=7.0 Hz), 1.20 (3H, t, J=7.0 Hz), 0.88 (3H, t, J=7.0 Hz).

EXAMPLE 18(2)

Ethyl 2'-(4-(N²-t-butoxycarbonyloxyamidino) phenylcarbamoyl)-2-biphenylcarboxylate

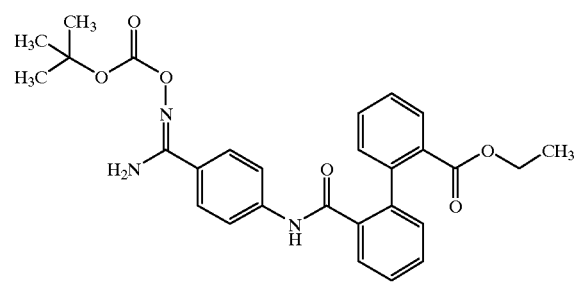

TLC: Rf 0.46 (Chloroform:Ethyl acetate=1:1); NMR (CDCl$_3$): δ 8.67 (1H, brs), 7.82–7.76 (2H, m), 7.53–7.35 (6H, m), 7.27–7.22 (3H, m), 7.13–7.09 (1H, m), 5.01 (2H, brs), 4.30–4.22 (2H, m), 1.54 (9H, s), 1.20 (3H, t, J=7.0 Hz).

EXAMPLE 18(3)

Benzyl 2'-(4-(N²-t-butoxycarbonyloxyamidino)phenylcarbamoyl)-2-biphenylcarboxylate

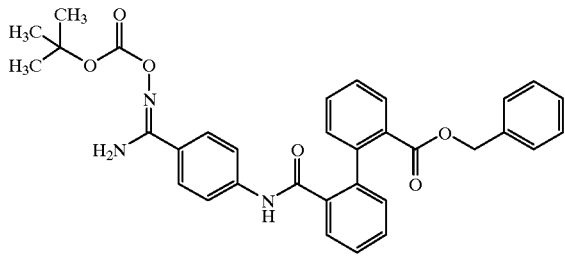

TLC: Rf 0.77 (Hexane:Ethyl acetate=1:2); NMR (CDCl$_3$): δ 8.40 (1H, brs), 7.82 (1H, dd, J=1.0, 8.0 Hz), 7.72 (1H, dd, J=1.0, 8.0 Hz), 7.51–7.30 (8H, m), 7.25–7.17 (2H, m), 7.10 (2H, brd, J=8.5 Hz), 5.22 (2H, d, J=12 Hz), 4.95 (2H, brs), 1.57 (9H, s).

EXAMPLE 18(4)

Ethyl 2'-(4-(N²-ethoxycarbonylamidino)phenyloarbamoyl)-4-((2-methylpropyl)carbamoyl)-2-biphenylcarboxylate

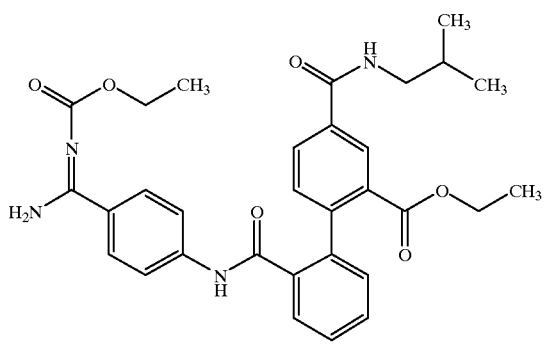

TLC: Rf 0.62 (Chloroform:Methanol=10:1); NMR (d$_6$-DMSO): δ 10.39 (1H, s), 9.2–8.8 (2H, br), 8.65 (1H, t, J=7.0 Hz), 8.23 (1H, d, J=2.0 Hz), 8.01 (1H, dd, J=2.0, 8.0 Hz), 7.89 (2H, d, J=8.8 Hz), 7.8–7.4 (5H, m), 7.39 (1H, d, J=8.0 Hz), 7.29 (1H, dd, J=2.0, 7.0 Hz), 4.05 (2H, q, J=7.2 Hz), 3.99 (2H, q, J=7.2 Hz), 3.08 (2H, t, J=7.0 Hz), 1.84 (1H, like septet, J=7.0H), 1.20 (3H, t, J=7.2 Hz), 0.89 (3H, t, J=7.2 Hz), 0.88 (6H, d, J=7.0 Hz).

EXAMPLE 18(5)

Ethyl 2'-(4-(N²-ethoxycarbonylamidino)phenyloarbamoyl)-4-((2-methylpropyl)carbamoyl)-2-biphenylcarboxylate methanesulfonate

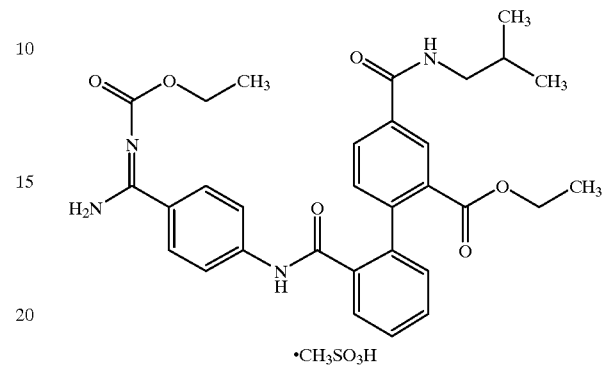

TLC: Rf 0.62 (Chloroform:Methanol=10:1); NMR (d$_6$-DMSO): δ 12.32 (1H, br), 11.12 (1H, br.s), 10.63 (1H, s), 10.43 (1H, br.s), 8.68 (1H, br.t, J=6.4 Hz), 8.23 (1H, d, J=1.6 Hz), 8.03 (1H, dd, J=1.6, 7.9 Hz), 7.74 (4H, like s), 7.8–7.6 (1H, m), 7.7–7.5 (2H, m), 7.41 (1H, d, J=7.8 Hz), 7.31 (1H, dd, J=1.6, 7.8 Hz), 4.33 (2H, q, J=6.8 Hz), 3.98 (2H, q, J=6.8 Hz), 3.09 (2H, t, J=6.4 Hz), 2.37 (3H, s), 1.84 (1H, like septet, J=6.4 Hz), 1.31 (3H, t, J=6.8 Hz), 0.89 (3H, t, J=6.8 Hz), 0.88 (6H, d, J=6.4 Hz).

EXAMPLE 18(6)

Ethyl 2'-(4-(N²-(2-propenyloxycarbonyl)amidino)phenylcarbamoyl)-2-biphenylcarboxylate

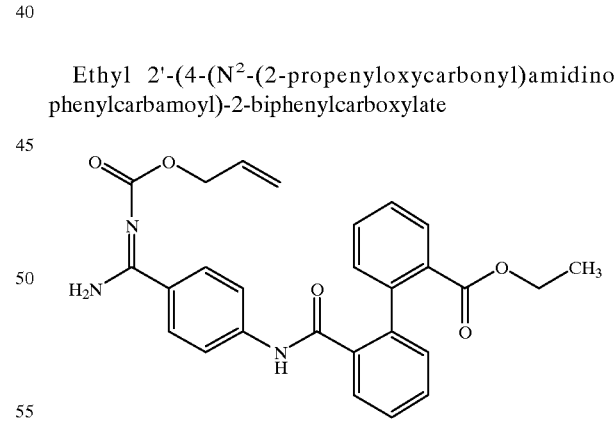

TLC: Rf 0.69 (Chloroform:Methanol:Water=9:1:0.1); NMR (CDCl$_3$): δ 8.95 (1H, s), 7.80 (2H, d, J=9.0 Hz), 7.76 (1H, m), 7.34–7.51 (4H, m), 7.33 (2H, d, J=9.0 Hz), 7.23 (1H, m), 7.12 (1H, m), 5.97 (1H, m), 5.22–5.42 (2H, m), 4.61–4.68 (2H, m), 4.28 (2H, q, J=7.2 Hz), 1.23 (3H, t, J=7.2 Hz).

EXAMPLE 18(7)

Benzyl 2'-(4-(N²-ethoxycarbonylamidino)phenylcarbamoyl)-2-biphenylcarboxylate

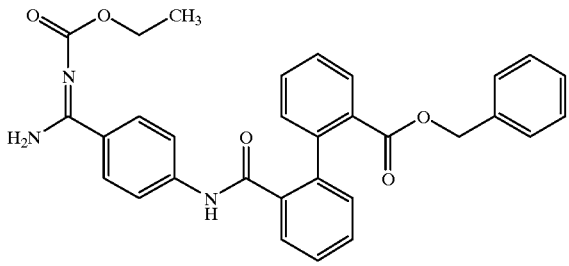

TLC: Rf 0.75 (Chloroform:Methanol=10:1); NMR (CDCl₃): δ 10.0–9.0 (1H, br), 8.5 (1H, s), 7.83 (1H, dd, J=1.6, 7.4 Hz), 7.8–7.6 (3H, m), 7.6–7.3 (6H, m), 7.3–7.0 (7H, m), 7.0–6.2 (1H, br), 5.24 (1H, d, J=14.6 Hz), 5.18 (1H, d, J=14.6 Hz), 4.19 (2H, q, J=7.4 Hz), 1.33 (3H, t, J=7.4 Hz).

EXAMPLE 18(8)

Benzyl 2-(3-(4-(N²-benzyloxycarbonylamidino)phenylcarbamoyl)-5-methoxybenzofuran-2-yl)benzoate

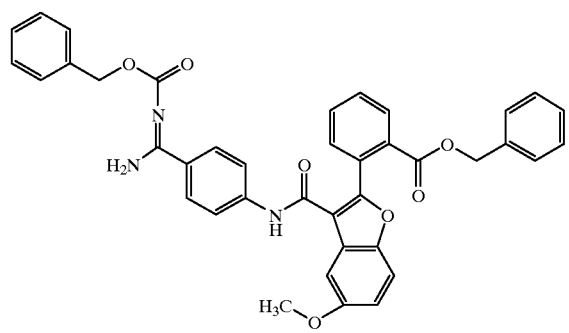

TLC: Rf 0.45 (Hexane:Ethyl acetate=1:1); NMR (d₆-DMSO): δ 10.30 (1H, s), 9.3–8.9 (2H, broad), 7.96 (2H, d, J=9.0 Hz), 7.91 (1H, dd, J=7.5 Hz, 2.0 Hz), 7.76–7.70 (4H, m), 7.64 (1H, td, J=7.5 Hz, 2.0 Hz), 7.53 (1H, d, J=9.0 Hz), 7.41–7.29 (5H, m), 7.25 (1H, d, J=2.0 Hz), 7.24–7.18 (3H, m), 7.16–7.13 (2H, m), 7.02 (1H, dd, J=9.0 Hz, 2.0 Hz), 5.10 (4H, s), 3.83 (3H, s).

EXAMPLE 18(9)

Benzyl 2'-(6-(N²-t-butoxycarbonylamidino)pyridin-3-ylcarbamoyl)-4-((2-methylpropyl)carbamoyl)-2-biphenylcarboxylate

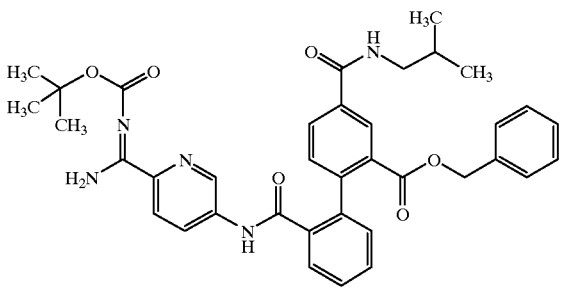

TLC: Rf 0.49 (Chloroform:Methanol=10:1); NMR (CDCl₃): δ 9.25 (1H, br s), 8.69 (1H, s), 8.28 (1H, d, J=1.6 Hz), 8.23 (1H, d, 6.2 Hz), 8.21 (1H, s), 8.10 (1H, br s), 7.81 (1H, dd, J=1.6, 7.6 Hz), 7.70–7.71 (2H, m), 7.58–7.42 (2H, m), 7.40–7.20 (6H, m), 7.09–7.04 (2H, m), 6.25 (1H, t, J=5.8 Hz), 5.29 (1H, d, J=11.6 Hz), 5.17 (1H, d, J=11.6 Hz), 3.26 (2H, t, J=6.2 Hz), 1.88 (1H, septet, J=6.2 Hz), 1.54 (9H, s), 0.96 (6H, d, J=6.2 Hz).

EXAMPLE 18(10)

Benzyl 2'-(6-(N²-t-butoxycarbonylamidino)pyridin-3-ylcarbamoyl)-4'-methoxy-4-((1,2,2-trimethylpropyl)carbamoyl)-2-biphenylcarboxylate

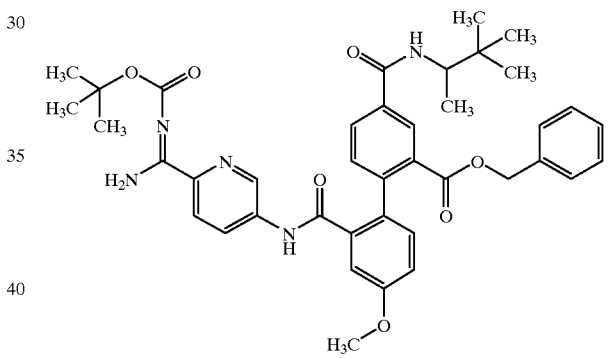

TLC: Rf 0.45 (Chloroform:Methanol:Water=9:1:0.1); NMR (CDCl₃): δ 9.3–9.2 (1H, broad), 8.77 and 8.73 (1H, s), 8.28–8.20 (2H, m), 8.20–8.08 (1H, broad), 7.81–7.70 (2H, m), 7.38–7.20 (7H, m), 6.99–6.92 (2H, m), 5.91 (1H, d, J=9.5 Hz), 5.31–5.09 (2H, m), 4.08 (1H, dq, J=9.5 Hz, 7.0 Hz), 3.90 (3H, s), 1.55 (9H, s), 1.14 (3H, d, J=7.0 Hz), 0.95 (9H, s).

EXAMPLE 19–EXAMPLE 19(182)

The following compounds were obtained by the same procedure as a series of reaction of Example 4, Example 2, Example 11 or Reference Example 8, using the compound prepared in Example 7–Example 7(83), Example 7(86) –Example 7(98), Example 8–Example 8(6), Example 9–Example 9–(31), Example 12–Example 12(3), Example 13, Example 14–Example 14(2), Example 15–Example 15(1), Example 16, Example 17–Example 17(5),Example 17(7)–Example 17(8), Example 18, Example 18(2) –Example 18(3), Example 18(7), Example 7(99)–Example 7(113), Example 8(7), Example 17(9), Example 18(8) –Example 18(9), Example 7(114)–Example 7(115), Example 17(10) and Example 18(10).

EXAMPLE 19

2'-(4-amidinophenylcarbamoyl)-2-biphenylcarboxylic acid methanesulfonate

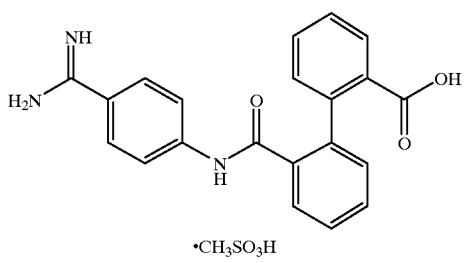

TLC: Rf 0.16 (Chloroform:Methanol:Water=8:2:0.2); NMR (d$_6$-DMSO): δ 10.39 (1H, s), 9.14 (2H, s), 8.79 (2H, s), 7.82 (1H, dd, J=1.4,7.6 Hz), 7.73 (2H, d, J=9.0 Hz), 7.64–7.69 (3H, m), 7.48–7.56 (3H, m), 7.40 (1H, dt, J=1.4, 7.6 Hz), 7.23–7.28 (2H, m), 2.35 (3H, s).

EXAMPLE 19(1)

2'-(4-amidinophenylcarbamoyl)-2-biphenylcarboxylic acid hydrochloride

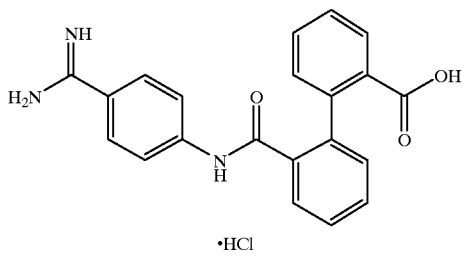

TLC: Rf 0.12 (Chloroform:Methanol:Acetic acid 10:2:1); NMR (d$_6$-DMSO): δ 13.2–12.2 (1H, broad), 10.46 (1H, s), 9.32 (2H, s), 9.16 (2H, s), 7.84–7.77 (3H, m), 7.72–7.64 (3H, m), 7.60–7.37 (4H, m), 7.28–7.20 (2H, m).

EXAMPLE 19(2)

3-(4-amidinophenylcarbamoyl)-4-biphenylcarboxylic acid

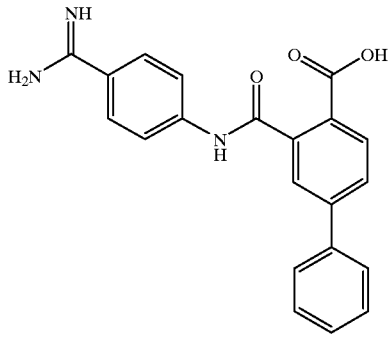

TLC: Rf 0.31 (Ethyl acetate:Acetic acid:Water=6:1:1); NMR (d$_6$-DMSO+1 drop of MeSO$_3$H): δ 10.90 (1H, s), 9.20 (2H, s), 9.02 (2H, s), 8.04–7.64 (9H, m), 7.60–7.38 (3H, m).

EXAMPLE 19(3)

4-(4-amidinophenylcarbamoyl)-3-biphenylcarboxylic acid

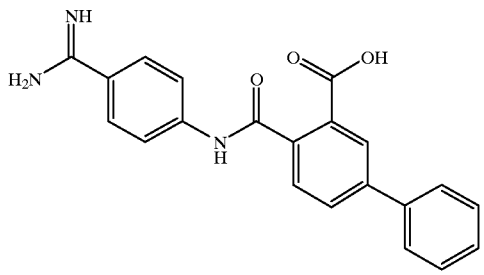

TLC: Rf 0.35 (Ethyl acetate:Acetic acid:Water=6:1:1); NMR (d$_6$-DMSO+1 drop of MeSO$_3$H): δ 11.59 (1H, s), 10.05 (2H, s), 9.05 (2H, s), 8.10 (1H, d, J=2 Hz), 8.00–7.62 (8H, m), 7.58–7.38 (3H, m).

EXAMPLE 19(4)

3'-(4-amidinophenylcarbamoyl)-2-biphenylcarboxylic acid methanesulfonate

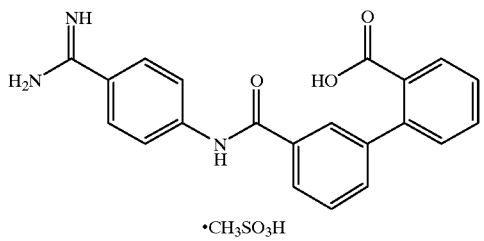

TLC: Rf 0.25 (Ethyl acetate:Acetic acid:Water=6:1:0.5); NMR (d$_6$-DMSO): δ 13.0–12.7 (1H, broad), 10.71 (1H, s), 9.23 (2H, s), 8.96 (2H, s), 8.06–7.96 (4H, m), 7.90–7.78 (3H, m), 7.68–7.43 (5H, m), 2.36 (3H, s).

EXAMPLE 19(5)

2,3-dihydro-2,2-dimethyl-5-(2-(4-amidinophenylcarbamoyl)phenyl)-6-benzofurancarboxylic acid methanesulfonate

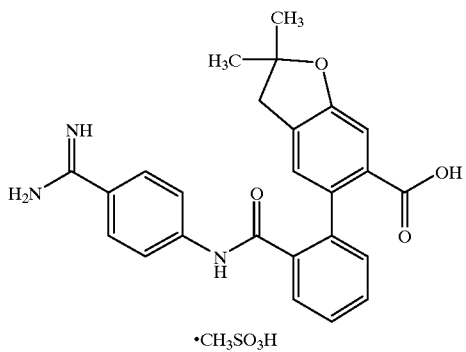

TLC: Rf 0.40 (Chloroform:Methanol:Acetic acid= 10:2:1); NMR (d$_6$-DMSO): δ 13.0–12.3 (1H, broad), 10.28 (1H, s), 9.16 (2H, s), 8.90 (2H, s), 7.75 (2H, d, J=9 Hz), 7.66 (2H, d, J=9 Hz), 7.62 (1H, dd, J=7 Hz, 2 Hz), 7.57–7.41 (2H, m), 7.22 (1H, dd, J=7 Hz, 2 Hz), 7.05 (1H, s), 7.04 (1H, s), 3.00 (2H, s), 2.36 (3H, s), 1.40 (6H, s).

EXAMPLE 19(6)

2'-(4-amidinophenylcarbamoyl)-3-biphenylcarboxylic acid methanesulfonate

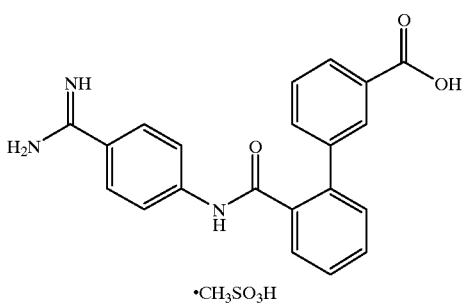

TLC: Rf 0.34 (Chloroform:Methanol:Acetic acid=10:2:1) NMR ($d_6$-DMSO): δ 13.3–12.7 (1H, broad), 10.71 (1H, s), 9.19 (2H, s), 8.98 (2H, s), 8.03 (1H, s), 7.88 (1H, d, J=8 Hz), 7.80–7.43 (10H, m), 2.38 (3H, s).

EXAMPLE 19(7)

2'-(4-amidinophenylcarbamoyl)-2,3-biphenyldicarboxylic acid

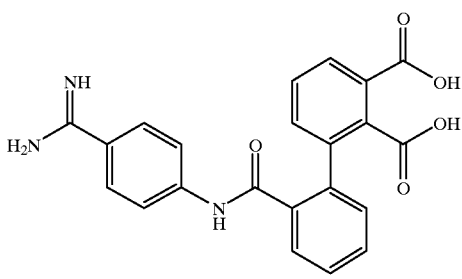

TLC: Rf 0.27 (Chloroform:Methanol:Water=6:4:1); NMR ($d_6$-DMSO): δ 14.0–12.0(1H, broad), 10.81 (1H, brs), 9.24(2H, brs), 8.20 (2H, brs), 7.84–7.24 (11H, m).

EXAMPLE 19(8)

2'-(4-amidinophenylcarbamoyl)-6-methyl-2-biphenylcarboxylic acid methanesulfonate

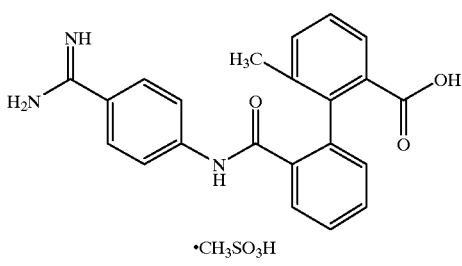

TLC: Rf 0.12 (Chloroform:Methanol:Acetic acid= 10:2:1); NMR ($d_6$-DMSO): δ 13.2–12.2 (1H, broad), 10.42 (1H, s), 9.15 (2H, brs), 8.91 (2H, brs), 7.75–7.50 (8H, m), 7.39 (1H, d, J=8 Hz), 7.30 (1H, t, J=8 Hz), 7.10 (1H, dd, J=8 Hz, 2 Hz), 2.35 (3H, s), 1.92 (3H, s).

EXAMPLE 19(9)

2'-(4-amidinophenylcarbamoyl)-5-methoxy-2-biphenylcarboxylic acid methanesulfonate

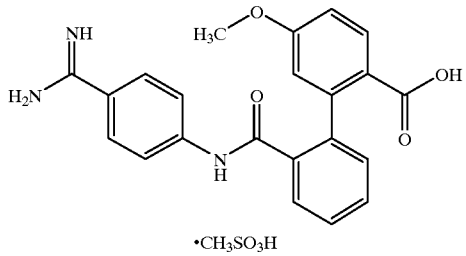

TLC: Rf 0.29 (Chloroform:Methanol:Water=7:3:0.3); NMR ($d_6$-DMSO): δ 10.40 (1H, s), 9.15 (2H, s), 8.82 (2H, s), 7.82 (1H, d, J=8.8 Hz), 7.73 (2H, d, J=9.0 Hz), 7.68 (2H, d, J=9.0 Hz), 7.66 (1H, d, J=8.8 Hz), 7.44–7.58 (2H, m), 7.26 (1H, d, J=7.8 Hz), 6.92 (1H, dd, J=2.2,8.8 Hz), 6.75 (1H, d, J=2.2 Hz), 3.76 (3H, s), 2.36 (3H, s).

EXAMPLE 19(10)

2'-(4-amidinophenylcarbamoyl)-4-methoxy-2-biphenylcarboxylic acid methanesulfonate

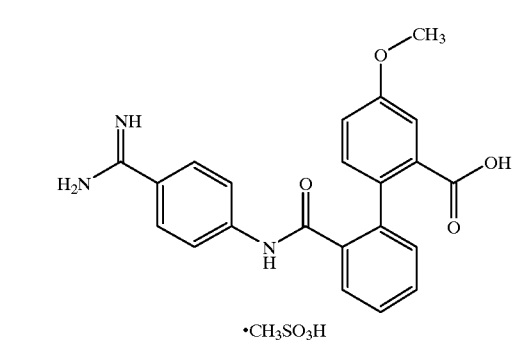

TLC: Rf 0.31 (Chloroform:Methanol:Water=7:3:0.3); NMR ($d_6$-DMSO): δ 10.38 (1H, s), 9.16 (2H, s), 8.87 (2H, s), 7.75 (2H, d, J=9.0 Hz), 7.69 (2H, d, J=9.0 Hz), 7.63 (1H, d, J=8.0 Hz), 7.53 (1H, t, J=8.0 Hz), 7.48 (1H, t, J=8.0 Hz), 7.32 (1H, d, J=2.2 Hz), 7.23 (1H, d, J=8.0 Hz), 7.17 (1H, d, J=8.6 Hz), 7.08 (1H, dd, J=2.2,8.6 Hz), 3.79 (3H, s), 2.35 (3H, s).

EXAMPLE 19(11)

2'-(4-amidinophenylcarbamoyl)-4-biphenylcarboxylic acid methanesulfonate

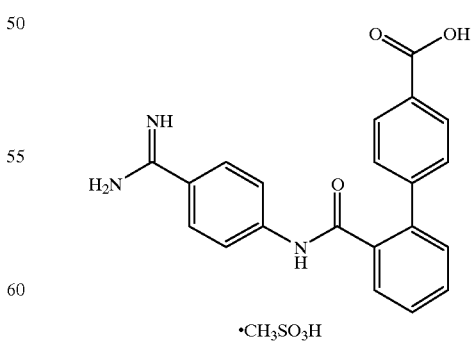

TLC: Rf 0.12 (Chloroform:Methanol:Acetic acid= 10:2:1); NMR ($d_6$-DMSO): δ 12.97 (1H, brs), 10.73 (1H, s), 9.18 (2H, brs), 8.95 (2H, brs), 7.91 (2H, d, J=8.5 Hz), 7.80–7.50 (10H, m), 2.34 (3H, s).

EXAMPLE 19(12)

2'-(4-amidinophenylcarbamoyl)-6-methoxy-2-biphenylcarboxylic acid methanesulfonate

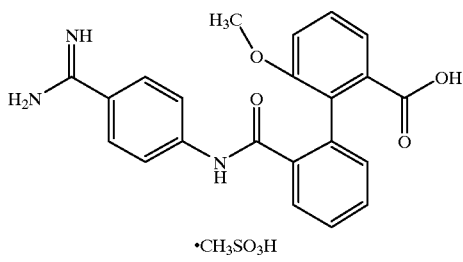

•CH₃SO₃H

TLC: Rf 0.30 (Chloroform:Methanol:Water=7:3:0.3); NMR (d₆-DMSO): δ 10.34 (1H, s), 9.15 (2H, s), 8.83 (2H, s), 7.73 (4H, s), 7.67 (1H, m), 7.45–7.54 (2H, m), 7.36–7.38 (2H, m), 7.11–7.16 (2H, m), 3.56 (3H, s), 2.34 (3H, s).

EXAMPLE 19(13)

2'-(4-amidinophenylcarbamoyl)-4-hydroxy-2-biphenylcarboxylic acid methanesulfonate

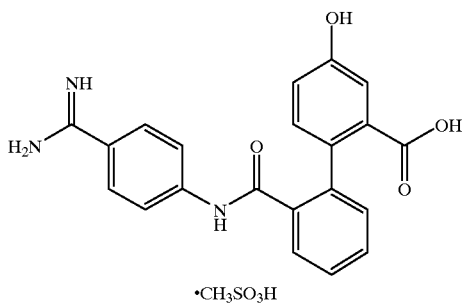

•CH₃SO₃H

TLC: Rf 0.1 9 (Chloroform:Methanol:Water=7:3:0.3); NMR (d₆-DMSO): δ 10.25 (1H, s), 9.76 (1H, s), 9.15 (2H, s), 8.82 (2H, s), 7.74 (2H, d, J=8.8 Hz), 7.66 (2H, d, J=8.8 Hz), 7.60 (1H, dd, J=2.0,7.6 Hz), 7.50 (1H, dt, J=2.0,7.6 Hz), 7.45 (1H, dt, J=2.0,7.6 Hz), 7.21 (1H, dd, J=2.0,7.6 Hz), 7.19 (1H, d, J=2.4 Hz), 7.03 (1H, d, J=8.2 Hz), 6.87 (1H, dd, J=2.4,8.2 Hz), 2.35 (3H, s).

EXAMPLE 19(14)

2'-(4-amidinophenylcarbamoyl)-5-hydroxy-2-biphenylcarboxylic acid methanesulfonate

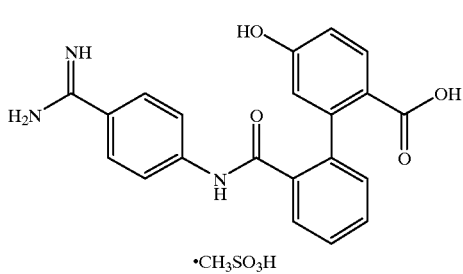

•CH₃SO₃H

TLC: Rf 0.19 (Chloroform:Methanol:Water=7:3:0.3); NMR (d₆-DMSO): δ 10.34 (1H, s), 10.16 (1H, s), 9.14 (2H, s), 8.78 (2H, s), 7.73 (2H, d, J=8.8 Hz), 7.72 (1H, d, J=8.6 Hz), 7.67 (2H, d, J=8.8 Hz), 7.63 (1H, dd, J=2.4,7.2 Hz), 7.47–7.53 (2H, m), 7.20 (1H, dd, J=2.4,7.2 Hz), 6.75 (1H, dd, J=2.4,8.6 Hz), 6.56 (1H, d, J=2.4 Hz), 2.34 (3H, s).

EXAMPLE 19(15)

2'-(4-amidinophenylcarbamoyl)-5-methyl-2-biphenylcarboxylic acid methanesulfonate

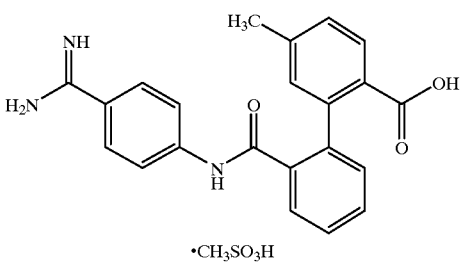

•CH₃SO₃H

TLC: Rf 0.15 (Chloroform:Methanol:Acetic acid=10:2:1); NMR (d₆-DMSO): δ 10.37 (1H, s), 9.13 (2H, brs), 8.80 (2H, brs), 7.72 (2H, d, J=8.0 Hz), 7.66 (2H, d, J=8.0 Hz), 7.70–7.60 (2H, m), 7.50 (1H, dt, J=1.5, 8.0 Hz), 7.45 (1H, dt, J=1.5, 8.0 Hz), 7.20 (1H, dd, J=2.0, 7.5 Hz), 7.16 (1H, dd, J=2.0, 8.0 Hz), 7.01 (1H, s), 5.00–3.60 (1H, m), 2.29 (3H, s), 2.27 (3H, s).

EXAMPLE 19(16)

2'-(4-amidinophenylcarbamoyl)-4-methyl-2-biphenylcarboxylic acid methanesulfonate

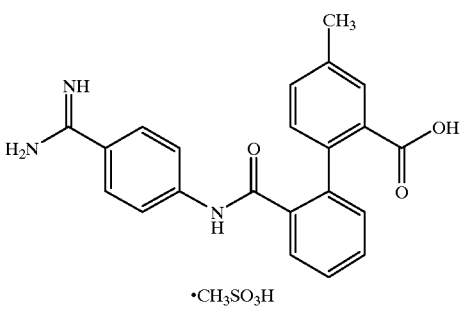

•CH₃SO₃H

TLC: Rf 0.14 (Chloroform:Methanol:Acetic acid=10:2:1); NMR (d₆-DMSO): δ 10.42 (1H, s), 9.14 (2H, brs), 8.81 (2H, brs), 7.70 (2H, d, J=8.0 Hz), 7.65 (2H, d, J=8.0 Hz), 7.66–7.60 (1H, m), 7.61 (1H, s), 7.50 (1H, brt, J=8.0 Hz), 7.45 (1H, brt, J=8.0 Hz), 7.30 (1H, d, J=7.5 Hz), 7.20 (1H, d, J=7.5 Hz), 7.10(1H, d, J=8.0 Hz), 4.20–3.50 (1H, m), 2.31 (6H, s).

EXAMPLE 19(17)

2'-(4-amidinophenylcarbamoyl)-3-hydroxy-2-biphenylcarboxylic acid methanesulfonate

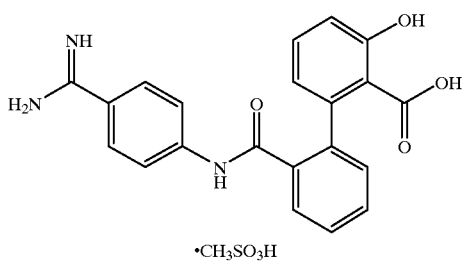

TLC: Rf 0.42 (Chloroform:Methanol:Water=7:3:0.3); NMR (d$_6$-DMSO): δ 10.36 (1H, s), 9.16 (2H, s), 8.81 (2H, s), 7.74 (2H, d, J=8.8 Hz), 7.65 (2H, d, J=8.8 Hz), 7.50–7.65 (3H, m), 7.19–7.30 (2H, m), 6.86 (1H, d, J=8.4 Hz), 6.61 (1H, d, J=7.0 Hz), 2.33 (3H, s).

EXAMPLE 19(18)

2'-(4-amidinophenylcarbamoyl)-4'-methyl-5-chloro-2-biphenylcarboxylic acid methanesulfonate

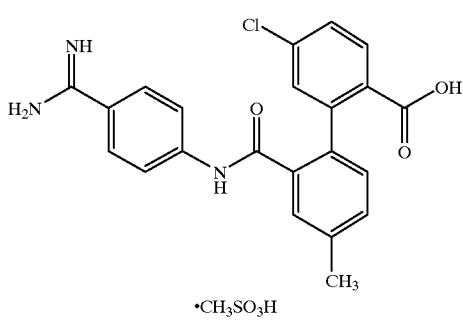

TLC: Rf 0.19 (Chloroform:Methanol:Acetic acid=4:1:0.1); NMR (d$_6$-DMSO): δ 13.2–12.0 (1H, br), 10.50 (1H, s), 9.17 (2H, s), 8.85 (2H, s), 7.82 (1H, d, J=8.4 Hz), 7.74 (4H, s), 7.5–7.3 (3H, m), 7.26 (1H, d, J=1.8 Hz), 7.18 (1H, d, J=7.8 Hz), 2.44 (3H, s), 2.35 (3H, s).

EXAMPLE 19(19)

2'-(4-amidinophenylcarbamoyl)-3-methoxy-2-biphenylcarboxylic acid methanesulfonate

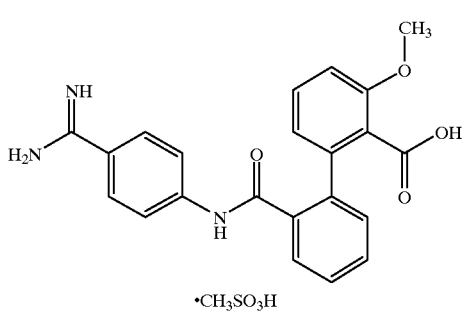

TLC: Rf 0.28 (Chloroform:Methanol:Water=7:3:0.3); NMR (d$_6$-DMSO): δ 10.32 (1H, br.s), 9.16 (2H, s), 8.85 (2H, s), 7.75 (2H, d, J=8.8 Hz), 7.67 (1H, m), 7.64 (2H, d, J=8.8 Hz), 7.53–7.57 (2H, m), 7.29–7.37 (2H, m), 7.05 (1H, d, J=8.4 Hz), 6.79 (1H, d, J=7.6 Hz), 3.83 (3H, s), 2.34 (3H, s).

EXAMPLE 19(20)

2'-(4-amidinophenylcarbamoyl)-4'-methyl-4-methoxy-2-biphenylcarboxylic acid methanesulfonate

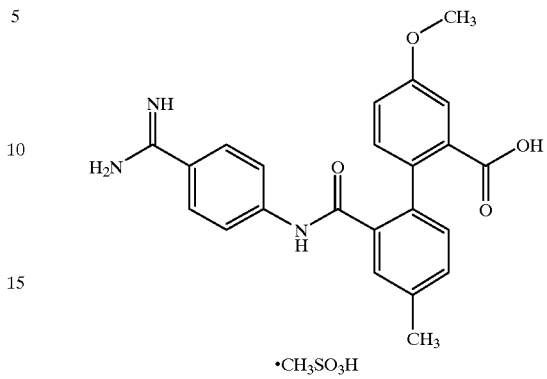

TLC: Rf 0.24 (Chloroform:Methanol:Acetic acid=4:1:0.1); NMR (d$_6$-DMSO): δ 13.4–12.0 (1H, br), 10.36 (1H, s), 9.14 (2H, s), 8.83 (2H, s), 7.7–7.6 (3H, m), 7.44 (1H, s), 7.4–7.2 (2H, m), 7.2–7.0 (4H, m), 3.78 (3H, s), 2.42 (3H, s), 2.37 (3H, s).

EXAMPLE 19(21)

2-(2-(4-amidinophenylcarbamoyl)phenyl)-1-naphthalenecarboxylic acid methanesulfonate

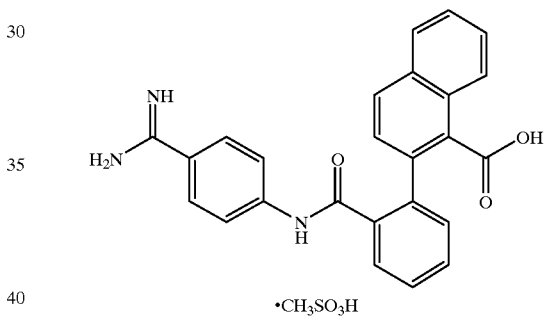

TLC: Rf 0.40 (Chloroform:Methanol:Water=7:3:0.3); NMR (d$_6$-DMSO): δ 10.50 (1H, br.s), 9.12 (2H, s), 8.83 (2H, s), 7.93–8.00 (3H, m), 7.58–7.79 (9H, m), 7.42 (1H, m), 7.37 (1H, d, J=8.4 Hz), 2.35 (3H, s).

EXAMPLE 19(22)

2'-(4-amidinophenylcarbamoyl)-3-methyl-2-biphenylcarboxylic acid methanesulfonate

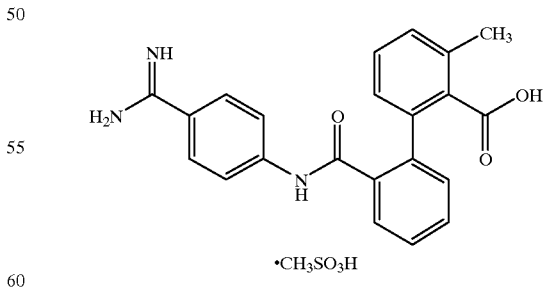

TLC: Rf 0.19 (Chloroform:Methanol:Acetic acid=4:1:0.1); NMR (d$_6$-DMSO): δ 13.7–12.7 (1H, br), 10.29 (1H, s), 9.16 (2H, s), 8.83 (2H, s), 7.74 (2H, d, J=8.8 Hz), 7.59 (2H, d, J=8.8 Hz), 7.8–7.6 (1H, m), 7.6–7.5 (2H, m), 7.4–7.2 (1H, m), 7.25 (2H, d, J=7 Hz), 7.03 (1H, dd, J=7.4, 2 Hz), 2.37 (3H, s), 2.34 (3H, s).

EXAMPLE 19(23)

3-(2-(4-amidinophenylcarbamoyl)phenyl)-7-methoxy-2-naphthalenecarboxylic acid methanesulfonate

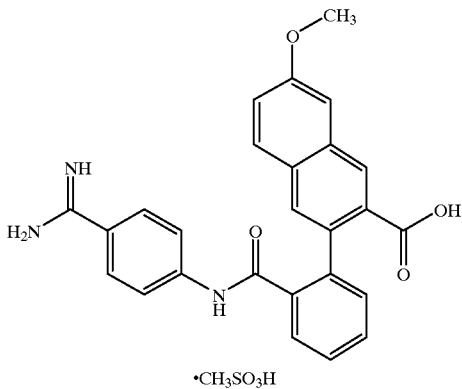

TLC: Rf 0.61 (Ethyl acetate: Acetic acid:Water=3:1:0.5); NMR (d$_6$-DMSO): δ 12.84 (1H, br.s), 10.40 (1H, s), 9.09 (2H, br.s), 8.78 (2H, br.s), 8.35 (1H, s), 7.84 (1H, d, J=9.4 Hz), 7.7–7.4 (9H, m), 7.34 (1H, dd, J=7.2, 1.4 Hz), 7.26 (1H, dd, J=9.4, 2.4 Hz), 3.87 (3H, s), 2.32 (3H, s).

EXAMPLE 19(24)

3-(2-(4-amidinophenylcarbamoyl)phenyl)-5-methoxy-2-naphthalenecarboxylic acid methanesulfonate

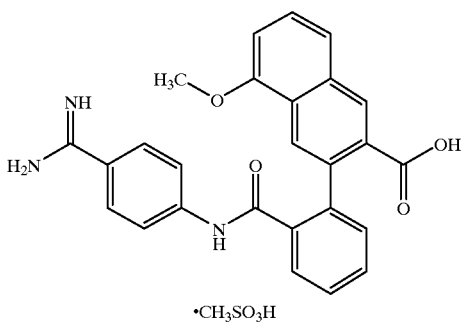

TLC: Rf 0.29 (Chloroform:Methanol:Water=10:3:0.2); NMR (d$_6$-DMSO): δ 12.88 (1H, br.s), 10.49 (1H, s), 9.10 (2H, br.s), 8.79 (2H, br.s), 8.40 (1H, s), 7.94 (1H, s), 7.8–7.4 (9H, m), 7.34 (1H, dd, J=2.0, 6.8 Hz), 7.07 (1H, d, J=7.4 Hz), 3.91 (3H, s), 2.32 (3H, s).

EXAMPLE 19(25)

2'-(4-amidinophenylcarbamoyl)-2,4-biphenyldicarboxylic acid methanesulfonate

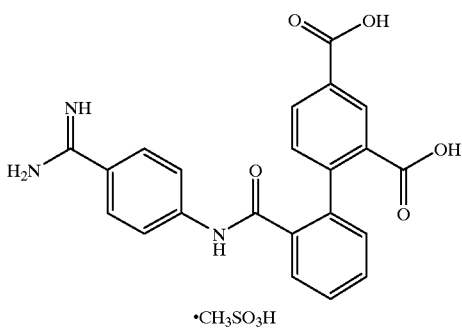

TLC: Rf 0.22 (Chloroform:Methanol:Water=6:4:1); NMR (d$_6$-DMSO): δ 13.02 (1H, br.s), 10.54 (1H, s), 9.16 (2H, s), 8.89 (2H, s), 8.38 (1H, d, J=2.0 Hz), 8.05 (1H, dd, J=2.0,7.8 Hz), 7.74 (4H, s), 7.73 (1H, dd, J=2.6,7.8 Hz), 7.53–7.60 (2H, m), 7.37 (1H, d, J=7.8 Hz), 7.29 (1H, dd, J=2.6,7.8 Hz), 2.38 (3H, s).

EXAMPLE 19(26)

2'-(4-amidinophenylcarbamoyl)-4-dimethylcarbamoyl-2-biphenylcarboxylic acid methanesulfonate

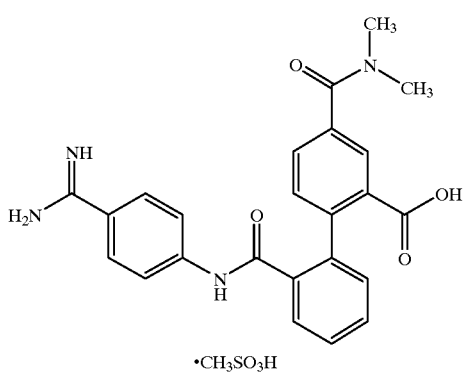

TLC: Rf 0.46 (Chloroform:Methanol:Water=7:3:0.3); NMR (d$_6$-DMSO): δ 10.43 (1H, s), 9.16 (2H, s), 8.88 (2H, s), 7.67–7.80 (6H, m), 7.52–7.59 (3H, m), 7.31 (2H, d, J=7.8 Hz), 2.98 (3H, br.s), 2.85 (3H, br.s), 2.37 (3H, s).

EXAMPLE 19(27)

3-(2-(4-amidinophenylcarbamoyl)phenyl)-6-methoxy-2-naphthalenecarboxylic acid methanesulfonate

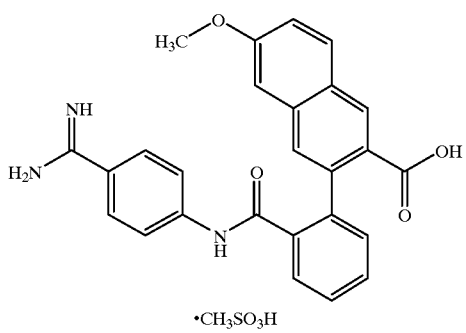

TLC: Rf 0.51 (Chloroform:Methanol:Water=10:3:0.2); NMR (d$_6$-DMSO): δ 13.0–12.0 (1H, br), 11.5–10.5 (1H, br), 9.05 (2H, br.s), 8.85 (2H, br.s), 8.29 (1H, s), 7.93 (1H, d, J=8.8 Hz), 7.7–7.5 (5H, m), 7.6–7.4 (3H, m), 7.4–7.1 (3H, m), 3.84 (3H, s), 2.30 (3H, s).

EXAMPLE 19(28)

2'-(4-amidinophenylcarbamoyl)-4-methylcarbamoyl-2-biphenylcarboxylic acid methanesulfonate

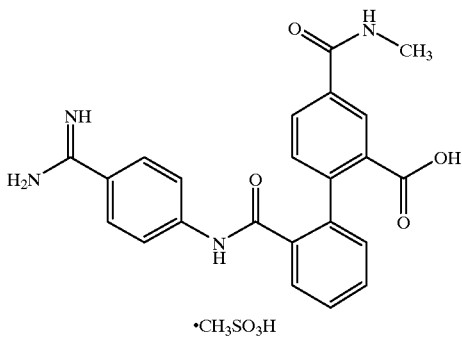

TLC: Rf 0.27 (Chloroform:Methanol:Water=7:3:0.3); NMR (d$_6$-DMSO): δ 10.49 (1H, s), 9.16 (2H, s), 8.89 (2H, s), 8.62 (1H, br.q, J=4.6 Hz), 8.30 (1H, d, J=1.8 Hz), 7.96 (1H, dd, J=1.8,8.2 Hz), 7.76 (2H, d, J=9.0 Hz), 7.71 (2H, d, J=9.0 Hz), 7.70 (1H, dd, J=2.0,7.6 Hz), 7.52–7.58 (2H, m), 7.33 (1H, d, J=8.2 Hz), 7.28 (1H, dd, J=2.0,7.6 Hz), 2.79 (3H, br.d, J=4.6 Hz), 2.39 (3H, s).

EXAMPLE 19(29)

3-(2-(4-amidinophenylcarbamoyl)phenyl)-8-methoxy-2-naphthalenecarboxylic acid methanesulfonate

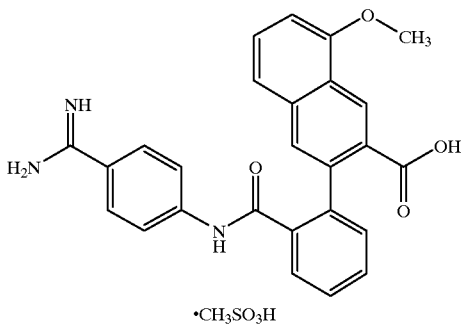

TLC: Rf 0.26 (Chloroform:Methanol:Water=10:3:0.2); NMR (d$_6$-DMSO): δ 12.76 (1H, br.s), 10.45 (1H, s), 9.09 (2H, br.s), 8.80 (2H, br.s), 8.68 (1H, s), 7.8–7.5 (10H, m), 7.35 (1H, m), 7.04 (1H, m), 4.00 (3H, s), 2.33 (3H, s).

EXAMPLE 19(30)

2'-(4-amidinophenylcarbamoyl)-3,4-dimethoxy-2-biphenylcarboxylic acid methanesulfonate

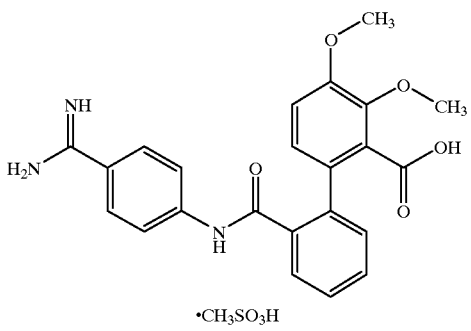

TLC: Rf 0.16 (Chloroform:Methanol:Acetic acid=10:2:1); NMR (d$_6$-DMSO): δ 13.7–13.2 (1H, broad), 10.30 (1H, s), 9.16 (2H, brs), 8.89 (2H, brs), 7.76 (2H, d, J=9.0 Hz), 7.69–7.62 (3H, m), 7.58–7.46 (2H, m), 7.33–7.27 (1H, m), 7.07 (1H, d, J=8.5 Hz), 6.92 (1H, d, J=8.5 Hz), 3.79 (3H, s), 3.77 (3H, s), 2.35 (3H, s).

EXAMPLE 19(31)

6-(2-(4-amidinophenylcarbamoyl)phenyl)-1,2-methylenedioxybenzen-5-carboxylic acid methanesulfonate

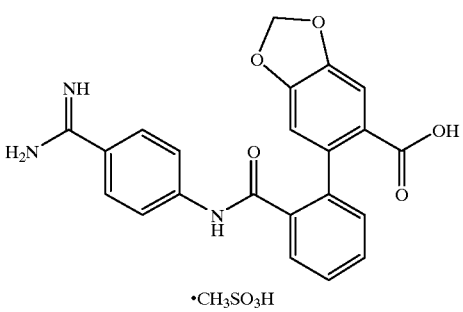

TLC: Rf 0.22 (Chloroform:Methanol:Acetic acid=10:2:1); NMR (d$_6$-DMSO): δ 12.8–12.2 (1H, broad), 10.39 (1H, s), 9.16 (2H, brs), 8.88 (2H, brs), 7.76 (2H, d, J=9.0 Hz), 7.70 (2H, d, J=9.0 Hz), 7.65–7.60 (1H, m), 7.56–7.42 (2H, m), 7.30 (1H, s), 7.24–7.19 (1H, m), 6.75 (1H, s), 6.10 (2H, s), 2.34 (3H, s).

EXAMPLE 19(32)

2'-(4-amidinophenylcarbamoyl)-4'-nitro-2-biphenylcarboxylic acid methanesulfonate

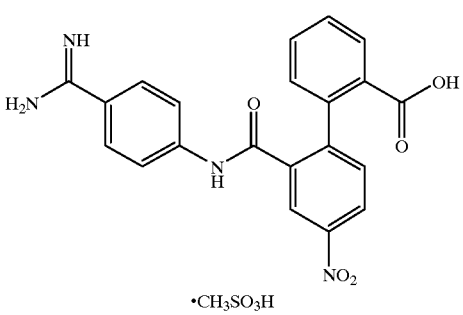

TLC: Rf 0.21 (Chloroform:Methanol:Acetic acid=10:2:1); NMR (d$_6$-DMSO): δ 13.0–12.5 (1H, broad), 10.77 (1H, s), 9.16 (2H, brs), 8.88 (2H, brs), 8.49 (1H, d, J=2.5 Hz), 8.39 (1H, dd, J=8.5 Hz, 2.5 Hz), 7.91 (1H, dd, J=8.0 Hz, 1.5 Hz), 7.76 (2H, d, J=9.0 Hz), 7.69 (2H, d, J=9.0 Hz), 7.59 (1H, td, J=8.0 Hz, 1.5 Hz), 7.58 (1H, d, J=8.5 Hz), 7.48 (1H, d, J=8.0 Hz, 1.5 Hz), 7.28 (1H, dd, J=8.0 Hz, 1.5 Hz), 2.34 (3H, s).

EXAMPLE 19(33)
2'-(4-amidinophenylcarbamoyl)-4-((carboxymethyl)carbamoyl)-2-biphenylcarboxylic acid methanesulfonate

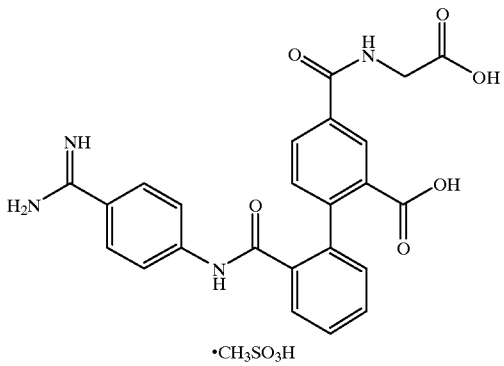

TLC: Rf 0.28 (Chloroform:Methanol:Water=6:4:1); NMR (d$_6$-DMSO): δ 10.54 (1H, s), 9.22 (2H, s), 9.07 (1H, br.t, J=5.6 Hz), 9.01 (2H, s), 8.35 (1H, d, J=1.2 Hz), 8.01 (1H, dd, J=1.2,7.6 Hz), 7.70–7.75 (5H, m), 7.50–7.62 (2H, m), 7.36 (1H, d, J=7.6 Hz), 7.30 (1H, d, J=7.6 Hz), 3.94 (2H, d, J=5.6 Hz), 2.42 (3H, s).

EXAMPLE 19(34)
2'-(4-amidinophenylcarbamoyl)-4-((1-carboxy-2-phenylethyl)carbamoyl)-2-biphenylcarboxylic acid methanesulfonate

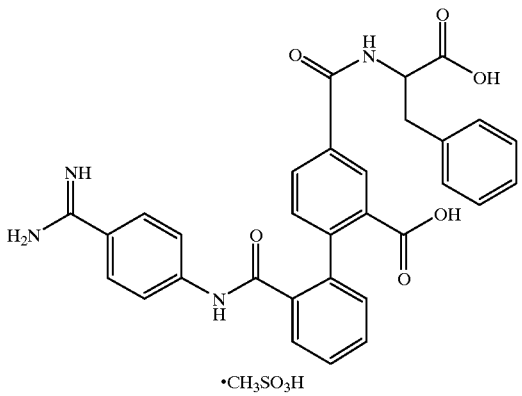

TLC: Rf 0.20 (Chloroform:Methanol:Water=7:3:0.3); NMR (d$_6$-DMSO): δ 10.53 (1H, s), 9.17 (2H, s), 8.95 (1H, d, J=5.0 Hz), 8.92 (2H, s), 8.28 (1H, d, J=1.6 Hz), 7.92 (1H, dd, J=1.6,8.0 Hz), 7.69–7.74 (5H, m), 7.53–7.58 (2H, m), 7.17–7.35 (7H, m), 4.64 (1H, m), 3.01–3.26 (2H, m), 2.39 (3H, s).

EXAMPLE 19(35)
2'-(4-amidinophenylcarbamoyl)-2-biphenylphosphoric acid methanesulfonate

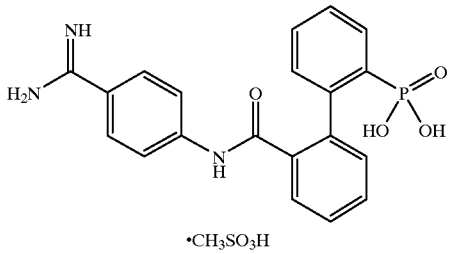

TLC: Rf 0.10 (Chloroform:Methanol:Acetic acid= 10:2:1); NMR (d$_6$-DMSO): δ 11.37 (1H, s), 9.10 (2H, brs), 8.85 (2H, brs), 7.87–7.74 (1H, m), 7.65 (2H, d, J=9.0 Hz), 7.59 (2H, d, J=9.0 Hz), 7.60–7.30 (5H, m), 7.26 (1H, dd, J=6.0 Hz, 3.0 Hz), 7.05–6.97 (1H, m), 2.33 (3H, s).

EXAMPLE 19(36)
2'-(4-amidinophenylcarbamoyl)-4-fluoro-2-biphenylcarboxylic acid methanesulfonate

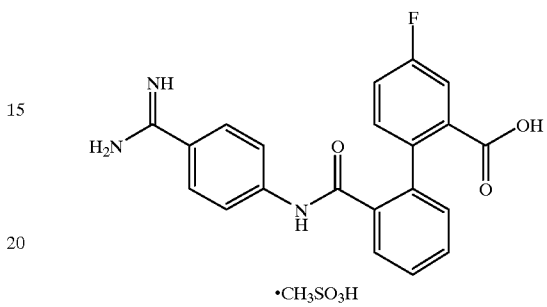

TLC: Rf 0.45 (Chloroform:Methanol:Water=7:3:0.3); NMR (d$_6$-DMSO): δ 10.45 (1H, s), 9.16 (2H, s), 8.84 (2H, s), 7.73 (4H, s), 7.67 (1H, dd, J=2.6,8.0 Hz), 7.50–7.61 (3H, m), 7.39 (1H, dt, J=2.6,8.0 Hz), 7.25–7.32 (2H, m), 2.36 (3H, s).

EXAMPLE 19(37)
2'-(4-amidinophenylcarbamoyl)-4-benzylcarbamoyl-2-biphenylcarboxylic acid methanesulfonate

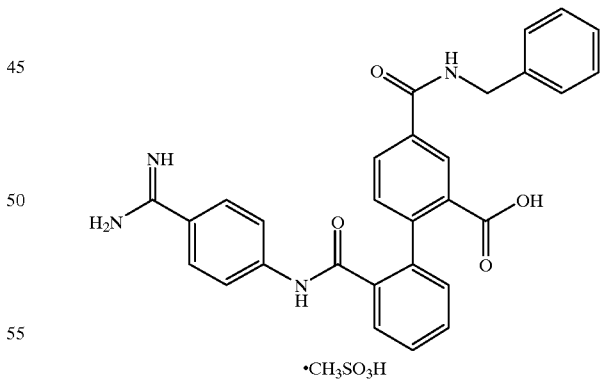

TLC: Rf 0.70 (Chloroform:Methanol:Water=7:3:0.3); NMR (d$_6$-DMSO): δ 10.54 (1H, s), 9.26 (1H, br.t, J=5.8 Hz), 9.17 (2H, s), 8.90 (2H, s), 8.37 (1H, d, J=1.8 Hz), 8.03 (1H, dd, J=1.8,8.0 Hz), 7.74 (4H, s), 7.71 (1H, dd, J=1.8,8.0 Hz), 7.53–7.59 (2H, m), 7.24–7.37 (7H, m), 4.48 (2H, d, J=5.8 Hz), 2.34 (3H, s).

EXAMPLE 19(38)

2'-(4-amidinophenylcarbamoyl)-4-phenylethylcarbamoyl-2-biphenylcarboxylic acid methanesulfonate

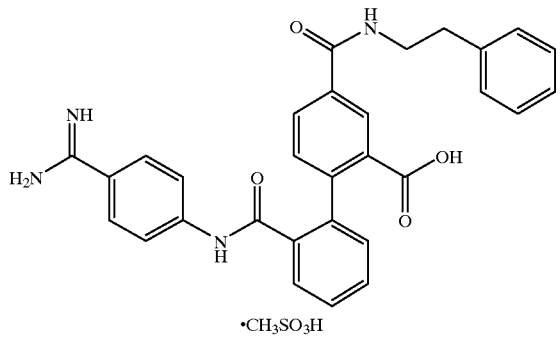

TLC: Rf 0.56 (Chloroform:Methanol:Water=7:3:0.3); NMR (d$_6$-DMSO): δ 10.52 (1H, s), 9.15 (2H, s), 8.83 (2H, s), 8.77 (1H, br.t, J=5.8 Hz), 8.30 (1H, d, J=1.8 Hz), 7.95 (1H, dd, J=1.8,8.0 Hz), 7.73 (4H, s), 7.70 (1H, dd, J=1.8,8.0 Hz), 7.52–7.59 (2H, m), 7.19–7.35 (7H, m), 3.50 (2H, m), 2.85 (2H, t, J=7.0 Hz), 2.34 (3H, s).

EXAMPLE 19(39)

2'-(4-amidinophenylcarbamoyl)-4-(2-methoxycarbonylethyl)-2-biphenylcarboxylic acid methanesulfonate

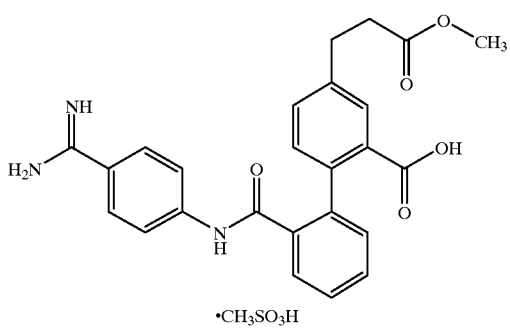

TLC: Rf 0.24 (Chloroform:Methanol=4:1); NMR (d$_6$-DMSO): δ 13.0–12.5 (1H, br), 10.41 (1H, s), 9.14 (2H, s), 8.82 (2H, s), 7.8–7.6 (6H, m), 7.6–7.4 (2H, m), 7.38–7.34 (1H, m), 7.25–7.21 (1H, m), 7.14 (1H, d, J=7.8 Hz), 3.56 (3H, s), 2.89 (2H, t, J=6.8 Hz), 2.64 (2H, t, J=6.8 Hz), 2.34 (3H, s).

EXAMPLE 19(40)

2'-(4-amidinophenylcarbamoyl)-4-(2-methoxyethoxy)-2-biphenylcarboxylic acid methanesulfonate

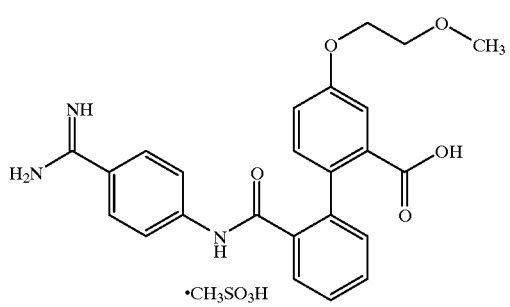

TLC: Rf 0.42 (Chloroform:Methanol:Acetic acid=10:2:1); NMR (d$_6$-DMSO): δ 13.8–12.5 (1H, br), 10.37 (1H, s), 9.13 (2H, br.s), 8.79 (2H, br.s), 7.80–7.55 (5H, m), 7.55–7.40 (2H, s), 7.30 (1H, d, J=2.4 Hz), 7.80–7.00 (3H, m), 4.11 (2H, t, J=4.4 Hz), 3.64 (2H, t, J=4.4 Hz), 3.28 (3H, s), 2.31 (3H, s).

EXAMPLE 19(41)

2'-(4-amidinophenylcarbamoyl)-4-((2-methylpropyl)carbamoyl)-2-biphenylcarboxylic acid methanesulfonate

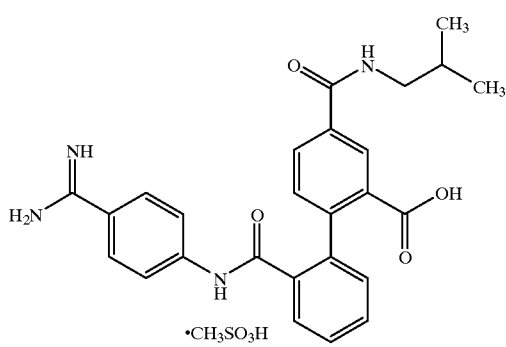

TLC: Rf 0.26 (Chloroform:Methanol:Water=8:2:0.2); NMR (d$_6$-DMSO): δ 10.53 (1H, s), 9.15 (2H, s), 8.85 (2H, s), 8.65 (1H, br.t, J=6.8 Hz), 8.31 (1H, d, J=1.8 Hz), 7.97 (1H, dd, J=1.8,7.8 Hz), 7.74 (4H, s), 7.70 (1H, dd, J=1.8,7.8 Hz), 7.52–7.59 (2H, m), 7.33 (1H, d, J=7.8 Hz), 7.28 (1H, dd, J=1.8,7.8 Hz), 3.09 (2H, br.t, J=6.8 Hz), 2.35 (3H, s), 1.85 (1H, m), 0.89 (6H, d, J=6.8 Hz).

EXAMPLE 19(42)

2'-(4-amidinophenylcarbamoyl)-4'-methoxy-4-((1-methoxycarbonyl-2-methylpropyl)carbamoyl)-2-biphenylcarboxylic acid methanesulfonate

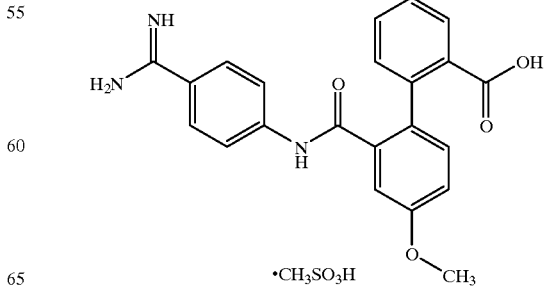

TLC: Rf 0.61 (Chloroform:Methanol:Water=7:3:0.3); NMR (d$_6$-DMSO): δ 10.53 (1H, s), 9.14 (2H, s), 8.82 (1H, d, J=7.8 Hz), 8.77 (2H, s), 8.31 (1H, d, J=1.6 Hz), 7.99 (1H, dd, J=1.6,8.0 Hz), 7.74 (4H, s), 7.32 (1H, d, J=8.0 Hz), 7.24 (1H, m), 7.13–7.19 (2H, m), 4.31 (1H, t, J=7.8 Hz), 3.89 (3H, s), 3.66 (3H, s), 2.32 (3H, s), 2.18 (1H, m), 0.98 (3H, d, J=6.6 Hz), 0.94 (3H, d, J=6.6 Hz).

EXAMPLE 19(43)

2'-(4-amidinophenylcarbamoyl)-4-trifluoromethoxy-2-biphenylcarboxylic acid methanesulfonate

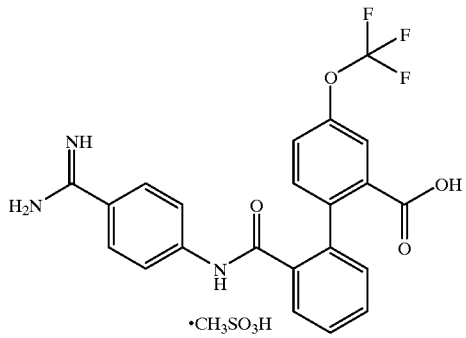

TLC: Rf 0.25 (Chloroform:Methanol:Water=8:2:0.2); NMR (d$_6$-DMSO): δ 10.5 (1H, s), 9.15 (2H, brs), 8.84 (2H, brs), 7.74–7.69 (6H, m), 7.59–7.53 (3H, m), 7.38 (1H, d, J=8.4 Hz), 7.33–7.28 (1H, m), 2.37 (3H, s).

EXAMPLE 19(44)

2-(3-(4-amidinophenylcarbamoyl)naphthalen-2-yl)-5-((1-methoxycarbonyl-2-methylpropyl)carbamoyl)benzoic acid methanesulfonate

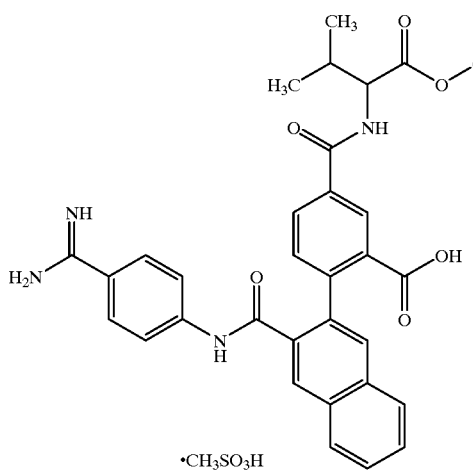

TLC: Rf 0.48 (Chloroform:Methanol:Water=8:2:0.2); NMR (d$_6$-DMSO): δ 10.78 (1H, s), 9.18 (2H, s), 8.89 (1H, d, J=7.6 Hz), 8.87 (2H, s), 8.40 (1H, d, J=1.8 Hz), 8.33 (1H, s), 8.01–8.14 (3H, m), 7.74–7.85 (5H, m), 7.64–7.69 (2H, m), 7.46 (1H, d, J=8.0 Hz), 4.34 (1H, t, J=7.6 Hz), 3.68 (3H, s), 2.35 (3H, s), 2.23 (1H, m), 1.00 (3H, d, J=7.0 Hz), 0.96 (3H, d, J=7.0 Hz).

EXAMPLE 19(45)

3-(2-(4-amidinophenylcarbamoyl)phenyl)-8-(2-methoxyethoxy)-2-naphthalenecarboxylic acid methanesulfonate

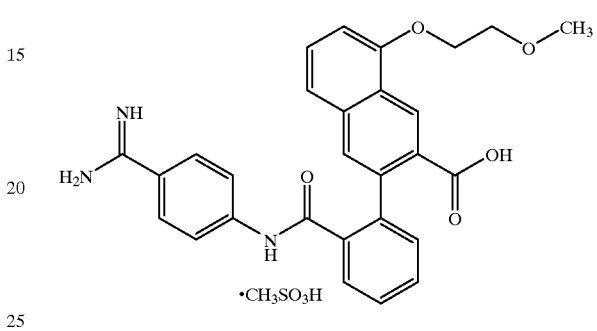

TLC: Rf 0.61 (Chloroform:Methanol:Acetic acid= 10:2:1); NMR (d$_6$-DMSO): δ 13.1–12.0 (1H, br), 10.44 (1H, s), 9.09(2H, brs), 8.80 (2H, brs), 8.67 (1H, s), 7.70 (1H, s), 7.67 (4H, likes), 7.7–7.4 (5H, m), 7.36 (1H, brd, J=7.8 Hz), 7.05 (1H, brd, J=5.4 Hz), 4.4–4.2 (2H, m), 3.9–3.7 (2H, m), 3.36 (3H, s), 2.32 (3H, s).

EXAMPLE 19(46)

2'-(4-amidinophenylcarbamoyl)-4-((isopropylcarbonyl)aminomethyl)-2-biphenylcarboxylic acid methanesulfonate

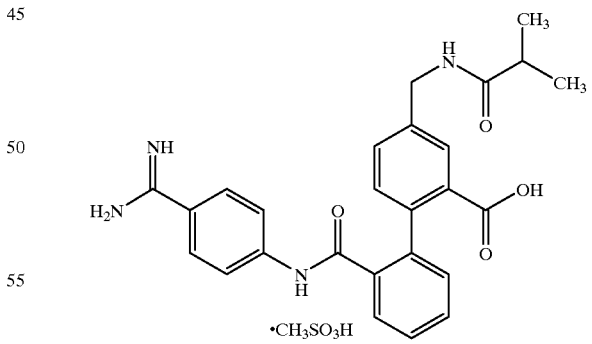

TLC: Rf 0.54 (Chloroform:Methanol:Water=8:2:0.1); NMR (d$_6$-DMSO): δ 10.5 (1H, s), 9.17 (2H, br s), 8.87 (2H, br s), 8.35 (1H, t, J=6.6 Hz), 7.78–7.64 (6H, m), 7.55–7.48 (2H, m), 7.36 (1H, dd, J=1.8, 8.0 Hz), 7.24–7.16 (2H, m), 4.30 (2H, d, J=6.0 Hz), 2.52–2.41 (1H, m ) 2.36 (3H, s), 1.04 (6H, d, J=7.0 Hz).

EXAMPLE 19(47)

2-(3-(4-amidinophenylcarbamoyl)naphthalen-2-yl)-5-((2-methylpropyl)carbamoyl)benzoic acid methanesulfonate

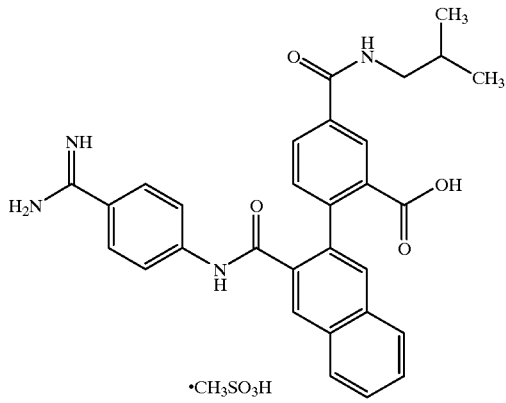

TLC: Rf 0.74 (Chloroform:Methanol:Water 7:3:0.3); NMR ($d_6$-DMSO): δ 10.76 (1H, s), 9.18 (2H, s), 8.86–8.93 (3H, m), 8.68 (1H, br.t, J=6.6 Hz), 8.36 (1H, s), 8.32 (1H, s), 8.00–8.14 (3H, m), 7.79 (4H, s), 7.63–7.68 (2H, m), 7.44 (1H, d, J=8.0 Hz), 3.11 (2H, br.t, J=6.6 Hz), 2.36 (3H, s), 1.88 (1H, m), 0.91 (6H, d, J=6.6 Hz).

EXAMPLE 19(48)

2'-(4-amidinophenylcarbamoyl)-4'-methoxy-4-((2-methylpropyl)carbamoyl)-2-biphenylcarboxylic acid methanesulfonate

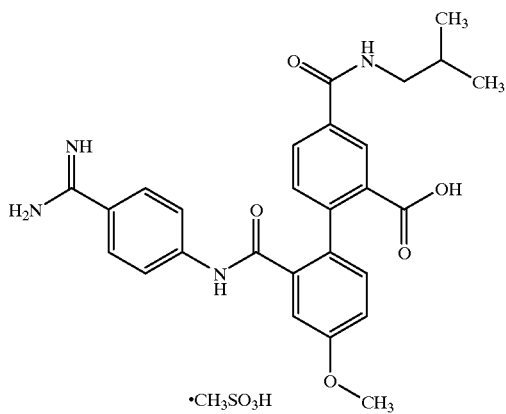

TLC: Rf 0.62 (Chloroform:Methanol:Water=7:3:0.3); NMR ($d_6$-DMSO): δ 10.51 (1H, s), 9.14 (2H, s), 8.83 (2H, s), 8.63 (1H, br.t, J=6.6 Hz), 8.28 (1H, d, J=2.0 Hz), 7.95 (1H, dd, J=2.0,8.0 Hz), 7.74 (4H, s), 7.30 (1H, d, J=8.0 Hz), 7.24 (1H, d, J=2.0 Hz), 7.21 (1H, d, J=8.0 Hz), 7.14 (1H, dd, J=2.0,8.0 Hz), 3.89 (3H, s), 3.09 (2H, t, J=6.6 Hz), 2.35 (3H, s), 1.85 (1H, m), 0.89 (6H, d, J=7.0 Hz).

EXAMPLE 19(49)

2'-(4-amidinophenylcarbamoyl)-4-isopropylcarbamoyl-2-biphenylcarboxylic acid methanesulfonate

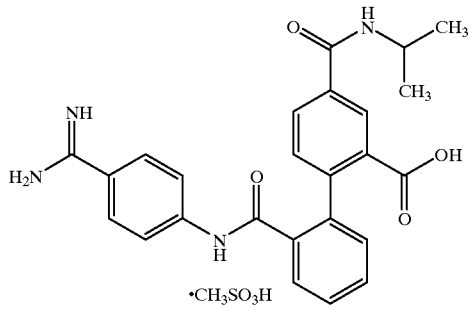

TLC: Rf 0.33 (Chloroform:Methanol:Acetic acid= 10:2:1); NMR ($d_6$-DMSO): δ 10.5 (1H, s), 9.16 (2H, br s), 8.86 (2H, br s), 8.43 (1H, d, J=7.6 Hz), 8.30 (1H, d, J=1.6 Hz), 7.97 (1H, dd, J=1.6, 8.0 Hz), 7.73–7.68 (5H, m), 7.59–7.52 (2H, m), 7.34–7.25 (2H, m), 4.20–4.02 (1H, m ), 2.34 (3H, s), 1.17 (6H, d, J=6.6 Hz).

EXAMPLE 19(50)

2'-(4-amidinophenylcarbamoyl)-4-((3-methylbutyl)carbamoyl)-2-biphenylcarboxylic acid methanesulfonate

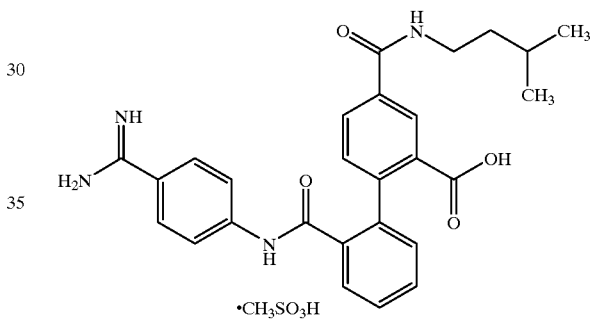

TLC: Rf 0.42 (Chloroform:Methanol:Acetic acid= 10:2:1); NMR ($d_6$-DMSO): δ 10.5 (1H, s), 9.14 (2H, brs), 8.83 (2H, brs), 8.61 (1H, t, J=6.0 Hz), 8.30 (1H, d, J=1.6 Hz), 7.96 (1H, dd, J=1.6, 8.0 Hz), 7.73–7.68 (5H, m), 7.62–7.53 (2H, m), 7.35–7.26 (2H, m), 3.34–3.24 (2H, m), 2.37 (3H, s), 1.69–1.53 (1H, m), 1.48–1.37 (2H, m), 0.90 (6H, d, J=6.2 Hz).

EXAMPLE 19(51)

2'-(4-amidinophenylcarbamoyl)-4-ethylcarbamoyl-2-biphenylcarboxylic acid methanesulfonate

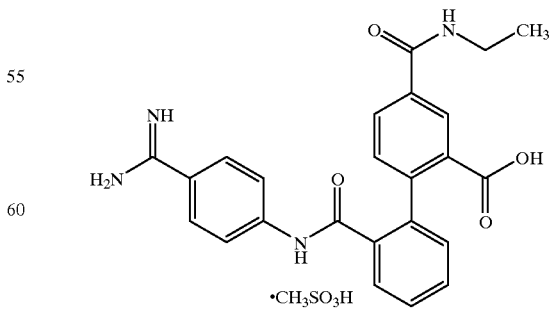

TLC: Rf 0.10 (Chloroform:Methanol:Acetic acid= 10:2:1); NMR ($d_6$-DMSO): δ 10.5 (1H, s), 9.17 (2H, br s), 8.86 (2H, br s), 8.66 (1H, t, J=5.4 Hz), 8.30 (1H, d, J=1.8 Hz), 7.97 (1H, dd, J=1.8, 7.6 Hz), 7.73–7.68 (5H, m), 7.59–7.52 (2H, m), 7.35–7.26 (2H, m), 3.36–3.23 (2H, m ), 2.36 (3H, s), 1.13 (3H, t, J=7.0 Hz).

EXAMPLE 19(52)

2'-(4-amidinophenylcarbamoyl)-4-butylcarbamoyl-2-biphenylcarboxylic acid methanesulfonate

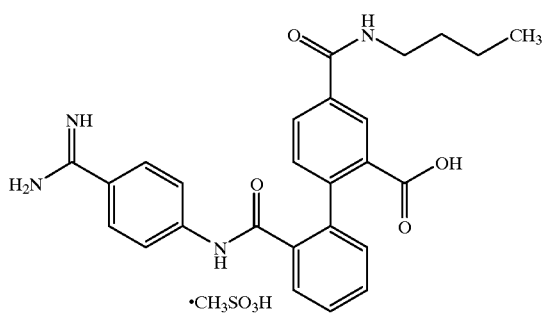

TLC: Rf 0.26 (Chloroform:Methanol:Acetic acid= 10:2:1); NMR (d$_6$-DMSO): δ 10.5 (1H, s), 9.16 (2H, br s), 8.85 (2H, br s), 8.63 (1H, t, J=5.4 Hz), 8.30 (1H, d, J=1.6 Hz), 7.97 (1H, dd, J=1.6, 8.2 Hz), 7.73–7.68 (5H, m), 7.58–7.53 (2H, m), 7.35–7.26 (2H, m), 3.32–3.22 (2H, m ),1.55–1.24 (4H, m), 2.36 (3H, s), 0.90 (3H, t, J=7.2 Hz).

EXAMPLE 19(53)

2'-(4-amidinophenylcarbamoyl)-4'-methyl-4-((2-methylpropyl)carbamoyl)-2-biphenylcarboxylic acid methanesulfonate

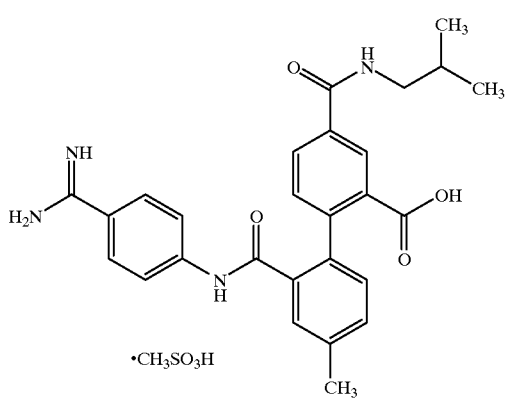

TLC: Rf 0.33 (Chloroform:Methanol:Water=8:2:0.2); NMR (d$_6$-DMSO): δ 10.51 (1H, s), 9.15 (2H, br.s), 8.83 (2H, br.s), 8.63 (1H, t, J=6.2 Hz), 8.29 (1H, d, J=1.8 Hz), 7.95 (1H, dd, J=1.8,8.0 Hz), 7.73 (4H, s), 7.51 (1H, s), 7.38 (1H, d, J=8.0 Hz), 7.29 (1H, d, J=8.0 Hz), 7.16 (1H, d, J=8.0 Hz), 3.09 (2H, t, J=6.2 Hz), 2.45 (3H, s), 2.36 (3H, s), 1.86 (1H, m), 0.89 (6H, d, J=6.6 Hz).

EXAMPLE 19(54)

2'-(4-amidinophenylcarbamoyl)-4-((cyclohexylmethyl)carbamoyl)-2-biphenylcarboxylic acid methanesulfonate

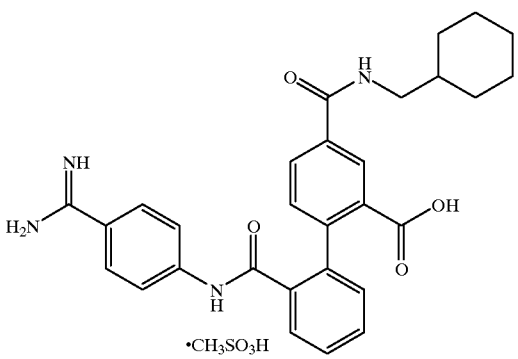

TLC: Rf 0.40 (Chloroform:Methanol:Acetic acid= 10:2:1); NMR (d$_6$-DMSO): δ 10.5 (1H, s), 9.17 (2H, br s), 8.87 (2H, br s), 8.60 (1H, t, J=5.4 Hz), 8.30 (1H, d, J=1.6 Hz), 7.97 (1H, dd, J=1.6, 8.0 Hz), 7.74–7.69 (5H, m), 7.62–7.50 (2H, m), 7.34–7.26 (2H, m), 3.11 (1H, t, J=5.8 Hz), 2.36 (3H, s), 1.8–1.40 (6H, m), 1.30–0.75 (5H, m).

EXAMPLE 19(55)

2'-(4-amidinophenylcarbamoyl)-4-((5-(t-butoxycarbonylamino)pentyl) carbamoyl)-2-biphenylcarboxylic acid methanesulfonate

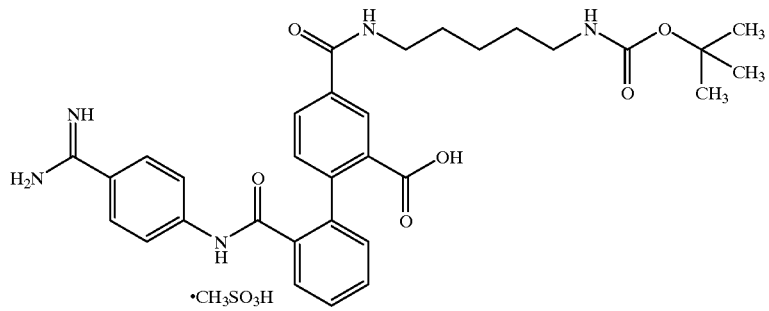

TLC: Rf 0.39 (Chloroform:Methanol:Acetic acid= 10:2:1); NMR (d₆-DMSO): δ 10.5 (1H, d, J=5.8 Hz), 9.17 (2H, br s), 8.86 (2H, m), 8.65 (1H, t, J=5.8 Hz), 8.30 (1H, s), 8.00–7.95 (1H, m), 7.74–7.60 (4H, m), 7.60–7.50 (2H, m), 7.35–7.25 (2H, m), 6.75 (1H, br s), 3.40–3.20 (2H, m), 3.00–2.70 (2H, m), 2.34 (3H, s), 1.60–1.20 (6H, m), 1.36 (9H, s).

EXAMPLE 19(56)

2'-(4-amidinophenylcarbamoyl)-4-((1-methylpropyl)carbamoyl)-2-biphenylcarboxylic acid methanesulfonate

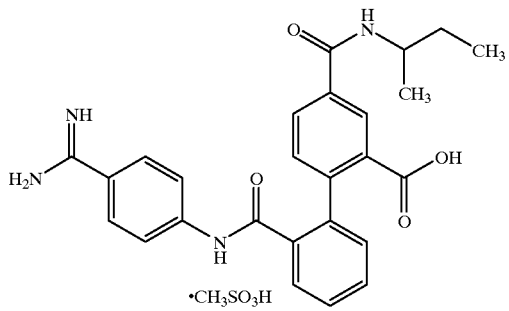

TLC: Rf 0.23 (Chloroform:Methanol:Acetic acid= 10:2:1); NMR (d₆-DMSO): δ 10.5 (1H, s), 9.18 (2H, br s), 8.89 (2H, br s), 8.36 (1H, d, J=8.2 Hz), 8.31 (1H, d, J=1.8 Hz), 7.98 (1H, dd, J=1.8, 8.2 Hz), 7.74–7.69 (4H, m), 7.59–7.52 (2H, m), 7.32 (1H, d, J=8.2 Hz), 7.30–7.26 (1H, m), 4.10–3.90 (1H, m), 2.37 (3H, s), 1.56–1.48 (2H, m), 1.14 (3H, d, J=6.6 Hz), 0.87 (3H, t, J=7.4 Hz.

EXAMPLE 19(57)

2'-(4-amidinophenylcarbamoyl)-4-((tetrahydropyran-4-ylmethyl)carbamoyl)-2-biphenylcarboxylic acid methanesulfonate

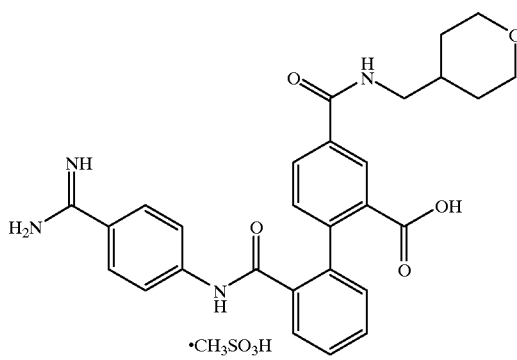

TLC: Rf 0.53 (Chloroform:Methanol:Water=7:3:0.3) NMR (d₆-DMSO): δ 13.3–12.5 (1H, broad), 10.54 (1H, s), 9.19 (2H, s), 8.95 (2H, s), 8.69 (1H, brt, J=6.0 Hz), 8.30 (1H, d, J=2.0 Hz), 7.97 (1H, dd, J=8.0 Hz, 2.0 Hz), 7.73 (4H, s), 7.70 (1H, dd, J=7.5 Hz, 1.5 Hz), 7.62–7.47 (2H, m), 7.32 (1H, d, J=8.0 Hz), 7.29–7.24 (1H, m), 3.83 (2H, dd, J=11 Hz, 2.5 Hz), 3.25 (2H, brt, J=11 Hz), 3.15 (2H, brt, J=6.0 Hz), 2.34 (3H, s), 1.90–1.65 (1H, m), 1.58 (2H, brd, J=13 Hz), 1.30–1.06 (2H, m).

EXAMPLE 19(58)

2'-(4-amidinophenylcarbamoyl)-4-((2-hydroxypropyl)carbamoyl)-2-biphenylcarboxylic acid methanesulfonate

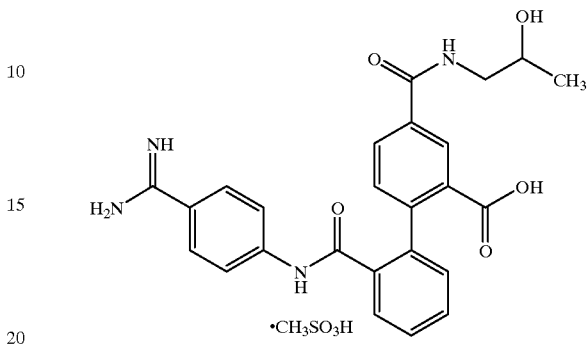

TLC: Rf 0.38 (Ethyl acetate:Acetic acid:Water=3:1:1); NMR (d₆-DMSO): δ 10.5 (1H, s), 9.17 (2H, br s), 8.87 (2H, br s), 8.61 (1H, t, J=5.6 Hz), 8.32 (1H, d, J=1.8 Hz), 7.99 (1H, dd, J=1.8, 7.6 Hz), 7.73–7.68 (5H, m), 7.62–7.52 (2H, m), 7.35–7.26 (2H, m), 4.20–3.60 (1H, br s), 3.90–3.70 (1H, m), 3.22 (2H, d, J=5.6 Hz), 2.36 (3H, s), 1.07 (3H, d, J=6.2 Hz).

EXAMPLE 19(59)

2'-(4-amidino-2-hydroxyphenylcarbamoyl)-4-((2-methylpropyl)carbamoyl)-2-biphenylcarboxylic acid methanesulfonate

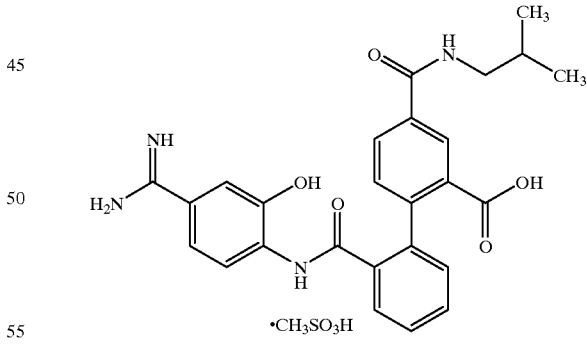

TLC: Rf 0.16 (Chloroform:Methanol:Acetic acid= 10:2:1); NMR (d₆-DMSO): δ 13.6–13.0 (1H, broad), 10.56 (1H, s), 9.08 (2H, brs), 8.91 (1H, s), 8.81 (2H, brs), 8.67 (1H, brt, J=5.5 Hz), 8.35 (1H, d, J=2.0 Hz), 8.20 (1H, d, J=8.5 Hz), 7.95 (1H, dd, J=8.5 Hz, 2.0 Hz), 7.77–7.71 (1H, m), 7.58–7.48 (2H, m), 7.28 (1H, d, J=8.5 Hz), 7.20–7.11 (2H, m), 7.08 (1H, d, J=2.0 Hz), 3.06 (2H, brt, J=6.0 Hz), 2.33 (3H, s), 1.93–1.73 (1H, m), 0.87 (6H, d, J=6.5 Hz).

EXAMPLE 19(60)

2'-(4-amidinophenylcarbamoyl)-4-(N-methyl-N-(2-methylpropyl)carbamoyl)-2-biphenylcarboxylic acid methanesulfonate

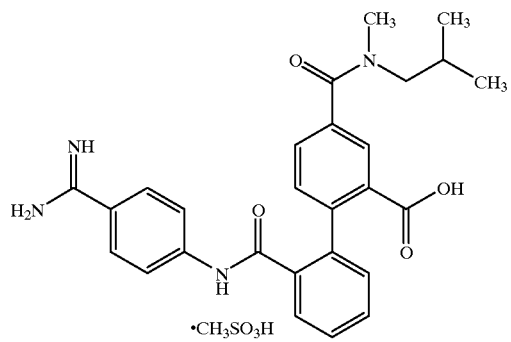

TLC: Rf 0.11 (Chloroform:Methanol:Acetic acid= 10:2:1); NMR (d$_6$-DMSO): δ 10.5 (1H, s), 9.17 (2H, brs), 8.91 (2H, brs), 7.73–7.40 (9H, m), 7.31 (2H, d, J=7.8 Hz), 3.30–2.94 (2H, m, rotamers), 2.94 (3H, s, each of rotamers), 2.84 (3H, s, each of rotamers), 2.39 (3H, s, each of rotamers), 2.38 (3H, s, each of rotamers), 0.91 (6H, d, J=6.6 Hz, each of rotamers), 0.62 (6H, m, each of rotamers).

EXAMPLE 19 (61)

2'-(4-amidinophenylcarbamoyl)-4-((2-methyl-1-(methylaminomethyl)propyl) carbamoyl)-2-biphenylcarboxylic acid dimethanesulfonate

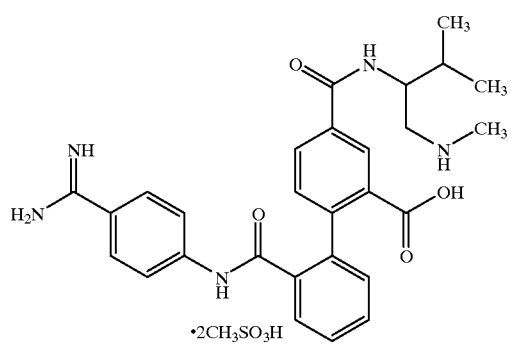

TLC: Rf 0.36 (Ethyl acetate:Acetic acid:Water=3:1:1); NMR (d$_6$-DMSO): δ 13.0–12.0 (1H, br), 10.62 (1H, s), 9.18 (2H, br.s), 8.96 (2H, br.s), 8.49 (1H, d, J=8.8 Hz), 8.6–8.3 (2H, br), 8.35 (1H, d, J=1.4 Hz), 8.03 (1H, dd, J=1.4, 8.0 Hz), 7.8–7.6 (1H, m), 7.75 (4H, like s), 7.55 (2H, m), 7.35 (1H, d, J=8.0 Hz), 7.25 (1H, dd, J=1.4, 6.8 Hz), 4.13 (1H, m), 3.3–2.9 (2H, br), 2.53 (3H, br.t, J=5.0 Hz), 2.36 (6H, s), 1.83 (1H, m), 0.92 (3H, d, J=6.4 Hz), 0.88 (3H, d, J=6.4 Hz).

EXAMPLE 19(62)

2'-(4-amidinophenylcarbamoyl)-4-((2-hydroxy-2-methylpropyl)carbamoyl)-2-biphenylcarboxylic acid methanesulfonate

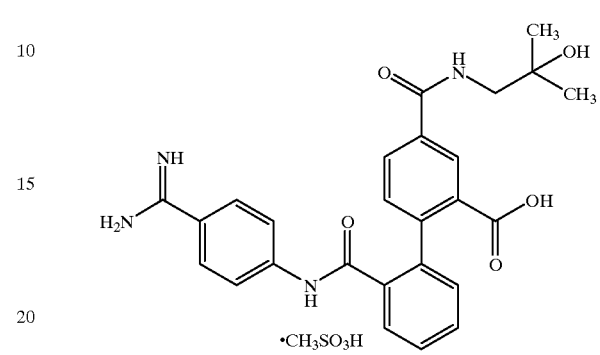

TLC: Rf 0.10 (Chloroform:Methanol:Water=8:2:0.1); NMR (d$_6$-DMSO): δ 10.5 (1H, s), 9.16 (2H, br s), 8.85 (2H, br s), 8.47 (1H, t, J=5.8 Hz), 8.32 (1H, d, J=1.8 Hz), 8.01 (1H, dd, J=1.8, 8.0 Hz), 7.74–7.69 (5H, m), 7.59–7.53 (2H, m), 7.35–7.26 (2H, m), 3.26 (2H, d, J=5.8 Hz), 2.35 (3H, s), 1.11 (6H, s).

EXAMPLE 19(63)

2'-(4-amidino-2-methylphenylcarbamoyl)-4-((2-methylpropyl)carbamoyl)-2-biphenylcarboxylic acid methanesulfonate

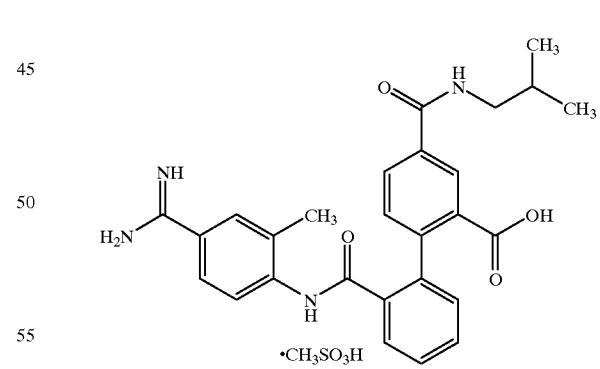

TLC: Rf 0.28 (Chloroform:Methanol:Acetic acid= 10:2:1); NMR (d$_6$-DMSO): δ 13.5–12.6 (1H, broad), 9.49 (1H, s), 9.18 (2H, brs), 8.94 (2H, brs), 8.67 (1H, brt, J=6.0 Hz), 8.30 (1H, d, J=1.5 Hz), 7.99 (1H, dd, J=8.0 Hz, 1.5 Hz), 7.75–7.70 (1H, m), 7.62–7.50 (5H, m), 7.36 (1H, d, J=8.0 Hz), 7.27–7.22 (1H, m), 3.08 (2H, brt, J=6.0 Hz), 2.32 (3H, s), 2.03 (3H, s), 1.96–1.74 (1H, m), 0.87 (6H, d, J=7.0 Hz).

EXAMPLE 19(64)

2'-(4-amidinophenylcarbamoyl)-4-((cyclopropylmethyl) carbamoyl)-2-biphenylcarboxylic acid methanesulfonate

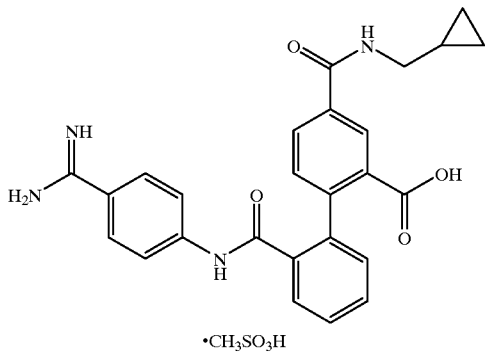

TLC: Rf 0.51 (Chloroform:Methanol:Water=7:3:0.3); NMR (d$_6$-DMSO): δ 10.52 (1H, s), 9.16 (2H, s), 8.77 (2H, s), 8.76 (1H, br.t, J=6.2 Hz), 8.32 (1H, d, J=2.0 Hz), 7.98 (1H, dd, J=2.0,8.0 Hz), 7.73 (4H, s), 7.70 (1H, dd, J=2.0,8.0 Hz), 7.58 (1H, dt, J=2.0,8.0 Hz), 7.53 (1H, dt, J=2.0,8.0 Hz), 7.33 (1H, d, J=8.0 Hz), 7.28 (1H, dd, J=2.0,8.0 Hz), 3:15 (2H, t, J=6.2 Hz, 2.35 (3H, s), 1.04 (1H, m), 0.40–0.48 (2H, m), 0.19–0.27 (2H, m).

EXAMPLE 19(65)

2'-(4-amidinophenylcarbamoyl)-4-((1-methylcarbamoyl-2-methylpropyl) carbamoyl)-2-biphenylcarboxylic acid methanesulfonate

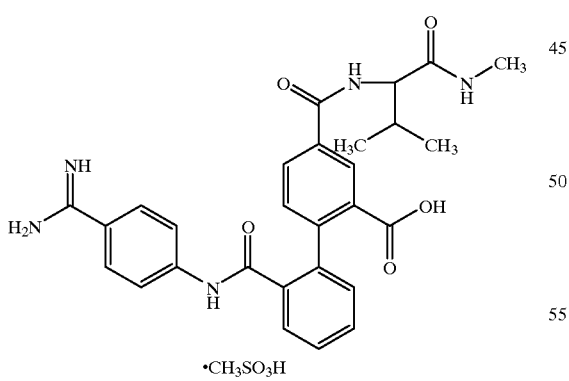

TLC: Rf 0.15 (Chloroform:Methanol:Acetic acid= 10:2:1); NMR (d$_6$-DMSO): δ 9.07 (4H, br s), 8.37 (1H, d, J=8.0 Hz), 8.06 (1H, s), 7.98 (1H, d, J=4.6 Hz), 7.74–7.57 (6H, m), 7.48–7.44 (2H, m), 7.07–7.02 (1H, m), 6.98 (1H, d, J=8.0 Hz), 4.15 (1H, t, J=8.2 Hz), 2.56 (3H, d, J=4.4 Hz), 2.32 (3H, s) 2.15–1.98 (1H, m), 0.88–0.83 (6H, m).

EXAMPLE 19(66)

2'-(4-amidinophenylcarbamoyl)-4-((cyclopentylmethyl) carbamoyl)-2-biphenylcarboxylic acid methanesulfonate

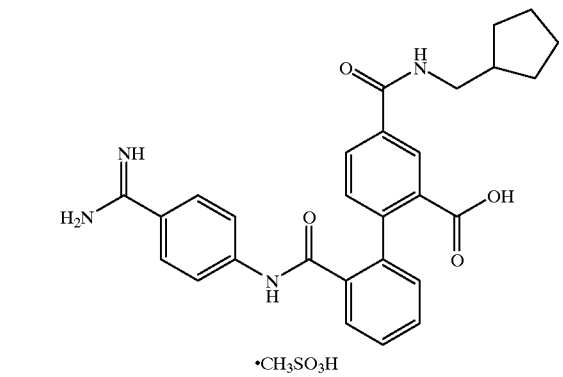

TLC: Rf 0.31 (Chloroform:Methanol:Acetic acid= 10:2:1); NMR (d$_6$-DMSO): δ 10.52 (1H, s), 9.16 (2H, s), 8.83 (2H, s), 8.66 (1H, br.d, J=6.2 Hz), 8.30 (1H, d, J=1.8 Hz), 7.97 (1H, dd, J=1.8,8.0 Hz), 7.73 (4H, s), 7.71 (1H, dd, J=1.8,8.0 Hz), 7.53–7.58 (2H, m), 7.32 (1H, d, J=8.0 Hz), 7.27 (1H, dd, J=1.8,8.0 Hz), 3.19 (2H, t, J=6.2 Hz), 2.35 (3H, s), 2.16 (1H, m), 1.53–1.69 (6H, m), 1.22–1.24 (2H, m).

EXAMPLE 19(67)

2'-(4-amidinophenylcarbamoyl)-4-((cyclobutylmethyl) carbamoyl)-2-biphenylcarboxylic acid methanesulfonate

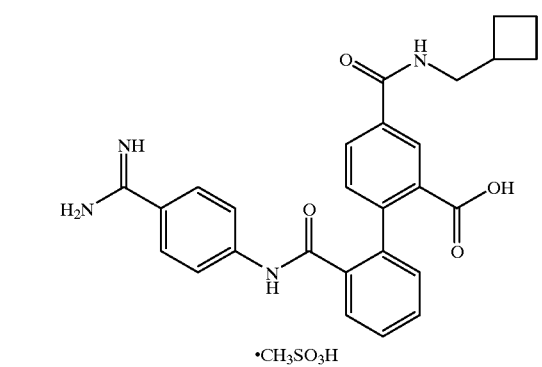

TLC: Rf 0.27 (Chloroform:Methanol:Acetic acid= 10:2:1); NMR (d$_6$-DMSO): δ 10.53 (1H, s), 9.17 (2H, s), 8.87 (2H, s), 8.64 (1H, br.d, J=6.6 Hz), 8.30 (1H, d, J=1.8 Hz), 7.96 (1H, dd, J=1.8,8.0 Hz), 7.74 (4H, s), 7.71 (1H, dd, J=1.8,8.0 Hz), 7.53–7.58 (2H, m), 7.32 (1H, d, J=8.0 Hz), 7.27 (1H, dd, J=1.8,8.0 Hz), 3.30 (2H, t, J=6.6 Hz), 2.58 (1H, m), 2.35 (3H, s), 1.66–2.00 (6H, m).

EXAMPLE 19(68)

2'-(4-amidinophenylcarbamoyl)-4-((2-methylpropyl)sulfamoyl)-2-biphenylcarboxylic acid methanesulfonate

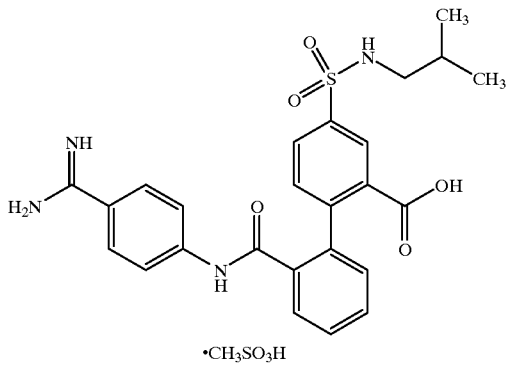

TLC: Rf 0.38 (Chloroform:Methanol:Water=8:2:0.1); NMR (d$_6$-DMSO): δ 10.6 (1H, br s), 9.14 (2H, br s), 8.79 (2H, br s), 8.20 (1H, d, J=1.8 Hz), 7.89 (1H, dd, J=1.8, 8.2 Hz), 7.80–7.62 (5H, m), 7.62–7.50 (2H, m), 7.45 (1H, d, J=8.2 Hz), 7.33–7.29 (1H, m), 2.60–2.40 (2H, m), 2.30 (3H, s), 1.70–1.50 (1H, m), 0.78 (6H, d, J=6.6 Hz).

EXAMPLE 19(69)

2'-(4-amidinophenylcarbamoyl)-5-chloro-2-biphenylcarboxylic acid methanesulfonate

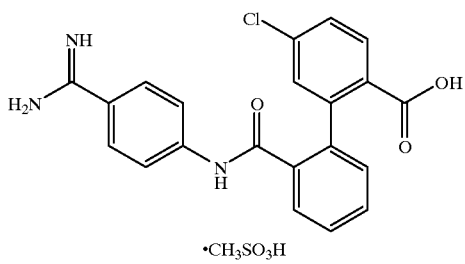

TLC: Rf 0.25 (Chloroform:Methanol:Acetic acid=10:2:1); NMR (d$_6$-DMSO): δ 13.2–12.4 (1H, broad), 10.50 (1H, s), 9.14 (2H, s), 8.87 (2H, s), 7.90–7.40 (9H, m), 7.40–7.26 (2H, m), 2.35 (3H, s).

EXAMPLE 19(70)

3-(2-(4-amidinophenylcarbamoyl)phenyl)-2-naphthalenecarboxylic acid methanesulfonate

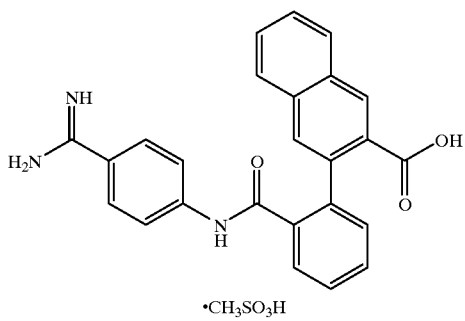

TLC: Rf 0.52 (Ethyl acetate:Acetic acid:Water=3:1:0.5); NMR (d$_6$-DMSO): δ 10.44 (1H, s), 9.09 (2H, br.s), 8.78 (2H, br.s), 8.46 (1H, s), 8.07 (1H, d, J=8.0 Hz), 7.92 (1H, d, J=8.0 Hz), 7.76 (1H, s), 7.8–7.5 (9H, m), 7.36 (1H, d, J=8.0 Hz), 4.31 (1H, br), 2.35 (3H, s).

EXAMPLE 19(71)

2'-(3-amidinophenylcarbamoyl)-2-biphenylcarboxylic acid methanesulfonate

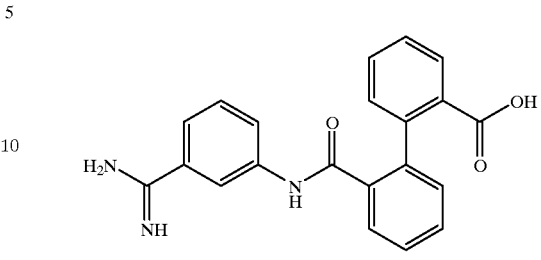

TLC: Rf 0.50 (Chloroform:Methanol:Water=7:3:0.3); NMR (d$_6$-DMSO): δ 10.37 (1H, s), 9.27 (2H, s), 8.93 (2H, s), 8.05 (1H, s), 7.83 (1H, d, J=7.8 Hz), 7.63–7.67 (2H, m), 7.48–7.54 (4H, m), 7.37–7.46 (2H, m), 7.22–7.25 (2H, m), 2.35 (3H, s).

EXAMPLE 19(72)

2-(2-(4-amidinophenylcarbamoyl)phenyl)cinnamic acid methanesulfonate

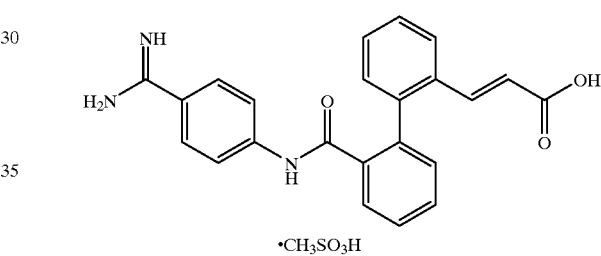

TLC: Rf 0.17 (Chloroform:Methanol:Acetic acid=10:2:1); NMR (d$_6$-DMSO): δ 12.6–12.0 (1H, broad), 10.68 (1H, s), 9.14 (2H, brs), 8.86 (2H, brs), 7.85–7.59 (8H, m), 7.45–7.24 (5H, m), 6.38 (1H, d, J=16 Hz), 2.34 (3H, s).

EXAMPLE 19(73)

2'-(4-amidinophenylcarbamoyl)biphenyl-2-yloxyacetic acid methanesulfonate

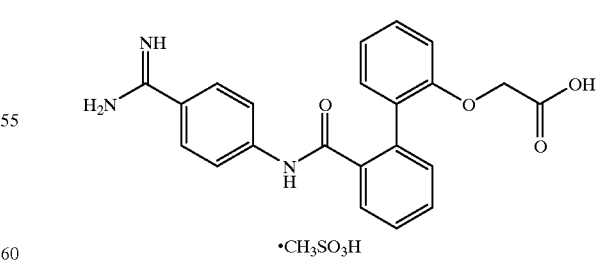

TLC: Rf 0.10 (Chloroform:Methanol:Acetic acid=10:2:1); NMR (d$_6$-DMSO): δ 13.3–12.6 (1H, broad), 10.42 (1H, s), 9.15 (2H, brs), 8.87 (2H, brs), 7.75 (4H, s), 7.65–7.44 (4H, m), 7.28–7.21 (2H, m), 6.98 (1H, t, J=8.0 Hz), 6.84 (1H, d, J=8.0 Hz), 4.45 (2H, s), 2.35 (3H, s).

EXAMPLE 19(74)

3-(2-(4-amidinophenylcarbamoyl)-4-methylphenyl)-2-naphthaleneoarboxylic acid methanesulfonate

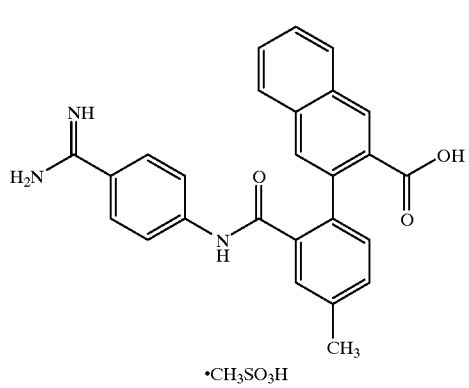

TLC: Rf 0.17 (Chloroform:Methanol:Acetic acid= 4:1:0.1); NMR (d$_6$DMSO): δ 13.0–12.6 (1H, br), 10.44 (1H, s), 9.09 (2H, s), 8.74 (2H, s), 8.45 (1H, s), 8.06 (1H, d, J=6.4 Hz), 7.92 (1H, d, J=8.8 Hz), 7.8–7.5 (5H, m), 7.73 (1H, s), 7.66 (2H, s), 7.40 (1H, d, J=8.4 Hz), 7.25 (1H, d, J=8.0 Hz), 2.46 (3H, s), 2.33 (3H, s).

EXAMPLE 19(75)

1-(2-(4-amidinophenylcarbamoyl)phenyl)-2-naphthalenecarboxylic acid methanesulfonate

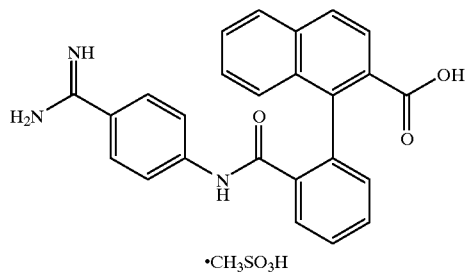

TLC: Rf 0.14 (Chloroform:Methanol:Acetic acid= 10:2:1); NMR (d$_6$-DMSO): δ 13.3–12.7 (1H, broad), 10.50 (1H, s), 9.09 (2H, brs), 8.81 (2H, brs), 7.99–7.95 (2H, m), 7.91–7.81 (2H, m), 7.67–7.51 (7H, m), 7.42 (1H, t, J=8.0 Hz), 7.26–7.20 (2H, m), 2.33 (3H, s).

EXAMPLE 19(76)

2-(3-(4-amidinophenylcarbamoyl)-6-methoxynaphthalen-2-yl)benzoic acid methanesulfonate

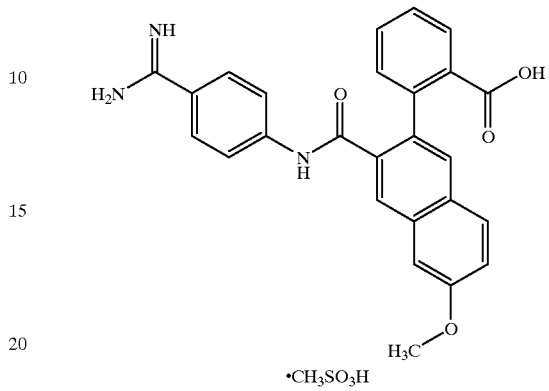

TLC: Rf 0.38 (Chloroform:Methanol:Water=10:3:0.2); NMR (d$_6$-DMSO): δ 12.62 (1H, br.s), 10.58 (1H, br.s), 9.14 (2H, br.s), 8.78 (2H, br.s), 8.15 (1H, s), 7.91 (1H, d, J=9.2 Hz), 7.84 (1H, d, J=7.8 Hz), 7.74 (4H, like s), 7.71 (1H, s), 7.6–7.2 (5H, m), 3.91 (3H, s), 2.31 (3H, s).

EXAMPLE 19(77)

3-(2-(4-amidinophenylcarbamoyl)-4-methoxyphenyl)-2-naphthalenecarboxylic acid methanesulfonate

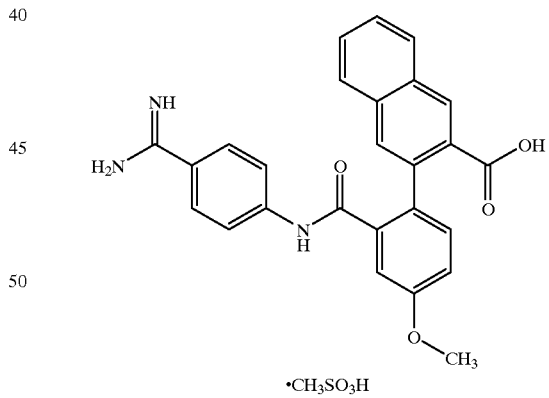

TLC: Rf 0.20 (Chloroform:Methanol:Acetic acid= 10:2:1); NMR (d$_6$-DMSO): δ 12.8 (1H, brs), 10.46 (1H, s), 9.10 (2H, brs), 8.82 (2H, brs), 8.43 (1H, s), 8.08–8.03 (1H, m), 7.94–7.88 (1H, m), 7.74–7.52 (7H, m), 7.28 (1H, d, J=8.0 Hz), 7.24 (1H, d, J=3.0 Hz), 7.15 (1H, dd, J=8.0 Hz, 3.0 Hz), 3.89 (3H, s), 2.33 (3H, s).

EXAMPLE 19(78)

3-(2-(4-amidinophenylcarbamoyl)-4-propoxyphenyl)-2-naphthalenecarboxylic acid methanesulfonate

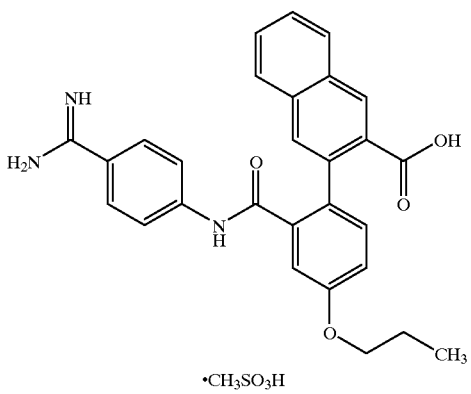

TLC: Rf 0.18 (Chloroform:Methanol:Acetic acid= 10:2:1); NMR (d$_6$-DMSO): δ 12.8 (1H, brs), 10.45 (1H, s), 9.10 (2H, brs), 8.83 (2H, brs), 8.43 (1H, s), 8.08–8.02 (1H, m), 7.94–7.89 (1H, m), 7.73 (1H, s), 7.67 (4H, s), 7.62–7.56 (2H, m), 7.26 (1H, d, J=8.0 Hz), 7.23 (1H, d, J=2.5 Hz), 7.14 (1H, dd, J=8.0 Hz, 2.5 Hz), 4.06 (2H, t, J=7.0 Hz), 2.34 (3H, s), 1.79 (2H, sextet, J=7.0 Hz), 1.03 (3H, t, J=7.0 Hz).

EXAMPLE 19(79)

2-(3-(4-amidinophenylcarbamoyl)-7-methoxynaphthalen-2-yl)benzoic acid methanesulfonate

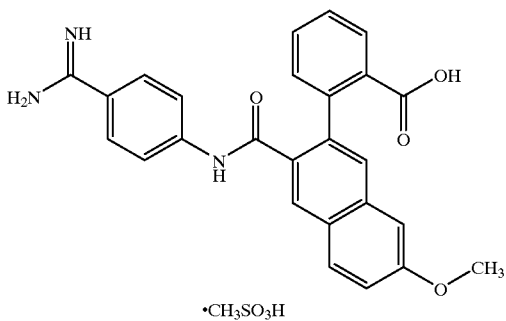

TLC: Rf 0.23 (Chloroform:Methanol:Water=10:3:0.2); NMR (d$_6$-DMSO): δ 12.6–11.9 (1H, br), 10.57 (1H, s), 9.15 (2H, br.s), 8.82 (2H, br.s), 8.20 (1H, s), 8.00 (1H, d, J=8.8 Hz), 7.85 (1H, d, J=7.4 Hz), 7.9–7.6 (5H, m), 7.55 (1H, m), 7.5–7.3 (2H, m), 7.4–7.1 (2H, m), 3.89 (3H, m), 2.33 (3H, s).

EXAMPLE 19(80)

2-(3-(4-amidinophenylcarbamoyl)-5-methoxynaphthalen-2-yl)benzoic acid methanesulfonate

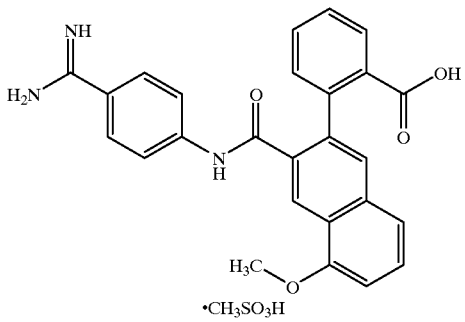

TLC: Rf 0.41 (Chloroform:Methanol:Water=10:3:0.2); NMR (d$_6$-DMSO): δ 12.70 (1H, br), 10.66 (1H, s), 9.16 (2H, br.s), 8.87 (2H, br.s), 8.44 (1H, s), 7.86 (1H, dd, J=1.4, 7.8 Hz), 7.75 (4H, s), 7.6–7.5 (4H, m), 7.43 (1H, dt, J=1.4, 7.8 Hz), 7.32 (1H, dd, J=1.4, 7.8 Hz), 7.09 (1H, m), 4.04 (3H, s), 2.34 (3H, s).

EXAMPLE 19(81)

2'-(4-amidinophenylcarbamoyl)-4-nitro-2-biphenylcarboxylic acid methanesulfonate

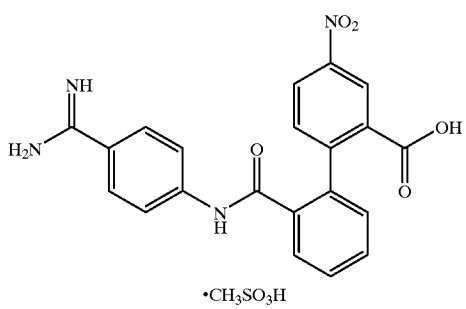

TLC: Rf 0.13 (Chloroform:Methanol:Acetic acid= 10:2:1); NMR (d$_6$-DMSO): δ 13.5–12.8 (1H, broad), 10.68 (1H, s), 9.15 (2H, brs), 8.87 (2H, brs), 8.56 (1H, d, J=2.5 Hz), 8.37 (1H, dd, J=8.0 Hz, 2.5 Hz), 7.81–7.70 (5H, m), 7.66–7.54 (2H, m), 7.53 (1H, d, J=8.0 Hz), 7.34–7.29 (1H, m), 2.35 (3H, s).

EXAMPLE 19(82)

2'-(4-amidinophenylcarbamoyl)-4-methylsulfonylamino-2-biphenylcarboxylic acid methanesulfonate

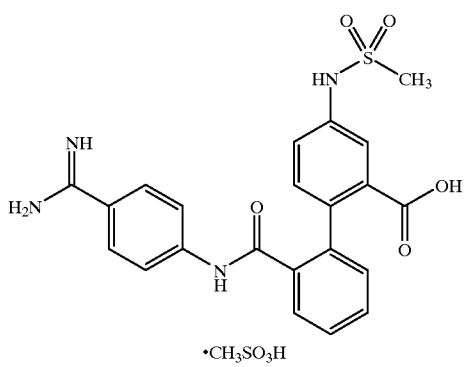

TLC: Rf 0.33 (Chloroform:Methanol:Water=7:3:0.3); NMR (d$_6$-DMSO): δ 10.40 (1H, s), 9.98 (1H, s), 9.14 (2H, brs), 8.89 (2H, brs), 7.74 (2H, d, J=9.0 Hz), 7.67 (2H, d, J=9.0 Hz), 7.66–7.60 (2H, m), 7.58–7.43 (2H, m), 7.32 (1H, dd, J=8.0 Hz, 2.0 Hz), 7.23 (1H, dd, J=8.0 Hz, 2.0 Hz), 7.20 (1H, d, J=8.0 Hz), 2.96 (3H, s), 2.34 (3H, s).

EXAMPLE 19(83)

2'-(4-amidinophenylcarbamoyl)-4-chloro-2-biphenylcarboxylic acid methanesulfonate

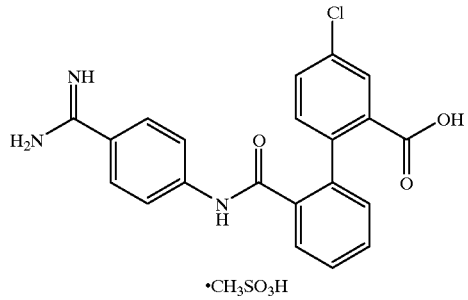

TLC: Rf 0.49 (Chloroform:Methanol:Water=7:3:0.3); NMR (d$_6$-DMSO): δ 10.52 (1H, s), 9.15 (2H, s), 8.86 (2H, s), 7.81 (1H, d, J=2.0 Hz), 7.74 (4H, s), 7.69 (1H, dd, J=2.0,7.6 Hz), 7.53–7.62 (3H, m), 7.27 (1H, dd, J=2.0,7.6 Hz), 7.26 (1H, d, J=7.6 Hz), 2.33 (3H, s).

EXAMPLE 19(84)

2'-(4-amidinophenylcarbamoyl)biphenyl-2-ylacetic acid methanesulfonate

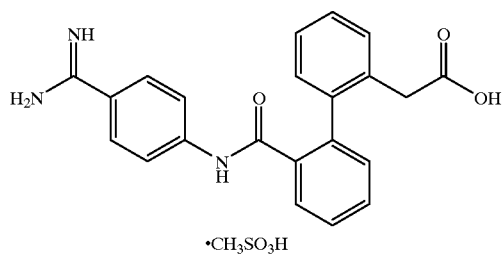

TLC: Rf 0.33 (Chloroform:Methanol:Acetic acid= 10:2:1); NMR (d$_6$-DMSO): δ 12.7–12.4 (1H, broad), 10.26 (1H, s), 9.14 (2H, brs), 8.91 (2H, brs), 7.72–7.65 (3H, m), 7.60–7.48 (4H, m), 7.39–7.32 (2H, m), 7.29–7.08 (3H, m), 3.77 (1H, d, J=17 Hz), 3.55 (1H, d, J=17 Hz), 2.33 (3H, s).

EXAMPLE 19(85)

2'-(4-amidinophenylcarbamoyl)-5-nitro-2-biphenylcarboxylic acid methanesulfonate

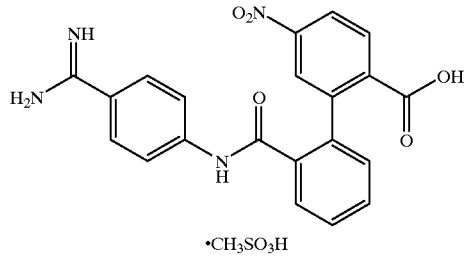

TLC: Rf 0.24 (Chloroform:Methanol:Water=8:2:0.1); NMR (d$_6$-DMSO): δ 10.6 (1H, s), 9.15 (2H, br s), 8.84 (2H, br s), 8.26 (1H, dd, J=2.6, 8.4 Hz), 8.07–8.02 (2H, m), 7.85–7.58 (7H, m), 7.38 (1H, dd, J=2.2, 7.8 Hz), 2.39 (3H, s).

EXAMPLE 19(86)

Benzyl 2'-(4-amidinophenylcarbamoyl)-4-methylaminomethyl-2-biphenylcarboxylic acid ditrifluoroacetate

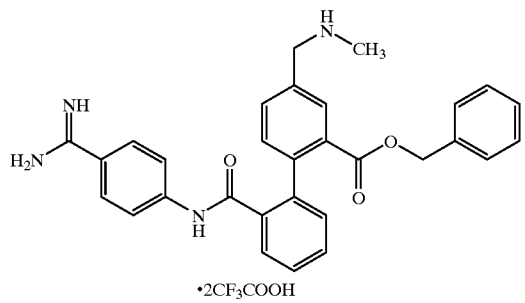

TLC: Rf 0.57 (Chloroform:Methanol:Water=7:3:0.3); NMR (CD$_3$OD): δ 8.02 (1H, d, J=1.6 Hz), 7.64–7.70 (6H, m), 7.54 (1H, dt, J=1.6,7.6 Hz), 7.50 (1H, dt, J=1.6,7.6 Hz), 7.42 (1H, d, J=8.0 Hz), 7.23–7.28 (4H, m), 7.10–7.15 (2H, m), 5.11 (2H, s), 4.23 (2H, s), 2.70 (3H, s).

EXAMPLE 19(87)

2'-(4-amidinophenylcarbamoyl)-4-ethoxycarbonylmethoxy-2-biphenyl carboxylic acid methanesulfonate

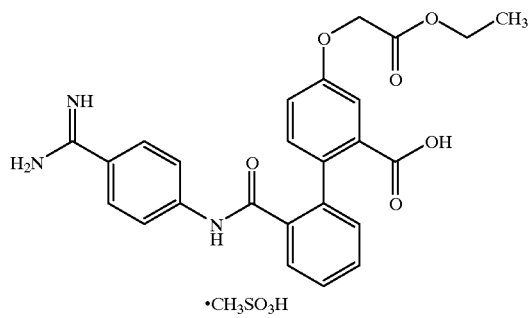

TLC: Rf 0.31 (Chloroform:Methanol:Water=10:3:0.2); NMR (d$_6$-DMSO): δ 13.4–12.4 (1H, br), 10.67 (1H, br.s), 9.21 (2H, br.s), 9.05 (2H, br.s), 7.8–7.5 (5H, m), 7.6–7.4 (2H, m), 7.3–7.0 (4H, m), 4.82 (2H, s), 4.14 (2H, q, J=7.4 Hz), 2.34 (3H, s), 1.17 (3H, t, J=7.4 Hz).

EXAMPLE 19(88)

2'-(4-amidinophenylcarbamoyl)-4-((1-methoxycarbonyl-2-methylpropyl) carbamoyl)-2-biphenylcarboxylic acid methanesulfonate

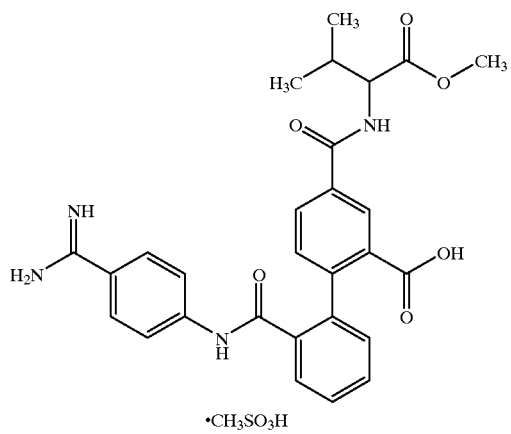

TLC: Rf 0.51 (Chloroform:Methanol:Water=7:3:0.3); NMR (CD$_3$OD): δ 9.04 (2H, br.s), 8.61 (2H, br.s), 8.34 (1H, d, J=1.6 Hz), 7.96 (1H, dd, J=1.6,7.8 Hz), 7.64–7.74 (5H, m), 7.53–7.59 (2H, m), 7.38 (1H, d, J=7.8 Hz), 7.26 (1H, dd, J=1.6,7.8 Hz), 4.47 (1H, d, J=6.6 Hz), 3.75 (3H, s), 2.71 (3H, s), 2.26 (1H, septet, J=6.6 Hz), 1.02 (3H, d, J=6.6 Hz), 1.00 (3H, d, J=6.6 Hz).

EXAMPLE 19(89)

2'-(4-amidinophenylcarbamoyl)-4-(2-(methoxymethoxy)ethoxy)-biphenylcarboxylic acid

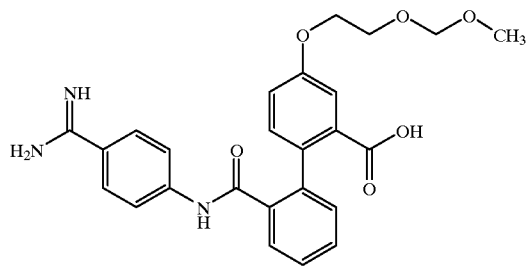

TLC: Rf 0.54 (Chloroform:Methanol:Water=10:3:0.2); NMR (d$_6$-DMSO): δ 13.0–12.0 (1H, br), 10.52 (1H, br.s), 9.3–9.0 (3H, br), 7.76 (2H, d, J=8.8 Hz), 7.67 (2H, d, J=8.8 Hz), 7.7–7.5 (1H, m), 7.6–7.4 (2H, m), 7.30 (1H, d, J=2.6 Hz), 7.3–7.0 (3H, m), 4.60 (2H, s), 4.14 (2H, t, J=4.4 Hz), 3.76 (2H, t, J=4.4 Hz), 3.25 (3H, s).

EXAMPLE 19(90)

3-(2-(4-amidinophenylcarbamoyl)phenyl)-5-methoxymethoxy-2-naphthalenecarboxylic acid

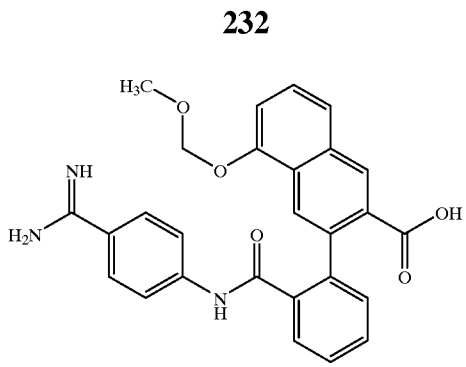

TLC: Rf 0.50 (Chloroform:Methanol:Acetic acid=10:2:1); NMR (d$_6$-DMSO): δ 10.80 (1H, br.s), 9.2–8.9 (3H, br), 8.39 (1H, s), 8.39 (1H, s), 7.95 (1H, s), 7.8–7.6 (6H, m), 7.6–7.4 (3H, m), 7.34 (1H, m), 7.18 (1H, d, J=8.0 Hz), 5.35 (2H, s), 3.30 (3H, s).

EXAMPLE 19(91)

3-(2-(4-amidinophenylcarbamoyl)phenyl)-8-methoxymethoxy-2-naphthalenecarboxylic acid

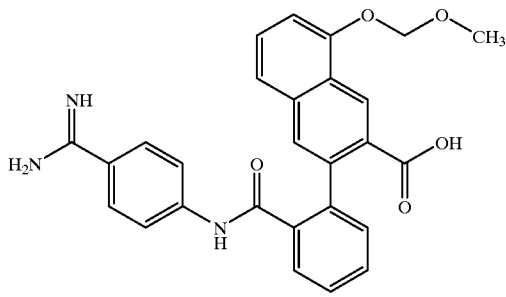

TLC: Rf 0.62 (Chloroform:Methanol:Acetic acid=10:2:1); NMR (d$_6$-DMSO): δ 10.69 (1H, br.s), 9.2–9.0 (3H, br), 8.69 (1H, s), 7.8–7.6 (6H, m), 7.6–7.4 (4H, m), 7.33 (1H, dd, J=2.2, 7.4 Hz), 7.15 (1H, dd, J=3.0, 5.4 Hz), 5.45 (2H, s), 3.46 (3H, s).

EXAMPLE 19(92)

Benzyl 2'-(4-amidinophenylcarbamoyl)-4-((2-methylpropyl)aminomethyl)-2-biphenylcarboxylic acid dimethanesulfonate

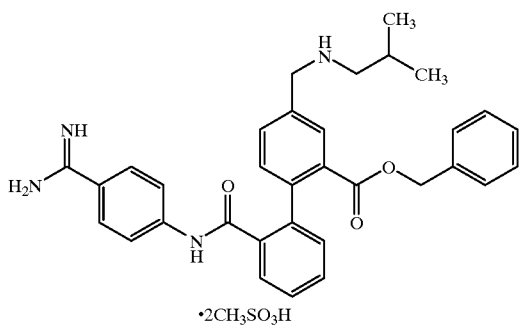

TLC: Rf 0.37 (Chloroform:Methanol:Water=8:2:0.1).

EXAMPLE 19(93)

2'-(4-amidinophenylcarbamoyl)-4-((2-methoxycarbonylethyl)carbamoyl)-2-biphenylcarboxylic acid methanesulfonate

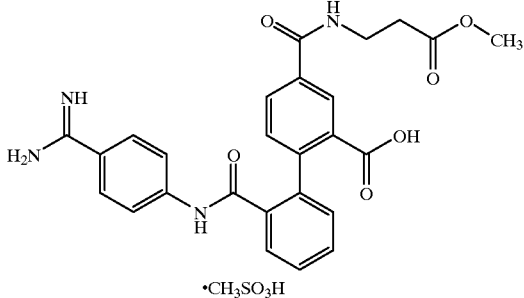

TLC: Rf 0.43 (Chloroform:Methanol:Water=7:3:0.3); NMR (d$_6$-DMSO): δ 13.1–12.7 (1H, broad), 10.54 (1H, s), 9.15 (2H, brs), 8.88 (2H, b rs), 8.75 (1H, brt, J=5.5Hz), 8.28 (1H, d, J=2.0 H z), 7.94 (1H, dd, J=8.0 Hz, 2.0 Hz), 7.72 (4H, s), 7.69 (1H, dd, J=7.5 Hz, 1.5 Hz), 7.62–7.47 (2H, m), 7.32 (1H, d, J=8.0 Hz), 7.27 (1H, dd, J=7.5 Hz, 1.5 Hz), 3.59 (3H, s), 3.49 (2H, q, J=7.0 Hz), 2.59 (2H, t, J=7.0 Hz), 2.34 (3H, s).

EXAMPLE 19(94)

2'-(4-amidinophenylcarbamoyl)-4-((3-ethoxycarbonylpropyl)carbamoyl)- 2-biphenylcarboxylic acid methanesulfonate

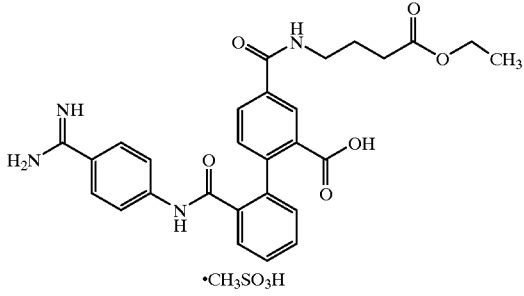

TLC: Rf 0.55 (Chloroform:Methanol:Water=7:3:0.3); NMR (d$_6$-DMSO): δ 13.1–12.6 (1H, broad), 10.54 (1H, s), 9.16 (2H, brs), 8.91 (2H, brs), 8.68 (1H, brt, J=5.5 Hz), 8.29 (1H, d, J=2.0 Hz), 7.96 (1H, dd, J=8.0 Hz, 2.0 Hz), 7.73 (4H, s), 7.70 (1H, dd, J=7.5 Hz, 1.5 Hz), 7.62–7.47 (2H, m), 7.32 (1H, d, J=8.0 Hz), 7.27 (1H, dd, J=7.5 Hz, 1.5 Hz), 4.03 (2H, q, J=7.0 Hz), 3.33–3.22 (2H, m), 2.34 (3H, s), 2.34 (2H, t, J=7.0 Hz), 1.77 (2H, quint, J=7.0 Hz), 1.15 (3H, t, J=7.0 Hz).

EXAMPLE 19(95)

2'-(4-amidinophenylcarbamoyl)-4-((1-t-butoxycarbonylpiperidin-4-ylmethyl) carbamoyl)-2-biphenylcarboxylic acid

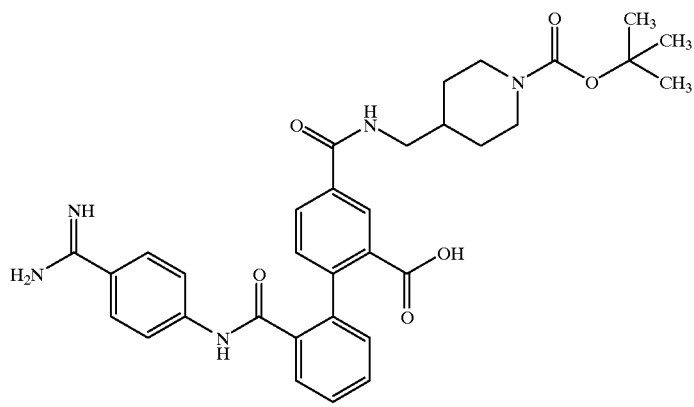

TLC: Rf 0.49 (Chloroform:Methanol:Acetic acid= 10:2:1); NMR (d$_6$-DMSO): δ 10.9 (1H, br s), 9.19 (2H, br s), 8.97 (2H, br s), 8.70 (1H, t, J=6.2 Hz), 8.27 (1H, d, J=1.8 Hz), 7.94 (1H, dd, J=1.8, 8.0 Hz), 7.80–7.60 (5H, m), 7.60–7.50 (2H, m), 7.30–7.23 (2H, m), 3.93 (2H, br d, J=12.0 Hz), 3.16 (2H, br s), 2.80–2.50 (2H, m), 1.80–1.60 (3H, m), 1.39 (9H, s), 1.10–0.99 (2H, m).

EXAMPLE 19(96)

2'-(4-amidinophenylcarbamoyl)-4-((2-methylthioethyl)carbamoyl)-2-biphenylcarboxylic acid methanesulfonate

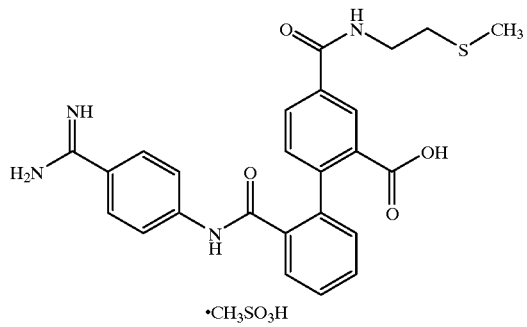

TLC: Rf 0.58 (Chloroform:Methanol:Water=10:3:0.2); NMR (d$_6$-DMSO): δ 13.0–12.0 (1H, br), 10.52 (1H, s), 9.14 (2H, br.s), 8.83 (2H, br.s), 8.79 (1H, br.t), 8.29 (1H, s), 7.96 (1H, d, J=8.0 Hz), 7.72 (4H, like s), 7.8–7.6 (1H, m), 7.6–7.5 (2H, m), 7.33 (1H, d, J=8.0 Hz), 7.4–7.2 (1H, m), 3.45 (2H, br.q), 2.64 (2H, t, J=6.8 Hz), 2.34 (3H, s), 2.08 (3H, s).

EXAMPLE 19(97)

2'-(4-amidinophenylcarbamoyl)-4-((2-methylsulfinylethyl)carbamoyl)-2-biphenylcarboxylic acid methanesulfonate

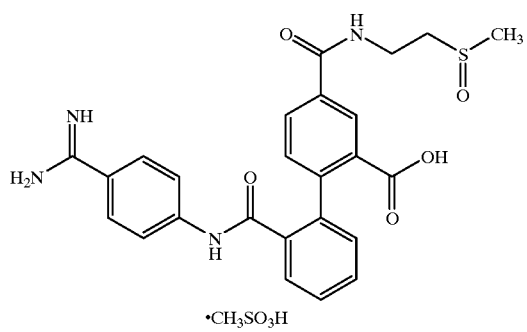

TLC: Rf 0.24 (Chloroform:Methanol:Water=10:0.2); NMR (d$_6$-DMSO): δ 10.52 (1H, s), 9.14 (2H, s), 8.96 (1H, br.t, J=1.4 Hz), 8.88 (2H, s), 8.30 (1H, s), 7.96 (1H, d, J=8.2 Hz), 7.72 (4H, like s), 7.8–7.6 (1H, m), 7.6–7.5 (2H, m), 7.34 (1H, d, J=8.2 Hz), 7.28 (1H, d, J=8.2 Hz), 6.0–4.6 (1H, br), 3.8–3.5 (2H, br), 3.06 (1H, dt, J=13.8, 6.4 Hz), 2.88 (1H, dt, J=13.8, 6..8 Hz), 2.58 (3H, s), 2.38 (3H, s).

EXAMPLE 19(98)

2-(3-(4-amidinophenylcarbamoyl)naphthalen-2-yl)-5-methylbenzoic acid methanesulfonate

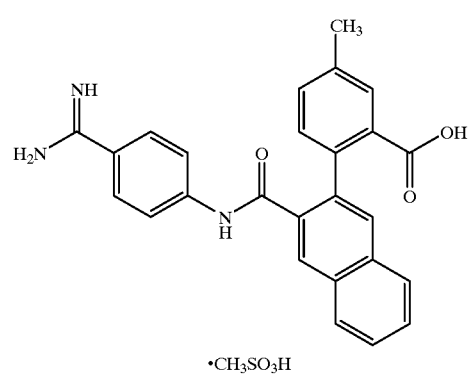

TLC: Rf 0.27 (Chloroform:Methanol:Acetic acid=4:1:0.1); NMR (d$_6$-DMSO): δ 12.6 (1H, brs), 10.7 (1H, s), 9.17 (2H, s), 8.83 (2H, s), 8.25 (1H, s), 8.15–8.05 (1H, m), 8.05–7.95 (1H, m), 7.77 (5H, s), 7.7–7.6 (3H, m), 7.37 (1H, dt, J=8.2, 1.0 Hz), 7.22 (1H, d, J=7.8 Hz), 2.37 (3H, s), 2.33 (3H, s).

EXAMPLE 19(99)

2-(2-(4-amidinophenylcarbamoyl)naphthalen-1-yl)benzoic acid methanesulfonate

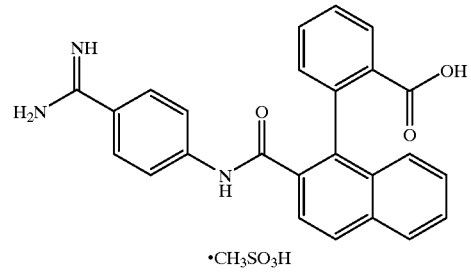

TLC: Rf 0.20 (Chloroform:Methanol:Acetic acid=10:2:1); NMR (d$_6$-DMSO): δ 13.0–12.5 (1H, broad), 10.40 (1H, s), 9.15 (2H, brs), 8.87 (2H, brs), 8.07 (1H, d, J=8.0 Hz), 8.05 (1H, d, J=8.0 Hz), 7.96 (1H, dd, J=7.5 Hz, 1.5 Hz), 7.73 (1H, d, J=8.0 Hz), 7.72 (2H, d, J=9.0 Hz), 7.62 (2H, d, J=9.z), 7.58–7.42 (4H, m), 7.27 (1H, dd, J=7.5 Hz, 1.5 Hz), 7.21 (1H, d, J=8.0 Hz), 2.33 (3H, s).

EXAMPLE 19(100)

2-(3-(4-amidinophenylcarbamoyl)naphthalen-2-yl)-5-methoxybenzoic acid methanesulfonate

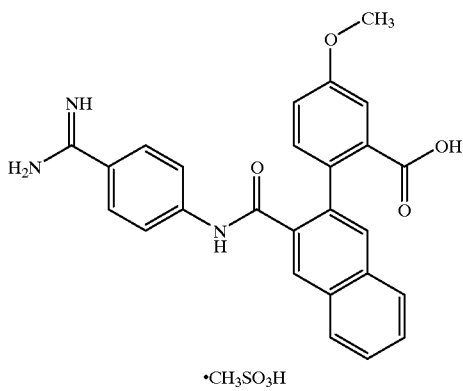

·CH₃SO₃H

TLC: Rf 0.13 (Chloroform:Methanol:Acetic acid= 10:2:1); NMR (d$_6$-DMSO): δ 12.7 (1H, brs), 10.63 (1H, s), 9.17 (2H, brs), 8.91 (2H, brs), 8.24 (1H, s), 8.11–8.05 (1H, m), 8.01–7.95 (1H, m), 7.77 (4H, s), 7.76 (1H, s), 7.65–7.59 (2H, m), 7.36 (1H, d, J=2.5 Hz), 7.26 (1H, d, J=8.5 Hz), 7.14 (1H, dd, J=8.5 Hz, 2.5 Hz), 3.81 (3H, s), 2.35 (3H, s).

EXAMPLE 19(101)

2-(3-(4-amidinophenylcarbamoyl)naphthalen-2-yl)-5-propoxybenzoic acid methanesulfonate

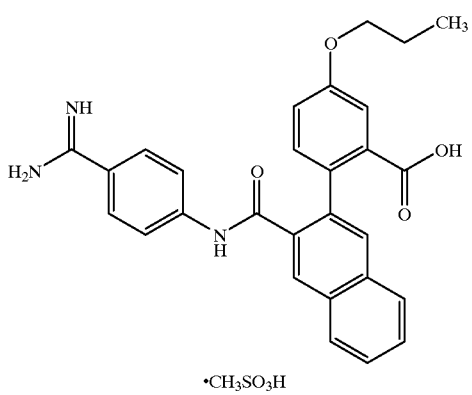

·CH₃SO₃H

TLC: Rf 0.20 (Chloroform:Methanol:Acetic acid= 10:2:1); NMR (d$_6$-DMSO): δ 12.7 (1H, brs), 10.63 (1H, s), 9.16 (2H, brs), 8.88 (2H, brs), 8.24 (1H, s), 8.10–8.05 (1H, m), 8.00–7.95 (1H, m), 7.77 (4H, s), 7.75 (1H, s), 7.67–7.59 (2H, m), 7.34 (1H, d, J=2.5 Hz), 7.24 (1H, d, J=8.0 Hz), 7.12 (1H, dd, J=8.0 Hz, 2.5 Hz), 3.98 (2H, t, J=7.0 Hz), 2.34 (3H, s), 1.74 (2H, sextet, J=7.0 Hz), 0.98 (3H, t, J=7.0 Hz).

EXAMPLE 19(102)

2'-(4-amidinophenylcarbamoyl)-4'-amino-2-biphenylcarboxylic acid methanesulfonate

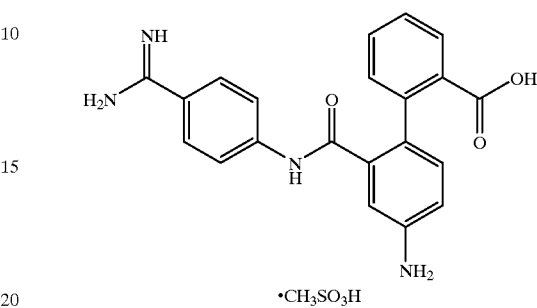

·CH₃SO₃H

TLC: Rf 0.22 (Chloroform:Methanol:Water=7:3:0.3); NMR (d$_6$-DMSO): δ 10.49 (1H, s), 9.21 (2H, brs), 9.03 (2H, brs), 7.81 (1H, dd, J=8.0 Hz, 1.5 Hz), 7.75 (2H, d, J=9.0 Hz), 7.64 (2H, d, J=9.0 Hz), 7.56–7.47 (2H, m), 7.44–7.35 (2H, m), 7.31 (1H, d, J=8.0 Hz), 7.26 (1H, d, J=8.0 Hz), 2.40 (3H, s).

EXAMPLE 19(103)

2'-(4-amidinophenylcarbamoyl)-4'-chloro-2-biphenylcarboxylic acid methanesulfonate

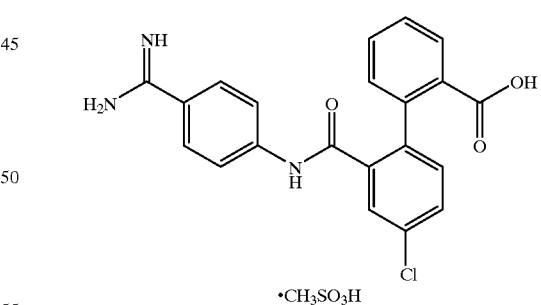

·CH₃SO₃H

TLC: Rf 0.48 (Chloroform:Methanol:Water=7:3:0.3); NMR (d$_6$-DMSO): δ 10.56 (1H, s), 9.14 (2H, s), 8.80 (2H, s), 7.85 (1H, dd, J=1.8,7.6 Hz), 7.73 (2H, d, J=9.2 Hz), 7.71 (1H, d, J=1.8 Hz), 7.68 (2H, d, J=9.2 Hz), 7.61 (1H, dd, J=1.8,7.6 Hz), 7.54 (1H, dt, J=1.8,7.6 Hz), 7.42 (1H, dt, J=1.8,7.6 Hz), 7.29 (1H, d, J=7.6 Hz), 7.24 (1H, dd, J=1.8, 7.6 Hz), 2.33 (3H, s).

EXAMPLE 19(104)

2'-(4-amidinophenylcarbamoyl)-4'-(2-methoxycarbonylethyl)-2-biphenylcarboxylic acid methanesulfonate

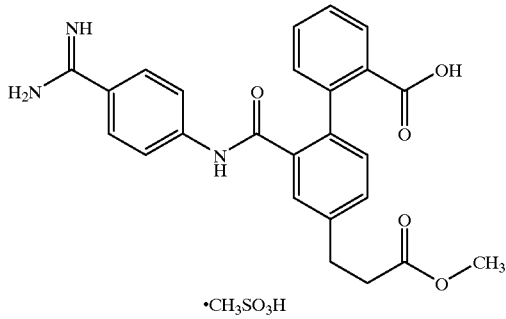

TLC: Rf 0.16 (Chloroform:Methanol=4:1); NMR ($d_6$-DMSO): δ 12.9–12.6 (1H, br), 10.4 (1H, s), 9.17 (2H, s), 9.0–8.8 (2H br), 7.79 (1H, d, J=7.8 Hz), 7.70 (2H, d, J=6.8 Hz), 7.68 (1H, s), 7.67 (1H, t, J=7.8 Hz), 7.51 (1H, d, J=7.8 Hz), 7.5–7.3 (1H, m), 7.40 (2H, d, J=6.8 Hz), 7.22 (1H, d, 7.8 Hz), 7.16 (1H, d, J=7.8 Hz), 3.62 (3H, s), 2.99 (2H, t, J=7.6 Hz), 2.75 (2H, t, J=7.6 Hz), 2.34 (3H, s).

EXAMPLE 19(105)

Benzyl 2'-(4-amidinophenylcarbamoyl)-3'-benzyloxy-2-biphenylcarboxylic acid trifluoroacetate

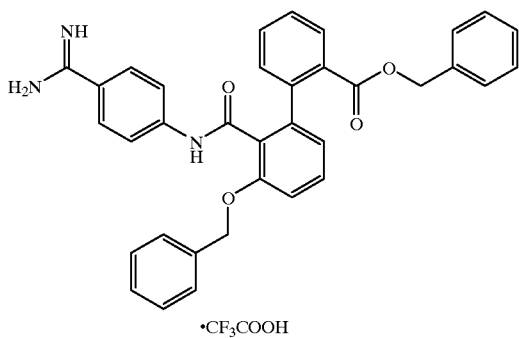

TLC: Rf 0.28 (Chloroform:Methanol:Acetic acid=10:2:1); NMR ($d_6$-DMSO): δ 10.53 (1H, s), 9.36 (2H, brs), 9.17 (2H, brs), 7.84 (1H, d, J=8 Hz), 7.74 (2H, d, J=9 Hz), 7.65 (2H, d, J=9 Hz), 7.60–7.10 (15H, m), 6.86 (1H, d, J=8 Hz), 5.20 (2H, s), 5.09 (2H, brs).

EXAMPLE 19(106)

2-(2,3-dihydro-2,2-dimethyl-6-(4-amidinophenylcarbamoyl)benzofuran-5-yl)benzoic acid trifluoroacetate

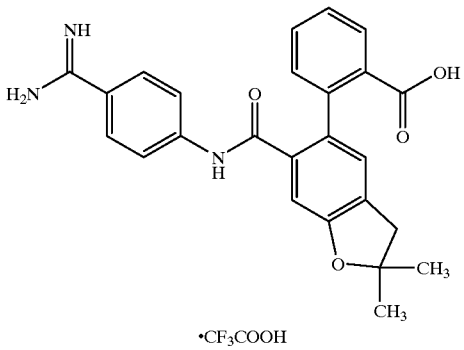

TLC: Rf 0.35 (Chloroform:Methanol:Acetic acid=10:2:1); NMR ($d_6$-DMSO): δ 10.59 (1H, brs), 9.19 (2H, s), 9.12 (2H, s), 7.72 (1H, d, J=7 Hz), 7.71 (2H, d, J=9 Hz), 7.62 (2H, d, J=9 Hz), 7.42 (1H, t, J=7 Hz), 7.33 (1H, t, J=7 Hz), 7.16 (1H, d, J=7 Hz), 7.02 (1H, s), 6.94 (1H, s), 3.07 (2H, s), 1.47 (6H, s).

EXAMPLE 19(107)

2'-(4-amidinophenylcarbamoyl)-6'-methyl-2-biphenylcarboxylic acid methanesulfonate

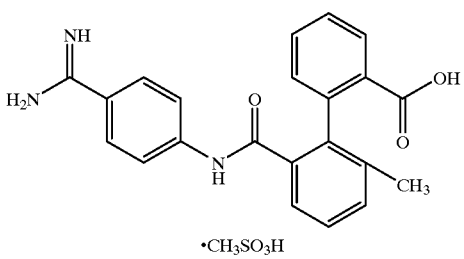

TLC: Rf 0.21 (Chloroform:Methanol:Acetic acid=10:2:1); NMR ($d_6$-DMSO): δ 13.0–12.5 (1H, broad), 10.36 (1H, s), 9.12 (2H, brs), 8.89 (2H, brs), 7.86 (1H, d, J=8 Hz), 7.70 (2H, d, J=9 Hz), 7.60 (2H, d, J=9 Hz), 7.57–7.35 (5H, m), 7.13 (1H, d, J=8 Hz), 2.37 (3H, s), 1.96 (3H, s).

EXAMPLE 19(108)

2'-(4-amidinophenylcarbamoyl)-5'-methyl-2-biphenylcarboxylic acid methanesulfonate

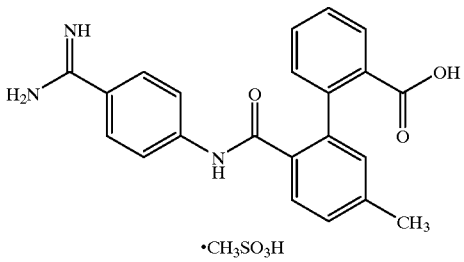

TLC: Rf 0.14 (Chloroform:Methanol:Acetic acid=10:2:1); NMR ($d_6$-DMSO): δ 13.3–12.3 (1H, broad), 10.30 (1H, s), 9.14 (2H, brs), 8.91 (2H, brs), 7.79 (1H, dd, J=8 Hz, 2 Hz), 7.73 (2H, d, J=9 Hz), 7.66 (2H, d, J=9 Hz), 7.58 (1H, d, J=8 Hz), 7.51 (1H, td, J=8 Hz, 2 Hz), 7.40 (1H, td, J=8 Hz, 2 Hz), 7.31 (1H, d, J=8 Hz), 7.21 (1H, d, J=8 Hz), 7.06 (1H, s), 2.38 (6H, s).

EXAMPLE 19(109)

2'-(4-amidinophenylcarbamoyl)-4'-isopropyl-2-biphenylcarboxylic acid methanesulfonate

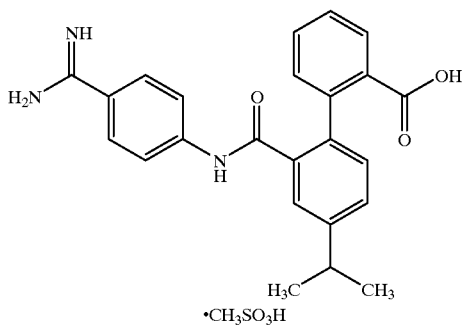

TLC: Rf 0.14 (Chloroform:Methanol:Acetic acid=10:2:1); NMR (d$_6$-DMSO): δ 13.3–12.5 (1H, broad), 10.55 (1H, s), 9.15 (2H, brs), 9.05 (2H, brs), 7.80–7.60 (5H, m), 7.52–7.32 (4H, m), 7.20 (1H, d, J=8 Hz), 7.16 (1H, d, J=8 Hz), 3.02 (1H, septet, J=7 Hz), 2.38 (3H, s), 1.30 (6H, d, J=7 Hz).

EXAMPLE 19(110)

2'-(4-amidinophenylcarbamoyl)-4'-t-butyl-2-biphenylcarboxylic acid methanesulfonate

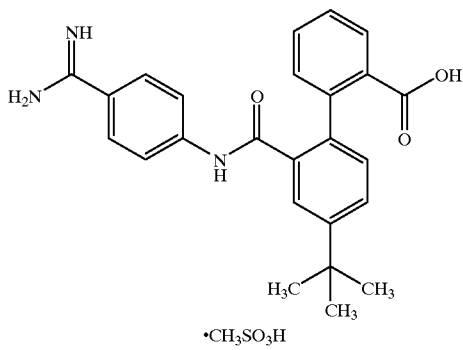

TLC: Rf 0.14 (Chloroform:Methanol:Acetic acid=10:2:1); NMR (d$_6$-DMSO): δ 13.0–12.6 (1H, broad), 10.35 (1H, s), 9.15 (2H, brs), 8.97 (2H, brs), 7.82–7.34 (9H, m), 7.24 (1H, d, J=8 Hz), 7.19 (1H, d, J=8 Hz), 2.37 (3H, s), 1.38 (9H, s).

EXAMPLE 19(111)

2'-(4-amidinophenylcarbamoyl)-4'-ethyl-2-biphenylcarboxylic acid methanesulfonate

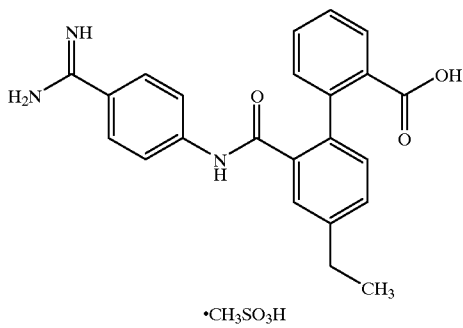

TLC: Rf 0.41 (Chloroform:Methanol:Water=7:3:0.3); NMR (d$_6$-DMSO): δ 12.73 (1H, brs), 10.42 (1H, s), 9.12 (2H, brs), 8.84 (2H, brs), 7.77 (1H, dd, J=7.6, 1.4 Hz), 7.74 (2H, d, J=9.0 Hz), 7.65 (2H, d, J=9.0 Hz), 7.54–7.30 (4H, m), 7.21 (1H, dd, J=7.6, 1.2 Hz), 7.15 (1H, d, J=7.6 Hz), 2.73 (2H, q, J=7.6 Hz), 2.33 (3H, s), 1.26 (3H, t, J=7.6 Hz).

EXAMPLE 19(112)

2'-(4-amidinophenylcarbamoyl)-4'-methoxy-2-biphenylcarboxylic acid methanesulfonate

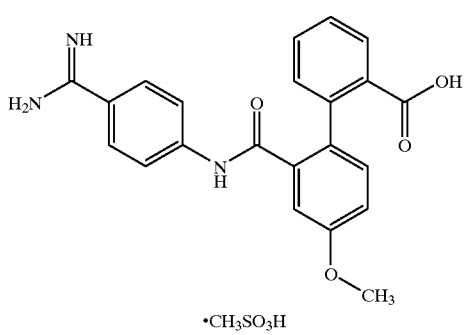

TLC: Rf 0.61 (Chloroform:Methanol:Water=6:4:1); NMR (d$_6$-DMSO): δ 13.2–12.5 (1H, broad), 10.51 (1H, s), 9.26 (2H, brs), 9.05 (2H, brs), 7.88 (1H, dd, J=8 Hz, 1 Hz), 7.85 (2H, d, J=9 Hz), 7.77 (2H, d, J=9 Hz), 7.59 (1H, td, J=8 Hz, 1 Hz), 7.49 (1H, td, J=8 Hz, 1 Hz), 7.32 (1H, dd, J=8 Hz, 1 Hz), 7.30 (1H, d, J=2 Hz), 7.23 (1H, d, J=8 Hz), 7.21 (1H, dd, J=8 Hz, 2 Hz), 3.97 (3H, s), 2.49 (3H, s).

EXAMPLE 19(113)

2-(5,6,7,8-tetrahydro-3-(4-amidinophenylcarbamoyl)naphthalen-2-yl)benzoic acid methanesulfonate

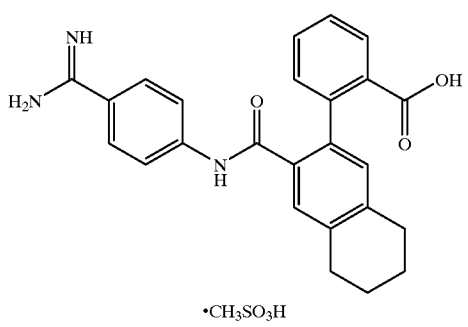

TLC: Rf 0.37 (Chloroform:Methanol:Water=7:3:0.3); NMR (d$_6$-DMSO): δ 13.0–12.6 (1H, broad), 10.32 (1H, s), 9.14 (2H, brs), 8.90 (2H, brs), 7.78 (1H, dd, J=8 Hz, 2 Hz), 7.73 (2H, d, J=9 Hz), 7.66 (2H, d, J=9 Hz), 7.56–7.36 (3H, m), 7.19 (1H, dd, J=8 Hz, 1 Hz), 6.92 (1H, s), 2.96–2.68 (4H, m), 2.37 (3H, s), 1.92–1.68 (4H, m).

EXAMPLE 19(114)

2'-(4-amidinophenylcarbamoyl)-4'-cyano-2-biphenylcarboxylic acid methanesulfonate

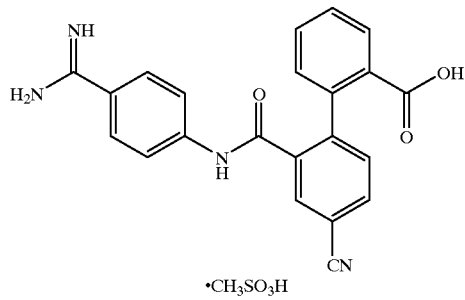

TLC: Rf 0.32 (Chloroform:Methanol:Water 7:3:0.3); NMR (d$_6$-DMSO): δ 13.0–12.5 (1H, broad), 10.66 (1H, s), 9.17 (2H, brs), 8.96 (2H, brs), 8.16 (1H, d, J=1 Hz), 8.01 (1H, dd, J=8 Hz, 2 Hz), 7.90 (1H, dd, J=8 Hz, 1 Hz), 7.76 (2H, d, J=9 Hz), 7.69 (2H, d, J=9 Hz), 7.62–7.40 (3H, m), 7.26 (1H, dd, J=8 Hz, 1 Hz), 2.39 (3H, s).

EXAMPLE 19(115)

2-(6-(4-amidinophenylcarbamoyl)indan-5-yl)benzoic acid methanesulfonate

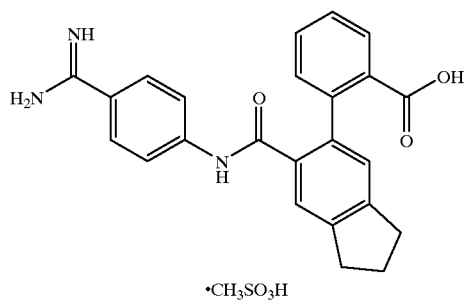

TLC: Rf 0.29 (Chloroform:Methanol:Water=7:3:0.3); NMR (d$_6$-DMSO): δ 12.9–12.6 (1H, broad), 10.32 (1H, s), 9.14 (2H, brs), 8.86 (2H, brs), 7.79 (1H, d, J=8 Hz), 7.73 (2H, d, J=9 Hz), 7.65 (2H, d, J=9 Hz), 7.54–7.30 (3H, m), 7.19 (1H, d, J=7 Hz), 7.08 (1H, s), 3.06–2.82 (4H, m), 2.35 (3H, s), 2.20–2.00 (2H, m).

EXAMPLE 19(116)

2'-(4-amidinophenylcarbamoyl)-5'-methoxy-2-biphenylcarboxylic acid methanesulfonate

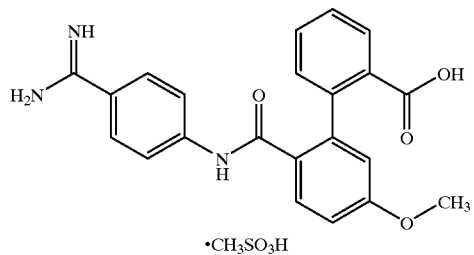

TLC: Rf 0.37 (Chloroform:Methanol:Water=7:3:0.3); NMR (d$_6$-DMSO): δ 10.23 (1H, s), 9.14 (2H, s), 8.79 (2H, s), 7.81 (1H, d, J=7.4 Hz), 7.72 (2H, d, J=8.8 Hz), 7.67 (1H, d, J=7.4 Hz), 7.66 (2H, d, J=8.8 Hz), 7.51 (1H, t, J=7.4 Hz), 7.40 (1H, t, J=7.4 Hz), 7.23 (1H, d, J=7.4 Hz), 7.05 (1H, dd, J=2.4,7.4 Hz), 6.76 (1H, d, J=2.4 Hz), 3.83 (3H, s), 2.33 (3H, s).

EXAMPLE 19(117)

2'-(4-amidinophenylcarbamoyl)-6'-methoxy-2-biphenylcarboxylic acid methanesulfonate

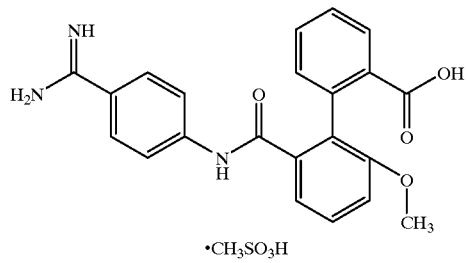

TLC: Rf 0.31 (Chloroform:Methanol:Water=7:3:0.3); NMR (d$_6$DMSO): δ 10.32 (1H, s), 9.13 (2H, s), 8.82 (2H, s), 7.83 (1H, dd, J=1.4,7.6 Hz), 7.71 (2H, d, J=9.0 Hz), 7.62 (2H, d, J=9.0 Hz), 7.46 (1H, t, J=8.0 Hz), 7.45 (1H, dt, J=1.4,7.6 Hz), 7.35 (1H, dt, J=1.4,7.6 Hz), 7.13–7.23 (3H, m), 3.67 (3H, s), 2.35 (3H, s).

EXAMPLE 19(118)

2'-(4-amidinophenylcarbamoyl)-5'-chloro-4-methyl-2-biphenylcarboxylic acid methanesulfonate

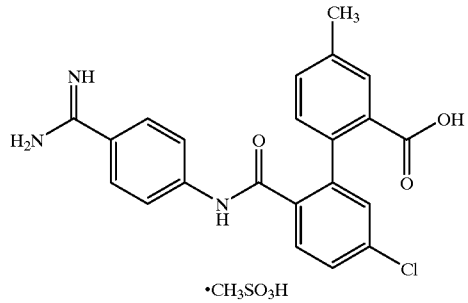

TLC: Rf 0.25 (Chloroform:Methanol:Acetic acid= 4:1:0.1); NMR (d₆-DMSO): δ 13.2–12.0 (1H, br), 10.5 (1H, s), 9.15 (2H, s), 8.84 (2H, s), 7.8–7.5 (6H, m), 7.4–7.0 (1H, m), 7.35 (1H, d, J=8.0 Hz), 7.28 (1H, s), 7.15 (1H, d, J=7.6 Hz), 2.37 (3H, s), 2.35 (3H, s).

EXAMPLE 19(119)

2'-(4-amidinophenylcarbamoyl)-4'-methoxy-4-methyl-2-biphenylcarboxylic acid methanesulfonate

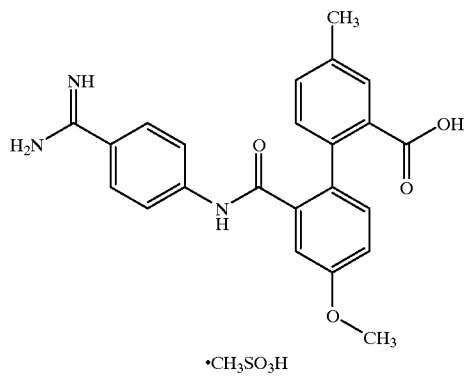

TLC: Rf 0.34 (Chloroform:Methanol:Acetic acid= 4:1:0.1); NMR (d₆-DMSO): δ 12.67 (1H, s), 10.40 (1H, s), 9.14 (2H, s), 8.83 (2H, s), 7.74 (2H, d, J=9.4 Hz), 7.68 (2H, d, J=9.4 Hz), 7.60 (1H, s), 7.29(1H, dd, J=8.4, 2.0 Hz), 7.18 (1H, d, J=2.4 Hz), 7.1–7.0 (3H, m), 3.87 (3H, s), 2.36 (3H, s), 2.33 (3H, s).

EXAMPLE 19(120)

2-(3-(4-amidinophenylcarbamoyl)-8-methoxynaphthalen-2-yl)benzoic acid methanesulfonate

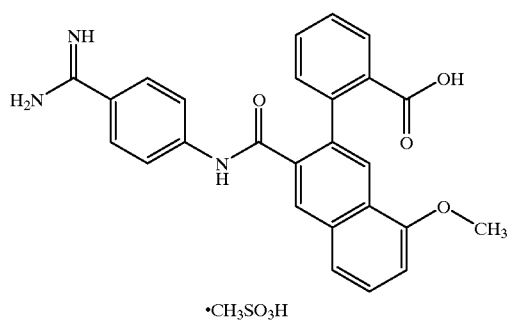

TLC: Rf 0.23 (Chloroform:Methanol:Water=10:3:0.2); NMR (d₆-DMSO): δ 13.0–12.0 (1H, br), 10.65 (1H, s), 9.16 (2H, br.s), 8.84 (2H, br.s), 8.22 (1H, s), 7.92 (1H, s), 7.85 (1H, dd, J=1.4, 7.4 Hz), 7.75 (4H, like s), 7.7–7.3 (4H, m), 7.32 (1H, dd, J=1.4, 7.4 Hz), 7.09 (1H, d, J=6.8 Hz), 3.96 (3H, s), 2.33 (3H, s).

EXAMPLE 19(121)

2'-(4-amidinophenylcarbamoyl)-4'-dimethylcarbamoyl-2-biphenylcarboxylic acid methanesulfonate

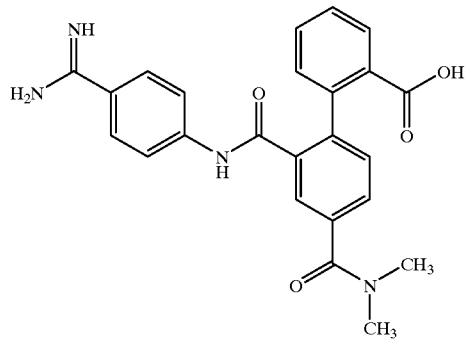

TLC: Rf 0.25 (Chloroform:Methanol:Water=8:2:0.2); NMR (d₆-DMSO): δ 10.52 (1H, s), 9.16 (2H, s), 8.34 (2H, s), 7.85 (1H, dd, J=1.4,7.8 Hz), 7.74 (2H, d, J=9.2 Hz), 7.69 (2H, d, J=9.2 Hz), 7.66 (1H, d, J=1.8 Hz), 7.57 (1H, dd, J=1.8,7.8 Hz), 7.55 (1H, dt, J=1.4, 7.8), 7.43 (1H, dt, J=1.4, 7.8), 7.36 (1H, d, J=7.8), 7.28 (1H, dd, J=1.4,7.8), 3.03 (6H, s), 2.34 (3H, s).

EXAMPLE 19(122)

2'-(4-amidinophenylcarbamoyl)-2,4'-biphenyldicarboxylic acid methanesulfonate

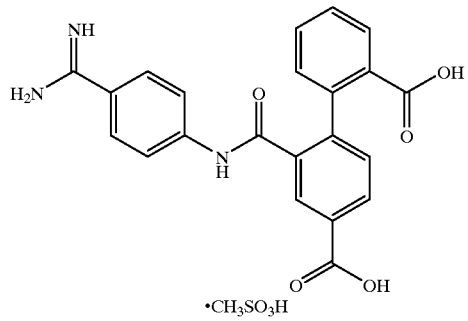

TLC: Rf 0.14 (Chloroform:Methanol:Water=6:4:1); NMR (d₆-DMSO): δ 10.62 (1H, s), 9.15 (2H, s), 8.86 (2H, s), 8.19 (1H, s), 8.08 (1H, d, J=7.8 Hz), 7.87 (1H, d, J=7.2), 7.75 (2H, d, J=9.0 Hz), 7.70 (2H, d, J=9.0), 7.56 (1H, t, J=7.2 Hz), 7.44 (1H, t, J=7.2 Hz), 7.41 (1H, d, J=7.8 Hz), 7.26 (1H, d, J=7.2 Hz), 2.34 (3H, s).

EXAMPLE 19(123)

2'-(4-amidinophenylcarbamoyl)-4'-methylcarbamoyl-2-biphenylcarboxylic acid methanesulfonate

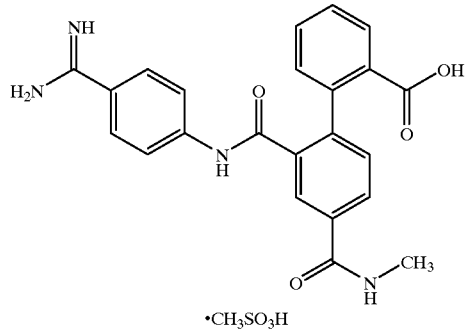

TLC: Rf 0.24 (Chloroform:Methanol:Water=7:3:0.3); NMR (d₆-DMSO): δ 10.54 (1H, s), 9.15 (2H, s), 8.87 (2H, s), 8.62 (1H, br.q, J=4.6 Hz), 8.13 (1H, d, J=1.4 Hz), 7.99 (1H, dd, J=1.4,7.8 Hz), 7.86 (1H, dd, J=1.4,7.8 Hz), 7.76 (2H, d, J=9.2 Hz), 7.71 (2H, d, J=9.2 Hz), 7.54(1H, dt, J=1.4,7.8 Hz), 7.43 (1H, dt, J=1.4,7.8 Hz), 7.35 (1H, d, J=7.8 Hz), 7.25 (1H, dd, J=1.4,7.8 Hz), 2.85 (3H, br.d, J=4.6 Hz), 2.39 (3H, s).

(1H, s), 9.12 (2H, brs), 8.84 (2H, brs), 7.78 (1H, dd, J=8.0 Hz, 1.5 Hz), 7.71 (2H, d, J=9.0 Hz), 7.61 (2H, d, J=9.0 Hz), 7.48 (1H, td, J=7.5 Hz, 1.5 Hz), 7.37 (1H, td, J=7.5 Hz, 1.5 Hz), 7.23 (1H, s), 7.21 (1H, dd, J=7.5 Hz, 1.5 Hz), 6.80 (1H, s), 6.15 (2H, s), 2.34 (3H, s).

EXAMPLE 19(124)

2'-(4-amidinophenylcarbamoyl)-4'-methylaminomethyl-2-biphenylcarboxylic acid dimethanesulfonate

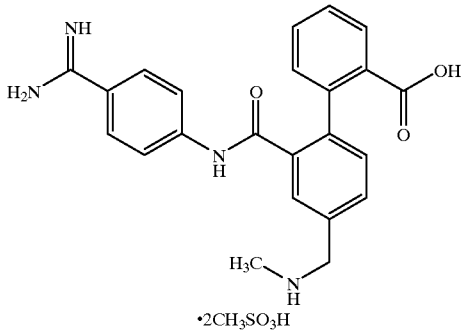

TLC: Rf 0.30 (Ethyl acetate:Acetic acid:Water=3:1:1); NMR (d₆-DMSO): δ 10.41 (1H, s), 9.15 (2H, s), 8.89 (4H, s), 7.85 (1H, dd, J=1.6,7.8 Hz), 7.83 (1H, d, J=1.6 Hz), 7.75 (2H, d, J=9.2 Hz), 7.67 (2H, d, J=9.2 Hz), 7.66 (1H, dd, J=1.6,7.8 Hz), 7.54 (1H, dt, J=1.6,7.8 Hz), 7.43 (1H, dt, J=1.6,7.8 Hz), 7.34 (1H, d, J=7.8 Hz), 7.23 (1H, dd, J=1.6, 7.8 Hz), 4.27 (2H, br.s), 2.65 (3H, t, J=5.2 Hz), 2.37 (6H, s).

EXAMPLE 19(125)

2-(6-(4-amidinophenylcarbamoyl)-1,2-methylenedioxybenzen-5-yl)benzoic acid methanesulfonate

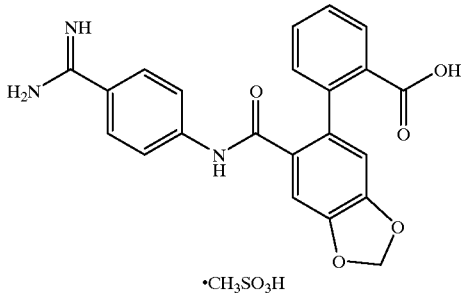

TLC: Rf 0.14 (Chloroform:Methanol:Acetic acid= 10:2:1); NMR (d₆-DMSO): δ 13.0–12.5 (1H, broad), 10.20

EXAMPLE 19(126)

2'-(4-amidinophenylcarbamoyl)-4'-(2-hydroxyethoxy)-2-biphenylcarboxylic acid methanesulfonate

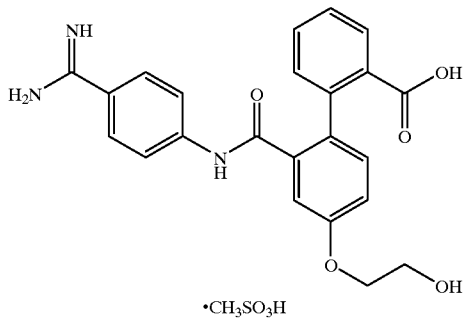

TLC: Rf 0.23 (Chloroform:Methanol:Water=10:3:0.2); NMR (d₆-DMSO): δ 13.0–11.8 (1H, br), 10.39 (1H, s), 9.13 (2H, br.s), 8.80 (2H, br.s), 7.8–7.6 (5H, m), 7.48 (1H, dt, J=1.0, 7.2 Hz), 7.37 (1H, dt, J=1.0, 7.2 Hz), 7.3–7.0 (4H, m), 4.10 (2H, t, J=4.4 Hz), 3.76 (2H, t, J=4.4 Hz), 3.8–3.3 (1H, br), 2.32 (3H, s).

EXAMPLE 19(127)

2'-(4-amidinophenylcarbamoyl)-4'-fluoro-2-biphenylcarboxylic acid methanesulfonate

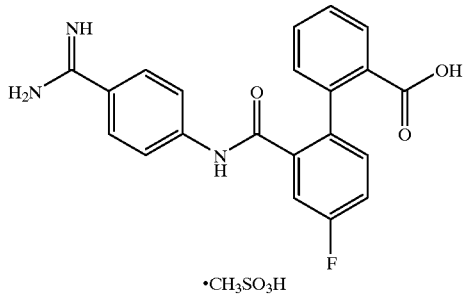

TLC: Rf 0.47 (Chloroform:Methanol:Water 7:3:0.3); NMR (d₆-DMSO): δ 10.48 (1H, s), 9.15 (2H, s), 8.87 (2H, ), 7.84 (1H, dd, J=1.6,7.8 Hz), 7.74 (2H, d, J=8.8 Hz), 7.67 (2H, d, J=8.8 Hz), 7.24–7.56 (6H, m), 2.37 (3H, s).

EXAMPLE 19(128)

2-(3-(4-amidinophenylcarbamoyl)-8-hydroxynaphthalen-2-yl)benzoic acid methanesulfonate

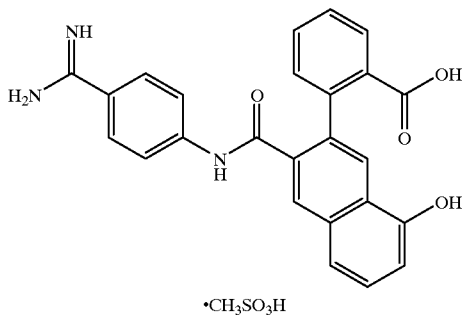

TLC: Rf 0.23 (Chloroform:Methanol:Acetic acid= 10:2:1); NMR (d$_6$-DMSO): δ 13.8–12.2 (1H, br), 10.62 (1H, s), 10.34 (1H, br.s), 9.17 (2H, br.s), 8.87 (2H, br.s), 8.16 (1H, s), 7.90 (1H, s), 7.84 (1H, d, J=7.4 Hz), 7.75 (4H, like s), 7.6–7.2 (5H, m), 6.99 (1H, d, J=6.4 Hz), 2.33 (3H, s).

EXAMPLE 19(129)

2'-(4-amidinophenylcarbamoyl)-4'-(2-methoxyethoxy)-2-biphenylcarboxylic acid methanesulfonate

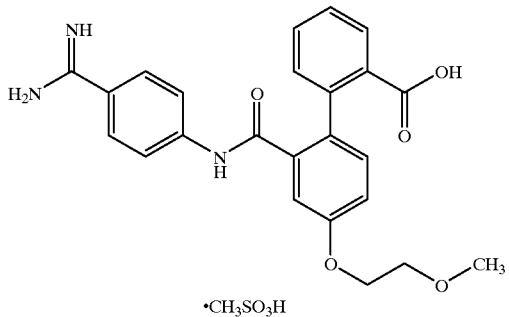

TLC: Rf 0.40 (Chloroform:Methanol:Acetic acid= 10:2:1); NMR (d$_6$-DMSO): δ 13.2–11.6 (1H, br), 10.39 (1H, s), 9.13 (2H, s), 8.81 (2H, s), 7.8–7.6 (5H, m), 7.46 (1H, dt, J=1.6, 7.4 Hz), 7.37 (1H, dt, J=1.6, 7.4 Hz), 7.25–7.10 (4H, m), 4.21 (2H, t, J=4.6 Hz), 3.70 (2H, t, J=4.6 Hz), 3.33 (3H, s), 2.33 (3H, s).

EXAMPLE 19(130)

2'-(4-amidinophenylcarbamoyl)-4'-trifluoromethoxy-2-biphenylcarboxylic acid methanesulfonate

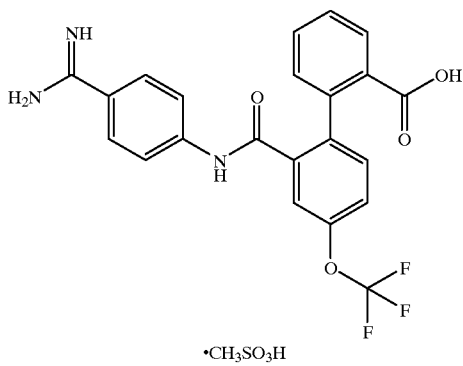

TLC: Rf 0.29 (Chloroform:Methanol:Water=8:2:0.2); NMR (d$_6$-DMSO): δ 10.5(1H, s), 9.15 (2H, br s), 8.83 (2H, br s), 7.86 (1H, dd, J=1.4, 7.0 Hz), 7.76–7.47 (8H, m), 7.41 (1H, d, J=8.6 Hz), 7.29 (1H, dd, J=1.4, 7.6 Hz), 2.36 (3H, s).

EXAMPLE 19(131)

2-(3-(4-amidinophenylcarbamoyl)-5-(2-methoxyethoxy)naphthalen-2-yl)benzoic acid methanesulfonate

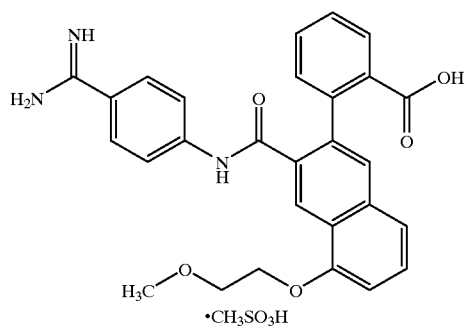

TLC: Rf 0.55 (Chloroform:Methanol:Acetic acid= 10:2:1); NMR (d$_6$-DMSO): δ 13.0–12.0 (1H, br), 10.61 (1H, s), 9.16 (2H, brs), 8.84 (2H, brs), 8.41 (1H, s), 7.85 (1H, d, J=6.3 Hz), 7.8–7.6 (4H, m), 7.6–7.4 (4H, m), 7.43 (1H, t, J=7.4 Hz), 7.33 (1H, d, J=6.3 Hz), 7.10 (1H, t, J=4.4 Hz), 4.36 (2H, t, J=4.4 Hz), 3.83 (2H, t, J=4.4 Hz), 3.37 (3H, s), 2.33 (3H, s).

EXAMPLE 19(132)

2-(3-(4-amidinophenylcarbamoyl)-5-hydroxynaphthalen-2-yl)benzoic acid methanesulfonate

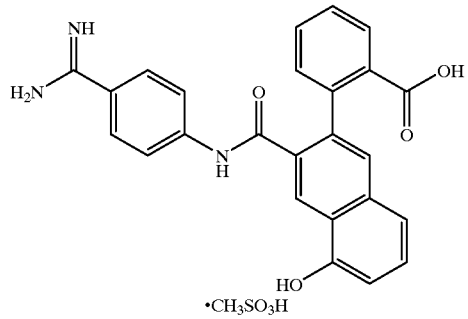

TLC: Rf 0.53 (Ethyl acetate:Acetic acid:Water=6:1:0.5); NMR (d$_6$-DMSO): δ 13.0–12.0 (1H, br), 10.64 (1H, s), 10.48 (1H, br.s), 9.15 (2H, br.s), 8.85 (2H, br.s), 8.43 (1H, s), 7.85 (1H, br.d, J=6.8 Hz), 7.51 (4H, like s), 7.67 (1H, s), 7.55 (1H, br.t, J=6.4 Hz), 7.5–7.3 (3H, m), 7.32 (1H, d, J=9.4 HZ), 6.97 (1H, dd, J=2.6, 6.0 Hz), 2.35 (3H, s).

EXAMPLE 19(133)

2'-(4-amidinophenylcarbamoyl)-4'-((methoxycarbonylmethyl)carbamoyl)-2-biphenylcarboxylic acid trifluoroacetate

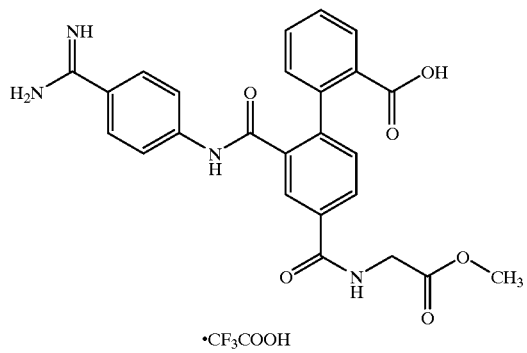

·CF$_3$COOH

TLC: Rf 0.34 (Chloroform:Methanol:Water=7:3:0.3); NMR (CD$_3$OD): δ 9.03 (1H, m), 8.19 (1H, d, J=1.6 Hz), 8.02 (1H, dd, J=1.6,7.8 Hz), 7.92 (1H, dd, J=1.6,7.8 Hz), 7.70 (2H, d, J=9.0 Hz), 7.62 (2H, d, J=9.0 Hz), 7.53 (1H, dt, J=1.6,7.8 Hz), 7.43 (1H, dt, J=1.6,7.8 Hz), 7.37 (1H, d, J=7.8 Hz), 7.28 (1H, dd, J=1.6,7.8 Hz), 4.16–4.18 (2H, m), 3.77 (3H, s).

EXAMPLE 19(134)

2'-(4-amidinophenylcarbamoyl)-4'-((1-methoxycarbonyl-2-phenylethyl) carbamoyl)-2-biphenylcarboxylic acid trifluoroacetate

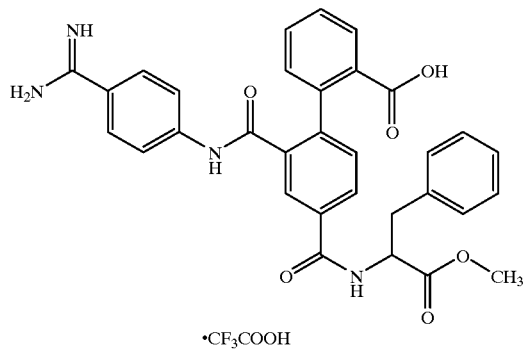

·CF$_3$COOH

TLC: Rf 0.60 (Chloroform:Methanol:Water=7:3:0.3); NMR (CD$_3$OD): δ 8.84 (1H, br.d, J=8.0 Hz), 8.06 (1H, s), 7.88–7.92 (2H, m), 7.70 (2H, d, J=9.2 Hz), 7.61 (2H, d, J=9.2 Hz), 7.39–7.56 (2H, m), 7.20–7.35 (7H, m), 4.92 (1H, m), 3.75 (3H, s), 3.08–3.38 (2H, m).

EXAMPLE 19(135)

2'-(4-amidinophenylcarbamoyl)-4'-ethoxycarbonylmethoxy-2-biphenylcarboxylic acid methanesulfonate

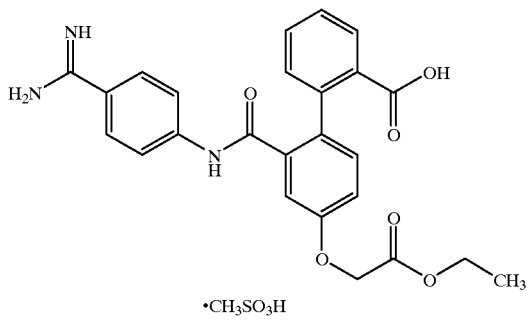

·CH$_3$SO$_3$H

TLC: Rf 0.30 (Chloroform:Methanol:Water=10:3:0.2); NMR (d$_6$-DMSO): δ 12.71 (1H, br), 10.38 (1H, s), 9.13 (2H, br.s), 8.77 (2H, br.s), 7.9–7.6 (5H, m), 7.49 (1H, m), 7.37 (1H, m), 7.3–7.0 (4H, m), 4.89 (2H, s), 4.20 (2H, q, J=7.4 Hz), 2.31 (3H, s), 1.23 (3H, t, J=7.4 Hz).

EXAMPLE 19(136)

A mixture of 2-(6-(4-amidinophenylcarbamoyl)-1-benzyloxymethyl benzoimidazol-5-yl)benzoic acid trifluoroacetate and 2-(5-(4-amidinophenylcarbamoyl)-1-benzyloxymethylbenzoimidazol-6-yl)benzoic acid trifluoroacetate

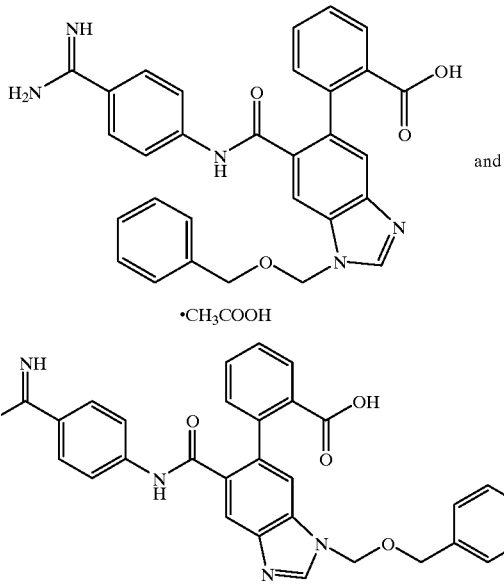

TLC: Rf 0.50 (Chloroform:Methanol:Water=7:3:0.3); NMR (CD$_3$OD): δ 8.52 (0.5H, s), 8.47 (0.5H, s), 8.03 (0.5H, s), 8.01 (0.5H, s), 7.89 (0.5H, d, J=8.0 Hz), 7.86 (0.5H, d, J=8.0 Hz), 7.40–7.70 (7H, m), 7.24–7.28 (6H, m), 5.86 (1H, s), 5.75 (1H, s), 4.62 (1H, s), 4.60 (1H, s).

EXAMPLE 19(137)

2'-(4-amidinophenylcarbamoyl)-4'-hydroxy-2-biphenylcarboxylic acid methanesulfonate

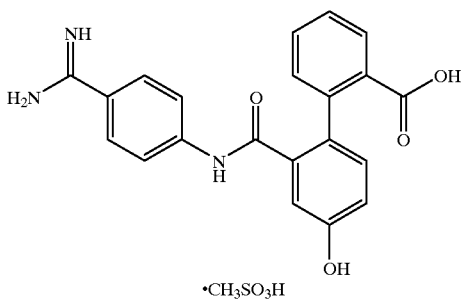

TLC: Rf 0.15 (Chloroform:Methanol:Water=7:3:0.3); NMR (d$_6$-DMSO): δ 10.35 (1H, s), 9.92 (1H, s), 9.22 (2H, s), 8.97 (2H, s), 7.75 (2H, d, J=8.8 Hz), 7.74 (1H, d, J=7.6 Hz), 7.65 (2H, d, J=8.8 Hz), 7.47 (1H, t, J=7.6 Hz), 7.35 (1H, t, J=7.6 Hz), 7.20 (1H, d, J=7.6 Hz), 7.04 (1H, d, J=8.6 Hz), 7.03 (1H, d, J=2.4 Hz), 6.94 (1H, dd, J=2.4,8.6 Hz), 2:33 (3H, s).

EXAMPLE 19(138)

2'-(4-amidinophenylcarbamoyl)-5'-hydroxy-2-biphenylcarboxylic acid methanesulfonate

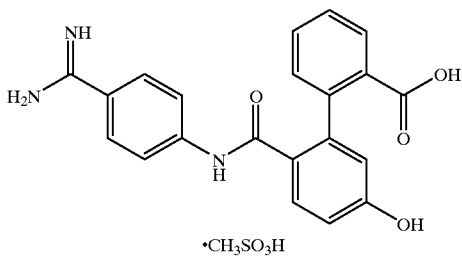

TLC: Rf 0.18 (Chloroform:Methanol:Water=7:3:0.3); NMR (d$_6$-DMSO): δ 10.16 (1H, s), 10.15 (1H, s), 9.20 (2H, s), 8.96 (2H, s), 7.78 (1H, dd, J=1.4,7.6 Hz), 7.74 (2H, d, J=9.0 Hz), 7.64 (2H, d, J=9.0 Hz), 7.56 (1H, d, J=8.4 Hz), 7.49 (1H, dt, J=1.4,7.6 Hz), 7.39 (1H, dt, J=1.4,7.6 Hz), 7.18 (1H, dd, J=1.4,7.6 Hz), 6 87 (1H, dd, J=2.6,8.4 Hz), 6.59 (1H, d, J=2.6 Hz), 2.34 (3H, s).

EXAMPLE 19(139)

2'-(4-amidinophenylcarbamoyl)-4'-bromo-2-biphenylcarboxylic acid methanesulfonate

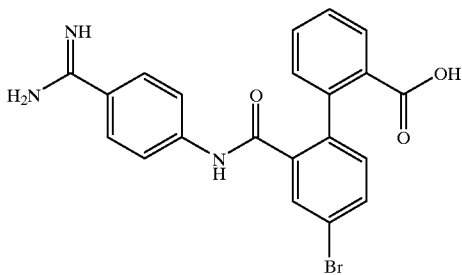

TLC: Rf 0.23 (Chloroform:Methanol:Water=8:2:0.2); NMR (d$_6$-DMSO): δ 10.58 (1H, s), 9.20 (2H, s), 8.93 (2H, s), 7.86 (1H, dd, J=1.6, 7.8 Hz), 7.84 (1H, d, J=1.6 Hz), 7.74–7.78 (3H, m), 7.68 (2H, d, J=9.2 Hz), 7.53 (1H, dt, J=1.6,7.8 Hz), 7.42 (1H, dt, J=1.6,7.8 Hz), 7.25 (1H, dd, J=1.6,7.8 Hz), 7.22 (1H, d, J=8.4 Hz), 2.35 (3H, s).

EXAMPLE 19(140)

2'-(4-amidinophenylcarbamoyl)-4-bromo-2-biphenylcarboxylic acid methanesulfonate

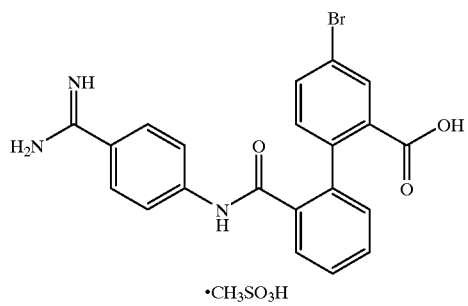

TLC: Rf 0.50 (Chloroform:Methanol:Water=7:3:0.3); NMR (d$_6$-DMSO): δ 10.53 (1H, s), 9.15 (2H, s), 8.79 (2H, s), 7.93–8.04 (3H, m), 7.74 (4H, s), 7.52–7.58 (2H, m), 7.28 (1H, dd, J=1.8,7.6 Hz), 7.20 (1H, d, J=8.4 Hz), 2.33 (3H, s).

EXAMPLE 19(141)

2'-(4-amidinophenylcarbamoyl)-3'-methoxy-2-biphenylcarboxylic acid methanesulfonate

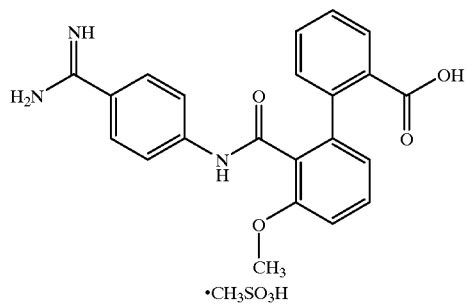

TLC: Rf 0.27 (Chloroform:Methanol:Water=7:3:0.3); NMR (d$_6$-DMSO): δ 10.40 (1H, br.s), 9.14 (2H, s), 8.86 (2H, s), 7.78 (1H, dd, J=1.8,7.6 Hz), 7.70 (2H, d, J=8.8 Hz), 7.61 (2H, d, J=8.8 Hz), 7.27–7.47 (4H, m), 7.13 (1H, d, J=8.0 Hz), 6.81 (1H, d, J=7.6 Hz), 3.84 (3H, s), 2.34 (3H, s).

EXAMPLE 19(142)

2'-(4-amidinophenylcarbamoyl)-4-((1-dimethylaminomethyl-2-methylpropyl) carbamoyl)-2-biphenylcarboxylic acid dimethanesulfonate

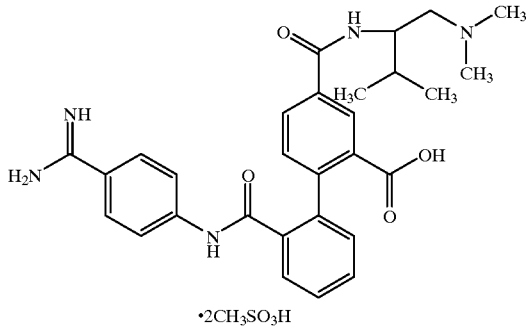

TLC: Rf 0.48 (Ethyl acetate:Acetic acid:Water=3:1:1); NMR (d$_6$-DMSO): δ 12.8–12.2(1H, br), 10.63 (1H, s), 9.21 (2H, s), 9.3–9.1 (1H, m), 9.00 (2H, s), 8.59 (1H, d, J=9.2 Hz), 8.35 (1H, d, J=2.0 Hz), 8.06 (1H, dd, J=2.0, 8.0 Hz), 7.76 (4H, like s), 7.8–7.7 (1H, m), 7.7–7.5 (2H, m), 7.35 (1H, d, J=8.0 Hz), 7.25 (1H, dd, J=2.0, 8.0 Hz), 4.20 (1H, m), 3.4–3.2 (2H, m), 2.80 (3H, s), 2.78 (3H, s), 2.33 (6H, s), 1.84 (1H, m), 0.92 (3H, d, J=7.4 Hz), 0.88 (3H, d, J=7.4 Hz).

EXAMPLE 19(143)

2'-(4-amidinophenylcarbamoyl)-4-((1-(pyrrolidin-1-ylmethyl)-2-methylpropyl) carbamoyl)-2-biphenylcarboxylic acid dimethanesulfonate

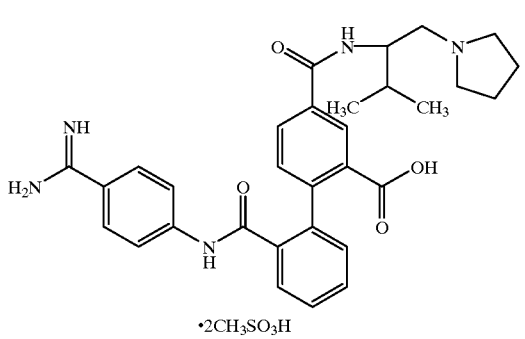

TLC: Rf 0.50 (Ethyl acetate:Acetic acid:Water=3:1:1); NMR (d$_6$-DMSO): δ 13.0–12.3 (1H, br), 10.61 (1H, br.s), 9.32 (1H, br), 9.17 (2H, br.s), 8.94 (2H, br.s), 8.53 (1H, br.d, J=5.1 Hz), 8.36 (1H, d, J=1.2 Hz), 8.05 (1H, dd, J=1.2, 7.8 Hz), 7.75 (4H, like s), 7.8–7.6 (1H, m), 7.6–7.5 (2H, m), 7.35 (1H, d, J=7.8 Hz), 7.24 (1H, dd, J=1.2, 7.8 Hz), 4.18 (1H, m), 3.8–3.3 (4H, m), 3.2–3.0 (2H, m), 2.32 (6H, s), 2.1–1.8 (5H, m), 0.93 (3H, d, J=6.6 Hz), 0.89 (3H, d, J=6.6 Hz).

EXAMPLE 19(144)

2'-(4-amidinophenylcarbamoyl)-4-((1-hydroxymethyl-2-methylpropyl) carbamoyl)-2-biphenylcarboxylic acid methanesulfonate

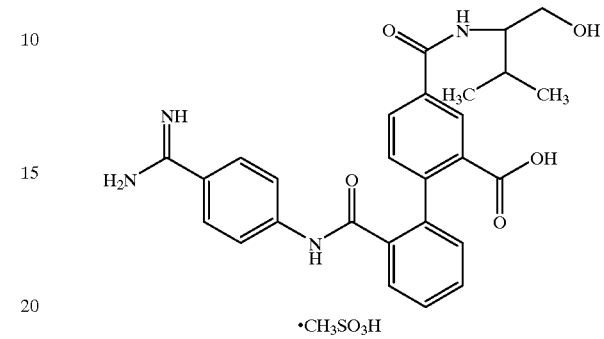

TLC: Rf 0.48 (Ethyl acetate:Acetic acid:Water=3:1:0.5); NMR (d$_6$-DMSO): δ 13.0–12.4 (1H, br), 10.52 (1H, br), 9.15 (2H, s), 8.89 (2H, s), 8.30 (1H, d, J=1.5 Hz), 8.17 (1H, br), 7.98 (1H, dd, J=1.5, 8.0 Hz), 7.73 (4H, like s), 7.8–7.6 (1H, m), 7.6–7.4 (2H, m), 7.31 (1H, d, J=8.0 Hz), 7.26 (1H, dd, J=1.5, 8.0 Hz), 5.4–4.5 (1H, br), 3.81 (1H, m), 3.6–3.3 (2H, m), 2.36 (3H, s), 1.90 (1H, like sextet, J=6.6 Hz), 0.90 (3H, d, J=6.6 Hz), 0.87 (3H, d, J=6.6 Hz).

EXAMPLE 19(145)

2-(6-(4-amidinophenylcarbamoyl)benzofuran-5-yl) benzoic acid methanesulfonate

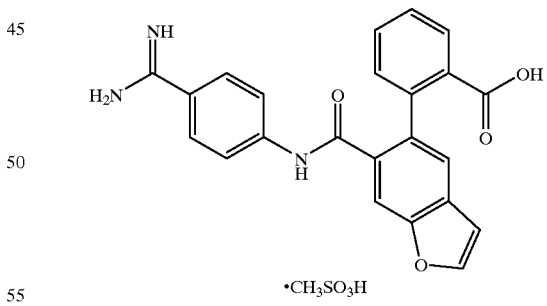

TLC: Rf 0.23 (Chloroform:Methanol:Acetic acid=10:2:1); NMR (d$_6$-DMSO): δ 13.0–12.6 (1H, broad), 10.42 (1H, s), 9.14 (2H, brs), 8.86 (2H, brs), 8.19 (1H, d, J=2.0 Hz), 7.94 (1H, d, J=1.0 Hz), 7.81 (1H, dd, J=8.0 Hz, 1.5 Hz), 7.73 (2H, d, J=9.0 Hz), 7.67 (2H, d, J=9.0 Hz), 7.51 (1H, td, J=8.0 Hz, 1.5 Hz), 7.50 (1H, s), 7.40 (1H, td, J=8.0 Hz, 1.5 Hz), 7.27 (1H, dd, J=8.0 Hz, 1.5 Hz), 7.05 (1H, dd, J=2.0 Hz, 1.0 Hz), 2.34 (3H, s).

EXAMPLE 19(146)

2-(5-(4-amidinophenylcarbamoyl)benzofuran-6-yl)benzoic acid methanesulfonate

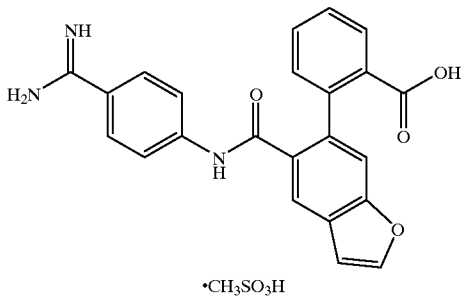

TLC:Rf 0.19 (Chloroform:Methanol:Acetic acid=10:2:1); NMR (d$_6$-DMSO): δ 13.0–12.4 (1H, broad), 10.44 (1H, s), 9.14 (2H, brs), 8.86 (2H, brs), 8.14 (1H, d, J=2.0 Hz), 7.98 (1H, s), 7.82 (1H, dd, J=8.0 Hz, 1.5 Hz), 7.74 (2H, d, J=9.0 Hz), 7.67 (2H, d, J=9.0 Hz), 7.52 (1H, td, J=8.0 Hz, 1.5 Hz), 7.48 (1H, d, J=1.0 Hz), 7.40 (1H, td, J=8.0 Hz, 1.5 Hz), 7.29 (1H, dd, J=8.0 Hz, 1.5 Hz), 7.12 (1H, dd, J=2.0 Hz, 1.0 Hz), 2.34 (3H, s).

EXAMPLE 19(147)

2'-(4-amidinophenylaminomethyl)-4-((2,2-dimethylpropyl)carbamoyl)-2-biphenylcarboxylic acid methanesulfonate

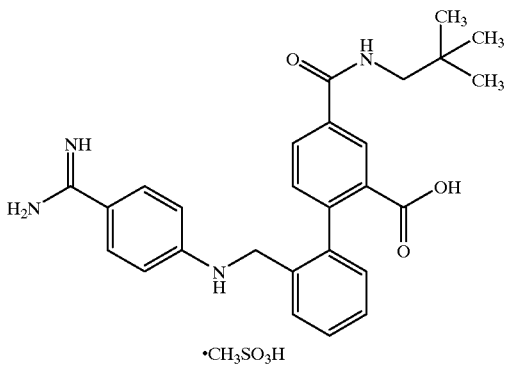

TLC:Rf 0.32 (Chloroform:Methanol:Acetic acid=10:2:1); NMR (d$_6$-DMSO): δ 12.97 (1H, br), 8.73 (2H, br.s), 8.56 (1H, br), 8.38 (2H, br.s), 8.36 (1H, d, J=1.8 Hz), 8.04 (1H, dd, J=1.8, 7.8 Hz), 7.53 (2H, d, J=8.4 Hz), 7.43 (1H, d, J=8.4 Hz), 7.4–7.2 (4H, m), 7.08 (1H, d, J=6.6 Hz), 6.55 (2H, d, J=8.4 Hz), 4.07 (2H, br.s), 3.13 (2H, d, J=6.6 Hz), 2.34 (3H, s), 0.91 (9H, s).

EXAMPLE 19(148)

2'-(4-amidinophenylaminomethyl)-2-biphenylcarboxylic acid methanesulfonate

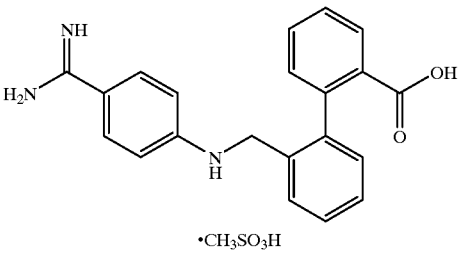

TLC:Rf 0.51 (Chloroform: Methanol:Water=7:3:0.3); NMR (d$_6$-DMSO): δ 12.9–12.6 (1H, broad), 8.74 (2H,s), 8.42 (2H, s), 7.89 (1H, d, J=8 Hz), 7.67–7.42 (4H, m), 7.40–7.18 (5H, m), 7.07 (1H, t, J=4 Hz), 6.54 (2H, d, J=8 Hz), 4.06 (2H, d, J=4 Hz), 2.35 (3H, s).

EXAMPLE 19(149)

2-(3-(4-amidinophenylaminomethyl)naphthalen-2-yl)benzoic acid methanesulfonate

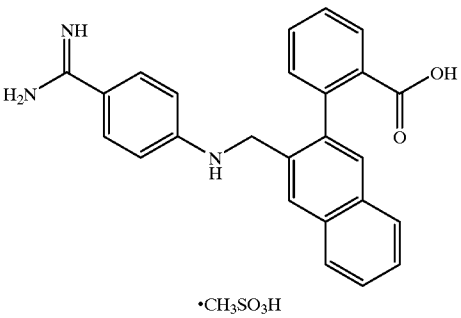

TLC:Rf 0.21 (Chloroform:Methanol:Water=10:3:0.2); NMR (d$_6$-DMSO): δ 13.2–12.5 (1H, br), 8.74 (2H, br.s), 8.34 (2H, br.s), 8.0–7.4 (10H, m), 7.53 (2H, d, J=8.8 Hz), 7.5–7.2 (1H, br), 6.59 (2H, d, J=8.8 Hz), 4.18 (2H, br.s), 2.32 (3H, s).

EXAMPLE 19(150)

2'-(4-amidinophenylaminomethyl)-4'-methoxy-2-biphenylcarboxylic acid methanesulfonate

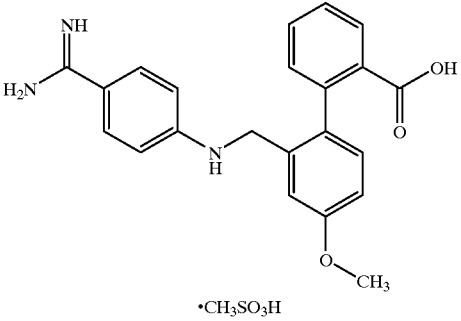

TLC:Rf 0.37 (Chloroform:Methanol:Acetic acid=10:2:1); NMR (d$_6$-DMSO): δ 13.1–12.5 (1H, broad), 8.75 (2H, brs), 8.44 (2H, brs), 7.85 (1H, dd, J=7.5 Hz, 1.5 Hz), 7.61–7.43 (4H, m), 7.31 (1H, d, J=7.5 Hz), 7.25 (1H, brs), 7.00 (1H, d, J=9.0 Hz), 6.86–6.80 (2H, m), 6.54 (2H, d, J=9.0 Hz), 4.02 (2H, brs), 3.70 (3H, s), 2.35 (3H, s).

EXAMPLE 19(151)

2-(3-(4-amidinophenylaminomethyl)naphthalen-2-yl)-5-((2-methylpropyl) carbamoyl) benzoic acid methanesulfonate

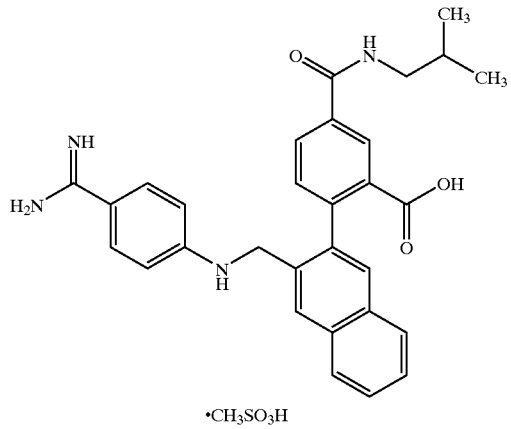

•CH₃SO₃H

TLC:Rf 0.30 (Chloroform:Methanol:Water=8:2:0.2); NMR (d₆-DMSO): δ 8.74 (3H, br.s), 8.44 (1H, s), 8.31 (2H, s), 8.10 (1H, d, J=8.0 Hz), 7.80–7.93 (2H, m), 7.75 (1H, s), 7.64 (1H, s), 7.47–7.56 (5H, m), 7.34 (1H, br.s), 6.60 (2H, d, J=8.8 Hz), 4.22 (2H, br.s), 3.14 (2H, t, J=7.0 Hz), 2.32 (3H, s), 1.89 (1H, m), 0.92 (6H, d, J=7.0 Hz).

EXAMPLE 19(152)

2'-(4-amidinophenylaminomethyl)-4'-methoxy-4-((2-methylpropyl)carbamoyl)-2-biphenylcarboxylic acid methanesulfonate

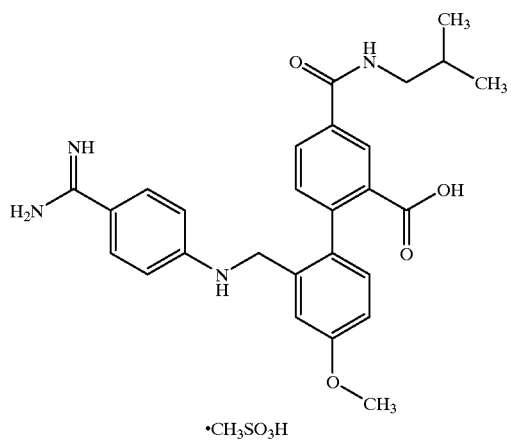

•CH₃SO₃H

TLC:Rf 0.30 (Chloroform:Methanol:Water=8:2:0.2); NMR (d₆-DMSO): δ 8.75 (2H, s), 8.67 (1H, t, J=6.0 Hz), 8.34 (1H, d, J=2.0 Hz), 8.31 (2H, s), 8.03 (1H, dd, J=2.0,8.0 Hz), 7.53 (2H, d, J=8.8 Hz), 7.41 (1H, d, J=8.0 Hz), 7.24 (1H, br.s), 7.02 (1H, d, J=9.2 Hz), 6.86–6.88 (2H, m), 6.55 (2H, d, J=8.8 Hz), 4.04 (2H, br.s), 3.72 (3H, s), 3.11 (2H, t, J=6.0 Hz), 2.33 (3H, s), 1.87 (1H, m), 0.90 (6H, d, J=6.6 Hz).

EXAMPLE 19(153)

2'-(4-amidinophenylaminomethyl)-4-((2-methylpropyl) carbamoyl)-2-biphenylcarboxylic acid methanesulfonate

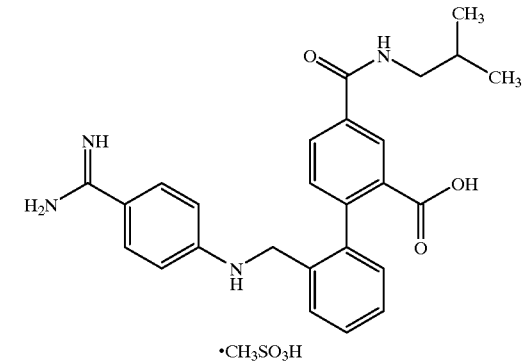

•CH₃SO₃H

TLC:Rf 0.42 (Chloroform:Methanol:Acetic acid=10:2:1); NMR (d₆-DMSO): δ 10.4–9.6 (2H, broad), 8.60 (1H, brt, J=6.0 Hz), 8.51 (2H, brs), 8.30 (1H, d, J=2.0 Hz), 7.87 (1H, dd, J=8.0 Hz, 2.0 Hz), 7.47 (2H, d, J=9.0 Hz), 7.48–7.35 (1H, broad), 7.32–7.15 (4H, m), 7.03–6.96 (1H, m), 6.66 (2H, d, J=9.0 Hz), 4.25–3.95 (2H, m), 3.08 (2H, t, J=6.5 Hz), 2.34 (3H, s), 1.96–1.75 (1H, m), 0.88 (6H, d, J=7.0 Hz).

EXAMPLE 19(154)

Ethyl 2'-(4-amidinophenylaminomethyl)-4-((2-methylpropyl)carbamoyl)-2-biphenylcarboxylate methanesulfonate

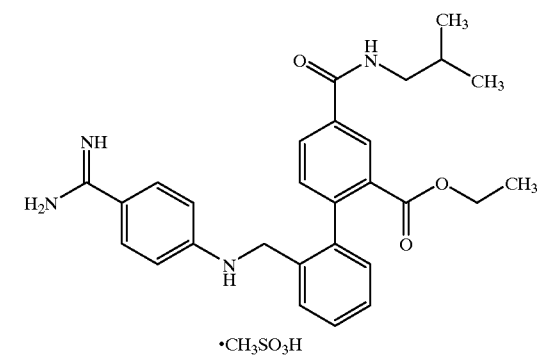

•CH₃SO₃H

TLC:Rf 0.58 (Chloroform:Methanol:Acetic acid=10:2:1); NMR (d₆-DMSO): δ 8.70 (1H, brt, J=6.0 Hz), 8.80–8.40 (4H, broad), 8.34 (1H, s), 8.07 (1H, d, J=8.0 Hz), 7.54 (2H, d, J=8.5 Hz), 7.50 (1H, d, J=8.0 Hz), 7.40–7.17 (4H, m), 7.06 (1H, d, J=7.5 Hz), 6.52 (2H, d, J=8.5 Hz), 4.17–3.90 (4H, m), 3.11 (2H, t, J=6.0 Hz), 2.32 (3H, s), 1.93–1.79 (1H, m), 0.91 (3H, t, J=0.89 (6H, d, J=7.0 Hz).

EXAMPLE 19(155)

Ethyl 2'-(4-(N²-hydroxyamidino)phenylaminomethyl)-4-((2-methylpropyl) carbamoyl)-2-biphenylcarboxylate methanesulfonate

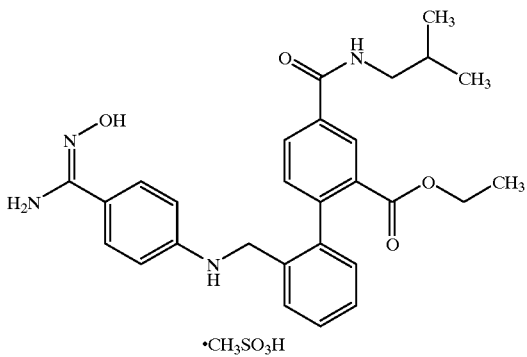

TLC:Rf 0.56 (Chloroform:Methanol:Water=9:1:0.1); NMR (d₆-DMSO): δ 12.26 (1H, brs), 11.2–10.3 (1H, broad), 8.93 (1H, brs), 8.73 (1H, brt, J=6.0 Hz), 8.56 (1H, brs), 8.34 (1H, d, J=2.0 Hz), 8.09 (1H, dd, 8.0 Hz, 2.0 Hz), 7.50 (1H, d, J=8.0 Hz), 7.43 (2H, d, J=9.0 Hz), 7.36–7.23 (3H, m), 7.06 (1H, d, J=7.0 Hz), 6.52 (2H, d, J=9.0 Hz), 4.16–3.90 (4H, m), 3.11 (2H, t, J=6.0 Hz), 2.35 (3H, s), 1.97–1.76 (1H, m), 0.91 (3H, t, J=7.0 Hz), 0.89 (6H, d, J=7.0 Hz).

EXAMPLE 19(156)

Ethyl 2'-(4-(N²-hydroxyamidino)phenylcarbamoyl)-4-((2-methylpropyl) carbamoyl)-2-biphenylcarboxylate methanesulfonate

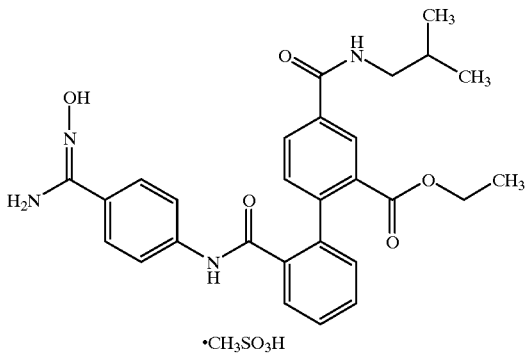

TLC:Rf 0.24 (Chloroform:Methanol=10:1); NMR (d₆-DMSO): δ 12.60 (1H, br), 11.05 (1H, br), 10.53 (1H, s), 9.3–8.8 (2H, br), 8.66 (1H, t, J=6.8 Hz), 8.22 (1H, d, J=2.0 Hz), 8.02 (1H, dd, J=2.0, 7.8 Hz), 7.8–7.5 (7H, m), 7.40 (1H, d, J=7.8 Hz), 7.31 (1H, br.d, J=7.8 Hz), 3.98 (2H, q, J=7.4 Hz), 3.08 (2H, t, J=6.8 Hz), 2.33 (3H, s), 1.84 (1H, like septet, J=6.8 Hz), 0.90 (3H, t, J=7.4 Hz), 0.88 (6H, d, J=6.8 Hz).

EXAMPLE 19(157)

Ethyl 2'-(4-(N²-hydroxyamidino)phenylcarbamoyl)-2-biphenylcarboxylate hydrochloride

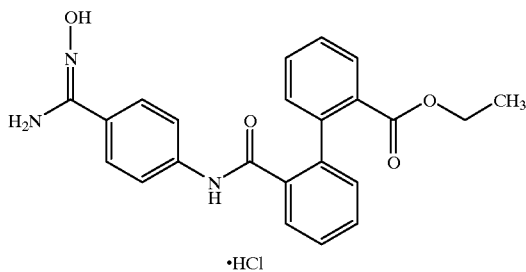

TLC:Rf 0.37 (Chloroform:Methanol:Water=9:1:0.1); NMR (d₆-DMSO): δ 11.16 (1H, brs), 10.42 (1H, s), 9.2–8.8 (3H, broad), 7.77 (1H, dd, J=8.0 Hz, 1.5 Hz), 7.69 (2H, d, J=9.0 Hz), 7.64 (2H, d, J=9.0 Hz), 7.65–7.61 (1H, m), 7.59–7.48 (3H, m), 7.47 (1H, td, J=8.0 Hz, 1.5 Hz), 7.34–7.25 (2H, m), 3.96 (2H, q, J=7.0 Hz), 0.88 (3H, t, J=7.0 Hz).

EXAMPLE 19(158)

2'-(4-(N²-t-butoxycarbonyloxyamidino) phenylcarbamoyl)-2-biphenylcarboxylic acid

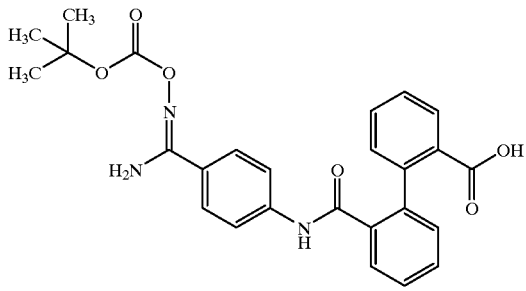

TLC:Rf 0.14 (Chloroform:Methanol:Water=9:1:0.1); NMR (d₆-DMSO): δ 10.09 (1H, brs), 7.80 (1H, brd, J=7.0 Hz), 7.70–7.30 (9H, m), 7.21 (2H, d, J=8.5 Hz), 6.59 (2H, brs), 1.44 (9H, s).

EXAMPLE 19(159)

2'-(4-(N²-ethoxycarbonylamidino)phenylcarbamoyl)-2-biphenylcarboxylic acid methanesulfonate

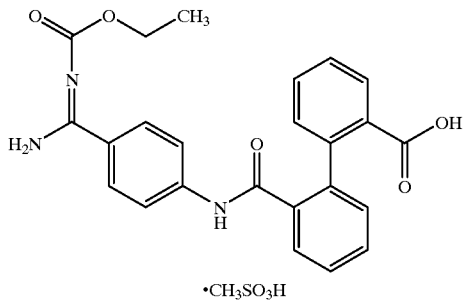

TLC:Rf 0.72 (Chloroform:Methanol:Acetic acid=10:2:1); NMR (d₆-DMSO): δ 13.0–12.0 (1H, br), 11.13 (1H, br), 10.46 (1H, s), 10.42 (1H, br.s), 7.81 (1H, dd, J=1.0, 7.4 Hz), 7.8–7.6 (5H, m), 7.6–7.3 (4H, m), 7.3–7.2 (2H, m), 4.33 (2H, q, J=7.4 Hz), 4.0–3.0 (1H, br), 2.30 (3H, s), 1.31 (3H, t, J=7.4 Hz).

EXAMPLE 19(160)

2-(4-(4-amidinophenylcarbamoyl)pyridin-3-yl)-5-((2-methylpropyl)carbamoyl) benzoic acid methanesulfonate

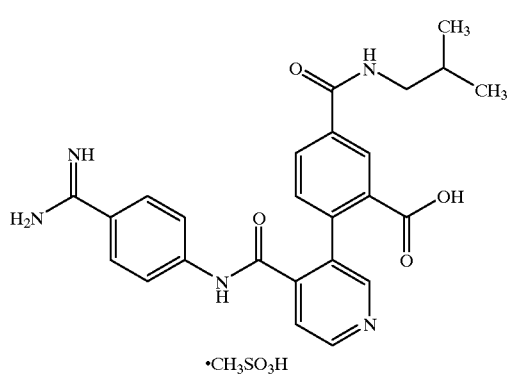

TLC:Rf 0.50 (Chloroform:Methanol:Water=7:3:0.3); NMR (d$_6$-DMSO): δ 11.03 (1H, s), 9.23 (2H, brs), 9.00 (2H, brs), 8.88 (1H, d, J=5.5 Hz), 8.73 (1H, brt, J=6.0 Hz), 8.71 (1H, s), 8.41 (1H, d, J=2.0 Hz), 8.05 (1H, dd, J=8.0 Hz, 2.0 Hz), 7.91 (1H, d, J=5.5 Hz), 7.78 (2H, d, J=9.5 Hz) 7.73 (2H, d, J=9.5 Hz), 7.47 (1H, d, J=8.0 Hz), 3.09 (2H, brt, J=6.5 Hz), 2.36 (3H, s), 1.97–1.75 (1H, m), 0.88 (6H, d, J=6.5 Hz).

EXAMPLE 19(161)

2-(2-(4-amidinophenylcarbamoyl)pyridin-3-yl)benzoic acid methanesulfonate

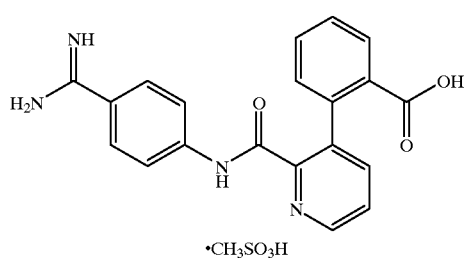

TLC:Rf 0.34 (Ethyl acetate:Acetic acid:Water=3:1:0.5); NMR (d$_6$-DMSO): δ 10.96 (1H,s), 9.21 (2H, br.s), 8.96 (2H, br.s), 8.71 (1H, m), 7.94 (2H, d, J=8.8 Hz), 8.0–7.8 (1H, m), 7.9–7.6 (2H, m), 7.77 (2H, d, J=8.8 Hz), 7.60 (1H, t, J=7.4 Hz), 7.48 (1H, t, J=7.4 Hz), 7.24 (1H, d, J=7.4 Hz), 5.6–4.2 (1H, br), 2.37 (3H, s).

EXAMPLE 19(162)

2'-(4-amidinophenylcarbamoyl)-4-propylcarbamoyl-2-biphenylcarboxylic acid methanesulfonate

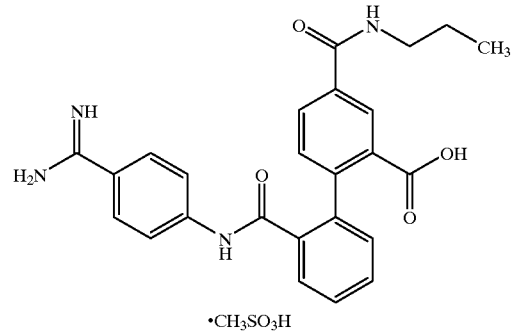

TLC:Rf 0.09 (Chloroform:Methanol:Acetic acid=10:2:1); NMR (d$_6$-DMSO): δ 10.5 (1H, s), 9.13 (2H,brs), 8.79 (2H,brs), 8.64 (1H, t, J=5.4 Hz), 8.29 (1H, d, J=1.8 Hz), 7.96 (1H, dd, J=1.8, 8.0 Hz), 7.80–7.60 (5H, m), 7.58–7.51 (2H, m), 7.32 (1H, d, J=8.4 Hz), 7.30–7.20 (1H, m), 3.21 (2H, q, J=6.6 Hz), 2.33 (3H, s), 1.52 (2H, sextet, J=7.0 Hz), 0.88 (3H, t, J=7.0 Hz).

EXAMPLE 19(163)

2'-(4-amidinophenylcarbamoyl)-4-((3-hydroxy-2,2-dimethylpropyl)carbamoyl)-2-biphenylcarboxylic acid methanesulfonate

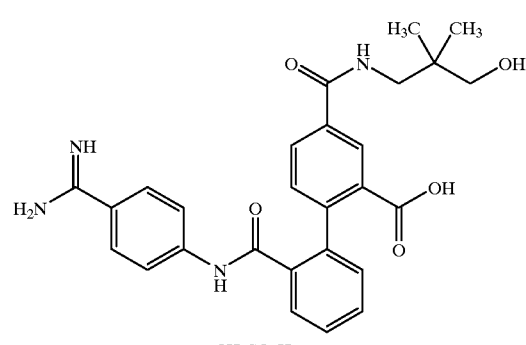

TLC:Rf 0.07 (Chloroform:Methanol:Acetic acid=10:2:1); NMR (d$_6$-DMSO): δ 9.06 (4H, br s), 8.96 (1H, d, J=8.0 Hz), 8.44 (1H, t, J=5.4 Hz), 8.01 (1H, s), 7.70–7.50 (6H, m), 7.50–7.40 (2H, m), 7.10–7.00 (1H, m), 6.97 (1H, d, J=8.0 Hz), 4.59 (1H, t, J=5.8 Hz), 3.10–3.07 (4H, m), 2.31 (3H, s), 0.79 (6H, s).

EXAMPLE 19(164)

2'-(4-amidinophenylcarbamoyl)-4-((1,2,2-trimethylpropyl)carbamoyl)-2-biphenylcarboxylic acid methanesulfonate

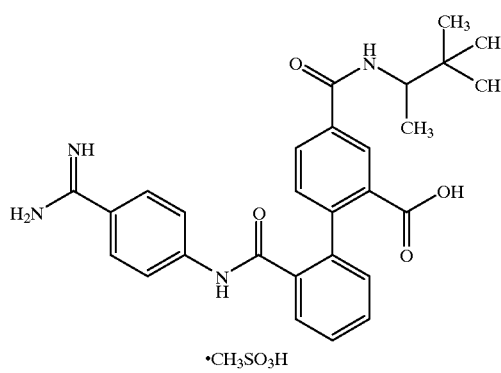

TLC:Rf 0.42 (Chloroform:Methanol:Acetic acid=10:2:1); NMR (d$_6$-DMSO): δ 10.54 (1H, s), 9.16 (2H, s), 8.83 (2H, s), 8.29 (1H, d, J=1.8 Hz), 8.17 (1H, br.d, J=9.4 Hz), 7.96 (1H, dd, J=1.8,8.0 Hz), 7.74 (4H, s), 7.71 (1H, dd, J=1.8,8.0 Hz), 7.52–7.59 (2H, m), 7.31 (1H, d, J=8.0 Hz), 7.26 (1H, m), 3.98 (1H, m), 2.36 (3H, s), 1.09 (3H, d, J=6.6 Hz), 0.91 (9H, s).

EXAMPLE 19(165)

2'-(4-amidinophenylcarbamoyl)-4-pentylcarbamoyl-2-biphenylcarboxylic acid methanesulfonate

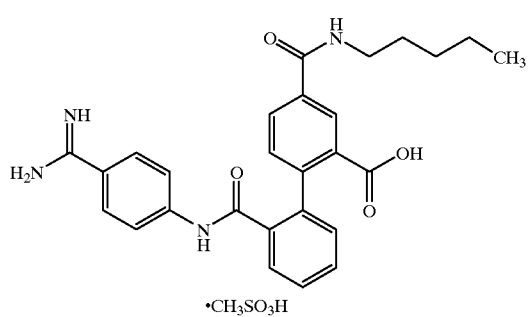

TLC:Rf 0.39 (Chloroform:Methanol:Acetic acid=10:2:1); NMR (d$_6$-DMSO): δ 10.52 (1H, s), 9.17 (2H, s), 8.89 (2H, s), 8.63 (1H, br.t, J=6.0 Hz), 8.31 (1H, d, J=1.8 Hz), 7.97 (1H, dd, J=1.8,8.0 Hz), 7.74 (4H, s), 7.71 (1H, dd, J=1.8,8.0 Hz), 7.52–7.59 (2H, m), 7.32 (1H, d, J=8.0 Hz), 7.28 (1, m), 3.26 (2H, dt, J=6.0,6.6 Hz), 2.36 (3H, s), 1.50–1.56 (2H, m), 1.26–1.33 (4H, m), 0.88 (3H, t, J=6.6 Hz).

EXAMPLE 19(166)

2'-(4-amidinophenylcarbamoyl)-4-hexylcarbamoyl-2-biphenylcarboxylic acid methanesulfonate

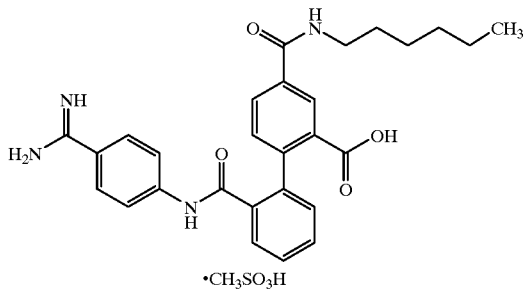

TLC:Rf 0.26 (Chloroform:Methanol:Acetic acid=10:2:1); NMR (d$_6$-DMSO): δ 10.5 (1H, s), 9.14 (2H, br s), 8.84 (2H, br s), 8.62 (1H, t, J=5.4 Hz), 8.28 (1H, d, J=2.1 Hz), 7.95 (1H, dd, J=2.1, 8.1 Hz), 7.75–7.67 (5H, m), 7.60–7.48 (2H, m), 7.31 (1H, d, J=8.1 Hz), 7.28–7.25 (1H, m), 3.24 (2H, q, J=6.3 Hz), 2.34 (3H, s), 1.58–1.42 (2H, m), 1.38–1.20 (6H, m), 0.85 (3H, t, J=6.3 Hz).

EXAMPLE 19(167)

2'-(4-amidinophenylcarbamoyl)-4-((1,2-dimethylpropyl)carbamoyl)-2-biphenylcarboxylic acid methanesulfonate

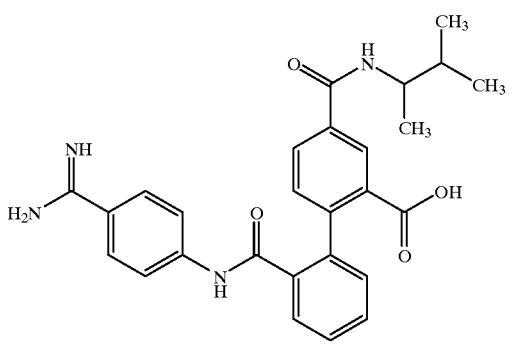

TLC:Rf 0.23 (Chloroform:Methanol:Acetic acid=10:2:1); NMR (d$_6$-DMSO): δ 10.5 (1H, s), 9.15 (2H, br s), 8.85 (2H, br s), 8.33 (1H, d, J=9.0 Hz), 9.0 Hz), 8.28 (1H, d, J=1.8 Hz), 7.96 (1H, dd, J=1.8, 7.8 Hz), 7.80–7.68 (5H, m), 7.60–7.49 (2H, m), 7.30 (1H, d, J=7.8 Hz), 7.28–7.25 (1H, m), 3.88–3.77 (1H, m), 2.34 (3H, s), 1.75 (1H, sextet, J=6.9 Hz), 1.09 (3H, d, J=6.9 Hz), 0.88 (6H, dd, J=2.7, 6.9 Hz).

EXAMPLE 19(168)

2'-(4-amidinophenylcarbamoyl)-4-(((1S)-1-hydroxymethyl-2-methylpropyl) carbamoyl)-2-biphenylcarboxylic acid methanesulfonate

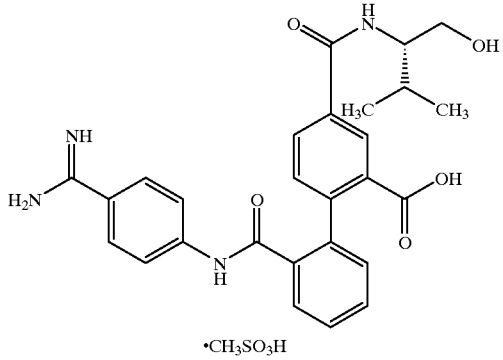

TLC:Rf 0.48 (Ethyl acetate:Acetic acid:Water=3:1:0.5); NMR (d$_6$-DMSO): δ 13.4–12.5 (1H, br), 10.54 (1H, s), 9.15 (2H, br.s), 8.91 (2H, br.s), 8.31 (1H, d, J=1.4 Hz), 8.19 (1H, d, J=8.8 Hz), 7.99 (1H, dd, J=1.4, 8.0 Hz), 7.73 (4H, like s), 7.8–7.5 (1H, m), 7.6–7.4 (2H, m), 7.32 (1H, d, J=8.0 Hz), 7.3–7.2 (1H, m), 5.2–3.6 (1H, br), 3.81 (1H, m), 3.6–3.4 (2H, m), 2.37 (3H, s), 1.90 (1H, like sextet, J=6.8 Hz), 0.90 (3H, d, J=6.8 Hz), 0.86 (3H, d, J=6.8 Hz).

EXAMPLE 19(169)

2'-(4-amidinophenylcarbamoyl)-4-((3,3-dimethylbutyl) carbamoyl)-2-biphenylcarboxylic acid methanesulfonate

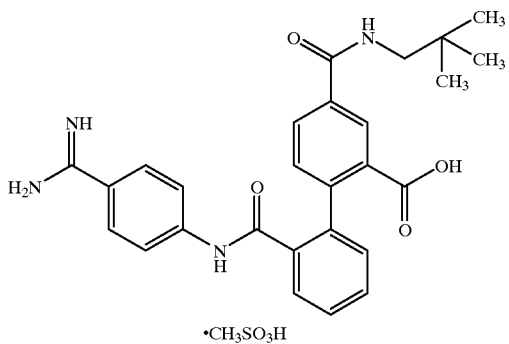

TLC:Rf 0.44 (Chloroform:Methanol:Acetic acid=10:2:1); NMR (d$_6$-DMSO): δ 12.83 (1H, br.s), 10.53 (1H, s), 9.18 (2H, s), 8.92 (2H, s), 8.61 (1H, br.t, J=6.0 Hz), 8.29 (1H, d, J=1.8 Hz), 7.95 (1H, dd, J=1.8,8.0 Hz), 7.74 (4H, s), 7.70 (1H, dd, J=1.8,8.0 Hz), 7.51–7.60 (2H, m), 7.32 (1H, d, J=8.0 Hz), 7.28 (1H, dd, J=1.8,8.0 Hz), 3.25–3.35 (2H, m), 2.36 (3H, s), 1.43–1.49 (2H, m), 0.93 (9H, s).

EXAMPLE 19(170)

2'-(4-amidinophenylcarbamoyl)-4-(((1R)-1-hydroxymethyl-2-methylpropyl) carbamoyl)-2-biphenylcarboxylic acid methanesulfonate

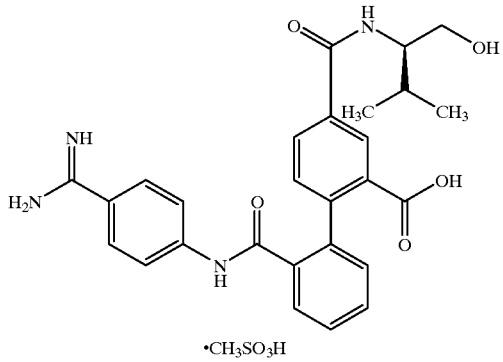

TLC:Rf 0.48 (Ethyl acetate:Acetic acid:Water=3:1:0.5); NMR (d$_6$-DMSO): δ 12.4–11.6 (1H, br), 10.54 (1H, s), 9.15 (2H, br.s), 8.89 (2H, br.s), 8.30 (1H, d, J=1.8 Hz), 8.19 (1H, d, J=9.0 Hz), 7.98 (1H, dd, J=1.8, 8.1 Hz), 7.73 (4H, like s), 7.8–7.6 (1H, m), 7.65–7.45 (2H, m), 7.31 (1H, d, J=8.1 Hz), 7.26 (1H, dd, J=1.8, 8.1 Hz), 4.5–3.8 (1H, br), 3.81 (1H, m), 3.6–3.4 (2H, m), 2.36 (3H, s), 1.90 (1H, like sextet, J=6.9 Hz), 0.89 (3H, d, J=6.9 Hz), 0.86 (3H, d, J=6.9 Hz).

EXAMPLE 19(171)

2'-(4-amidinophenylcarbamoyl)-4-(((1S)-1-methoxycarbonyl-2-methylpropyl) carbamoyl)-2-biphenylcarboxylic acid methanesulfonate

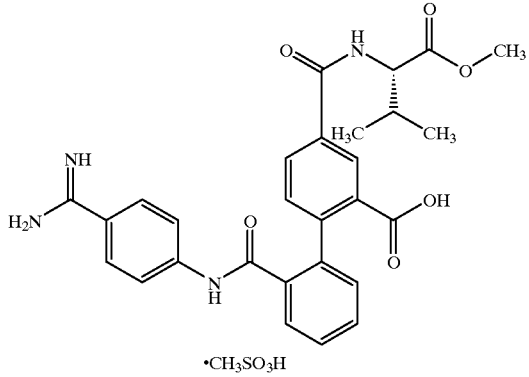

TLC:Rf 0.36 (Chloroform:Methanol:Acetic acid=10:2:1); NMR (d$_6$-DMSO): δ 10.5 (1H, s), 9.14 (2H, br s), 8.85 (1H, d, J=7.6 Hz), 8.83 (2H, br s), 8.33 (1H, d, J=1.8 Hz), 8.01 (1H, dd, J=1.8, 8.0 Hz), 7.80–7.68 (5H, m), 7.59–7.52 (2H, m), 7.33 (1H, d, J=8.0 Hz), 7.30–7.25 (1H, m), 4.30 (1H, t, J=7.4 Hz), 3.65 (3H, s), 2.32 (3H, s), 2.32–2.10 (1H, m), 0.98–0.91 (6H, m).

EXAMPLE 19(172)

2'-(4-amidinophenylcarbamoyl)-4-(((1R)-1-methoxycarbonyl-2-methylpropyl) carbamoyl)-2-biphenylcarboxylic acid methanesulfonate

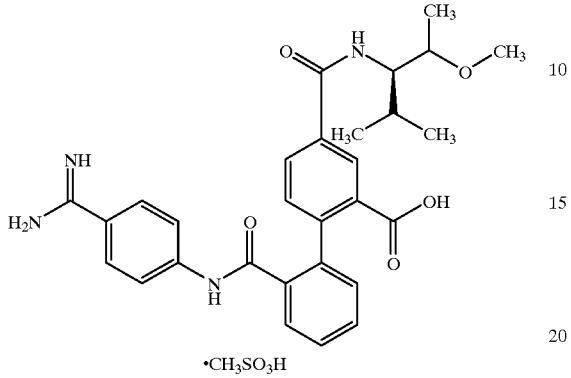

TLC:Rf 0.36 (Chloroform:Methanol:Acetic acid=10:2:1); NMR (d₆-DMSO): δ 10.5 (1H, s), 9.15 (2H, br s), 8.85 (1H, d, J=7.4 Hz), 8.83 (2H, br s), 8.33 (1H, d, J=1.8 Hz), 8.01 (1H, dd, J=1.8, 8.0 Hz), 7.80–7.68 (5H, m), 7.59–7.50 (2H, m), 7.33 (1H, d, J=8.0 Hz), 7.30–7.25 (1H, m), 4.30 (1H, t, J=7.8 Hz), 3.65 (3H, s), 2.33 (3H, s), 2.33–2.10 (1H, m), 0.98–0.91 (6H, m).

EXAMPLE 19(173)

2'-(4-amidinophenylcarbamoyl)-4-(3-methylbutoxy)-2-biphenylcarboxylic acid methanesulfonate

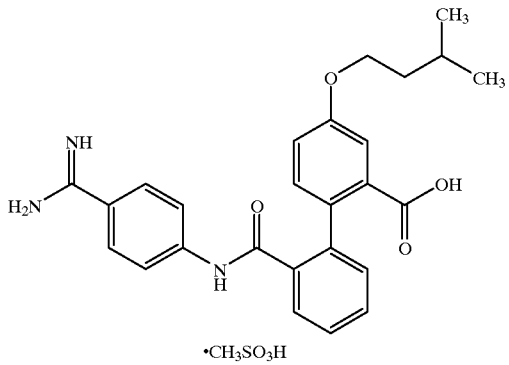

TLC:Rf 0.26 (Chloroform:Methanol:Acetic acid=10:2:1); NMR (d₆-DMSO): δ 10.4 (1H, s), 9.14 (2H, br s), 8.83 (2H, br s), 7.76–7.60 (5H, m), 7.52–7.46 (2H, m), 7.30–7.05 (4H, m), 4.01 (2H, t, J=6.6 Hz), 2.33 (3H, s), 1.85–1.54 (3H, m), 0.91 (6H, d, J=6.6 Hz).

EXAMPLE 19(174)

2-(3-(4-amidinophenylcarbamoyl)pyridin-4-yl)-5-((2-methylpropyl)carbamoyl) benzoic acid methanesulfonate

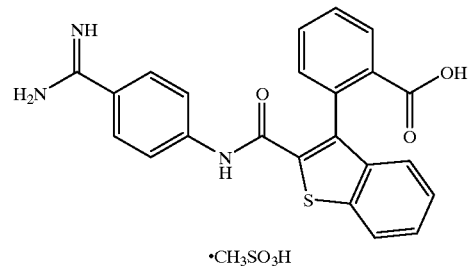

TLC:Rf 0.23 (Chloroform:Methanol:Water=7:3:0.3); NMR (d₆-DMSO): δ 11.12 (1H, s), 9.24 (2H, brs), 9.10 (1H, s), 9.03 (2H, brs), 8.90 (1H, d, J=5.5 Hz), 8.76 (1H, brt, J=5.5 Hz), 8.42 (1H, d, J=2.0 Hz) 8.08 (1H, dd, J=8.0 Hz, 2.0 Hz), 7.77 (4H, s), 7.70 (1H, d, J 5.5 Hz), 7.40 (1H, d, J=8.0 Hz), 3.09 (2H, t, J=6.0 Hz), 2.38 (3H, s), 1.95–1.75 (1H, m), 0.88 (6H, d, J=6.5 Hz).

EXAMPLE 19(175)

2-(2-(4-amidinophenylcarbamoyl)benzothiophene-3-yl) benzoic acid methanesulfonate

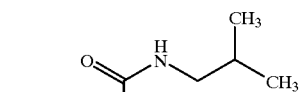

TLC:Rf 0.36 (Chloroform:Methanol:Acetic acid=10:2:1); NMR (d₆-DMSO): δ 12.8 (1H, brs), 10.03 (1H, s), 9.17 (2H, brs), 8.89 (2H, brs), 8.13 (1H, d, J=8.0 Hz), 7.99 (1H, dd, J=7.5 Hz, 1.5 Hz), 7.76 (2H, d, J=9.0 Hz), 7.69–7.48 (5H, m), 7.45–7.36 (2H, m), 7.23 (1H, d, J=8.0 Hz), 2.34 (3H, s).

EXAMPLE 19(176)

Ethyl 2'-(4-amidinophenoxymethyl)-4-((2-methylpropyl) carbamoyl)-2-biphenylcarboxylate

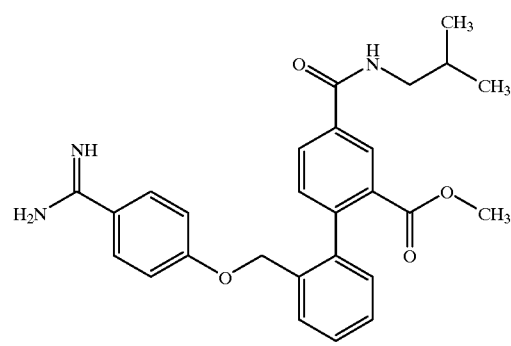

TLC:Rf 0.56 (Chloroform:Methanol:Acetic acid=10:2:1); NMR (d₆-DMSO): δ 9.15 (2H, brs), 8.92 (2H, brs), 8.71

(1H, brt, J=6.0 Hz), 8.31 (1H, d, J=2.0 Hz), 8.04 (1H, dd, J=8.0 Hz, 2.0 Hz), 7.74 (2H, d, J=9.0 Hz), 7.59–7.53 (1H, m), 7.44 (1H, d, J=8.0 Hz), 7.49–7.36 (2H, m), 7.17–7.12 (1H, m), 7.01 (2H, d, J=9.0 Hz), 4.92 (1H, d, J=12 Hz), 4.85 (1H, d, J=12 Hz), 3.98 (2H, q, J=7.0 Hz), 3.08 (2H, t, J=6.0 Hz), 1.97–1.72 (1H, m), 0.88 (6H, d, J=7.0 Hz), 0.84 (3H, t, J=7.0 Hz).

EXAMPLE 19(177)

2-(3-(4-amidinophenylcarbamoyl)-5-methoxybenzofuran-2-yl)benzoic acid methanesulfonate

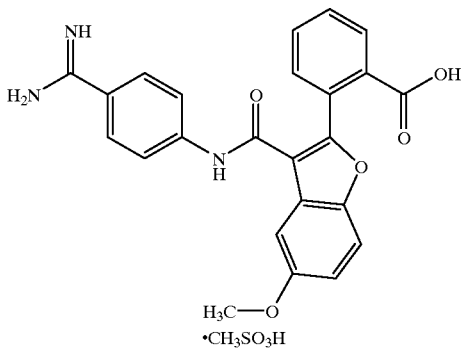

TLC:Rf 0.14 (Chloroform:Methanol:Acetic acid=10:2:1); NMR (d$_6$-DMSO): δ 13.2–12.8 (1H, broad), 10.48 (1H, brs), 9.17 (2H, brs), 8.89 (2H, brs), 7.91 (1H, dd, J=7.5 Hz, 1.5 Hz), 7.83 (2H, d, J=9.0 Hz), 7.78 (2H, d, J=9.0 Hz), 7.74 (1H, dd, J=7.5 Hz, 1.5 Hz), 7.70 (1H, td, J=7.5 Hz, 1.5 Hz), 7.62 (1H, td, J=7.5 Hz, 1.5 Hz), 7.60 (1H, d, J=9.0 Hz), 7.26 (1H, d, J=2.5 Hz), 7.03 (1H, dd, J=9.0 Hz, 2.5 Hz), 3.83 (3H, s), 2.34 (3H, s).

EXAMPLE 19(178)

Benzyl 2'-(6-amidinopyridin-3-ylcarbamoyl)-4-((2-methylpropyl)carbamoyl)-2-biphenylcarboxylate

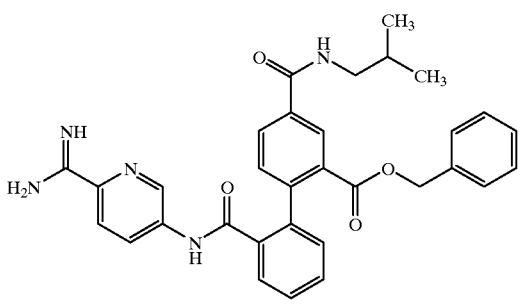

TLC:Rf 0.33 (Chloroform:Methanol:Acetic acid= 8:2:0.1); NMR (CD$_3$OD): δ 8.78 (1H, d, J=1.8 Hz), 8.33 (1H, d, J=1.8 Hz), 8.19 (1H, dd, J=2.6, 8.8 Hz), 8.04 (1H, s), 7.99 (1H, dd, J=2.0, 8.0 Hz), 7.60–7.48 (2H, m), 7.44 (1H, d, J=8.0 Hz), 7.33–7.29 (1H, m), 7.25–7.21 (3H, m), 7.14–7.09 (2H, m), 5.10 (2H, s), 3.18 (2H, d, J=7.0 Hz), 2.02–1.81 (1H, m), 0.95 (6H, d, J=6.6 Hz).

EXAMPLE 19(179)

2'-(4-amidinophenylcarbamoyl)-4'-methoxy-4-((1,2,2-trimethylpropyl) carbamoyl)-2-biphenylcarboxylic acid methanesulfonate

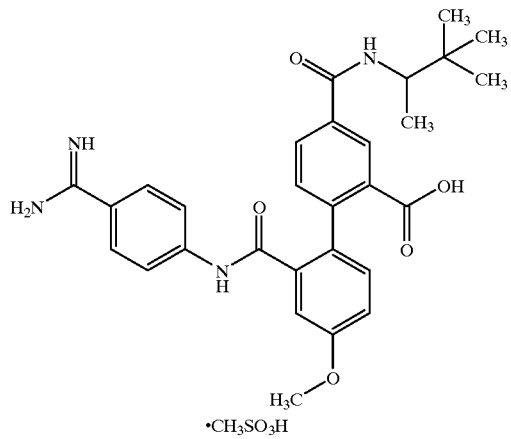

TLC:Rf 0.17 (Chloroform:Methanol:Water=10:2:1); NMR (d$_6$-DMSO): δ 12.9–12.7 (1H, broad), 10.55 (1H, s), 9.17 (2H, brs), 8.91 (2H, brs), 8.23 (1H, d, J=2.0 Hz), 8.16 (1H, d, J=9.5 Hz), 7.92 (1H, dd, J=8.0 Hz, 2.0 Hz), 7.73 (4H, s), 7.28 (1H, d, J=8.0 Hz), 7.23 (1H, d, J=2.5 Hz), 7.18 (1H, d, J=8.5 Hz), 7.13 (1H, dd, J=8.5 Hz, 2.5 Hz), 3.97 (1H, dq, J=9.5 Hz, 7.0 Hz), 3.87 (3H, s), 2.33 (3H, s), 1.08 (3H, t, J=7.0 Hz), 0.89 (9H, s).

EXAMPLE 19(180)

2'-(4-amidinophenylcarbamoyl)-4-(((1S)-1-hydroxymethyl-2,2-dimethylpropyl) carbamoyl)-2-biphenylcarboxylic acid methanesulfonate

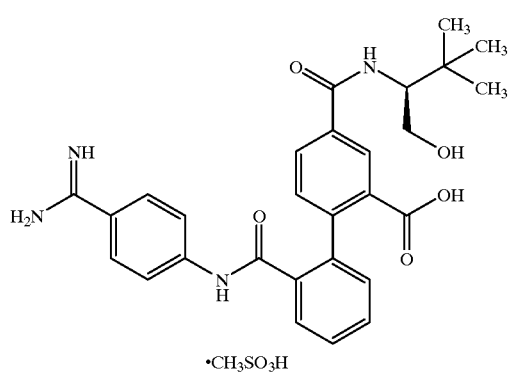

TLC:Rf 0.40 (Ethyl acetate:Acetic acid:Water=3:1:1); NMR (d$_6$-DMSO): δ 10.5 (1H, s), 9.16 (2H, br s), 8.86 (2H, br s), 8.86 (1H, d, J=51.8 Hz), 8.09 (1H, d, J=9.6 Hz), 7.98 (1H, dd, J=1.8, 8.0 Hz), 7.73–7.67 (5H, m), 7.67–7.52 (2H, m), 7.31 (1H, d, J=8.0 Hz), 7.28–7.24 (1H, m), 4.40 (1H, br, s), 3.96–3.82 (1H, m), 3.70–3.62 (1H, m), 3.51–3.41 (1H, m), 2.33 (3H, s), 0.88 (9H, s).

EXAMPLE 19(181)

Ethyl 2'-(4-amidinophenylthiomethyl)-4-((2-methylpropyl)carbamoyl)-2-biphenylcarboxylate

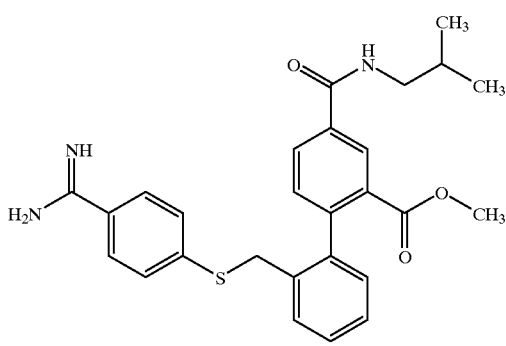

TLC:Rf 0.67 (Chloroform:Methanol:Water=7:3:0.3); NMR (d$_6$-DMSO): δ 9.25 (2H, s), 8.97 (2H, s), 8.73 (1H, br.t, J=6.6 Hz), 8.37 (1H, d, J=1.8 Hz), 8.08 (1H, dd, J=1.8, 8.0 Hz), 7.67 (2H, d, J=8.8 Hz), 7.53 (1H, m), 7.45 (1H, d, J=8.0 Hz), 7.30–7.38 (4H, m), 7.10 (1H, m), 4.13 (1H, d, J=13.0 Hz), 4.04 (1H, d, J=13.0 Hz), 4.02 (2H, q, J=7.2 Hz), 3.12 (2H, t, J=6.6 Hz), 1.87 (1H, m), 0.91 (6H, d, J=6.6 Hz), 0.89 (3H, t, J=7.2 Hz).

EXAMPLE 19(182)

Benzyl 2'-(6-amidinopyridin-3-ylcarbamoyl)-2-((1,2,2-trimethylpropyl) carbamoyl)-2-biphenylcarboxylate

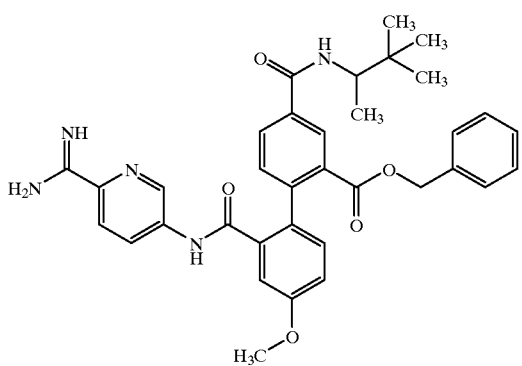

TLC:Rf 0.67 (Chloroform:Methanol:Acetic acid=10:2:1); NMR (CD$_3$OD): δ 8.77 (1H, d, J=2.5 Hz), 8.25 (1H, d, J=2.0 Hz), 8.18 (1H, dd, J=8.5 Hz, 2.5 Hz), 8.02 (1H, d, J=8.5 Hz), 7.93 (1H, dd, J=8.0 Hz, 2.0 Hz), 7.42 (1H, d, J=8.0 Hz), 7.27–7.17 (5H, m), 7.26–7.09 (2H, m), 7.08 (1H, dd, J=8.5 Hz, 2.5 Hz), 5.10 (2H, s), 4.05 (1H, q, J=7.0 Hz), 3.89 (3H, s), 1.15 (3H, d, J=7.0 Hz), 0.95 (9H, s).

EXAMPLE 20–EXAMPLE 20(20)

The following compounds were obtained by the same procedure as a series of reaction of Example 4, Example 2, Example 11 or Reference Example 8, using a compound prepared in Example 19(86)–Example 19(94), Example 19(55), Example 19(95), Example 19(105), Example 19(133)–Example 19(136), Example 19(158), Example 19(176), Example 19(178) and Example 19(181)–Example 19(182).

EXAMPLE 20

2'-(4-amidinophenylcarbamoyl)-4-methylaminomethyl-2-biphenylcarboxylic acid dimethanesulfonate

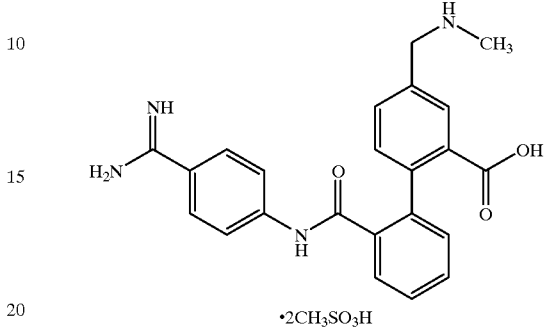

TLC:Rf 0.29 (Ethyl acetate:Acetic acid:Water=3:1:1); NMR (d$_6$-DMSO): δ 10.55 (1H, s), 9.15 (2H, s), 8.92 (2H, s), 8.85 (2H, br.s), 8.01 (1H, d, J=1.8 Hz), 7.75 (4H, s), 7.70 (1H, dd, J=1.8,7.8 Hz), 7.62 (1H, dd, J=1.8,8.0 Hz), 7.52–7.58 (2H, m), 7.32 (1H, d, J=8.0 Hz), 7.25 (1H, dd, J=1.8,7.8 Hz), 4.20 (2H, t, J=5.6 Hz), 2.57 (3H, t, J=5.6 Hz), 2.37 (6H, s).

EXAMPLE 20(1)

2'-(4-amidinophenylcarbamoyl)-4-carboxymethoxy-2-biphenylcarboxylic acid methanesulfonate

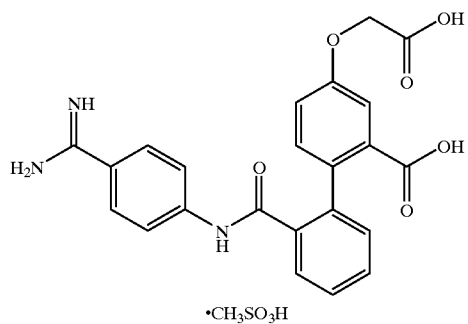

TLC:Rf 0.45 (Ethyl acetate:Acetic acid:Water=6:1:0.5); NMR (d$_6$-DMSO): δ 13.4–12.5 (2H, br), 10.41 (1H, s), 9.20 (2H, br.s), 8.97 (2H, br.s), 7.76 (2H, d, J=8.8 Hz), 7.69 (2H, d, J=8.8 Hz), 7.7–7.6 (1H, m), 7.6–7.4 (2H, m), 7.28 (1H, d, J=2.8 Hz), 7.3–7.1 (2H, m), 7.06 (1H, dd, J=8.8, 2.8 Hz), 4.72 (2H, s), 2.31 (3H, s).

EXAMPLE 20(2)

2'-(4-amidinophenylcarbamoyl)-4-((1-carboxy-2-methylpropyl)carbamoyl)-2-biphenylcarboxylic acid methanesulfonate

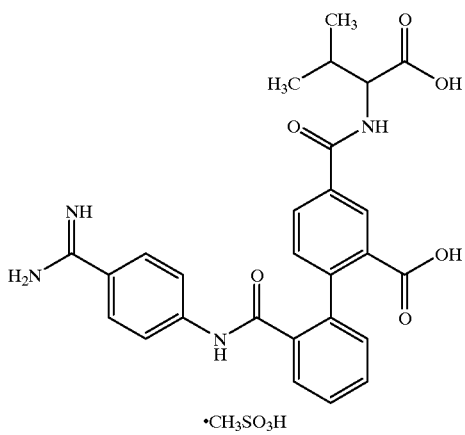

TLC:Rf 0.12 (Chloroform:Methanol:Water=7:3:0.3); NMR (d$_6$-DMSO): δ 10.57 (1H, s), 9.24 (2H, s), 9.04 (?H, s), 8.68 (1H, d, J=7.8 Hz), 8.34 (1H, s), 8.02 (1H, d, J=7.8 Hz), 7.76 (5H, br.s), 7.52–7.60 (2H, m), 7.26–7.36 (2H, m), 4.31 (1H, t, J=7.0 Hz), 2.37 (3H, s), 2.19 (1H, m), 0.99 (3H, d, J=6.0 Hz), 0.97 (3H, d, J=6.0 Hz).

EXAMPLE 20(3)

2'-(4-amidinophenylcarbamoyl)-4-(2-hydroxyethoxy)-2-biphenylcarboxylic acid methanesulfonate

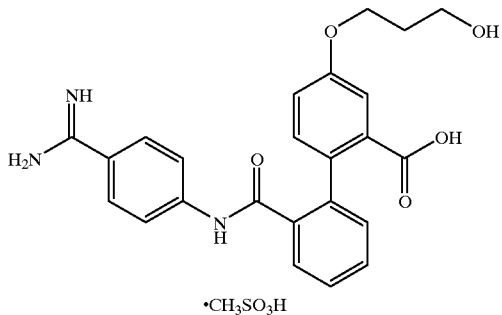

TLC:Rf 0.22 (Chloroform:Methanol:Water=10:3:0.2); NMR (d$_6$-DMSO): δ 13.1–12.0 (1H, br), 10.36 (1H, s), 9.13 (2H, br.s), 8.78 (2H, br.s), 7.8–7.5 (5H, m), 7.6–7.4 (2H, m), 7.4–7.0 (4H, m), 4.00 (2H, t, J=4.8 Hz), 3.69 (2H, t, J=4.8 Hz), 3.6–3.2 (1H, br), 2.31 (3H, s).

EXAMPLE 20(4)

3-(2-(4-amidinophenylcarbamoyl)phenyl)-5-hydroxy-2-naphthalenecarboxylic acid methanesulfonate

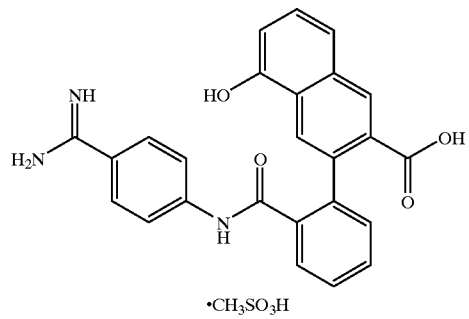

TLC:Rf 0.23 (Chloroform:Methanol:Acetic acid=10:2:1); NMR (d$_6$-DMSO): δ 13.0–12.2 (1H, br), 10.45 (1H, s), 10.31 (1H, br.s), 9.09 (2H, br.s), 8.75 (2H, br.s), 8.35 (1H, s), 7.91 (1H, s), 7.75–7.3 (10H, m), 6.94 (1H, d, J=7.4 Hz), 2.31 (3H, s).

EXAMPLE 20(5)

3-(2-(4-amidinophenylcarbamoyl)phenyl)-8-hydroxy-2-naphthalenecarboxylic acid methanesulfonate

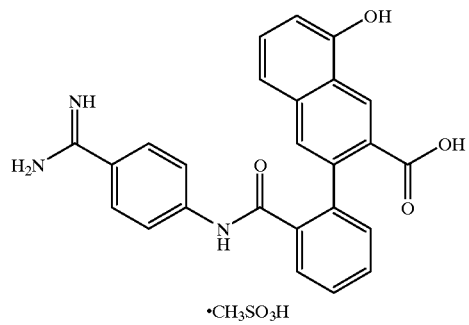

TLC:Rf 0.34 (Chloroform:Methanol:Acetic acid=10:2:1); NMR (d$_6$-DMSO): δ 13.2–12.0 (1H, br), 10.6–10.4 (1H, br), 10.43 (1H, s), 9.12 (2H, brs), 8.85 (2H, brs), 8.66 (1H, s), 7.8–7.5 (8H, m), 7.5–7.3 (3H, m), 6.92 (1H, d, J=6.4 Hz), 2.32 (3H, s).

EXAMPLE 20(6)

2'-(4-amidinophenylcarbamoyl)-4-((2-methylpropyl)aminomethyl)-2-biphenylcarboxylic acid dimethanesulfonate

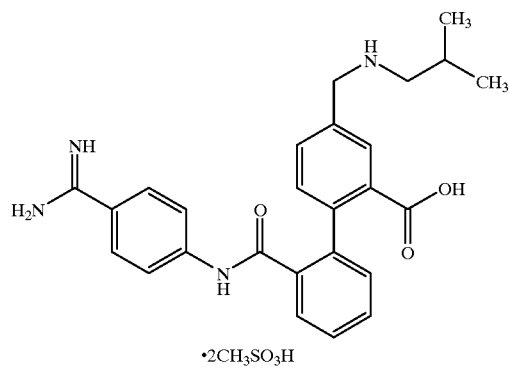

TLC:Rf 0.16 (Chloroform:Methanol:Water=8:2:0.1); NMR (d$_6$-DMSO): δ 10.6 (1H, s), 9.16 (2H, br s), 8.94 (2H, br s), 8.75 (2H, br s), 8.05 (1H, s), 7.80–7.60 (6H, m), 7.60–7.50 (2H, m), 7.34–7.23 (2H, m), 4.22 (2H, br s), 2.79 (2H, br s), 2.39 (3H, s), 2.37 (3H, s), 2.06–1.93 (1H, m), 0.94 (6H, d, J=6.6 Hz).

EXAMPLE 20(7)

2'-(4-amidinophenylcarbamoyl)-4-((2-carboxyethyl)carbamoyl)-2-biphenylcarboxylic acid methanesulfonate

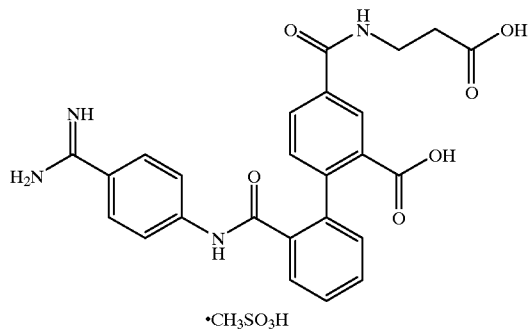

·CH$_3$SO$_3$H

TLC:Rf 0.60 (Ethyl acetate:Acetic acid:Water=3:1:1); NMR (d$_6$-DMSO): δ 13.0–12.0 (2H, broad), 10.53 (1H, s), 9.18 (2H, brs), 8.92 (2H, brs), 8.74 (1H, brt, J=5.5 Hz), 8.29 (1H, d, J=2.0 Hz), 7.95 (1H, dd, J=8.0 Hz, 2.0 Hz), 7.28 (4H, s), 7.70 (1H, dd, J=7.5 Hz, 2.0 Hz), 7.62–7.47 (2H, m), 7.32 (1H, d, J=8.0 Hz), 7.27 (1H, dd, J=7.5 Hz, 2.0 Hz), 3.45 (2H, q, J=7.0 Hz), 2.51 (2H, t, J=7.0 Hz), 2.34 (3H, s).

EXAMPLE 20(8)

2'-(4-amidinophenylcarbamoyl)-4-((3-carboxypropyl)carbamoyl)-2-biphenylcarboxylic acid hydrochloride

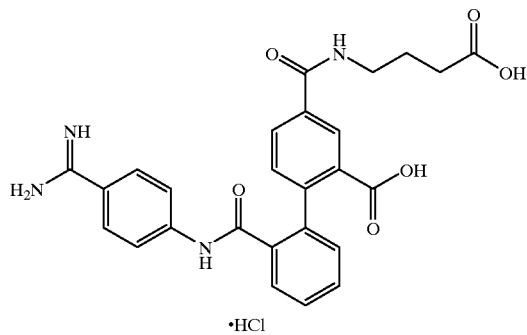

·HCl

TLC:Rf 0.65 (Ethyl acetate:Acetic acid:Water=3:1:1); NMR (d$_6$-DMSO): δ 12.8–12.1 (2H, broad), 10.57 (1H, s), 9.25 (2H, brs), 9.04 (2H, brs), 8.71 (1H, brt, J=6.0 Hz), 8.30 (1H, d, J=2.0 Hz), 7.97 (1H, dd, J=7.5 Hz, 2.0 Hz), 7.77 (2H, d, J=9.0 Hz), 7.71 (2H, d, J=9.0 Hz), 7.70 (1H, dd, J=7.5 Hz, 2.0 Hz), 7.62–7.47 (2H, m), 7.31 (1H, d, J=8.0 Hz), 7.26 (1H, dd, J=7.5 Hz, 2.0 Hz), 3.27 (2H, q, J=6.0 Hz), 2.27 (2H, t, J=7.0 Hz), 1.74 (2H, quint, J=7.0 Hz).

EXAMPLE 20(9)

2'-(4-amidinophenylcarbamoyl)-4-((5-aminopentyl)carbamoyl)-2-biphenylcarboxylic acid dimethanesulfonate

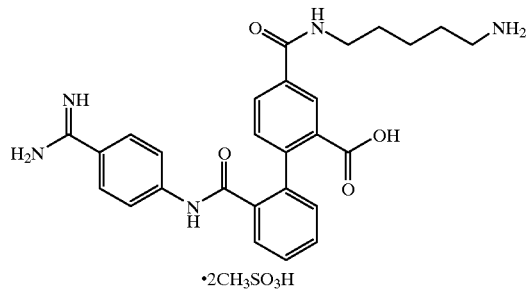

·2CH$_3$SO$_3$H

TLC:Rf 0.11 (Ethyl acetate:Acetic acid:Water=3:1:1); NMR (d$_6$-DMSO): δ 10.6 (1H, s), 9.15 (2H, br s), 8.90 (2H, br s), 8.66 (1H, t, J=5.6 Hz), 8.31 (1H, d, J=1.8 Hz), 7.98 (1H, dd, J=1.8, 8.0 Hz), 7.81–7.35 (7H, m), 7.35–7.26 (2H, m), 4.20 (3H, br s), 3.28 (2H, q, J=6.2 Hz), 2.79 (2H, q, J=7.4 Hz), 2.37 (3H, s), 2.36 (3H, s), 1.70–1.20 (6H, m).

EXAMPLE 20(10)

2'-(4-amidinophenylcarbamoyl)-4-((piperidin-4-ylmethyl)carbamoyl)-2-biphenylcarboxylic acid dimethanesulfonate

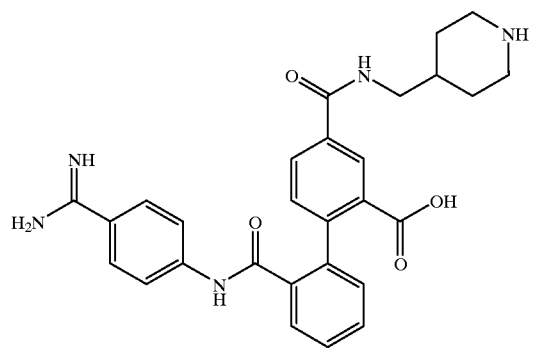

·2CH$_3$SO$_3$H

TLC:Rf 0.16 (Ethyl acetate:Acetic acid:Water=3:1:1); NMR (d$_6$-DMSO): δ 10.6 (1H, s), 9.17 (2H, br s), 8.95 (2H, br s), 8.78 (1H, t, J=6.0 Hz), 8.58–8.55 (1H, m), 8.32 (1H, d, J=1.8 Hz), 8.25–8.21 (1H, m), 7.99 (1H, dd, J=1.8, 7.8 Hz), 7.78–7.70 (5H, m), 7.60–7.53 (2H, m), 7.35–7.27 (2H, m), 3.29–3.17 (4H, m), 2.89–2.79 (2H, m), 2.39 (6H, s), 1.84–1.80 (3H, m), 1.42–1.30 (2H, m).

EXAMPLE 20(11)

2'-(4-amidinophenylcarbamoyl)-3'-hydroxy-2-biphenylcarboxylic acid methanesulfonate

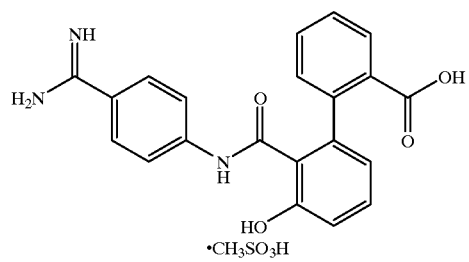

·CH$_3$SO$_3$H

TLC:Rf 0.27 (Chloroform:Methanol:Water=7:3:0.3); NMR (d$_6$-DMSO): δ 13.0–12.0 (1H, broad), 10.34 (1H, s), 10.20–9.85 (1H, broad), 9.13 (2H, brs), 8.94 (2H, brs), 7.76 (1H, d, J=7 Hz), 7.72 (2H, d, J=9 Hz), 7.63 (2H, d, J=9 Hz), 7.50–7.18 (4H, m), 6.95 (1H, d, J=8 Hz), 6.63 (1H, d, J=8 Hz), 2.41 (3H, s).

EXAMPLE 20(12)

2'-(4-amidinophenylcarbamoyl)-4'-((carboxymethyl)carbamoyl)-2-biphenylcarboxylic acid methanesulfonate

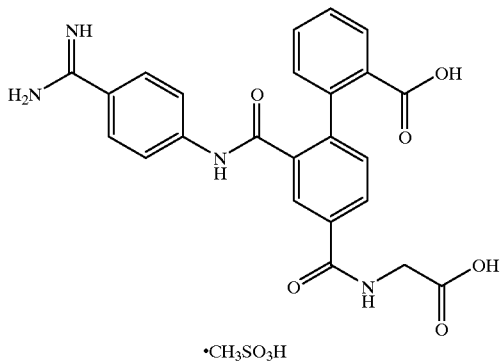

TLC:Rf 0.56 (Ethyl acetate:Acetic acid:Water=3:1:1); NMR (d$_6$-DMSO): δ 10.60 (1H, s), 9.15 (2H, s), 9.03 (1H, br.t, J=5.4 Hz), 8.81 (2H, s), 8.17 (1H, d, J=1.6 Hz), 8.03 (1H, dd, J=1.8,8.0 Hz), 7.87 (1H, dd, J=1.6,7.8 Hz), 7.75 (2H, d, J=9.2 Hz), 7.70 (2H, d, J=9.2 Hz), 7.55 (1H, dd, J=1.8,8.0 Hz), 7.44 (1H, dt, J=1.8,8.0 Hz), 7.39 (1H, d, J=7.8 Hz), 7.27 (1H, dd, J=1.8,8.0 Hz), 3.99 (2H, br.d, J=5.4 Hz), 2.34 (3H, s).

EXAMPLE 20(13)

2'-(4-amidinophenylcarbamoyl)-4'-((1-carboxy-2-phenylethyl)carbamoyl)-2-biphenylcarboxylic acid methanesulfonate

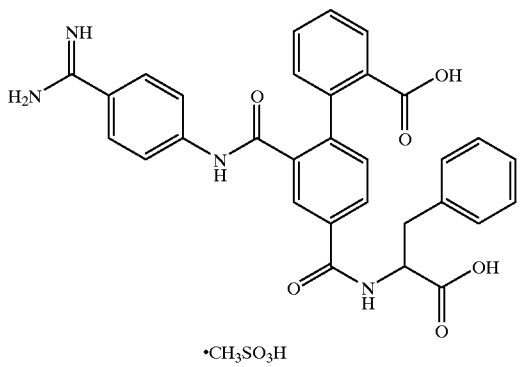

TLC:Rf 0.76 (Ethyl acetate:Acetic acid:Water=3:1:1); NMR (d$_6$-DMSO): δ 10.57 (1H, s), 9.16 (2H, s), 8.92 (1H, br.d, J=5.4 Hz), 8.87 (2H, s), 8.09 (1H, s), 7.97 (1H, d, J=7.8 Hz), 7.87 (1H, d, J=7.8 Hz), 7.75 (2H, d, J=9.2 Hz), 7.70 (2H, d, J=9.2 Hz), 7.55 (1H, t, J=7.8 Hz), 7.44 (1H, t, J=7.8 Hz), 7.19–7.38 (7H, m), 4.70 (1H, m), 3.04–3.29 (2H, m), 2.35 (3H, s).

EXAMPLE 20(14)

2'-(4-amidinophenylcarbamoyl)-4'-carboxymethoxy-2-biphenylcarboxylic acid methanesulfonate

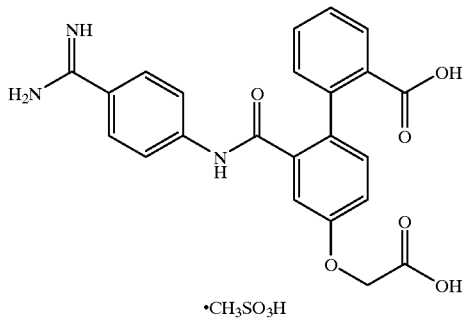

TLC:Rf 0.44 (Ethyl acetate:Acetic acid:Water=6:1:0.5); NMR (d$_6$-DMSO): δ 10.37 (1H, s), 9.14 (2H, br.s), 8.84 (2H, br.s), 7.8–7.6 (5H, m), 7.49 (1H, t, J=6.8 Hz), 7.37 (1H, t, J=6.8 Hz), 7.3–7.0 (4H, m), 4.79 (2H, s), 4.4–2.8 (2H, br), 2.35 (3H, s).

EXAMPLE 20(15)

2-(6-(4-amidinophenylcarbamoyl)benzoimidazol-5-yl)benzoic acid dimethanesulfonate

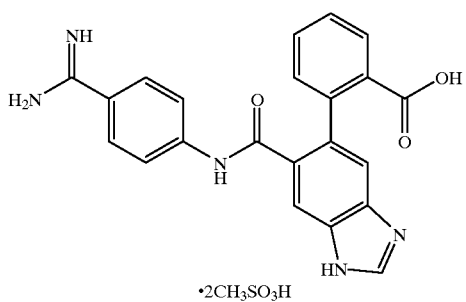

TLC:Rf 0.16 (Chloroform:Methanol:Water=7:3:0.3); NMR (d$_6$-DMSO): δ 10.57 (1H, s), 9.37 (1H, s), 9.17 (2H, s), 8.82 (2H, s), 8.10 (1H, s), 7.86 (1H, d, J=7.8 Hz), 7.75 (2H, d, J=9.0 Hz), 7.68 (2H, d, J=9.0 Hz), 7.63 (1H, s), 7.56 (1H, t, J=7.8 Hz), 7.44 (1H, t, J=7.8 Hz), 7.30 (1H, d, J=7.8 Hz), 2.35 (6H, s).

EXAMPLE 20(16)

2'-(4-(N$^2$-hydroxyamidino)phenylcarbamoyl)-2-biphenylcarboxylic acid hydrochloride

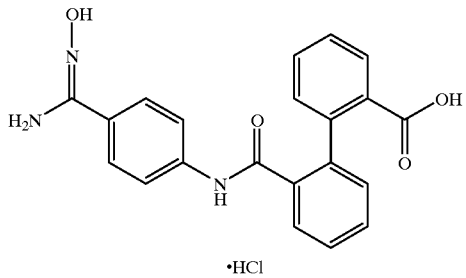

TLC:Rf 0.31 (Chloroform:Methanol:Acetic acid=10:2:1); NMR (d$_6$-DMSO): δ 10.47 (1H, s), 8.92 (2H, brs), 7.80 (1H, dd, J=1.0, 8.0 Hz), 7.70–7.30 (9H, m), 7.28–7.18 (2H, m), 3.80–3.00 (2H, m).

EXAMPLE 20(17)

2'-(4-amidinophenoxymethyl)-4-((2-methylpropyl)carbamoyl)-2-biphenylcarboxylic acid methanesulfonate

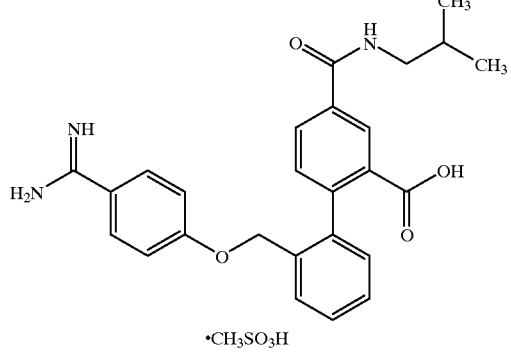

TLC:Rf 0.43 (Chloroform:Methanol:Acetic acid=10:2:1); NMR (d$_6$-DMSO): δ 13.0–12.7 (1H, broad), 9.08 (2H, brs), 8.84 (2H, brs), 8.67 (1H, brt, J=6.0 Hz), 8.33 (1H, d, J=2.0 Hz), 7.98 (1H, dd, J=8.0 Hz, 2.0 Hz), 7.70 (2H, d, J=9.0 Hz), 7.54–7.48 (1H, m), 7.39 (1H, d, J=8.0 Hz), 7.44–7.33 (2H, m), 7.18–7.12 (1H, m), 7.04 (2H, d, J=9.0 Hz), 4.92 (2H, s), 3.08 (2H, t, J=6.0 Hz), 2.31 (3H, s), 1.95–1.75 (1H, m), 0.88 (6H, d, J=7.0 Hz).

EXAMPLE 20(18)

2'-(6-amidinopyridin-3-ylcarbamoyl)-4-((2-methylpropyl)carbamoyl)-2-biphenylcarboxylic acid methanesulfonate

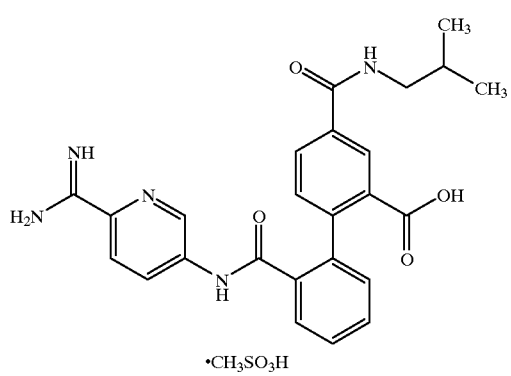

TLC:Rf 0.51 (Chloroform:Methanol:Water=7:3:0.3); NMR (d$_6$-DMSO): δ 10.9 (1H, s), 9.38 (2H, brs), 9.12 (2H, br s), 8.90 (1H, d, J=2.2 Hz), 8.66 (1H, t, J=6.0 Hz), 8.29 (1H, d, J=1.8 Hz), 8.26–8.16 (2H, m), 7.98 (1H, dd, J=1.8, 8.0 Hz), 7.75 (1H, dd, J=1.8, 7.0 Hz), 7.68–7.52 (2H, m), 7.35–7.28 (2H, m), 3.08 (1H, t, J=6.2 Hz), 2.34 (3H, s), 1.91–1.77 (1H, m), 0.88 (6H, d, J=6.6 Hz).

EXAMPLE 20(19)

2'-(4-amidinophenylthiomethyl)-4-((2-methylpropyl)carbamoyl)-2-biphenylcarboxylic acid methanesulfonate

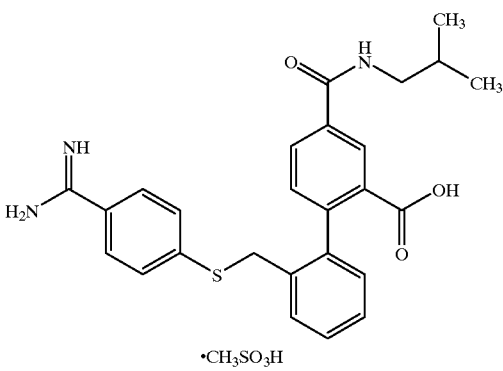

TLC:Rf 0.47 (Chloroform:Methanol:Water=7:3:0.3); NMR (d$_6$-DMSO): δ 9.18 (2H, s), 8.89 (2H, s), 8.70 (1H, br.t, J=6.3 Hz), 8.38 (1H, s), 8.03 (1H, d, J=8.0 Hz), 7.64 (2H, d, J=8.8 Hz), 7.52 (1H, d, J=8.0 Hz), 7.40 (1H, d, J=8.0 Hz), 7.30–7.38 (4H, m), 7.11 (1H, d, J=8.0 Hz), 4.17 (1H, d, J=13.6 Hz), 4.02 (1H, d, J=13.6 Hz), 3.11 (2H, t, J=6.3 Hz), 2.36 (3H, s), 1.87 (1H, m), 0.90 (6H, d, J=6.3 Hz).

EXAMPLE 20(20)

2'-(6-amidinopyridin-3-ylcarbamoyl)-4'-methoxy-4-((1,2,2-trimethylpropyl) carbamoyl)-2-biphenylcarboxylic acid methanesulfonate

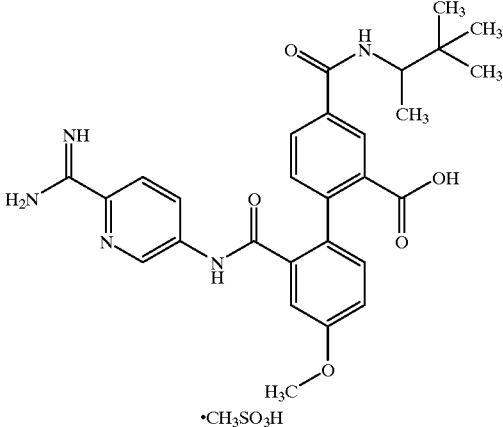

TLC:Rf 0.19 (Chloroform:Methanol:Water=10:2:1); NMR (d$_6$-DMSO): δ 13.0–12.0 (1H, broad), 10.88 (1H, s), 9.36 (2H, brs), 9.10 (2H, brs), 8.91 (1H, d, J=2.5 Hz), 8.27 (1H, dd, J=9.0 Hz, 2.5 Hz), 8.23 (1H, d, J=2.0 Hz), 8.17 (1H, d, J=9.0 Hz), 8.15 (1H, d, J=9.0 Hz), 7.94 (1H, dd, J=8.0 Hz, 2.0 Hz), 7.30 (1H, d, J=8.0 Hz), 7.29 (1H, d, J=2.0 Hz), 7.22 (1H, d, J=8.5 Hz), 7.16 (1H, dd, J=8.5 Hz, 2.0 Hz), 3.98 (1H, dq, J=9.0 Hz, 7.0 Hz), 3.88 (3H, s), 2.34 (3H, s), 1.07 (3H, d, J=7.0 Hz), 0.89 (9H, s).

EXAMPLE 21

N-benzyloxy-2'-(4-amidinophenylcarbamoyl)-2-biphenylcarboxamide

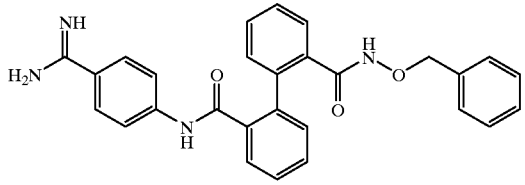

The compound prepared in Example 19(1) (147 mg) and O-benzylhydroxyamine hydrochloride (178 mg) were dissolved into dimethylformamide (1 ml) and pyridine (1 ml). Dicyclohexylcarbodiimide (115 mg) was added to the mixture. The mixture was stirred for 18 hours at room temperature. The reaction mixture was filtered, and the solid was washed with dimethylformamide. The solution of washings and filtrate was concentrated. The residue was purified by column chromatography on silica gel (Chloroform:Methanol:Water=9:1:0.1→8:2 0.1) to give the present compound having the following physical data.

TLC:Rf 0.40 (Chloroform:Methanol:Acetic acid=10:2:1); NMR ($d_6$-DMSO): δ 10.88 (1H, brs), 9.40–8.70 (3H, broad), 7.75–7.63 (3H, m), 7.60–7.46 (4H, m), 7.46–7.32 (8H, m), 7.18–7.10 (2H, m), 4.73 (2H, s).

EXAMPLE 21(1)–EXAMPLE 21(10)

The following compounds were obtained by the same procedure as a series of reaction of Example 21, using a compound prepared in Example 19(1), Example 19(41), Example 19(47)–Example 19(48), Example 6, Example 19(100), Example 4, Example 19(112), Example 19(159) and Example 19(1), subject to using N-methyl-O-benzylhydroxyamine instead of O-benzylhydroxyamine in Example 21(1), and using cyanamide instead of O-benzylhydroxyamine in Example 21(10).

EXAMPLE 21(1)

N-benzyloxy-N-methyl-2'-(4-amidinophenylcarbamoyl)-2-biphenyl carboxamide

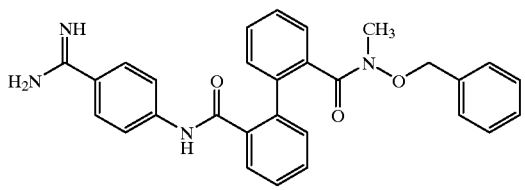

TLC:Rf 0.24 (Chloroform:Methanol:Acetic acid=20:2:1); NMR ($d_6$-DMSO): δ 10.9–10.3 (1H, broad), 9.17 (3H, brs), 7.76–7.00 (17H, m), 4.84 (2H, brs), 3.17 (3H, brs).

EXAMPLE 21(2)

N-benzyloxy-2'-(4-amidinophenylcarbamoyl)-4-((2-methylpropyl)carbamoyl)-2-biphenylcarboxamide

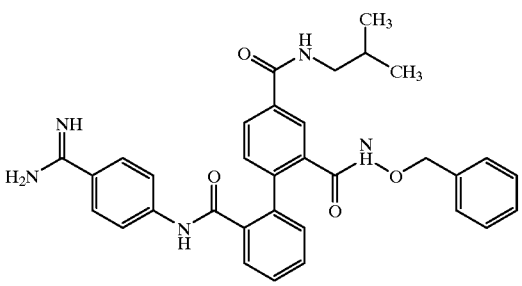

TLC:Rf 0.31 (Chloroform:Methanol:Water=8:2:0.2); NMR ($d_6$-DMSO) δ 10.92 (1H, br.s), 9.08 (3H, br.s), 8.63 (1H, br.t, J=6.6 Hz), 8.01 (1H, d, J=1.8 Hz), 7.90 (1H, dd, J=1.8,8.0 Hz), 7.69–7.76 (3H, m), 7.55–7.62 (4H, m), 7.37 (5H, s), 7.26 (1H, d, J=8.0 Hz), 7.16 (1H, m), 4.75 (2H, s), 3.07 (2H, t, J=6.6 Hz), 1.84 (1H, m), 0.88 (6H, d, J=6.6 Hz).

EXAMPLE 21(3)

N-benzyloxy-2-(3-(4-amidinophenylcarbamoyl)naphthalen-2-yl)-5-((2-methylpropyl)carbamoyl)benzcarboxamide

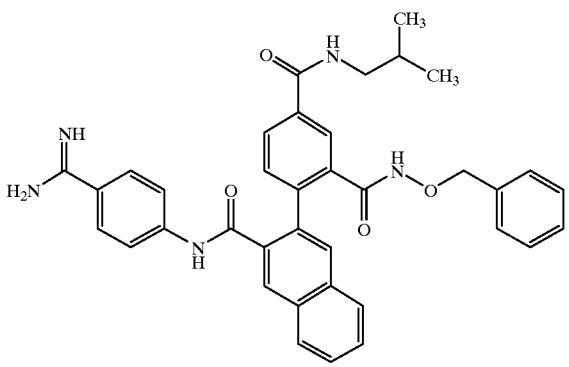

TLC:Rf 0.28 (Chloroform:Methanol:Water=8:2:0.2); NMR (CD$_3$OD): δ 8.24 (1H, s), 8.06 (1H, m), 8.00 (1H, d, J=1.8 Hz), 7.94 (1H, m), 7.87 (1H, dd, J=1.8,8.0 Hz), 7.64–7.70 (7H, m), 7.35 (1H, d, J=8.0 Hz), 7.16–7.29 (5H, m), 4.65 (2H, br.s), 3.18 (2H, d, J=7.0 Hz), 1.91 (1H, m), 0.95 (6, d, J=6.6 Hz).

EXAMPLE 21(4)

N-benzyloxy-2'-(4-amidinophenylcarbamoyl)-4'-methoxy-4-((2-methylpropyl) carbamoyl)-2-biphenylcarboxamide

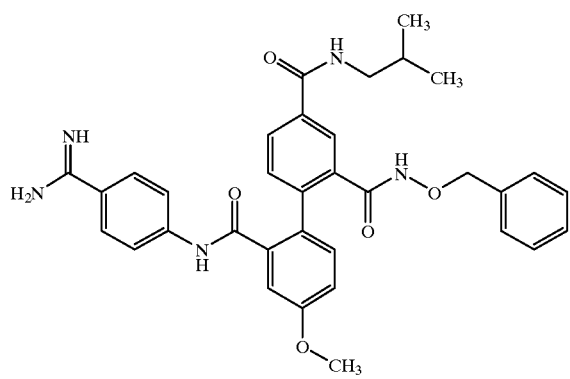

TLC:Rf 0.28 (Chloroform:Methanol:Water=8:2:0.2); NMR (CD$_3$OD): δ 7.93 (1H, d, J=1.8 Hz), 7.82 (1H, dd, J=1.8,8.0 Hz), 7.68 (2H, d, J=9.2 Hz), 7.61 (2H, d, J=9.2 Hz), 7.39 (5H, s), 7.26 (1H, d, J=8.0 Hz), 7.22 (1H, t, J=1.4 Hz), 7.10 (2H, d, J=1.4 Hz), 4.84 (2H, s), 3.90 (3H, s), 3.16 (2H, d, J=7.4 Hz), 1.89 (1H, m), 0.94 (6H, d, J=6.6 Hz).

EXAMPLE 21(5)

N-benzyloxy-2-(3-(4-amidinophenylcarbamoyl) naphthalen-2-yl) benzcarboxamide

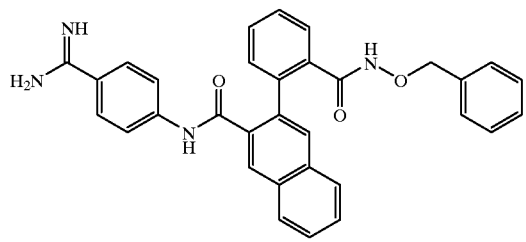

TLC:Rf 0.48 (Chloroform:Methanol:Water=10:3:0.2); NMR (d$_6$-DMSO): δ 11.21 (1H, br), 9.11 (3H, br), 8.29 (1H, s), 8.11 (1H, m), 7.95 (1H, m), 7.8–7.5 (7H, m), 7.6–7.3 (4H, m), 7.4–7.1 (6H, m), 4.63 (2H, s).

EXAMPLE 21(6)

N-benzyloxy-2-(3-(4-amidinophenylcarbamoyl) naphthalen-2-yl)-5-methoxy benzcarboxamide

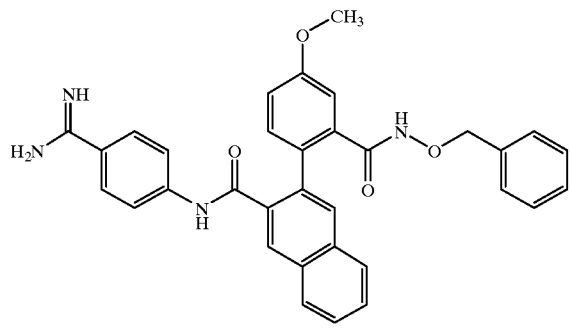

TLC:Rf 0.39 (Chloroform:Methanol:Water=10:3:0.2); NMR (d$_6$-DMSO): δ 11.87 (1H, s), 11.04 (1H, s), 9.3–9.0 (3H, s), 8.27 (1H, s), 8.10 (1H, m), 7.96 (1H, m), 7.78 (2H, d, J=9.4 Hz), 7.8–7.5 (4H, m), 7.5–7.1 (7H, m), 7.1–6.9 (2H, m), 4.64 (2H, s), 3.77 (3H, s).

EXAMPLE 21(7)

N-benzyloxy-2'-(4-amidinophenylcarbamoyl)-4'-methyl-2-biphenyl carboxamide

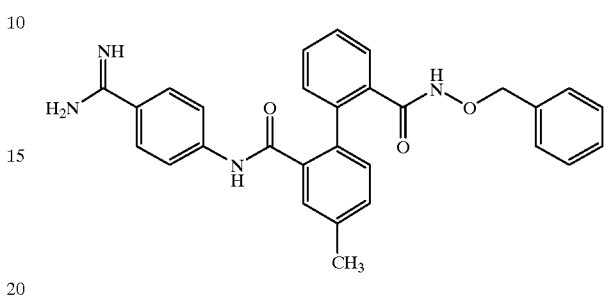

TLC:Rf 0.52 (Chloroform:Methanol:Water=10:3:0.2); NMR (d$_6$-DMSO): δ 11.92 (1H, br.s), 10.83 (1H, s), 9.4–8.8 (3H, br), 7.72 (3H, J=8.8 Hz), 7.52 (2H, d, J=8.8 Hz), 7.6–7.2 (9H, m), 7.10 (1H, d, J=7.8 Hz), 7.03 (1H, d, J=7.8 Hz), 4.75 (2H, s), 2.40 (3H, s).

EXAMPLE 21(8)

N-benzyloxy-2'-(4-amidinophenylcarbamoyl)-4'-methoxy-2-biphenyl carboxamide methanesulfonate

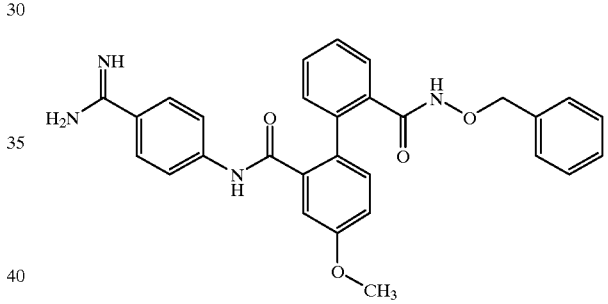

TLC:Rf 0.62 (Chloroform:Methanol:Acetic acid=10:2:1); NMR (CD$_3$OD): δ 7.68 (2H, d, J=9.0 Hz), 7.58 (2H, d, J=9.0 Hz), 7.45–7.28 (8H, m), 7.22–7.11 (2H, m), 7.09–7.07 (2H, m), 4.82 (2H, s), 3.88 (3H, s).

EXAMPLE 21(9)

N-benzyloxy-2'-(4-(N$^2$-ethoxycarbonylamidino) phenylcarbamoyl)-2-biphenyl carboxamide

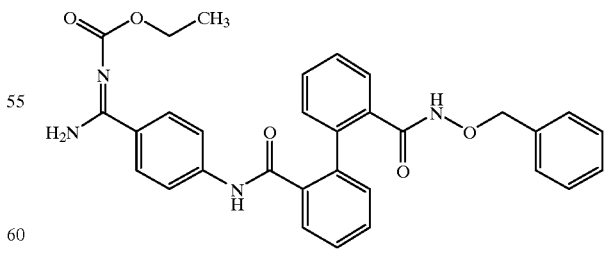

TLC:Rf 0.58 (Toluene:Ethyl acetate=1:1); NMR (d$_6$-DMSO): δ 11.85 (1H, br.s), 10.70 (1H, s), 9.2–8.8 (2H, br), 7.85 (2H, d, J=8.8 Hz), 7.66 (1H, m), 7.6–7.5 (2H, m), 7.5–7.3 (10H, m), 7.2–7.1 (2H, m), 4.71 (2H, s), 4.03 (2H, q, J=7.4 Hz), 1.20 (3H, t, J=7.4 Hz).

EXAMPLE 21(10)

N-cyano-2'-(4-amidinophenylcarbamoyl)-2-biphenylcarboxamide methanesulfonate

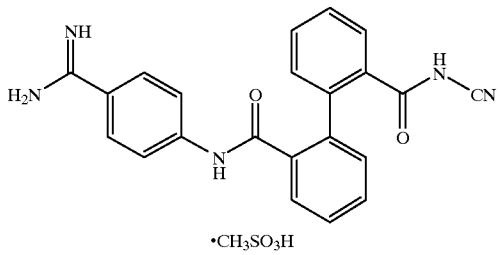

TLC:Rf 0.34 (Ethyl acetate:Acetic acid:Water=6:1:0.5); NMR (d$_6$-DMSO): δ 10.81 (1H, s), 9.17 (2H, br.s), 8.89 (2H, br.s), 7.74 (4H, like s), 7.8–7.4 (6H, m), 7.29 (2H, t, J=8.0 Hz), 6.0–4.0 (1H, br), 2.35 (3H, s).

EXAMPLE 22–EXAMPLE 22(9)

The following compounds were obtained by the same procedure as a series of reaction of Example 2, using the compound prepared in Example 21–Example 21(9).

Example 22

N-hydroxy-2'-(4-amidinophenylcarbamoyl)-2-biphenylcarboxamide

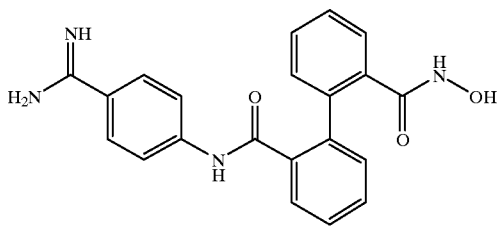

TLC:Rf 0.14 (Chloroform:Methanol:Acetic acid=10:2:1); NMR (d$_6$-DMSO): δ 11.8–11.2 (1H, broad), 11.21 (1H, s), 9.7–8.7 (4H, broad), 7.77–7.60 (3H, m), 7.60–7.30 (7H, m), 7.20–7.04 (2H, m).

EXAMPLE 22(1)

N-hydroxy-N-methyl-2'-(4-amidinophenylcarbamoyl)-2-biphenylcarboxamide methanesulfonate

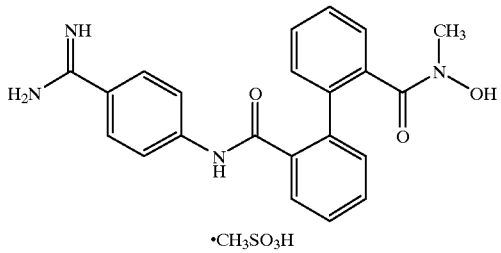

TLC:Rf 0.29 (Chloroform:Methanol:Acetic acid=10:2:1); NMR (d$_6$-DMSO): δ 10.41 (1H, brs), 10.03 (1H, brs), 9.10–8.55 (4H, broad), 7.70 (2H, d, J=7.0 Hz), 7.67–7.65 (1H, m), 7.53–7.47 (5H, m), 7.37–7.32 (2H, m), 7.31–7.28 (1H, m), 7.15–7.13 (1H, m), 3.21 (3H, s), 2.37 (3H; s).

EXAMPLE 22(2)

N-hydroxy-2'-(4-amidinophenylcarbamoyl)-4-((2-methylpropyl)carbamoyl)-2-biphenylcarboxamide methanesulfonate

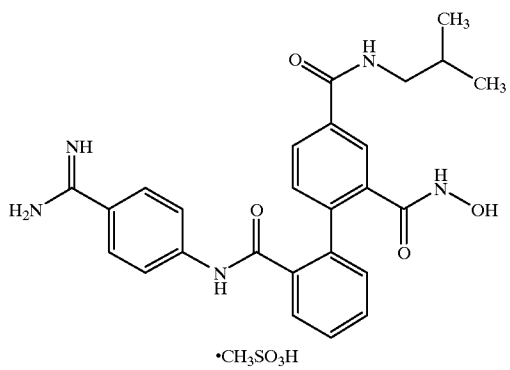

TLC:Rf 0.42 (Chloroform:Methanol:Water=7:3:0.3); NMR (d$_6$-DMSO): δ 11.53 (1H, s), 11.18 (1H, s), 9.13 (2H, s), 8.85 (2H, s), 8.61 (1H, br.t, J=6.2 Hz), 8.02 (1H, d, J=1.8 Hz), 7.90 (1H, dd, J=1.8,8.0 Hz), 7.68–7.73 (3H, m), 7.54–7.59 (4H, m), 7.23 (1H, d, J=8.0 Hz), 7.14 (1H, m), 3.0 (2H, t, J=6.2 Hz), 2.34 (3H, s), 1.82 (1H, m), 0.87 (6H, d, J=6.6 Hz).

EXAMPLE 22(3)

N-hydroxy-2-(3-(4-amidinophenylcarbamoyl)naphthalen-2-yl)-5-((2-methylpropyl)carbamoyl)benzcarboxamide methanesulfonate

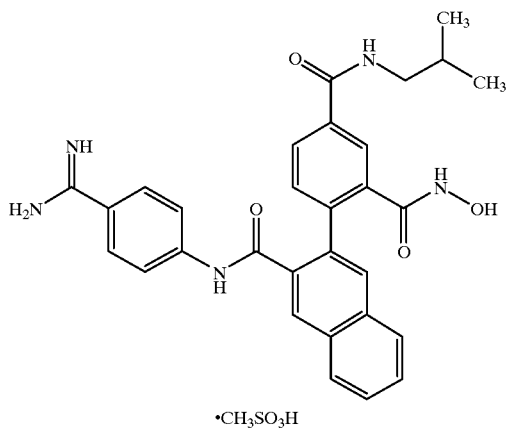

TLC:Rf 0.19 (Chloroform:Methanol:Water=8:2:0.2); NMR (d$_6$-DMSO): δ 11.49 (1H, s), 11.31 (1H, s), 9.15 (2H, s), 8.81 (2H, s), 8.62 (1H, br.t, J=5.8 Hz), 8.33 (1H, s), 8.13 (1H, m), 8.06 (1H, d, J=1.8 Hz), 8.00 (1H, m), 7.93 (1H, dd, J=1.8,8.0 Hz), 7.61–7.75 (7H, m), 7.32 (1H, d, J=8.0 Hz), 3.08 (2H, t, J=5.8 Hz), 2.34 (3H, s), 1.84 (1H, m), 0.89 (6H, d, J=6.6 Hz).

EXAMPLE 22(4)

N-hydroxy-2'-(4-amidinophenylcarbamoyl)-4'-methoxy-4-((2-methylpropyl) carbamoyl)-2-biphenylcarboxamide methanesulfonate

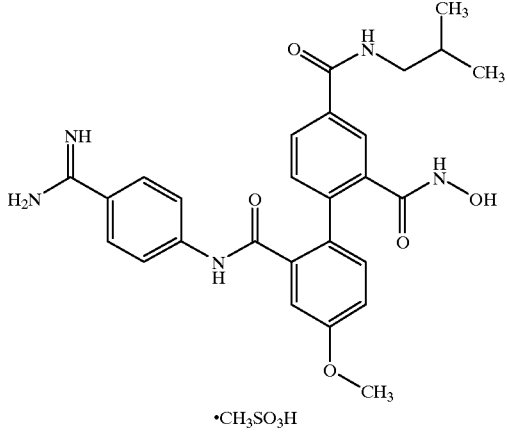

TLC:Rf 0.33 (Chloroform:Methanol:Water=7:3:0.3); NMR (d$_6$-DMSO): δ 11.47 (1H, s), 11.18 (1H, s), 9.14 (2H, s), 8.85 (2H, s), 8.60 (1H, br.t, J=5.8 Hz), 7.99 (1H, d, J=1.6 Hz), 7.87 (1H, dd, J=1.6,8.0 Hz), 7.70 (2H, d, J=8.8 Hz), 7.57 (2H, d, J=8.8 Hz), 7.21 (1H, d, J=2.6 Hz), 7.20 (1H, d, J=8.0 Hz), 7.14 (1H, dd, J=2.6,8.4 Hz), 7.06 (1H, d, J=8.4 Hz), 3.86 (3H, s), 3.06 (2H, t, J=5.8 Hz), 2.34 (3H, s), 1.82 (1H, m), 0.87 (6H, d, J=6.6 Hz).

EXAMPLE 22(5)

N-hydroxy-2-(3-(4-amidinophenylcarbamoyl) naphthalen-2-yl) benzcarboxamide methanesulfonate

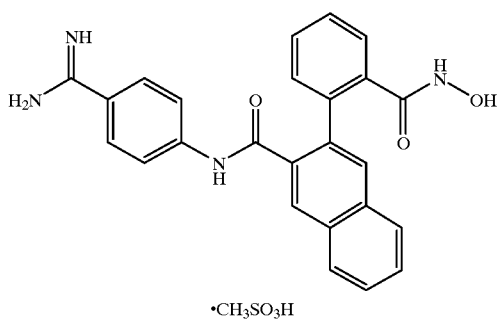

TLC Rf 0.60 (Ethyl acetate:Acetic acid:Water=3:1:0.5); NMR (d$_6$-DMSO): δ 11.49 (1H, s), 11.35 (1H, s), 9.5–9.2 (1H, br), 9.15 (2H, br.s), 8.82 (2H, br.s), 8.30 (1H, s), 8.11 (1H, m), 7.98 (1H, m), 7.8–7.2 (10H, m), 7.19 (1H, m), 2.30 (3H, s).

EXAMPLE 22(6)

N-hydroxy-2-(3-(4-amidinophenylcarbamoyl) naphthalen-2-yl)-5-methoxy benzcarboxamide methanesulfonate

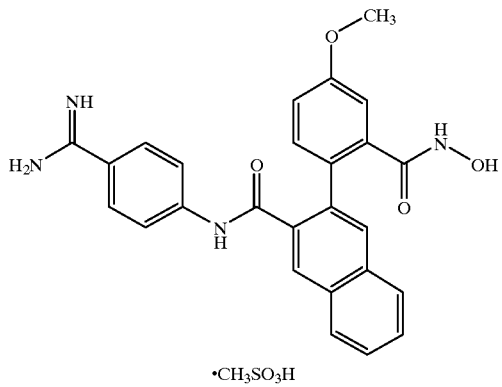

TLC:Rf 0.26 (Chloroform:Methanol:Water=10:3:0.2); NMR (d$_6$-DMSO): δ 11.46 (1H, br.s), 11.33 (1H, s), 9.16 (2H, br.s), 8.87 (2H, br.s), 8.27 (1H, s), 8.10 (1H, t, J=4.4 Hz), 7.96 (1H, t, J=4.4 Hz), 7.8–7.5 (7H, m), 7.2–6.9 (3H, m), 5.5–4.2 (1H, br), 3.77 (3H, s), 2.35 (3H, s).

EXAMPLE 22(7)

N-hydroxy-2'-(4-amidinophenylcarbamoyl)-4'-methyl-2-biphenylcarboxamide methanesulfonate

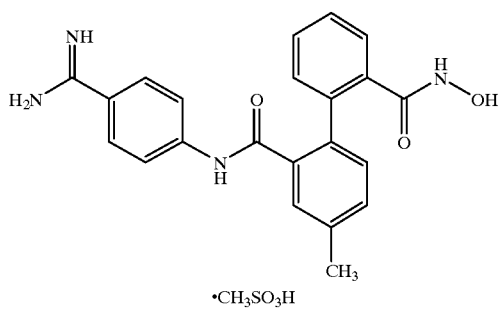

TLC:Rf 0.29 (Chloroform:Methanol:Water=10:3:0.2); NMR (d$_6$-DMSO): δ 11.46 (1H, s), 11.17 (1H, s), 9.41 (1H, br), 9.12 (2H, br.s), 8.81 (2H, br.s), 7.68 (2H, d, J=8.8 Hz), 7.51 (2H, d, J=8.8 Hz), 7.46 (1H, s), 7.5–7.3 (4H, m), 7.07 (1H, m), 7.01 (1H, d, J=7.8 Hz), 2.40 (3H, s), 2.31 (3H, s).

EXAMPLE 22(8)

N-hydroxy-2'-(4-amidinophenylcarbamoyl)-4'-methoxy-2-biphenyl carboxamide methanesulfonate

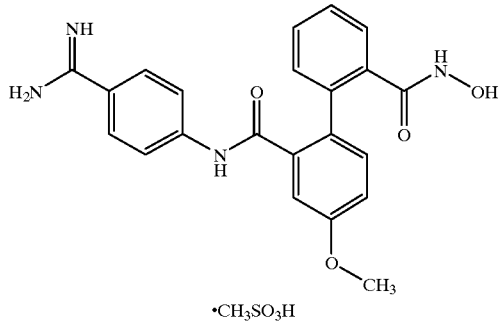

TLC:Rf 0.18 (Chloroform:Methanol:Acetic acid=10:2:1); NMR (d$_6$-DMSO): δ 11.46 (1H, s), 11.21 (1H, s), 9.70–9.10

(1H, broad), 9.13 (2H, brs), 8.89 (2H, brs), 7.69 (2H, d, J=9.0 Hz), 7.52 (2H, d, J=9.0 Hz), 7.50–7.34 (3H, m), 7.20–7.02 (4H, m), 3.84 (3H, s), 2.35 (3H, s).

EXAMPLE 22(9)

N-hydroxy-2'-(4-(N²-ethoxycarbonylamidino) phenylcarbamoyl)-2-biphenyl carboxamide

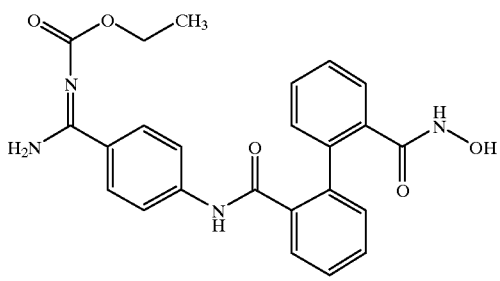

TLC:Rf 0.59 (Chloroform:Methanol:Acetic acid=10:2:1); NMR (d₆-DMSO): δ 11.44 (1H, br.s), 10.99 (1H, s), 9.42 (1H, s), 9.3–8.7 (2H, br), 7.83 (2H, d, J=8.8 Hz), 7.65 (1H, m), 7.6–7.4 (3H, m), 7.5–7.3 (4H, m), 7.2–7.0 (2H, m), 4.03 (2H, q, J=7.4 Hz), 1.19 (3H, t, J=7.4 Hz).

EXAMPLE 23–EXAMPLE 23(1)

The following compounds were obtained by the same procedure as a series of reaction of Reference Example 12, using compounds prepared in Example 19(81) and Example 19(72).

EXAMPLE 23

2'-(4-amidinophenylcarbamoyl)-4-amino-2-biphenylcarboxylic acid methanesulfonate

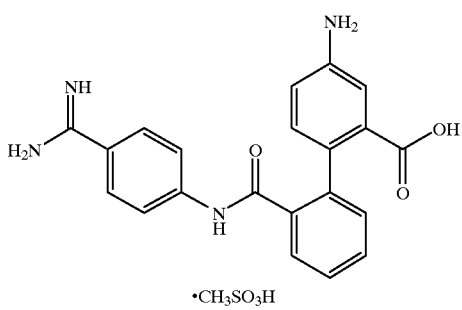

TLC:Rf 0.11 (Chloroform:Methanol:Water=7:3:0.3); NMR (d₆-DMSO): δ 10.19 (1H, s), 9.13 (2H, brs), 8.88 (2H, brs), 7.73 (2H, d, J=9.0 Hz), 7.63 (2H, d, J=9.0 Hz), 7.57 (1H, dd, J=7.0 Hz, 1.5 Hz), 7.51–7.36 (2H, m), 7.16 (1H, dd, J=7.0 Hz, 1.5 Hz), 6.98 (1H, d, J=2.0 Hz), 6.85 (1H, d, J=8.0 Hz), 6.62 (1H, dd, J=8.0 Hz, 2.0 Hz), 2.35 (3H, s).

EXAMPLE 23(1)

3-(2'-(4-amidinophenylcarbamoyl)biphenyl-2-yl) propanoic acid methanesulfonate

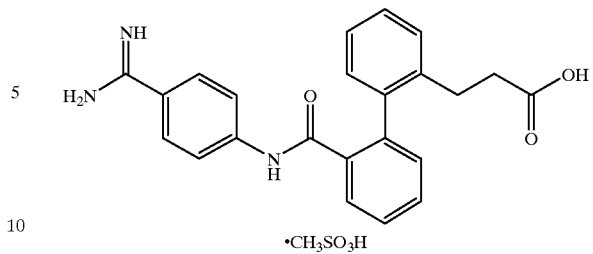

TLC:Rf 0.21 (Chloroform:Methanol:Acetic acid=10:2:1); NMR (d₆-DMSO): δ 12.2–11.9 (1H, broad), 10.55 (1H, s), 9.13 (2H, brs), 8.94 (2H, brs), 7.76–7.50 (7H, m), 7.34–7.12 (5H, m), 2.76–2.62 (2H, m), 2.45–2.34 (2H, m), 2.36 (3H, s).

EXAMPLE 24

2'-(4-amidinophenylcarbamoyl)-4-methylcarbonylamino-2-biphenylcarboxylic acid methanesulfonate

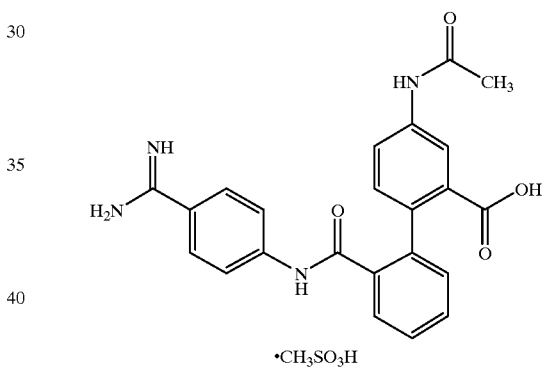

To a solution of the compound prepared in Example 23 (376 mg) in dimethylformamide (3.2 ml) and pyridine (0.8 ml), acetic acid anhydrous (75.5 μl) was added. The mixture was stirred for 1 hour at room temperature. The reaction mixture was concentrated. The residue was crystallized with ethyl acetate, furthermore, was crystallized with ethyl acetate-methanol to give the present compound (407 mg) having the following physical data. TLC:Rf 0.12 (Chloroform:Methanol:Acetic acid=10:2:1); NMR (d₆-DMSO): δ 13.0–12.5 (1H, broad), 10.43 (1H, s), 10.12 (1H, s), 9.13 (2H, brs), 8.86 (2H, brs), 8.05 (1H, d, J=2.5 Hz), 7.76–7.60 (6H, m), 7.58–7.42 (2H, m), 7.26–7.20 (1H, m), 7.15 (1H, d, J=8.0 Hz), 2.34 (3H, s), 2.04 (3H, s).

EXAMPLE 24(1)–EXAMPLE 24(2)

The following compounds were obtained by the same procedure as a series of reaction of Example 24, using compounds prepared in Example 19(102) and Example 23.

EXAMPLE 24(1)

2'-(4-amidinophenylcarbamoyl)-4'-methylcarbonylamino-2-biphenylcarboxylic acid methanesulfonate

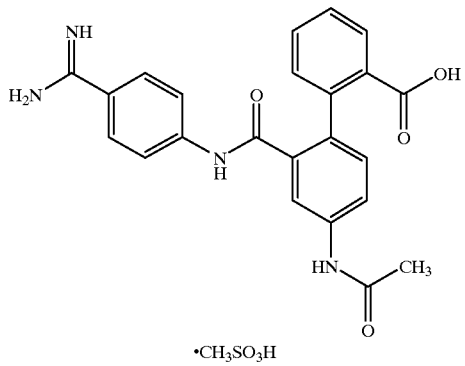

TLC:Rf 0.10 (Chloroform:Methanol:Acetic acid=10:2:1); NMR (d$_6$-DMSO): δ 10.39 (1H, s), 10.28 (1H, s), 9.19 (2H, brs), 8.96 (2H, brs), 7.89 (1H, d, J=2.0 Hz), 7.80–7.60 (6H, m), 7.49 (1H, td, J=7.5 Hz, 1.5 Hz), 7.37 (1H, td, J=7.5 Hz, 1.5 Hz), 7.22 (1H, dd, J=7.5 Hz, 1.5 Hz), 7.17 (1H, d, J=8.0 Hz), 2.35 (3H, s), 2.09 (3H, s).

EXAMPLE 24(2)

2'-(4-amidinophenylcarbamoyl)-4-((2-methylpropylcarbonyl)amino)-2-biphenylcarboxylic acid methanesulfonate

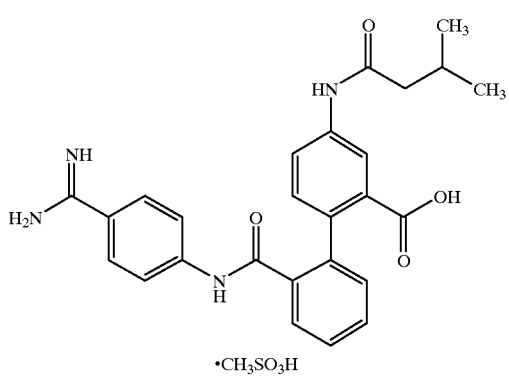

TLC:Rf 0.25 (Chloroform:Methanol:Acetic acid=10:2:1); NMR (d$_6$-DMSO): δ 13.3–12.2 (1H, broad), 10.43 (1H, s), 10.13 (1H, s), 9.19 (2H, brs), 8.98 (2H, brs), 8.10 (1H, d, J=2.5 Hz), 7.78–7.60 (6H, m), 7.56–7.42 (2H, m), 7.26–7.19 (1H, m), 7.15 (1H, d, J=8.0 Hz), 2.36 (3H, s), 2.19 (2H, d, J=6.5 Hz), 2.15–1.95 (1H, m), 0.92 (6H, d, J=6.5 Hz).

EXAMPLE 25

N-hydroxy-2'-(4-(N$^2$-hydroxyamidino)phenylcarbamoyl)-2-biphenyl carboxamide hydrochloride

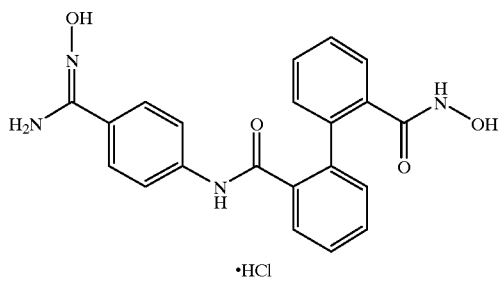

1-Ethyl-3-(3-dimethylaminopropyl)-carbodiimide (183 mg), 1-hydroxybenzotriazole (129 mg) and N-(1-methoxy-1-methylethoxy)amine (333 mg) were added to a solution of the compound prepared in Example 19(158) (302 mg) in dimethylformamide (5 ml). The mixture was stirred for 3 hours at room temperature. The reaction mixture was distilled off an azeotropic mixture with toluene. Methylene chloride (2 ml), methanol (0.5 ml) and 4N hydrochloric acid—dioxane (2 ml) were added to the residue, and the mixture was stirred for 1 hour at room temperature. The reaction mixture was concentrated. The residue was purified by column chromatography on silica gel (Methylene chloride:Methanol:Acetic acid=10:2:1). The purified product was dissolved into methanol (2 ml), and then 4N hydrochloric acid—ethyl acetate (0.16 ml) was added to the solution. The mixture was concentrated. The obtained compound hydrochloride was washed with ether to give the present compound (197 mg) having the following physical data.
TLC:Rf 0.38 (Chloroform:Methanol:Acetic acid=10:2:1); NMR (d$_6$-DMSO): δ 12.79 (1H, br), 11.51 (1H, s), 11.19 (1H, s), 11.2–11.0 (1H, br), 9.4–8.7 (3H, br), 7.7–7.4 (8H, m), 7.45–7.35 (2H, m), 7.2–7.0 (2H, m).

EXAMPLE 26

2'-(4-(N$^2$-(2-propenyl)oxycarbonylamidino)phenylcarbamoyl)-2-biphenyl carboxylic acid

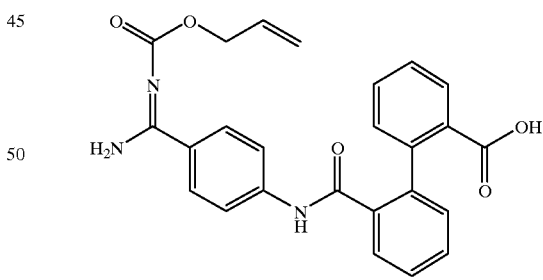

The compound prepared in Example 19 (300 mg) was dissolved into a mixed solution of 2N aqueous solution of sodium hydroxide and tetrahydrofuran (2:1, 15 ml), and then allyloxycarbonyl chloride (140 μl) was added to the solution. The mixture was stirred for 30 minutes at room temperature. 2N hydrochloric acid (10 ml) was added to the reaction mixture. The precipitate obtained by filtration was washed with water, and dried. The precipitate was crystallized with methanol to give the present compound (47 mg) having the following physical data.

TLC:Rf 0.41 (Chloroform:Methanol:Water=8:2:0.2); NMR ($d_6$-DMSO): δ 10.32 (1H, s), 9.10 (2H, br.s), 7.89 (2H, d, J=8.8 Hz), 7.81 (1H, dd, J=1.8,7.8 Hz), 7.66 (1H, m), 7.56 (2H, d, J=8.8 Hz), 7.46–7.54 (3H, m), 7.39 (1H, dt, J=1.8,7.8 Hz), 7.21–7.25 (2H, m), 5.96 (1H, m), 5.17–5.35 (2H, m), 4.53–4.56 (2H, m).

EXAMPLE 27 t-Butyl 2'-(1-(4-($N^2$-benzyloxycarbonylamidino)phenylamino)-1-methoxy carbonylmethyl)-2-biphenylcarboxylate

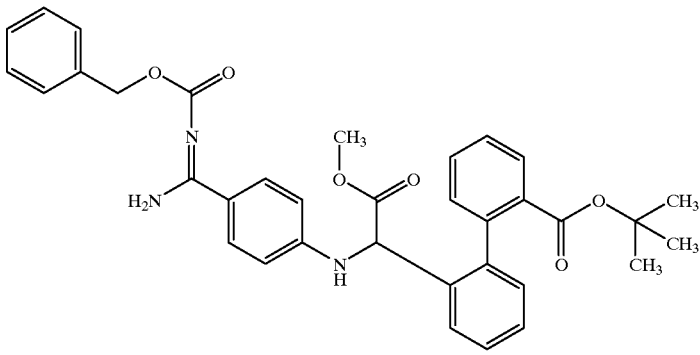

t-Butyl 2'-(1-methoxycarbonyl-1-methylsulfonyloxymethyl)-2-biphenyl carboxylate (3.36 g) and 4-($N^2$-benzyloxycarbonylamidino)aniline (5.38 g) was dissolved into dimethylformamide (5 ml). The mixture was stirred for 19 hours at 60° C., and then for 6 hours at 80° C. After the reaction mixture was cooled to room temperature, water was added to the reaction mixture. The solution was extracted with ethyl acetate. The extract was washed with water, 0.5 N hydrochloric acid, a saturated aqueous solution of sodium bicarbonate and a saturated aqueous solution of sodium chloride, successively, dried over anhydrous sodium sulfate and concentrated. The residue was purified by column chromatography on silica gel (hexane:ethyl acetate=1:1) to give the title compound (2.03 g) having the following physical data.

TLC:Rf 0.53 (Hexane:Ethyl acetate=1:1).

EXAMPLE 27(1)–EXAMPLE 27(2)

The following compounds were obtained by the same procedure as a series of reaction of Example 27, using a corresponding compound instead of t-butyl 2'-(1-methoxycarbonyl-1-methylsulfonyloxymethyl)-2-biphenylcarboxylate.

EXAMPLE 27(1)

t-Butyl 2'-(1-(4-($N^2$-benzyoxycarbonylamidino)phenylamino)-1-methyl carbamoylmethyl)-2-biphenylcarboxylate

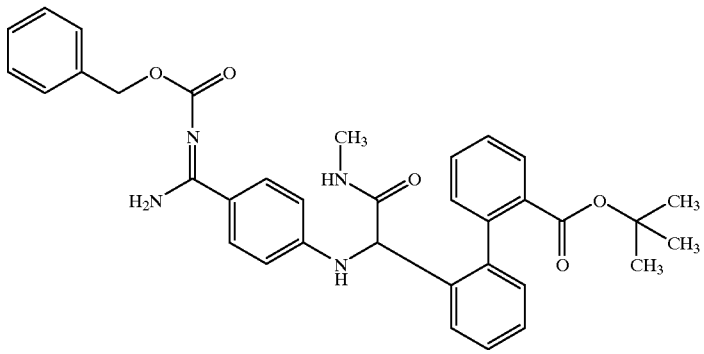

TLC:Rf 0.36 (Chloroform:Ethyl acetate=1:1); NMR (CDCl$_3$) δ 10.0–9.0 (2H, broad), 8.0–7.9 (1H, broad), 7.69–7.24 (13H, m), 7.15–7.04 (2H, m), 6.43 and 6.23 (2H, d, J=9.0 Hz), 5.70 (0.6H, d, J=2.0 Hz), 5.52 (0.4H, d, J=5.0 Hz), 5.19 (2H, s), 4.89 (0.4H, d, J=5.0 Hz), 4.83 (0.6H, d, J=2.0 Hz), 2.92 and 2.63 (3H, d, J=5.0 Hz), 1.41 (9H, s).

EXAMPLE 27(2)

t-Butyl 2'-(1-(4-(N²-benzyoxycarbonylamidino)phenylamino)-1-cyanomethyl)-2-biphenylcarboxylate

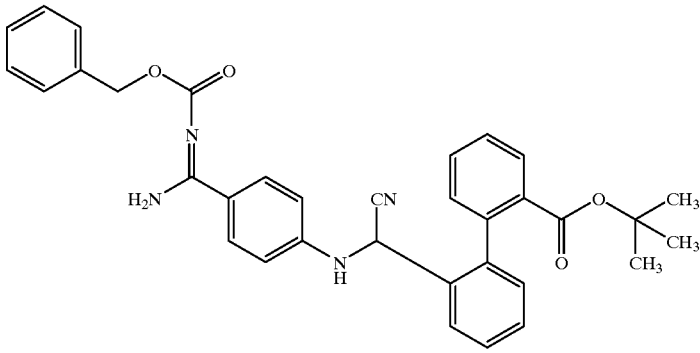

TLC:Rf 0.79 (Chloroform:Ethyl acetate=7:3); NMR (CDCl$_3$): δ 7.97–7.09 (15H, m), 6.47 and 6.36 (2H, d, J=9.0 Hz), 5.34–5.11 (3H, m), 4.60–4.34 (1H, m), 1.37 and 1.22 (9H, s).

REFERENCE EXAMPLE 17

Methyl 2'-ethynyl-4-((2-methylpropyl)carbamoyl)-2-biphenylcarboxylate

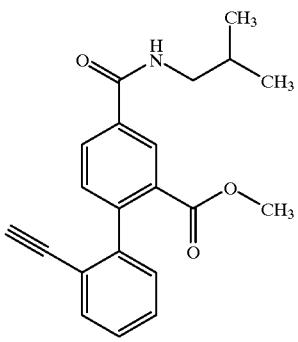

A solution of potassium t-butoxide (1.43 g) in anhydrous tetrahydrofuran (5 ml) was added to a solution of (bromomethyl)triphenylphosphonium bromide (2.78 g) in anhydrous tetrahydrofuran (20 ml). The mixture was stirred for 30 minutes. Methyl 2'-formyl-4-((2-methylpropyl)carbamoyl)-2-biphenylcarboxylate (1.8 g) which was prepared by the same procedure as a series of reaction of Reference Example 3 (using 2-methylpropylamine instead of 2,2-dimethylpropylamine)→Reference Example 4, using 3-methoxycarbonyl-4-trifluoromethylsulfonyloxybenzoic acid; in anhydrous tetrahydrofuran (20 ml) was added to the mixture. After the mixture was warmed to room temperature, it was stirred for 12 minutes. Water (100 ml) was added to the reaction mixture, and the solution was extracted with ethyl acetate. The extract was washed with a saturated aqueous solution of sodium chloride, dried over anhydrous magnesium sulfate and concentrated. The residue was purified by column chromatography on silica gel (hexane:ethyl acetate=2:1) to give the title compound (1.20 g) having the following physical data.

TLC:Rf 0.37 (Hexane:Ethyl acetate=1:1); NMR (CDCl$_3$): δ 8.32 (1H, d, J=2.0 Hz), 8.01 (1H, dd, J=2.0,8.0 Hz), 7.57 (1H, dd, J=2.0,8.0 Hz), 7.43 (1H, d, J=8.0 Hz), 7.42 (1H, dt, J=2.0,8.0 Hz), 7.34 (1H, dt, J=2.0,8.0 Hz), 7.24 (1H, dd, J=2.0,8.0 Hz), 6.30 (1H, br.t, J=6.0 Hz), 3.67 (3H, s), 3.33 (2H, t, J=6.0 Hz), 2.91 (1H, s), 1.94 (1H, m), 1.01 (6H, d, J=6.6 Hz).

REFERENCE EXAMPLE 18

Methyl 2'-(4-cyanophenylethynyl)-4-((2-methylpropyl)carbamoyl)-2-biphenylcarboxylate

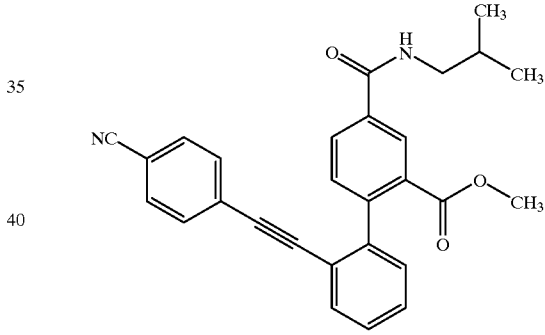

To a solution of the compound prepared in Reference Example 17 (1.07 g) and p-cyanobromobenzene (640 mg) in dimethylformamide-triethylamine (5:1, 6 ml), dichlorobis(triphenylphosphine)palladium (II) (45 mg) was added. The mixture was stirred for 30 minutes 90° C. Water (100 ml) was added to the reaction mixture, and the solution was extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=2:1→3:2) to give the title compound (1.23 g) having the following physical data.

TLC:Rf 0.32 (Hexane:Ethyl acetate=2:1); NMR (CDCl$_3$): δ 8.38 (1H, d, J=2.0 Hz), 8.03 (1H, dd, J=2.0,8.0 Hz), 7.61 (1H, d, J=8.0 Hz), 7.53 (2H, d, J=8.8 Hz), 7.44–7.50 (2H, m), 7.40 (1H, dt, J=2.0,8.0 Hz), 7.27–7.34 (3H, m), 6.36 (1H, br.t, J=6.4 Hz), 3.63 (3H, s), 3.34 (2H, t, J=6.4 Hz), 1.95 (1H, m), 1.01 (6H, d, J=6.6 Hz).

EXAMPLE 28

Methyl 2'-(4-amidinophenyletynyl)-4-((2-methylpropyl)carbamoyl)-2-biphenylcarboxylate

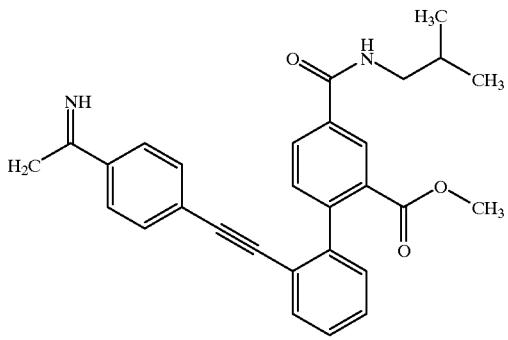

To a solution of the compound prepared in Reference Example 18 (704 mg) in methanol (20 ml), hydrogen chloride gas was introduced below 10° C. The solution was stirred for 12 hours at room temperature. The reaction solution was concentrated. To a solution of the residue in methanol (20 ml), ammonium gas was introduced below 10° C. The solution was stirred for 12 hours at room temperature. The reaction solution was concentrated. The residue was purified by column chromatography on silica gel (Chloroform:Methanol:Water=9:1:0.1→8:2:0.2) to give the present compound (0.41 g) having the following physical data.

TLC:Rf 0.42 (Chloroform:Methanol:Water=8:2:0.2); NMR (CD$_3$OD): δ 8.45 (1H, d, J=2.0 Hz), 8.08 (1H, dd, J=2.0,8.0 Hz), 7.71 (2H, d, J=8.0 Hz), 7.52 (1H, d, J=8.0 Hz), 7.53 (1H, t, J=8.0 Hz), 7.50 (1H, t, J=8.0 Hz), 7.39–7.46 (4H, m), 3.61 (3H, s), 3.25 (2H, d, J=7.2 Hz), 1.97 (1H, t, J=1.00 (6H, d, J=6.6 Hz).

EXAMPLE 29

Methyl 2'-(4-amidinophenyletynyl)-2-biphenylcarboxyate hydrochloride

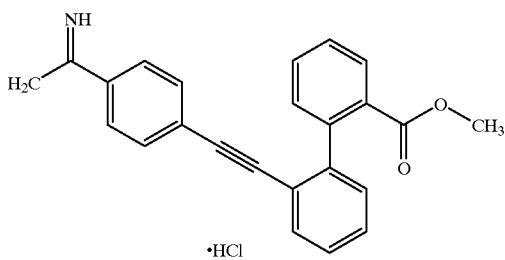

The present compound having the following physical data was obtained by the same procedure as a series of reaction of Reference Example 17→Reference Example 18→Example 28, using methyl 2'-formyl-2-biphenylcarboxylate.

TLC:Rf 0.41 (Chloroform:Methanol:Acetic acid=20:2:1); NMR (d$_6$-DMSO): δ 9.30 (4H, brs), 7.94 (1H, dd, J=2.0, 8.0 Hz), 7.79 (2H, d, J=8.5 Hz), 7.74–7.38 (7H, m), 7.39 (2H, d, J=8.5 Hz), 3.52 (3H, s).

REFERENCE EXAMPLE 19

2'-((1E)-2-(4-cyanophenyl)ethenyl)-4-((2-methylpropyl)carbarmoyl)-2-biphenylcarboxylic acid

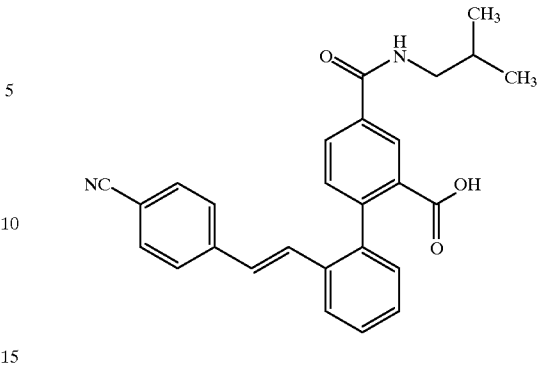

A solution of p-tolunitrile (1.7 g) and ethyl 2'-formyl-4-((2-methylpropyl)carbamoyl)-2-biphenylcarboxylate (2.58 g) which was prepared by the same procedure as a series of reaction of Reference Example 3 (using 2-methylpropylamine instead of 2,2-dimethylpropylamine) Reference Example 4, using 3-ethoxycarbonyl-4-trifluoromethylsulfonyloxybenzoic acid; in anhydrous hexamethylphosphoramide (3 ml) was added to a solution of potassium t-butoxide in anhydrous hexamethylphosphoramide (30 ml). The mixture was stirred for 12 hours at room temperature. The reaction mixture was diluted with water (100 ml), and extracted with ethyl acetate. The extract was washed with water and a saturated aqueous solution of sodium chloride, successively, dried over anhydrous magnesium sulfate and concentrated. The residue was purified by column chromatography on silica gel (Chloroform:Methanol=20:1 Chloroform:Methanol:Water= 9:1:0.1) to give the title compound (0.96 g) having the following physical data.

TLC:Rf 0.26 (Chloroform:Methanol:Water=9:1:0.1); NMR (CDCl$_3$): δ 8.40 (1H, s), 8.02 (1H, d, J=8.0 Hz), 7.71 (1H, d, J=7.0 Hz), 7.51 (2H, d, J=8.4 Hz), 7.42 (1H, t, J=7.0 Hz), 7.36 (1H, t, J=7.0 Hz), 7.29–7.34 (3H, m), 7.16 (1H, d, J=7.0 Hz), 6.95 (1H, d, J=16.0 Hz), 6.85 (1H, d, J=16 Hz), 6.37 (1H, br.t, J=6.6 Hz), 3.32 (2H, t, J=6.6 Hz), 1.94 (1H, m), 1.01 (6H, d, J=6.6 Hz).

EXAMPLE 30

Methyl 2'-((1E)-2-(4-amidinophenyl)ethenyl)-4-((2-methylpropyl)carbamoyl)-2-biphenylcarboxylate

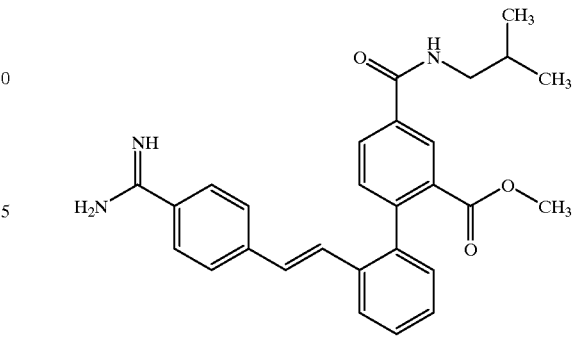

To a solution of the compound prepared in Reference Example 19 (560 mg) in methanol (20 ml), hydrogen chloride gas was introduced below 10° C. The solution was stirred for 12 hours at room temperature. The reaction solution was concentrated. To a solution of the residue in methanol (20 ml), ammonium gas was introduced below 10°

C. The solution was stirred for 12 hours at room temperature. The reaction solution was concentrated. The residue was purified by column chromatography on silica gel (Chloroform:Methanol:Water=9:1:0.1→8:2:0.2) to give the present compound (0.41 g) having the following physical data.

TLC:Rf 0.21 (Chloroform:Methanol:Water=8:2:0.2); NMR (d$_6$-DMSO): δ 9.23 (2H, s), 8.90 (2H, s), 8.74 (1H, t, J=6.2 Hz), 8.34 (1H, d, J=1.8 Hz), 8.13 (1H, dd, J=1.8,8.0 Hz), 7.85 (1H, dd, J=1.8,8.0 Hz), 7.75 (2H, d, J=8.8 Hz), 7.54 (2H, d, J=8.8 Hz), 7.35–7.47 (3H, m), 7.23–7.28 (2H, m), 6.90 (1H, d, J=16.2 Hz), 3.46 (3H, s), 3.13 (2H, t, J=6.2 Hz), 2.33 (3H, s), 1.89 (1H, m), 0.92 (6H, d, J=6.6 Hz).

EXAMPLE 31

Methyl 2'-((1E)-2-(4-amidinophenyl)ethenyl)-2-biphenylcarboxylate

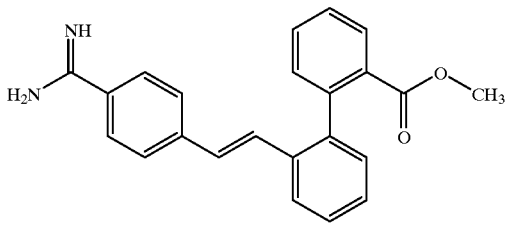

The present compound having the following physical data was obtained by the same procedure as a series of reaction of Reference Example 19–Example 30, using ethyl 2'-formyl-2-biphenylcarboxylate. NMR (d$_6$-DMSO): δ 9.60 (2H, brs), 9.20 (2H, brs), 7.88 (1H, dd, J=1.5, 8.0 Hz), 7.84 (1H, dd, J=1.5, 8.0 Hz), 7.73 (2H, d, J=8.5 Hz), 7.60–7.40 (2H, m), 7.46 (2H, d, J=8.5 Hz), 7.36 (2H, brt, J=8.0 Hz), 7.30–7.14 (2H, m), 7.24 (1H, d, J=16.5 Hz), 6.79 (1H, d, J=16.5 Hz), 3.58 (3H, s).

EXAMPLE 32

Methyl 2-(6-(4-amidinophenylcarbamoyl)isoquinolin-7-yl)benzoate

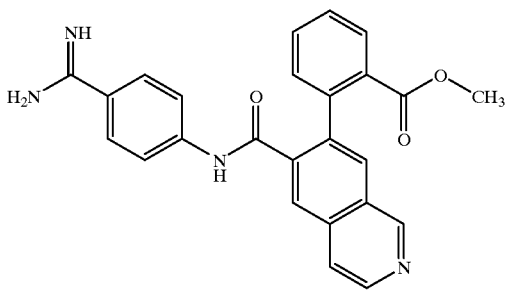

The present compound having the following physical data was obtained by the same procedure as a series of reaction of Reference Example 4→Reference Example 5→Reference Example 10→Reference Example 12→Example 1, using benzyl 7-trifluoromethylsulfonyloxy-6-isoquinolinecarboxylate.

TLC:Rf 0.36 (Chloroform:Methanol:Acetic acid=10:2:1); NMR (CD$_3$OD): δ 9.34 (1H, s), 8.56 (1H, d, J=6.0 Hz), 8.26 (1H, s), 8.04 (1H, s), 8.00 (1H, d, J=6.0 Hz), 7.93 (1H, dd, J=7.5 Hz, 1.5 Hz), 7.73 (4H, s), 7.64 (1H, td, J=7.5 Hz, 1.5 Hz), 7.52–7.43 (2H, m), 3.61 (3H, s).

EXAMPLE 33–EXAMPLE 33(7)

The following compounds were obtained by the same procedure as a series of reaction of Reference Example 19, using a compound prepared in Example 27–Example 32.

EXAMPLE 33 t-Butyl 2'-(1-(4-amidinophenylamino)-1-methoxycarbonylmethyl)-2-biphenylcarboxylate

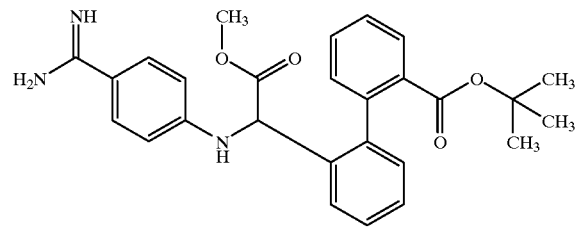

TLC:Rf 0.48 (Chloroform:Methanol:Acetic acid=10:2:1); NMR (d$_6$-DMSO): δ 7.92–7.83 (1H, m), 7.72–7.10 (9H, m), 6.49–6.39 (2H, m), 4.97 (0.4H, d, J=9.0 Hz), 4.75 (0.6H, d, J=7.5 Hz), 3.57 (3H, s), 1.69 (3H, s), 1.11 (5.4H, s), 1.02 (3.6H, s).

EXAMPLE 33(1)

t-Butyl 2'-(1-(4-amidinophenylamino)-1-methylcarbamoylmethyl)-2-biphenylcarboxylate

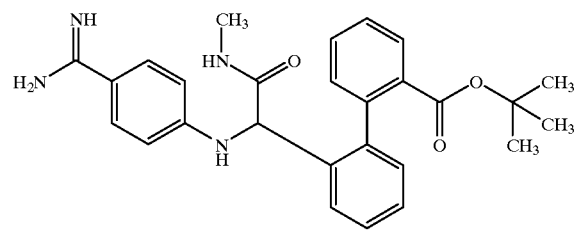

TLC:Rf 0.65 (Chloroform:Methanol:Acetic acid=10:2:1); NMR (CD$_3$OD): δ 7.83 (0.4H, dd, J=8.0 Hz, 1.5 Hz), 7.65 (0.6H, d, J=8.0 Hz), 7.56–7.08 (9H, m), 6.50 and 6.37 (2H, d, J=9.0 Hz), 4.93 and 4.68 (1H, s), 2.80 and 2.71 (3H, s), 1.91 (3H, s), 1.32 and 1.27 (9H, s).

EXAMPLE 33(2)

t-Butyl 2'-(1-(4-amidinophenylamino)-1-cyanomethyl)-2-biphenylcarboxylate

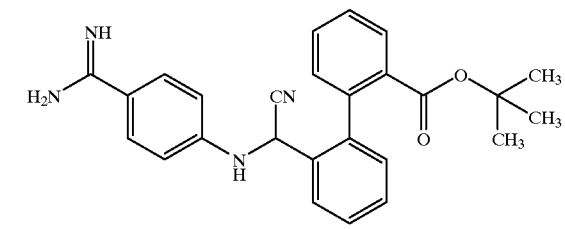

TLC:Rf 0.48 and 0.55 (Chloroform:Methanol:Acetic acid=10:2:1); NMR (d$_6$-DMSO): δ 7.85–7.10 (10H, m), 6.69 and 6.56 (2H, d, J=9.0 Hz), 5.52–5.14 (1H, m), 1.10 and 1.13 (9H, s).

EXAMPLE 33(3)

2'-(4-amidinophenylethynyl)-4-((2-methylpropyl)carbamoyl)-2-biphenyl carboxylic acid methanesulfonate

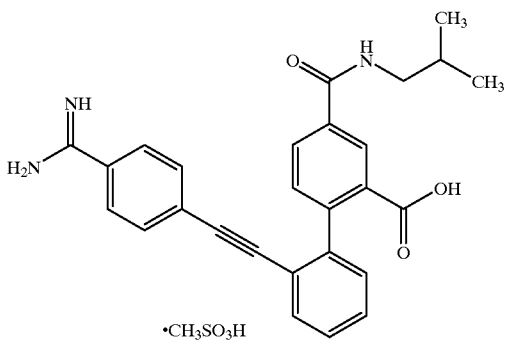

TLC:Rf 0.46 (Chloroform:Methanol:Water=8:2:0.2); NMR (d$_6$-DMSO): δ 12.85 (1H, s), 9.33 (2H, s), 9.05 (2H, s), 8.72 (1H, br.t, J=6.4 Hz), 8.44 (1H, d, J=1.8 Hz), 8.11 (1H, dd, J=1.8,8.4 Hz), 7.77 (2H, d, J=8.8 Hz), 7.63 (1H, 1H, d, J=7.2 Hz), 7.39–7.55 (6H, m), 3.13 (2H, t, J=6.4 Hz), 2.35 (3H, s), 1.89 (1H, m), 0.92 (6H, d, J=6.8 Hz).

EXAMPLE 33(4)

2'-(4-amidinophenylethynyl)-2-biphenylcarboxylate acetic acetate

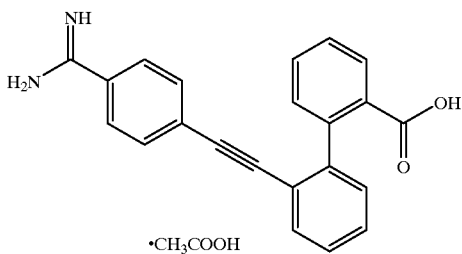

TLC:Rf 0.37 (Chloroform:Methanol:Acetic acid=10:2:1); NMR (CDCl$_3$): δ 11.6–9.00 (4H, m), 7.90 (1H, dd, J=2.0, 7.5 Hz), 7.73 (2H, d, J=8.0 Hz), 7.54 (1H, brd, J=7.5 Hz), 7.50–7.20 (8H, m), 1.84 (3H, s).

EXAMPLE 33(5)

2'-((1E)-2-(4-amidinophenyl)ethenyl)-4-((2-methylpropyl)carbamoyl)-2-biphenylcarboxylic acid methanesulfonate

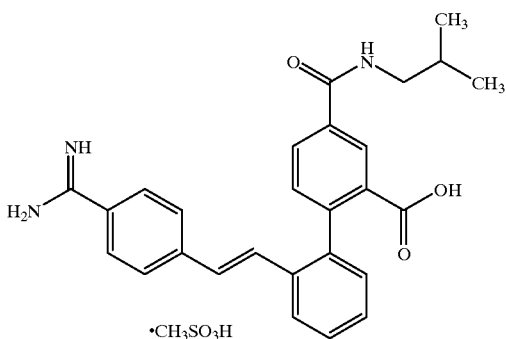

TLC:Rf 0.39 (Chloroform:Methanol:Acetic acid=10:2:1); NMR (d$_6$-DMSO): δ 12.78 (1H, s), 9.30 (2H, s), 9.09 (2H, s), 8.75 (1H, br.t, J=6.0 Hz), 8.39 (1H, s), 8.09 (1H, d, J=8.0 Hz), 7.87 (1H, d, J=8.0 Hz), 7.77 (2H, d, J=8.8 Hz), 7.51 (2H, d, J=8.8 Hz), 7.44 (1H, t, J=8.0 Hz), 7.35–7.41 (2H, m), 7.26 (1H, d, J=16.2 Hz), 7.21 (1H, d, J=8.0 Hz), 6.93 (1H, d, J=16.2 Hz), 3.14 (2H, t, J=6.0 Hz), 2.38 (3H, s), 1.90 (1H, m), 0.92 (6H, d, J=6.6 Hz).

EXAMPLE 33(6)

2'-((1E)-2-(4-amidinophenyl)ethenyl)-2-biphenylcarboxylic acid trifluoroacetate

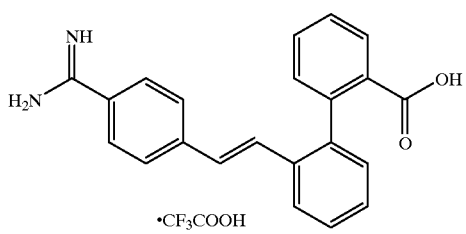

TLC:Rf 0.25 (Chloroform:Methanol:Acetic acid=10:2:1); NMR (d$_6$-DMSO): δ 9.60 (2H, brs), 9.20 (2H, brs), 7.88 (1H, dd, J=1.5, 8.0 Hz), 7.84 (1H, dd, J=1.5, 8.0 Hz), 7.73 (2H, d, J=8.5 Hz), 7.60–7.40 (2H, m), 7.46 (2H, d, J=8.5 Hz), 7.36 (2H, brt, J=8.0 Hz), 7.30–7.14 (2H, m), 7.24 (1H, d, J=16.5 Hz), 6.79 (1H, d, J=16.5 Hz).

EXAMPLE 33(7)

2-(6-(4-amidinophenylcarbamoyl)isoquinolin-7-yl)benzoic acid methanesulfonate

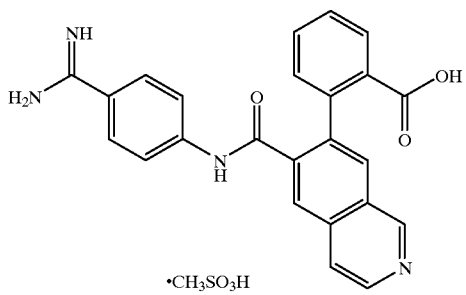

TLC:Rf 0.45 (Ethyl acetate:Acetic acid:Water=3:1:1); NMR (d$_6$-DMSO): δ 13.0–12.0 (1H, broad), 10.91 (1H, s), 9.71 (1H, s), 9.20 (2H, brs), 8.94 (2H, brs), 8.72 (1H, d, J=6.0 Hz), 8.49 (1H, s), 8.38 (1H, d, J=6.0 Hz), 8.26 (1H, s), 7.93 (1H, dd, J=7.5 Hz, 1.5 Hz), 7.78 (2H, d, J=9.0 Hz), 7.73 (2H, d, J=9.0 Hz), 7.63 (1H, td, J=7.5 Hz, 1.5 Hz), 7.50 (1H, td, J=7.5 Hz, 1.5 Hz), 7.39 (1H, dd, J=7.5 Hz, 1.5 Hz), 2.34 (3H, s).

EXAMPLE 34–EXAMPLE 34(2)

The following compounds were obtained by the same procedure as a series of reaction of Reference Example 19, using a compound prepared in Example 33–Example 33(2).

EXAMPLE 34

2'-(1-(4-amidinophenylamino)-1-methoxycarbonylmethyl)-2-biphenyl carboxylic acid hydrochloride

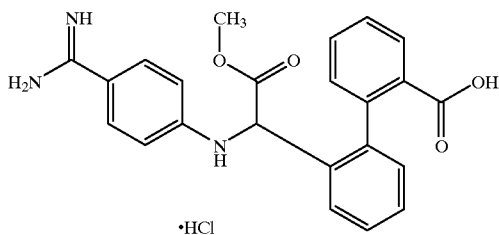

TLC:Rf 0.39 (Chloroform:Methanol:Acetic acid=10:2:1); NMR (d$_6$-DMSO): δ 12.6 (1H, brs), 8.81 (2H, brs), 8.55 (2H, brs), 7.99–7.87 (1H, m), 7.70–7.10 (9H, m), 6.52 and 6.47 (2H, d, J=9.0 Hz), 4.94 and 4.76 (1H, d, J=7.0 Hz), 3.55 (3H, s).

EXAMPLE 34(1)

2'-(1-(4-amidinophenylamino)-1-methylcarbamoylmethyl)-2-biphenyl carboxylic acid methanesulfonate

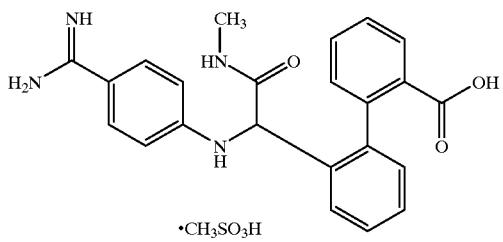

TLC:Rf 0.30 (Chloroform:Methanol:Acetic acid=10:2:1); NMR (CD$_3$OD): δ 7.90 (0.4H, dd, J=8.0 Hz, 2.0 Hz), 7.74 (0.6H, dd, J=8.0 Hz, 1.0 Hz), 7.54–7.08 (9H, m), 6.48 (0.8H, d, J=9.0 Hz), 6.39 (1.2H, d, J=9.0 Hz), 4.84 (0.6H, s), 4.81 (0.4H, s), 2.79 (1.8H, s), 2.71 (3H, s), 2.68 (1.2H, s).

EXAMPLE 34(2)

2'-(1-(4-amidinophenylamino)-1-cyanomethyl)-2-biphenylcarboxylic acid hydrochloride

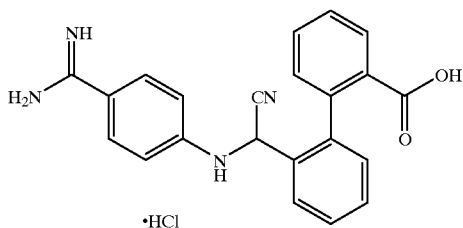

TLC:Rf 0.28 (Chloroform:Methanol:Acetic acid=10:2:1); NMR (CD$_3$OD): δ 7.86–7.11 (10H, m), 6.61 (2H, d, J=8.0 Hz), 5.50 and 5.43 (1H, s).

EXAMPLE 35

2'-(1-(4-amidinophenylamino)-1-carboxymethyl)-2-biphenylcarboxylic acid hydrochloride

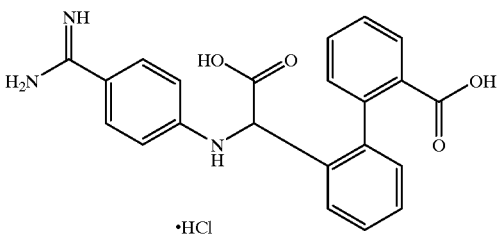

The present compound having the following physical data was obtained by the same procedure as a series of reaction of Reference Example 19, using a compound prepared in Example 34.

TLC:Rf 0.09 (Chloroform:Methanol:Acetic acid=10:2:1); NMR (d$_6$-DMSO): δ 13.8–11.6 (1H, broad), 8.81 and 8.87 (2H, brs), 8.70 (2H, brs), 7.95–7.86 (1H, m), 7.65–7.30 (7H, m), 7.25–7.11 (2H, m), 6.48 and 6.45 (2H, d, J=8.5 Hz), 4.83 and 4.65 (1H, s).

EXAMPLE 36–EXAMPLE 36(1)

The following compounds were obtained by the same procedure as a series of reaction of Example 2, using a compound prepared in Example 33(3) and Example 33(4).

EXAMPLE 36

2'-(2-(4-amidinophenyl)ethyl)-4-((2-methylpropyl)carbamoyl)-2-biphenyl carboxylic acid methanesulfonate

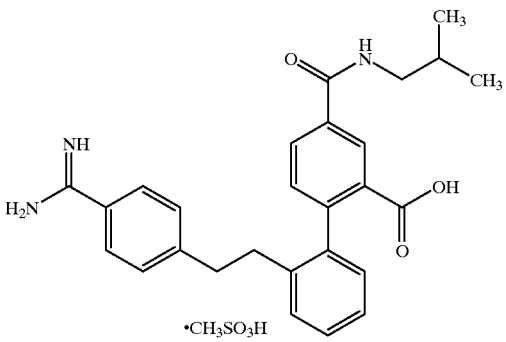

TLC:Rf 0.46 (Chloroform:Methanol:Water=7:3:0.3); NMR (d$_6$-DMSO): δ 12.83 (1H, s), 9.19 (2H, s), 9.02 (2H, s), 8.71 (1H, br.t, J=6.8 Hz), 8.35 (1H, d, J=2.0 Hz), 8.03 (1H, dd, J=2.0,8.0 Hz), 7.64 (2H, d, J=8.0 Hz), 7.16–7.31 (6H, m), 7.06 (1H, d, J=8.0 Hz), 3.12 (2H, t, J=6.8 Hz), 2.61–2.77 (4H, m), 2.33 (3H, s), 1.88 (1H, m), 0.92 (6H, d, J=7.0 Hz).

EXAMPLE 36(1)

2'-(2-(4-amidinophenyl)ethyl)-2-biphenylcarboxylic acid acetate

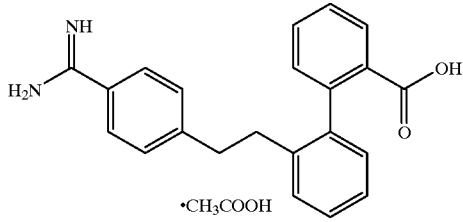

TLC:Rf 0.42 (Chloroform:Methanol:Acetic acid=10:2:1); NMR (CDCl₃): δ 11.6–9.80 (2H, m), 9.80–8.00 (1H, m), 7.79 (1H, dd, J=2.0, 7.5 Hz), 7.59 (2H, d, J=8.0 Hz), 7.40–7.30 (2H, m), 7.22–7.10 (5H, m), 7.10–7.00 (2H, m), 1.84 (3H, s).

REFERENCE EXAMPLE 20

4-(2'-methoxycarbonylbiphenyl-2-yloxymethyl)phenylmethylthioimidate hydroiodide

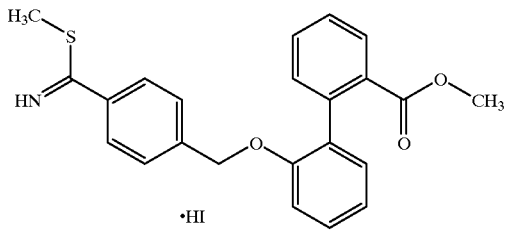

To a solution of methyl 2'-(4-cyanobenzyloxy)-2-biphenylcarboxylate (2.14 g) which was prepared by the same procedure as a series of reaction of Example 16 (using 4-cyanobenzyl bromide instead of a compound prepared in Reference Example 16, and using 2-bromophenol instead of 4-amidinoaniline)→Reference Example 4→Reference Example 5→Reference Example 14; in dimethylformamide (40 ml), magnesium chloride hexahydroxide (1.39 mg) and sodium hydrogensulfide (629 mg) was added. The mixture was stirred for 4 hours at room temperature. The reaction mixture was diluted with ethyl acetate (100 ml), and the solution was washed with a saturated aqueous solution of sodium chloride (50 ml, 2 times). The organic layer was dried over anhydrous sodium sulfate and concentrated. The residue was purified by column chromatography on silica gel (hexane:ethyl acetate=3:1) to give thioamide compound (2.74 g). Thioamide compound (2.74 g) was dissolved into acetone (50 ml), and then methyl iodide (1.94 ml) was added to the solution at room temperature. The mixture was refluxed for 1 hour. The reaction mixture was concentrated to give the title compound (3.42 g) having the following physical data.

TLC:Rf 0.69 (Chloroform:Methanol=10:1); NMR (CDCl₃): δ 8.01 (2H, d, J=8.5 Hz), 7.94 (1H, dd, J=1.5, 7.5 Hz), 7.58 (1H, dt, J=1.5, 7.5 Hz), 7.44 (1H, dt, J=1.5, 7.5 Hz), 7.38 (2H, d, J=8.5 Hz), 7.4–7.25 (5H, m), 7.09 (1H, dt, J=1.5, 7.5 Hz), 6.90 (1H, br.d, J=7.5 Hz), 5.07 (2H, s), 3.60 (3H, s), 3.13 (3H, s).

EXAMPLE 37

Methyl 2'-(4-amidinobenzyloxy)-2-biphenylcarboxylate

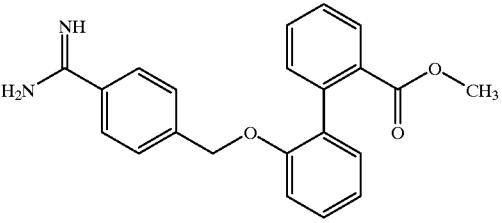

The compound prepared in Reference Example 20 (3.23 g) and ammonium acetate (959 mg) was dissolved into ethanol (50 ml). The mixture was refluxed for 1 hour. The reaction mixture was cooled to room temperature, and concentrated. The residue was purified by column chromatography on silica gel (Chloroform:Methanol=10:1→Chloroform:Methanol:Water=10:2:0.1) to give the present compound (2.15 g) having the following physical data.

TLC:Rf 0.38 (Chloroform:Methanol:Acetic acid=10:1:0.2); NMR (d₆-DMSO): δ 9.4–8.83 (4H, br), 7.80 (1H, dd, J=1.0, 8.0 Hz), 7.73 (2H, d, J=8.4 Hz), 7.63 (1H, dt, J=1.0, 8.0 Hz), 7.48 (1H, dt, J=1.0, 8.0 Hz), 7.42 (2H, d, J=8.4 Hz), 7.4–7.25 (2H, m), 7.21 (1H, dd, J=1.0, 8.0 Hz), 7.1–7.0 (2H, m), 5.15 (2H, s), 3.52 (3H, s).

EXAMPLE 38

2'-(4-amidinobenzyloxy)-2-biphenylcarboxylic acid methanesulfonate

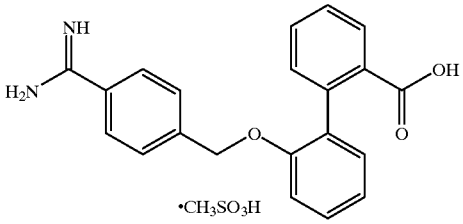

The present compound having the following physical data was obtained by the same procedure as a series of reaction of Example 19, using the compound prepared in Example 37.

TLC:Rf 0.60 (Chloroform:Methanol:Acetic acid=10:2:1); NMR (d₆-DMSO): δ 12.46 (1H, br.s), 9.24 (2H, s), 8.91 (2H, s), 7.82 (1H, dd, J=1.0, 7.5 Hz), 7.72 (2H, d, J=8.4 Hz), 7.58 (1H, dt, J=1.0, 7.5 Hz), 7.5–7.4 (1H, m), 7.46 (2H, d, J=8.4 Hz), 7.35–7.25 (2H, m), 7.18 (1H, dd, J=1.0, 7.5 Hz), 7.05–6.95 (2H, m), 5.15 (2H, s), 2.31 (3H, s).

REFERENCE EXAMPLE 21

Benzyl 2'-(tetrazol-5-yl)-2-biphenylcarboxylate

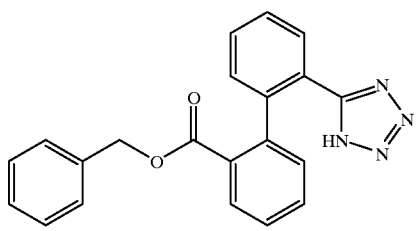

To a solution of benzyl 2'-cyano-2-bipheylcarboxylate (560 mg) in toluene (10 ml), azidotrimethyltin (810 mg) was added. The mixture was refluxed for 12 hours. The reaction mixture was concentrated. 5% aqueous solution of potassium fluoride (4 ml) was added to the residue. The solution was filtered. The filtrate was diluted with ethyl acetate, and the solution was washed with a saturated aqueous solution of sodium chloride. The organic layer was dried over anhydrous sodium sulfate and concentrated. The residue was purified by column chromatography on silica gel (hexane:ethyl acetate=2:1→chloroform:methanol=10:1) to give the title compound (545 mg) having the following physical data.

TLC:Rf 0.08 (Hexane:Ethyl acetate=2:1).

REFERENCE EXAMPLE 22

Benzyl 2'-(triphenylmethyltetrazol-5-yl)-2-biphenylcarboxylate

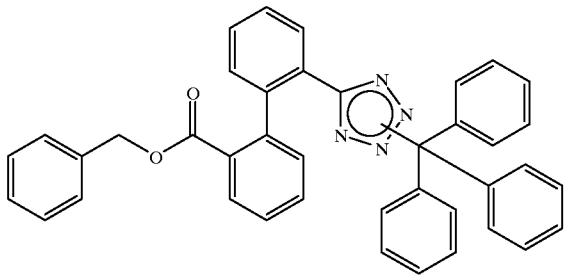

Triethylamine (2.74 ml) and trityl chloride (549 mg) were added to a solution of the compound prepared in Reference Example 21 (545 mg) in methylene chloride (10 ml). The mixture was stirred for 1 hour at room temperature. The reaction mixture was diluted with chloroform (50 ml), and the solution was washed with water (50 ml). The organic layer was dried over anhydrous sodium sulfate and concentrated. The residue was purified by column chromatography on silica gel (hexane:ethyl acetate=8:1) to give the title compound (713 mg) having the following physical data.

TLC:Rf 0.71 (Hexane:Ethyl acetate=2:1).

EXAMPLE 39

2'-(4-amidinophenylcarbamoyl)-2-(tetrazol-5-yl)biphenyl methanesulfonate

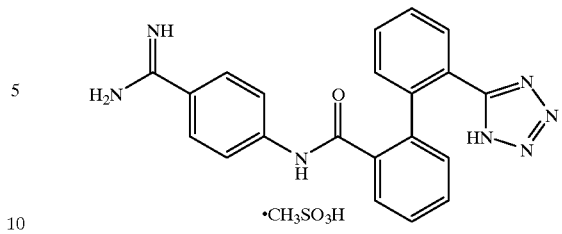

The present compound having the following physical data was obtained by the same procedure as a series of reaction of Example 11→Example 1→Example 2, using a compound prepared in Reference Example 22.

TLC:Rf 0.35 (Chloroform:Methanol:Acetic acid=10:2:1); NMR ($d_6$-DMSO): δ 10.32 (1H, s), 9.14 (2H, s), 8.80 (2H, s), 7.71 (2H, d, J=9.0 Hz), 7.7–7.45 (6H, m), 7.63 (2H, d, J=9.0 Hz), 7.42 (1H, dd, J=1.2, 7.5 Hz), 7.24 (1H, dd, J=1.2, 7.5 Hz), 4.2–3.5 (1H, br), 2.32 (3H, s).

REFERENCE EXAMPLE 23

Benzyl 4'-benzyloxycarbonylamino-2'-methoxymethyloxycarbonyl-4-hydroxymethyl-2-biphenylcarboxylate

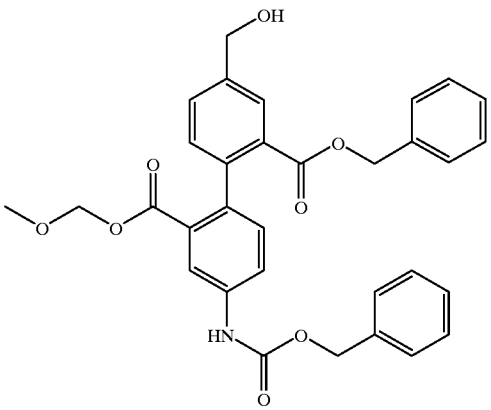

To a solution of benzyl 4'-benzyloxycarbonylamino-2'-methoxymethyloxycarbonyl-4-t-butyidiphenylsilyloxymethyl-2-biphenyl carboxylate (777 mg) which was prepared by the same procedure as a series of reaction of Reference Example 6→Reference Example 1 (without an esterfication of benzyl)→Reference Example 4→Reference Example 5→Reference Example 7, using 5-benzyloxycarbonylaminosalicylic acid; in anhydrous tetrahydrofuran (10 ml), a solution of 1.0 M tetrabutylammonium fluoride in anhydrous tetrahydrofuran (1.0 ml) was added. The mixture was stirred for 2 hours at room temperature. Water (100 ml) was added to the reaction mixture, the solution was extracted with ethyl acetate. The organic layer was washed with a saturated aqueous solution of sodium chloride, successively, dried over anhydrous magnesium sulfate and concentrated. The residue was purified by column chromatography on silica gel (n-hexane:ethyl acetate=2:3) to give the title compound (370 mg) having the following physical data.

TLC:Rf 0.29 (n-Hexane:Ethyl acetate=1:1); NMR (200 MHz, $CDCl_3$): δ 8.02 (d, J=2.0 Hz, 1H), 7.81 (d, J=2.0 Hz, 1H), 7.65 (dd, J=8.0,2.0 Hz, 1H), 7.54 (dd, J=8.0,2.0 Hz, 1H), 7.45–7.38 (m, 5H), 7.28–7.07 (m, 7H), 6.78 (s, 1H), 5.25 (s, 2H), 5.16 (d, J=6.0 Hz, 1H), 5.10 (d, J=6.0 Hz, 1H), 5.04 (s, 2H), 4.76 (s, 2H), 3.21 (s, 3H).

REFERENCE EXAMPLE 24

Benzyl 4'-benzyloxycarbonylamino-2'-methoxymethyloxycarbonyl-4-formyl-2-biphenylcarboxylate

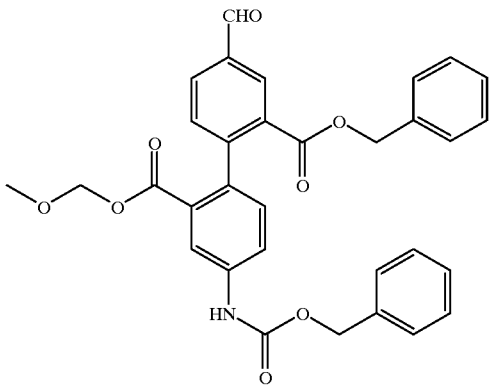

Dimethylsulfoxide (124 μl) was added to a solution of oxalyl chloride (120 μl) in anhydrous methylene chloride (5 ml) at −78° C. The mixture was stirred for 10 minutes. The compound prepared in Reference Example 23 (370 mg) in anhydrous methylene chloride (5 ml) was added to the above solution at −78° C. The mixture was stirred for 1 hour. Triethylamine (0.38 ml) was added to the reaction mixture at −78° C. The mixture was stirred for 1 hour at room temperature. Water (50 ml) was added to the reaction mixture at −78 ° C. The solution was extracted with ethyl acetate. The organic layer was washed with a saturated aqueous solution of sodium chloride, successively, dried over anhydrous magnesium sulfate and concentrated to give the title compound (356 mg) having the following physical data.

TLC:Rf 0.65 (n-Hexane:Ethyl acetate=1:1); NMR (200 MHz, CDCl₃): δ 10.09 (s, 1H), 8.53 (d, J=2.0 Hz, 1H), 8.04 (dd, J=8.0,2.0 Hz, 1H), 7.86 (d, J=2.0 Hz, 1H), 7.71 (dd, J=8.0,2.0 Hz, 1H), 7.46–7.35 (m, 5H), 7.26–7.24 (m, 4H), 7.17–7.08 (m, 3H), 6.75 (s, 1H), 5.26 (s, 2H), 5.16 (d, J=6.4 Hz, 1H), 5.12 (d, J=6.4 Hz, 1H), 5.08 (s, 2H), 3.25 (s, 3H).

REFERENCE EXAMPLE 25

Benzyl 2-(2-formyl-6-methoxy-3-pyridyl)-5-((1(S)-t-butyldimethylsilyloxymethyl-2,2-dimethylpropyl)carbamoyl)benzoate

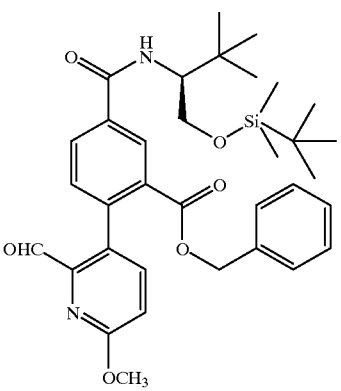

To a solution of 3-tributyltin-2-formyl-6-methoxypyridine (2.45 g) and benzyl 2-trofluoromethylsulfonyloxy-5-((1(R)-t-butylmethylsilyloxymethyl-2,2-dimethylpropyl)carbamoyl)benzoate (2.36 g) which was prepared by the same procedure as a series of reaction of Reference Example 1 Reference Example 2→Reference Example 3, using a corresponding compound; in dimethylformamide (15 ml), copper oxide (II) (305 mg) and dichlorobis(triphenylphosphine)palladium (II) (134 mg) were added. The mixture was stirred for 1 hour at 110° C. The reaction mixture was cooled to room temperature, and ethyl acetate and water were added to the reaction solution. Insoluble solid was removed by filtration. The filtrate was extracted. The organic layer was washed two times with water, and a saturated aqueous solution of sodium chloride, dried over anhydrous magnesium sulfate and concentrated. The residue was purified by column chromatography on silica gel (hexane:ethyl acetate=7:3) to give the present compound (2.02 g) having the following physical data.

TLC:Rf 0.51 (Hexane:Ethyl acetate=7:3); NMR (300 MHz, CDCl₃): δ 9.78 (s, 1H), 8.49 and 8.46 (d, J=2.0 Hz, 1H), 8.00 and 7.97 (dd, J=8.0, 2.0 Hz, 1H), 7.39 (d, J=8.0 Hz, 1H), 7.32–7.27 (m, 4H), 7.19–7.12 (m, 2H), 6.87 (d, J=8.0 Hz, 1H), 6.63 (d, J=9.6 Hz, 1H), 5.08 (2H, m), 4.06–4.00 (m, 1H), 4.03 (s, 3H), 3.91 (dd, J=10.5, 3.3 Hz, 1H), 3.76 (dd, J=10.5, 4.5 Hz, 1H), 1.04 (s, 9H), 0.88 (s, 9H), 0.07 (s, 3H), 0.04 (s, 3H).

EXAMPLE 40(1)–40(88)

The following compounds were obtained by the same procedure as a series of reaction of Example 1, using a compound prepared by the same procedure as a series of reaction of Reference Example 1→Reference Example 2→Reference Example 3→Reference Example 4 or Reference Example 25→Reference Example 5 using a corresponding compound instead of a compound prepared in Reference Example 5, or using a compound prepared by the same procedure as a series of reaction of Reference Example 5→Reference Example 3→Example 4 using the compound prepared in Reference Example 24 or a compound prepared by the same procedure as it, and using a corresponding compound instead of 4-amidinoaniline.

EXAMPLE 40(1)

Benzyl 2-[4-(4-amidinophenylcarbamoyl)-3-pyridyl]-5-[(1,2,2-trimethyl propyl)carbamoyl]benzoate

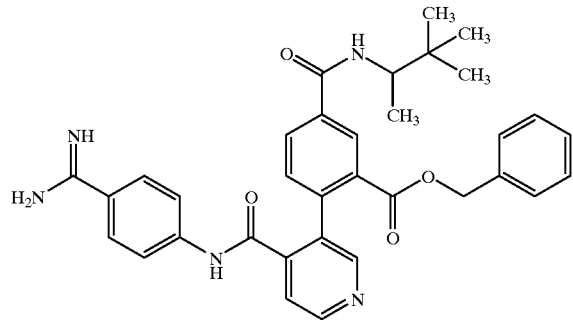

TLC:Rf 0.27 (Chloroform:Methanol:Acetic acid=10:2:1); NMR (200 MHz, CD$_3$OD): δ 8.64 (1H, d, J=5.0 Hz), 8.50 (1H, s), 8.39 (1H, d, J=2.0 Hz), 8.00 (1H, dd, J=8.0 Hz, 2.0 Hz), 7.70 (4H, s), 7.61 (1H, d, J=5.0 Hz), 7.47 (1H, d, J=8.0 Hz), 7.30–7.23 (3H, m), 7.23–7.13 (2H, m), 5.11 (2H, s), 4.05 (1H, q, J=7.0 Hz), 1.16 (3H, d, J=7.0 Hz), 0.96 (9H, s).

EXAMPLE 40(2)

Benzyl 2-[2-(4-amidinophenylcarbamoyl)-6-methyl-3-pyridyl]-5-[(2-methyl propyl)carbamoyl]benzoate

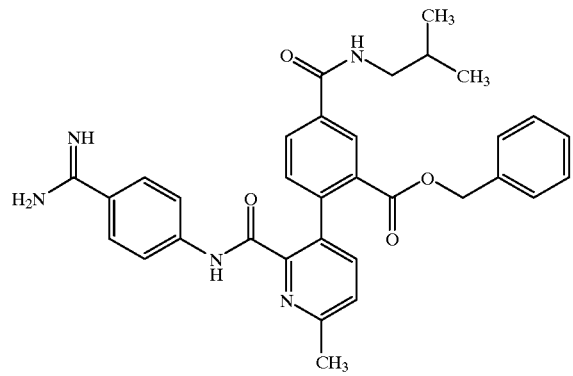

TLC:Rf 0.49 (Chloroform:Methanol:Acetic acid=10:2:1); NMR (300 MHz, CD$_3$OD): δ 8.52 (1H, d, J=2.0 Hz), 8.03 (1H, dd, J=8.0 Hz, 2.0 Hz), 7.85 (2H, d, J=9.0 Hz), 7.76 (2H, d, J=9.0 Hz), 7.55 (1H, d, J=7.5 Hz), 7.43 (1H, d, J=7.5 Hz), 7.32 (1H, d, J=8.0 Hz), 7.27–7.16 (3H, m), 7.09–7.03 (2H, m), 5.04 (1H, brd, J=12 Hz), 4.98 (1H, brd, J=12 Hz), 3.23 (2H, d, J=7.0 Hz), 2.64 (3H, s), 2.03–1.88 (1H, m), 0.98 (6H, d, J=6.5 Hz).

EXAMPLE 40(3)

Benzyl 2-[2-(4-amidinophenylcarbamoyl)-6-methyl-3-pyridyl]-5-[(1,2,2-trimethylpropyl)carbamoyl]benzoate

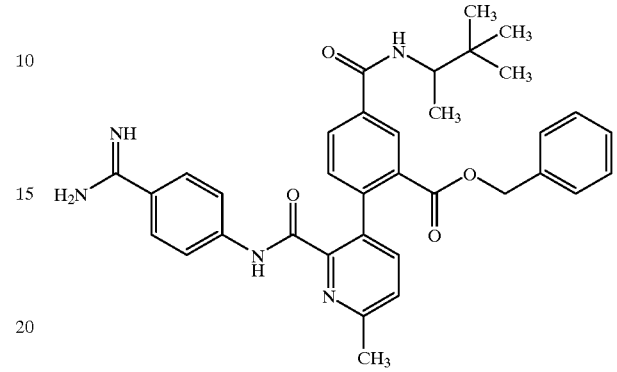

TLC:Rf 0.51 (Chloroform:Methanol:Acetic acid=10:2:1); NMR (300 MHz, CD$_3$OD): δ 8.48 (1H, d, J=2.0 Hz), 8.00 (1H, dd, J=8.0 Hz, 2.0 Hz), 7.85 (2H, d, J=9.0 Hz), 7.76 (2H, d, J=9.0 Hz), 7.56 (1H, d, J=8.0 Hz), 7.43 (1H, d, J=8.0 Hz), 7.32 (1H, d, J=8.0 Hz), 7.28–7.16 (3H, m), 7.10–7.06 (2H, m), 5.05 (1H, brd, J=12 Hz), 4.98 (1H, brd, J=12 Hz), 4.10 (1H, q, J=7.0 Hz), 2.64 (3H, s), 1.20 (3H, d, J=7.0 Hz), 1.00 (9H, s).

EXAMPLE 40(4)

Benzyl 2'-(4-amidinophenylcarbamoyl)-4-(1,1-dimethylpropylcarbamoyl)-2-biphenylcarboxylate

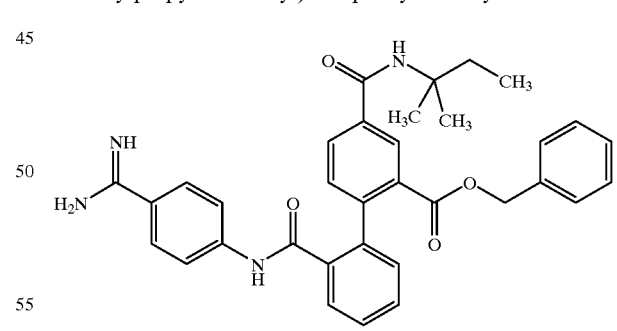

TLC:Rf 0.39 (Chloroform:Methanol:Water=8:2:0.1); NMR (300 MHz, CD$_3$OD): δ 8.21 (d, J=1.8 Hz, 1H), 7.88 (dd, J=7.8, 1.8 Hz, 1H), 7.67 (d, J=9.0 Hz, 2H), 7.68–7.64 (m, 1H), 7.60 (d, J=9.0 Hz, 2H), 7.56–7.46 (m, 2H), 7.39 (d, J=7.8 Hz, 1H), 7.28–7.24 (m, 4H), 7.16–7.13 (m, 2H), 5.12 (s, 2H), 1.85 (q, J=7.5 Hz, 2H), 1.38 (s, 6H), 0.88 (t, J=7.5 Hz, 3H).

EXAMPLE 40(5)

Benzyl 2'-(4-amidinophenylcarbamoyl)-4-[(1(S)-t-butyl-2-methoxycarbonyl ethyl)carbamoyl]-2-biphenylcarboxylate

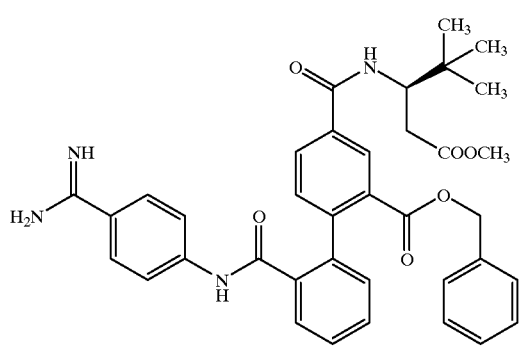

TLC:Rf 0.37 (Chloroform:Methanol:Water=8:2:0.1); NMR (200 MHz, CD$_3$OD): δ 8.25 (d, J=1.8 Hz, 1H), 7.92 (dd, J=8.0, 1.8 Hz, 1H), 7.70–7.49 (m, 7H), 7.42 (d, J=7.8 Hz, 1H), 7.29–7.25 (m, 4H), 7.18–7.15 (m, 2H), 5.12 (s, 2H), 4.39 (dd, J=11.4,3.2 Hz, 1H), 3.56 (s, 3H), 2.72 (dd, J=14.6, 3.2 Hz, 1H), 2.53 (dd, J=14.6, 11.4 Hz, 1H), 0.97 (s, 9H).

EXAMPLE 40(6)

Benzyl 2'-(4-amidinophenylcarbamoyl)-4-(2,2-dimethylcyclohexylcarbamoyl)-2-biphenylcarboxylate

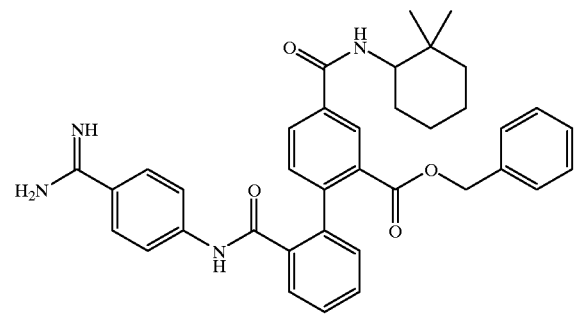

TLC:Rf 0.75 (Chloroform:Methanol:Acetic acid=10:2:1); NMR (d$_6$-DMSO): δ 10.65 (1H, s), 9.3–8.8 (3H, br), 8.21 (1H, d, J=1.5 Hz), 8.13 (1H, d, J=9.0 Hz), 8.01 (1H, dd, J=8.0, 1.5 Hz), 7.75 (4H, like s), 7.70 (1H, dd, J=8.0, 1.5 Hz), 7.6–7.5 (2H, m), 7.38 (1H, d, J=8.0 Hz), 7.35–7.20 (4H, m), 7.10–7.00 (2H, m), 5.03 (2H, br.s), 3.79 (1H, m), 1.8–1.6 (1H, m), 1.6–1.3 (4H, m), 1.4–1.2 (3H, m), 0.89 (3H, s), 0.83 (3H, s).

EXAMPLE 40(7)

Benzyl 2'-(4-amidinophenylcarbamoyl)-4-(1-isopropyl-2-methylpropyl carbamoyl)-2-biphenylcarboxylate

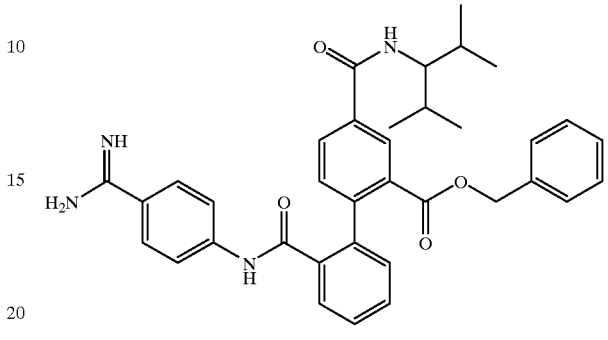

TLC:RF 0.41 (Chloroform:Methanol:Water 8:2:0.2); NMR (200 MHz, CD$_3$OD): δ 8.31 (d, J=2.0 Hz, 1H), 7.96 (dd, J=8.0,2.0 Hz, 1H), 7.70–7.59 (m, 5H), 7.55–7.50 (m, 2H), 7.42 (d, J=8.0 Hz, 1H), 7.29–7.26 (m, 4H), 7.18–7.13 (m, 2H), 5.14 (s, 2H), 3.72 (t, J=7.0 Hz, 1H), 1.95 (m, 2H), 0.95 (d, J=7.0 Hz, 6H), 0.90 (d, J=7.0 Hz, 6H).

EXAMPLE 40(8)

Benzyl 2'-(4-amidinophenylcarbamoyl)-4-[(4,4-dimethyloxolan-3(S)-yl) carbamoyl]-2-biphenylcarboxylic acid

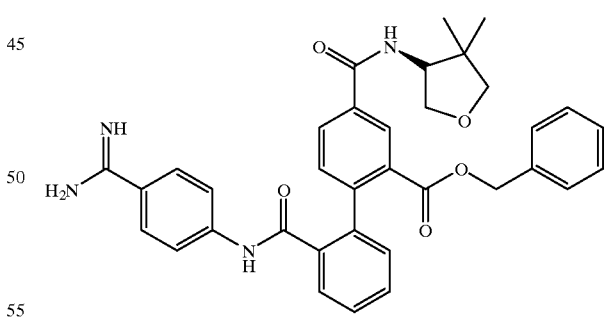

TLC:Rf 0.31 (Chloroform:Methanol:Water=8:2:0.1); NMR (200 MHz, CD$_3$OD): δ 8.31 (d, J=1.8 Hz, 1H), 7.98 (dd, J=8.0, 1.8 Hz, 1H), 7.71–7.59 (m, 6H), 7.59–7.49 (m, 2H), 7.42 (d, J=8.0 Hz, 1H), 7.28–7.25 (m, 3H), 7.16–7.11 (m, 2H), 5.12 (s, 2H), 4.44 (dd, J=7.4, 5.4 Hz, 1H), 4.20 (dd, J=9.2, 7.4 Hz, 1H), 3.72 (dd, J=9.2, 5.4 Hz, 1H), 3.63–3.53 (m, 2H), 1.16 (s, 3H), 1.02 (s, 3H).

EXAMPLE 40(9)

Benzyl 2-[2-(4-amidinophenylcarbamoyl)-3-pyridyl]-5-[(2-methylpropyl) carbamoyl]benzoate

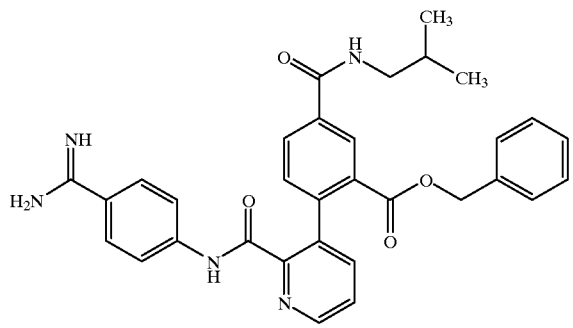

TLC:Rf 0.62 (Chloroform:Methanol:Acetic acid=10:2:1); NMR (300 MHz, $d_6$-DMSO): δ 10.98 (s, 1H), 9.4–9.0 (br, 3H), 8.76 (br.t, J=6.6 Hz, 1H), 8.70 (dd, J=4.5, 1.8 Hz, 1H), 8.42 (d, J=1.8 Hz, 1H), 8.11 (dd, J=7.8, 1.8 Hz, 1H), 7.93 (d, J=8.7 Hz, 2H), 7.85–7.75 (m, 1H), 7.79 (d, J=8.7 Hz, 2H), 7.68 (dd, J=7.8, 4.5 Hz, 1H), 7.39 (d, J=7.8 Hz, 1H), 7.3–7.15 (m, 3H), 7.15–7.05 (m, 2H), 5.02 (s, 2H), 3.11 (t, J=6.6 Hz, 2H), 1.87 (like septet, J=6.6 Hz, 1H), 0.90 (d, J=6.6 Hz, 6H).

EXAMPLE 40(10)

Benzyl 2-[2-(4-amidinophenylcarbamoyl)-6-methyl-3-pyridyl]-5-[(3-hydroxy methyl-2,2-dimethylpropyl) carbamoyl]benzoate

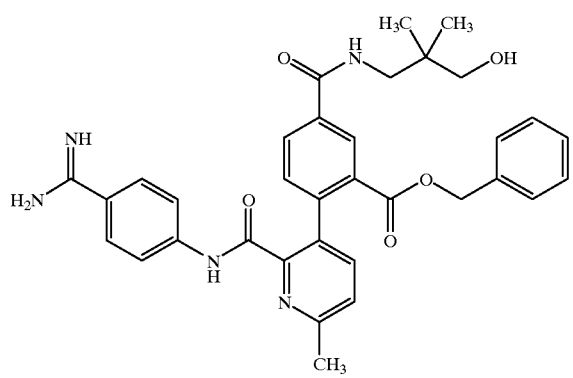

TLC:Rf 0.44 (Chloroform:Methanol:Acetic acid=10:2:1); NMR (300 MHz, $CD_3OD$) δ 8.52 (d, J=2.0 Hz, 1H), 8.04 (dd, J=8.0, 2.0 Hz, 1H), 7.85 (d, J=9.0 Hz, 2H), 7.76 (d, J=9.0 Hz, 2H), 7.56 (d, J=8.0 Hz, 1H), 7.43 (d, J=8.0 Hz, 1H), 7.33 (d, J=8.0 Hz, 1H), 7.27–7.16 (m, 3H), 7.09–7.03 (m, 2H), 5.04 (d, J=12 Hz, 1H), 4.98 (d, J=12 Hz, 1H), 3.34 (s, 2H), 3.33–3.30 (m, 2H), 2.64 (s, 3H), 0.96 (s, 6H).

EXAMPLE 40(11)

Benzyl 2-[2-(4-amidinophenylcarbamoyl)-3-pyridyl]-5-[(1,2,2-trimethylpropyl) carbamoyl]benzoate

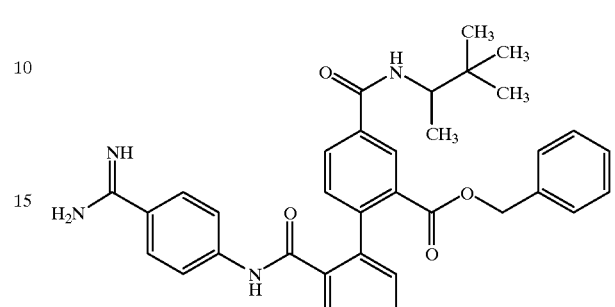

TLC:Rf 0.77 (Chloroform:Methanol:Acetic acid=10:2:1); NMR ($d_6$-DMSO): δ 10.98 (1H, s), 9.3–8.8 (3H, br), 8.71 (1H, dd, J=4.2, 1.2 Hz), 8.38 (1H, d, J=1.2 Hz), 8.27 (1H, br.d, J=9.0 Hz), 8.09 (1H, dd, J=7.8, 1.2 Hz), 7.93 (2H, d, J=8.7 Hz), 7.8–7.75 (3H, m), 7.69 (1H, dd, J=7.8, 4.2 Hz), 7.38 (1H, d, J=7.8 Hz), 7.3–7.15 (3H, m), 7.15–7.05 (2H, m), 5.03 (2H, s), 4.00 (1H, m), 1.10 (3H, d, J=6.4 Hz), 0.92 (9H, s).

EXAMPLE 40(12)

Benzyl 2'-(4-amidinophenylcarbamoyl)-4-[(1 (R), 2,2-trimethylpropyl)carbamoyl]-2-biphenylcarboxylate

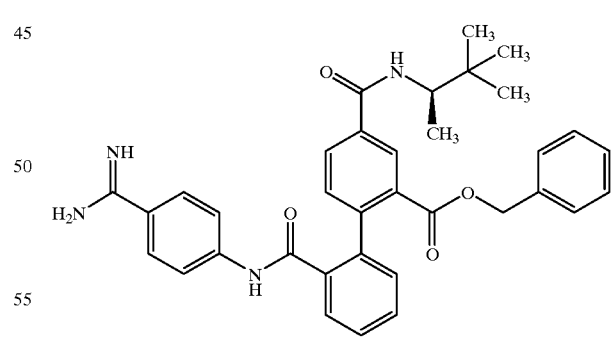

TLC:Rf 0.30 (Chloroform:Methanol:Water=8:2:0.1); NMR (200 MHz, $CD_3OD$): δ 8.27 (d, J=2.0 Hz, 1H), 7.94 (dd, J=8.2, 2.0 Hz, 1H), 7.70–7.58 (m, 5H), 7.55–7.49 (m, 2H), 7.42 (d, J=8.0 Hz, 1H), 7.29–7.25 (m, 4H), 7.17–7.12 (m, 2H), 5.12 (s, 2H), 4.10–3.99 (m, 1H), 1.15 (d, J=7.0 Hz, 3H), 0.95 (s, 9H).

EXAMPLE 40(13)

Benzyl 2'-(4-amidinophenylcarbamoyl)-4-[(1(S), 2,2-trimethylpropyl)carbamoyl]-2-biphenylcarboxylate

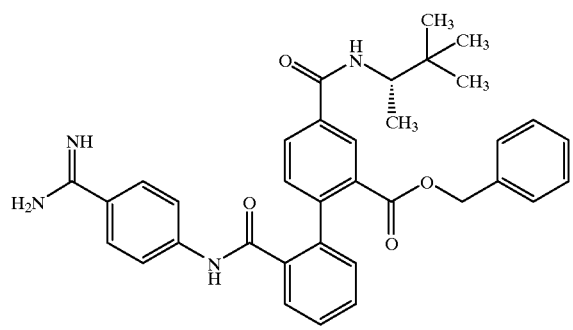

TLC:Rf 0.30 (Chloroform:Methanol:Water=8:2:0.1); NMR (200 MHz, CD$_3$OD): δ 8.27 (d, J=2.0 Hz, 1H), 7.94 (dd, J=8.2, 2.0 Hz, 1H), 7.70–7.58 (m, 5H), 7.55–7.49 (m, 2H), 7.44 (d, J=8.2 Hz, 1H), 7.29–7.25 (m, 4H), 7.17–7.12 (m, 2H), 5.13 (s, 2H), 4.10–3.99 (m, 1H), 1.15 (d, J=6.8 Hz, 3H), 0.95 (s, 9H).

EXAMPLE 40(14)

Benzyl 2-[2-(4-amidinophenylcarbamoyl)-6-methyl-3-pyridyl]-5-[(2,2-dimethylpropyl)carbamoyl]benzoate

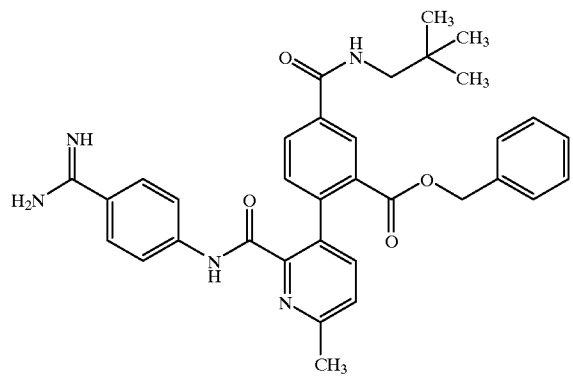

TLC:Rf 0.56 (Chloroform:Methanol:Acetic acid=10:2:1); NMR (300 MHz, CD$_3$OD): δ 8.51 (d, J=2.0 Hz, 1H), 8.03 (dd, J=8.0, 2.0 Hz, 1H), 7.85 (d, J=9.0 Hz, 2H), 7.76 (d, J=9.0 Hz, 2H), 7.55 (d, J=7.8 Hz, 1H), 7.43 (d, J=7.8 Hz, 1H), 7.33 (d, J=8.0 Hz, 1H), 7.28–7.16 (m, 3H), 7.09–7.04 (m, 2H), 5.04 (d, J=12 Hz, 1H), 4.98 (d, J=12 Hz, 1H), 3.25 (s, 2H), 2.64 (s, 3H), 0.99 (s, 9H).

EXAMPLE 40(15)

Benzyl 2-[2-(4-amidinophenylcarbamoyl)-6-methoxy-3-pyridyl]-5-[(2-methylpropyl)carbamoyl]benzoic acid

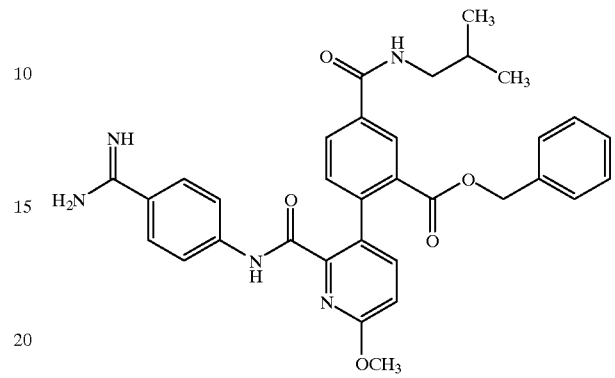

TLC:Rf 0.58 (Chloroform:Methanol:Acetic acid=10:2:1); NMR (300 MHz, CD$_3$OD): δ 8.51 (d, J=2.0 Hz, 1H), 8.02 (dd, J=8.0, 2.0 Hz, 1H), 7.83 (d, J=9.0 Hz, 2H), 7.77 (d, J=9.0 Hz, 2H), 7.54 (d, J=8.4 Hz, 1H), 7.31 (d, J=8.0 Hz, 1H), 7.28–7.16 (m, 3H), 7.10–7.04 (m, 2H), 6.98 (d, J=8.4 Hz, 1H), 1H), 5.07 (brd, J=12 Hz, 1H), 4.98 (brd, J=12 Hz, 1H), 4.06 (s, 3H), 3.23 (d, J=6.8 Hz, 2H), 2.03–1.88 (m, 1H), 0.98 (d, J=6.8 Hz, 6H).

EXAMPLE 40(16)

Benzyl 2'-(4-amidinophenylcarbamoyl)-4-(1-methoxycarbonylcyclopentyl carbamoyl)-2-biphenylcarboxylate

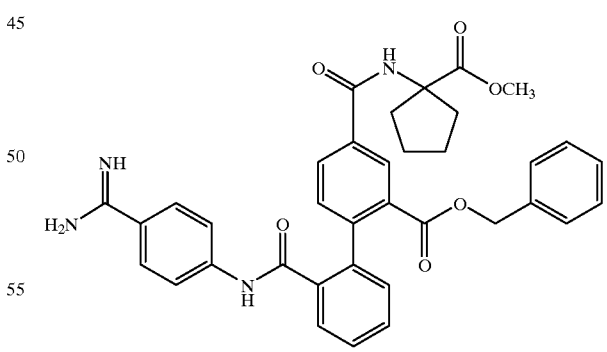

TLC:Rf 0.40 (Chloroform:Methanol:Water=8:2:0.1); NMR (200 MHz, CD$_3$OD): δ 8.30 (d, J=1.8 Hz, 1H), 7.97 (dd, J=8.0, 1.8 Hz, 1H), 7.70–7.62 (m, 5H), 7.55–7.48 (m, 2H), 7.41 (d, J=7.6 Hz, 1H), 7.28–7.22 (m, 4H), 7.17–7.12 (m, 2H), 5.12 (s, 2H), 3.68 (s, 3H), 2.36–2.21 (m, 2H), 2.13–2.00 (m, 2H), 1.86–1.75 (m, 4H).

EXAMPLE 40(17)

Benzyl 2-[4-(4-amidinophenylcarbamoyl)-3-pyridyl]-5-[(1(S)-hydroxymethyl-2-methylpropyl)carbamoyl]benzoate

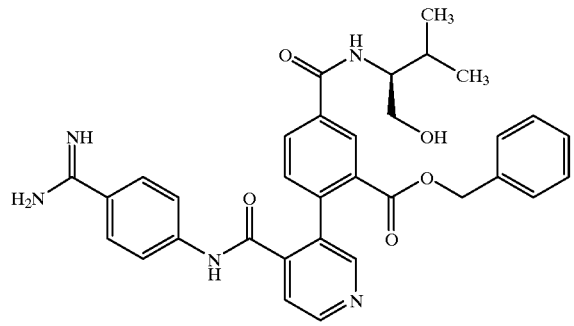

TLC:Rf 0.22 (Chloroform:Methanol:Acetic acid=10:2:1); NMR (300 MHz, CD$_3$OD): δ 8.63 (d, J=5.1 Hz, 1H), 8.50 (d, J=1.0 Hz, 1H), 8.45 (d, J=2.0 Hz, 1H), 8.06 (dd, J=8.0, 2.0 Hz, 1H), 7.71 (d, J=9.0 Hz, 2H), 7.67 (d, J=9.0 Hz, 2H), 7.60 (dd, J=5.1, 1.0 Hz, 1H), 7.48 (d, J=8.0 Hz, 1H), 7.30–7.26 (m, 3H), 7.20–7.16 (m, 2H), 5.14 (brd, J=12 Hz, 1H), 5.09 (brd, J=12 Hz, 1H), 3.91 (ddd, J=6.9, 6.6, 4.2 Hz, 1H), 3.73 (dd, J=11.4, 4.2 Hz, 1H), 3.65 (dd, J=11.4, 6.6 Hz, 1H), 2.05–1.94 (m, 1H), 1.00 (d, J=6.6 Hz, 3H), 0.96 (d, J=6.9 Hz, 3H).

EXAMPLE 40(18)

Benzyl 2-[2-(4-amidinophenylcarbamoyl)-6-methyl-3-pyridyl]-5-[(1(S)-hydroxymethyl-2-methylpropyl)carbamoyl]benzoate

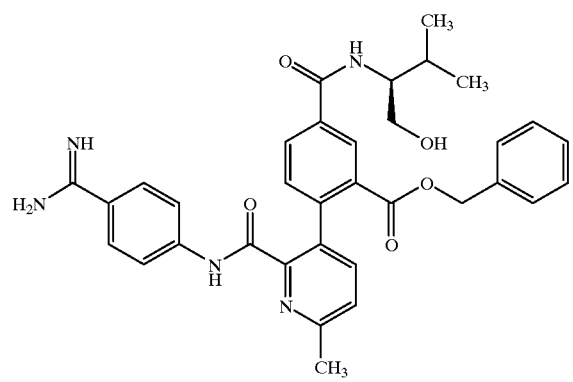

TLC:Rf 0.43 (Chloroform:Methanol:Acetic acid=10:2:1); NMR (300 MHz, CD$_3$OD): δ 8.54 (d, J=2.0 Hz, 1H), 8.05 (dd, J=8.0, 2.0 Hz, 1H), 7.85 (d, J=9.0 Hz, 2H), 7.76 (d, J=9.0 Hz, 2H), 7.55 (d, J=8.0 Hz, 1H), 7.43 (d, J=8.0 Hz, 1H), 7.32 (d, J=8.0 Hz, 1H), 7.28–7.16 (m, 3H), 7.10–7.03 (m, 2H), 5.04 (brd, J=12 Hz, 1H), 4.98 (brd, J=12 Hz, 1H), 3.96 (ddd, J=6.9, 6.6, 4.2 Hz, 1H), 3.76 (dd, J=11.4, 4.2 Hz, 1H), 3.70 (dd, J=11.4, 6.6 Hz, 1H), 2.64 (s, 3H), 2.09–1.93 (m, 1H), 1.03 (d, J=6.6 Hz, 3H), 1.00 (d, J=6.9 Hz, 3H).

EXAMPLE 40(19)

Benzyl 2-[2-(4-amidinophenylcarbamoyl)-3-pyridyl]-5-[(1(S)-hydroxymethyl-2-methylpropyl)carbamoyl]benzoate

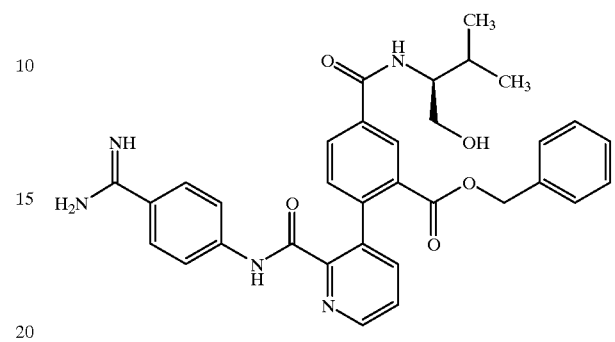

TLC:Rf 0.83 (Chloroform:Methanol:Acetic acid=10:2:1); NMR (d6-DMSO): δ 10.97 (s, 1H), 9.3–8.8 (br, 3H), 8.71 (dd, J=4.4, 2.1 Hz, 1H), 8.42 (d, J=2.1 Hz, 1H), 8.28 (d, J=9.6 Hz, 1H), 8.13 (dd, J=8.0, 2.1 Hz, 1H), 7.94 (d, J=9.0 Hz, 2H), 7.77 (d, J=9.0 Hz, 2H), 7.8–7.7 (m, 1H), 7.68 (dd, J=8.0, 4.4 Hz, 1H), 7.38 (d, J=8.0 Hz, 1H), 7.3–7.2 (m, 3H), 7.15–7.0 (m, 2H), 5.02 (s, 2H), 4.61 (t, J=5.5 Hz, 1H), 3.83 (m, 1H), 3.53 (t, J=5.5 Hz, 2H), 1.90 like sextet, J=6.6 Hz, 1H), 0.92 (d, J=6.6 Hz, 3H), 0.88 (d, J=6.6 Hz, 3H).

EXAMPLE 40(20)

Benzyl 2'-(4-amidinophenylcarbamoyl)-4-[(2-methoxycarbonyl-2,2-dimethyl ethyl)carbamoyl]-2-biphenylcarboxylate

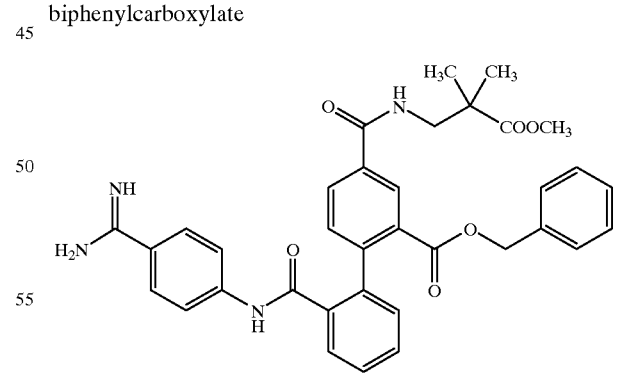

TLC:Rf 0.49 (Chloroform:Methanol:Water=8:2:0.1); NMR (200 MHz, CDCl$_3$): δ 8.27 (d, J=2.0 Hz, 1H), 7.95 (dd, J=8.0, 2.0 Hz, 1H), 7.70–7.58 (m, 5H), 7.55–7.49 (m, 2H), 7.42 (d, J=8.0 Hz, 1H), 7.30–7.22 (m, 4H), 7.17–7.12 (m, 2H), 5.12 (s, 2H), 3.64 (s, 3H), 3.52 (s, 2H), 1.21 (s, 6H).

EXAMPLE 40(21)

Benzyl 2-[2-(4-amidinophenylcarbamoyl)-6-methyl-3-pyridyl]-5-[(1(S)-methoxycarbonyl-2-methylpropyl)carbamoyl]benzoate

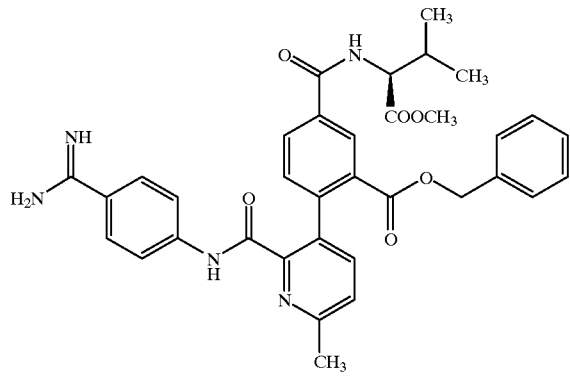

TLC:Rf 0.71 (Chloroform:Methanol:Acetic acid=10:2:1); NMR (300 MHz, CD$_3$OD): δ 8.52 (d, J=2.0 Hz, 1H), 8.05 (dd, J=8.0, 2.0 Hz, 1H), 7.85 (d, J=9.0 Hz, 2H), 7.76 (d, J=9.0 Hz, 2H), 7.56 (d, J=8.0 Hz, 1H), 7.43 (d, J=8.0 Hz, 1H), 7.33 (d, J=8.0 Hz, 1H), 7.26–7.16 (m, 3H), 7.10–7.06 (m, 2H), 5.04 (brd, J=12 Hz, 1H), 4.98 (brd, J=12 Hz, 1H), 4.52 (d, J=6.9 Hz, 1H), 3.76 (s, 3H), 2.64 (s, 3H), 2.34–2.23 (m, 1H), 1.06 (d, J=6.3 Hz, 3H), 1.04 (d, J=6.6 Hz, 3H).

EXAMPLE 40(22)

Benzyl 2-[4-(4-amidinophenylcarbamoyl)-3-pyridyl]-5-[(1(S)-methoxycarbonyl-2-methylpropyl)carbamoyl]benzoate

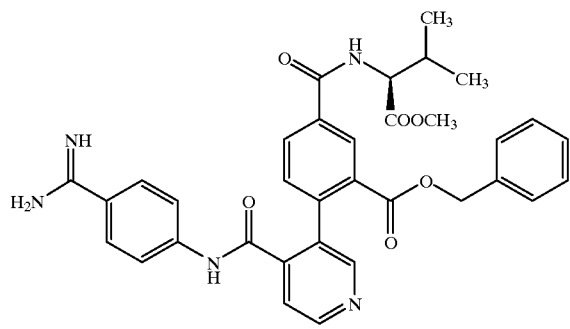

TLC:Rf 0.63 (Chloroform:Methanol:Acetic acid=10:2:1); NMR (300 MHz, CD$_3$OD): δ 8.64 (d, J=5.0 Hz, 1H), 8.51 (s, 1H), 8.44 (d, J=2.0 Hz, 1H), 8.06 (dd, J=8.0, 2.0 Hz, 1H), 7.71 (d, J=9.0 Hz, 2H), 7.67 (d, J=9.0 Hz, 2H), 7.60 (d, J=5.0 Hz, 1H), 7.49 (d, J=8.0 Hz, 1H), 7.30–7.24 (m, 3H), 7.20–7.14 (m, 2H), 5.14 (brd, J=12 Hz, 1H), 5.10 (brd, J=12 Hz, 1H), 4.47 (d, J=7.0 Hz, 1H), 3.74 (s, 3H), 2.31–2.19 (m, 1H), 1.02 (d, J=6.6 Hz, 3H), 1.00 (d, J=6.9 Hz, 3H).

EXAMPLE 40(23)

Benzyl 2'-(4-amidino-3-benzyloxyphenylcarbamoyl)-4-(2-methylpropylcarbamoyl)-2-biphenylcarboxylate

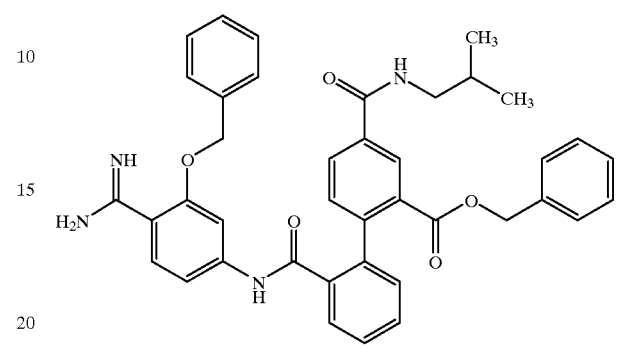

TLC:Rf 0.31 (Chloroform:Methanol:Water=8:2:0.2); NMR (200 MHz, CD$_3$OD): δ 8.34 (d, J=2.0 Hz, 1H), 7.98 (dd, J=8.0, 2.0 Hz, 1H), 7.67 (dd, J=8.0,2.0 Hz, 1H), 7.55–7.24 (m, 14H), 7.17–7.12 (m, 2H), 7.01 (dd, J=8.0,2.0 Hz, 1H), 5.12 (s, 2H), 5.10 (s, 2H), 3.18 (d, J=7.0 Hz, 2H), 1.91 (m, 1H), 0.95 (d, J=6.6 Hz, 6H).

EXAMPLE 40(24)

Benzyl 2'-(4-amidino-3-benzyloxyphenylcarbamoyl)-4-(1,2,2-trimethylpropyl carbamoyl)-2-biphenylcarboxylate

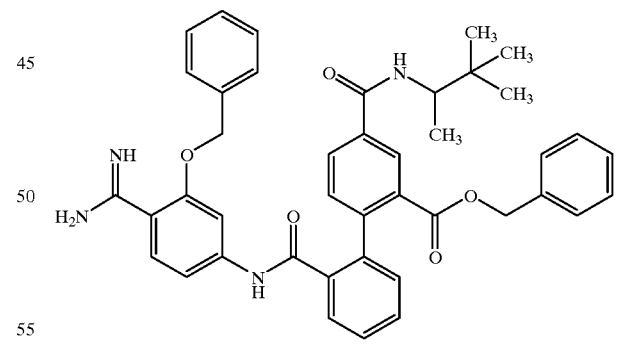

TLC:Rf 0.38 (Chloroform:Methanol:Water=8:2:0.2); NMR (300 MHz, CD$_3$OD): δ 8.31 (d, J=2.0 Hz, 1H), 8.17 (br.d, J=9.0 Hz, 1H), 7.95 (dd, J=8.0,2.0 Hz, 1H), 7.66 (dd, J=8.0,2.0 Hz, 1H), 7.58 (d, J=2.0 Hz, 1H), 7.54–7.50 (m, 2H), 7.46 (d, J=8.0 Hz, 1H), 7.43–7.31 (m, 5H), 7.29–7.24 (m, 4H), 7.15–7.12 (m, 2H), 7.02 (d, J=8.0 Hz, 1H), 5.10 (s, 4H), 4.06 (m, 1H), 1.16 (d, J=7.0 Hz, 3H), 0.96 (s, 9H).

EXAMPLE 40(25)

Benzyl 2'-(4-amidinophenylcarbamoyl)-4-(1,3-dimethylbutylcarbamoyl)-2-biphenylcarboxylate

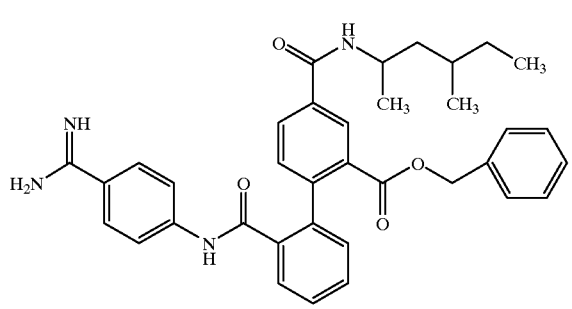

TLC:Rf 0.30 (Chloroform:Ethyl acetate:Water=8:2:0.2); NMR (300 MHz, CD$_3$OD): δ 8.30 (d, J=2.0 Hz, 1H), 7.95 (dd, J=8.1, 2.0 Hz, 1H), 7.69–7.65 (m, 4H), 7.62–7.59 (m, 2H), 7.52 (m, 2H), 7.41 (d, J=8.1 Hz, 1H), 7.28–7.26 (m, 3H), 7.17–7.14 (m, 2H), 5.13 (s, 2H), 4.22 (m, 1H), 1.70–1.52 (m, 2H), 1.25 (m, 1H), 1.19 (d, J=6.6 Hz, 3H), 0.93 (d, J=6.6 Hz, 6H).

EXAMPLE 40(26)

Benzyl 2'-(4-amidinophenylcarbamoyl)-4-(2,2-dimethyl-1(R)-cyclopentyl carbamoyl)-2-biphenylcarboxylate

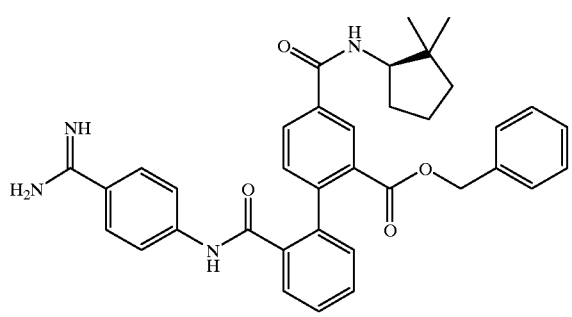

TLC:Rf 0.50 (Chloroform:Methanol:Acetic acid=10:2:1); NMR (300 MHz, CD$_3$OD): δ 8.28 (d, J=1.8 Hz, 1H), 7.95 (dd, J=7.8, 1.8 Hz, 1H), 7.70–7.58 (m, 5H), 7.53 (td, J=6.0, 1.8 Hz, 1H), 7.50 (td, J=6.0, 1.8 Hz, 1H), 7.41 (d, J=7.8 Hz, 1H, 7.30–7.22 (m, 4H), 7.18–7.12 (m, 2H), 5.12 (s, 2H), 4.17 (q, J=7.8 Hz, 1H), 2.08–1.98 (m, 1H), 1.80–1.52 (m, 5H), 1.05 (s, 3H), 0.93 (s, 3H).

EXAMPLE 40(27)

Benzyl 2-[2-(4-amidinophenylcarbamoyl)-3-pyridyl]-5-[(1(S)-carboxy-2-methylpropyl)carbamoyl]benzoate

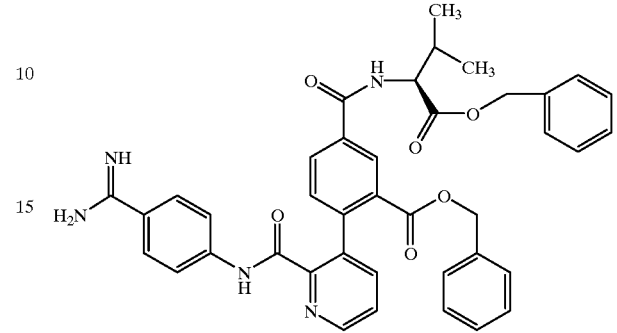

TLC:Rf 0.73 (Chloroform:Methanol:Acetic acid=10:2:1); NMR (d$_6$-DMSO): δ 810.40 (1H, br.s), 9.10 (3H, br.s), 8.97 (1H, br.s, J=7.5 Hz), 8.71 (1H, dd, J=4.5, 1.5 Hz), 8.43 (1H, d, J=1.5 Hz), 8.14 (1H, dd, J=8.0, 1.5 Hz), 7.94 (2H, d, J=9.0 Hz), 7.78 (2H, d, J=9.0 Hz), 7.8–7.7 (1H, m), 7.69 (1H, dd, J=7.5, 4.5 Hz), 7.41 (1H, d, J=8.0 Hz), 7.4–7.3 (5H, m), 7.25–7.15 (3H, m), 7.15–7.05 (2H, m), 5.20 (1H, d, J=12.6 Hz), 5.14 (1H, d, J=12.6 Hz), 5.03 (2H, s), 4.37 (1H, t, J=7.5 Hz), 2.23 (1H, m), 0.99 (3H, d, J=6.6 Hz), 0.94 (3H, d, J=6.6 Hz).

EXAMPLE 40(28)

Benzyl 2-[3-(4-amidinophenylcarbamoyl)-2-furyl]-5-(2-methylpropylcarbamoyl) benzoate

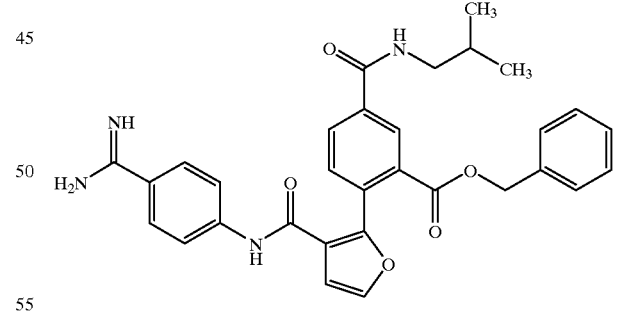

TLC:Rf 0.61 (Chloroform:Methanol:Acetic acid=10:2:1); NMR (300 MHz, DMSO-d$_6$): δ 8.38 (d, J=2.0 Hz, 1H), 8.04 (dd, J=8.0, 2.0 Hz, 1H), 7.85 (d, J=9.3 Hz, 2H), 7.76 (d, J=9.3 Hz, 2H), 7.70 (d, J=8.0 Hz, 1H), 7.60 (d, J=2.1 Hz, 1H), 7.27 (s, 5H), 7.02 (d, J=2.1 Hz, 1H), 5.15 (s, 2H), 3.21 (d, J=6.9 Hz, 2H), 2.01–1.87 (m, 1H), 0.97 (d, J=6.6 Hz, 6H).

EXAMPLE 40(29)

Benzyl 2-[2-(4-amidinophenylcarbamoyl)-3-thienyl]-5-(2-methylpropyl carbamoyl)benzoate

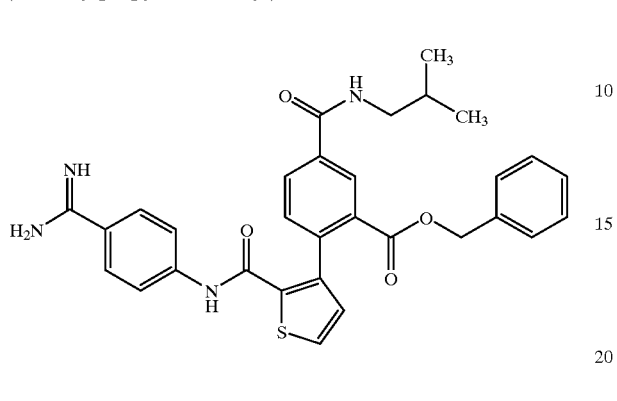

TLC:Rf 0.71 (Chloroform:Methanol:Acetic acid=10:2:1); NMR (300 MHz, DMSO-$d_6$): δ 8.35 (d, J=1.8 Hz, 1H), 8.01 (dd, J=8.0, 1.8 Hz, 1H), 7.70 (d, J=9.0 Hz, 2H), 7.67 (d, J=5.0 Hz, 1H), 7.60 (d, J=9.0 Hz, 2H), 7.49 (d, J=8.0 Hz, 1H), 7.29–7.17 (m, 5H), 7.06 (d, J=5.0 Hz, 1H), 5.12 (s, 2H), 3.20 (d, J=6.9 Hz, 2H), 2.00–1.86 (m, 1H), 0.96 (d, J=6.6 Hz, 6H).

EXAMPLE 40(30)

Benzyl 2'-(4-amidinophenylcarbamoyl)-4-[(1-methoxycarbonyl-1-methylethyl) carbamoyl]-2-biphenylcarboxylate

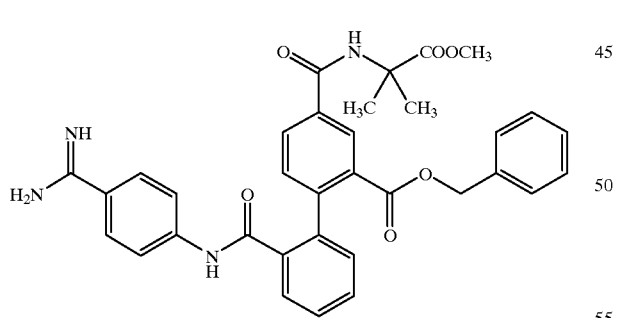

TLC:RF 0.40 (Chloroform:Ethyl acetate:Water=8:2:0.2); NMR (300 MHz, CD$_3$OD): δ 8.32 (d, J=2.0 Hz, 1H), 7.96 (dd, J=6.9, 2.0 Hz, 2H), 7.68–7.66 (m, 3H), 7.62–7.58 (m, 2H), 7.53–7.50 (m, 2H), 7.42 (d, J=7.8 Hz, 1H), 7.28–7.25 (m, 3H), 7.17–7.13 (m, 2H), 5.13 (s, 2H), 3.70 (s, 3H), 1.55 (s, 6H).

EXAMPLE 40(31)

Benzyl 2'-(4-amidinophenylcarbamoyl)-4-(1(S)-carboxy-3-methylbutyl carbamoyl)-2-biphenylcarboxylate

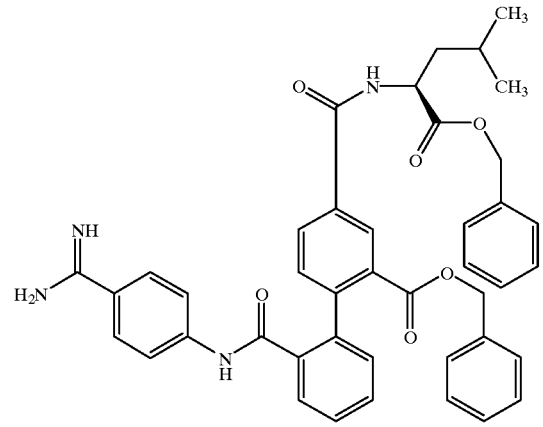

TLC:Rf 0.40 (Chloroform:Ethyl acetate:Water=8:2:0.2); NMR (300 MHz, DMSO-$d_6$): δ 10.64 (s, 1H), 9.12 (br, 1H), 9.01 (d, J=7.5 Hz, 1H), 8.87 (br, 1H), 8.29 (d, J=2.1 Hz, 1H), 8.07 (dd, J=8.1, 2.1 Hz, 1H), 7.78–7.59 (m, 4H), 7.59 (m, 1H), 7.55 (m, 1H), 7.44 (d, J=8.1 Hz, 1H), 7.35–7.23 (m, 6H), 7.07–7.03 (m, 2H), 5.14 (s, 2H), 5.05 (s, 2H), 4.54 (m, 1H), 1.84–1.50 (m, 3H), 0.92 (d, J=6.3 Hz, 3H), 0.87 (d, J=6.0 Hz, 3H).

EXAMPLE 40(32)

Benzyl 2-[2-(4-amidinophenylcarbamoyl)-3-pyridyl]-5-(2,2-dimethylpropyl carbamoyl)benzoate

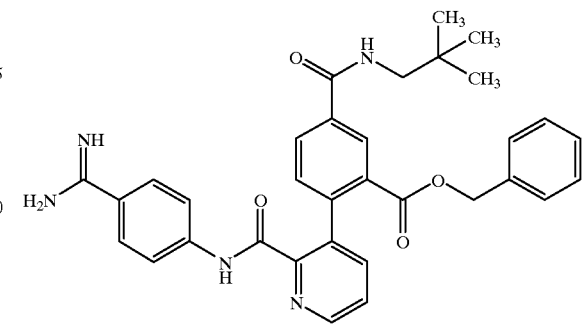

TLC:Rf 0.80 (Chloroform:Methanol:Acetic acid=10:2:1); NMR (d$_6$-DMSO): δ 10.98 (br.s, 1H), 9.11 (br.s, 3H), 8.71 (dd, J=4.5, 1.5 Hz, 1H), 8.65 (t, J=6.3 Hz, 1H), 8.42 (d, J=1.5 Hz, 1H), 8.11 (dd, J=8.0, 1.5 Hz, 1H), 7.93 (d, J=9.0 Hz, 2H), 7.78 (d, J=9.0 Hz, 2H), 7.85–7.75 (m, 1H), 7.68 (dd, J=8.0, 4.5 Hz, 1H), 7.39 (d, J=8.0 Hz, 1H), 7.25–7.15 (m, 3H), 7.15–7.05 (m, 2H), 5.03 (s, 2H), 3.14 (d, J=6.3 Hz, 2H), 0.91 (s, 9H).

EXAMPLE 40(33)

Benzyl 2-[2-(4-amidinophenylcarbamoyl)-6-methoxy-3-pyridyl]-5-(2,2-dimethylpropylcarbamoyl)benzoate

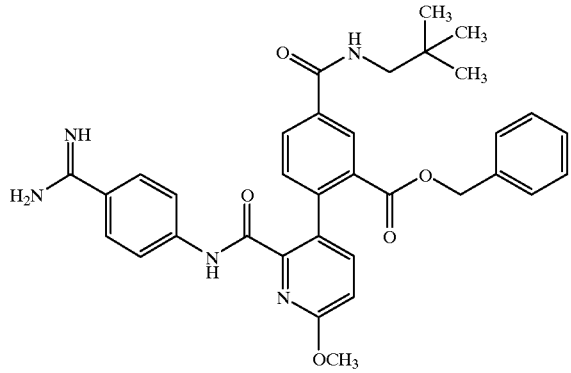

TLC:Rf 0.72 (Chloroform:Methanol:Acetic acid=10:2:1); NMR (300 MHz, DMSO-$d_6$): δ 8.50 (d, J=2.0 Hz, 1H), 8.01 (dd, J=8.0, 2.0 Hz, 1H), 7.83 (d, J=9.3 Hz, 2H), 7.77 (d, J=9.3 Hz, 2H), 7.55 (d, J=8.3 Hz, 1H), 7.32 (d, J=8.0 Hz, 1H), 7.26–7.16 (m, 3H), 7.10–7.05 (m, 2H), 6.98 (d, J=8.3 Hz, 1H), 5.07 (brd, J=12 Hz, 1H), 4.98 (brd, J=12 Hz, 1H), 4.06 (s, 3H), 3.25 (s, 2H), 0.99 (s, 9H).

EXAMPLE 40(34)

Benzyl 2'-(4-amidinophenylcarbamoyl)-4-(2,2-dimethyl-1(S)-cyclopentyl carbamoyl)-2-biphenylcarboxylate

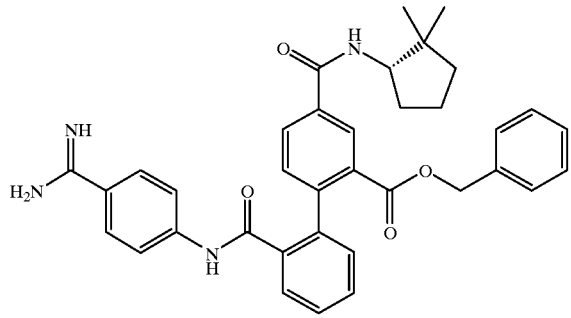

TLC:Rf 0.5 (Chloroform:Methanol:Acetic acid=10:2:1); NMR (300 MHz, $CD_3OD$): δ 8.28 (d, J=1.8 Hz, 1H), 7.95 (dd, J=7.8, 1.8 Hz, 1H), 7.70–7.58 (m, 5H), 7.53 (td, J=6.0, 1.8 Hz, 1H), 7.50 (td, J=6.0, 1.8 Hz, 1H), 7.41 (d, J=7.8 Hz, 1H), 7.30–7.22 (m, 4H), 7.18–7.12 (m, 2H), 5.12 (s, 2H), 4.17 (q, J=7.8 Hz, 1H), 2.08–1.98 (m, 1H), 1.80–1.52 (m, 5H), 1.05 (s, 3H), 0.93 (s, 3H).

EXAMPLE 40(35)

Benzyl 2–3-(4-amidinophenylcarbamoyl)-2-thienyl-5-(2,2-dimethylpropyl carbamoyl)benzoate

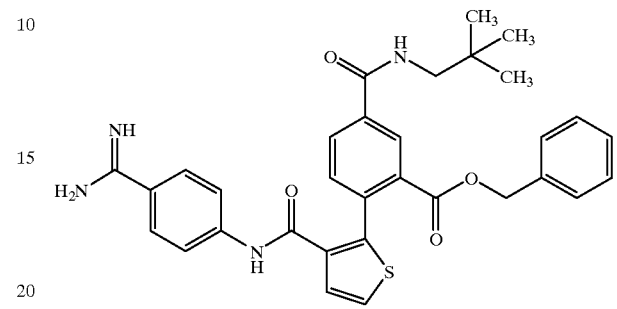

TLC:Rf 0.51 (Chloroform:Methanol:Acetic acid=10:2:1); NMR (300 MHz, $d_6$-DMSO): δ 10.38 (s, 1H), 9.3–8.9 (br, 3H), 8.65 (br.t, J=6.3 Hz, 1H), 8.29 (d, J=1.8 Hz, 1H), 8.06 (dd, J=8.1, 1.8 Hz, 1H), 7.83 (d, J=9.0 Hz, 2H), 7.77 (d, J=9.0 Hz, 2H), 7.73 (d, J=5.4 Hz, 1H), 7.68 (d, J=5.4 Hz, 1H), 7.54 (d, J=8.1 Hz, 1H), 7.3–7.2 (m, 3H), 7.2–7.1 (m, 2H), 5.06 (s, 2H), 3.12 (d, J=6.3 Hz, 2H), 0.90 (s, 9H).

EXAMPLE 40(36)

Benzyl 2-[2-(4-amidinophenylcarbamoyl)-3-thienyl]-5-(2,2-dimethylpropyl carbamoyl)benzoate

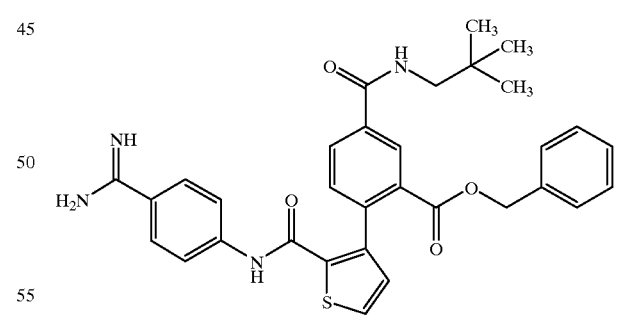

TLC:Rf 0.44 (Chloroform:Methanol:Acetic acid=10:2:1); NMR (200 MHz, $d_6$-DMSO): δ 10.29 (s, 1H), 9.07 (br.s, 3H), 8.59 (br.t, J=6.2 Hz, 1H), 8.28 (d, J=1.8 Hz, 1H), 8.06 (dd, J=8.0, 1.8 Hz, 1H), 7.85 (d, J=5.2 Hz, 1H), 7.77 (d, J=9.6 Hz, 2H), 7.71 (d, J=9.6 Hz, 2H), 7.47 (d, J=8.0 Hz, 1H), 7.3–7.2 (m, 3H), 7.2–7.1 (m, 2H), 7.15 (d, J=5.2 Hz, 1H), 5.08 (s, 2H), 3.11 (d, J=6.2 Hz, 2H), 0.89 (s, 9H).

EXAMPLE 40(37)

Benzyl 2-[4-(4-amidinophenylcarbamoyl)-3-pyridyl]-5-(2,2-dimethylpropyl carbamoyl)benzoate

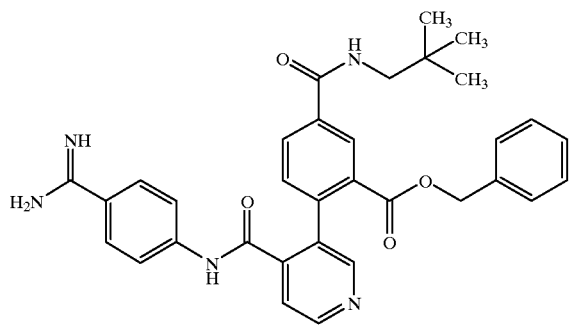

TLC:Rf 0.60 (Chloroform:Ethyl acetate:Water=7:3:0.3); NMR (200 MHz, DMSO-$d_6$): δ 10.94 (brs, 1H), 9.24 (br, 2H), 9.02 (br, 2H), 8.76 (d, J=4.4 Hz, 1H), 8.16–8.57 (m, 2H), 8.35 (s, 1H), 8.10 (d, J=7.4 Hz, 1H), 7.77 (s, 3H), 7.69 (d, J=4.4 Hz, 1H), 7.49 (d, J=8.0 Hz, 1H), 7.28 (m; 3H), 7.13 (m, 2H), 5.07 (s, 2H), 4.11 (d, J=5.0 Hz, 1H), 3.17 (d, J=4.8 Hz, 2H), 0.90 (s, 9H).

EXAMPLE 40(38)

Benzyl 2-[2-(4-benzyloxycarbonylamidinophenylcarbamoyl)-5-methyl-3-thienyl]-5-(2,2-dimethylpropylcarbamoyl)benzoate

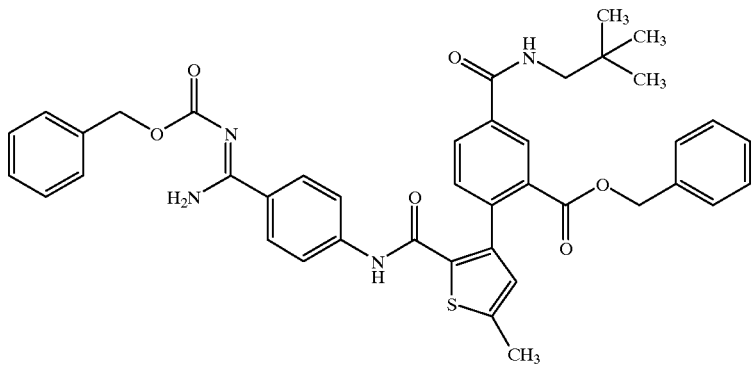

TLC:Rf 0.62 (Chloroform:Methanol=10:1); NMR (300 MHz, CDCl$_3$): δ 10.0–9.20 (br, 1H), 8.35 (d, J=1.8 Hz, 1H), 7.95 (dd, J=8.0, 1.8 Hz, 1H), 7.71 (d, J=9.0 Hz, 2H), 7.60 (s, 1H), 7.45–7.40 (m, 3H), 7.40–7.25 (m, 7H), 7.25–7.15 (m, 3H), 6.53 (s, 1H), 6.60–6.00 (br, 1H), 6.28 (br.t, J=6.0 Hz, 1H), 5.20 (s, 2H), 5.18 (s, 2H), 3.30 (d, J=6.0 Hz, 2H), 2.47 (s, 3H), 0.99 (s, 9H).

EXAMPLE 40(39)

Benzyl 2'-(4-amidinophenylcarbamoyl)-4'-nitro-4-(2,2-dimethylpropyl carbamoyl)-2-biphenylcarboxylate

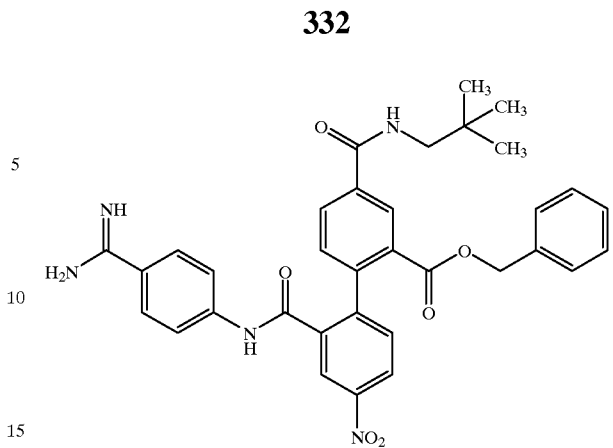

TLC:Rf 0.40 (Chloroform:Methanol:Water=8:2:0.2); NMR (300 MHz, CD$_3$OD): δ 8.45 (d, J=2.0 Hz, 1H), 8.37 (d, J=2.0 Hz, 1H), 8.23 (dd, J=8.0,2.0 Hz, 1H), 8.02 (dd, J=8.0,2.0 Hz, 1H), 7.72 (d, J=9.0 Hz, 2H), 7.68 (d, J=9.0 Hz, 2H), 7.48 (d, J=8.0 Hz, 1H), 7.43 (d, J=8.0 Hz, 1H), 7.23–7.19 (m, 3H), 7.14–7.11 (m, 2H), 5.10 (d, J=12.0 Hz, 1H), 5.05 (d, J=12.0 Hz, 1H), 3.22 (s, 2H), 0.97 (s, 9H).

EXAMPLE 40(40)

Benzyl 2-[2-(4-amidinophenylcarbamoyl)-5-methyl-3-furyl]-5-(2,2-dimethylpropylcarbamoyl)benzoate

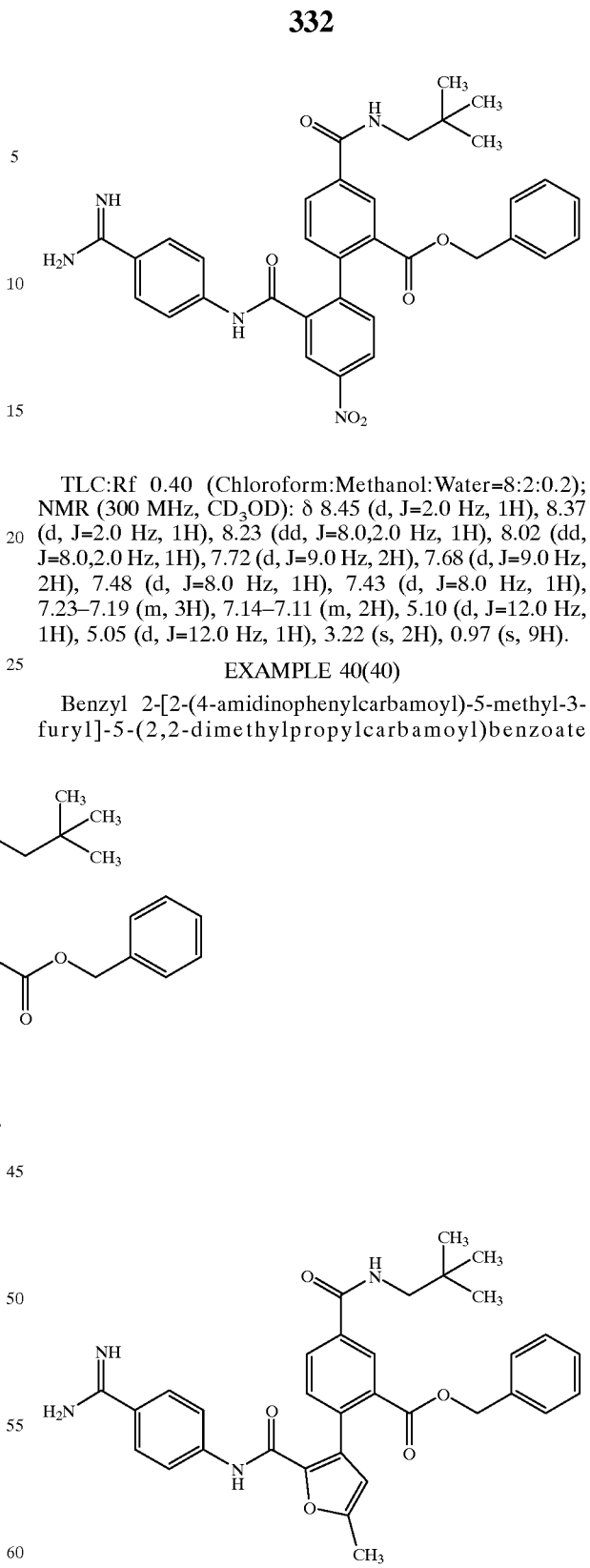

TLC:Rf 0.61 (Chloroform:Methanol:Acetic acid=10:2:1); NMR (200 MHz, d$_6$-DMSO): δ 13.38 (br.s, 1H), 9.09 (br.s, 3H), 8.60 (t, J=6.2 Hz, 1H), 8.34 (d, J=1.6 Hz, 1H), 8.03 (dd, J=8.0, 1.6 Hz, 1H), 7.92 (d, J=8.8 Hz, 2H), 7.78 (d, J=8.8 Hz, 2H), 7.48 (d, J=8.0 Hz, 1H), 7.4–7.2 (m, 5H), 6.42 (s, 1H), 5.11 (s, 2H), 3.13 (d, J=6.2 Hz, 2H), 2.42 (s, 3H), 0.91 (s, 9H).

EXAMPLE 40(41)

Benzyl 2-[4-(4-amidinophenylcarbamoyl)-2-methyl-pyrimidin-5-yl]-5-(2,2-dimethylpropylcarbamoyl)benzoate

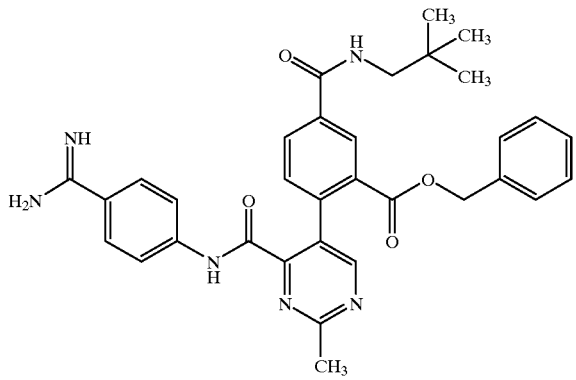

TLC:Rf 0.71 (Chloroform:Methanol:Acetic acid=10:2:1); NMR (300 MHz, CD$_3$OD): δ 8.64 (s, 1H), 8.57 (d, J=2.0 Hz, 1H), 8.08 (dd, J=8.0,2.0 Hz, 1H), 7.89 (d, J=9.0 Hz, 2H), 7.78 (d, J=9.0 Hz, 2H), 7.40 (d, J=8.0 Hz, 1H), 7.28–7.19 (m, 3H), 7.16–7.10 (m, 2H), 5.08 (brd, J=12 Hz, 1H), 5.02 (brd, J=12 Hz, 1H), 3.25 (s, 2H), 2.80 (s, 3H), 0.99 (s, 9H).

EXAMPLE 40(42)

Benzyl 2-[2-(4-amidinophenylcarbamoyl)-6-methyl-3-pyridyl]-5-(1(S)-morpholinocarbonyl-3-methylbutylcarbamoyl)benzoate

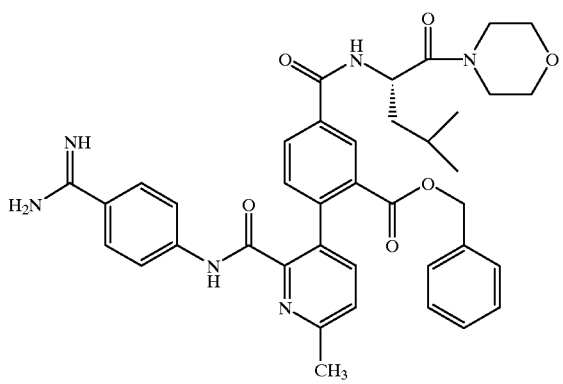

TLC:Rf 0.53 (Chloroform:Methanol:Acetic acid= 10:1:0.2); NMR (200 MHz, CD$_3$OD): δ 8.54 (d, J=1.8 Hz, 1H), 8.07 (dd, J=8.2, 1.8 Hz, 1H), 7.85 (d, J=9.0 Hz, 2H), 7.76 (d, J=9.0 Hz, 2H), 7.56 (d, J=8.2 Hz, 1H), 7.43 (d, J=8.2 Hz, 1H), 7.33 (d, J=8.2 Hz, 1H), 7.25–7.15 (m, 3H), 7.20–7.10 (m, 2H), 5.13 (dd, J=12.0, 4.8 Hz, 1H), 5.01 (like d, 2H), 3.9–3.6 (m, 6H), 3.60–3.40 (m, 2H), 2.64 (s, 3H), 1.90–1.70 (m, 2H), 1.70–1.50 (m, 1H), 1.01 (d, J=6.2 Hz, 3H), 1.00 (d, J=6.2 Hz, 3H).

EXAMPLE 40(43)

Benzyl 2-[2-(4-amidinophenylcarbamoyl)-6-methyl-3-pyridyl]-5-(1(S)-methoxymethyl-2,2-dimethylpropylcarbamoyl)benzoate

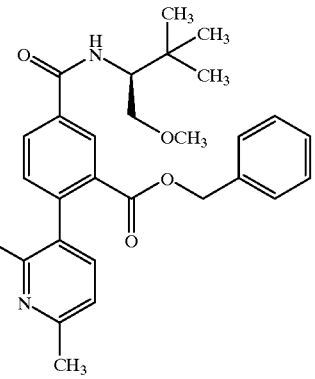

TLC:Rf 0.50 (Chloroform:Methanol:Water=8:2:0.1); NMR (200 MHz, CD$_3$OD): δ 8.50 (d, J=1.8 Hz, 1H), 8.03 (dd, J=8.2, 1.8 Hz, 1H), 7.85 (d, J=8.6 Hz, 2H), 7.76 (d, J=8.6 Hz, 2H), 7.56 (d, J=8.0 Hz, 1H), 7.43 (d, J=8.0 Hz, 1H), 7.33 (d, J=8.0 Hz, 1H), 7.26–7.16 (m, 3H), 7.09–7.04 (m, 2H), 5.01 (d, J=3.2 Hz, 2H), 4.20 (dd, J=9.2, 4.0 Hz, 1H), 3.72–3.50 (m, 2H), 3.34 (s, 3H), 2.64 (s, 3H), 1.02 (s, 9H).

EXAMPLE 40(44)

Benzyl 2-[2-(4-amidinophenylcarbamoyl)-6-methoxy-3-pyridyl]-5-(1(S)-methoxymethyl-2,2-dimethylpropylcarbamoyl)benzoate

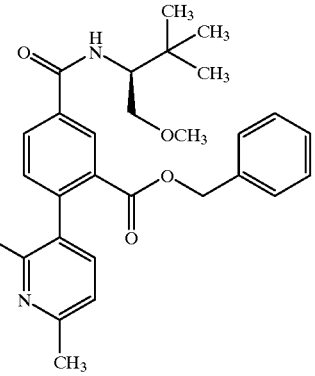

TLC:Rf 0.45 (Chloroform:Methanol:Water=8:2:0.1); NMR (200 MHz, CD$_3$OD): δ 8.49 (d, J=2.2 Hz, 1H), 8.01 (dd, J=8.0, 2.2 Hz, 1H), 7.84 (d, J=9.6 Hz, 2H), 7.76 (d, J=9.6 Hz, 2H), 7.56 (d, J=8.4 Hz, 1H), 7.32 (d, J=8.2 Hz, 1H), 7.26–7.14 (m, 3H), 7.11–7.06 (m, 2H), 6.99 (d, J=8.6 Hz, 1H), 5.03 (d, J=8.8 Hz, 2H), 4.21 (dd, J=8.8, 3.6 Hz, 1H), 3.68 (dd, J=10.4, 4.2 Hz, 1H), 3.61–3.51 (m, 1H), 3.34 (s, 3H), 1.02 (s, 9H).

EXAMPLE 40(45)

Benzyl 2-[2-(4-amidinophenylcarbamoyl)-6-methyl-3-pyridyl]-5-(2,2-dimethylpropylcarbamoyl)benzoate

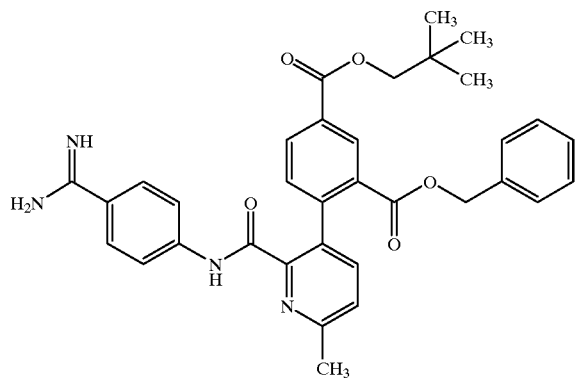

TLC:Rf 0.38 (Chloroform:Methanol:Water=9:1:0.1); NMR (200 MHz, CD$_3$OD): δ 8.72 (d, J=2.0 Hz, 1H), 8.23 (dd, J=8.2, 2.0 Hz, 1H), 7.87 (dt, J=9.2, 2.0 Hz, 2H), 7.78 (dt, J=9.2,2.0H, 2H), 7.56 (d, J=8.2, 2.0 Hz, 1H), 7.44 (d, J=8.2 Hz, 1H), 7.37 (d, J=8.2 Hz, 1H), 7.26–7.16 (m, 3H), 7.10–7.06 (m, 2H), 4.98 (d, J=11.2 Hz, 1H), 4.94 (d, J=11.2 Hz, 1H), 4.08 (s, 2H), 2.66 (s, 3H), 1.07 (s, 9H).

EXAMPLE 40(46)

Benzyl 2-[2-(4-amidino-3-fluorophenylcarbamoyl)-6-methyl-3-pyridyl]-5-(2,2-dimethylpropylcarbamoyl)benzoate

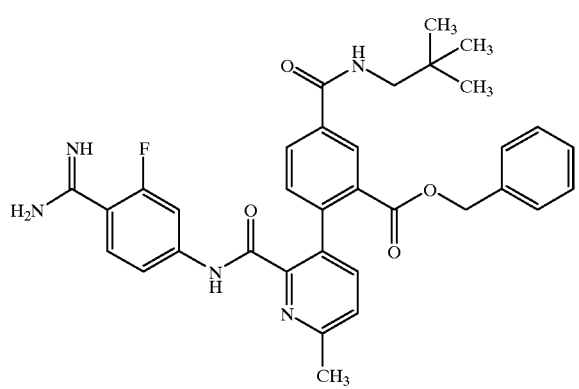

TLC:Rf 0.37 (Chloroform:Methanol:Water=8:2:0.1); NMR (300 MHz, d$_6$-DMSO): δ 9.22 (br s, 3H), 8.63 (t, J=6.3 Hz, 1H), 8.40 (d, J=1.8 Hz, 1H), 8.09 (dd, J=7.8, 1.8 Hz, 1H), 7.82 (dd, J=13.5, 1.8 Hz, 1H), 7.72–7.60 (m, 3H), 7.52 (d, J=8.1 Hz, 1H), 7.36 (d, J=8.1 Hz, 1H), 7.28–7.20 (m, 3H), 7.12–7.08 (m, 2H), 5.03 (s, 2H), 3.13 (d, J=6.3 Hz, 2H), 2.64 (s, 3H), 0.91 (s, 9H).

EXAMPLE 40(47)

Dibenzyl 4-[2-(4-amidinophenylcarbamoyl)-6-methyl-3-pyridyl]isophthalate

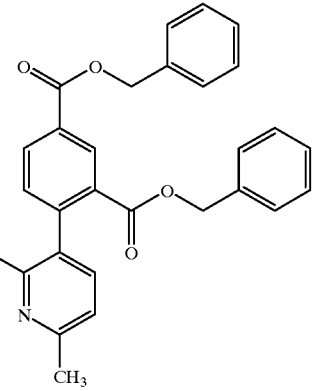

TLC:Rf 0.50 (Chloroform:Methanol:Water=10:2:0.5); NMR (200 MHz, CD$_3$OD): δ 8.67 (d, J=1.8 Hz, 1H), 8.18 (dd, J=7.6, 1.8 Hz, 1H), 7.83–7.72 (m, 4H), 7.50–7.29 (m, 9H), 7.20–7.17 (m, 2H), 7.04–6.98 (m, 2H), 5.38 (s, 2H), 4.97 (d, J=4.0 Hz, 2H), 2.62 (s, 3H).

EXAMPLE 40(48)

Benzyl 2'-(4-amidinophenylcarbamoyl)-5'-benzyloxycarbonylamino-4-(2,2-dimethylpropylcarbamoyl)-2-biphenylcarboxylate

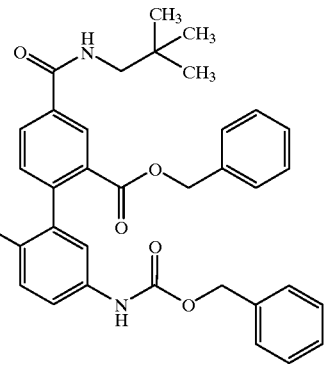

TLC:RF 0.29 (Chloroform:Methanol:Water=8:2:0.2); NMR (200 MHz, CD$_3$OD): δ 8.32 (d, J=2.0 Hz, 1H), 7.96 (dd, J=8.0,2.0 Hz, 1H), 7.70–7.58 (m, 6H), 7.46–7.35 (m, 6H), 7.23–7.10 (m, 6H), 5.21 (s, 2H), 5.13 (s, 2H), 3.21 (s, 2H), 0.96 (s, 9H).

EXAMPLE 40(49)

Benzyl 2-[2-(4-amidinophenylcarbamoyl)-6-methyl-3-pyridyl]-5-(1,1,3,3-tetramethylbutylcarbamoyl)benzoate

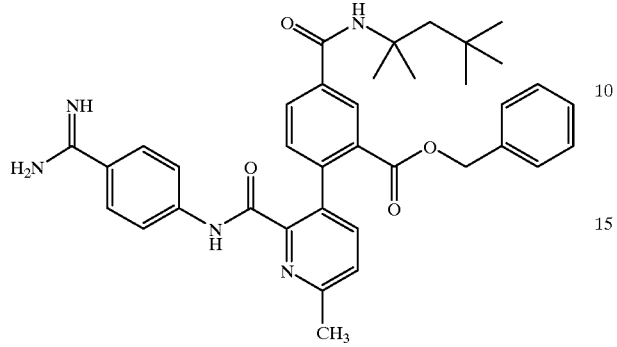

TLC:Rf 0.64 (Chloroform:Methanol:Acetic acid=10:2:1); NMR (300 MHz, CD$_3$OD): δ 8.40 (d, J=1.8 Hz, 1H), 7.92 (dd, J=8.0, 1.8 Hz, 1H), 7.84 (d, J=9.0 Hz, 2H), 7.76 (d, J=9.0 Hz, 2H), 7.54 (d, J=8.0 Hz, 1H), 7.43 (d, J=8.0 Hz, 1H), 7.29 (d, J=8.0 Hz, 1H), 7.25–7.16 (m, 3H), 7.10–7.04 (m, 2H), 5.04 (brd, J=12 Hz, 1H), 4.97 (brd, J=12 Hz, 1H), 2.64 (s, 3H), 2.00 (s, 2H), 1.51 (s, 6H), 1.05 (s, 9H).

EXAMPLE 40(50)

Benzyl 2-[2-(4-amidinophenylcarbamoyl)-5-methyl-3-pyridyl]-5-(2,2-dimethyl propylcarbamoyl)benzoate

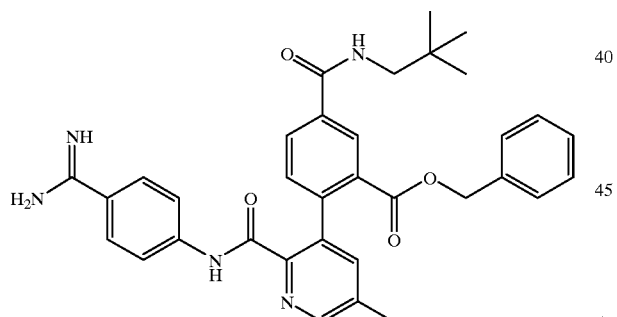

TLC:Rf 0.29 (Chloroform:Methanol:Water=8:2:0.2) NMR (200 MHz, CD$_3$OD): δ 8.54 (d, J=2.0 Hz, 1H), 8.44 (d, J=2.0 Hz, 1H), 8.05 (dd, J=8.0,2.0 Hz, 1H), 7.85 (d, J=9.0 Hz, 2H), 7.75 (d, J=9.0 Hz, 2H), 7.49 (d, J=2.0 Hz, 1H), 7.34 (d, J=8.0 Hz, 1H), 7.24–7.18 (m, 3H), 7.11–7.06 (m, 2H), 5.03 (s, 2H), 3.27 (s, 2H), 2.41 (s, 3H), 1.00 (s, 9H).

EXAMPLE 40(51)

Benzyl 2-[2-(4-amidinophenylcarbamoyl)-6-methoxy-3-pyridyl]-5-[[5-(1-methylethyl)-2,2-dimethyldioxan-5-yl]carbamoyl]benzoate

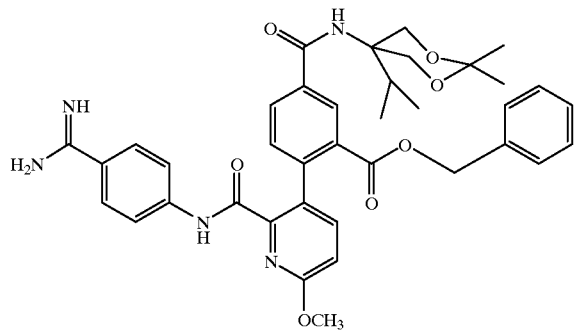

TLC:Rf 0.75 (Chloroform:Methanol:Acetic acid=10:2:1); NMR (300 MHz, CD$_3$OD): δ 8.47 (d, J=1.8 Hz, 1H), 7.98 (dd, J=7.8, 1.8 Hz, 1H), 7.85–7.75 (m, 4H), 7.55 (d, J=8.1 Hz, 1H), 7.31 (d, J=8.1 Hz, 1H), 7.23–7.20 (m, 3H), 7.07 (d, J=7.5 Hz, 1H), 7.07 (d, J=8.4 Hz, 1H), 7.00 (d, J=8.7 Hz, 1H), 5.02 (d, J=13.4 Hz, 2H), 4.23 (d, J=12.0 Hz, 2H), 4.07 (d, J=12.0 Hz, 2H), 4.06 (s, 3H), 2.50 (m, 1H), 1.44 (s, 3H), 1.37 (s, 3H), 1.02 (d, J=7.2 Hz, 6H).

EXAMPLE 40(52)

Benzyl 2-[2-(4-amidinophenylcarbamoyl)-6-methoxy-3-pyridyl]-5-[1(S)-(4-ethoxycarbonyloxazol-2-yl)-3-methylbutyl)carbamoyl]benzoate

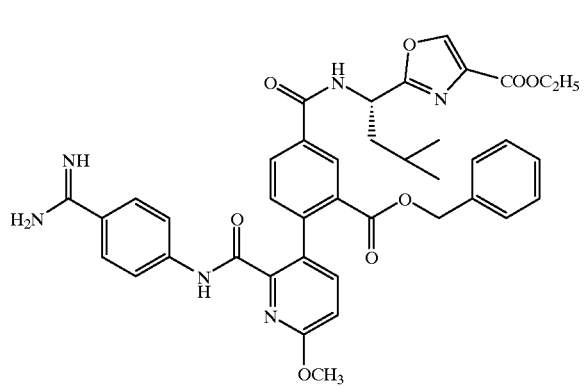

TLC:Rf 0.86 (Chloroform:Methanol:Acetic acid=10:2:1); NMR (300 MHz, CD$_3$OD): δ 8.55 (d, J=2.0 Hz, 1H), 8.50 (s, 1H), 8.07 (dd, J=8.0, 2.0 Hz, 1H), 7.83 (d, J=9.0 Hz, 2H), 7.77 (d, J=9.0 Hz, 2H), 7.55 (d, J=8.4 Hz, 1H), 7.33 (d, J=8.0 Hz, 1H), 7.26–7.16 (m, 3H), 7.10–7.05 (m, 2H), 6.99 (d, J=8.4 Hz, 1H), 5.45 (dd, J=9.6, 6.3 Hz, 1H), 5.02 (brd, J=12 Hz, 1H), 4.97 (brd, J=12 Hz, 1H), 4.34 (q, J=7.2 Hz, 2H), 4.06 (s, 3H), 2.07–1.87 (m, 2H), 1.83–1.68 (m, 1H), 1.35 (t, J=7.2 Hz, 3H), 1.03 (d, J=6.6 Hz, 3H), 1.01 (d, J=6.3 Hz, 3H).

EXAMPLE 40(53)

Benzyl 2-[2-(4-amidinophenylcarbamoyl)-6-methoxy-3-pyridyl]-5-[(1(S)-N-benzyloxycarbamoyl)-3-methylbutylcarbamoyl]benzoate

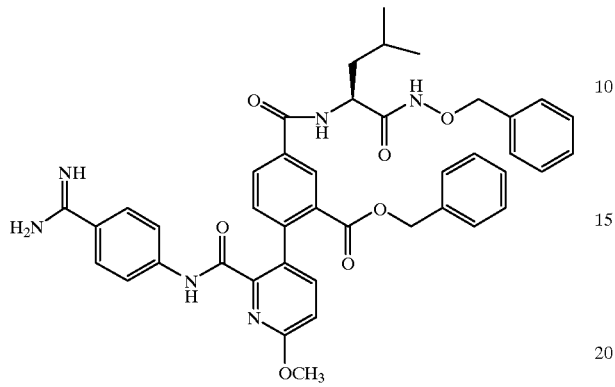

TLC:Rf 0.58 (Chloroform:Methanol:Water=8:2:0.2); NMR (300 MHz, DMSO-d$_6$): δ 10.55 (s, 1H), 9.10 (br, 3H), 8.81 (d, J=7.2 Hz, 1H), 8.45 (dd, J=8.1, 1.5 Hz, 1H), 7.90 (d, J=9.0 Hz, 2H), 7.81 (d, J=9.0 Hz, 2H), 7.66 (d, J=8.4 Hz, 1H), 7.39–7.34 (m, 5H), 7.27–7.19 (m, 3H), 7.12–7.06 (m, 3H), 5.05 (s, 2H), 4.80 (s, 2H), 4.43 (m, 1H), 4.08 (s, 3H), 1.80–1.60 (m, 2H), 1.49 (m, 1H), 0.90 (d, J=6.3 Hz, 3H), 0.87 (d, J=6.6 Hz, 3H).

EXAMPLE 40(54)

Benzyl 2-[2-(4-amidinophenylcarbamoyl)-6-methoxy-3-pyridyl]-5-(2,2-dimethyl propylcarbamoyl)-4-methylbenzoate

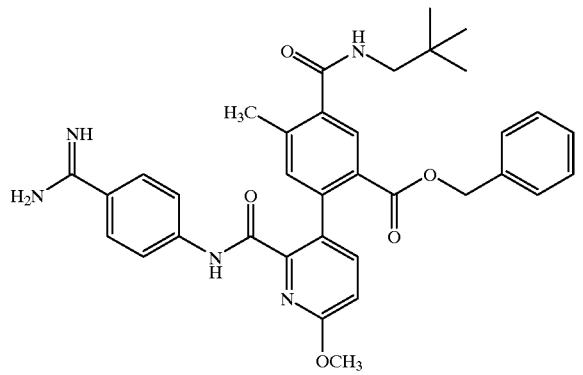

TLC:Rf 0.47 (Chloroform:Methanol:Water=8:2:0.2); NMR (200 MHz, CD$_3$OD): δ 8.05 (s, 1H), 7.84 (d, J=9.0 Hz, 2H), 7.77 (d, J=9.0 Hz, 2H), 7.52 (d, J=8.4 Hz, 1H), 7.26–7.17 (m, 3H)., 7.12 (s, 1H), 7.09–7.04 (m, 2H), 6.98 (d, J=8.4 Hz, 1H), 5.04 (d, J=12.0 Hz, 1H), 4.95 (d, J=12.0 Hz, 1H), 4.06 (s, 3H), 3.23 (s, 2H), 2.46 (s, 3H), 1.01 (s, 9H).

EXAMPLE 40(55)

Dibenzyl 4-[2-(4-amidinophenylcarbamoyl)-6-methoxy-3-pyridyl]isophthalate

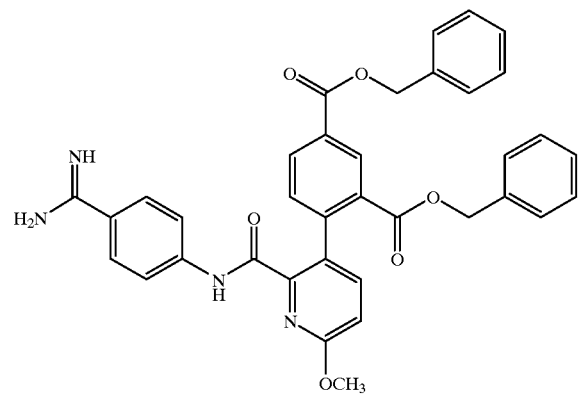

TLC:Rf 0.17 (Chloroform:Methanol:Water=9:1:0.1); NMR (200 MHz, CD$_3$OD): δ 8.07 (d, J=1.8 Hz, 1H), 8.23 (dd, J=8.0, 1.8 Hz, 1H), 7.84 (d, J=9.4 Hz, 2H), 7.77 (d, J=9.4 Hz, 2H), 7.54 (d, J=8.4 Hz, 1H), 7.50–7.32 (m, 5H), 7.26–7.14 (m, 3H), 7.09–7.04 (m, 2H), 6.99 (d, J=8.4 Hz, 1H), 5.42 (s, 2H), 5.05 (m, 1H), 5.00 (m, 1H), 4.07 (s, 3H).

EXAMPLE 40(56)

Benzyl 2-[2-(4-amidinophenylcarbamoyl)-6-methoxy-3-pyridyl]-5-(1(S)-hydroxymethyl-3-methylbutylcarbamoyl)-4-methylbenzoate TLC:Rf 0.58 (Chloroform:Methanol:Acetic acid=10:2:1); NMR (300 MHz, CD$_3$OD): δ 8.51 (d, J=1.8 Hz, 1H), 8.03 (dd, J=8.0, 1.8 Hz, 1H), 7.83 (d, J=9.0 Hz, 2H), 7.77 (d, J=9.0 Hz, 2H), 7.55 (d, J=8.4 Hz, 1H), 7.31 (d, J=8.0 Hz, 1H), 7.25–7.16 (m, 3H), 7.12–7.05 (m, 2H), 6.99 (d, J=8.4 Hz, 1H), 5.07 (brd, J=12 Hz, 1H), 4.98 (brd, J=12 Hz, 1H), 4.32–4.22 (m, 1H), 4.06 (s, 3H), 3.61 (d, J=5.7 Hz, 2H), 1.80–1.65 (m, 1H), 1.65–1.40 (m, 2H), 0.98 (d, J=6.6 Hz, 6H).

EXAMPLE 40(57)

Benzyl 2-[2-(4-amidinophenylcarbamoyl)-6-methoxy-3-pyridyl]-5-[(4,4-dimethyloxolan-3(S)-yl)carbamoyl]-4-methylbenzoate

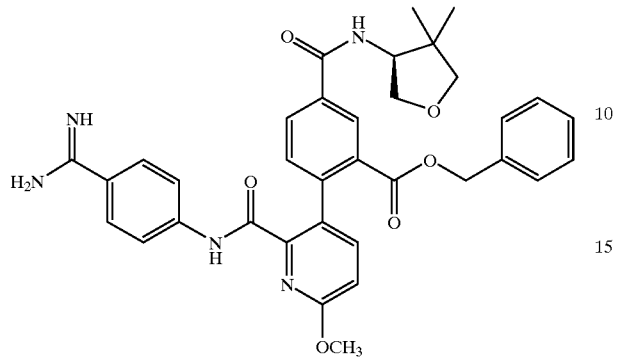

TLC:Rf 0.70 (Chloroform:Methanol:Acetic acid=10:2:1); NMR (300 MHz, CD$_3$OD): δ 8.50 (d, J=1.8 Hz, 1H), 8.02 (dd, J=8.0, 1.8 Hz, 1H), 7.83 (d, J=9.0 Hz, 2H), 7.77 (d, J=9.0 Hz, 2H), 7.55 (d, J=8.4 Hz, 1H), 7.33 (d, J=8.0 Hz, 1H), 7.24–7.17 (m, 3H), 7.12–7.05 (m, 2H), 6.99 (d, J=8.4 Hz, 1H), 5.07 (brd, J=12 Hz, 1H), 4.98 (brd, J=12 Hz, 1H), 4.48 (dd, J=7.5, 5.4 Hz, 1H), 4.23 (dd, J=9.3, 7.5 Hz, 1H), 4.06 (s, 3H), 3.77 (dd, J=9.3, 5.4 Hz, 1H), 3.64 (d, J=8.4 Hz, 1H), 3.59 (d, J=8.4 Hz, 1H), 1.21 (s, 3H), 1.08 (s, 3H).

EXAMPLE 40(58)

Benzyl 2-[2-(4-amidinophenylcarbamoyl)-6-methoxy-3-pyridyl]-5-(1(R), 2,2-trimethylpropylcarbamoyl)benzoate

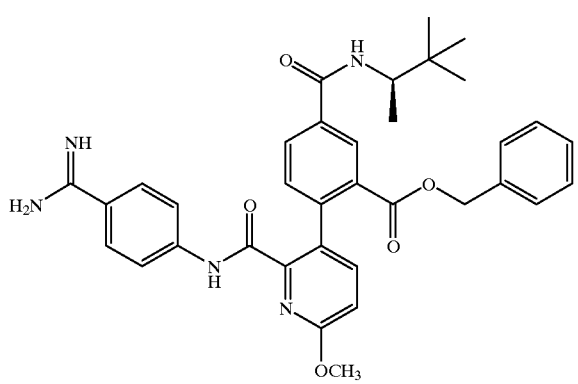

TLC:Rf 0.65 (Chloroform:Methanol:Acetic acid=10:2:1); NMR (300 MHz, CD$_3$OD): δ 8.46 (d, J=1.8 Hz, 1H), 7.99 (dd, J=8.0, 1.8 Hz, 1H), 7.83 (d, J=9.0 Hz, 2H), 7.77 (d, J=9.0 Hz, 2H), 7.55 (d, J=8.4 Hz, 1H), 7.31 (d, J=8.0 Hz, 1H), 7.25–7.16 (m, 3H), 7.10–7.06 (m, 2H), 6.99 (d, J=8.4 Hz, 1H), 5.07 (brd, J=12 Hz, 1H), 4.98 (brd, J=12 Hz, 1H), 4.10 (q, J=7.0 Hz, 1H), 4.06 (s, 3H), 1.20 (d, J=7.0 Hz, 3H), 1.00 (s, 9H).

EXAMPLE 40(59)

Benzyl 2-[2-(4-amidinophenylcarbamoyl)-6-methoxy-3-pyridyl]-5-[(1(R)- 2,2-dimethylcyclopentyl)carbamoyl]benzoate

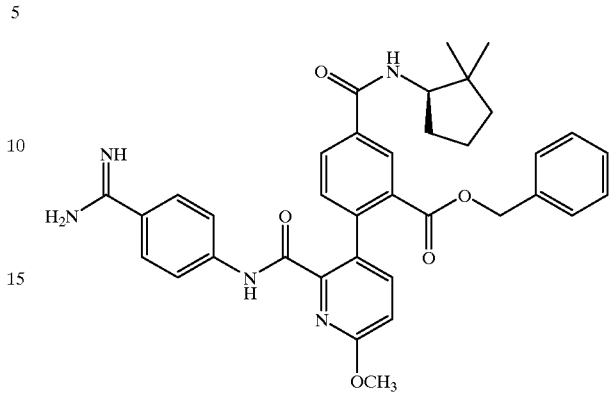

TLC:Rf 0.70 (Chloroform:Methanol:Acetic acid=10:2:1); NMR (300 MHz, CD$_3$OD): δ 8.48 (d, J=1.8 Hz, 1H), 8.00 (dd, J=8.0, 1.8 Hz, 1H), 7.83 (d, J=9.0 Hz, 2H), 7.77 (d, J=9.0 Hz, 2H), 7.54 (d, J=8.4 Hz, 1H), 7.31 (d, J=8.0 Hz, 1H), 7.26–7.16 (m, 3H), 7.10–7.05 (m, 2H), 6.98 (d, J=8.4 Hz, 1H), 5.07 (brd, J=12 Hz, 1H), 4.98 (brd, J=12 Hz, 1H), 4.21 (brt, J=7.0 Hz, 1H), 4.06 (s, 3H), 2.15–2.03 (m, 1H), 1.84–1.54 (m, 5H), 1.09 (s, 3H), 0.98 (s, 3H).

EXAMPLE 40(60)

Benzyl 2-[2-(4-amidinophenylcarbamoyl)-6-methoxy-3-pyridyl]-5-[(1(S)-methylaminomethyl-3-methylbutyl)carbamoyl]benzoate dihydrochloride

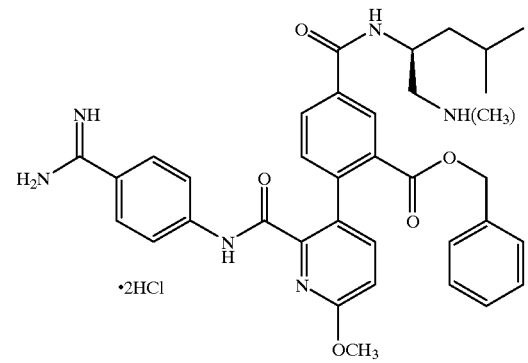

TLC:Rf 0.38 (Chloroform:Methanol:Acetic acid=10:2:1); NMR (300 MHz, CD$_3$OD): δ 8.60 (d, J=1.8 Hz, 1H), 8.12 (dd, J=8.2, 1.8 Hz, 1H), 7.78 (d, J=9.1 Hz, 2H), 7.55 (d, J=8.4 Hz, 1H), 7.36 (d, J=8.2 Hz, 1H), 7.24–7.18 (m, 3H), 7.10–7.05 (m, 2H), 7.01 (d, J=8.4 Hz, 1H), 5.04 (d, J=8.2 Hz, 1H), 2H), 4.54 (m, 1H), 4.07 (s, 3H), 2.76 (s, 3H), 1.80–1.64 (m, 2H), 1.40 (m, 1H), 1.01 (d, J=6.3 Hz, 3H), 0.99 (d, J=6.6 Hz, 3H).

EXAMPLE 40(61)

Benzyl 2-[2-(4-amidinophenylcarbamoyl)-6-methoxy-3-pyridyl]-5-[(4,4-dimethyl-2-oxooxolan-3(S)-yl)carbamoyl]benzoate

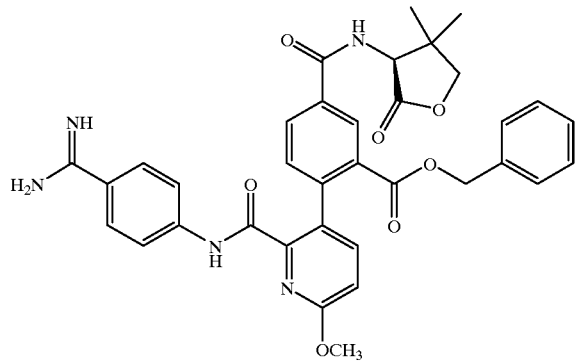

TLC:Rf 0.70 (Chloroform:Methanol:Acetic acid=10:2:1); NMR (300 MHz, CD$_3$OD): δ 8.57 (d, J=1.8 Hz, 1H), 8.09 (dd, J=8.0, 1.8 Hz, 1H), 7.83 (d, J=9.0 Hz, 2H), 7.77 (d, J=9.0 Hz, 2H), 7.56 (d, J=8.4 Hz, 1H), 7.35 (d, J=8.0 Hz, 1H), 7.28–7.17 (m, 3H), 7.10–7.04 (m, 2H), 6.99 (d, J=8.4 Hz, 1H), 5.07 (brd, J=12 Hz, 1H), 5.00 (s, 1H), 4.99 (brd, J=12 Hz, 1H), 4.19 (d, J=9.0 Hz, 1H), 4.14 (d, J=9.0 Hz, 1H), 1.27 (s, 3H), 1.12 (s, 3H).

EXAMPLE 40(62)

Benzyl 2-[2-(4-amidinophenylcarbamoyl) -3-thienyl]-5-[(1(S) -acetyloxymethyl- 2,2-dimethylpropyl)carbamoyl]benzoate

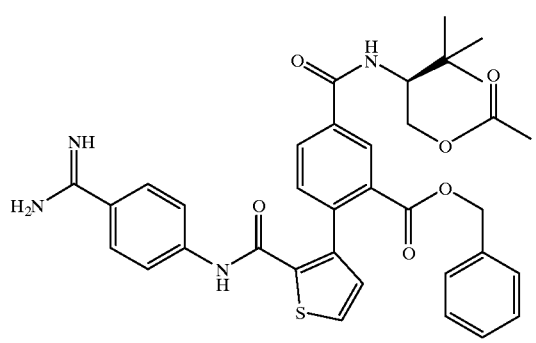

TLC:Rf 0.30 (Chloroform:Methanol:Acetic acid= 10:1:0.2); NMR (200 MHz, CD$_3$OD): δ 8.33 (d, J=2.0 Hz, 1H), 7.99 (dd, J=8.0, 2.0 Hz, 1H), 7.71 (d, J=9.2 Hz, 2H), 7.70–7.60 (m, 1H), 7.62 (d, J=9.2 Hz, 2H), 7.49 (d, J=8.0 Hz, 1H), 7.30–7.15 (m, 5H), 7.06 (d, J=5.2 Hz, 1H), 5.13 (s, 2H), 4.46 (dd, J=10.4, 3.0 Hz, 1H), 4.26 (dd, J=10.4, 3.0 Hz, 1H), 4.13 (t, J=10.4 Hz, 1H), 1.95 (s, 3H), 1.03 (s, 9H).

EXAMPLE 40(63)

Benzyl 2-[2-(4-amidinophenylcarbamoyl)-6-methoxy-3-pyridyl]-5-[[4-benyzloxy carbonyl-4-(2-methyl-2-propenyl)piperidinyl]carbonyl]benzoate

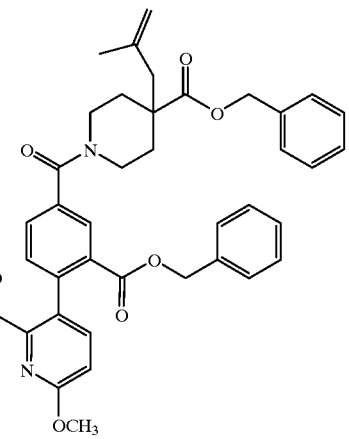

TLC:Rf 0.58 (Chloroform:Methanol:Water=8:2:0.1); NMR (300 MHz, CD$_3$OD): δ 8.05 (d, J=2.1 Hz, 1H), 7.83 (d, J=9.0 Hz, 2H), 7.77 (d, J=9.0 Hz, 2H), 7.61 (dd, J=8.1, 2.1 Hz, 1H), 7.55 (d, J=8.4 Hz, 1H), 7.44–7.29 (m, 5H), 7.31 (d, J=7.8 Hz, 1H), 7.26–7.16 (m, 3H), 7.09–7.05 (m, 2H), 6.99 (d, J=8.7 Hz, 1H), 5.18 (s, 2H), 5.01 (d, J=17.1 Hz, 2H), 4.80 (m, 1H), 4.67 (s, 1H), 4.45–4.30 (m, 2H*½, each of rotamers), 4.06 (s, 3H), 3.80–3.70 (m, 2H*½, each of rotamers), 3.31–3.20 (m, 2H*½, each of rotamers), 3.10–3.00 (m, 2H*½, each of rotamers), 2.40 (m, 2H), 2.40–2.20 (m, 2H*1/2, each of rotamers), 2.20–2.10 (m, 2H*½, each of rotamers), 1.62 (s, 3H), 1.62–1.50 (m, 2H).

EXAMPLE 40(64)

Benzyl 2-[2-(4-amidinophenylcarbamoyl)-6-methoxy-3-pyridyl]-5-[1(S)-[N-methyl-N-(1-iminoethyl)aminomethyl]-3-methylbutyl]benzoate acetic acetate

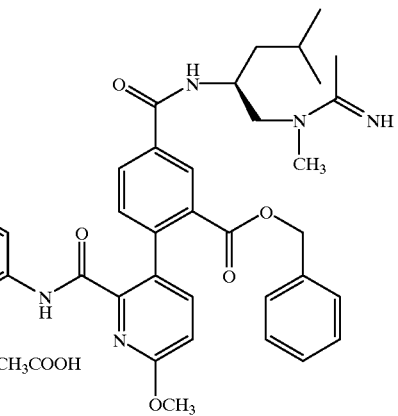

TLC:Rf 0.25 (Chloroform:Methanol:Acetic acid=10:2:1); NMR (300 MHz, CD$_3$OD): δ 8.52 and 8.49 (s, 1H), 8.04 (m, 1H), 7.84 (d, J=9.0 Hz, 2H), 7.79 (d, J=9.0 Hz, 2H), 7.53 (d, J=8.4 Hz, 1H), 7.26–7.06 (m, 5H), 7.00 (d, J=8.4 Hz, 1H), 5.08 (d, J=12.6 Hz, 1H), 4.97 (d, J=12.6 Hz, 1H), 4.50 (m, 1H), 4.07 (s, 3H), 3.64 (d, J=6.9 Hz, 2H), 3.21 (s, 3H), 2.35 and 2.32 (s, 3H), 1.99 (s, 3H), 1.90–1.62 (m, 2H), 1.41 (m, 1H), 0.99 (m, 6H).

EXAMPLE 40(65)

Benzyl 2'-(4-amidinophenylcarbamoyl)-4'-benzyloxycarbonylamino-4-(1(R), 2,2-trimethylpropylcarbamoyl)-2-biphenylcarboxylate

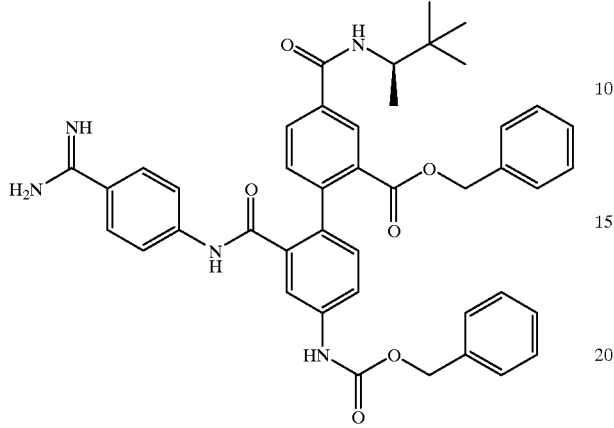

TLC:RF 0.46 (Chloroform:Methanol:Water=8:2:0.2); NMR (200 MHz, CDCl₃): δ 8.25 (d, J=2.0 Hz, 1H), 8.15 (br.d, J=9.6 Hz, 1H), 7.90 (dd, J=8.0, 2.0 Hz, 1H), 7.81 (d, J=2.0 Hz, 1H), 7.67 (d, J=9.0 Hz, 2H), 7.60 (d, J=9.0 Hz, 2H), 7.51–7.31 (m, 7H), 7.22–7.08 (m, 6H), 5.23 (s, 2H), 5.10 (s, 2H), 4.05 (m, 1H), 1.15 (d, J=7.0 Hz, 3H), 0.94 (s, 9H).

EXAMPLE 40(66)

Benzyl 2-[2-(4-amidinophenylcarbamoyl)-6-methoxy-3-pyridyl]-5-[1-(2,2-dimethylpropyl)tetrazol-5-yl]benzoate

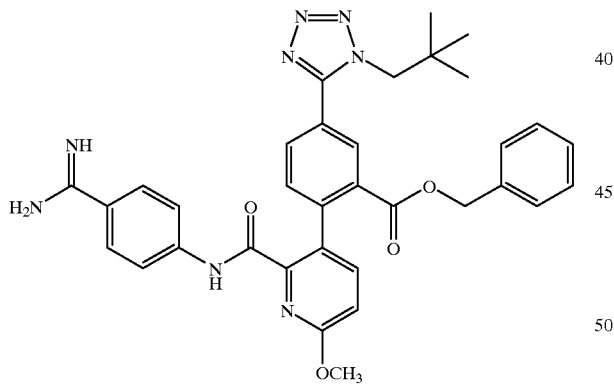

TLC:Rf 0.48 (Chloroform:Methanol:Acetic acid= 10:1:0.2); NMR (300 MHz, CD₃OD): δ 8.38 (d, J=2.0 Hz, 1H), 7.95 (dd, J=8.0, 2.0 Hz, 1H), 7.85 (d, J=9.0 Hz, 2H), 7.78 (d, J=9.0 Hz, 2H), 7.62 (d, J=8.4 Hz, 1H), 7.48 (d, J=8.0 Hz, 1H), 7.3–7.1 (m, 3H), 7.15–7.05 (m, 2H), 7.01 (d, J=8.4 Hz, 1H), 5.09 (d, J=11.7 Hz, 1H), 4.99 (d, J=11.7 Hz, 1H), 4.44 (s, 2H), 4.07 (s, 3H), 0.90 (s, 9H).

EXAMPLE 40(67)

Benzyl 2-[2-(4-amidinophenylcarbamoyl)-6-methoxy-3-pyridyl]-5-[[1-(1-iminoethyl)-4-(2-methylpropyl)piperidin-4-yl]carbamoyl]benzoate

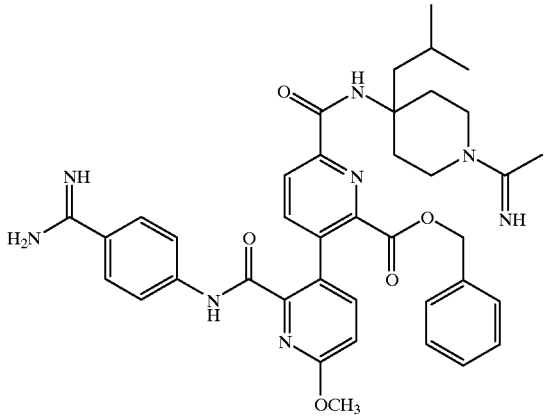

TLC:Rf 0.87 (Ethyl acetate:Acetic acid:Water=3:1:1); NMR (300 MHz, CD₃OD): δ 8.46 (d, J=1.8 Hz, 1H), 8.01 (dd, J=8.1, 1.8 Hz, 1H), 7.83 (d, J=9.3 Hz, 2H), 7.78 (d, J=9.3 Hz, 2H), 7.53 (d, J=8.7 Hz, 1H), 7.33 (d, J=8.1 Hz, 1H), 7.25–7.17 (m, 3H), 7.08–7.05 (m, 2H), 6.99 (d, J=8.7 Hz, 1H), 5.02 (d, J=18.6 Hz, 2H), 4.06 (s, 3H), 3.96–3.84 (m, 2H), 3.59–3.37 (m, 2H), 2.73–2.62 (m, 2H), 2.34 (s, 3H), 1.86–1.73 (m, 5H), 0.98 (d, J=6.0 Hz, 6H).

EXAMPLE 40(68)

Benzyl 3-[2-(4-amidinophenylcarbamoyl)-6-methoxy-3-pyridyl]-6-[(1(R), 2,2-trimethylpropyl)carbamoyl]-2-pyridinecarboxylate

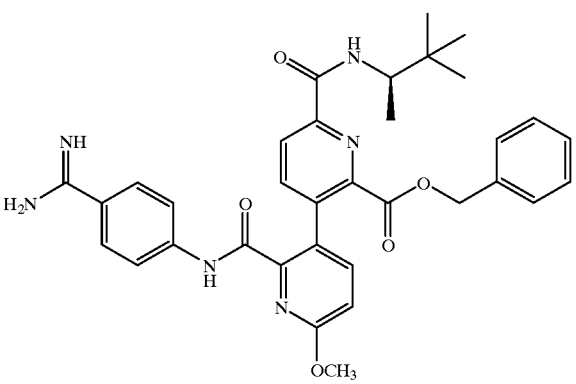

TLC:Rf 0.30 (Chloroform:Methanol:Water=8:2:0.2); NMR (200 MHz, CD₃OD): δ 8.29 (d, J=8.0 Hz, 1H), 7.87 (d, J=8.0 Hz, 1H), 7.85 (d, J=9.0 Hz, 2H), 7.77 (d, J=9.0 Hz, 2H), 7.61 (d, J=8.4 Hz, 1H), 7.28–7.17 (m, 3H), 7.09–7.04 (m, 2H), 7.02 (d, J=8.4 Hz, 1H), 5.20–4.94 (m, 2H), 4.07 (s, 3H), 4.06 (m, 1H), 1.24 (d, J=7.0 Hz, 3H), 1.00 (s, 9H).

EXAMPLE 40(69)

Benzyl 2-[2-(4-amidinophenylcarbamoyl)-6-methoxy-3-pyridyl]-5-(t-butyl carbamoyl)benzoate

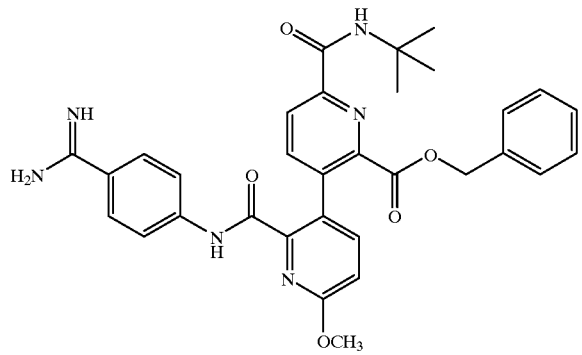

TLC:Rf 0.40 (Chloroform:Methanol:Acetic acid= 10:1:0.5); NMR (200 MHz, CD$_3$OD): δ 8.41 (d, J=1.8 Hz, 1H), 7.93 (dd, J=8.4, 1.8 Hz, 1H), 7.83 (d, J=9.0 Hz, 2H), 7.82 (d, J=9.0 Hz, 2H), 7.53 (d, J=8.4 Hz, 1H), 7.27 (d, J=8.4 Hz, 1H), 7.20–7.04 (m, 5H), 6.97 (d, J=8.4 Hz, 1H), 5.01 (d, J=8.2 Hz, 2H), 4.06 (s, 3H), 1.48 (s, 9H).

EXAMPLE 40(70)

Benzyl 2-[2-(4-amidinophenylcarbamoyl)-6-methoxy-3-pyridyl]-5-(2,2,2-trichloroethylcarbamoyl)benzoate

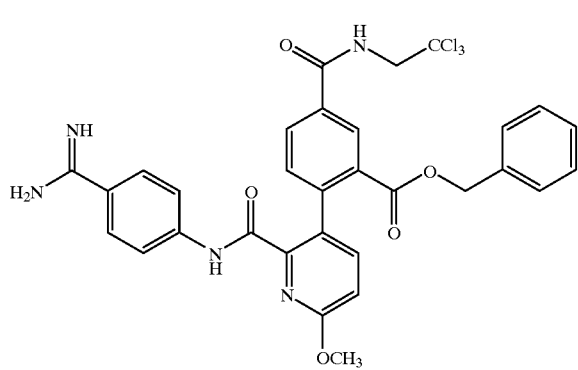

TLC:Rf 0.25 (Chloroform:Methanol:Acetic acid= 10:1:0.5); NMR (300 MHz, CD$_3$OD): δ 8.57 (d, J=1.8 Hz, 1H), 8.08 (dd, J=7.8, 1.8 Hz, 1H), 7.83 (d, J=9.0 Hz, 2H), 7.77 (d, J=9.0 Hz, 2H), 7.56 (d, J=8.4 Hz, 1H), 7.36 (d, J=7.8 Hz, 1H), 7.25–7.07 (m, 6H), 7.00 (d, J=8.4 Hz, 1H), 5.03 (d, J=17.7 Hz, 2H), 4.49 (s, 2H), 4.07 (s, 3H).

EXAMPLE 40 (71)

Benzyl 2-[3-(4-amidinophenylcarbamoyl)-2-thienyl]-6-(t-butylcarbamoyl)-2-pyridinecarboxylate

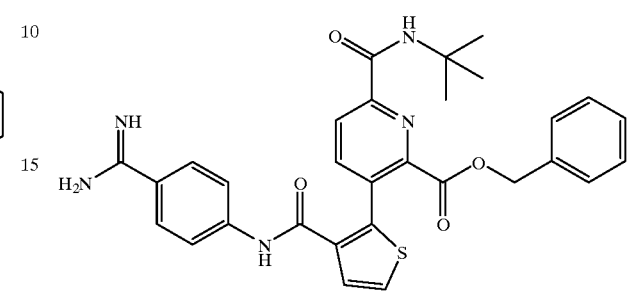

TLC:Rf 0.30 (Chloroform:Methanol:Water=8:2:0.2); NMR (300 MHz, CD$_3$OD): δ 8.23 (d, J=8.0 Hz, 1H), 8.04 (d, J=8.0 Hz, 1H), 7.79 (d, J=9.0 Hz, 2H), 7.74 (d, J=9.0 Hz, 2H), 7.59 (d, J=5.4 Hz, 1H), 7.52 (d, J=5.4 Hz, 1H), 7.25–7.21 (m, 3H), 7.16–7.13 (m, 2H), 5 13 (s, 2H), 1.48 (s, 9H).

EXAMPLE 40(72)

Benzyl 2-[2-(4-amidinophenylcarbamoyl)-6-methoxy-3-pyridyl]-5-(2,2,2-trifluoroethylcarbamoyl)benzoate

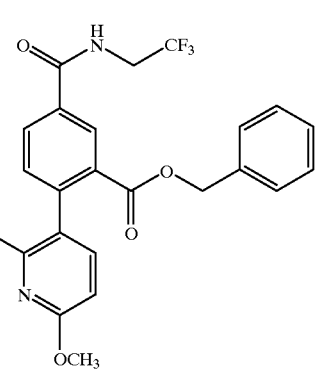

TLC:Rf 0.41 (Chloroform:Methanol:Water=8:2:0.2); NMR (300 MHz, CD$_3$OD): δ 8.56 (d, J=1.8 Hz, 1H), 8.06 (dd, J=8.1, 1.8 Hz, 1H), 7.83 (d, J=9.0 Hz, 2H), 7.78 (d, J=9.0 Hz, 2H), 7.54 (d, J=8.7 Hz, 1H), 7.35 (d, J=8.1 Hz, 1H), 7.25–7.17 (m, 3H), 7.07 (d, J=8.7 Hz, 1H), 6.99 (d, J=J=8.7 Hz, 1H), 5.07 (d, J=11.7 Hz, 1H), 4.99 (d, J=11.7 Hz, 1H), 4.13 (q, J=9.3 Hz, 2H), 4.07 (s, 3H).

EXAMPLE 40(73)

Benzyl 2-[2-[(2-amidinopyrimidin-5-yl)carbamoyl]-6-methoxy-3-pyridyl]-5-(2,2-dimethylpropylcarbamoyl)benzoate

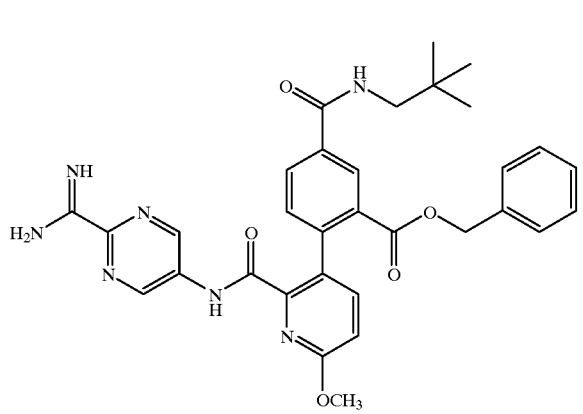

TLC:Rf 0.57 (Chloroform:Methanol:Acetic acid=10:2:1); NMR (300 MHz, $d_6$-DMSO): δ 11.05–10.85 (br, 1H), 9.45 (br.s, 3H), 9.30 (s, 2H), 8.61 (t, J=6.6 Hz, 1H), 8.40 (d, J=1.8 Hz, 1H), 8.09 (dd, J=7.8, 1.8 Hz, 1H), 7.69 (d, J=8.7 Hz, 1H), 7.38 (d, J=7.8 Hz, 1H), 7.30–7.15 (m, 3H), 7.20–7.05 (m, 3H), 5.05 (s, 2H), 4.09 (s, 3H), 3.13 (d, J=6.6 Hz, 2H), 0.97 (s, 9H).

EXAMPLE 40(74)

Benzyl 2-[2-(4-amidinophenylcarbamoyl)-6-methoxy-3-pyridyl]-5-[[1(S)-(2-benzyloxycarbonylaminoethyl)-3-methylbutyl]carbamoyl]benzoate

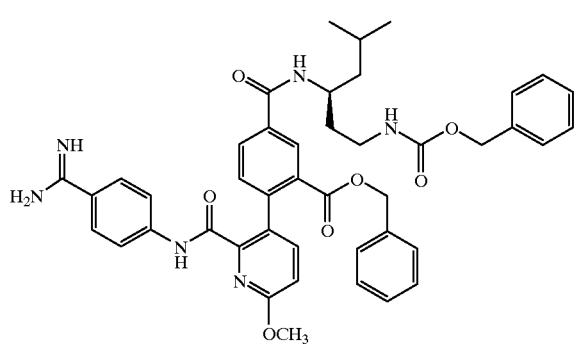

TLC:Rf 0.32 (Chloroform:Methanol:Water=8:2:0.2); NMR (300 MHz, $CD_3OD$): δ 8.51 (d, J=2.0 Hz, 1H), 8.02 (dd, J=8.0, 2.0 Hz, 1H), 7.83 (d, J=9.0 Hz, 2H), 7.76 (d, J=9.0 Hz, 2H), 7.54 (d, J=8.0 Hz, 1H), 7.33–7.16 (m, 9H), 7.09–7.06 (m, 2H), 6.99 (d, J=8.0 Hz, 1H), 5.15–5.00 (m, 4H), 4.27 (m, 1H), 4.06 (s, 3H), 3.34–3.07 (m, 2H), 1.85–1.30 (m, 5H), 0.95 (d, J=6.3 Hz, 6H).

EXAMPLE 40(75)

Benzyl 2-[2-(4-amidinophenylcarbamoyl)-6-methoxy-3-pyridyl]-5-[(2,2-diethylbutyloxy)carbamoyl]benzoate

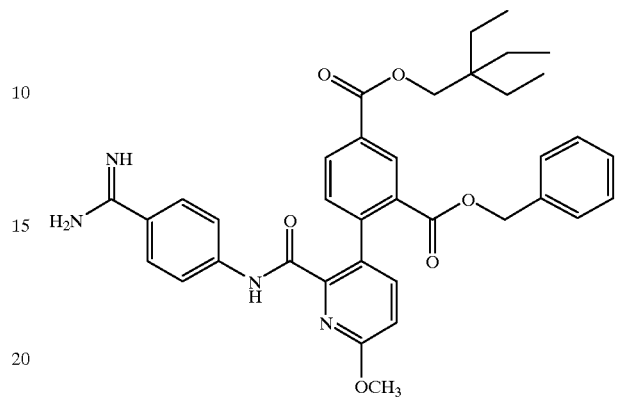

TLC:Rf 0.54 (Chloroform:Methanol:Water=8:2:0.2); NMR (200 MHz, $CD_3OD$): δ8.68 (d, J=1.8 Hz, 1H), 8.19 (d, J=8.0, 1.8 Hz, 1H), 7.85 (d, J=8.8 Hz, 2H), 7.77 (d, J=8.8 Hz, 2H), 7.56 (d, J=8.6 Hz, 1H), 7.36 (d, J=8.0 Hz, 1H), 7.28–7.18 (m, 3H), 7.13–7.08 (m, 2H), 6.99 (d, J=8.6 Hz, 1H), 5.09 (d, J=12.0 Hz, 1H), 4.97 (d, J=12.0 Hz, 1H), 4.16 (s, 2H), 4.08 (s, 3H), 1.43 (q, J=7.6 Hz, 6H), 0.88 (t, J=7.6 Hz, 9H).

EXAMPLE 40(76)

Benzyl 2-[2-(4-amidinophenylcarbamoyl)-6-methoxy-3-pyridyl]-5-[(2,2-dimethyl-3-hydroxypropyl)carbamoyl]benzoate

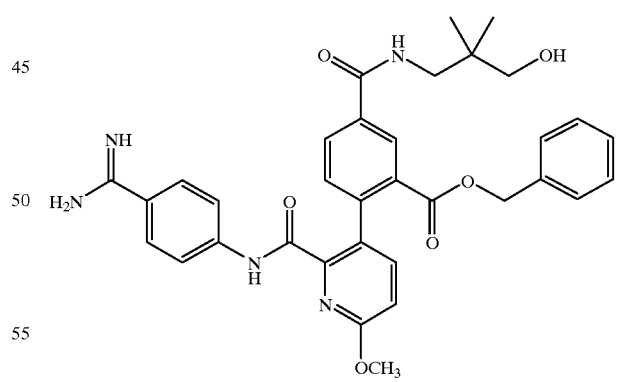

TLC:Rf 0.29 (Chloroform:Methanol:Water=8:2:0.1); NMR (200 MHz, $CD_3OD$): δ 8.51 (d, J=2.0 Hz, 1H), 8.03 (dd, J=8.0, 2.0 Hz, 1H), 7.84 (d, J=9.2 Hz, 2H), 7.76 (d, J=9.2 Hz, 2H), 7.55 (d, J=8.4 Hz, 1H), 7.33 (d, J=8.0 Hz, 1H), 7.23–7.17 (m, 3H), 7.10–7.05 (m, 2H), 6.99 (d, J=8.4 Hz, 1H), 5.03 (d, J=8.8 Hz, 2H), 4.06 (s, 3H), 3.34–3.28 (m, 4H), 0.96 (s, 6H).

EXAMPLE 40(77)

Benzyl 2-[2-(4-amidinophenylcarbamoyl)-6-methoxy-3-pyridyl]-5-[(2,2-diethylbutyl)carbamoyl]benzoate

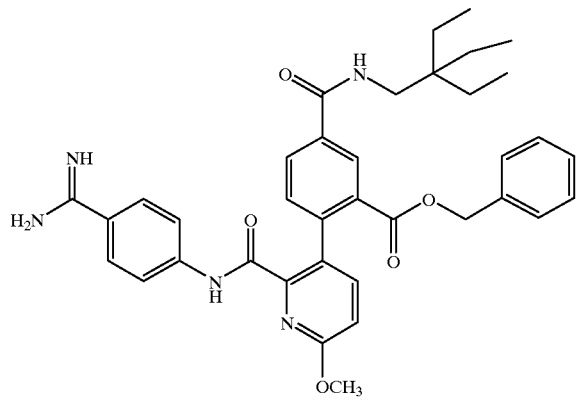

TLC:Rf 0.56 (Chloroform:Methanol:Water=8:2:0.2); NMR (300 MHz, CD$_3$OD): δ 8.45 (d, J=1.8 Hz, 1H), 7.97 (dd, J=8.1, 1.8 Hz, 1H), 7.83 (d, J=9.0 Hz, 2H), 7.78 (d, J=9.0 Hz, 2H), 7.53 (d, J=8.4 Hz, 1H), 7.31 (d, J=8.1 Hz, 1H), 7.25–7.17 (m, 3H), 7.09–7.07 (m, 2H), 6.98 (d, J=8.4 Hz, 1H), 5.07 (d, J=11.4 Hz, 1H), 4.97 (d, J=11.4 Hz, 1H), 4.06 (s, 3H), 3.35 (s, 2H), 1.33 (q, J=7.5 Hz, 6H), 0.88 (t, J=7.5 Hz, 9H).

EXAMPLE 40(78)

Benzyl 2-[2-(4-amidinophenylcarbamoyl)-6-methoxy-3-pyridyl]-5-[((1-hydroxymethyl)cyclobutylmethyl)carbamoyl]benzoate

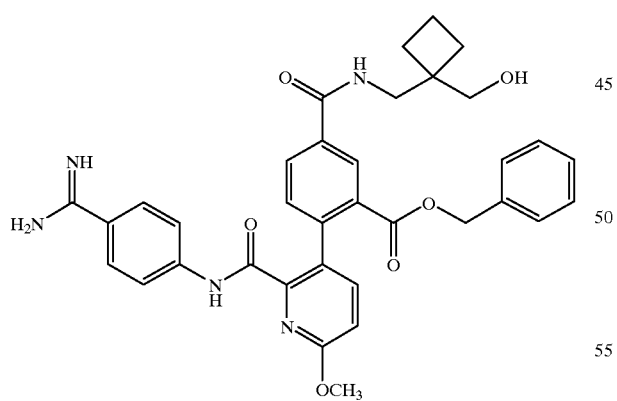

TLC:Rf 0.30 (Chloroform:Methanol:Water=8:2:0.1); NMR (300 MHz, CD$_3$OD): δ 8.50 (d, J=1.8 Hz, 1H), 8.01 (dd, J=7.8, 1.8 Hz, 1H), 7.83 (d, J=9.0 Hz, 2H), 7.77 (d, J=9.0 Hz, 2H), 7.54 (dd, J=8.4, 1.8 Hz, 1H), 7.32 (d, J=7.8 Hz, 1H), 7.24–7.17 (m, 3H), 7.08–7.06 (m, 2H), 6.99 (dd, J=8.4, 1.8 Hz, 1H), 5.02 (br d, J=16.5 Hz, 2H), 4.06 (s, 3H), 3.57 (s, 2H), 3.56 (s, 2H), 1.93–1.82 (m, 6H).

EXAMPLE 40(79)

Benzyl 2-[2-(4-amidinophenylcarbamoyl)-6-methoxy-3-pyridyl]-5-[(2-ethyl-2-hydroxymethylbutyl)carbamoyl]benzoate

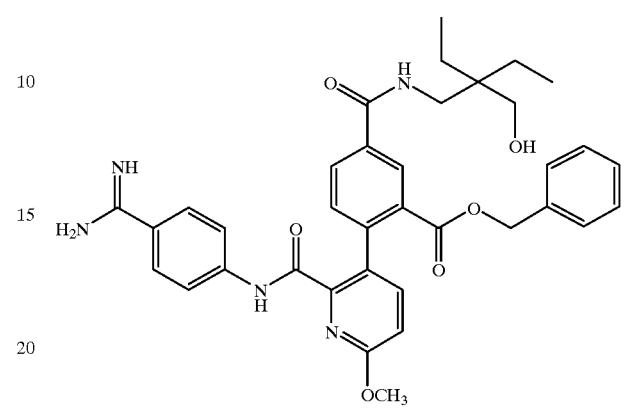

TLC:Rf 0.31 (Chloroform:Methanol:Water=8:2:0.1); NMR (300 MHz, CD$_3$OD): δ 8.50 (d, J=1.8 Hz, 1H), 8.01 (dd, J=8.1, 1.8 Hz, 1H), 7.83 (d, J=9.0 Hz, 2H), 7.77 (d, J=9.0 Hz, 2H), 7.55 (d, J=8.4 Hz, 1H), 7.33 (d, J=8.1 Hz, 1H), 7.24–7.17 (m, 3H), 7.08–7.06 (m, 2H), 6.99 (d, J=8.4 Hz, 1H), 5.02 (br d, J=17.4 Hz, 2H), 4.06 (s, 3H), 3.36 (s, 2H), 3.35 (s, 2H), 1.35 (septet, J=7.5 Hz, 4H), 0.90 (t, J=7.5 Hz, 6H).

EXAMPLE 40(80)

Benzyl 2-[2-(4-amidinophenylcarbamoyl)-6-methoxy-3-pyridyl]-5-[(( 1-hydroxymethyl)cyclopentylmethyl)carbamoyl]benzoate

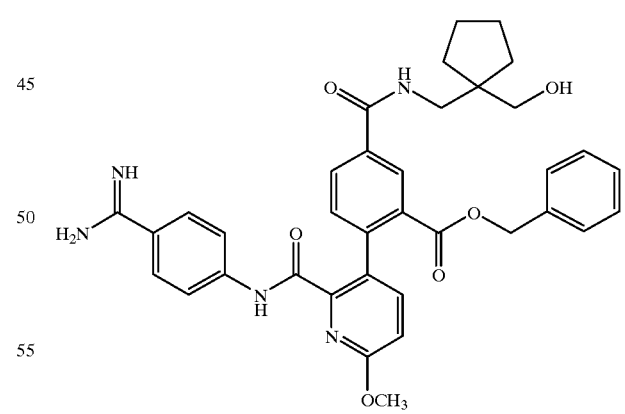

TLC:Rf 0.28 (Chloroform:Methanol:Water=8:2:0.1); NMR (300 MHz, CD$_3$OD): δ 8.50 (d, J=1.8 Hz, 1H), 8.02 (dd, J=8.1, 1.8 Hz, 1H), 7.83 (d, J=9.3 Hz, 2H), 7.77 (d, J=9.3 Hz, 2H), 7.54 (d, J=8.4 Hz, 1H), 7.33 (d, J=8.1 Hz, 1H), 7.25–7.16 (m, 3H), 7.09–7.06 (m, 2H), 6.99 (d, J=8.4 Hz, 1H), 5.02 (d, J=16.8 Hz, 2H), 4.06 (s, 3H), 3.44 (s, 2H), 3.39 (s, 2H), 1.80–1.60 (m, 4H), 1.60–1.40 (m, 2H).

EXAMPLE 40(81)

Benzyl 2-[2-(4-amidinophenylcarbamoyl)-6-methoxy-3-pyridyl]-5-[(2-propyl-2-hydroxymethylpentyl)carbamoyl]benzoate

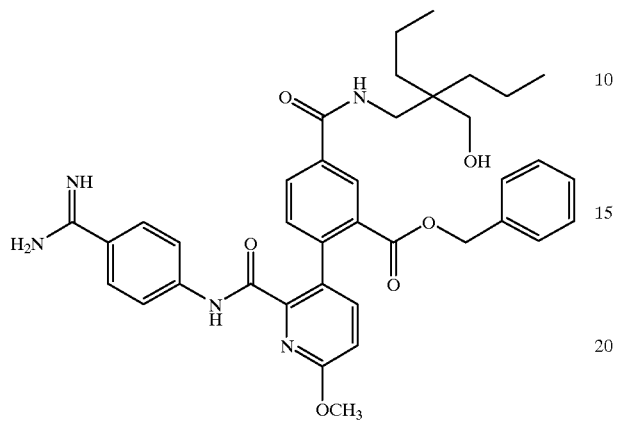

TLC:Rf 0.60 (Chloroform:Methanol:Acetic acid=10:2:1); NMR (300 MHz, CD$_3$OD): δ 8.49 (d, J=1.8 Hz, 1H), 8.00 (dd, J=8.1, 1.8 Hz, 1H), 7.85–7.75 (m, 4H), 7.55 (d, J=8.7 Hz, 1H), 7.32 (d, J=8.1 Hz, 1H), 7.23–7.20 (m, 3H), 7.09–7.06 (m, 2H), 6.99 (d, J=8.7 Hz, 1H), 5.02 (d, J=17.4 Hz, 2H), 4.06 (s, 3H), 3.60 (m, 1H), 3.39–3.25 (m, 3H), 1.40–1.20 (m, 8H), 0.93 (t, J=6.9 Hz, 6H).

EXAMPLE 40(82)

Benzyl 2-[2-(4-amidinophenylcarbamoyl)-6-methoxy-3-pyridyl]-5-[(2-(2-methylpropyl)-2-hydroxymethyl-4-methylpentyl)carbamoyl]benzoate

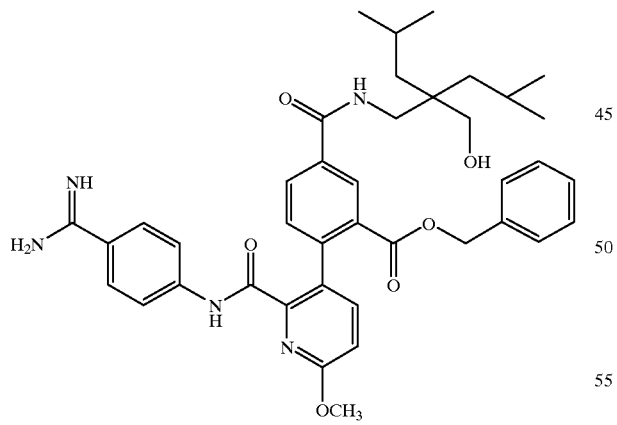

TLC:Rf 0.38 (Chloroform:Methanol:Water=8:2:0.2); NMR (300 MHz, CD$_3$OD): δ 8.49 (d, J=2.1 Hz, 1H), 8.00 (dd, J=8.1, 2.1 Hz, 1H), 7.83 (d, J=9.0 Hz, 2H), 7.77 (d, J=9.0 Hz, 2H), 7.55 (d, J=8.7 Hz, 1H), 7.34 (d, J=8.1 Hz, 1H), 7.24–7.20 (m, 3H), 7.09–7.06 (m, 2H), 6.99 (d, J=8.7 Hz, 1H), 1H), 5.15–4.95 (m, 2H), 4.07 (s, 3H), 3.49 (s, 2H), 3.45 (s, 2H), 1.86–1.76 (2H), 1.50–1.30 (m, 4H), 0.98 (d, J=6.6 Hz, 12H).

EXAMPLE 40(83)

Benzyl 2-[2-(4-amidinophenylcarbamoyl)-6-methoxy-3-pyridyl]-5-[(1-hydroxy methylcyclopentyl)carbamoyl]benzoate

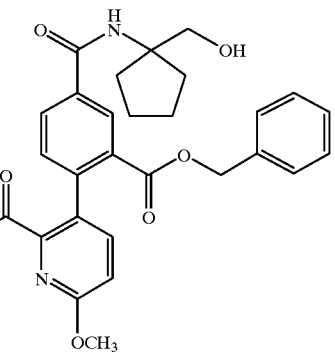

TLC:Rf 0.38 (Chloroform:Methanol:Water=8 8:2:0.2); NMR (300 MHz, CD$_3$OD): δ 8.45 (d, J=2.1 Hz, 1H), 7.98 (dd, J=7.8, 2.1 Hz, 1H), 7.83 (d, J=9.0 Hz, 2H), 7.77 (d, J=9.0 Hz, 2H), 7.53 (d, J=8.4 Hz, 1H), 7.29 (d, J=7.8 Hz, 1H), 7.25–7.17 (m, 3H), 7.09–7.06 (m, 2H), 6.98 (d, J=8.4 Hz, 1H), 5.15–4.90 (m, 2H), 4.60 (s, 3H), 3.80 (s, 2H), 2.18–2.01 (m, 2H), 1.96–1.70 (m, 4H), 1.70–1.52 (m, 2H).

EXAMPLE 40(84)

Benzyl 2-[2-(4-amidinophenylcarbamoyl)-6-methoxy-3-pyridyl)-5-[(1-( 2-methylpropyl)-1-hydroxymethyl-3-methylbutyl)carbamoyl]benzoate

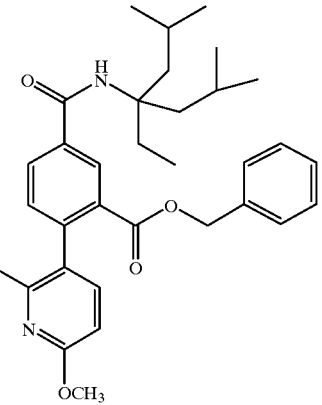

TLC:Rf 0.38 (Chloroform:Methanol:Water=8:2:0.2); NMR (300 MHz, CD$_3$OD): δ 8.42 (d, J=2.1 Hz, 1H), 7.93 (dd, J=7.8, 2.1 Hz, 1H), 7.83 (d, J=9.0 Hz, 2H), 7.78 (d, J=9.0 Hz, 2H), 7.53 (d, J=8.4 Hz, 1H), 7.30 (d, J=7.8 Hz, 1H), 7.23–7.18 (m, 3H), 7.09–7.06 (m, 2H), 6.98 (d, J=8.4 Hz, 1H), 5.15–4.90 (m, 2H), 4.06 (s, 3H), 3.80 (s, 2H), 1.92–1.76 (m, 6H), 0.99 (d, J=6.0 Hz, 6H), 0.98 (d, J=6.3 Hz, 6H).

EXAMPLE 40(85)

Benzyl 2-[2-(4-amidinophenylcarbamoyl)-6-methoxy-3-pyridyl]-5-[(1(S)-(hydroxymethyl)-2(S)-methylbutyl)carbamoyl]benzoate.

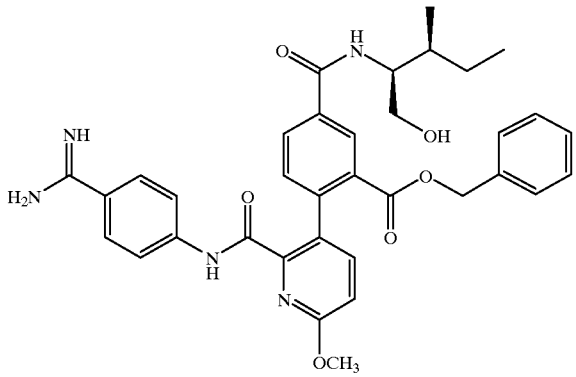

TLC:Rf 0.20, (Chloroform:Methanol:Acetic acid=10:1:0.5); NMR (300 MHz, CD$_3$OD): δ 8.52 (d, J=1.8 Hz, 1H), 8.04 (dd, J=7.8, 1.8 Hz, 1H), 7.83 (d, J=9.0 Hz, 2H), 7.77 (d, J=9.0 Hz, 2H), 7.55 (d, J=8.4 Hz, 1H), 7.32 (d, J=7.8 Hz, 1H), 7.30–7.03 (m, 5H), 6.98 (d, J=8.4 Hz, 1H), 5.03 (d, J=15.6 Hz, 2H), 4.06 (s, 3H), 4.03 (m, 1H), 3.78 (m, 2H), 1.80 (m, 1H), 1.60 (m, 1H), 1.23 (m, 1H), 1.00 (d, J=6.9 Hz, 3H), 0.95 (t, J=7.5 Hz, 3H).

EXAMPLE 40(86)

Benzyl 2-[2-(4-amidinophenylcarbamoyl)-6-ethoxy-3-pyridyl]-5-[(1(S)-isopropyl-3-benzyloxycarbonylaminopropyl)carbamoyl]benzoate

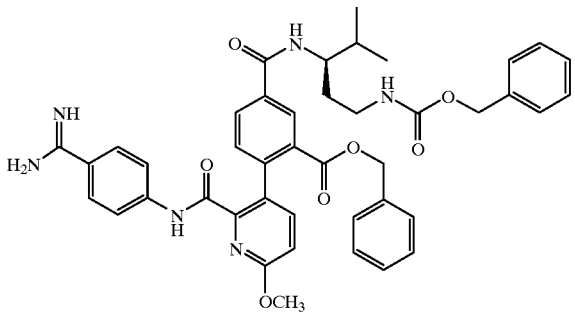

TLC:Rf 0.40 (Chloroform:Methanol:Acetic acid=10:1:0.5); NMR (200 MHz, CD$_3$OD): δ 8.51 (d, J=1.8 Hz, 1H), 8.05 (m, 1H), 7.81–7.77 (m, 4H), 7.50 (d, J=8.4 Hz, 1H), 7.39–7.02 (m, 11H), 6.93 (d, J=8.4 Hz, 1H), 5.02 (m, 4H), 4.46 (dd, J=14.0,7.4 Hz, 2H), 3.95 (m, 1H), 3.69 (m, 1H), 3.10 (m, 1H), 1.83 (m, 2H), 1.70 (m, 1H), 1.48 (t, J=7.0 Hz, 3H), 0.97 (d, J=7.0 Hz, 6H).

EXAMPLE 40(87)

Benzyl 2-[2-(4-amidinophenylcarbamoyl)-6-ethoxy-3-pyridyl]-5-[(1(S)-(2-benzyloxycarbonylaminoethyl)-3-methylbutyl)carbamoyl]benzoate TLC:Rf 0.27 (Chloroform:Methanol:Acetic acid=20:2:1); NMR (300 MHz, CD$_3$OD): δ 8.51 (d, J=2.0 Hz, 1H), 8.02 (dd, J=8.0, 2.0 Hz, 1H), 7.81 (d, J=9.0 Hz, 2H), 7.76 (d, J=9.0 Hz, 2H), 7.53 (d, J=8.4 Hz, 1H), 7.36–7.16 (m, 9H), 7.10–7.05 (m, 2H), 6.96 (d, J=8.4 Hz, 1H), 5.07 (brd, J=12 Hz, 1H), 5.05 (s, 2H), 4.98 (brd, J=12 Hz, 1H), 4.52–4.42 (m, 2H), 4.33–4.20 (m, 1H), 3.36–3.25 (m, 1H), 3.20–3.05 (m, 1H), 1.90–1.50 (m, 4H), 1.48 (t, J=7.2 Hz, 3H), 1.42–1.30 (m, 1H), 0.95 (d, J=6.0 Hz, 6H).

EXAMPLE 40(88)

Benzyl 2-[2-(4-amidinophenylcarbamoyl)-6-ethoxy-3-pyridyl]-5-[(1(S)-(2-benzyloxycarbonylaminoethyl)-2(S)-methylbutyl)carbamoyl]benzoate

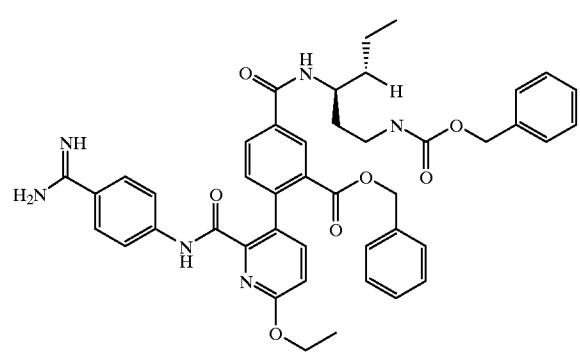

TLC:Rf 0.30 (Chloroform:Methanol:Acetic acid=20:2:1); NMR (300 MHz, CD$_3$OD): δ 8.51 (d, J=2.0 Hz, 1H), 8.02 (dd, J=8.0, 2.0 Hz, 1H), 7.82 (d, J=9.0 Hz, 2H), 7.76 (d, J=9.0 Hz, 2H), 7.53 (d, J=8.4 Hz, 1H), 7.36–7.16 (m, 9H), 7.12–7.05 (m, 2H), 6.97 (d, J=8.4 Hz, 1H), 5.07 (brd, J=12 Hz, 1H), 5.04 (s, 2H), 4.97 (brd, J=12 Hz, 1H), 4.52–4.42 (m, 2H), 4.12–3.98 (m, 1H), 3.33–3.20 (m, 1H), 3.15–3.00 (m, 1H), 1.95–1.80 (m, 1H), 1.75–1.45 (m, 3H), 1.49 (t, J=7.2 Hz, 3H), 1.30–1.18 (m, 1H), 0.97 (d, J=6.6 Hz, 3H), 0.94 (t, J=7.5 Hz, 3H).

EXAMPLE 41(1)–41(90)

The following compounds were obtained by the same procedure as a series of reaction of Example 2, with the proviso that some compounds were not converted to salt thereof, or were converted to different salt thereof; using the compound prepared in Reference Example 40(1)–40(88).

EXAMPLE 41(1)

2-[4-(4-amidinophenylcarbamoyl)-3-pyridyl]-5-[(1,2,2-trimethylpropyl) carbamoyl]benzoic acid methanesulfonate

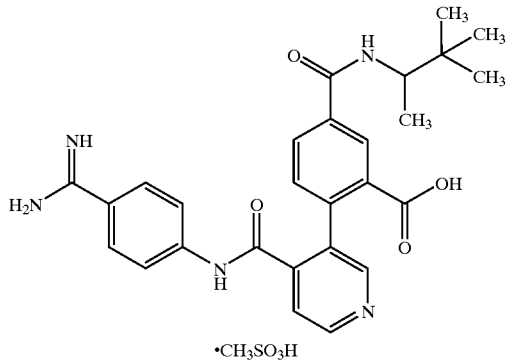

TLC:Rf 0.35 (Chloroform:Methanol:Water=7:3:0.3); NMR ($d_6$-DMSO): δ 11.05 (1H, s), 9.23 (2H, brs), 9.00 (2H, brs), 8.89 (1H, brd, J=5.5 Hz), 8.70 (1H, s), 8.38 (1H, d, J=2.0 Hz), 8.25 (1H, d, J=9.0 Hz), 8.03 (1H, dd, J=8.0 Hz, 2.0 Hz), 7.92 (1H, d, J=5.5 Hz), 7.78 (2H, d, J=9.0 Hz), 7.74 (2H, d, J=9.0 Hz), 7.45 (1H, d, J=8.0 Hz), 3.99 (1H, dq, J=9.0 Hz, 7.0 Hz), 2.36 (3H, s), 1.08 (3H, d, J=7.0 Hz), 0.89 (9H, s).

EXAMPLE 41(2)

2-[2-(4-amidinophenylcarbamoyl)-6-methyl-3-pyridyl]-5-[(2-methylpropyl) carbamoyl]benzoic acid methanesulfonate

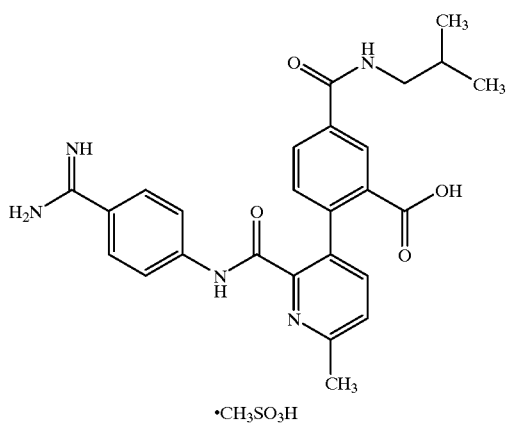

TLC:Rf 0.13 (Chloroform:Methanol:Acetic acid=10:2:1); NMR ($d_6$-DMSO): δ 10.85 (1H, s), 9.21 (2H, brs), 8.96 (2H, brs), 8.71 (1H, brt, J=5.5 Hz), 8.42 (1H, d, J=2.0 Hz), 8.03 (1H, dd, J=8.0 Hz, 2.0 Hz), 7.92 (2H, d, J=8.5 Hz), 7.78 (2H, d, J=8.5 Hz), 7.64 (1H, d, J=8.0 Hz), 7.55 (1H, d, J=8.0 Hz), 7.30 (1H, d, J=8.0 Hz), 3.11 (2H, brt, J=6.5 Hz), 2.67 (3H, s), 2.37 (3H, s), 1.94–1.80 (1H, m), 0.90 (6H, d, J=6.5 Hz).

EXAMPLE 41(3)

2-[2-(4-amidinophenylcarbamoyl)-6-methyl-3-pyridyl]-5-[(1,2,2-trimethylpropyl) carbamoyl]benzoic acid methanesulfonate

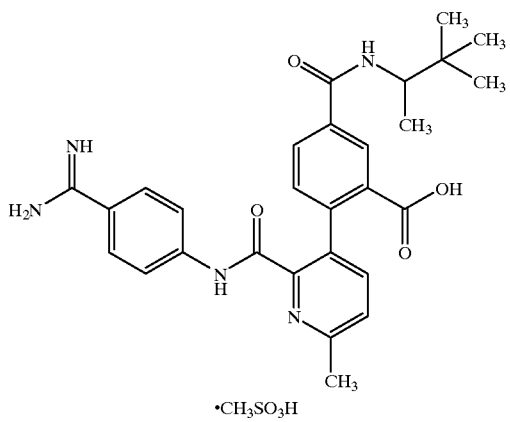

TLC:Rf 0.16 (Chloroform:Methanol:Acetic acid=10:2:1); NMR ($d_6$-DMSO): δ 10.86 (1H, s), 9.22 (2H, brs), 8.98 (2H, brs), 8.38 (1H, d, J=1.5 Hz), 8.23 (1H, brd, J=9.0 Hz), 8.02 (1H, dd, J=8.0 Hz, 1.5 Hz), 7.93 (2H, d, J=8.5 Hz), 7.79 (2H, d, J=8.5 Hz), 7.62 (1H, d, J=8.0 Hz), 7.56 (1H, d, J=8.0 Hz), 7.29 (1H, d, J=8.0 Hz), 4.01 (1H, dq, J=9.0 Hz, 7.0 Hz), 2.67 (3H, s), 2.38 (3H, s), 1.10 (3H, d, J=7.0 Hz), 0.92 (9H, s).

EXAMPLE 41(4)

2'-(4-amidinophenylcarbamoyl)-4-(1,1-dimethylpropylcarbamoyl)-2-biphenylcarboxylic acid methanesulfonate

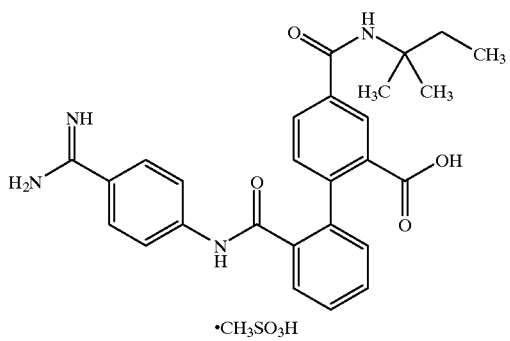

TLC:Rf 0.15 (Chloroform:Methanol:Acetic acid=10:2:1); NMR ($d_6$-DMSO): δ 10.5 (1H, s), 9.15 (2H, br s), 8.84 (2H, br s), 8.20 (1H, d, J=2.1 Hz), 7.90 (1H, dd, J=2.1, 7.8 Hz), 7.81 (1H, s), 7.72 (4H, s), 7.72–7.67 (1H, m), 7.59–7.49 (2H, m), 7.28 (1H, d, J=8.1 Hz), 7.26–7.23 (1H, m), 2.33 (3H, s), 1.77 (2H, q, J=7.5 Hz), 1.31 (6H, s), 0.79 (3H, t, J=7.5 Hz).

EXAMPLE 41(5)

2'-(4-amidinophenylcarbamoyl)-4-[(1(S)-t-butyl-2-methoxycarbonylethyl) carbamoyl]-2-biphenylcarboxylic acid methanesulfonate

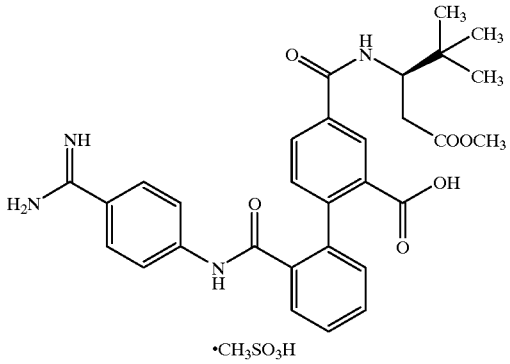

TLC:Rf 0.18 (Chloroform:Methanol:Water=10:2:1); NMR (d$_6$-DMSO): δ 10.6 (1H, s), 9.14 (2H, br s), 8.80 (2H, br s), 8.29 (1H, d, J=9.3 Hz), 8.23 (1H, s), 7.90 (1H, d, J=8.8 Hz), 7.73–7.68 (5H, m), 7.60–7.48 (2H, m), 7.32–7.25 (2H, m), 4.28 (1H, t, J=8.8 Hz), 3.51 (3H, s), 2.72–2.40 (2H, m), 2.30 (3H, s), 0.89 (9H, s).

EXAMPLE 41(6)

2'-(4-amidinophenylcarbamoyl)-4-(2,2-dimethylcyclohexylcarbamoyl)-2-biphenylcarboxylic acid methanesulfonate

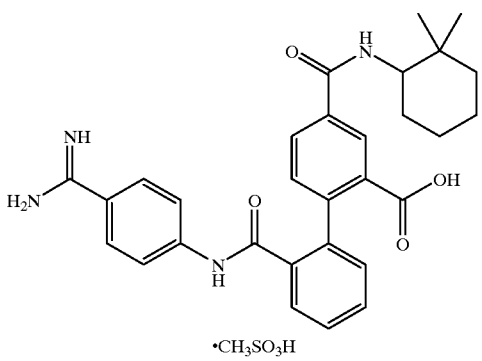

TLC:Rf 0.36 (Chloroform:Methanol:Acetic acid=10:2:1); NMR (d$_6$-DMSO): δ 13.0–12.0 (1H, br), 10.56 (1H, s), 9.16 (2H, s), 8.89 (2H, s), 8.25 (1H, d, J=2.0 Hz), 8.10 (1H, d, J=9.0 Hz), 7.94 (1H, dd, J=2.0, 8.0 Hz), 7.73 (4H, like s), 7.69 (1H, dd, J=2.0, 8.0 Hz), 7.5–7.45 (2H, m), 7.30 (1H, d, J=8.0 Hz), 7.25 (1H, dd, J=2.0, 8.0 Hz), 3.81 (1H, m), 2.36 (3H, s), 1.8–1.6 (1H, m), 1.7–1.3 (4H, m), 1.4–1.2 (3H, m), 0.89 (3H, s), 0.84 (3H, s).

EXAMPLE 41(7)

2'-(4-amidinophenylcarbamoyl)-4-(1-isopropyl-2-methylpropylcarbamoyl)-2-biphenylcarboxylic acid methanesulfonate

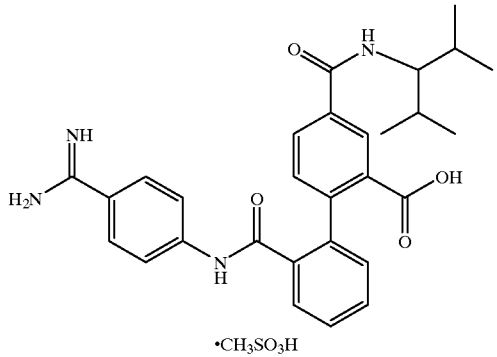

TLC:Rf 0.31(Chloroform:Methanol:Acetic acid=10:2:1); NMR (d$_6$-DMSO): δ 10.57 (1H, s), 9.15 (2H, s), 8.81 (2H, s), 8.29 (1H, d, J=2.0 Hz), 8.02 (1H, d, J=10.0 Hz), 7.97 (1H, dd, J=2.0,8.0 Hz), 7.74 (4H, s), 7.71 (1H, dd, J=2.0,8.0 Hz), 7.58 (1H, dt, J=2.0,8.0 Hz), 7.54 (1H, dt, J=2.0,8.0 Hz), 7.32 (1H, d, J=8.0 Hz), 7.27 (1H, dd, J=2.0,8.0 Hz), 3.67 (1H, dt, J=7.2, 10.0 Hz), 2.33 (3H, s), 1.91 (2H, m), 0.87 (6H, d, J=7.5 Hz), 0.85 (6H, d, J=7.5 Hz).

EXAMPLE 41(8)

2'-(4-amidinophenylcarbamoyl)-4-[(4,4-dimethyloxolan-3(S)-yl)carbamoyl]-2-biphenylcarboxylic acid methanesulfonate

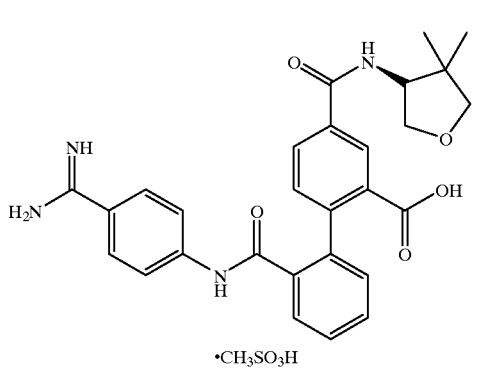

TLC:Rf 0.15 (Chloroform:Methanol:Acetic acid=10:2:1); NMR (d$_6$-DMSO): δ 10.5 (s, 1H), 9.14 (br s, 2H), 8.78 (br s, 2H), 8.51 (d, J=8.8 Hz, 1H), 8.31 (d, J=1.4 Hz, 1H), 7.98 (dd, J=8.0,1.4 Hz, 1H), 7.72–7.68 (m, 5H), 7.60–7.50 (m, 2H), 7.32 (d, J=8.0 Hz, 1H), 7.30–7.25 (m, 1H), 7.30–7.25 (m, 1H), 4.40–4.25 (m, 1H), 4.12–4.03 (m, 1H), 3.70–3.60 (m, 1H), 3.54–3.39 (m, 2H, 2.29 (s, 3H), 1.08 (s, 3H), 0.93 (s, 3H).

EXAMPLE 41(9)

2-[2-(4-amidinophenylcarbamoyl)-3-pyridyl]-5-[(2-methylpropyl)carbamoyl]benzoic acid methanesulfonate

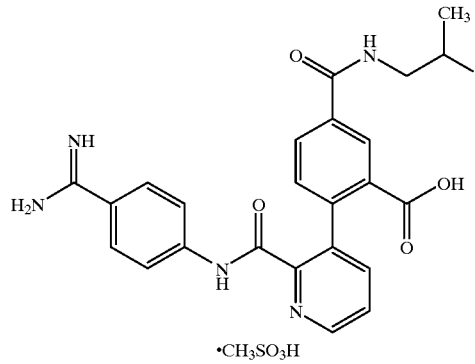

TLC:Rf 0.34 (Chloroform:Methanol:Acetic acid=10:2:1); NMR (d$_6$-DMSO): δ 11.00 (s, 1H), 9.12 (s, 2H), 8.92 (s, 2H), 8.73 (dd, J=4.8, 2.1 Hz, 1H), 8.71 (br.d, J=6.3 Hz, 1H), 8.43 (d, J=1.8 Hz, 1H), 8.05 (dd, J=7.8, 1.8 Hz, 1H), 7.95 (d, J=9.0 Hz, 2H), 7.8–7.7 (m, 1H), 7.77 (d, J=9.0 Hz, 2H), 7.71 (dd, J=7.8, 4.8 Hz, 1H), 7.34 (d, J=7.8 Hz, 1H), 5.0–4.2 (br, 1H), 3.12 (t, J=6.3 Hz, 2H), 2.36 (s, 3H), 1.88 (like septet, J=6.3 Hz, 1H), 0.91 (d, J=6.3 Hz, 6H).

EXAMPLE 41(10)

2-[2-(4-amidinophenylcarbamoyl)-6-methyl-3-pyridyl]-5-[(3-hydroxymethyl-2,2-dimethylpropyl)carbamoyl]benzoic acid methanesulfonate

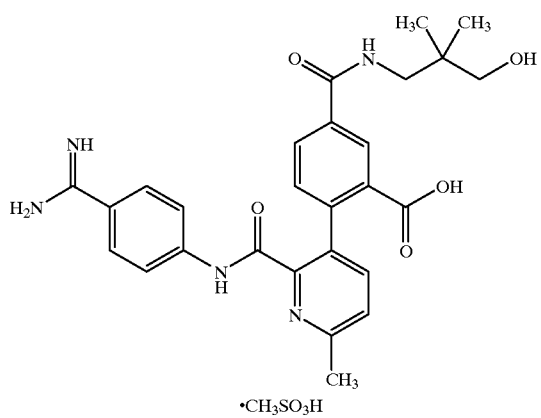

TLC:Rf 0.25 (Chloroform:Methanol:Water=7:3:0.3); NMR (d$_6$-DMSO): δ 10.86 (s, 1H), 9.22 (brs, 2H), 8.97 (brs, 2H), 8.66 (brt, J=6.5 Hz, 1H), 8.41 (d, J=1.8 Hz, 1H), 8.04 (dd, J=8.0, 1.8 Hz, 1H), 7.93 (d, J=8.7 Hz, 2H), 7.79 (d, J=8.7 Hz, 2H), 7.64 (d, J=8.0 Hz, 1H), 9.56 (d, J=8.0 Hz, 1H), 7.31 (d, J=8.0 Hz, 1H), 3.19 (d, J=6.5 Hz, 2H), 3.15 (s, 2H), 2.67 (s, 3H), 2.38 (s, 3H), 0.84 (s, 6H).

EXAMPLE 41(11)

2-[2-(4-amidinophenylcarbamoyl)-3-pyridyl]-5-[(1,2,2-trimethylpropyl) carbamoyl]benzoic acid methanesulfonate

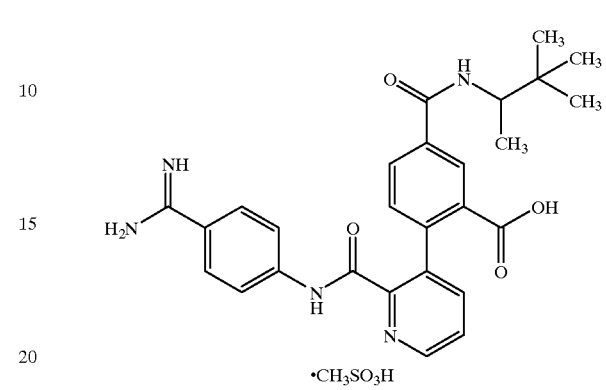

TLC:Rf 0.36 (Chloroform:Methanol:Acetic acid=10:2:1); NMR (d$_6$-DMSO): δ 11.00 (s, 1H), 9.20 (br.s, 2H), 8.93 (br.s, 2H), 8.73 (dd, J=4.8, 2.1 Hz, 1H), 8.40 (d, J=1.8 Hz, 1H), 8.25 (d, J=9.6 Hz, 1H), 8.04 (dd, J=7.8, 1.8 Hz, 1H), 7.95 (d, J=9.0 Hz, 2H), 7.77 (d, J=9.0 Hz, 2H), 7.75–7.65 (m, 2H), 7.33 (d, J=7.8 Hz, 1H), 6.5–5.0 (br, 1H), 4.01 (m, 1H), 2.36 (s, 3H), 1.11 (d, J=6.6 Hz, 3H), 0.92 (s, 9H).

EXAMPLE 41(12)

2'-(4-amidinophenylcarbamoyl)-4-[(1(R), 2,2-trimethylpropyl)carbamoyl]-2-biphenylcarboxylic acid methanesulfonate

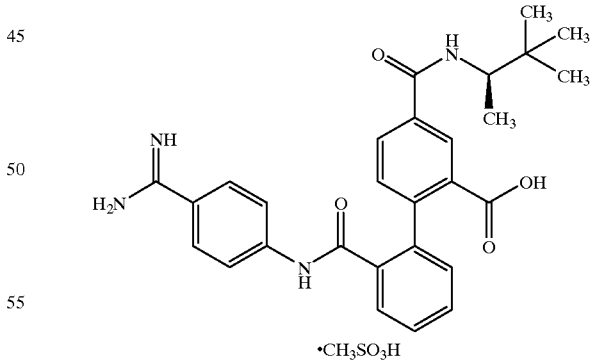

TLC:Rf 0.14 (Chloroform:Methanol:Acetic acid=10:2:1); NMR (d$_6$-DMSO): δ 10.6 (s, 1H), 9.15 (br s, 2H), 8.85 (br s, 2H), 8.26 (d, J=1.8 Hz, 1H), 8.18 (d, J=8.6 Hz, 1H), 7.95 (dd, J=8.0, 1.8 Hz, 1H), 7.73–7.58 (m, 5H), 7.60–7.48 (m, 2H), 7.30 (d, J=8.2 Hz, 1H), 7.28–7.24 (m, 1H), 4.05–3.90 (m, 1H), 2.33 (s, 3H), 1.07 (d, J=6.8 Hz, 3H), 0.89 (s, 9H).

EXAMPLE 41(13)

2'-(4-amidinophenylcarbamoyl)-4-[(1(S), 2,2-trimethylpropyl)carbamoyl]-2-biphenylcarboxylic acid methanesulfonate

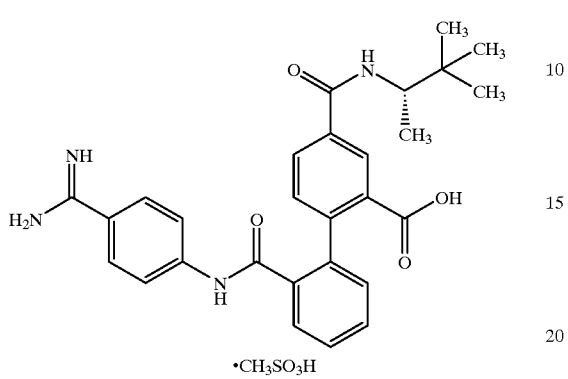

TLC:Rf 0.14 (Chloroform:Methanol:Acetic acid=10:2:1); NMR (d$_6$-DMSO): δ 10.5 (s, 1H), 9.15 (br s, 2H), 8.83 (br s, 2H), 8.26 (d, J=1.8 Hz, 1H), 8.17 (d, J=9.2 Hz, 1H), 7.95 (dd, J=8.0, 1.8 Hz, 1H), 7.73–7.67 (m, 5H), 7.60–7.48 (m, 2H), 7.30 (d, J=8.2 Hz, 1H), 7.28–7.24 (m, 1H), 4.05–3.90 (m, 1H), 2.32 (s, 3H), 1.07 (d, J=6.8 Hz, 3H), 0.89 (s, 9H).

EXAMPLE 41(14)

2-[2-(4-amidinophenylcarbamoyl)-6-methyl-3-pyridyl]-5-[(2,2-dimethylpropyl) carbamoyl]benzoic acid methanesulfonate

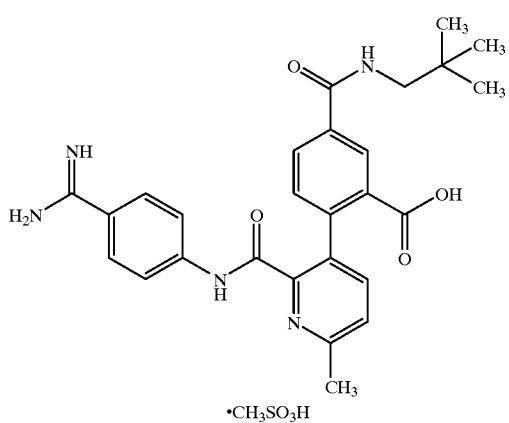

TLC:Rf 0.15 (Chloroform:Methanol:Acetic acid=10:2:1); NMR (d$_6$-DMSO): δ 10.85 (s, 1H), 9.22 (brs, 2H), 8.97 (brs, 2H), 8.61 (brt, J=6.5 Hz, 1H), 8.42 (d, J=2.0 Hz, 1H), 8.04 (dd, J=8.0,2.0 Hz, 1H), 7.93 (d, J=8.7 Hz, 2H), 7.79 (d, J=8.7 Hz, 2H), 7.64 (d, J=7.8 Hz, 1H), 7.55 (d, J=7.8 Hz, 1H), 7.30 (d, J=8.0 Hz, 1H), 3.13 (d, J=6.5 Hz, 2H), 2.67 (s, 3H), 2.37 (s, 3H), 0.91 (s, 9H).

EXAMPLE 41(15)

2-[2-(4-amidinophenylcarbamoyl)-6-methyl-3-pyridyl]-5-[(2,2-dimethylpropyl) carbamoyl]benzoic acid

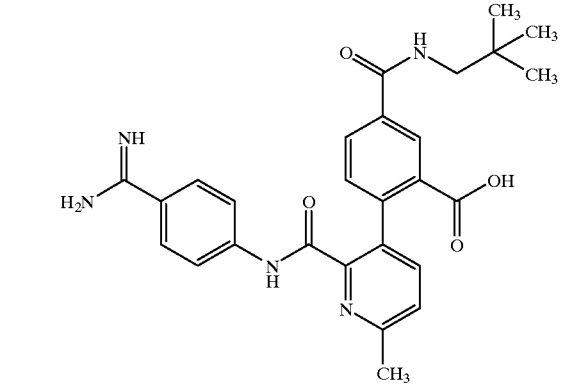

TLC:Rf 0.49 (Chloroform:Methanol:Acetic acid=10:2:1); NMR (300 MHz, DMSO-d$_6$): δ 13.6 (brs, 1H), 9.01 (brs, 4H), 8.38 (brt, J=6.3 Hz, 1H), 8.04 (d, J=1.5 Hz, 1H), 7.64 (dd, J=8.0, 1.5 Hz, 1H), 7.59 (s, 4H), 7.39 (d, J=8.0 Hz, 1H), 7.35 (d, J=8.0 Hz, 1H), 6.98 (d, J=8.0 Hz, 1H), 3.05 (d, J=6.3 Hz, 2H), 2.56 (s, 3H), 0.87 (s, 9H).

EXAMPLE 41(16)

2-[2-(4-amidinophenylcarbamoyl)-6-methyl-3-pyridyl]-5-[(2,2-dimethylpropyl) carbamoyl]benzoic acid dihydrochloride

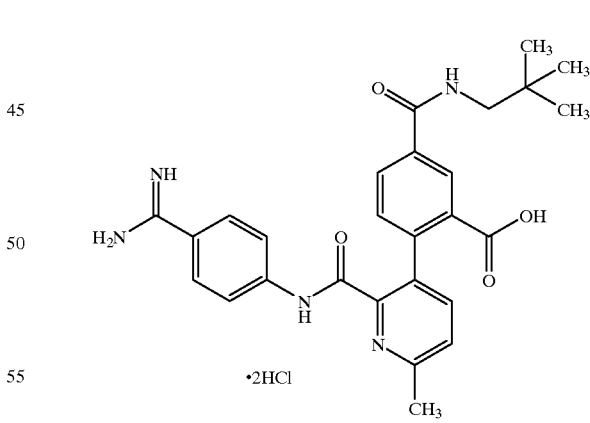

TLC:Rf 0.39 (Chloroform:Methanol:Acetic acid=10:2:1); NMR (300 MHz, DMSO-d$_6$): δ 10.85 (s, 1H), 9.26 (brs, 2H), 9.03 (brs, 2H), 8.61 (brt, J=6.3 Hz, 1), 8.41 (d, J=1.8 Hz, 1H), 8.04 (dd, J=8.0, 1.8 Hz, 1H), 7.93 (d, J=8.7 Hz, 2H), 7.80 (d, J=8.7 Hz, 2H), 7.63 (d, J=8.0 Hz, 1H), 7.55 (d, J=8.0 Hz, 1H), 7.30 (d, J=8.0 Hz, 1H), 3.13 (d, J=6.3 Hz, 2H), 2.67 (s, 3H), 0.91 (s, 9H).

EXAMPLE 41(17)

2-[2-(4-amidinophenylcarbamoyl)-6-methoxy-3-pyridyl]-5-[(2-methylpropyl) carbamoyl]benzoic acid methanesulfonate

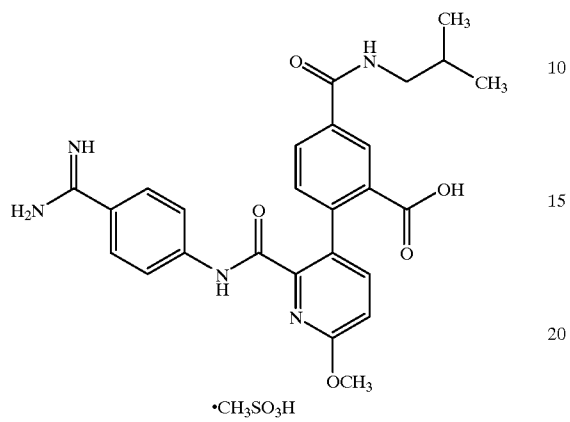

TLC:Rf 0.33 (Chloroform:Methanol:Acetic acid=10:2:1); NMR (d$_6$-DMSO): δ 13.0–12.5 (broad, 1H), 10.61 (s, 1H), 9.21 (brs, 2H), 8.92 (brs, 2H), 8.70 (brt, J=6.0 Hz, 1H), 8.41 (d, J=1.8 Hz, 1H), 8.02 (dd, J=8.0, 1.8 Hz, 1H), 7.90 (d, J=9.0 Hz, 2H), 7.79 (d, J=9.0 Hz, 2H), 7.65 (d, J=8.4 Hz, 1H), 7.30 (d, J=8.0 Hz, 1H), 7.12 (d, J=8.4 Hz, 1H), 4.09 (s, 3H), 3.11 (t, J=6.5 Hz, 2H), 2.34 (s, 3H), 1.94–1.80 (m, 1H), 0.90 (d, J=6.5 Hz, 6H).

EXAMPLE 41(18)

2'-(4-amidinophenylcarbamoyl)-4-(1-methoxycarbonylcyclopentylcarbamoyl)-2-biphenylcarboxylic acid methanesulfonate

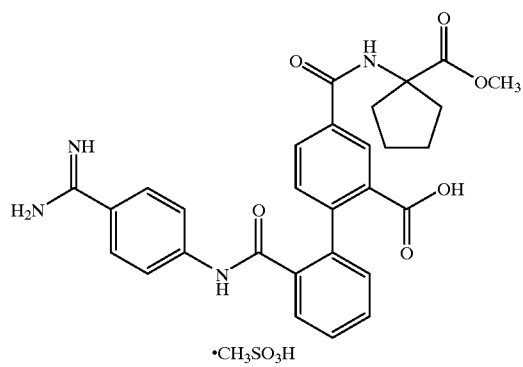

TLC:Rf 0.21 (Chloroform:Methanol:Acetic acid=10:2:1); NMR (d$_6$-DMSO): δ 10.6 (s, 1H), 9.15 (br s, 2H), 8.87 (s, 1H), 8.83 (br s, 2H), 8.30 (d, J=1.8 Hz, 1H), 7.97 (dd, J=8.0, 1.8 Hz, 1H), 7.73–7.68 (m, 5H), 7.63–7.48 (m, 2H), 7.32 (d, J=8.0 Hz, 1H), 7.30–7.24 (m, 1H), 3.57 (s, 3H), 2.32 (s, 3H), 2.20–2.00 (m, 4H), 1.80–1.60 (m, 4H).

EXAMPLE 41(19)

2-[4-(4-amidinophenylcarbamoyl)-3-pyridyl]-5-[(1(S)-hydroxymethyl-2-methyl propyl)carbamoyl]benzoic acid methanesulfonate

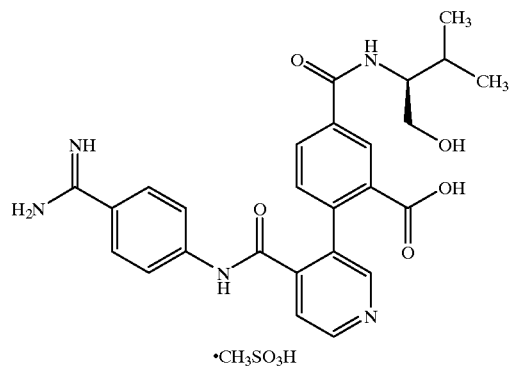

TLC:Rf 0.12 (Chloroform:Methanol:Water=7:3:0.3); NMR (d$_6$-DMSO): δ 11.04 (s, 1H), 9.23 (brs, 2H), 8.99 (brs, 2H), 8.88 (d, J=5.4 Hz, 1H), 8.70 (s, 1H), 8.42 (d, J=1.8 Hz, 1H), 8.28 (d, J=9.0 Hz, 1H), 8.07 (dd, J=8.0, 1.8 Hz, 1H), 7.90 (d, J=5.4 Hz, 1H), 7.77 (d, J=9.3 Hz, 2H), 7.73 (d, J=9.3 Hz, 2H), 7.46 (d, J=8.0 Hz, 1H), 3.86–3.76 (m, 1H), 3.56–3.45 (m, 2H), 2.36 (s, 3H), 1.98–1.82 (m, 1H), 0.90 (d, J=6.9 Hz, 3H), 0.86 (d, J=6.9 Hz, 3H).

EXAMPLE 41(20)

2-[2-(4-amidinophenylcarbamoyl)-6-methyl-3-pyridyl]-5-[(1(S)-hydroxymethyl-2-methylpropyl)carbamoyl]benzoic acid methanesulfonate

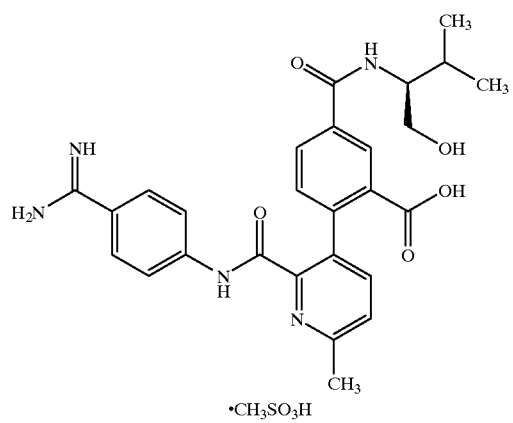

TLC:Rf 0.19 (Chloroform:Methanol:Water=7:3:0.3); NMR (d$_6$-DMSO): δ 10.85 (s, 1H), 9.22 (brs, 2H), 8.97 (brs, 2H), 8.43 (d, J=1.8 Hz, 1H), 8.25 (d, J=9.0 Hz, 1H), 8.06 (dd, J=8.0, 1.8 Hz, 1H), 7.93 (d, J=9.0 Hz, 2H), 7.79 (d, J=9.0 Hz, 2H), 7.63 (d, J=8.0 Hz, 1H), 7.55 (d, J=8.0 Hz, 1H), 7.30 (d, J=8.0 Hz, 1H), 3.90–3.80 (m, 1H), 3.58–3.48 (m, 2H), 2.67 (s, 3H), 2.37 (s, 3H), 2.01–1.86 (m, 1H), 0.92 (d, J=6.9 Hz, 3H), 0.89 (d, J=6.6 Hz, 3H).

EXAMPLE 41(21)

2-[2-(4-amidinophenylcarbamoyl)-3-pyridyl]-5-[(1(S)-hydroxymethyl-2-methyl propyl)carbamoyl]benzoic acid methanesulfonate

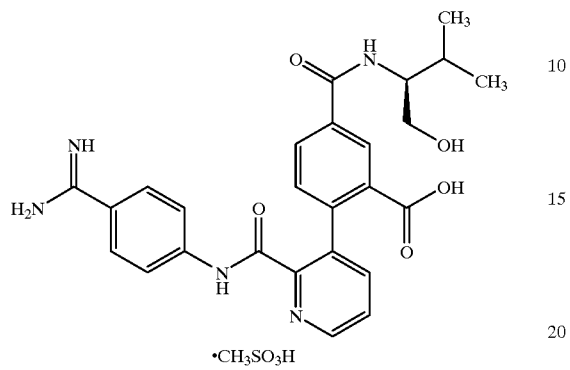

TLC:Rf 0.45 (Chloroform:Methanol:Acetic acid=10:2:1); NMR (d$_6$-DMSO): δ 11.00 (s, 1H), 9.19 (s, 2H), 8.90 (s, 2H), 8.73 (dd, J=4.5, 1.8 Hz, 1H), 8.44 (d, J=1.8 Hz, 1H), 8.25 (br.d, J=8.7 Hz, 1H), 8.08 (dd, J=8.0, 1.8 Hz, 1H), 7.95 (d, J=8.7 Hz, 2H), 7.76 (d, J=8.7 Hz, 2H), 7.80–7.65 (m, 2H), 7.33 (d, J=8.0 Hz, 1H), 4.80–4.20 (br, 2H), 3.86 (m, 1H), 3.60–3.50 (m, 2H), 2.34 Hz, 3H), 1.94 (like sextet, J=7.0 Hz, 1H), 0.93 (d, J=7.0 Hz, 3H), 0.90 (d, J=7.0 Hz, 3H).

EXAMPLE 41(22)

2'-(4-amidinophenylcarbamoyl)-4-[(2-methoxycarbonyl-2,2-dimethylethyl) carbamoyl]-2-biphenylcarboxylic acid methanesulfonate

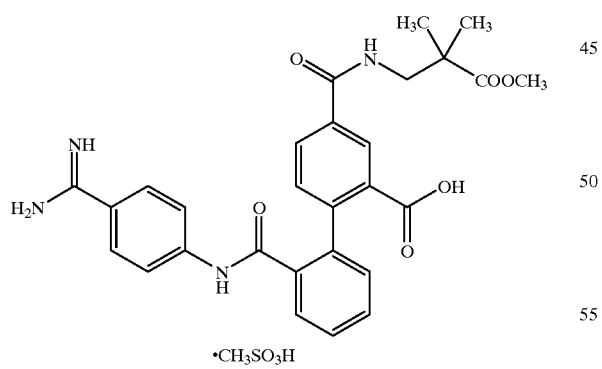

TLC:Rf 0.25 (Chloroform:Methanol:Acetic acid=10:2:1); NMR (300 MHz, d$_6$-DMSO): δ 10.6 (s, 1H), 9.15 (br s, 2H), 8.83 (br s, 2H), 8.61 (t, J=6.3 Hz, 1H), 8.25 (d, J=1.5 Hz, 1H), 7.92 (dd, J=8.1, 1.5 Hz, 1H), 7.72–7.68 (m, 5H), 7.65–7.50 (m, 2H), 7.32 (d, J=8.1 Hz, 1H), 7.27 (dd, J=7.2, 1.5 Hz, 1H), 3.58 (s, 3H), 3.42 (d, J=6.3 Hz, 2H), 2.31 (s, 3H), 1.13 (s, 6H).

EXAMPLE 41(23)

2-[2-(4-amidinophenylcarbamoyl)-6-methyl-3-pyridyl]-5-[(1(S)-methoxycarbonyl-2-methylpropyl)carbamoyl]benzoic acid

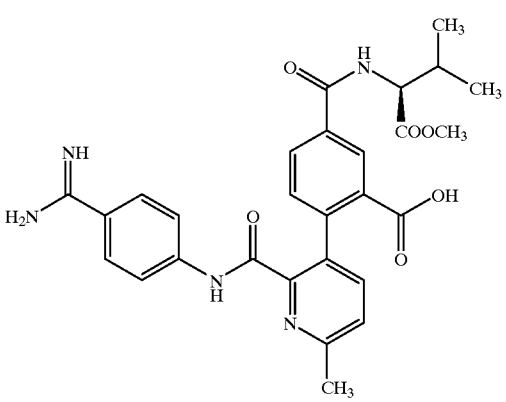

TLC:Rf 0.39 (Chloroform:Methanol:Acetic acid=10:2:1); NMR (300 MHz, CD$_3$OD): δ 8.51 (d, J=1.8 Hz, 1H), 8.03 (dd, J=8.0, 1.8 Hz, 1H), 7.88 (d, J=9.0 Hz, 2H), 7.76 (d, J=9.0 Hz, 2H), 7.61 (d, J=8.3 Hz, 1H), 7.52 (d, J=8.3 Hz, 1H), 7.34 (d, J=8.0 Hz, 1H), 4.53 (d, J=6.9 Hz, 1H), 3.77 (s, 3H), 2.70 (s, 3H), 2.37–2.21 (m, 1H), 1.06 (d, J=6.9 Hz, 3H), 1.04 (d, J=3H).

EXAMPLE 41(24)

2-[4-(4-amidinophenylcarbamoyl)-3-pyridyl]-5-[(1(S)-methoxycarbonyl-2-methylpropyl)carbamoyl]benzoic acid

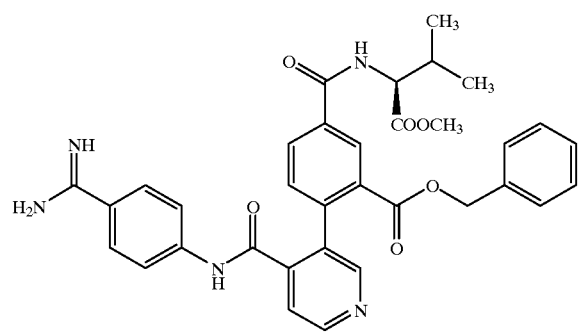

TLC:Rf 0.39 (Chloroform:Methanol:Acetic acid=10:2:1); NMR (300 MHz, CD$_3$OD): δ 8.73 (d, J=5.4 Hz, 1H), 8.51 (s, 1H), 8.42 (d, J=1.8 Hz, 1H), 8.00 (dd, J=8.1, 1.8 Hz, 1H), 7.71 (s, 4H), 7.70 (d, J=5.4 Hz, 1H), 7.44 (d, J=8.1 Hz, 1H), 4.48 (d, J=6.9 Hz, 1H), 3.74 (s, 3H), 2.33–2.16 (m, 1H), 1.03 (d, J=6.9 Hz, 3H), 1.01 (d, J=6.6 Hz, 3H).

EXAMPLE 41(25)

2'-(4-amidino-3-hydroxyphenylcarbamoyl)-4-(2-methylpropylcarbamoyl)-2-biphenylcarboxylic acid methanesulfonate

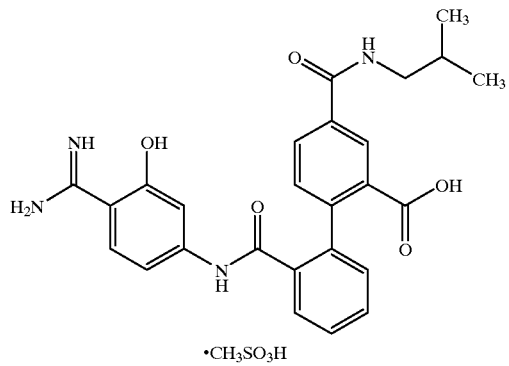

TLC:Rf 0.60 (Chloroform:Methanol:Water=7:3:0.3); NMR ($d_6$-DMSO): δ 11.15 (s, 1H), 10.39 (s, 1H), 8.79 (s, 2H), 8.66 (t, J=6.0 Hz, 1H), 8.61 (s, 2H), 8.32 (d, J=1.8 Hz, 1H), 7.96 (dd, J=8.0, 1.8 Hz, 1H), 7.68 (dd, J=8.0, 1.8 Hz, 1H), 7.59–7.52 (m, 3H), 7.48 (d, J=8.0 Hz, 1H), 7.31 (d, J=8.0 Hz, 1H), 7.26 (dd, J=8.0, 1.8 Hz, 1H), 7.00 (dd, J=8.0, 1.8 Hz, 1H), 3.10 (t, J=6.0 Hz, 2H), 2.34 (s, 3H), 1.86 (m, 1H), 0.89 (d, J=6.3 Hz, 6H).

EXAMPLE 41(26)

2'-(4-amidino-3-hydroxyphenylcarbamoyl)-4-(1,2,2-trimethylpropylcarbamoyl)-2-biphenylcarboxylic acid methanesulfonate

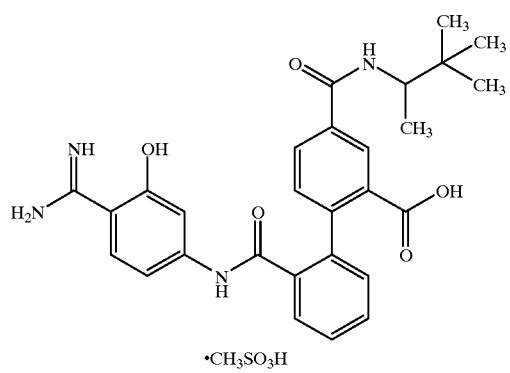

TLC:Rf 0.68 (Chloroform:Methanol:Water=7:3:0.3); NMR ($d_6$-DMSO): δ 11.14 (br.s, 1H), 10.42 (s, 1H), 8.79 (s, 2H), 8.54 (s, 2H), 8.29 (s, 1H), 8.18 (d, J=9.0 Hz, 1H), 7.95 (d, J=8.0 Hz, 1H), 7.68 (d, J=8.0 Hz, 1H), 7.58–7.52 (m, 3H), 7.48 (d, J=8.0 Hz, 1H), 7.30 (d, J=8.0 Hz, 1H), 7.25 (d, J=8.0 Hz, 1H), 7.01 (d, J=8.0 Hz, 1H), 4.00 (m, 1H), 2.31 (s, 3H), 1.09 (d, J=7.0 Hz, 3H), 0.91 (s, 9H).

EXAMPLE 41(27)

2'-(4-amidinophenylcarbamoyl)-4-(1,3-dimethylbutylcarbamoyl)-2-biphenyl carboxylic acid methanesulfonate

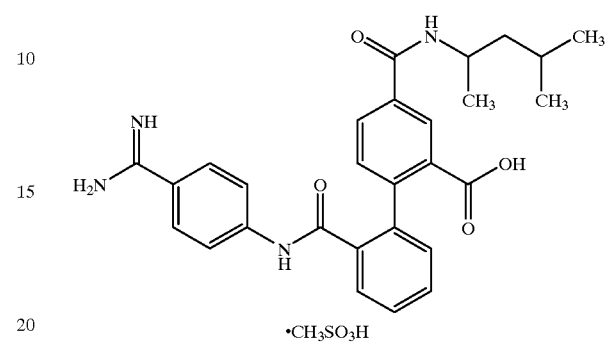

TLC:Rf 0.27 (Chloroform:Methanol:Water=7:3:0.3); NMR ($d_6$-DMSO): δ 12.84 (br, 1H), 10.53 (s, 1H), 9.15 (s, 2H), 8.82 (s, 2H), 8.34 (d, J=8.4 Hz, 1H), 8.30 (d, J=1.5 Hz, 1H), 7.96, (dd, J=7.8, 1.5 Hz, 1H), 7.74 (dd, J=6.9, 1.5 Hz, 1H), 7.73 (s, 4H), 7.58 (dt, J=6.0, 1.8 Hz, 1H), 7.53 (dt, J=7.8, 1.8 Hz, 1H), 7.32 (d, J=8.4 Hz, 1H), 7.27 (d, J=7.8 Hz, 1H), 4.13 (m, 1H), 2.35 (s, 3H), 1.68–1.48 (m, 2H), 1.24 (m, 1H), 1.13 (d, J=6.3 Hz, 3H), 0.8 (d, J=6.3 Hz, 6H)

EXAMPLE 41(28)

2'-(4-amidinophenylcarbamoyl)-4-(2,2-dimethyl-1(R)-cyclopentylcarbamoyl)-2-biphenylcarboxylic acid methanesulfonate

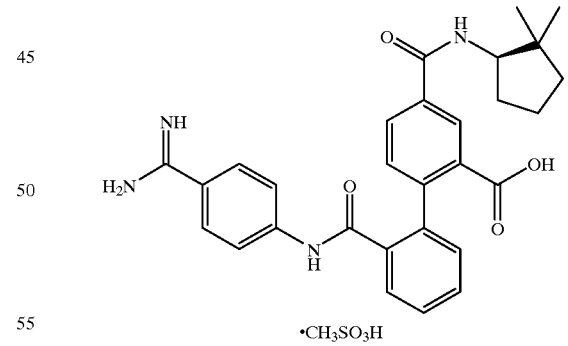

TLC:Rf 0.30 (Chloroform:Methanol:Acetic acid=10:2:1); NMR ($d_6$-DMSO): δ 13.0–12.0 (br, 1H), 10.54 (s, 1H), 9.14 (s, 2H), 8.83 (s, 2H), 8.27 (d, J=1.8 Hz, 1H), 8.19 (d, J=8.7 Hz, 1H), 7.95 (dd, J=9.7, 1.8 Hz, 1H), 7.72 (m, 5H), 7.55 (td, J=7.8, 1.5 Hz, 1H), 7.54 (td, J=7.8, 1.5 Hz, 1H), 7.31 (d, J=9.7 Hz, 1H), 7.26 (dd, J=7.8,1.5 Hz, 1H), 4.08 (q, J=8.7 Hz, 1H), 2.33 (s, 3H), 1.90 (m, 1H), 1.74–1.40 (m, 5H), 0.98 (s, 3H), 0.87 (s, 3H)

EXAMPLE 41(29)

2-[2-(4-amidinophenylcarbamoyl)-3-pyridyl]-5-[(1(S)-carboxy-2-methylpropyl) carbamoyl]benzoic acid methanesulfonate

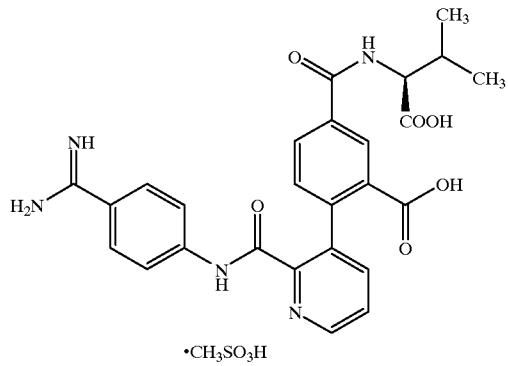

TLC:Rf 0.60 (Ethyl acetate:Acetic acid:Water=3:1:0.5); NMR (d$_6$-DMSO): δ 11.01 (s, 1H), 9.20 (br.s, 2H), 8.95 (br.s, 2H), 8.80–8.70 (m, 2H), 8.47 (d, J=1.8 Hz, 1H), 8.10 (dd, J=7.8, 1.8 Hz, 1H), 7.96 (d, J=8.8 Hz, 2H), 7.77 (d, J=8.8 Hz, 2H), 7.80–7.65 (m, 2H), 7.35 (d, J=7.8 Hz, 1H), 6.40–4.40 (br, 2H), 4.33 (t, J=7.4 Hz, 1H), 2.37 (s, 3H), 2.22 (like sextet, J=7.4 Hz, 1H), 0.99 (d, J=7.4 Hz, 3H), 0.98 (d, J=7.4 Hz, 3H).

EXAMPLE 41(30)

2-[3-(4-amidinophenylcarbamoyl)-2-furyl]-5-(2-methylpropylcarbamoyl)benzoic acid methanesulfonate

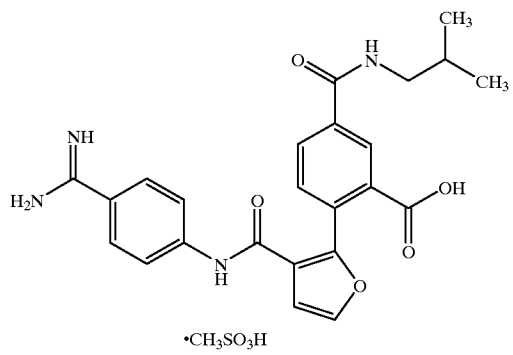

TLC:Rf 0.39 (Chloroform:Methanol:Water=7:3:0.3); NMR (d$_6$-DMSO): δ 13.0 (brs, 1H), 10.29 (s, 1H), 9.20 (brs, 2H), 8.89 (brs, 2H), 8.74 (brt, J=6.0 Hz, 1H), 8.32 (d, J=2.0 Hz, 1H), 8.05 (dd, J=8.0, 2.0 Hz, 1H), 7.91 (d, J=8.7 Hz, 2H), 7.89 (d, J=2.0 Hz, 1H), 7.79 (d, J=8.7 Hz, 2H), 7.69 (d, J=8.0 Hz, 1H), 7.29 (d, J=2.0 Hz, 1H), 3.11 (brt, J=6.5 Hz, 2H), 2.33 (s, 3H), 1.94–1.79 (m, 1H), 0.90 (d, J=6.5 Hz, 6H).

EXAMPLE 41(31)

2-[2-(4-amidinophenylcarbamoyl)-3-thienyl]-5-(2-methylpropylcarbamoyl) benzoic acid methanesulfonate

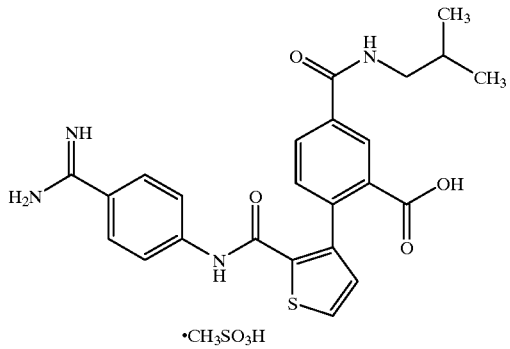

TLC:Rf 0.56 (Chloroform:Methanol:Water 7:3:0.3); NMR (d$_6$-DMSO): δ 12.9 (brs, 1H), 10.18 (s, 1H), 9.18 (brs, 2H), 8.87 (brs, 2H), 8.67 (brt, J=6.0 Hz, 1H), 8.30 (d, J=2.0 Hz, 1H), 8.00 (dd, J=8.0, 2.0 Hz, 1H), 7.84 (d, J=5.0 Hz, 1H), 7.75 (d, J=9.3 Hz, 2H), 7.70 (d, J=9.3 Hz, 2H), 7.41 (d, J=8.0 Hz, 1H), 7.11 (d, J=5.0 Hz, 1H), 3.09 (brt, J=6.5 Hz, 2H), 2.32 (s, 3H), 1.92–1.78 (m, 1H), 0.89 (d, J=6.5 Hz, 6H).

EXAMPLE 41(32)

2'-(4-amidinophenylcarbamoyl)-4-[(1-methoxycarbonyl-1-methylethyl) carbamoyl]-2-biphenylcarboxylic acid

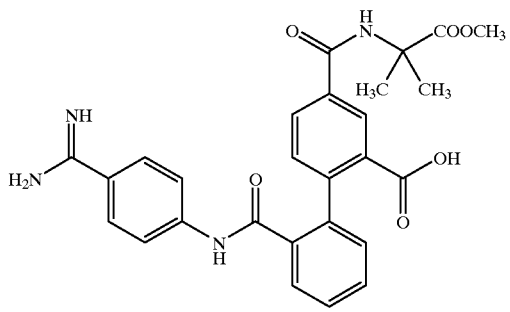

TLC:Rf 0.25 (Chloroform:Methanol:Acetic acid=20:2:1); NMR (300 MHz, DMSO-d$_6$): δ 12.82 (brs, 1H), 10.56 (s, 1H), 9.15 (s, 2H), 8.84 (s, 2H), 8.82 (s, 1H), 8.31 (d, J=2.0 Hz, 1H), 7.98 (dd, J=8.1, 2.0 Hz, 1H), 7.74 (s, 2H), 7.67 (dd, J=6.6, 2.0 Hz, 1H), 7.59 (dt, J=7.2, 2.0 Hz, 1H), 7.53 (dt, J=7.2, 2.0 Hz, 1H), 7.33 (d, J=8.1 Hz, 1H), 7.28 (dd, J=7.8, 2.0 Hz, 1H), 3.59 (s, 3H), 2.34 (s, 3H), 1.47 (s, 6H).

EXAMPLE 41(33)

2'-(4-amidinophenylcarbamoyl)-4-(1(S)-carboxy-3-methylbutylcarbamoyl)-2-biphenylcarboxylic acid methanesulfonate

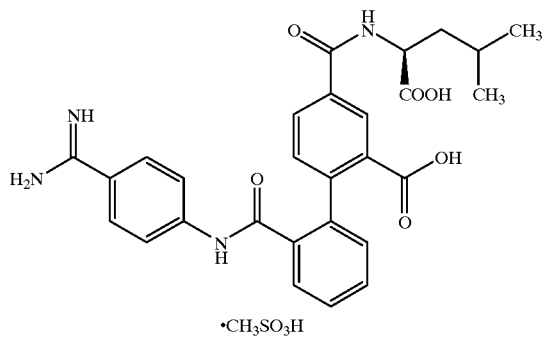

TLC:Rf 0.56 (Chloroform:Methanol:Water=6:4:1); NMR (d$_6$-DMSO): δ 12.79 (br, 2H), 10.54 (s, 1H), 9.14 (s, 2H), 8.81 (d, J=8.4 Hz, 1H), 8.77 (s, 2H), 8.:35 (d, J=1.8 Hz, 1H), 8.01 (dd, J=7.8, 1.8 Hz, 1H), 7.73 7.70, (m, 5H), 7.63 (dt, J=7.8, 1.2 Hz, 1H), 7.54 (dt, J=6.6, 1.8 Hz, 1H), 7.35 J=7.8 Hz, 1H), 7.29 (dd, J=6.6, 1.8 Hz, 1H), 4.45 (m, 1H), 1.82–1.55 (m, 3H), 0.92 (d, J=6.6 Hz, 3H), 0.88 (d, J=6.0 Hz, 3H)

EXAMPLE 41(34)

2-[2-(4-amidinophenylcarbamoyl)-3-pyridyl]-5-(2,2-dimethylpropylcarbamoyl) benzoic acid methanesulfonate

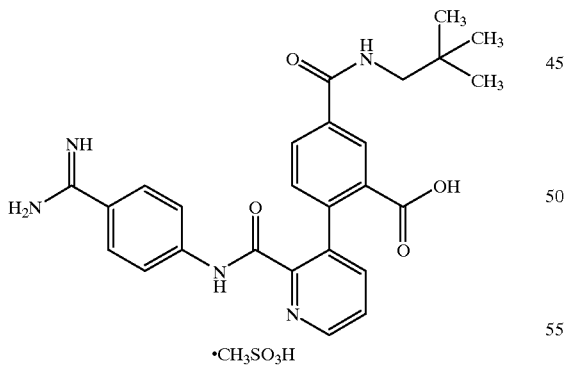

TLC:Rf 0.35 (Chloroform:Methanol:Acetic acid=10:2:1); NMR (d$_6$-DMSO): δ 11.00 (s, 1H), 9.18 (s, 2H), 8.86 (s, 2H), 8.73 (dd, J=4.8, 2.1 Hz, 1H), 8.61 (br.t, J=6.6 Hz, 1H), 8.43 (d, J=1.8 Hz, 1H), 8.06 (dd, J=7.8, 1.8 Hz, 1H), 7.95 (d, J=9.0 Hz, 2H), 7.76 (d, J=9.0 Hz, 2H), 7.80–7.65 (m, 2H), 7.34 (d, J=7.8 Hz, 1H), 3.90–3.70 (br, 1H), 3.14 (d, J=6.6 Hz, 2H), 2.34 (s, 3H), 0.92 (s, 9H).

EXAMPLE 41(35)

2-[2-(4-amidinophenylcarbamoyl)-6-methoxy-3-pyridyl]-5-(2,2-dimethylpropyl carbamoyl)benzoic acid methanesulfonate

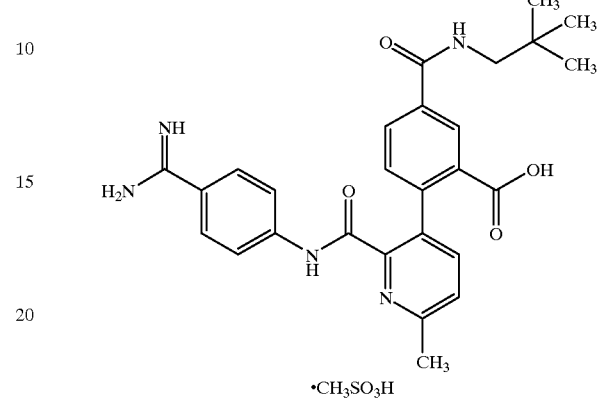

TLC:Rf 0.40 (Chloroform:Methanol:Acetic acid=10:2:1); NMR (d$_6$-DMSO): δ 12.9–12.5 (broad, 1H), 10.61 (s, 1H), 9.19 (brs, 2H), 8.90 (brs, 2H), 8.59 (brt, J=6.3 Hz, 1H), 8.41 (d, J=1.8 Hz, 1H), 8.02 (dd, J=8.0, 1.8 Hz, 1H), 7.90 (d, J=9.0 Hz, 2H), 7.78 (d, J=9.0 Hz, 2H), 7.65 (d, J=8.4 Hz, 1H), 7.30 (d, J=8.0 Hz, 1H), 7.12 (d, J=8.4 Hz, 1H), 4.09 (s, 3H), 3.13 (brd, J=6.3 Hz, 2H), 2.34 (s, 3H), 0.91 (s, 9H).

EXAMPLE 41(36)

2'-(4-amidinophenylcarbamoyl)-4-(2,2-dimethyl-1(S)-cyclopentylcarbamoyl)-2-biphenylcarboxylic acid methanesulfonate

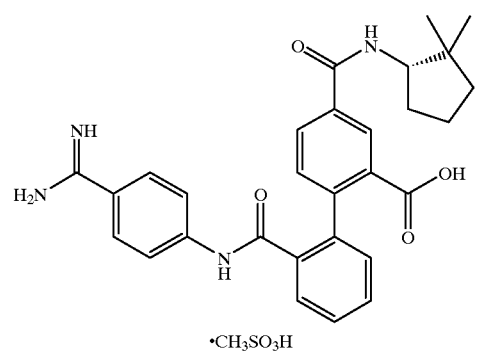

TLC:Rf 0.30 (Chloroform:Methanol:Acetic acid=10:2:1); NMR (d$_6$-DMSO): δ 13.0–12.6 (br, 1H), 10.54 (s, 1H), 9.13 (s, 2H), 8.80 (s, 2H), 8.27 (d, J=1.8 Hz, 1H), 8.18 (d, J=8.7 Hz, 1H), 7.95 (dd, J=8.1, 1.8 Hz, 1H), 7.72 (m, 4H), 7.69 (dd, J=6.9, 1.2 Hz, 1H), 7.57 (td, J=6.9, 1.2 Hz, 1H), 7.52 (td, J=6.9, 1.2 Hz, 1H), 7.31 (d, J=8.1 Hz, 1H), 7.26 (dd, J=6.9, 1.2 Hz, 1H), 4.08 (q, J=8.7 Hz, 1H), 2.31 (s, 3H), 1.90 (m, 1H), 1.80–1.40 (m, 5H), 0.97 (s, 3H), 0.87 (s, 3H).

EXAMPLE 41(37)

2-[3-(4-amidinophenylcarbamoyl)-2-thienyl]-5-(2,2-dimethylpropylcarbamoyl) benzoic acid methanesulfonate

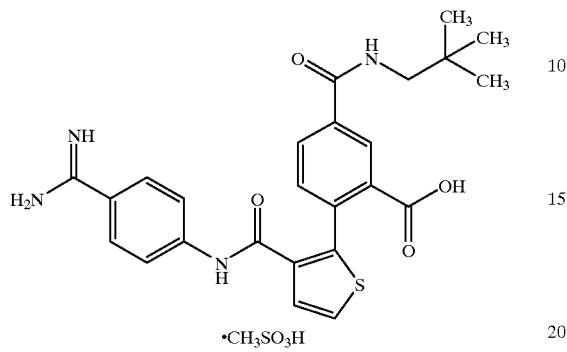

TLC:Rf 0.21 (Chloroform:Methanol:Acetic acid=10:2:1); NMR (d$_6$-DMSO): δ 13.2–12.6 (br, 1H), 10.31 (s, 1H), 9.16 (s, 2H), 8.82 (s, 2H), 8.59 (br.t, J=6.3 Hz, 1H), 8.31 (d, J=1.8 Hz, 1H), 8.01 (dd, J=8.0, 1.8 Hz, 1H), 7.82 (d, J=8.7 Hz, 2H), 7.75 (d, J=8.7 Hz, 2H), 7.73 (d, J=5.4 Hz, 1H), 7.64 (d, J=5.4 Hz, 1H), 7.49 (d, J=8.0 Hz, 1H), 3.12 (d, J=6.3 Hz, 2H), 2.32 (s, 3H), 0.90 (s, 9H).

EXAMPLE 41(38)

2-[2-(4-amidinophenylcarbamoyl)-3-thienyl]-5-(2,2-dimethylpropylcarbamoyl) benzoic acid methanesulfonate

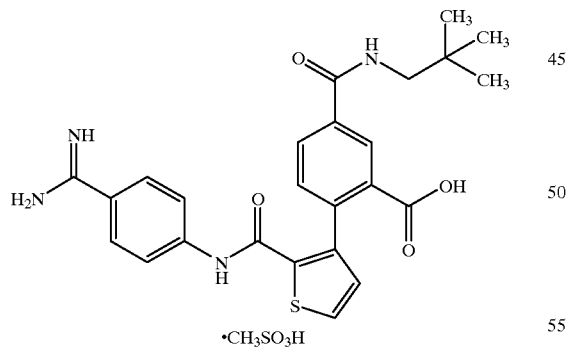

TLC:Rf 0.21 (Chloroform:Methanol:Acetic acid=10:2:1); NMR (d$_6$-DMSO): δ 13.0–12.4 (br, 1H), 10.18 (s, 1H), 9.16 (s, 2H), 8.84 (s, 2H), 8.57 (br.t, J=6.6 Hz, 1H), 8.30 (d, J=1.8 Hz, 1H), 8.01 (dd, J=8.0, 1.8 Hz, 1H), 7.84 (d, J=5.1 Hz, 1H), 7.74 (d, J=9.0 Hz, 2H), 7.70 (d, J=9.0 Hz, 2H), 7.42 (d, J=8.0 Hz, 1H), 7.12 (d, J=5.1 Hz, 1H), 3.12 (d, J=6.6 Hz, 2H), 2.32 (s, 3H), 0.90 (s, 9H).

EXAMPLE 41(39)

2-[4-(4-amidinophenylcarbamoyl)-3-pyridyl]-5-(2,2-dimethylpropylcarbamoyl) benzoic acid methanesulfonate

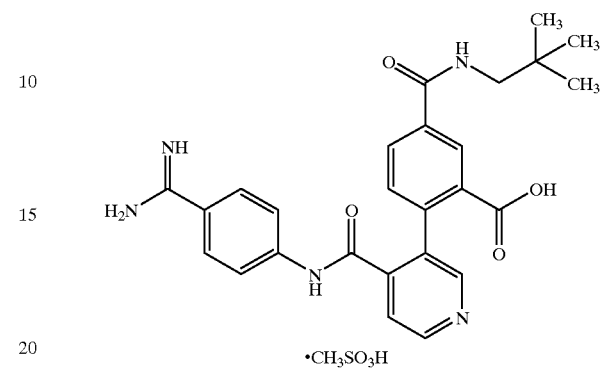

TLC:Rf 0.60 (Chloroform:Methanol:Water=a7:3:0.3); NMR (d$_6$-DMSO): δ 10.96 (s, 1H), 9.21 (s, 2H), 8.93 (s, 2H), 8.86 (d, J=5.1 Hz, 1H), 8.66 (s, 1H), 8.62 (t, J=6.2 Hz, 1H), 8.41 (d, J=1.8 Hz, 1H), 8.06 (dd, J=8.1, 2.1 Hz, 1H), 7.85 (d, J=5.1 Hz, 1H), 7.76 (s, 4H), 7.46 (d, J=8.1 Hz, 1H), 3.12 (d, J=6.2 Hz, 1H), 2.37 (s, 3H), 0.91 (s, 9H).

EXAMPLE 41(40)

2-[2-(4-amidinophenylcarbamoyl)-5-methyl-3-thienyl]-5-(2,2-dimethylpropyl carbamoyl)benzoic acid methanesulfonate

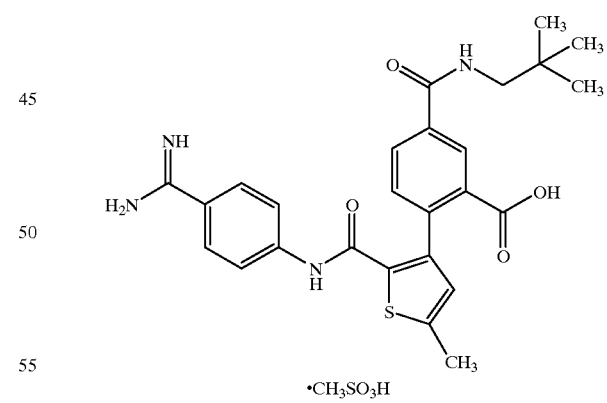

TLC:Rf 0.61 (Chloroform:Methanol:Acetic acid=10:2:1); NMR (d$_6$-DMSO): δ 12.87 (br, 1H), 9.97 (s, 1H), 9.15 (s, 2H), 8.80 (s, 2H), 8.56 (t, J=6.6 Hz, 1H), 8.28 (d, J=1.5 Hz, 1H), 8.00 (dd, J=8.0, 1.5 Hz, 1H), 7.73 (d, J=9.0 Hz, 2H), 7.67 (d, J=9.0 Hz, 2H), 7.39 (d, J=8.0 Hz, 1H), 6.85 (s, 1H), 3.11 (d, J=6.6 Hz, 2H), 2.54 (s, 3H), 2.31 (s, 3H), 0.90 (s, 9H).

EXAMPLE 41(41)

2'-(4-amidinophenylcarbamoyl)-4'-amino-4-(2,2-dimethylpropylcarbamoyl)-2-biphenylcarboxylic acid dimethanesulfonate

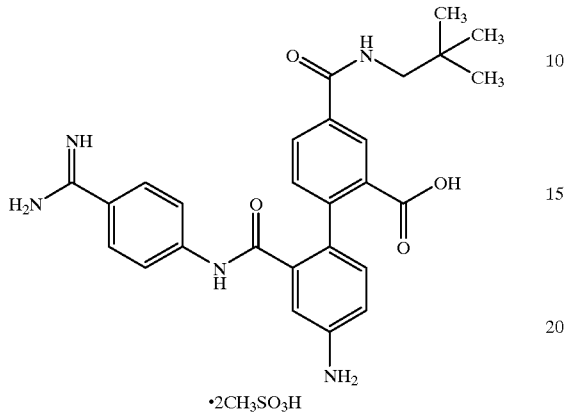

TLC:Rf 0.35 (Chloroform:Methanol:Water=7:3:0.3); NMR (d$_6$-DMSO): δ 10.49 (s, 1H), 9.13 (s, 2H), 8.78 (s, 2H), 8.50 (br.t, J=6.3 Hz, 1H), 8.24 (d, J=1.8 Hz, 1H), 7.92 (dd, J=8.0,1.8 Hz, 1H), 7.71 (s, 4H), 7.29 (d, J=8.0 Hz, 1H), 7.11–7.01 (m, 3H), 3.10 (d, J=6.3 Hz, 2H), 2.35 (s, 6H), 0.89 (s, 9H).

EXAMPLE 41(42)

2-[2-(4-amidinophenylcarbamoyl)-5-methyl-3-furyl]-5-(2,2-dimethylpropyl carbamoyl)benzoic acid methanesulfonate

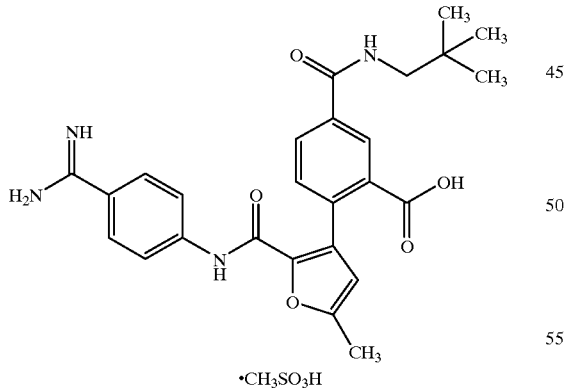

TLC:Rf 0.29 (Chloroform:Methanol:Acetic acid=10:2:1); NMR (d$_6$-DMSO): δ 13.0–12.4 (br, 1H), 10.42 (s, 1H), 9.18 (s, 2H), 8.87 (s, 2H), 8.57 (br.t, J=6.6 Hz, 1H), 8.33 (d, J=1.5 Hz, 1H), 8.00 (dd, J=7.8, 1.5 Hz, 1H), 7.93 (d, J=9.0 Hz, 2H), 7.77 (d, J=9.0 Hz, 2H), 7.45 (d, J=7.8 Hz, 1H), 6.43 (s, 1H), 3.13 (d, J=6.6 Hz, 2H), 2.46 (s, 3H), 2.33 (s, 3H), 0.91 (s, 9H).

EXAMPLE 41(43)

2-[4-(4-amidinophenylcarbamoyl)-2-methyl-pyrimidin-5-yl]-5-(2,2-dimethylpropyl carbamoyl)benzoic acid methanesulfonate

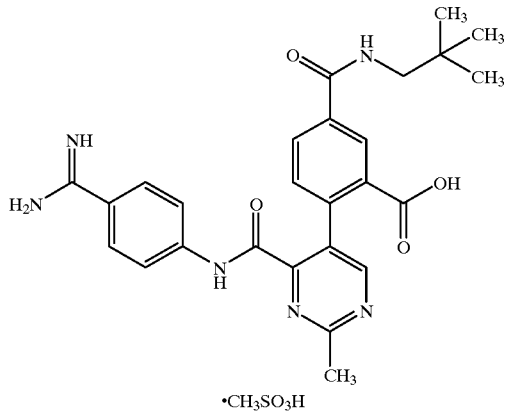

TLC:Rf 0.40 (Chloroform:Methanol:Acetic acid=10:2:1); NMR (d$_6$-DMSO): δ 11.02 (s, 1H), 9.20 (brs, 2H), 8.85 (brs, 2H), 8.73 (s, 1H), 8.62 (brt, J=6.5 Hz, 1H), 8.46 (d, J=1.8 Hz, 1H), 8.09 (dd, J=8.0, 1.8 Hz, 1H), 7.91 (d, J=9.0 Hz, 2H), 7.78 (d, J=9.0 Hz, 2H), 7.43 (d, J=8.0 Hz, 1H), 3.14 (d, J=6.5 Hz, 2H), 2.83 (s, 3H), 2.30 (s, 3H), 0.91 (s, 9H).

EXAMPLE 41(44)

2-[2-(4-amidinophenylcarbamoyl)-6-methyl-3-pyridyl]-5-(1(S)-morpholino carbonyl-3-methylbutylcarbamoyl) benzoic acid methanesulfonate

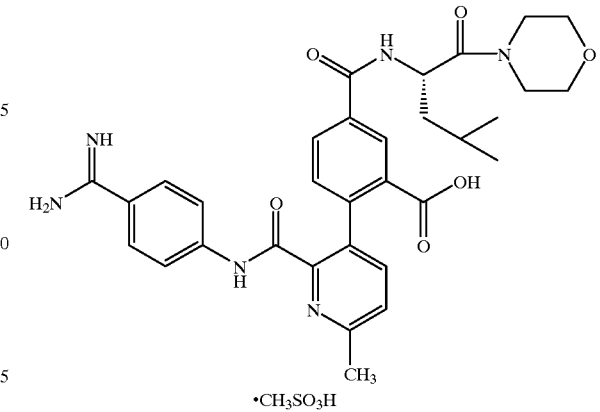

TLC:Rf 0.78 (Chloroform:Methanol:Acetic acid=10:2:1); NMR (d$_6$-DMSO): δ 10.84 (s, 1H), 9.20 (s, 2H), 8.93 (s, 2H), 8.90 (d, J=8.1 Hz, 1H), 8.46 (d, J=1.8 Hz, 1H), 8.08 (dd, J=8.1, 1.8 Hz, 1H), 7.83 (d, J=9.0 Hz, 2H), 7.78 (d, J=9.0 Hz, 2H), 7.64 (d, J=8.1 Hz, 1H), 7.55 (d, J=8.1 Hz, 1H), 7.31 (d, J=8.1 Hz, 1H), 4.97 (m, 1H), 4.46 (br, 1H), 3.7–3.4 (m, 8H), 2.67 (s, 3H), 2.36 (s, 3H), 1.8–1.6 (m, 2H), 1.47 (m, 1H), 0.91 (d, J=6.6 Hz, 3H), 0.91 (d, J=6.6 Hz, 3H).

EXAMPLE 41(45)

2-[2-(4-amidinophenylcarbamoyl)-6-methyl-3-pyridyl]-5-(1(S)-methoxymethyl-2,2-dimethylpropylcarbamoyl)benzoic acid methanesulfonate

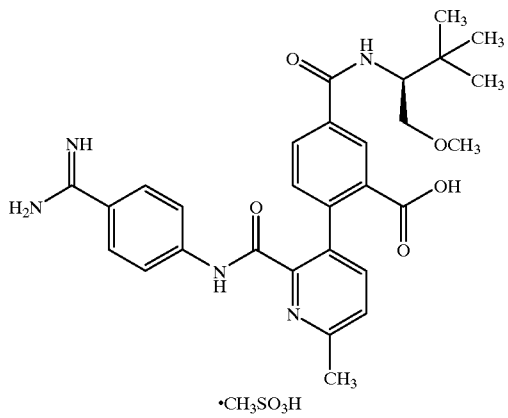

TLC:Rf 0.45 (Chloroform:Methanol:Acetic acid=10:2:1); NMR (d$_6$-DMSO): δ 10.8 (s, 1H), 9.19 (br s, 2H), 8.84 (br s, 2H), 8.41 (d, J=1.8 Hz, 1H), 8.27 (d, J=9.3 Hz, 1H), 8.04 (dd, J=8.1, 1.8 Hz, 1H), 7.93 (d, J=9.0 Hz, 2H), 7.77 (d, J=9.0 Hz, 2H), 7.63 (d, J=7.8 Hz, 1H), 7.56 (d, J=7.8 Hz, 1H), 7.30 (d, J=8.1 Hz, 1H), 4.10 (dt, J=9.3, 3.3 Hz, 1H), 3.70–3.40 (m, 2H), 3.23 (s, 3H), 2.67 (s, 3H), 2.32 (s, 3H), 0.93 (s, 9H).

EXAMPLE 41(46)

2-[2-(4-amidinophenylcarbamoyl)-6-methoxy-3-pyridyl]-5-(1(S)-methoxymethyl-2,2-dimethylpropylcarbamoyl)benzoic acid methanesulfonate

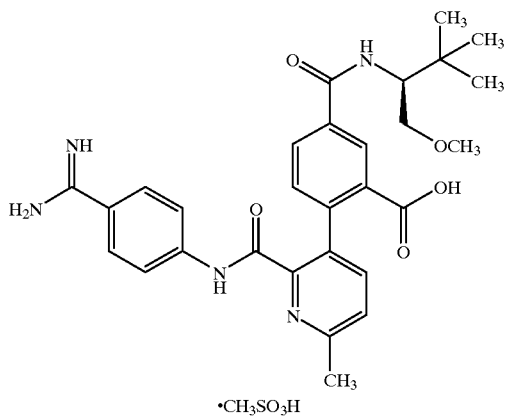

TLC:Rf 0.48 (Chloroform:Methanol:Acetic acid=10:2:1); NMR (d$_6$-DMSO): δ 10.6 (s, 1H), 9.18 (br s, 2H), 8.80 (br s, 2H), 8.40 (d, J=2.1 Hz, 1H), 8.26 (d, J=9.3 Hz, 1H), 8.02 (dd, J=8.1, 2.1 Hz, 1H), 7.90 (d, J=9.0 Hz, 2H), 7.77 (d, J=9.0 Hz, 2H), 7.65 (d, J=8.1 Hz, 1H), 7.30 (d, J=8.1 Hz, 1H), 7.13 (d, J=8.1 Hz, 1H), 4.15–4.05 (m, 1H), 4.09 (s, 3H), 3.59–3.46 (m, 2H), 3.23 (s, 3H), 2.30 (s, 3H), 0.93 (s, 9H).

EXAMPLE 41(47)

2-[2-(4-amidinophenylcarbamoyl)-6-methyl-3-pyridyl]-5-(2,2-dimethylpropyloxy carbonyl)benzoic acid methanesulfonate

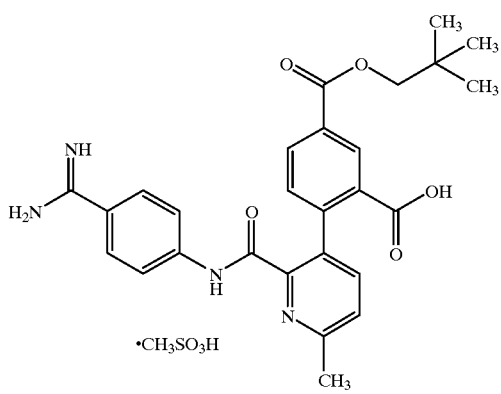

TLC:Rf 0.28 (Chloroform:Methanol:Acetic acid=20:2:1); NMR (d$_6$-DMSO): δ 10.86 (s, 1H), 9.20 (s, 2H), 8.62 (brs, 2H), 8.54 (d, J=1.8 Hz, 1H), 8.17, (dd, J=8.4, 1.8 Hz, 1H), 7.94 (d, J=8.7 Hz, 2H), 7.79 (d, J=8.7 Hz, 2H), 7.58 (d, J=7.8 Hz, 1H), 7.65 (d, J=8.4 Hz, 1H), 7.39 (d, J=7.8 Hz, 1H), 4.05 (s, 2H), 2.70 (s, 3H), 2.37 (s, 3H), 1.04 (s, 9H).

EXAMPLE 41(48)

2-[2-(4-amidino-3-fluorophenylcarbamoyl)-6-methyl-3-pyridyl]-5-(2,2-dimethyl propylcarbamoyl)benzoic acid methanesulfonate

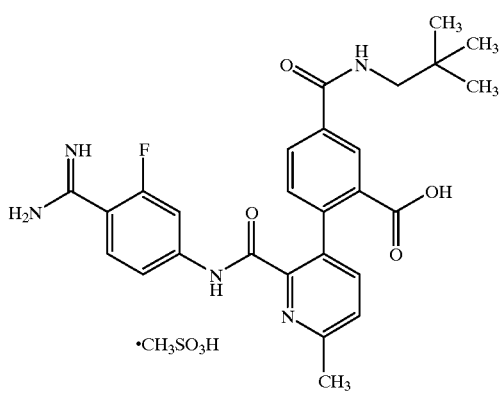

TLC:Rf 0.44 (Chloroform:Methanol:Acetic acid=10:2:1); NMR (d$_6$-DMSO): δ 11.0 (s, 1H), 9.30 (br s, 2H), 9.17 (br s, 2H*3/5), 9.10 (br s, 2H*2/5), 8.60 (t, J=6.3 Hz, 1H), 8.41 (d, J=2.1 Hz, 1H), 8.05 (dd, J=7.8, 2.1 Hz, 1H), 7.85 (dd, J=14, 2.1 Hz, 1H), 7.74 (dd, J=9.0, 2.1 Hz, 1H), 7.65–7.60 (m, 1H), 7.64 (d, J=7.8 Hz, 1H), 7.56 (d, J=7.8 Hz, 1H), 7.30 (d, J=8.1 Hz, 1H), 3.13 (d, J=6.3 Hz, 2H), 2.67 (s, 3H), 2.36 (s, 3H*3/5), 2.33 (s, 3H*2/5), 0.91 (s, 9H).

EXAMPLE 41(49)

4-[2-(4-amidinophenylcarbamoyl)-6-methyl-3-pyridyl] isophthalic acid methanesulfonate

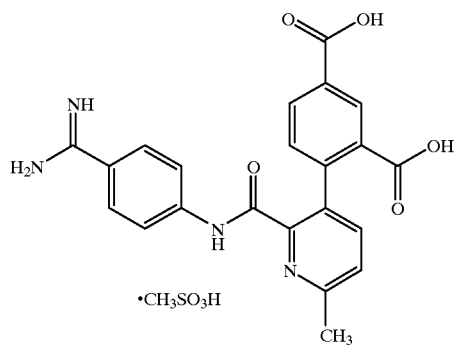

TLC:Rf 0.3 (Chloroform:Methanol:Acetic acid=10:2:1); NMR (d$_6$-DMSO): δ 10.83 (s, 1H), 9.20 (s, 2H), 8.90 (s, 2H), 8.48 (d, J=1.8 Hz, 1H), 8.10 (dd, J=8.1, 1.8 Hz, 1H), 7.91 (d, J=8.7 Hz, 2H), 7.78 (d, J=8.7 Hz, 2H), 7.64 (d, J=7.8 Hz, 1H), 7.56 (d, J=7.8 Hz, 1H), 7.34 (d, J=8.1 Hz, 1H), 2.68 (s, 3H), 2.35 (s, 3H).

EXAMPLE 41(50)

2'-(4-amidinophenylcarbamoyl)-5'-amino-4-(2,2-dimethylpropylcarbamoyl)-2-biphenylcarboxylic acid dimethanesulfonate

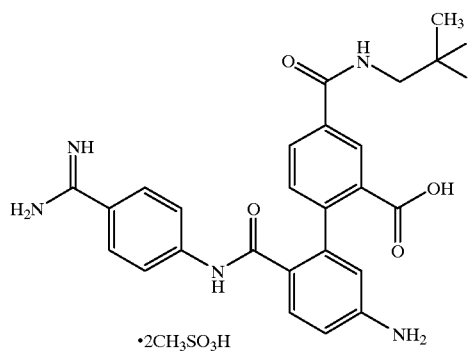

TLC:Rf 0.42 (Chloroform:Methanol:Water=7:3:0.3); NMR (d$_6$-DMSO): δ 10.24 (s, 1H), 9.10 (s, 2H), 8.80 (s, 2H), 8.51 (br.t, J=6.0 Hz, 1H), 8.27 (d, J=2.0 Hz, 1H), 7.94 (dd, J=8.0,2.0 Hz, 1H), 7.69 (s, 4H), 7.58 (d, J=8.0 Hz, 1H), 7.24 (d, J=8.0 Hz, 1H), 6.91 (d, J=8.0 Hz, 1H), 6.64 (s, 1H), 3.10 (d, J=6.0 Hz, 2H), 2.38 (s, 6H), 0.89 (s, 9H).

EXAMPLE 41(51)

2-[2-(4-amidinophenylcarbamoyl)-6-methyl-3-pyridyl]-5-(1,1,3,3-tetramethyl butylcarbamoyl)benzoic acid methanesulfonate

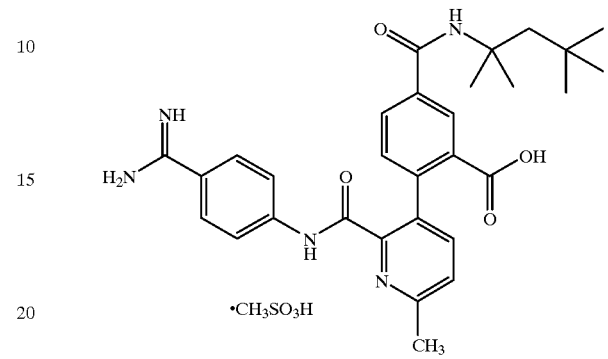

TLC:Rf 0.48 (Chloroform:Methanol:Acetic acid=10:2:1); NMR (d-DMSO): δ 10.84 (s, 1H), 9.21 (brs, 2H), 8.94 (brs, 2H), 8.31 (d, J=1.8 Hz, 1H), 7.95 (dd, J=8.0, 1.8 Hz, 1H), 7.92 (d, J=9.0 Hz, 2H), 7.89 (brs, 1H), 7.79 (d, J=9.0 Hz, 2H), 7.61 (d, J=8.0 Hz, 1H), 7.54 (d, J=8.0 Hz, 1H), 7.26 (d, J=8.0 Hz, 1H), 2.67 (s, 3H), 2.36 (s, 3H), 1.87 (s, 2H), 1.43 (s, 6H), 0.98 (s, 9H).

EXAMPLE 41(52)

2-[2-(4-amidinophenylcarbamoyl)-5-methyl-3-pyridyl]-5-(2,2-dimethylpropyl carbamoyl)benzoic acid methanesulfonate

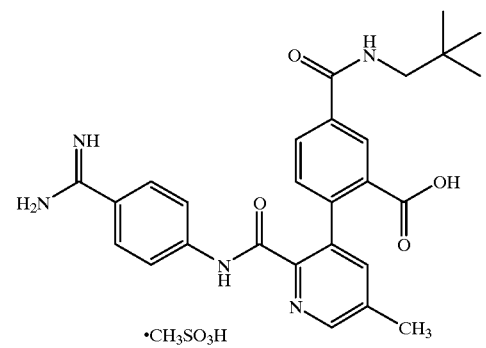

TLC:Rf 0.50 (Chloroform:Methanol:Water=7:3:0.3); NMR (d$_6$-DMSO): δ 10.93 (s, 1H), 9.18 (s, 2H), 8.88 (s, 2H), 8.60 (br.t, J=6.2 Hz, 1H), 8.56 (d, J=2.0 Hz, 1H), 8.43 (d, J=2.0 Hz, 1H), 8.06 (dd, J=8.0,2.0 Hz, 1H), 7.95 (d, J=9.0 Hz, 2H), 7.76 (d, J=9.0 Hz, 2H), 7.57 (d, J=2.0 Hz, 1H), 7.31 (d, J=8.0 Hz, 1H), 3.14 (d, J=6.2 Hz, 2H), 2.44 (s, 3H), 2.36 (s, 3H), 0.92 (s, 9H).

EXAMPLE 41(53)

2-[2-(4-amidinophenylcarbamoyl)-6-methoxy-3-pyridyl]-5-[[5-(1-methylethyl)-2,2-dimethyldioxan-5-yl]carbamoyl]benzoic acid hydrochloride

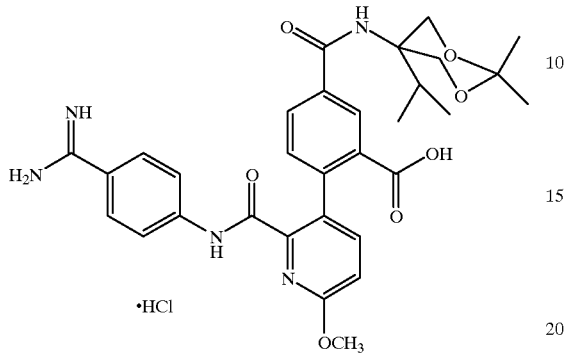

TLC:Rf 0.40 (Chloroform:Methanol:Acetic acid=10:2:1); NMR (d$_6$-DMSO): δ 12.8–12.5 (br, 1H), 9.24 (s, 2H), 9.07 (s, 2H), 8.33 (d, J=1.8 Hz, 1H), 8.03 (s, 1H), 7.95 (dd, J=8.1, 1.8 Hz, 1H), 7.88 (d, J=8.7 Hz, 2H), 7.78 (d, J=8.7 Hz, 2H), 7.62 (d, J=8.4 Hz, 1H), 7.27 (d, J=8.1 Hz, 1H), 7.10 (d, J=8.4 Hz, 1H), 4.14 (d, J=12.0 Hz, 2H), 4.08 (s, 3H), 3.93 (d, J=11.7 Hz, 2H), 2.39 (m, 1H), 1.33 (s, 3H), 1.29 (s, 3H), 0.93 (d, J=7.2 Hz, 6H).

EXAMPLE 41(54)

2-[2-(4-amidinophenylcarbamoyl)-6-methoxy-3-pyridyl]-5-[1(S)-(4-ethoxy carbonyloxazol-2-yl)-3-methylbutyl)carbamoyl]benzoic acid

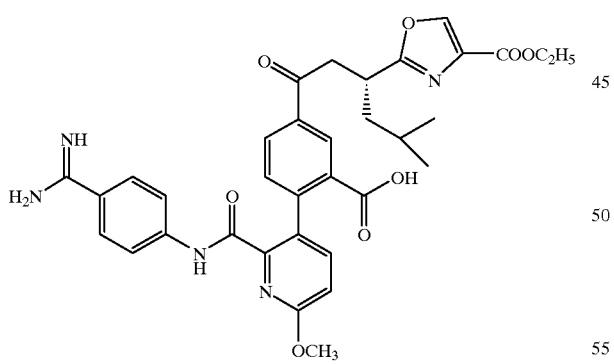

TLC:Rf 0.57 (Chloroform:Methanol:Acetic acid=10:2:1); NMR (300 MHz, CD$_3$OD): δ 8.52 (d, J=1.8 Hz, 1H), 8.03 (dd, J=8.0, 1.8 Hz, 1H), 7.85 (d, J=9.0 Hz, 2H), 7.75 (d, J=9.0 Hz, 2H), 7.59 (d, J=8.0 Hz, 1H), 7.33 (d, J=8.0 Hz, 1H), 7.06 (d, J=8.0 Hz, 1H), 5.45 (dd, J=9.3, 6.0 Hz, 1H), 4.34 (q, J=7.2 Hz, 2H), 4.12 (s, 3H), 2.07–1.87 (m, 2H), 1.82–1.68 (m, 1H), 1.35 (t, J=7.2 Hz, 3H), 1.03 (d, J=6.6 Hz, 3H), 1.01 (d, J=6.9 Hz, 3H).

EXAMPLE 41(55)

2-[2-(4-amidinophenylcarbamoyl)-6-methoxy-3-pyridyl]-5-[(1(S)-N-hydroxy carbamoyl)-3-methylbutylcarbamoyl]benzoic acid methanesulfonate

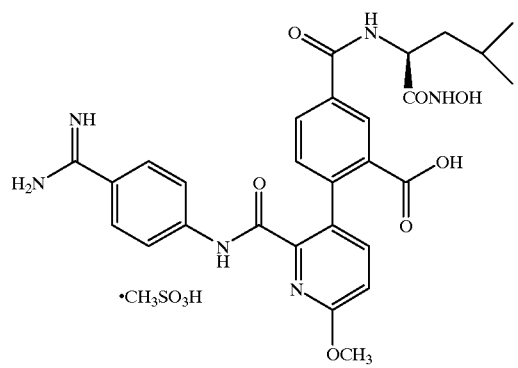

TLC:Rf 0.39 (Chloroform:Methanol:Water=8:2:0.2); NMR (d$_6$-DMSO): δ 10.77 (s, 1H), 10.61 (s, 1H), 9.20 (s, 2H), 8.86 (s, 2H), 8.73 (d, J=7.8 Hz, 1H), 8.47 (d, J=1.8 Hz, 1H), 8.08 (dd, J=7.8, 1.8 Hz, 1H), 7.91 (d, J=9.0 Hz, 2H), 7.79 (d, J=9.0 Hz, 2H), 7.65 (d, J=8.1 Hz, 1H), 7.30 (d, J=7.8 Hz, 1H), 7.12 (d, J=8.1 Hz, 1H), 4.49 (m, 1H), 4.11 (s, 3H), 2.35 (s, 3H), 1.80–1.60 (m, 2H), 1.51 (m, 1H), 0.93 (d, J=6.6 Hz, 3H), 0.89 (d, J=6.3 Hz, 3H).

EXAMPLE 41(56)

2-[2-(4-amidinophenylcarbamoyl)-6-methoxy-3-pyridyl]-5-(2,2-dimethylpropyl carbamoyl)-4-methylbenzoic acid methanesulfonate

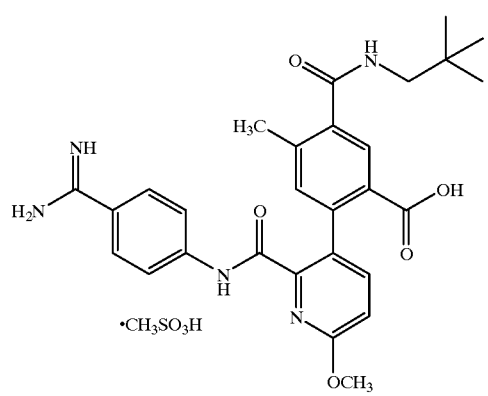

TLC:Rf 0.20 (Chloroform:Methanol:Acetic acid=20:2:1); NMR (d$_6$-DMSO): δ 10.59 (s, 1H), 9.21 (s, 2H), 8.90 (s, 2H), 8.45 (br.t, J=6.6 Hz, 1H), 7.93 (d, J=9.0 Hz, 2H), 7.90 (s, 1H), 7.80 (d, J=9.0 Hz, 2H), 7.59 (d, J=8.0 Hz, 1H), 7.11 (d, J=8.0 Hz, 1H), 7.09 (s, 1H), 4.11 (s, 3H), 3.11 (d, J=6.6 Hz, 2H), 2.40 (s, 6H), 0.94 (s, 9H).

EXAMPLE 41(57)

4-[2-(4-amidinophenylcarbamoyl)-6-methoxy-3-pyridyl]isophthalic acid methanesulfonate

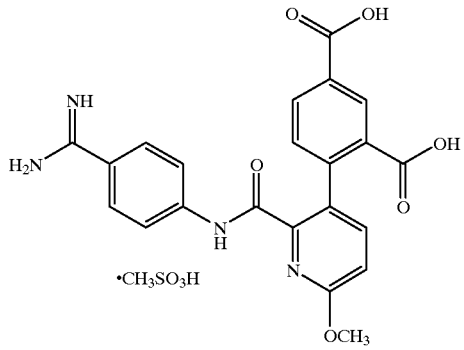

TLC:Rf 0.20 (Chloroform:Methanol:Acetic acid=3:1:1); NMR (d$_6$-DMSO): δ 10.61 (s, 1H), 9.18 (s, 2H), 8.75 (s, 2H), 8.50 (d, J=1.8 Hz, 1H), 8.10 (dd, J=8.0, 1.8 Hz, 1H), 7.91 (d, J=8.7 Hz, 2H), 7.78 (d, J=8.7 Hz, 2H), 7.67 (d, J=8.6 Hz, 1H), 7.35 (d, J=8.0 Hz, 1H), 7.14 (d, J=8.6 Hz, 1H), 4.11 (s, 3H), 2.32 (s, 3H).

EXAMPLE 41(58)

2-[2-(4-amidinophenylcarbamoyl)-6-methoxy-3-pyridyl]-5-(1(S)-hydroxymethyl-3-methylbutylcarbamoyl)-4-methylbenzoic acid methanesulfonate

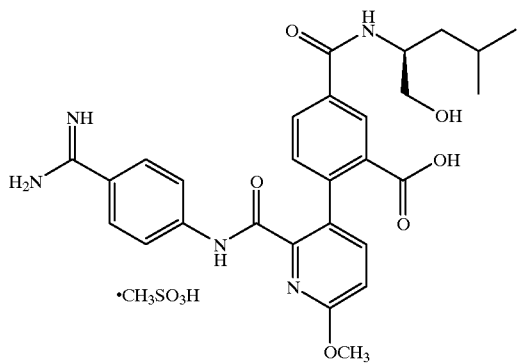

TLC:Rf 0.25 (Chloroform:Methanol:Acetic acid=10:2:1); NMR (d$_6$-DMSO): δ 12.9–12.5 (broad, 1H), 10.60 (s, 1H), 9.19 (brs, 2H), 8.86 (brs, 2H), 8.41 (d, J=2.0 Hz, 1H), 8.25 (brd, J=8.4 Hz, 1H), 8.02 (dd, J=8.0, 2.0 Hz, 1H), 7.90 (d, J=9.0 Hz, 2H), 7.78 (d, J=9.0 Hz, 2H), 7.64 (d, J=8.4 Hz, 1H), 7.29 (d, J=8.0 Hz, 1H), 7.12 (d, J=8.4 Hz, 1H), 4.15–4.05 (m, 1H), 4.09 (s, 3H), 3.47–3.32 (m, 2H), 2.32 (s, 3H), 1.72–1.56 (m, 1H), 1.55–1.30 (m, 2H), 0.90 (d, J=6.6 Hz, 3H), 0.89 (d, J=6.6 Hz, 3H).

EXAMPLE 41(59)

2-[2-(4-amidinophenylcarbamoyl)-6-methoxy-3-pyridyl]-5-[(4,4-dimethyloxolan-3(S)-yl)carbamoyl]-4-methylbenzoic acid methanesulfonate

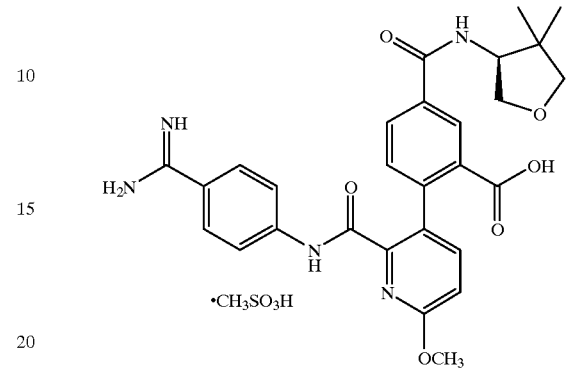

TLC:Rf 0.25 (Chloroform:Methanol:Acetic acid 10:2:1); NMR (d$_6$-DMSO): δ 12.9–12.6 (broad, 1H), 10.61 (s, 1H), 9.18 (brs, 2H), 8.84 (brs, 2H), 8.55 (brd, J=8.4 Hz, 1H), 8.42 (d, J=2.0 Hz, 1H), 8.03 (dd, J=8.0, 2.0 Hz, 1H), 7.89 (d, J=9.0 Hz, 2H), 7.78 (d, J=9.0 Hz, 2H), 7.65 (d, J=8.4 Hz, 1H), 7.30 (d, J=8.0 Hz, 1H), 7.12 (d, J=8.4 Hz, 1H), 4.40–4.32 (m, 1H), 4.09 (s, 3), 3.69 (dd, J=9.0, 6.0 Hz, 1H), 3.53 (d, J=5.4 Hz, 1H), 3.48 (d, J=5.4 Hz, 1H), 2.31 (s, 3H), 1.10 (s, 3H), 0.96 (s, 3H).

EXAMPLE 41(60)

2-[2-(4-amidinophenylcarbamoyl)-6-methoxy-3-pyridyl]-5-(1(R), 2,2-trimethyl propylcarbamoyl)benzoic acid methanesulfonate

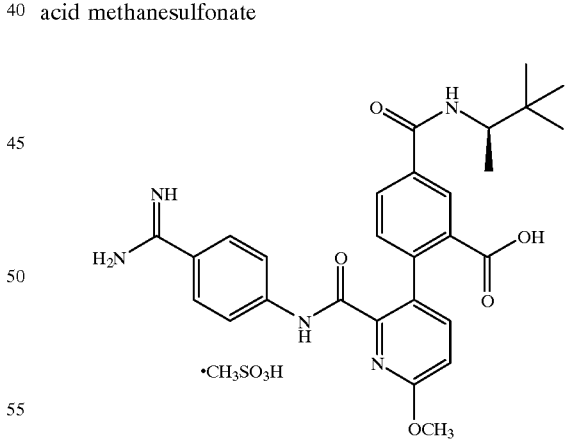

TLC:Rf 0.40 (Chloroform:Methanol:Acetic acid=10:2:1); NMR (d$_6$-DMSO): δ 12.9–12.5 (broad, 1H), 10.61 (s, 1H), 9.20 (brs, 2H), 8.90 (brs, 2H), 8.37 (d, J=1.8 Hz, 1H), 8.21 (brd, J=9.0 Hz, 1H), 8.00 (dd, J=8.0, 1.8 Hz, 1H), 7.90 (d, J=9.0 Hz, 2H), 7.78 (d, J=9.0 Hz, 2H), 7.63 (d, J=8.4 Hz, 1H), 7.28 (d, J=8.0 Hz, 1H), 7.12 (d, J=8.4 Hz, 1H), 4.09 (s, 3H), 4.06–3.96 (m, 1H), 2.33 (s, 3H), 1.10 (d, J=6.6 Hz, 3H), 0.92 (s, 9H).

EXAMPLE 41(61)

2-[2-(4-amidinophenylcarbamoyl)-6-methoxy-3-pyridyl]-5-[(1(R)-2,2-dimethyl cyclopentyl)carbamoyl] benzoic acid methanesulfonate

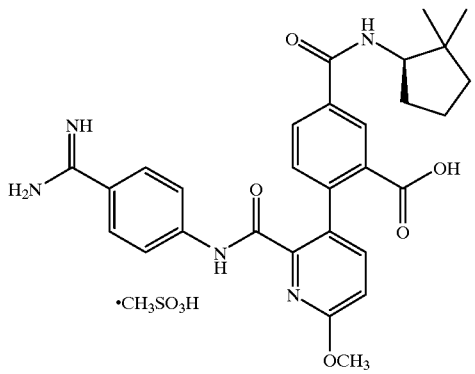

TLC:Rf 0.42 (Chloroform:Methanol:Acetic acid=10:2:1); NMR (d$_6$-DMSO): δ 12.9–12.5 (broad, 1H), 10.61 (s, 1H), 9.20 (brs, 2H), 8.89 (brs, 2H), 8.38 (d, J=1.8 Hz, 1H), 8.22 (brd, J=8.7 Hz, 1H), 8.01 (dd, J=8.0, 1.8 Hz, 1H), 7.90 (d, J=9.0 Hz, 2H), 7.78 (d, J=9.0 Hz, 2H), 7.64 (d, J=8.4 Hz, 1H), 7.29 (d, J=8.0 Hz, 1H), 7.12 (d, J=8.4 Hz, 1H), 4.16–4.08 (m, 1H), 4.09 (s, 3H), 2.32 (s, 3H), 2.00–1.88 (m, 1H), 1.83–1.42 (m, 5H), 1.00 (s, 3H), 0.90 (s, 3H).

EXAMPLE 41(62)

2-[2-(4-amidinophenylcarbamoyl)-6-methoxy-3-pyridyl]-5-[(1(S)-methylamino methyl-3-methylbutyl)carbamoyl]benzoic acid dimethanesulfonate

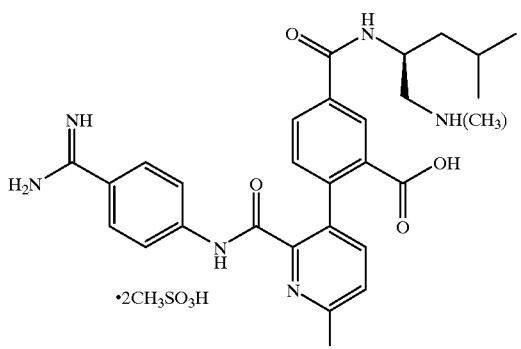

TLC:Rf 0.17 (Chloroform:Methanol:Acetic acid=10:2:1); NMR (d$_6$-DMSO): δ 12.75 (br, 1H), 10.62 (s, 1H), 9.21 (s, 2H), 8.91 (s, 2H), 8.57 (d, J=8.7 Hz, 1H), 8.60–8.40 (br, 2H), 8.48 (d, J=1.7 Hz, 1H), 8.09 (dd. J=8.0, 1.7 Hz, 1H), 7.91 (d, J=9.0 Hz, 2H), 7.81 (d, J=9.0 Hz, 2H), 7.63 (d, J=8.7 Hz, 1H), 7.34 (d, J=8.0 Hz, 1H), 7.14 (d, J=8.7 Hz, 1H), 4.43 (m, 1H), 4.12 (3H), 3.20–3.00 (m, 2H), 2.60 (t, J=5.4 Hz, 3H), 2.35 (s, 6H), 1.71–1.52 (m, 2H), 1.33 (m, 1H), 0.93 (d, J=6.3 Hz, 3H), 0.92 (d, J=6.3 Hz, 3H).

EXAMPLE 41(63)

2-[2-(4-amidinophenylcarbamoyl)-6-methoxy-3-pyridyl]-5-[(4,4-dimethyl-2-oxooxolan-3(S)-yl)carbamoyl] benzoic acid methanesulfonate

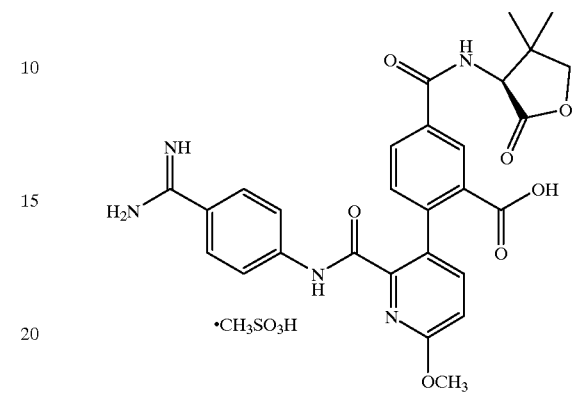

TLC:Rf 0.36 (Chloroform:Methanol:Acetic acid 10:2:1); NMR (d$_6$-DMSO): δ 12.9–12.6 (broad, 1H), 10.62 (s, 1H), 9.19 (brs, 2H), 9.05 (brd, J=9.0 Hz, 1H), 8.86 (brs, 2H), 8.50 (d, J=1.8 Hz, 1H), 8.09 (dd, J=8.0, 1.8 Hz, 1H), 7.90 (d, J=9.0 Hz, 2H), 7.78 (d, J=9.0 Hz, 2H), 7.67 (d, J=8.4 Hz, 1H), 7.35 (d, J=8.0 Hz, 1H), 7.13 (d, J=8.4 Hz, 1H), 4.99 (d, J=9.0 Hz, 1H), 4.16 (d, J=9.0 Hz, 1H), 4.10 (s, 3H), 4.08 (d, J 9.0 Hz, 1H), 2.32 (s, 3H), 1.15 (s, 3H), 1.02 (s, 3H).

EXAMPLE 41(64)

2-[2-(4-amidinophenylcarbamoyl)-3-thienyl]-5-[(1(S)-acetyloxymethyl-2,2-dimethylpropyl)carbamoyl]benzoic acid methanesulfonate

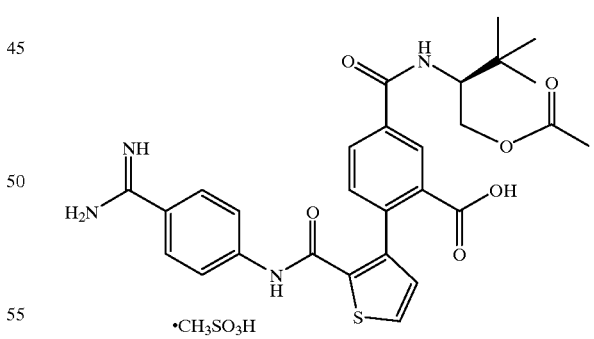

TLC:Rf 0.58 (Chloroform:Methanol:Acetic acid=10:2:1); NMR (d$_6$-DMSO): δ 12.8–12.0 (br, 1H), 10.24 (s, 1H), 9.17 (s, 2H), 8.86 (s, 2H), 8.34 (d, J=8.4 Hz, 1H), 8.29 (d, J=1.8 Hz, 1H), 8.00 (dd, J=8.4, 1.8 Hz, 1H), 7.84 (d, J=5.1 Hz, 1H), 7.74 (like s, 4H), 7.42 (d, J=8.4 Hz, 1H), 7.11 (d, J=5.1 Hz, 1H), 4.34 (dd, J=10.2, 1.6 Hz, 1H), 4.13 (dd, J=10.2, 1.6 Hz, 1H), 4.06 (t, J=10.2 Hz, 1H), 2.33 (s, 3H), 1.93 (s, 3H), 0.94 (s, 9H).

EXAMPLE 41(65)

2-[2-(4-amidinophenylcarbamoyl)-6-methoxy-3-pyridyl]-5-[[4-carboxy-4-(2-methyl-2-propenyl)piperidinyl]carbonyl]benzoic acid methanesulfonate

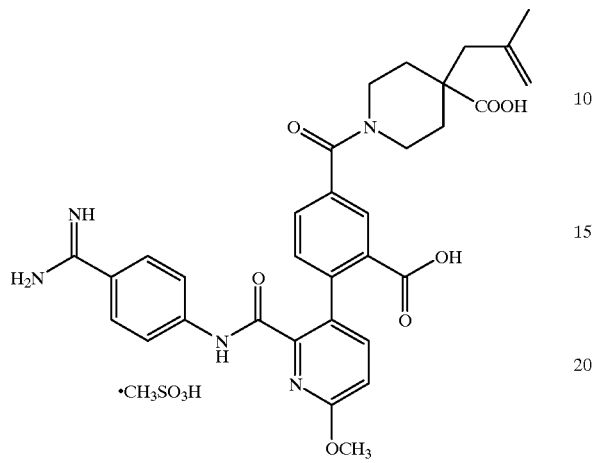

TLC:Rf 0.37 (Chloroform:Methanol:Acetic acid=10:2:1); NMR ($d_6$-DMSO): δ 10.6 (s, 1H), 9.19 (br s, 2H), 8.85 (br s, 2H), 7.91–7.88 (m, 3H), 7.78 (d, J=8.7 Hz, 2H), 7.67 (d, J=8.1 Hz, 1H), 7.58 (dd, J=8.1, 1.8 Hz, 1H), 7.27 (d, J=8.1 Hz, 1H), 7.11 (d, J=8.1 Hz, 1H), 4.81 (s, 1H), 4.72 (s, 1H), 4.30–4.10 (m, 2H*1/2, each of isomers), 4.09 (s, 3H), 3.60–3.40 (m, 2H*1/2, each of isomers), 3.40–3.00 (m, 2H), 2.31 (s, 3H), 2.30 (s, 2H), 2.10–1.90 (m, 2H), 1.66 (s, 3H), 1.50–1.30 (m, 2H).

EXAMPLE 41(66)

2-[2-(4-amidinophenylcarbamoyl)-6-methoxy-3-pyridyl]-5-[1(S)-[N-methyl-N-(1-iminoethyl)aminomethyl]-3-methylbutyl]benzoic acid dimethanesulfonate

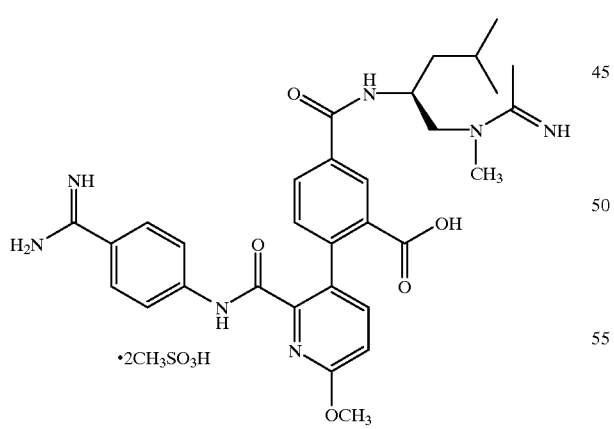

TLC:Rf 0.42 (Ethyl acetate:Acetic acid:Water=3:1:1); NMR ($D_2O$): δ 8.13 (d, J=1.8 Hz, 1H), 7.84 (d, J=8.4 Hz, 1H), 7.72 (d, J=8.7 Hz, 1H), 7.70 (d, J=8.7 Hz, 2H), 7.60 (d, J=8.7 Hz, 2H), 7.41 (d, J=8.7 Hz, 1H), 7.13 (d, J=8.4 Hz, 1H), 4.73 (m, 1H), 4.03 (s, 3H), 3.62 and 3.57 (d, J=7.5 Hz, 1H), 3.21 and 3.14 (s, 3H), 2.75 (s, 6H), 2.25 and 2.18 (s, 3H), 1.76–1.54 (m, 2H), 1.39 (m, 1H), 0.92–0.85 (m, 6H).

EXAMPLE 41(67)

2'-(4-amidinophenylcarbamoyl)-4'-amino-4-(1(R), 2,2-trimethylpropyl carbamoyl)-2-biphenylcarboxylic acid dimethanesulfonate

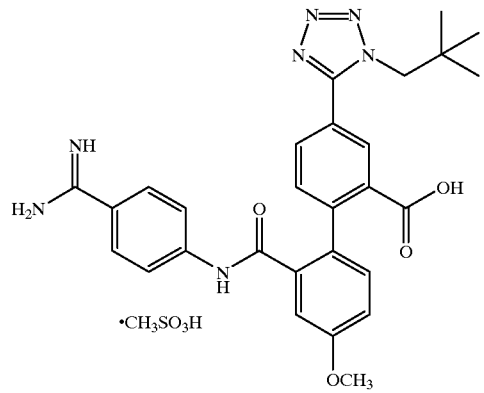

TLC:Rf 0.52 (Chloroform:Methanol:Water 7:3:0.3); NMR ($d_6$-DMSO): δ 10.55 (s, 1H), 9.14 (s, 2H), 8.85 (s, 2H), 8.24 (d, J=2.0 Hz, 1H), 8.15 (br.d, J=6.3 Hz, 1H), 7.93 (dd, J=8.0,2.0 Hz, 1H), 7.74 (d, J=9.0 Hz, 2H), 7.70 (d, J=9.0 Hz, 2H), 7.30 (d, J=8.0 Hz, 1H), 7.29 (s, 1H), 7.17 (s, 2H), 3.98 (m, 1H), 2.37 (s, 6H), 1.08 (d, J=7.0 Hz, 3H), 0.90 (s, 9H).

EXAMPLE 41(68)

2-[2-(4-amidinophenylcarbamoyl)-6-methoxy-3-pyridyl]-5-[1-(2,2-dimethyl propyl)tetrazol-5-yl]benzoic acid methanesulfonate TLC:Rf 0.24 (Chloroform:Methanol:Acetic acid= 10:1:0.2); NMR ($d_6$-DMSO): δ 13.2–12.3 (br, 1H), 10.62 (s, 11H), 9.19 (s, 2H), 8.88 (s, 2H), 8.27 (d, J=1.8 Hz, 1H), 7.99 (dd, J=7.8, 1.8 Hz, 1H), 7.90 (d, J=9.0 Hz, 2H), 7.79 (d, J=9.0 Hz, 2H), 7.74 (d, J=8.4 Hz, 1H), 7.46 (d, J=7.8 Hz, 1H), 7.15 (d, J=8.4 Hz, 1H), 4.38 (s, 2H), 4.10 (s, 3H), 2.32 (s, 3H), 0.80 (s, 9H).

EXAMPLE 41(69)

2-[2-(4-amidinophenylcarbamoyl)-6-methoxy-3-pyridyl]-5-[[1-(1-iminoethyl)-4-(2-methylpropyl)piperidin-4-yl]carbamoyl]benzoic acid dimethanesulfonate

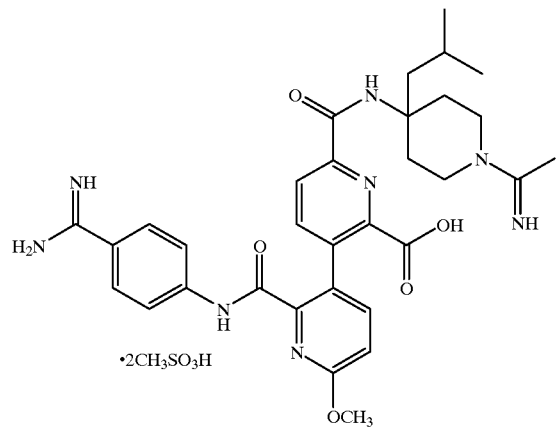

TLC:Rf 0.48 (Ethyl acetate:Acetic acid:Water=3:1:1); NMR (d$_6$-DMSO): δ 10.6 (s, 1H), 9.20 (br s, 2H), 9.08 (br s, 1H), 8.89 (br s, 2H), 8.53 (br s, 1H), 8.36 (d, J=1.8 Hz, 1H), 8.08 (s, 1H), 8.02 (dd, J=8.1, 1.8 Hz, 1H), 7.90 (d, J=8.7 Hz, 2H), 7.79 (d, J=8.7 Hz, 2H), 7.63 (d, J=8.7 Hz, 1H), 7.30 (d, J=8.1 Hz, 1H), 7.13 (d, J=8.7 Hz, 1H), 4.10 (s, 3H), 3.93–3.76 (m, 2H), 3.40–3.20 (m, 2H), 2.61–2.44 (m, 2H), 2.31 (s, 6H), 2.26 (s, 3H), 1.74–1.49 (m, 5H), 0.90 (d, J=6.0 Hz, 6H).

EXAMPLE 41(70)

3-[2-(4-amidinophenylcarbamoyl)-6-methoxy-3-pyridyl]-6-[(1(R), 2,2-trimethyl propyl)carbamoyl]-2-pyridinecarboxylic acid methanesulfonate

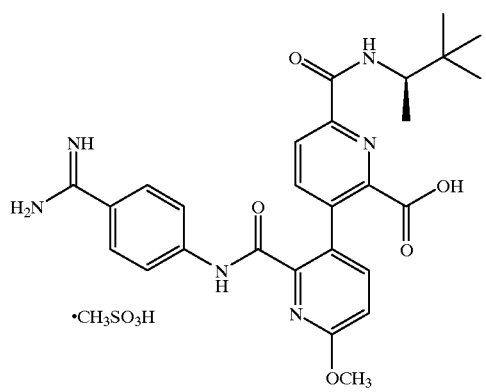

TLC:Rf 0.40 (Chloroform:Methanol:Water=8:2:0.2); NMR (d$_6$-DMSO): δ 12.95 (br.s, 1H), 10.65 (s 1H), 9.20 (s, 2H), 8.89 (s, 2H), 8.69 (d, J=10.0 Hz, 1H), 8.26 (d, J=8.0 Hz, 1H), 7.94 (d, J=8.0 Hz, 1H), 7.90 (d, J=9.0 Hz, 2H), 7.78 (d, J=9.0 Hz, 2H), 7.74 (d, J=8.0 Hz, 1H), 7.19 (d, J=8.0 Hz, 1H), 4.12 (s, 3H), 4.02 (dq, J=10.0,7.2 Hz, 1H), 2.33 (s, 3H), 1.17 (d, J=7.2 Hz, 3H), 0.94 (s, 9H).

EXAMPLE 41(71)

2-[2-(4-amidinophenylcarbamoyl)-6-methoxy-3-pyridyl]-5-(t-butylcarbamoyl) benzoic acid methanesulfonate

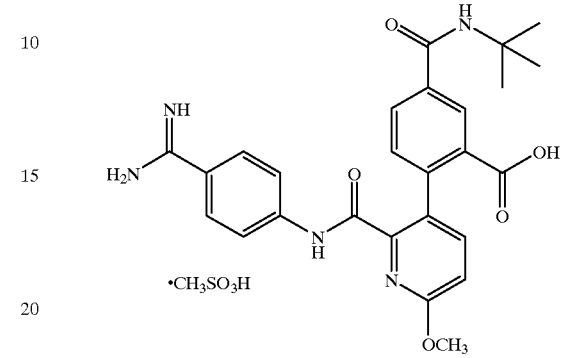

TLC:Rf 0.50 (Chloroform:Methanol:Acetic acid=10:2:1); NMR (d$_6$-DMSO): δ 10.60 (s, 1H), 9.20 (s, 2H), 8.88 (s, 2H), 8.32 (d, J=1.8 Hz, 1H), 8.00 (s, 1H), 7.95 (dd, J=7.8,1.8 Hz, 1H), 7.88 (di J=9.3 Hz, 2H), 7.78 (d, J=9.3 Hz, 2H), 7.62 (d, J=8.4 Hz, 1H), 7.26 (d, J=7.8 Hz, 1H), 7.11 (d, J=8.4 Hz, 1H), 4.09 (s, 3H), 2.32 (s, 3H), 1.40 (s, 9H).

EXAMPLE 41(72)

2-[2-(4-amidinophenylcarbamoyl)-6-methoxy-3-pyridyl]-5-(2,2,2-trichloroethyl carbamoyl)benzoic acid methanesulfonate

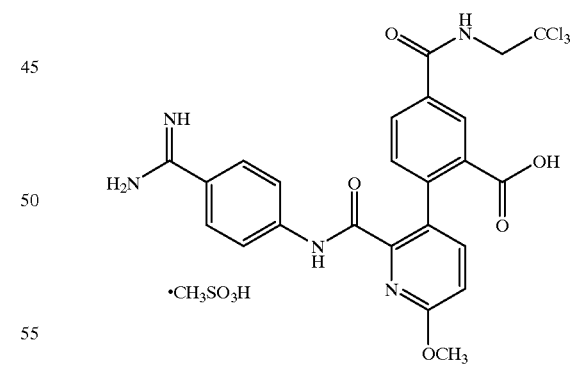

TLC:Rf 0.40 (Chloroform:Methanol:Acetic acid=10:2:1); NMR (d$_6$-DMSO): δ 12.81 (s, 1H), 10.62 (s, 1H), 9.56 (t, J=6.4 Hz, 1H), 9.20 (s, 2H), 8.86 (s, 2H), 8.49 (d, J=1.8 Hz, 1H), 8.04 (dd, J=8.0, 1.8 Hz, 1H), 7.90 (d, J=9.2 Hz, 2H), 7.79 (d, J=9.2 Hz, 2H), 7.67 (d, J=8.6 Hz, 1H), 7.35 (d, J=8.0 Hz, 1H), 7.13 (d, J=8.6 Hz, 1H), 4.42 (d, J=6.0 Hz, 2H), 4.10 (s, 3H), 2.31 (s, 3H).

EXAMPLE 41(73)

2-[3-(4-amidinophenylcarbamoyl)-2-thienyl]-6-(t-butylcarbamoyl)-2-pyridine carboxylic acid methanesulfonate

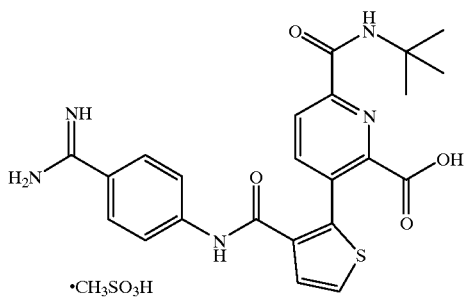

TLC:Rf 0.15 (Chloroform:Methanol:Acetic acid=10:2:1); NMR (d$_6$-DMSO): δ 13.05 (br.s, 1H), 10.41 (s 1H), 9.17 (s, 2H), 8.82 (s, 2H), 8.31 (s, 1H), 8.19 (d, J=8.0 Hz, 1H), 8.07 (d, J=8.0 Hz, 1H), 7.84 (d, J=9.0 Hz, 2H), 7.82 (d, J=5.4 Hz, 1H), 7.75 (d, J=9.0 Hz, 2H), 7.73 (d, J=5.4 Hz, 1H), 2.31 (s, 3H), 1.44 (s, 9H).

EXAMPLE 41(74)

2-[2-(4-amidinophenylcarbamoyl)-6-methoxy-3-pyridyl]-5-(2,2,2-trifluoroeth carbamoyl)benzoic acid methanesulfonate

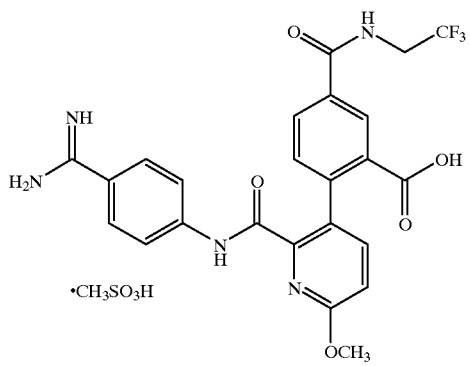

TLC:Rf 0.30 (Chloroform:Methanol:Water=8:2:0.2); NMR (d$_6$-DMSO): δ 12.79 (brs, 1H), 10.62 (s, 1H), 9.34 (t, J=6.3 Hz, 1H), 9.19 (s, 2H), 8.81 (s, 2H), 8.48 (d, J=1.8 Hz, 1H), 8.08 (dd, J=7.8, 1.8 Hz, 1H), 7.91 (d, J=8.7 Hz, 2H), 7.78 (d, J=8.7 Hz, 2H), 7.67 (d, J=8.4 Hz, 1H), 7.36 (d, J=7.8 Hz, 1H), 7.14 (d, J=8.4 Hz, 1H), 4.22–4.10 (m, 2H), 4.11 (s, 3H), 2.32 (s, 3H).

EXAMPLE 41(75)

2-[2-[(2-amidinopyrimidin-5-yl)carbamoyl]-6-methoxy-3-pyridyl]-5-(2,2-dimethyl propyicarbamoyl)benzoic acid methanesulfonate

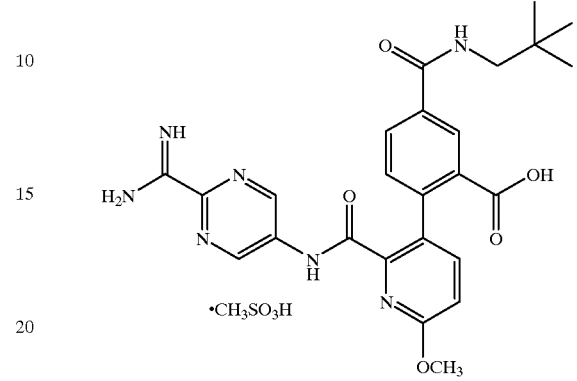

TLC:Rf 0.38 (Chloroform:Methanol:Acetic acid=10:2:1); NMR (d$_6$-DMSO): δ 13.0–12.6 (br, 1H), 11.05 (s, 1H), 9.59 (s, 2H), 9.35 (s, 2H), 9.29 (s, 2H), 8.59 (t, J=6.0 Hz, 1H), 8.41 (d, J=1.5 Hz, 1H), 8.04 (dd, J=8.0, 1.5 Hz, 1H), 7.69 (d, J=8.7 Hz, 1H), 7.34 (d, J=8.0 Hz, 1H), 7.18 (d, J=8.7 Hz, 1H), 4.11 (s, 3H), 3.13 (d, J=6.0 Hz, 2H), 2.29 (s, 3H), 0.91 (s, 9H).

EXAMPLE 41(76)

2-[2-(4-amidinophenylcarbamoyl)-6-methoxy-3-pyridyl]-5-[[1(S)-(2-aminoethyl)-3-methylbutylcarbamoyl]benzoic acid dimethanesulfonate TLC:Rf 0.17 (Chloroform:Methanol:Water=7:3:0.3); NMR (d$_6$-DMSO): δ 12.80 (br.s, 1H), 10.62 (s 1H), 9.19 (s, 2H), 8.90 (s, 2H), 8.51 (d, J=9.0 Hz, 1H), 8.42 (d, J=2.0 Hz, 1H), 8.04 (dd, J=8.0,2.0 Hz, 1H), 7.90 (d, J=9.0 Hz, 2H), 7.79 (d, J=9.0 Hz, 2H), 7.69 (br.s, 3H), 7.64 (d, J=8.4 Hz, 1H), 7.32 (d, J=8.0 Hz, 1H), 7.13 (d, J=8.4 Hz, 1H ), 4.15 (m, 1H), 4.10 (s, 3H), 2.90–2.78 (m, 2H), 2.34 (s, 6H), 1.83–1.60 (m, 4H), 1.27 (m, 1H), 0.90 (d, J=6.8 Hz, 3H), 0.88 (d, J=6.8 Hz, 3H).

EXAMPLE 41(77)

2-[2-(4-amidinophenylcarbamoyl)-6-methoxy-3-pyridyl]-5-[(2,2-diethylbutyloxy) carbamoyl]benzoic acid methanesulfonate

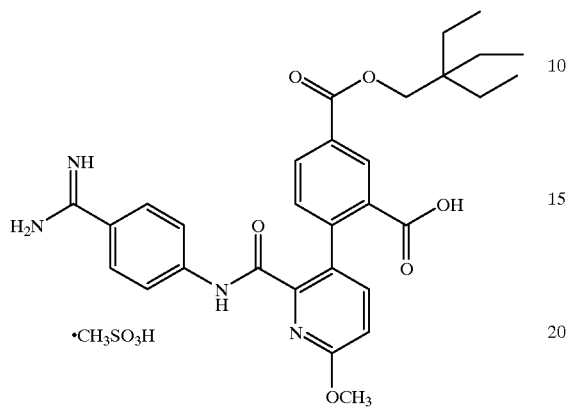

TLC:Rf 0.80 (Chloroform:Methanol:Water=7:3:0.3); NMR (d$_6$-DMSO): δ 12.86 (s, 1H), 10.63 (s, 1H), 9.20 (s, 2H), 8.86 (s, 2H), 8.50 (d, J=1.5 Hz, 1H), 8.11 (dd, J=8.1, 1.5 Hz, 1H), 7.91 (d, J=9.0 Hz, 2H), 7.80 (d, J=9.0 Hz, 2H), 7.68 (d, J=8.7 Hz, 1H), 7.40 (d, J=8.1 Hz, 1H), 7.15 (d, J=8.7 Hz, 1H), 4.12 (s, 3H), 4.10 (s, 2H), 2.33 (s, 3H), 1.36 (q, J=7.5 Hz, 6H), 0.82 (t, J=7.5 Hz, 9H).

EXAMPLE 41(78)

2-[2-(4-amidinophenylcarbamoyl)-6-methoxy-3-pyridyl]-5-[(2,2-dimethyl-3-hydroxypropyl)carbamoyl]benzoic acid methanesulfonate

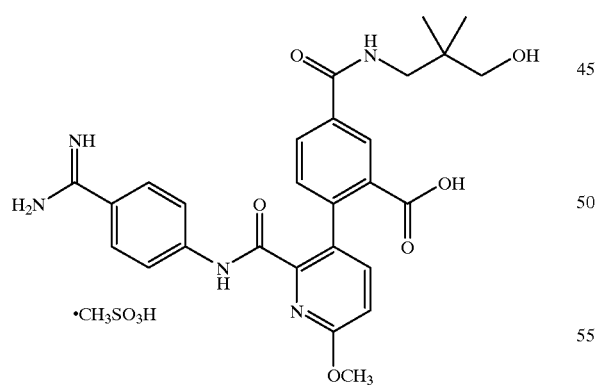

TLC:Rf 0.10 (Chloroform:Methanol:Acetic acid=10:2:1); NMR (d$_6$-DMSO): δ 10.6 (s, 1H), 9.19 (br s, 2H), 8.82 (br s, 2H), 8.62 (t, J=5.8 Hz, 1H), 8.40 (d, J=1.8 Hz, 1H), 8.02 (dd, J=8.2, 1.8 Hz, 1H), 7.90 (d, J=9.2 Hz, 2H), 7.78 (d, J=9.2 Hz, 2H), 7.66 (d, J=8.4 Hz, 1H), 7.31 (d, J=8.2 Hz, 1H, 7.13 (d, J=8.4 Hz, 1H), 4.10 (s, 3H), 3.19 (d, J=6.2 Hz, 2H), 3.15 (s, 2H), 2.31 (s, 3H), 0.85 (s, 6H).

EXAMPLE 41(79)

2-[2-(4-amidinophenylcarbamoyl)-6-methoxy-3-pyridyl]-5-[(2,2-diethylbutyl) carbamoyl]benzoic acid methanesulfonate

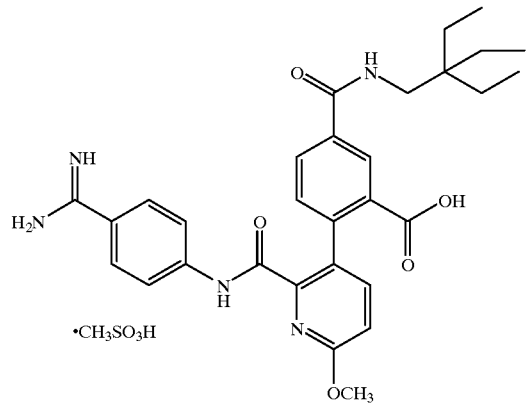

TLC:Rf 0.31 (Chloroform:Methanol:Acetic acid=10:2:1); NMR (d$_6$-DMSO): δ 10.62 (s, 1H), 9.21 (s, 2H), 8.89 (s, 2H), 8.36 (d, J=1.8 Hz, 1H), 8.24 (t, J=6.6 Hz, 1H), 7.99 (dd, J=8.4, 1.8 Hz, 1H), 7.91 (d, J=9.0 Hz, 2H), 7.80 (d, J=9.0 Hz, 2H), 7.65 (d, J=8.4 Hz, 1H), 7.30 (d, J=8.4 Hz, 1H), 7.13 (d, J=8.4 Hz, 1H), 4.11 (s, 3H), 3.18 (d, J=6.6 Hz, 2H), 2.34 (s, 3H), 1.24 (q, J=7.5 Hz, 6H), 0.81 (t, J=7.5 Hz, 9H).

EXAMPLE 41(80)

2-[2-(4-amidinophenylcarbamoyl)-6-methoxy-3-pyridyl]-5-[((1-hydroxymethyl) cyclobutylmethyl) carbamoyl]benzoic acid methanesulfonate TLC Rf 0.16 (Chloroform:Methanol:Acetic acid=10:2:1); NMR (d$_6$-DMSO): δ 10.6 (s, 1H), 9.17 (br s, 2H), 8.77 (br s, 2H), 8.66 (t, J=6.0 Hz, 1H), 8.41 (d, J=2.1 Hz, 1H), 8.02 (dd, J=7.8, 2.1 Hz, 1H), 7.90 (d, J=8.7 Hz, 2H), 7.77 (d, J=8.7 Hz, 2H), 7.65 (d, J=8.1 Hz, 1H), 7.31 (d, J=7.8 Hz, 1H), 7.12 (d, J=8.1 Hz, 1H), 4.09 (s, 3H), 3.41–3.36 (m, 4H), 2.29 (s, 3H), 1.90–1.70 (m, 6H).

EXAMPLE 41(81)

2-[2-(4-amidinophenylcarbamoyl)-6-methoxy-3-pyridyl]-5-[(2-ethyl-2-hydroxy methylbutyl)carbamoyl]benzoic acid methanesulfonate

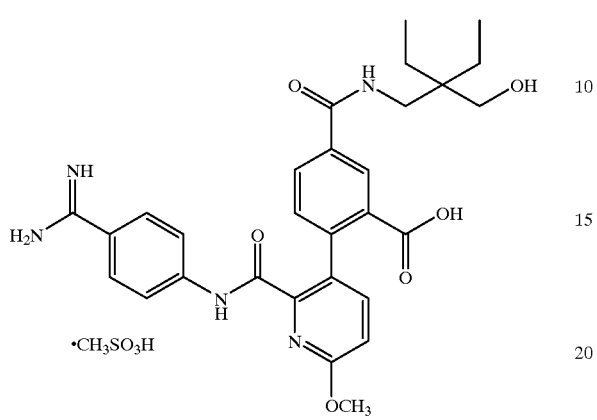

TLC:Rf 0.24 (Chloroform:Methanol:Acetic acid=10:2:1); NMR (d$_6$-DMSO): δ 10.6 (s, 1H), 9.18 (br s, 2H), 8.80 (br s, 2H), 8.49 (t, J=6.0 Hz, 1H), 8.38 (d, J=2.1 Hz, 1H), 8.00 (dd, J=8.1, 2.1 Hz, 1H), 7.90 (d, J=8.7 Hz, 2H), 7.77 (d, J=8.7 Hz, 2H), 7.65 (d, J=8.4 Hz, 1H), 7.31 (d, J=8.1 Hz, 1H), 7.13 (d, J=8.4 Hz, 1H), 4.10 (s, 3H), 3.20–3.18 (m, 4H), 2.30 (s, 3H), 1.22 (septet, J=6.6 Hz, 4H), 0.81 (t, J=6.6 Hz, 6H).

EXAMPLE 41(82)

2-[2-(4-amidinophenylcarbamoyl)-6-methoxy-3-pyridyl]-5-[((1-hydroxymethyl) cyclopentylmethyl)carbamoyl]benzoic acid methanesulfonate

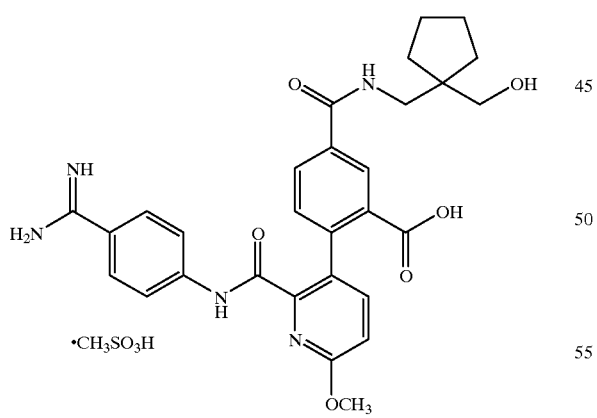

TLC:Rf 0.20 (Chloroform:Methanol:Acetic acid=10:2:1); NMR (300 MHz, d$_6$-DMSO): δ 10.6 (s, 1H), 9.19 (br s, 2H), 8.84 (br s, 2H), 8.67 (t, J=6.3 Hz, 1H), 8.40 (d, J=1.5 Hz, 1H), 8.02 (dd, J=7.8, 1.5 Hz, 1H), 7.90 (d, J=9.0 Hz, 2H), 7.78 (d, J=9.0 Hz, 2H), 7.66 (d, J=8.4 Hz, 1H), 7.31 (d, J=7.8 Hz, 1H), 7.12 (d, J=8.4 Hz, 1H), 4.10 (s, 3H), 3.36–3.22 (m, 4H), 2.30 (s, 3H), 1.57–1.38 (m, 8H).

EXAMPLE 41(83)

2-[2-(4-amidinophenylcarbamoyl)-6-methoxy-3-pyridyl]-5-[(2-propyl-2-hydroxy methylpentyl)carbamoyl]benzoic acid methanesulfonate

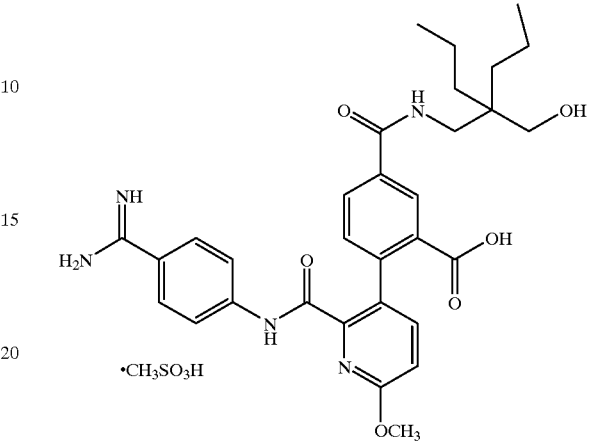

TLC:Rf 0.50 (Chloroform:Methanol:Acetic acid=10:2:1); NMR (300 MHz, d$_6$-DMSO): δ 12.8–12.3 (brd, 1H), 10.61 (s, 1H), 9.19 (s, 2H), 8.83 (s, 2H), 8.50 (t, J=5.7 Hz, 1H), 8.37 (d, J=1.8 Hz, 1H), 8.00 (dd, J=8.1, 1.8 Hz, 1H), 7.90 (d, J=8.7 Hz, 2H), 7.71 (d, J=8.7 Hz, 2H), 7.65 (d, J=8.7 Hz, 1H), 7.31 (d, J=8.1 Hz, 1H), 7.12 (d, J=8.7 Hz, 1H), 4.09 (s, 3H), 3.21–3.18 (m, 4H), 2.31 (s, 3H), 1.18–1.02 (m, 8H), 0.86 (t, J=6.6 Hz, 6H).

EXAMPLE 41(84)

2-(2-(4-amidinophenylcarbamoyl)-6-methoxy-3-pyridyl]-5-[(2-(2-methylpropyl)-2-hydroxymethyl-4-methylpentyl)carbamoyl]benzoic acid methanesulfonate

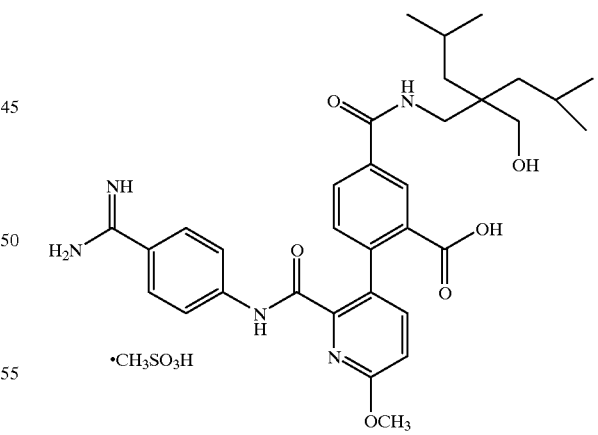

TLC:Rf 0.23 (Chloroform:Methanol:Acetic acid=10:2:1); NMR(300 MHz, DMSO-d$_6$) :δ 12.74 (br, 1H), 10.62:(s, 1H), 9.19 (s, 2H), 8.12 (s, 2H), 8.42 (m, 1H), 8.37 (d, J=1.8 Hz, 1H), 7.97 (dd, J=8.1, 1.8 Hz, 1H), 7.91 (d,J=9.0 Hz,2H), 7.79 (d, J=9.0 Hz, 2H), 7.66 (d, J=8.4 Hz, 1H), 7.33 (d, J=8.1 Hz, 1H), 7.13 (d, J=8.4 Hz, 1H), 4.77 (br, 1H), 4.11 (s, 3H), 2.32 (s, 3H), 1.82–1.70 (m, 2H), 1.40–1.20 (m, 4H), 0.92 (d, J=6.9 Hz, 6H).

EXAMPLE 41(85)

2-[2-(4-amidinophenylcarbamoyl)-6-methoxy-3-pyridyl]-5-[(1-hydroxymethyl cyclopentyl)carbamoyl]benzoic acid methanesulfonate

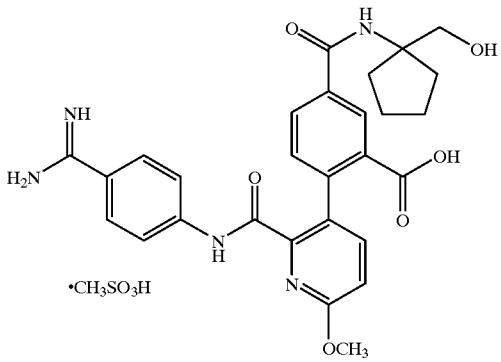

TLC:Rf 0.23 (Chloroform:Methanol:Acetic acid=10:2:1); NMR (300 MHz, DMSO-$d_6$): δ 10.61 (s, 1H), 9.20 (s, 2H), 8.87 (s, 2H), 8.36 (d, J=1.8 Hz, 1H), 7.99 (dd, J=8.4, 1.8 Hz, 1H), 7.98 (s, 1H), 7.91 (d, J=9.0 Hz, 2H), 7.79 (d, J=9.0 Hz, 2H), 7.64 (d, J=8.4 Hz, 1H), 7.27 (d, J=8.4 Hz, 1H), 7.13 (d, J=8.4 Hz, 1H), 4.10 (s, 3H), 3.61 (s, 2H), 2.33 (s, 3H), 2.09–2.00 (m, 2H), 1.80–1.62 (m, 4H), 1.62–1.54 (m, 2H).

EXAMPLE 41(86)

2-[2-(4-amidinophenylcarbamoyl)-6-methoxy-3-pyridyl]-5-[(1-(2-methylpropyl)-1-hydroxymethyl-3-methylbutyl)carbamoyl]benzoic acid methanesulfonate

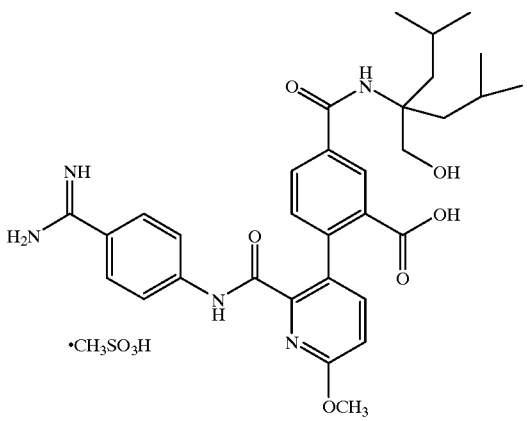

TLC:Rf 0.23 (Chloroform:Methanol:Acetic acid=10:2:1); NMR (300 MHz, DMSO-$d_6$): δ 10.59 (s, 1H), 9.16 (s, 2H), 8.77 (s, 2H), 8.28 (d, J=2.1 Hz, 1H), 7.90 (dd, J=8.1, 2.1 Hz, 1H), 7.89 (d, J=8.7 Hz, 2H), 7.76 (d, J=8.7 Hz, 2H), 7.62 (d, J=8.7 Hz, 1H), 7.46 (s, 1H), 7.25 (d, J=8.1 Hz, 1H), 7.10 (d, J=8.7 Hz, 1H), 4.08 (s, 3H), 3.61 (s, 2H), 2.29 (s, 3H), 1.87 (dd, J=13.8, 5.7 Hz, 2H), 1.80–1.68 (m, 2H), 1.59 (dd, J=13.8, 5.1 Hz, 2H), 0.89 (d, J=6.6 Hz, 6H), 0.88 (dd, J=6.3 Hz, 6H).

EXAMPLE 41(87)

2-[2-(4-amidinophenylcarbamoyl)-6-methoxy-3-pyridyl]-5-[(1(S)-(hydroxymethyl)-2(S)-methylbutyl)carbamoyl]benzoic acid methanesulfonate

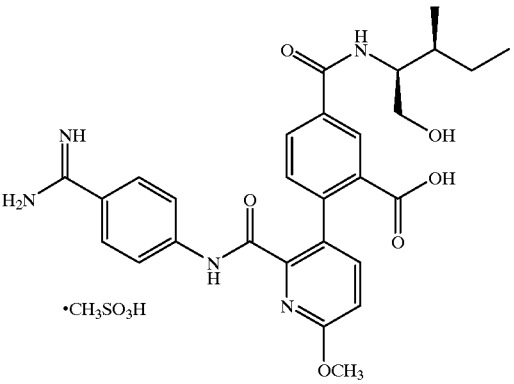

TLC:Rf 0.35 (Chloroform:Methanol:Acetic acid=10:2:1); NMR (300 MHz, $d_6$-DMSO): δ 12.8–12.3 (brd, 1H), 10.60 (s, 1H), 9.18 (s, 2H), 8.82 (s, 2H), 8.41 (d, J=1.8 Hz, 1H), 8.25 (d, J=8.7 Hz, 1H), 8.04 (dd, J=8.1, 1.8 Hz, 1H), 7.90 (d, J=9.0 Hz, 2H), 7.77 (d, J=9.0 Hz, 2H), 7.64 (d, J=8.1 Hz, 1H), 7.29 (d, J=8.1 Hz, 1H), 7.11 (d, J=8.1 Hz, 1H), 4.09 (s, 3H), 3.88 (m, 1H), 3.52 (m, 1H), 3.00 (m, 1H), 2.31 (s, 3H), 1.74 (m, 1H), 1.50 (m, 1H), 1.18 (m, 1H), 0.90 (d, J=6.6 Hz, 3H), 0.86 (t, J=7.5 Hz, 3H).

EXAMPLE 41(88)

2-[2-(4-amidinophenylcarbamoyl)-6-ethoxy-3-pyridyl]-5-[(1(S)-isopropyl-3-amino propyl)carbamoyl benzoic acid dimethanesulfonate

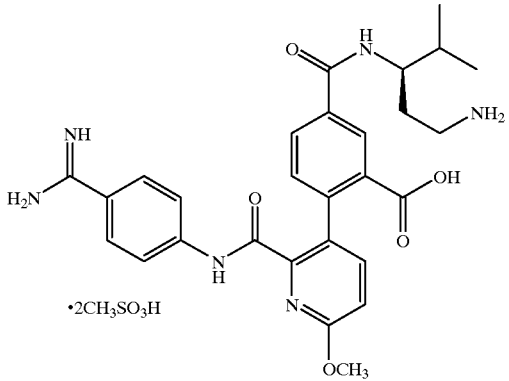

TLC:Rf 0.60 (Ethyl acetate:Acetic acid:Water=3:3:1); NMR (300 MHz, $d_6$-DMSO): δ 12.8–12.3 (brd, 1H), 10.58 (s, 1H), 9.19 (s, 2H), 8.91 (s, 2H), 8.45 (d, J=8.7 Hz, 1H), 8.41 (d, J=1.8 Hz, 1H), 8.04 (dd, J=8.1, 1.8 Hz, 1H), 7.88 (d, J=9.0 Hz, 2H), 7.78 (d, J=9.0 Hz, 2H), 7.72 (brd, 2H), 7.61 (d, J=8.4 Hz, 1H), 7.32 (d, J=8.1 Hz, 1H), 7.19 (dd, J=19.8, 6.9 Hz, 1H), 7.10 (d, J=8.4 Hz, 1H), 4.56 (m, 2H), 3.83 (m, 1H), 2.85–2.70 (m, 2H), 2.33 (s, 6H), 1.95–1.70 (m, 3H), 1.41 (t, J=6.9 Hz, 3H), 0.94 (d, J=6.0 Hz, 3H), 0.92 (d, J=6.0 Hz, 3H).

EXAMPLE 41(89)

2-[2-(4-amidinophenylcarbamoyl)-6-ethoxy-3-pyridyl]-5-[(1(S)-(2-aminoethyl)-3-methylbutyl)carbamoyl]benzoic acid dimethanesulfonate

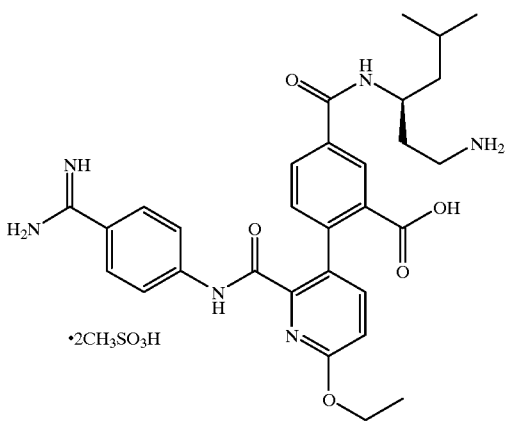

TLC:Rf 0.65 (Ethyl acetate:Acetic acid:Water=3:1:1); NMR (300 MHz, $d_6$-DMSO): δ 13.0–12.5 (broad, 1H), 10.57 (s, 1H), 9.20 (brs, 2H), 8.91 (brs, 2H), 8.51 (brd, J=9.0 Hz, 1H), 8.42 (d, J=1.8 Hz, 1H), 8.03 (dd, J=8.0, 1.8 Hz, 1H), 7.89 (d, J=9.0 Hz, 2H), 7.79 (d, J=9.0 Hz, 2H), 7.82–7.68 (broad, 3H), 7.62 (d, J=8.4 Hz, 1H), 7.32 (d, J=8.0 Hz, 1H), 7.10 (d, J=8.4 Hz, 1H), 4.56 (brq, J=7.0 Hz, 2H), 4.21–4.28 (m, 1H), 2.90–2.75 (m, 2H), 2.33 (s, 6H), 1.88–1.57 (m, 4H), 1.41 (t, J=7.0 Hz, 3H), 1.34–1.22 (m, 1H), 0.91 (d, J=6.6 Hz, 3H), 0.89 (d, J=6.9 Hz, 3H).

EXAMPLE 41(90)

2-[2-(4-amidinophenylcarbamoyl)-6-ethoxy-3-pyridyl]-5-[(1(S)-(2-aminoethyl)-2(S)-methylbutyl)carbamoyl]benzoic acid dimethanesulfonate

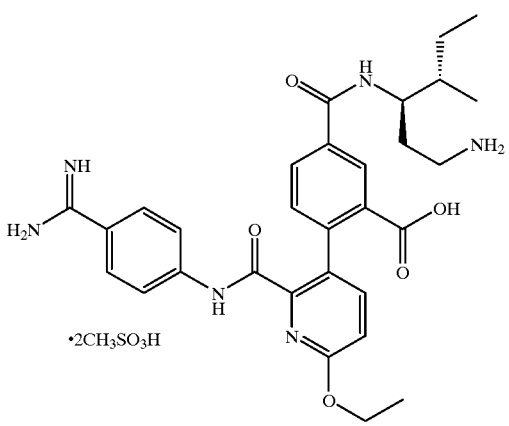

TLC:Rf 0.64 (Ethyl acetate:Acetic acid:Water=3:1:1); NMR (300 MHz, $d_6$-DMSO): δ 13.0–12.5 (broad, 1H), 10.57 (s, 1H), 9.20 (brs, 2H), 8.91 (brs, 2H), 8.48 (brd, J=9.0 Hz, 1H), 8.41 (d, J=1.8 Hz, 1H), 8.04 (dd, J=8.0, 1.8 Hz, 1H), 7.89 (d, J=8.7 Hz, 2H), 7.79 (d, J=8.7 Hz, 2H), 7.82–7.68 (broad, 3H), 7.62 (d, J=8.4 Hz, 1H), 7.32 (d, J=8.0 Hz, 1H), 7.10 (d, J=8.4 Hz, 1H), 4.56 (brq, J=7.0 Hz, 2H), 3.98–3.85 (m, 1H), 2.90–2.70 (m, 2H), 2.33 (s, 6H), 1.95–1.58 (m, 3H), 1.41 (t, J=7.0 Hz, 3H), 1.24–1.08 (m, 1H), 0.91 (d, J=6.6 Hz, 3H), 0.89 (d, J=7.2 Hz, 3H).

EXAMPLE 42(1)–42(7)

The following compounds were obtained by the same procedure as a series of reaction of Reference Example 8 or Example 11, using a compound prepared in Example 41(5), 41(18), 41(22), 41(23), 41(24), 41(32) or 41(54).

EXAMPLE 42(1)

2'-(4-amidinophenylcarbamoyl)-4-[(1(S)-carboxymethyl-2,2-dimethylpropyl) carbamoyl]-2-biphenylcarboxylic acid methanesulfonate

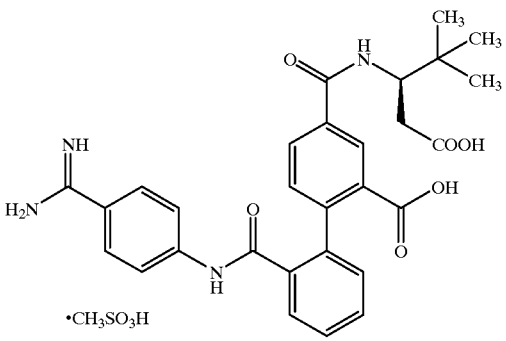

TLC:Rf 0.41 (Ethyl acetate:Acetic acid:Water=3:1:1); NMR ($d_6$-DMSO): δ 10.6 (1H, s), 9.15 (2H, br s), 8.80 (2H, br s), 8.28 (1H, d, J=8.8 Hz), 8.26 (1H, s), 7.92 (1H, d, J=6.0 Hz), 7.73–7.68 (5H, m), 7.60–7.48 (2H, m), 7.33–7.25 (2H, m), 4.29 (1H, t, J=8.8 Hz), 2.60–2.40 (2H, m), 2.30 (3H, s), 0.89 (9H, s).

EXAMPLE 42 (2)

2'-(4-amidinophenylcarbamoyl)-4-(1-carboxycyclopentylcarbamoyl)-2-biphenyl carboxylic acid methanesulfonate

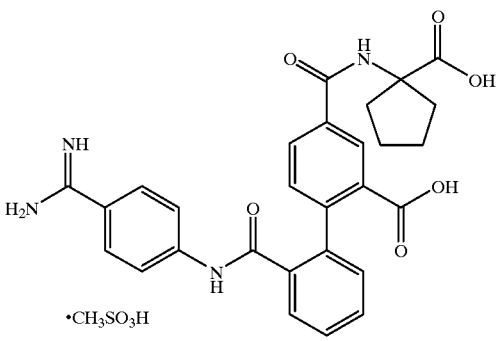

TLC:Rf 0.11 (Chloroform:Methanol:Acetic acid=10:2:1); NMR ($d_6$-DMSO): δ 10.5 (s, 1H), 9.15 (br s, 2H), 8.83 (br s, 2H), 8.72 (s, 1H), 8.29 (d, J=1.8 Hz, 1H), 7.96 (dd, J=7.8, 1.8 Hz, 1H), 7.73–7.68 (m, 5H), 7.60–7.50 (m, 2H), 7.31 (d, J=7.8 Hz, 1H), 7.28–7.24 (m, 1H), 2.31 (s, 3H), 2.20–2.00 (m, 4H), 1.80–1.60 (m, 4H).

EXAMPLE 42 (3)

2'-(4-amidinophenylcarbamoyl)-4-[(2-carboxy-2,2-dimethylethyl)carbamoyl]-2-biphenylcarboxylic acid methanesulfonate

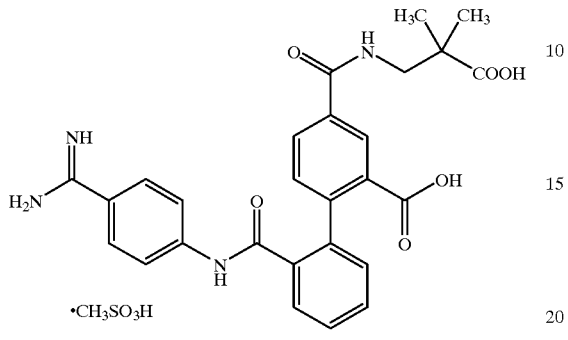

TLC:Rf 0.20 (Chloroform:Methanol:Acetic acid=10:2:1); NMR (d$_6$-DMSO): δ 10.5 (s, 1H), 9.16 (br s, 2H), 8.87 (br s, 2H), 8.53 (t, J=5.0 Hz, 1H), 8.27 (d, J=2.0 Hz, 1H), 7.94 (dd, J=8.4, 2.0 Hz, 1H), 7.73–7.67 (m, 5H), 7.58–7.52 (m, 2H), 7.32 (d, J=8.4 Hz, 1H), 7.30–7.24 (m, 1H), 3.43 (d, J=5.0 Hz, 2H), 2.32 (s, 3H), 1.10 (s, 6H).

EXAMPLE 42(4)

2-[2-(4-amidinophenylcarbamoyl)-6-methyl-3-pyrdyl]-5-[(1(S)-carboxy-2-methylpropyl)carbamoyl]benzoic acid methanesulfonate

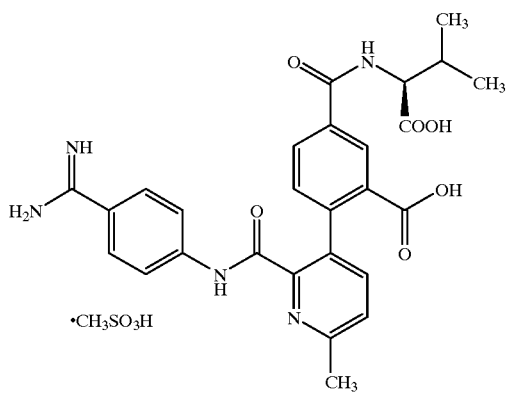

TLC:Rf 0.79 (Ethyl acetate:Acetic acid:Water=3:1:1); NMR (d$_6$-DMSO): δ 13.0–12.4 (broad, 2H), 10.84 (s, 1H), 9.17 (brs, 2H), 8.90 (brs, 2H), 8.72 (br d, J=7.5 Hz, 1H), 8.44 (brs, 1H), 8.07 (brd, J=7.8 Hz, 1H), 7.93 (brd, J=8.4 Hz, 2H), 7.77 (brd, J=8.4 Hz, 2H), 7.63 (brd, J=7.8 Hz, 1H), 7.55 (brd, J=7.8 Hz, 1H), 7.31 (d, J=7.8 Hz, 1H), 4.33 (brt, J=7.5 Hz, 1H), 2.67 (brs, 3H), 2.36 (brs, 3H), 2.30–2.10 (m, 1H), 0.98 (brs, 6H).

EXAMPLE 42(5)

2-[4-(4-amidinophenylcarbamoyl)-3-pyridyl]-5-[(1(S)-carboxy-2-methylpropyl) carbamoyl]benzoic acid methanesulfonanate

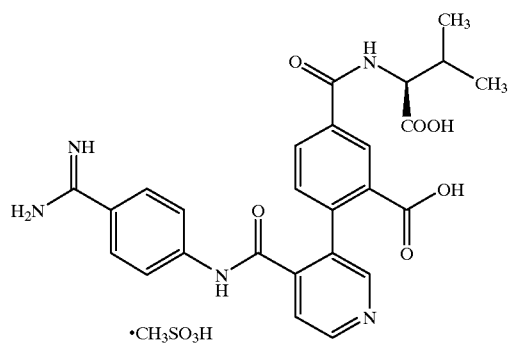

TLC:Rf 0.69 (Ethyl acetate:Acetic acid:Water=3:1:1); NMR (d$_6$-DMSO): δ 13.2–12.4 (broad, 2H), 10.86 (brs, 1H), 9.16 (brs, 2H), 8.87 (brs, 2H), 8.80–8.68 (m, 2H), 8.52 (brs, 1H), 8.39 (brs, 1H), 8.05 (brd, J=7.5 Hz, 1H), 7.73 (s, 4H), 7.70 (brd, J=7.5 Hz, 1H), 7.41 (brd, J=7.5 Hz, 1H), 4.29 (brt, J=7.0 Hz, 1H), 2.34 (brs, 3H), 2.30–2.10 (m, 1H), 0.97 (brs, 6H).

EXAMPLE 42(6)

2'-(4-amidinophenylcarbamoyl)-4-[(1-carboxy-1-methylethyl)carbamoyl]-2-biphenylcarboxylic acid methanesulfonate

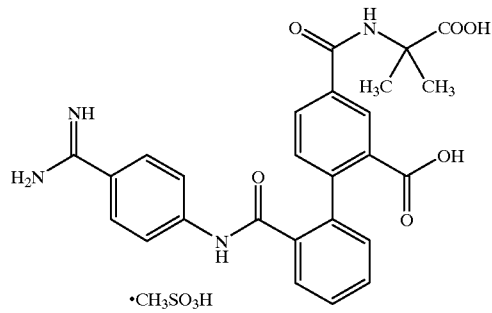

TLC:Rf 0.51 (Ethyl acetate:Acetic acid:Water=6:2:1); NMR (d$_6$-DMSO): δ 12.50 (br, 2H), 10.55 (s, 1H), 9.16 (s, 2H), 8.87 (s, 2H), 8.67 (s, 1H), 8.30 (d, J=1.8 Hz, 1H), 7.97, (dd, J=7.8, 1.8 Hz, 1H), 7.74 (s, 4H), 7.70 (dd, J=7.2, 1.2 Hz, 1H), 7.57 (dt, J=7.2, 1.2 Hz, 1H), 7.53 (dt, J=7.2, 1.2 Hz, 1H), 7.33 (d, J=8.4 Hz, 1H), 7.27 (dd, J=7.2, 1.2 Hz, 1H), 2.35 (s, 3H), 1.46 (s, 6H).

EXAMPLE 42(7)

2-[2-(4-amidinophenylcarbamoyl)-6-methoxy-3-pyridyl]-5-[1(S)-(4-carboxy oxazol-2-yl)-3-methylbutyl)carbamoyl]benzoic acid methanesulfonate

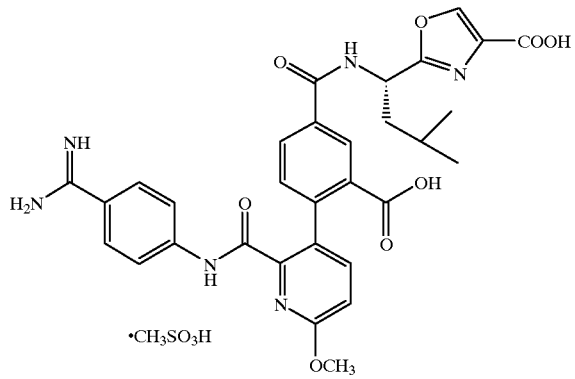

TLC:Rf 0.09 (Chloroform:Methanol:Water=7 3:0.3); NMR (d$_6$-DMSO): δ 13.2–12.6 (broad, 2H), 10.61 (s, 1H), 9.25 (brd, J=8.0 Hz, 1H), 9.18 (brs, 2H), 8.86 (brs, 2H), 8.69 (s, 1H), 8.47 (d, J=1.8 Hz, 1H), 8.07 (dd, J=7.8, 1.8 Hz, 1H), 7.90 (d, J=9.0 Hz, 2H), 7.78 (d, J=9.0 Hz, 2H), 7.65 (d, J=8.4 Hz, 1H), 7.33 (d, J=7.8 Hz, 1H), 7.13 (d, J=8.4 Hz, 1H), 5.38–5.29 (m, 1H), 4.10 (s, 3H), 2.33 (s, 3H), 2.05–1.62 (m, 3H), 0.95 (d, J=6.3 Hz, 3H), 0.94 (d, J=6.3 Hz, 3H).

EXAMPLE 43(1)–43(6)

The following compounds were obtained by the same procedure as a series of reaction of Example 1, using a corresponding compound instead of a compound prepared in Reference Example 5.

EXAMPLE 43(1)

Methyl 2'-(4-amidinophenylcarbamoyl)-4-(2,2-dimethylcyclopentylcarbamoyl)-2-biphenylcarboxylate

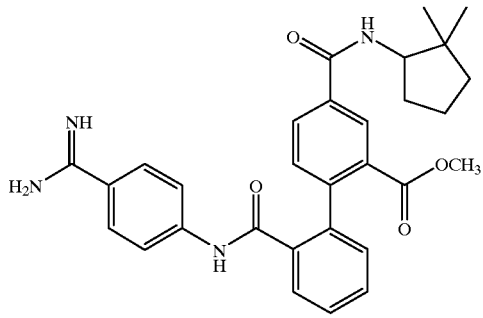

TLC:Rf 0.42 (Chloroform:Methanol:Acetic acid=10:2:1); NMR (d$_6$-DMSO): δ 10.63 (1H, br.s), 9.05 (3H, br.d), 8.25–8.15 (2H, m), 8.03 (1H, dd, J=8.0, 2.0 Hz), 7.74 (4H, like s), 7.69 (1H, dd, J=8.0, 2.0 Hz), 7.60 (1H, dt, J=8.0, 2.0 Hz), 7.54 (1H, dt, J=8.0, 2.0 Hz), 7.40 (1H, d, J=8.0 Hz), 7.31 (1H, dd, J=8.0, 2.0 Hz), 4.09 (1H, q, J=9.0 Hz), 3.54 (3H, s), 1.92 (1H, m), 1.8–1.5 (2H, m), 1.6–1.4 (3H, m), 0.98 (3H, s), 0.87 (3H, s).

EXAMPLE 43(2)

Methyl 2'-(4-amidinophenylcarbamoyl)-4-(3-methylbutylcarbonyl)-2-biphenylcarboxylate

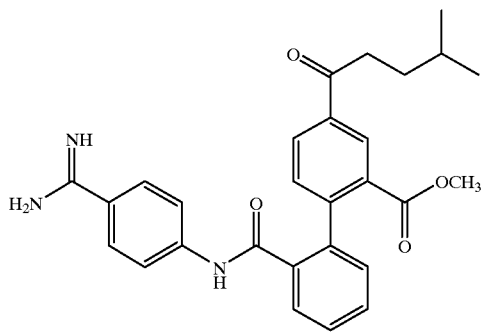

TLC:Rf 0.64 (Chloroform:Methanol:Acetic acid=10:2:1); NMR (300 MHz, d$_6$-DMSO): δ 10.67 (br.s, 1H), 9.3–8.9 (br, 3H), 8.28 (d, J=1.8 Hz, 1H), 8.17 (dd, J=1.8, 7.8 Hz, 1H), 7.75 (like s, 4H), 7.71 (dd, J=1.8, 7.8 Hz, 1H), 7.61 (dt, J=1.8, 7.8 Hz, 1H), 7.55 (dt, J=1.8, 7.8 Hz, 1H), 7.46 (d, J=7.8 Hz, 1H), 7.32 (dd, J=1.8, 7.8 Hz, 1H), 3.54 (s, 3H), 3.05 (t, J=7.0 Hz, 2H), 1.57 (like septet, J=7.0 Hz, 1H), 1.51 (q, J=7.0 Hz, 2H), 0.89 (d, J=7.0 Hz, 6H).

EXAMPLE 43(3)

Methyl 2'-(4-amidinophenylcarbamoyl)-4-[(N-methyl-N-t-butylamino)carbamoyl]-2-biphenylcarboxylate

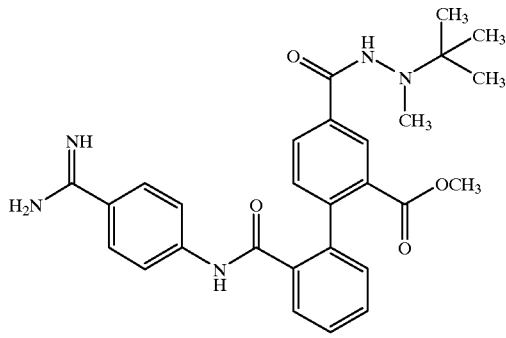

TLC:Rf 0.23 (Chloroform:Methanol:Water=8:2:0.2); NMR (200 MHz, CD$_3$OD): δ 8.25 (d, J=2.0 Hz, 1H), 7.94 (dd, J=8.0, 2.0 Hz, 1H), 7.73–7.65 (m, 5H), 7.61 (dt, J=8.0, 2.0 Hz, 1H), 7.55 (dt, J=8.0, 2.0 Hz, 1H), 7.45 (d, J=8.0 Hz, 1H), 7.30 (dd, J=8.0, 2.0 Hz, 1H), 3.69 (s, 3H), 2.57 (s, 3H), 1.17 (s, 9H).

EXAMPLE 43(4)

Benzyl 2-[2-(4-amidinophenylcarbamoyl)-6-methyl-3-pyridyl]-5-[(3-methyl-2-butenyl)carbamoyl]benzoate

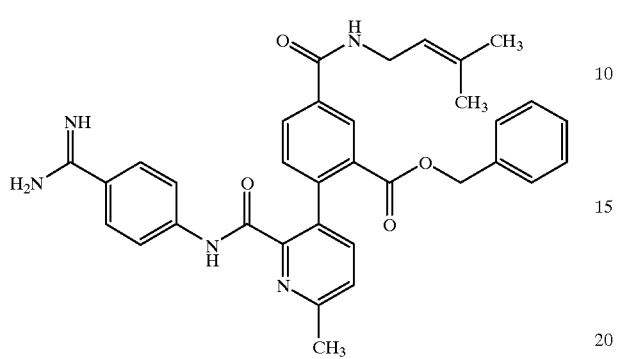

TLC:Rf 0.8 (Chloroform:Methanol:Acetic acid=10:2:1); NMR (300 MHz, CD$_3$OD): δ 8.51 (d, J=1.8 Hz, 1H), 8.02 (dd, J=7.8, 1.8 Hz, 1H), 7.84 (d, J=9.0 Hz, 2H), 7.75 (d, J=9.0 Hz, 2H), 7.54 (d, J=7.8 Hz, 1H), 7.43 (d, J=7.8 Hz, 1H), 7.31 (d, J=7.8 Hz, 1H), 7.25–7.17 (m, 3H), 7.05 (brt, J=6.3 Hz, 1H), 5.32 (brt, J=7.2 Hz, 1H), 5.00 (d, J=6.0 Hz, 2H), 4.00 (d, J=7.2 Hz, 2H), 2.64 (s, 3H), 1.76 (s, 6H).

EXAMPLE 43(5)

Benzyl 2'-(4-amidinophenylcarbamoyl)-5'-nitro-4-(2,2-dimethylpropylcarbamoyl)-2-biphenylcarboxylate

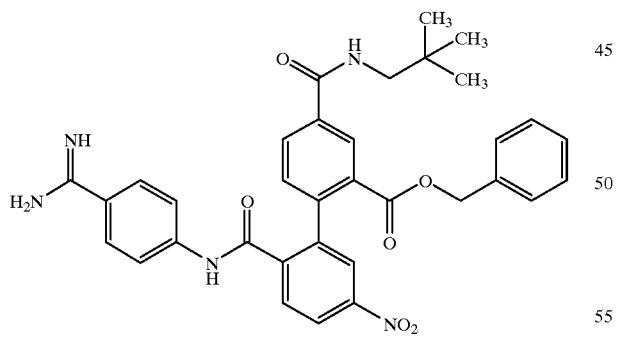

TLC:Rf 0.25 (Chloroform:Methanol:Water=8:2:0.2); NMR (200 MHz, CD$_3$OD): δ 8.44 (d, J=2.0 Hz, 1H), 8.21 (dd, J=8.0, 2.0 Hz, 1H), 8.08 (d, J=2.0 Hz, 1H), 8.02 (dd, J=8.0,2.0 Hz, 1H), 7.78 (d, J=8.0 Hz, 1H), 7.72 (d, J=9.0 Hz, 2H), 7.66 (d, J=9.0 Hz, 2H), 7.47 (d, J=8.0 Hz, 1H), 7.21 (m, 3H), 7.15–7.10 (m, 2H), 5.10 (s, 2H), 3.21 (s, 2H), 0.96 (s, 9H).

EXAMPLE 43(6)

Methyl 3-[2-(4-amidinophenylcarbamoyl)-6-methoxy-3-pyridyl]-6-[(1-isopropyl-2-methylpropyl)carbamoyl]-2-pyridinecarboxylate

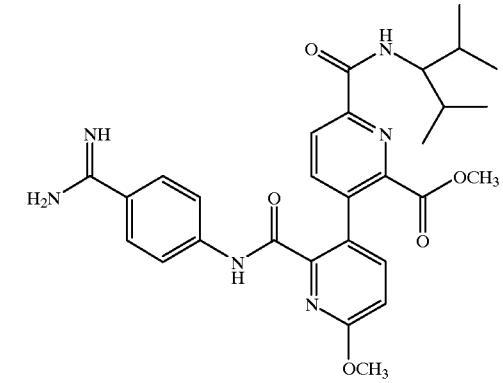

TLC:Rf 0.28 (Chloroform:Methanol:Water=8:2:0.2); NMR (200 MHz, CD$_3$OD): δ 8.32 (d, J=8.0 Hz, 1H), 7.93 (d, J=8.0 Hz, 1H), 7.90 (d, J=9.0 Hz, 2H), 7.78 (d, J=9.0 Hz, 2H), 7.70 (d, J=8.4 Hz, 1H), 7.15 (d, J=8.4 Hz, 1H), 4.17 (s, 3H), 3.74 (t, J=7.0 Hz, 1H), 3.67 (s, 3H), 2.04 (m, 2H), 0.98 (d, J=6.6 Hz, 6H), 0.96 (d, J=6.6 Hz, 6H).

EXAMPLE 44(1)–44(6)

The following compounds were obtained by the same procedure as a series of reaction of Example 11, using a compound prepared in Example 43 (1)–43 (6).

EXAMPLE 44(1)

2'-(4-amidinophenylcarbamoyl)-4-(2,2-dimethylcyclopentylcarbamoyl)-2-biphenylcarboxylic acid methanesulfonate

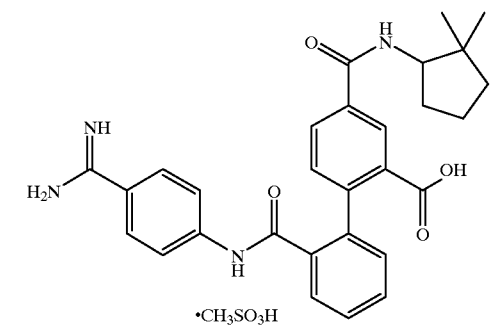

TLC:Rf 0.36 (Chloroform:Methanol:Acetic acid=10:2:1); NMR (d$_6$-DMSO): δ 12.6–11.8 (1H, br), 10.55 (1H, br.s), 9.14 (2H, br.s), 8.88 (2H, br.s), 8.27 (1H, d, J=1.8 Hz), 8.19 (1H, d, J=9.0 Hz), 7.96 (1H, dd, J=1.8, 8.1 Hz), 7.73 (4H, like s), 7.75–7.65 (1 H , m), 7.6–7.5 (2H, m), 7.31 (1H, d, J=8.1 Hz), 7.26 (1H, dd, J=1.8, 8.1 Hz), 4.08 (1H, like q, J=9.0 Hz), 2.36 (3H, s), 1.91 (1H, m), 1.8–1.6 (2H, m), 1.6–1.4 (3H, m), 0.97 (3H, s), 0.87 (3H, s).

EXAMPLE 44(2)

2'-(4-amidinophenylcarbamoyl)-4-(3-methylbutylcarbonyl)-2-biphenylcarboxylic

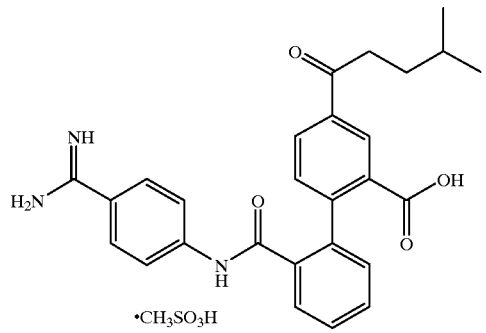

TLC:Rf 0.33 (Chloroform:Methanol:Acetic acid=10:2:1); NMR (d$_6$-DMSO): δ 12.90 (br.s, 1H), 10.59 (s, 11H), 9.13 (s, 2H), 8.81 (s, 2H), 8.34 (d, J=1.8 Hz, 1H), 8.10 (dd, J=1.8, 7.8 Hz, 1H), 7.8–7.65 (m, 5H), 7.65–7.5 (m, 2H), 7.38 (d, J=7.8 Hz, 1H), 7.28 (dd, J=1.8, 7.8 Hz, 1H), 3.04 (t, J=7.0 Hz, 2H), 2.32 (s, 3H), 1.59 (like septet, J=7.0 Hz, 1H), 1.50 (q, J=7.0 Hz, 2H), 0.89 (d, J=7.0 Hz, 6H).

EXAMPLE 44(3)

2'-(4-amidinophenylcarbamoyl)-4-[(N-methyl-N-t-butylamino)carbamoyl]-2-biphenylcarboxylic acid dimethanesulfonate

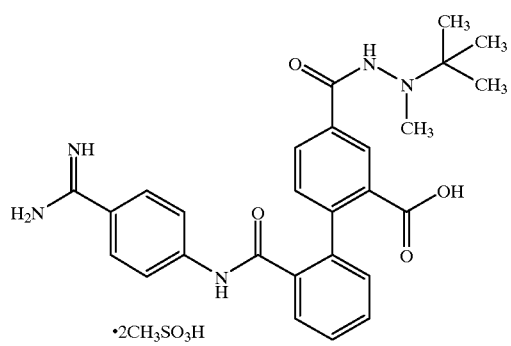

TLC:Rf 0.33 (Chloroform:Methanol:Water=7:3:0.3); NMR (d$_6$-DMSO): δ 10.65 (s, 1H), 9.23 (s, 2H), 9.01 (s, 2H), 8.32 (d, J=2.0 Hz, 1H), 8.04 (dd, J=8.0, 2.0 Hz, 1H), 7.77 (s, 4H), 7.74 (dd, J=8.0, 2.0 Hz, 1H), 7.59 (dt, J=8.0, 2.0 Hz, 1H), 7.54 (dt, J=8.0, 2.0 Hz, 1H), 7.38 (d, J=8.0 Hz, 1H), 7.26 (dd, J=8.0, 2.0 Hz, 1H), 2.89 (s, 3H), 2.36 (s, 6H), 1.29 (s, 9H).

EXAMPLE 44(4)

2-[2-(4-amidinophenylcarbamoyl)-6-methyl-3-pyridyl)-5-[(3-methyl-2-butenyl) carbamoyl]benzoic acid methanesulfonate

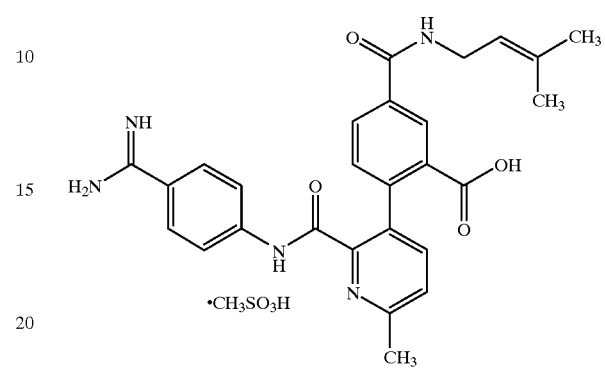

TLC:Rf 0.30 (Chloroform:Methanol:Acetic acid 10:2:1); NMR (d$_6$-DMSO): δ 10.83 (s, 1H), 9.20 (S, 2H), 8.90 (s, 2H), 8.78 (t, J=5.4 Hz, 1H), 8.42 (d, J=1.8 Hz, 1H), 8.02, (dd, J=8.4, 1.8 Hz, 1H), 7.92 (d, J=8.7 Hz, 2H), 7.78 (d, J=8.7 Hz, 2H), 7.63 (d, J=7.8 Hz, 1H), 7.55 (d, J=7.8 Hz, 1H), 7.29 (d, J=8.4 Hz, 1H), 5.25 (brt, J=5.4 Hz, 1H), 3.88 (t, J=5.4 Hz, 2H), 2.67 (s, 3H), 2.33 (s, 3H), 1.69 (s, 6H).

EXAMPLE 44(5)

2'-(4-amidinophenylcarbamoyl)-5'-nitro-4-(2,2-dimethylpropylcarbamoyl)-2-biphenylcarboxylic acid methanesulfonate

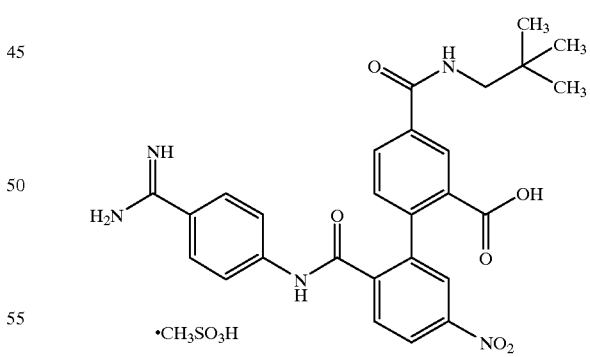

TLC:Rf 0.30 (Chloroform2:Methanol:Water=8:2:0.2); NMR (d$_6$-DMSO): δ 12.90 (br.s, 1H), 10.84 (s, 1H), 9.15 (s, 2H), 8.78 (s, 2H), 8.59 (br.t, J=6.3 Hz, 1H) 8.40 (dd, J=8.0,2.0 Hz), 8.39 (d, J=2.0 Hz, 1H), 8.10 (d, J=2.0 Hz, 1H), 8.05 (dd, J=8.0,2.0 Hz, 1H), 7.96 (d, J=8.0 Hz, 1H), 7.73 (s, 4H), 7.43 (d, J=8.0 Hz, 1H), 3.12 (d, J=6.3 Hz, 2H), 2.33 (s, 3H), 0.91 (s, 9H).

EXAMPLE 44(6)

3-[2-(4-amidinophenylcarbamoyl)-6-methoxy-3-pyridyl]-6-[(1-isopropyl-2-imethylpropyl)carbamoyl]-2-pyridinecarboxylic acid methanesulfonate

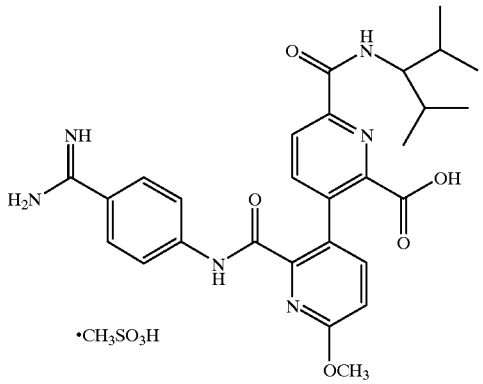

TLC:Rf 0.30 (Chloroform:Methanol:Water=8:2:0.2); NMR (d$_6$-DMSO): δ 12.95 (br.s, 1H), 10.66 (s 1H), 9.18 (s, 2H), 8.81 (s, 2H), 8.59 (d, J=10.0 Hz, 1H), 8.27 (d, J=8.0 Hz, 1H), 7.94 (d, J=8.0 Hz, 1H), 7.91 (d, J=9.0 Hz, 2H), 7.77 (d, J=9.0 Hz, 2H ), 7.76 (d, J=8.0 Hz, 1H), 7.19 (d, J=8.0 Hz, 1H ), 4.13 (s, 3H), 3.70 (dt, J=10.0,7.0 Hz, 1H), 2.31 (s, 3H), 1.98 (m, 2H), 0.91 (d, J=6.0 Hz, 6H ), 0.89 (d, J=6.0 Hz, 6H).

REFERENCE EXAMPLE 26

Benzyl 2-[2-(4-amidinophenylcarbamoyl)-6-methoxy-3-pyridyl]-5-[(1(S)-t-butyl dimethylsilyloxymethyl-2,2-dimethylpropyl)carbamoyl]benzoate

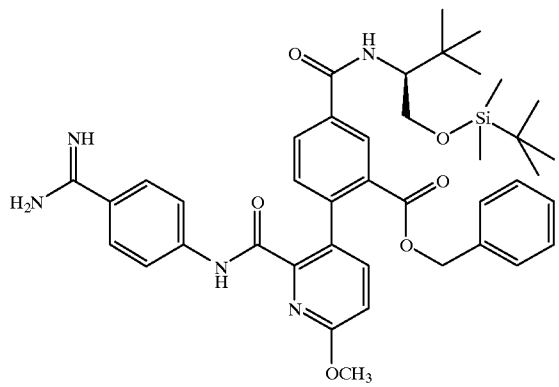

The title compound was obtained by the same procedure as a series of reaction of Example 1, using 3-[4-(1(S)-t-butyidimethylsilyloxy-2,2-dimethylpropylcarbamoyl)-2-benzyloxycarbonylphenyl]-6-methoxy-2-pyridinecarboxylic acid which was obtained by the same procedure as a series of reaction of Reference Example 5, using a compound prepared in Reference Example 25.

TLC:Rf 0.58 (Chloroform:Methanol:Acetic acid=20:2:1); NMR (300 MHz, CD$_3$OD): δ 8.46 (d, J=1.8 Hz, 1H), 7.98 (dd, J=8.0, 1.8 Hz, 1H), 7.83 (d, J=9.3 Hz, 2H), 7.77 (d, J=9.3 Hz, 2H), 7.56 (d, J=8.4 Hz, 1H), 7.32 (d, J=8.0 Hz, 1H), 7.28–7.16 (m, 3H), 7.12–7.06 (m, 2H), 6.99 (d, J=8.4 Hz, 1H), 5.08 (brd, J=12 Hz, 1H), 4.99 (brd, J=12 Hz, 1H), 4.07 (dd, J=8.7, 3.9 Hz, 1H), 3.95 (dd, J=10.5, 3.9 Hz, 1H), 3.74 (dd, J=10.5, 8.7 Hz, 1H), 1.03 (s, 9H), 0.86 (s, 9H), 0.08 (s, 3H), 0.07 (s, 3H).

EXAMPLE 45

Benzyl 2-[2-(4-amidinophenylcarbamoyl)-6-methoxy-3-pyridyl]-5-[(1(S)-hydroxy methyl-2,2-dimethylpropyl)carbamoyl]benzoate

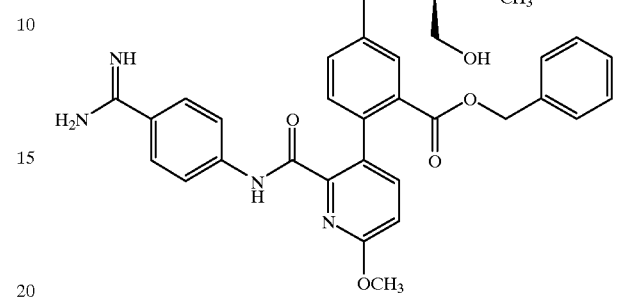

A solution of a compound prepared in Reference Example 26 (2.15 g) in acetic acid (9 ml)/water (3 ml) was stirred for 16 hours at room temperature. The reaction mixture was concentrated. The residue was purified by column chromatography on silica gel (Chloroform:Methanol:Water= 7:3:0.3) to give the title compound (1.52 g) having the following physical data.

TLC:Rf 0.32 (Chloroform:Methanol:Acetic acid=20:2:1); NMR (300 MHz, CD$_3$OD): δ 8.52 (d, J=2.0 Hz, 1H), 8.04 (dd, J=8.0, 2.0 Hz, 1H), 7.83 (d, J=9.0 Hz, 2H), 7.77 (d, J=9.0 Hz, 2H), 7.55 (d, J=8.4 Hz, 1H), 7.32 (d, J=8.0 Hz, 1H), 7.28–7.16 (m, 3H), 7.10–7.05 (m, 2H), 6.99 (d, J=8.4 Hz, 1H), 5.07 (brd, J=12 Hz, 1H), 4.98 (brd, J=12 Hz, 1H), 4.09 (dd, J=9.0, 3.3 Hz, 1H), 4.06 (s, 3H), 3.90 (dd, J=10.4, 3.3 Hz, 1H), 3.65 (dd, J=10.4, 9.0 Hz, 1H), 1.02 (s, 9H).

EXAMPLE 46

2-[2-(4-amidinophenylcarbamoyl)-6-methoxy-3-pyridyl]-5-[(1(S)-hydroxymethyl-2,2-dimethylpropyl)carbamoyl]benzoic acid methanesulfonate

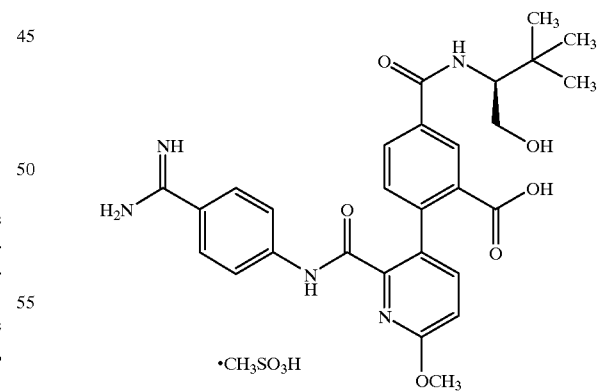

The title compound (1.48 g) having the following physical data was obtained by the same procedure as a series of reaction of Example 2, using a compound prepared in Example 45 (1.51 g).

TLC:Rf 0.21 (Chloroform:Methanol:Acetic acid=10:2:1) NMR (d$_6$-DMSO): δ 13.0–12.4 (broad, 1H), 10.61 (s, 1H), 9.19 (brs, 2H), 8.88 (brs, 2H), 8.41 (d, J=1.8 Hz, 1H), 8.12

(d, J=9.0 Hz, 1H), 8.03 (dd, J=8.0, 1.8 Hz, 1H), 7.90 (d, J=9.0 Hz, 2H), 7.78 (d, J=9.0 Hz, 2H), 7.64 (d, J=8.5 Hz, 1H), 7.30 (d, J=8.0 Hz, H), 7.12 (d, J=8.0 Hz, 1H), 4.09 (s, 3H), 3.93 (td, J=9.0, 3.5 Hz, 1H), 3.67 (dd, J=10.8, 3.5 Hz, 1H), 3.50 (dd, J=10.8, 9.0 Hz, 1H), 2.33 (s, 3H), 0.92 (s, 9H).

EXAMPLE 47(1)–47(32)

The following compounds were obtained by the same procedure as a series of reaction of Reference Example 26 Example 45 Example 46, using a corresponding compound.

EXAMPLE 47(1)

2'-[(2-amidino-5-pyridyl)carbamoyl]-4'-methoxy-4-[(1 (S)-hydroxymethyl- 2,2-dimethylpropyl)carbamoyl]-2-biphenylcarboxylic acid methanesulfonate

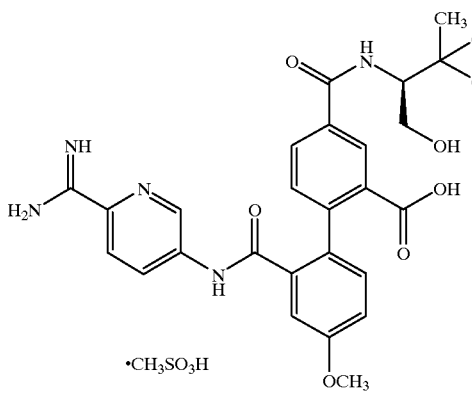

TLC:Rf 0.42 (Chloroform:Methanol:Water=7:3:0.3); NMR (d$_6$-DMSO+2 drops of CD$_3$OD): δ 10.89 (s, 1H), 9.38 (s, 2H), 9.07 (s, 2H), 8.93 (d, J=2.0 Hz, 1H), 8.30–8.28 (m, 2H), 8.20 (d, J=8.0 Hz, 1H), 8.07 (d, J=9.6 Hz, 1H), 7.98 (dd, J=8.0, 2.0 Hz, 1H), 7.33–7.30 (m, 2H), 7.24 (d, J=8.0 Hz, 1H), 7.17 (dd, J=8.0, 2.0 Hz, 1H), 3.90 (s, 3H), 3.67 (dd, J=11.4, 3.0 Hz, 1H), 3.48 (dd, J=11.4, 9.3 Hz, 1H), 2.35 (s, 3H), 0.91 (s, 9H).

EXAMPLE 47(2)

2'-[(2-amidino-5-pyridyl)carbamoyl]-4-[(1(S)-hydroxymethyl-2,2-dimethylpropyl) carbamoyl]-2-biphenylcarboxylic acid methanesulfonate

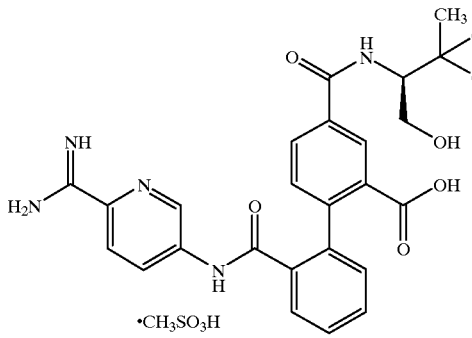

TLC:Rf 0.11 (Chloroform:Methanol:Acetic acid=10:2:1); NMR (d$_6$-DMSO): δ 10.9 (s, 1H), 9.37 (br s, 2H), 9.07–9.05 (m, 2H), 8.91 (d, J=2.6 Hz, 1H), 8.28 (dd, J'6.6,2.6 Hz, 1H), 8.18 (d, J=8.8 Hz, 1H), 8.08 (d, J=9.4 Hz, 1H), 8.00 (dd, J=8.0, 1.8 Hz, 1H), 7.77–7.72 (m, 1H), 7.64–7.51 (m, 2H), 7.33 (d, J=8.0 Hz, 1H), 7.31–7.28 (m, 1H), 3.90–3.85 (m, 1H), 3.80–3.40 (m, 2H), 3.50–3.40 (m, 1H), 2.31 (s, 3H), 0.90 (s, 9H).

EXAMPLE 47(3)

2-[4-(4-amidinophenylcarbamoyl)-3-pyridyl]-5-[(1(S) hydroxymethyl-2,2-dimethylpropyl)carbamoyl]benzoic acid methanesulfonate

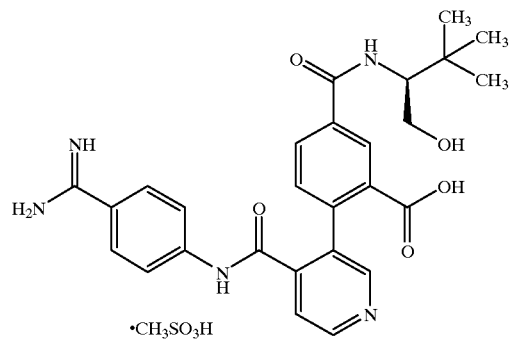

TLC:Rf 0.18 (Chloroform:Methanol:Water=7:3:0.3); NMR (d$_6$-DMSO): δ 11.05 (s, 1H), 9.22 (brs, 2H), 8.99 (brs, 2H), 8.90 (d, J=5.5 Hz, 1H), 8.72 (s, 1H), 8.41 (d, J=1.5 Hz, 1H), 8.17 (d, J=9.5 Hz, 1H), 8.07 (dd, J=8.0, 1.5 Hz, 1H), 7.93 (d, J=5.5 Hz, 1H), 7.76 (like s, 4H), 7.46 (d, J=8.0 Hz, 1H), 3.90 (td, J=9.5, 3.5 Hz, 1H), 3.66 (dd, J=11.0, 3.5 Hz, 1H), 3.47 (dd, J=11.0, 9.5 Hz, 1H), 2.36 (s, 3H), 0.90 (s, 9H).

EXAMPLE 47(4)

2-[4-[(2-amidino-5-pyridyl)carbamoyl]-3-pyridyl]-5-[(1 (S)-hydroxymethyl- 2,2-dimethylpropyl)carbamoyl]benzoic acid methanesulfonate

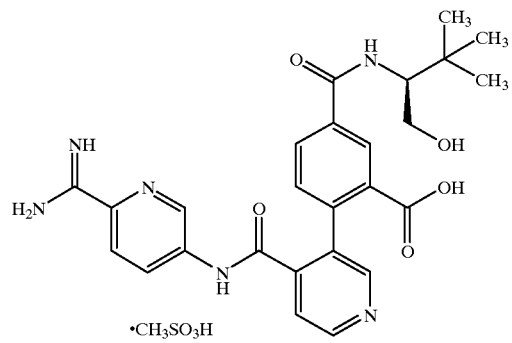

TLC:Rf 0.18 (Chloroform:Methanol:Water=7:3:0.3); NMR (d$_6$-DMSO): δ 11.38 (s, 1H), 9.44 (brs, 2H), 9.23 (brs, 2H), 8.94 (d, J=2.0 Hz, 1H), 8.90 (d, J=5.0 Hz, 1H), 8.70 (s, 1H), 8.40 (d, J=1.5 Hz, 1H), 8.29 (dd, J=9.0, 2.0 Hz, 1H), 8.23 (d, J=9.0 Hz, 1H), 8.16 (d, J=9.0 Hz, 1H), 8.08 (dd, J=8.0,1.5 Hz, 1H), 7.93 (d, J=5.0 Hz, 1H), 7.47 (d, J=8.0 Hz, 1H), 3.90 (td, J=9.0, 3.5 Hz, 1H), 3.66 (dd, J=11.0, 3.5 Hz, 1H), 3.47 (dd, J=11.0, 9.0 Hz, 1H), 2.36 (s, 3H), 0.90 (s, 9H).

EXAMPLE 47(5)

2-[2-(4-amidinophenylcarbamoyl)-3-pyridyl]-5-[(1(S)-hydroxymethyl-2,2-dimethylpropyl)carbamoyl]benzoic acid methanesulfonate

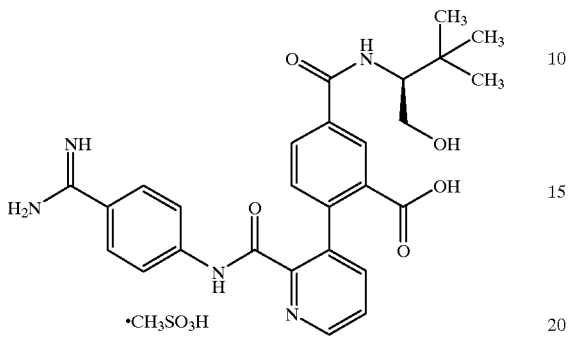

TLC:Rf 0.30 (Chloroform:Methanol:Acetic acid=10:2:1); NMR (d$_6$-DMSO): δ 11.00 (s, 1H), 9.20 (s, 2H), 8.94 (s, 2H), 8.73 (dd, J=4.5, 2.1 Hz, 1H), 8.43 (d, J=2.1 Hz, 1H), 8.15 (br.d, J=9.0 Hz, 1H), 8.08 (dd, J=8.1, 2.1 Hz, 1H), 7.95 (d, J=9.0 Hz, 2H), 7.8–7.65 (m, 4H), 733 (d, J=8.1 Hz, 1H), 5.4–4.6 (br, 2H), 3.94 (td, J=9.0, 3.6 Hz, 1H), 3.68 (dd, J=11.1, 3.6 Hz, 1H), 3.51 (dd, J=11.1, 9.0 Hz, 1H), 2.37 (s, 3H), 0.93 (s, 9H).

EXAMPLE 47(6)

2-[2-[(2-amidino-5-pyridyl)carbamoyl]-3-pyridyl]-5-[(1(S)-hydroxymethyl-2,2-dimethylpropyl)carbamoyl]benzoic acid methanesulfonate

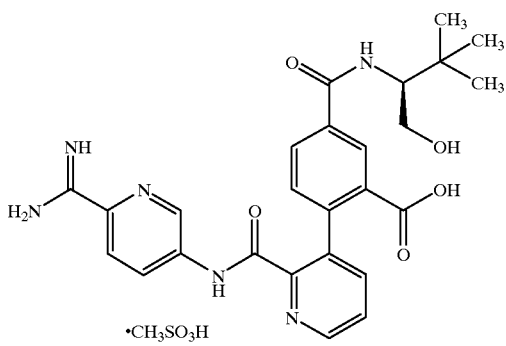

TLC:Rf 0.26 (Chloroform:Methanol:Acetic acid 10:2:1); NMR (d$_6$-DMSO): δ 13.0–12.4 (br, 1H), 11.34 (s, 1H), 9.40 (br.s, 2H), 9.12 (d, J=2.0 Hz, 1H), 9.09 (br.s, 2H), 8.76 (dd, J=4.2, 2.1 Hz, 1H), 8.49 (dd, J=9.0, 2.0 Hz, 1H), 8.44 (d, J=2.0 Hz, 1H), 8.20 (d, J=9.0 Hz, 1H), 8.15 (br.d, J=9.3 Hz, 1H), 8.09 (dd, J=8.0, 2.0 Hz, 1H), 7.8–7.7 (m, 2H), 7.35 (d, J=8.0 Hz, 1H), 3.94 (td, J=9.3, 3.3 Hz, 1H), 3.9–3.7 (br, 1H), 3.69 (dd, J=10.8, 3.3 Hz, 1H), 3.50 (dd, J=10.8, 9.3 Hz, 1H), 2.31 (s, 3H), 0.93 (s, 9H).

EXAMPLE 47 (7)

2-[2-(4-amidinophenylcarbamoyl)-6-methyl-3-pyridyl]-5-[(1(S)-hydroxymethyl-2,2-dimethylpropyl)carbamoyl]benzoic acid methanesulfonate

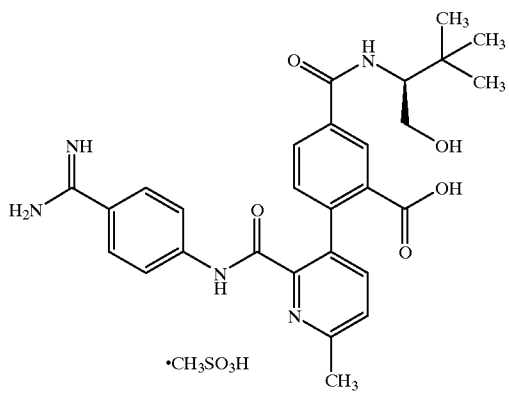

TLC:Rf 0.09 (Chloroform:Methanol:Acetic acid=10:2:1); NMR (d$_6$-DMSO): δ 10.85 (s, 1H), 9.21 (brs, 2H), 8.94 (brs, 2H), 8.42 (d, J=1.8 Hz, 1H), 8.14 (d, J=9.3 Hz, 1H), 8.05 (dd, J=8.0, 1.8 Hz, 1H), 7.93 (d, J=9.0 Hz, 2H), 7.78 (d, J=9.0 Hz, 2H), 7.63 (d, J=8.0 Hz, 1H), 7.56 (d, J=8.0 Hz, 1H), 7.30 (d, J=8.0 Hz, 1H), 3.93 (td, J=9.3, 3.5 Hz, 1H), 3.68 (dd, J=11.0, 3.5 Hz, 1H), 3.50 (dd, J=11.0, 9.3 Hz, 1H), 2.67 (s, 3H), 2.36 (s, 3H), 0.93 (s, 9H).

EXAMPLE 47(8)

2-[2-(4-amidinophenylcarbamoyl)-6-methyl-3-pyridyl]-5-[(1(S)-hydroxymethyl-3-methylbutyl)carbamoyl]benzoic acid methanesulfonate

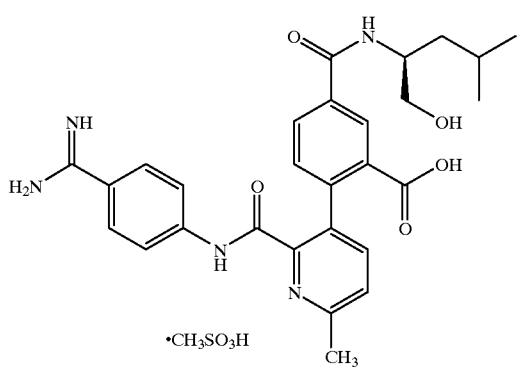

TLC:Rf 0.23 (Chloroform:Methanol:Acetic acid=10:2:1); NMR (d$_6$-DMSO): δ 10.8 (s, 1H), 9.21 (br s, 2H), 8.93 (br s, 2H), 8.42 (d, J=1.8 Hz, 1H), 8.27 (d, J=8.7 Hz, 1H), 8.05 (dd, J=8.1, 1.8 Hz, 1H), 7.93 (d, J=8.1 Hz, 2H), 7.78 (d, J=8.1 Hz, 2H), 7.63 (d, J=8.1 Hz, 1H), 7.55 (d, J=8.1 Hz, 1H), 7.29 (d, J=8.1 Hz, 1H) 4.20–4.10 (m, 1H), 3.47–3.33 (m, 2H), 2.67 (s, 3H), 2.36 (s, 3H), 1.70–1.30 (m, 3H), 0.91–0.87 (m, 6H).

EXAMPLE 47(9)

2-[2-(4-amidinophenylcarbamoyl)-6-methoxy-3-pyridyl]-4-methyl-5-[(1(S)-hydroxymethyl-2,2-dimethylpropyl)carbamoyl]benzoic acid methanesulfonate

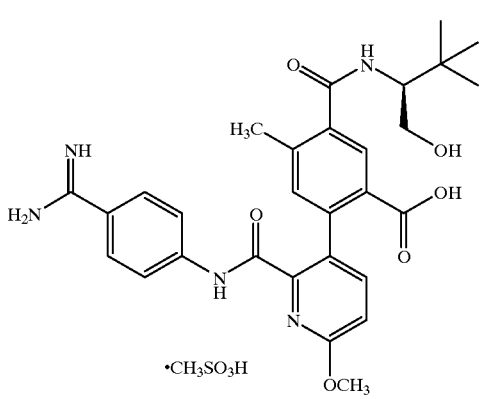

TLC:Rf 0.37 (Chloroform:Methanol:Water=8:2:0.2); NMR (d$_6$-DMSO): δ 10.59 (s, 1H), 9.21 (s, 2H), 8.89 (s, 2H), 8.07 (d, J=9.0 Hz, 1H), 7.91 (d, J=9.0 Hz, 2H), 7.89 (s, 1H), 7.79 (d, J=9.0 Hz, 2H), 7.58 (d, J=8.0 Hz, 1H), 7.10 (d, J=8.0 Hz, 1H), 7.08 (s, 1H), 4.09 (s, 3H), 3.40 (t, J=9.0 Hz, 1H), 2.38 (s, 3H), 2.33 (s, 3H), 0.94 (s, 9H).

EXAMPLE 47(10)

2-[3-(4-amidinophenylcarbamoyl)-2-thienyl]-5-[(1(S)-hydroxymethyl-2,2-dimethylpropyl)carbamoyl]benzoic acid methanesulfonate

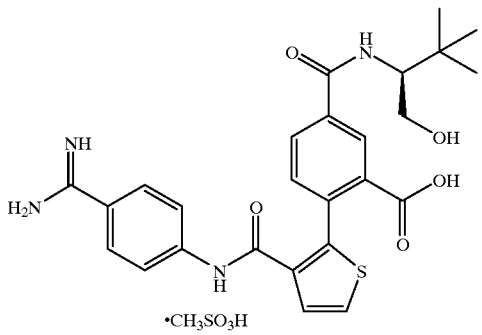

TLC:Rf 0.31 (Chloroform:Methanol:Water=8:2:0.2); NMR (d$_6$-DMSO): δ 10.32 (s, 1H), 9.18 (s, 2H), 8.89 (s, 2H), 8.30 (d, J=2.0 Hz, 1H), 8.13 (br.d, J=9.3 Hz, 1H), 8.01 (dd, J=8.0,2.0 Hz, 1H), 7.83 (d, J=9.0 Hz, 2H), 7.75 (d, J=9.0 Hz, 2H), 7.72 (d, J=5.6 Hz, 1H), 7.65 (d, J=5.6 Hz, 1H), 7.48 (d, J=8.0 Hz, 1H), 3.90 (m, 1H), 3.67 (dd, J=11.5,3.3 Hz, 1H), 3.48 (dd, J=11.5,9.0 Hz, 1H), 2.33 (s, 3H), 0.91 (s, 9H).

EXAMPLE 47(11)

2-[2-(4-amidinophenylcarbamoyl)-3-thienyl]-5-[(1(S)-hydroxymethyl-2,2-dimethylpropyl)carbamoyl]benzoic acid methanesulfonate

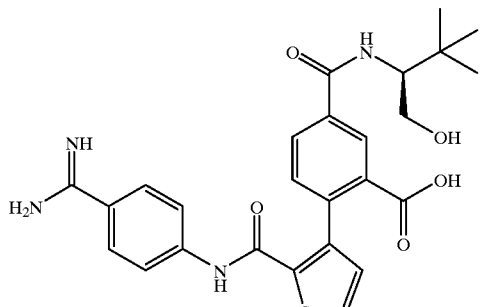

TLC:Rf 0.35 (Chloroform:Methanol:Acetic acid=10:2:1); NMR (d$_6$-DMSO): δ 13.0–12.4 (br, 1H), 10.18 (s, 1H), 9.18 (s, 2H), 8.87 (s, 2H), 8.30 (d, J=1.8 Hz, 1H), 8.09 (br.d, J=9.6 Hz, 1H), 8.02 (dd, J=8.0, 1.8 Hz, 1H), 7.84 (d, J=5.0 Hz, 1H), 7.74 (d, J=9.0 Hz, 2H), 7.70 (d, J=9.0 Hz, 2H), 7.41 (d, J=8.0 Hz, 1H), 7.11 (d, J=5.0 Hz, 1H), 3.91 (m, 1H), 3.66 (m, 1H), 3.65–3.45 (br, 1H), 3.48 (m, 1H), 2.32 (s, 3H), 0.91 (s, 9H).

EXAMPLE 47(12)

2-[2-(4-amidinophenylcarbamoyl)-6-methoxy-3-pyridyl]-5-[(1-hydroxymethyl-1-methoxycarbonyl-3-methylbutyl)carbamoyl]benzoic acid methanesulfonate

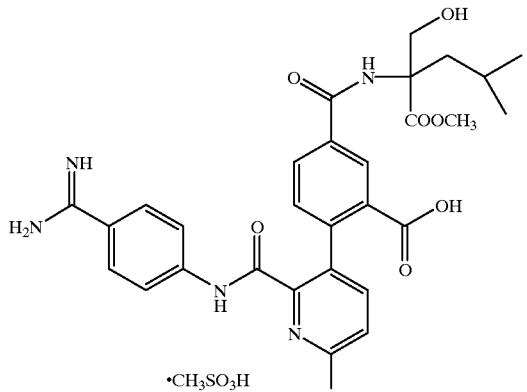

TLC:Rf 0.54 (Chloroform:Methanol:Water=8:2:0.2); NMR (d$_6$-DMSO): δ 12.75 (br.s, 1H), 10.61 (s, 1H), 9.19 (s, 2H), 8.86 (s, 2H), 8.38 (d, J=2.0 Hz, 1H), 8.25 (s, 1H), 8.00 (dd, J=8.0,2.0 Hz, 1H), 7.90 (d, J=9.0 Hz, 2H), 7.78 (d, J=9.0 Hz, 2H), 7.65 (d, J=8.0 Hz, 1H), 7.31 (d, J=8.0 Hz, 1H), 7.13 (d, J=8.0 Hz, 1H), 4.10 (s, 3H), 3.82 (s, 2H), 3.62 (s, 3H), 2.31 (s, 3H), 1.96 (dd, J=13.6,6.3 Hz, 1H), 1.87 (dd, J=13.6, 6.3 Hz, 1H), 1.65 (m, 1H), 0.87 (d, J=5.7 Hz, 3H), 0.85 (d, J=5.7 Hz, 3H).

EXAMPLE 47(13)

2-[2-(N-(4-amidinophenyl)-N-methylcarbamoyl]-6-methoxy-3-pyridyl]-5-[(1(S)-hydroxymethyl-2,2-dimethylpropyl)carbamoyl]benzeic acid methanesulfonate

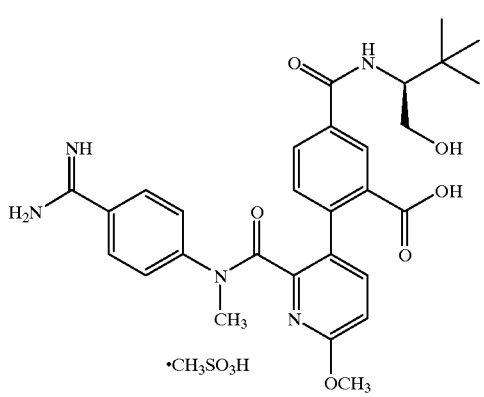

TLC:Rf 0.35 (Chloroform:Methanol:Acetic acid=10:2:1); NMR (CD$_3$OD): δ 8.48 (d, J=2.0 Hz, 1H), 8.01 (dd, J=8.2, 2.0 Hz, 1H), 7.67 (d, J=8.4 Hz, 2H), 7.54 (d, J=8.4 Hz, 1H), 7.34 (d, J=8.4 Hz, 1H), 7.20 (d, J=8.4 Hz, 2H), 6.82 (d, J=8.4 Hz, 1H), 4.09 (dd, J=9.0, 3.6 Hz, 1H), 3.90 (dd, J=11.6, 3.6 Hz, 1H), 3.83 (s, 3H), 3.43 (dd, J=11.6, 9.0 Hz, 1H), 3.28 (s, 3H), 2.70 (s, 3H), 1.02 (s, 9H).

EXAMPLE 47(14)

2-[2-(4-amidinophenylcarbamoyl)-6-ethoxy-3-pyridyl]-5-[(1(S)-hydroxymethyl-2,2-dimethylpropyl)carbamoyl]benzoic acid methanesulfonate

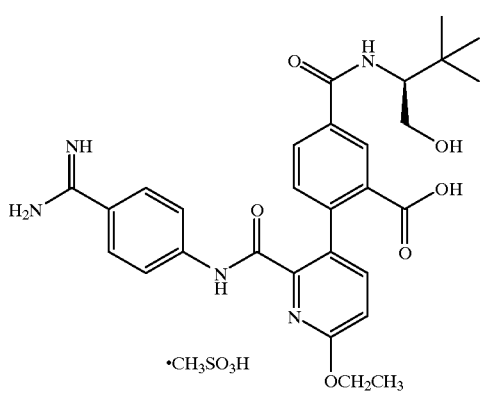

TLC:Rf 0.38 (Chloroform:Methanol:Acetic acid=10:2:1); NMR (d$_6$-DMSO): δ 10.6 (s, 1H), 9.19 (br s, 2H), 8.87 (br s, 2H), 8.40 (d, J=1.5 Hz, 1H), 8.11 (d, J=9.3 Hz, 1H), 8.03 (dd, J=8.1, 1.5 Hz, 1H), 7.89 (d, J=9.0 Hz, 2H), 7.77 (d, J=9.0 Hz, 2H), 7.63 (d, J=8.7 Hz, 1H), 7.29 (d, J=8.1 Hz, 1H), 7.10 (d, J=8.7 Hz, 1H), 4.56 (q, J=6.9 Hz, 2H), 3.93 (dt, J=3.9, 9.3 Hz, 1H), 3.68 (dd, J=11.1, 3.9 Hz, 1H), 3.53–3.34 (m, 1H), 2.31 (s, 3H), 1.41 (t, J=6.9 Hz, 3H), 0.92 (s, 9H).

EXAMPLE 47(15)

2-[2-(4-amidinophenylcarbamoyl)-6-isopropyloxy-3-pyridyl]-5-[(1(S)-hydroxy methyl-2,2-dimethylpropyl)carbamoyl]benzoic acid methanesulfonate

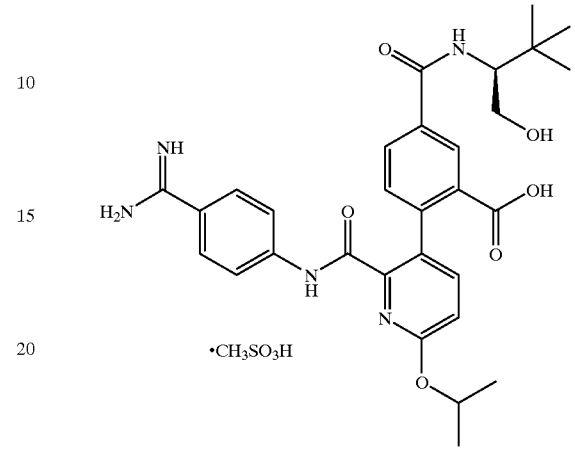

TLC:Rf 0.50 (Chloroform:Methanol:Acetic acid=10:2:1); NMR (d$_6$-DMSO): δ 10.5 (s, 1H), 9.19 (br s, 2H), 8.85 (br s, 2H), 8.40 (d, J=2.1 Hz, 1H), 8.11 (d, J=9.6 Hz, 1H), 8.03 (dd, J=8.1, 2.1 Hz, 1H), 7.88 (d, J=8.7 Hz, 2H), 7.77 (d, J=8.7 Hz, 2H), 7.61 (d, J=8.4 Hz, 1H), 7.30 (d, J=8.1 Hz, 1H), 7.04 (d, J=8.4 Hz, 1H), 5.59 (quintet, J=6.0 Hz, 1H), 3.93 (dt, J=3.9, 9.0 Hz, 1H), 3.68 (dd, J=11.1, 3.9 Hz, 1H), 3.53–3.34 (m, 1H), 2.31 (s, 3H), 1.38 (d, J=6.0 Hz, 6H), 0.92 (s, 9H).

EXAMPLE 47 (16)

2-(2-(4-amidinophenylcarbamoyl)-6-chloro-3-pyridyl]-5-[(1(S)-hydroxymethyl-2,2-dimethylpropyl)carbamoyl]benzoic acid methanesulfonate

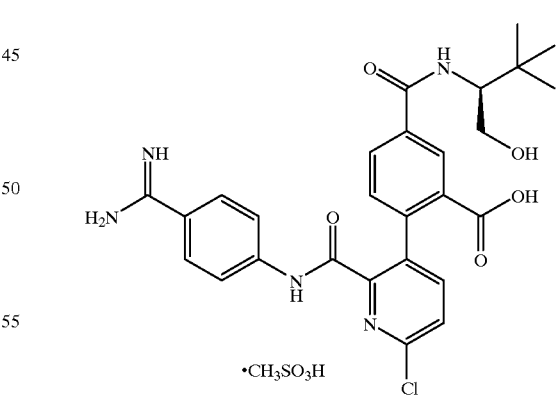

TLC:Rf 0.40 (Chloroform:Methanol:Acetic acid=10:2:1); NMR (d$_6$-DMSO): δ 10.86 (s, 1H), 9.19 (s, 2H), 8.89 (s, 2H), 8.43 (d, J=1.2 Hz, 1H), 8.15 (d, J=9.0 Hz, 1H), 8.07 (dd, J=8.1, 1.2 Hz, 1H), 7.89 (d, J=8.7 Hz, 2H), 7.84 (d, J=8.7 Hz, 1H), 7.80 (J=8.7 Hz, 1H), 7.75 (d, J=8.7 Hz, 2H), 7.35 (d, J=8.1 Hz, 1H), 3.93 (dt, J=3.3, 9.0 Hz, 1H), 3.67 (dd, J=11.4, 3.3 Hz, 1H), 3.45 (m, 1H), 2.32 (s, 3H), 0.92 (s, 9H).

EXAMPLE 47(17)

2-[2-(4-amidinophenylcarbamoyl)-6-methoxy-3-pyridyl]-5-[(1(S)-(2-hydroxy ethyl)-2,2-dimethylpropyl)carbamoyl]benzoic acid methanesulfonate

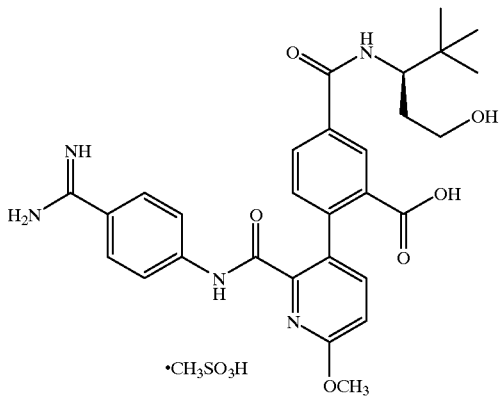

TLC:Rf 0.71 (Chloroform:Ethyl acetate:Water=3:1:1); NMR (d$_6$-DMSO): δ 12.70 (brs, 1H), 10.62 (s, 1H), 9.18 (s, 2H), 8.79 (s, 2H), 8.40 (d, J=1.8 Hz, 1H), 8.13 (d, J=9.3 Hz, 2H), 8.02 (dd, J=7.8,1.8 Hz, 1H), 7.92 (d, J=9.0 Hz, 2H), 7.78 (d, J=9.0 Hz, 2H), 7.65 (d, J=8.1 Hz, 1H), 7.30 (d, J=7.8 Hz, 1H), 7.13 (d, J=8.1 Hz, 1H), 4.35 (m, 1H), 4.11 (s, 3H), 3.94 (t, J=10.8 Hz, 1H), 3.42 (t, J=9.9 Hz, 1H), 2.31 (s, 3H), 1.74 (m, 1H), 1.65 (m, 1H), 0.93 (s, 9H).

EXAMPLE 47(18)

3-[3-(4-amidinophenylcarbamoyl)-2-thienyl]-6-[(1(S)-hydroxymethyl- 2,2-dimethyl propyl)carbamoyl]-2-pyridinecarboxylic acid methanesulfonate

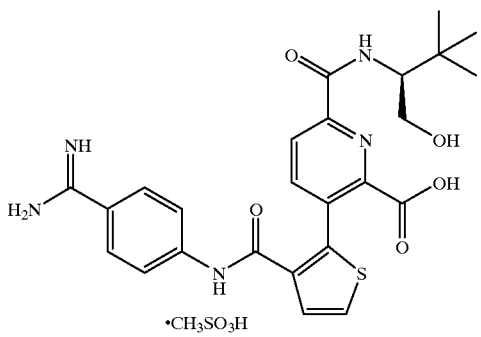

TLC Rf 0.31 (Chloroform:Methanol:Water=8:2:0.2); NMR (d$_6$-DMSO): δ 10.45 (s 1H), 9.20 (s, 2H), 8.93 (s, 2H), 8.50 (d, J=10.2 Hz, 1H), 8.21 (d, J=8.0 Hz, 1H), 8.09 (d, J=8.0 Hz, 1H), 7.86 (d, J=9.0 Hz, 2H), 7.82 (d, J=5.7 Hz, 1H ), 7.77 (d, J=9.0 Hz, 2H ), 7.76 (d, J=5.7 Hz, 1H ), 3.89 (m, 1H), 3.71 (dd, J=11.4,3.3 Hz, 1H), 3.55 (dd, J=11.4,8.0 Hz, 1H), 2.35 (s, 3H), 0.94 (s, 9H).

EXAMPLE 47(19)

3-[2-(4-amidinophenylcarbamoyl)-6-methoxy-3-pyridyl]-6-[(1(S)-hydroxymethyl-2,2-dimethylpropyl)carbamoyl]-2-pyridinecarboxylic acid methanesulfonate

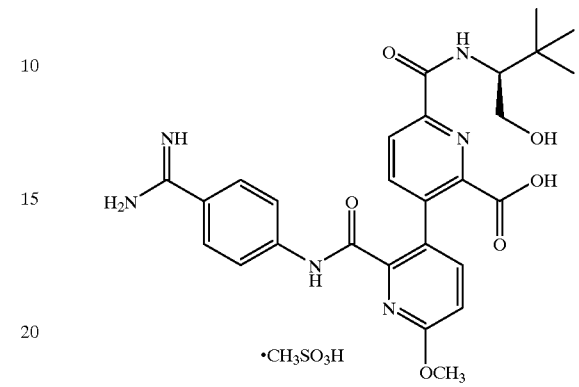

TLC:Rf 0.33 (Chloroform:Methanol:Water=8:2:0.2); NMR (d$_6$-DMSO): δ 12.95 (br.s, 1H), 10.66 (s 1H), 9.21 (s, 2H), 8.91 (s, 2H), 8.67 (d, J=10.0 Hz, 1H), 8.26 (d, J=8.0 Hz, 1H), 7.94 (d, J=8.0 Hz, 1H), 7.91 (d, J=9.0 Hz, 2H), 7.79 (d, J=9.0 Hz, 2H ), 7.76 (d, J=8.0 Hz, 1H), 7.19 (d, J=8.0 Hz, 1H ), 4.12 (s, 3H), 3.93 (m, 1H), 3.74 (dd, J=11.0,3.6 Hz, 1H), 3.56 (dd, J=11.0,8.7 Hz, 1H), 2.33 (s, 3H), 0.95 (s, 9H).

EXAMPLE 47(20)

2-[2-(4-amidinophenylcarbamoyl)-6-methoxy-3-pyridyl]-5-[[1(S)-(2-hydroxy ethylcarbamoyl)-3-methylbutyl]carbamoyl]benzoic acid methanesulfonate

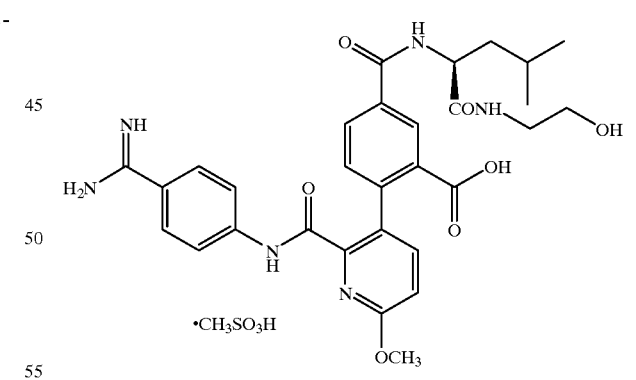

TLC:Rf 0.16 (Chloroform:Methanol:Water=8:2:0.2); NMR (d$_6$-DMSO): δ 12.71 (br, 1H), 10.60 (s, 1H), 9.25 (s, 2H), 9.01 (s, 2H), 8.70 (d, J=5.4 Hz, 1H), 8.45 (d, J=2.1 Hz, 1H), 8.08 (dd, J=8.1, 2.1 Hz, 1H), 7.97 (t, J=5.7 Hz, 1H), 7.89 (d, J=8.7 Hz, 2H), 7.80 (d, J=8.7 Hz, 2H), 7.63 (d, J=8.4 Hz, 1H), 7.29 (d, J=8.1 Hz, 1H), 7.10 (d, J=8.4 Hz, 1H), 4.53 (m, 1H), 3.44–3.20 (m, 2H), 3.18–3.04 (m, 2H), 2.33 (s, 3H), 1.75–1.62 (m, 2H), 1.51 (m, 1H), 0.89 (d, J=6.3 Hz, 3H), 0.87 (d, J=6.0 Hz, 3H).

EXAMPLE 47(21)

3-[2-(2-amidino-5-pyridylcarbamoyl)-6-methoxy-3-pyridyl]-6-[(1(S)-hydroxy methyl-2,2-dimethylpropyl) carbamoyl]-2-pyridinecarboxylic acid methanesulfonate

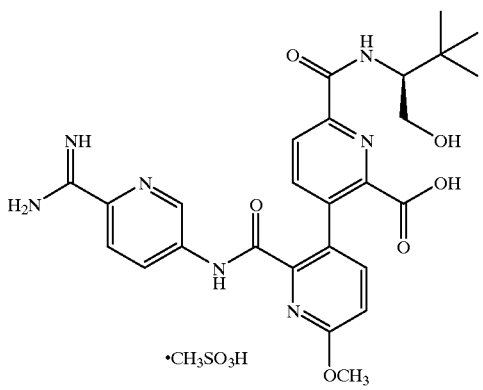

TLC:Rf 0.22 (Chloroform:Methanol:Water=8:2:0.2); NMR (d$_6$-DMSO): δ 12.95 (br.s, 1H), 10.92 (s 1H), 9.40 (s, 2H), 9.14 (s, 2H), 9.05 (d, J=2.0 Hz, 1H), 8.66 (d, J=10.0 Hz, 1H), 8.42 (dd, J=9.0,2.0 Hz, 1H), 8.27 (d, J=8.0 Hz, 1H), 8.22 (d, J=9.0 Hz, 1 H ), 7.96 (d, J=8.0 Hz, 1H), 7.78 (br.d, J=8.4 Hz, 1H ), 7.22 (d, J=8.4 Hz, 1H), 4.13 (s, 3H, 3.92 (m, 1H), 3.76 (m, 1H), 3.56 (m, 1H), 2.32 (s, 3H), 0.95 (s, 9H).

EXAMPLE 47(22)

2-[2-(4-amidinophenylcarbamoyl)-6-dimethylamino-3-pyridyl]-5-[(1(S)-hydroxy methyl-2,2-dimethylpropyl) carbamoyl]benzoic acid dimethanesulfonate

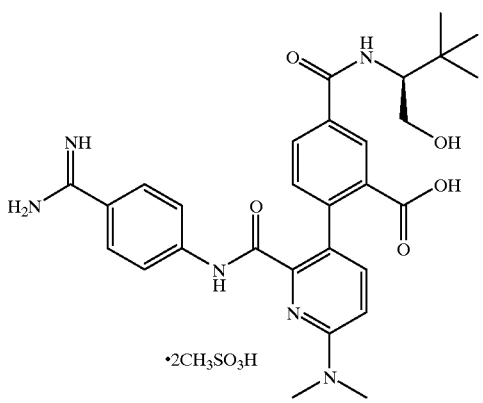

TLC:Rf 0.21 (Chloroform:Methanol:Acetic acid=10:2:1); NMR (d$_6$-DMSO): δ 10.6 (s, 1H), 9.17 (br s, 2H), 8.82 (br s, 2H), 8.35 (d, J=2.1 Hz, 1H), 8.07 (d, J=9.6 Hz, 1H), 7.99 (dd, J=8.1, 2.1 Hz, 1H), 7.89 (d, J=9.0 Hz, 2H), 7.76 (d, J=9.0 Hz, 2H), 7.40 (d, J=8.7 Hz, 1H), 7.25 (d, J=8.1 Hz, 1H), 6.93 (d, J=8.7 Hz, 1H), 3.92 (dt, J=3.6, 9.0 Hz, 1H), 3.88–3.54 (m, 1H), 3.49 (dd, J=10.5, 9.0 Hz, 1H), 3.17 (s, 6H), 2.33 (s, 6H), 0.92 (s, 9H).

EXAMPLE 47(23)

2-[2-(4-amidinophenoxycarbonyl)-6-methoxy-3-pyridyl]-5-[(1(S)-hydroxymethyl-2,2-dimethylpropyl) carbamoyl]benzoic acid methanesulfonate

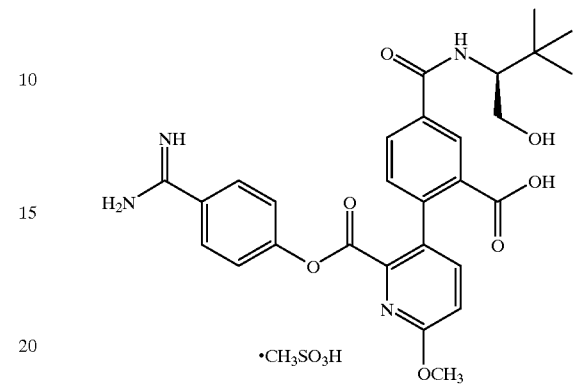

TLC:Rf 0.13 (Chloroform:Methanol:Acetic acid=10:2:1); NMR (d$_6$-DMSO): δ 13.01 (brs, 1H), 9.30 (brs, 2H), 8.99 (brs, 2H), 8.40 (d, J=1.8 Hz, 1H), 8.12 (brd, J=9.3 Hz, 1H), 8.08 (brd, J=8.0 Hz, 1H), 7.80 (d, J=8.7 Hz, 2H), 7.74 (d, J=8.4 Hz, 1H), 7.42 (d, J=8.0 Hz, 1H), 7.20 (d, J=8.4 Hz, 1H), 7.19 (d, J=8.7 Hz, 2H), 4.60–4.30 (broad, 1H), 3.99 (s, 3H), 3.90 (dt, J=3.3, 9.3 Hz, 1H), 3.66 (dd, J=10.8, 3.3 Hz, 1H), 3.47 (dd, J=10.8, 9.3 Hz, 1H), 2.30 (s, 3H), 0.90 (s, 9H).

EXAMPLE 47(24)

2-[2-(4-amidinophenylcarbamoyl)-6-butoxy-3-pyridyl]-5-[(1(S)-hydroxymethyl-2,2-dimethylpropyl)carbamoyl] benzoic acid methanesulfonate

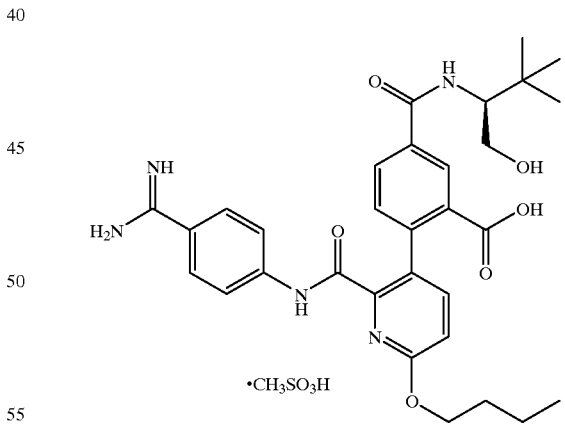

TLC:Rf 0.29 (Chloroform:Methanol:Acetic acid=10:2:1); NMR (d$_6$-DMSO): δ 10.6 (s, 1H), 9.18 (br s, 2H), 8.82 (br s, 2H), 8.40 (d, J=1.8 Hz, 1H), 8.11 (d, J=6.3 Hz, 1H), 8.03 (dd, J=8.1, 6.3 Hz, 1H), 7.89 (d, J=9.0 Hz, 2H), 7.77 (d, J=9.0 Hz, 2H), 7.63 (d, J=8.4 Hz, 1H), 7.29 (d, J=8.1 Hz, 1H), 7.10 (d, J=8.4 Hz, 1H), 4.51 (t, J=6.6 Hz, 2H), 3.93 (dt, J=3.3, 9.0 Hz, 1H), 3.68 (dd, J=3.3, 8.1 Hz, 1H), 3.53–3.34 (m, 1H), 2.30 (s, 3H), 1.78 (quintet, J=6.6 Hz, 2H), 1.49 (sextet, J=6.6 Hz, 2H), 0.97 (t, J=6.6 Hz, 3H), 0.92 (s, 9H).

EXAMPLE 47(25)

2-[2-(2-amidinopyrimidin-5-yl)carbamoyl-6-methoxy-3-pyridyl]-5-[(1(S)-hydroxy methyl-2,2-dimethylpropyl)carbamoyl]benzoic acid methanesulfonate

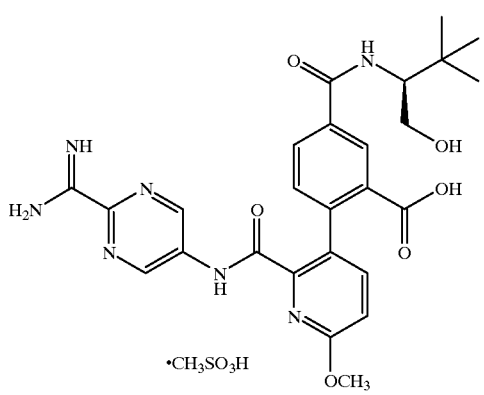

TLC:Rf 0.24 (Chloroform:Methanol:Acetic acid=10:2:1); NMR (d$_6$-DMSO): δ 13.0–12.4 (br, 1H), 11.05 (s, 1H), 9.59 (s, 2H), 9.35 (s, 2H), 9.32 (s, 2H), 8.41 (d, J=1.5 Hz, 1H), 8.12 (d, J=9.0 Hz, 1H), 8.06 (dd, J=8.4 Hz, 1H), Hz, 1H), 7.69 (d, J=8.4 Hz, 1H), 7.33 (d, J=7.8 Hz, 1H), 7.18 (d, J=8.4 Hz, 1H), 4.11 (s, 3H), 3.93 (dt, J=3.3, 9.0 Hz, 1H), 3.75–3.60 (m, 1H), 3.65–3.30 (m, 2H), 2.30 (s, 3H), 0.92 (s, 9H).

EXAMPLE 47(26)

2-[2-(4-amidinophenylcarbamoyl)-6-propoxy-3-pyridyl]-5-[(1(S)-hydroxymethyl-2,2-dimethylpropyl)carbamoyl]benzoic acid methanesulfonate

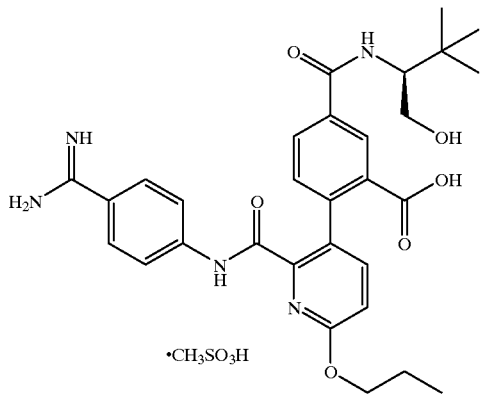

TLC:Rf 0.20 (Chloroform:Methanol:Acetic acid=10:2:1); NMR (d$_6$-DMSO): δ 10.6 (s, 1H), 9.19 (br s, 2H), 8.86 (br s, 2H), 8.40 (d, J=1.5 Hz, 1H), 8.11 (d, J=9.3 Hz, 1H), 8.03 (dd, J=8.1, 1.5 Hz, 1H), 7.89 (d, J=9.0 Hz, 2H), 7.77 (d, J=9.0 Hz, 2H), 7.63 (d, J=8.7 Hz, 1H), 7.29 (d, J=8.1 Hz, 1H), 7.10 (d, J=8.7 Hz, 1H), 4.46 (t, J=6.6 Hz, 2H), 3.93 (dt, J=3.3, 9.3 Hz, 1H), 3.68 (dd, J=11.1, 3.3 Hz, 1H), 3.51 (dd, J=11.1, 9.3 Hz, 1H), 2.31 (s, 3H), 1.81 (sextet, J=6.6 Hz, 2H), 1.04 (t, J=6.6 Hz, 3H), 0.92 (s, 9H).

EXAMPLE 47(27)

2-[2-(4-amidinophenylcarbamoyl)-6-methoxy-3-pyridyl]-5-[(1(S), 2-bishydroxy methyl-2-methylpropyl)carbamoyl]benzoic acid methanesulfonate

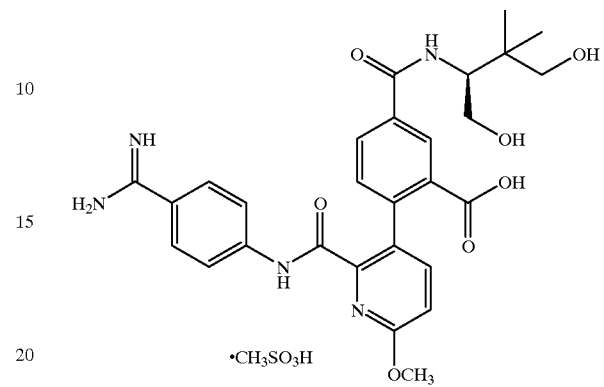

TLC:Rf 0.60 (Ethyl acetate:Acetic acid:Water=3:1:0.5); NMR (d$_6$-DMSO): δ 12.71 (br.s, 1H), 10.61 (s, 1H), 9.18 (s, 2H), 8.82 (s, 2H), 8.41 (d, J=1.8 Hz, 1H), 8.23 (d, J=8.7 Hz, 1H), 8.03 (dd, J=8.1, 1.8 Hz, 1H), 7.90 (d, J=9.0 Hz, 2H), 7.78 (d, J=9.0 Hz, 2H), 7.65 (d, J=8.7 Hz, 1H), 7.31 (d, J=8.1 Hz, 1H), 7.13 (d, J=8.7 Hz, 1H), 4.10 (s, 3H), 4.01 (m, 1H), 3.70 (dd, J=10.8, 3.3 Hz, 1H), 3.57 (dd, J=10.8, 9.0 Hz, 1H), 3.80–3.20 (br, 2H), 3.27 (d, J=10.8 Hz, 1H), 3.11 (d, J=10.8 Hz, 1H), 2.31 (s, 3H), 0.92 (s, 3H), 0.83 (s, 3H).

EXAMPLE 47(28)

2-[2-(4-amidinophenylcarbamoyl)-6-ethoxy-3-pyridyl]-5-[(1(S), 2-bishydroxy methyl-2-methylpropyl)carbamoyl]benzoic acid methanesulfonate

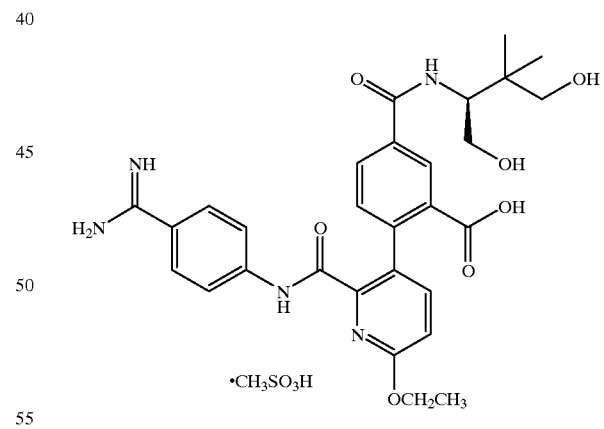

TLC:Rf 0.60 (Ethyl acetate:Acetic acid:Water=3:1:0.5); NMR (d$_6$-DMSO): δ 12.72 (br, 1H), 10.57 (s, 1H), 9.19 (s, 2H), 8.84 (s, 2H), 8.40 (d, J=1.8 Hz, 1H), 8.23 (d, J=9.0 Hz, 1H), 8.02 (dd, J=8.1, 1.8 Hz, 1H), 7.89 (d, J=9.0 Hz, 2H), 7.77 (d, J=9.0 Hz, 2H), 7.64 (d, J=8.4 Hz, 1H), 7.31 (d, J=8.1 Hz, 1H), 7.10 (d, J=8.4 Hz, 1H), 4.56 (q, J=6.9 Hz, 2H), 4.01 (d, J=3.6, 9.0 Hz, 1H), 3.69 (dd, J=11.0, 3.6 Hz, 1H), 3.57 (dd, J=11.0, 9.0 Hz, 1H), 3.80–3.20 (br, 2H), 3.27 (d, J=11.0 Hz, 1H), 3.11 (d, J=11.0 Hz, 1H), 2.30 (s, 3H), 1.41 (t, J=6.9 Hz, 3H), 0.92 (s, 3H), 0.82 (s, 3H).

EXAMPLE 47(29)

5-[2-(4-amidinophenylcarbamoyl)-6-methoxy-3-pyridyl]-2-[(1(S)-hydroxymethyl-2,2-dimethylpropyl)carbamoyl]-4-pyridinecarboxylic acid methanesulfonate

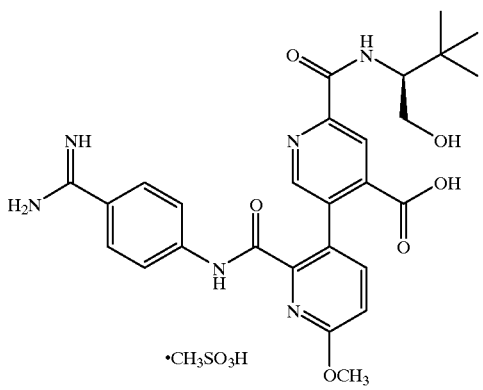

TLC:Rf 0.26 (Chloroform:Methanol:Water=7:3:0.3); NMR (300 MHz, DMSO-$d_6$): δ 13.47 (br.s, 1H), 10.66 (s 1H), 9.24 (s, 2H), 8.99 (s, 2H), 8.58 (s, 1H), 8.41 (s, 1H), 8.32 (d, J=10.0 Hz, 1H), 7.91 (d, J=9.0 Hz, 2H), 7.81–7.78 (m, 3H), 7.20 (d, J=8.8 Hz, 1H), 4.12 (s, 3H), 3.86 (m, 1H), 3.63–3.60 (m, 2H), 2.32 (s, 3H), 0.94 (s, 9H).

EXAMPLE 47(30)

2-[2-(4-amidinophenylcarbamoyl)-6-methoxy-3-pyridyl]-5-[(1(S)-hydroxymethyl-2-methylpropyl)carbamoyl]benzoic acid methanesulfonate

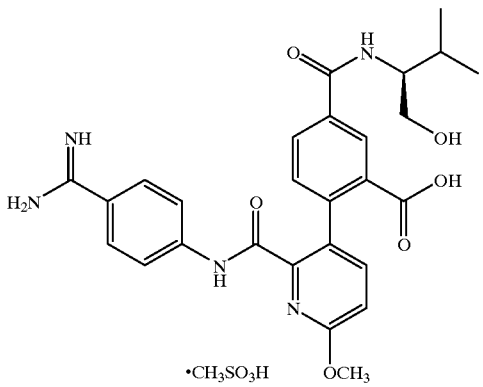

TLC:Rf 0.09 (Chloroform:Methanol:Acetic acid=10:2:1); NMR (300 MHz, $d_6$-DMSO): δ 12.8–12.5 (broad, 1H), 10.61 (s, 1H), 9.17 (brs, 2H), 8.81 (brs, 2H), 8.42 (d, J=2.0 Hz, 1H), 8.21 (brd, J=9.0 Hz, 1H), 8.04 (dd, J=8.0, 2.0 Hz, 1H), 7.90 (d, J=8.7 Hz, 2H), 7.77 (d, J=8.7 Hz, 2H), 7.65 (d, 8.4 Hz, 1H), 7.29 (d, J=8.0 Hz, 1H), 7.12 (d, J=8.4 Hz, 1H), 4.09 (s, 3), 3.90–3.80 (m, 1H), 3.58–3.47 (m, 2H), 2.32 (s, 3H), 1.99–1.87 (m, 1H), 0.92 (d, J=6.9 Hz, 3H), 0.90 (d, J=6.9 Hz, 3H).

EXAMPLE 47(31)

2-[2-(4-amidinophenylcarbamoyl)-6-ethoxy-3-pyridyl]-5-[(1(S)-hydroxymethyl-3,3-dimethylbutyl)carbamoyl]benzoic acid methanesulfonate

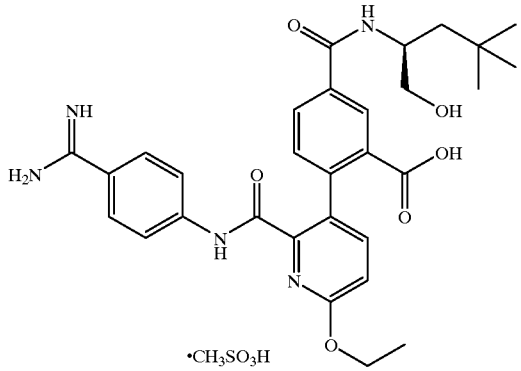

TLC:Rf 0.35 (Chloroform:Methanol:Water=7:3:0.3); NMR (300 MHz, DMSO-$d_6$): δ 12.68 (br.s, 1H), 10.57 (s 1H), 9.19 (s, 2H), 8.85 (s, 2H), 8.39 (d, J=2.0 Hz, 1H), 8.28 (br.d, J=9.0 Hz, 1H), 8.00 (dd, J=8.0,2.0 Hz, 1H), 7.89 (d, J=9.0 Hz, 2H), 7.77 (d, J=9.0 Hz, 2H), 7.63 (d, J=8.0 Hz, 1H), 7.28 (d, J=8.0 Hz, 1H), 7.09 (d, J=8.0 Hz, 1H), 4.55 (q, J=7.0 Hz, 2H), 4.12 (m, 1H), 3.41–3.22 (m, 3H), 2.31 (s, 3H), 1.52 (d, J=5.4 Hz, 2H), 1.41 (t, J=7.0 Hz, 3H), 0.91 (s, 9H).

EXAMPLE 47(32)

2-[2-(4-amidinophenylcarbamoyl)-6-methoxy-3-pyridyl]-5-[(1(S)-hydroxymethyl-3,3-dimethylbutyl)carbamoyl]benzoic acid methanesulfonate

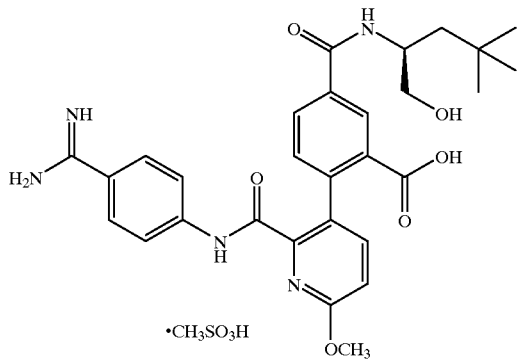

TLC:Rf 0.50 (Chloroform:Methanol:Water=7:3:0.3); NMR (300 MHz, DMSO-$d_6$): δ 12.68 (br.s, 1H), 10.57 (s 1H), 9.19 (s, 2H), 8.85 (s, 2H), 8.39 (d, J=2.0 Hz, 1H), 8.28 (br.d, J=9.0 Hz, 1H), 8.00 (dd, J=8.0,2.0 Hz, 1H), 7.89 (d, J=9.0 Hz, 2H), 7.77 (d, J=9.0 Hz, 2H), 7.63 (d, J=8.0 Hz, 1H), 7.28 (d, J=8.0 Hz, 1H), 7.09 (d, J=8.0 Hz, 1H), 4.55 (q, J=7.0 Hz, 2H), 4.12 (m, 1H), 3.41–3.22 (m, 3H), 2.31 (s, 3H), 1.52 (d, J=5.4 Hz, 2H), 1.41 (t, J=7.0 Hz, 3H), 0.91 (s, 9H).

EXAMPLE 48(1)–48(3)

The following compounds were obtained by the same procedure as a series of reaction of Reference Example 26→Example 45→Example 11, using a corresponding compound.

EXAMPLE 48(1)

2'-(4-amidinophenylcarbamoyl)-4'-hydroxymethyl-4-(2-methylpropylcarbamoyl)-2-biphenylcarboxylic acid methanesulfonate

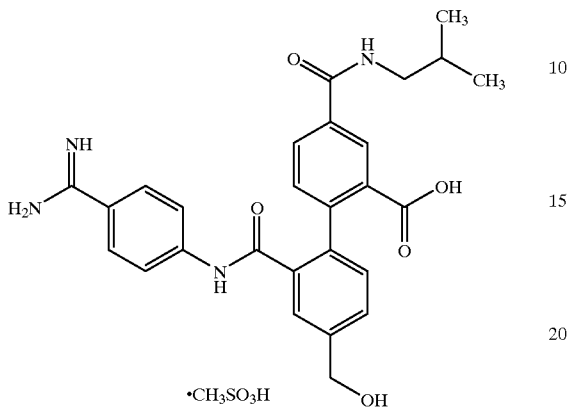

TLC:Rf 0.50 (Chloroform:Methanol:Water=7:3:0.3); NMR (d$_6$-DMSO): δ 10.53 (s, 1H), 9.13 (s, 2H), 8.75 (s, 2H), 8.64 (br.t, J=6.3 Hz, 1H), 8.30 (d, J=2.0 Hz, 1H), 7.95 (dd, J=8.0, 2.0 Hz, 1H), 7.72 (s, 4H), 7.62 (s, 1H), 7.51 (d, J=8.0 Hz, 1H), 7.31 (d, J=8.0 Hz, 1H), 7.23 (d, J=8.0 Hz, 1H), 4.65 (s, 2H), 3.09 (t, J=6.3 Hz, 2H), 2.32 (s, 3H), 1.85 (m, 1H), 0.89 (d, J=6.6 Hz, 6H).

EXAMPLE 48(2)

2'-(4-amidinophenylcarbamoyl)-4'-hydroxymethyl-4-(1,2,2-trimethylpropyl carbamoyl)-2-biphenylcarboxylic acid methanesulfonate

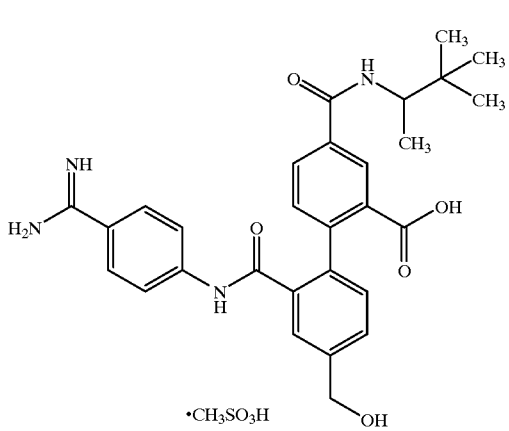

TLC:Rf 0.18 (Chloroform:Methanol:Water=8:2:0.2); NMR (d$_6$-DMSO): δ 10.57 (s, 1H), 9.13 (s, 2H), 8.79 (s, 2H), 8.26 (d, J=2.0 Hz, 1H), 8.17 (d, J=6.3 Hz, 1H), 7.93 (dd, J=8.0,2.0 Hz, 1H), 7.73 (s, 4H), 7.63 (s, 1H), 7.51 (d, J=8.0 Hz, 1H), 7.29 (d, J=8.0 Hz, 1H), 7.22 (d, J=8.0 Hz, 1H), 5.42 (br.s, 1H), 4.65 (s, 2H), 3.99 (m, 1H), 2.33 (s, 3H), 1.08 (d, J=6.6 Hz 3H), 0.90 (s, 9H).

EXAMPLE 48(3)

3-[2-(4-amidinophenylcarbamoyl)-4-methoxyphenyl]-6-[(1(S)-hydroxymethyl-2,2-dimethylpropyl)carbamoyl]-2-pyridinecarboxylic acid methanesulfonate

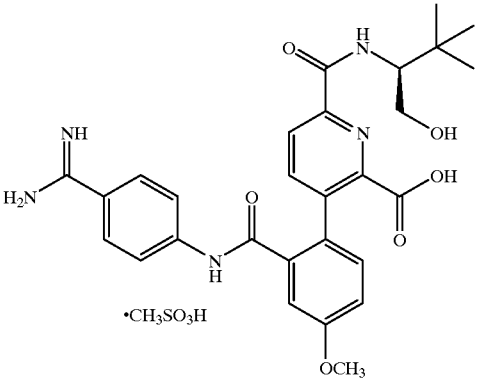

TLC:Rf 0.27 (Chloroform:Methanol:Water=8:2:0.2); NMR (d$_6$-DMSO): δ 13.04 (br.s, 1H), 10.82 (br.s 1H), 9.14 (s, 2H), 8.81 (s, 2H), 8.48 (br.d, J=10.2 Hz, 1H), 8.16 (d, J=8.0 Hz, 1H), 7.89 (d, J=8.0 Hz, 1H), 7.75 (s, 4H), 7.33–7.17 (m, 3H), 4.62 (br.s, 1H), 3.90 (s, 3H), 3.85–3.40 (m, 3H), 2.31 (s, 3H), 0.92 (s, 9H).

REFERENCE EXAMPLE 27

4-[(2-trifluoromethylsulfonyloxyphenyl)carbonylamino]phenylnitrile

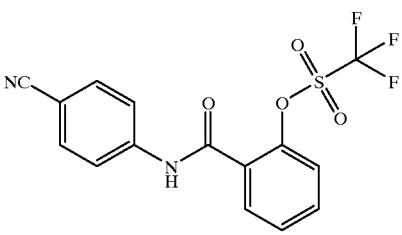

Trifluoromethanesulfonic acid anhydrous (0.75 ml) was dropped into a solution of 2-(4-cyanophenylcarbamoyl)phenol (895 mg) in pyridine (5 ml) at 0° C. The mixture was stirred for 1 hour at 0° C. The reaction mixture was diluted with water, and extracted with ethyl acetate. The organic layer was washed with a saturated aqueous solution of sodium chloride, dried over anhydrous sodium sulfate and concentrated. The residue was purified by column chromatography on silica gel (hexane:ethyl acetate=2:1→1:1) to give the present compound (1.25 g) having the following physical data.

TLC:Rf 0.20 (Hexane:Ethyl acetate=2:1); NMR (200 MHz, CDCl$_3$): δ 8.09 (br.s, 1H), 7.92 (dd, J=8.0, 1.5 Hz, 1H), 7.78 (d, J=8.8 Hz, 2H), 7.67 (d, J=8.8 Hz, 2H), 7.70–7.60 (m, 1H), 7.56 (dt, J=1.5, 8.0 Hz, 1H), 7.42 (dd, J=8.0, 1.5 Hz, 1H).

EXAMPLE 49

Ethyl 2-[2-(4-amidinophenylcarbamoyl)phenyl]-5-(2,2-dimethylpropyl carbamoyl)-3-furancarboxylate

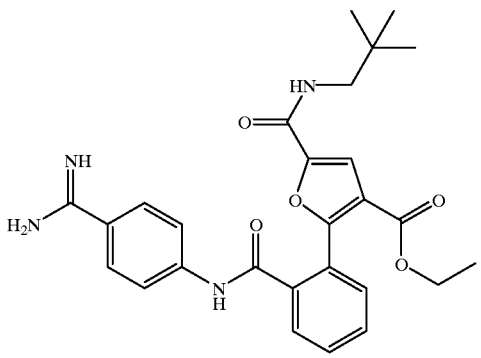

The title compound having the following physical data was obtained by the same procedure as a series of reaction of Example 37, using 4-[2-[5-(2,2-dimethylpropylcarbamoyl)-3-ethoxycarbonyl-2-furyl]phenylcarbonylamino]phenylmethylthioimidatel which was obtained by the same procedure as a series of reaction of Reference Example 4→Reference Example 8→Reference Example 5→Reference Example 3→Reference Example 20, using a compound prepared in Reference Example 27.

TLC:Rf 0.63 (Chloroform:Methanol:Acetic acid=10:2:1); NMR (300 MHz, $d_6$-DMSO): δ 11.0–10.4 (br, 1H), 10.4–9.6 (br, 3H), 8.19 (t, J=6.6 Hz, 1H), 7.85–7.75 (m, 2H), 7.75 (like s, 4H), 7.7–7.65 (m, 2H), 7.51 (s, 1H), 4.06 (q, J=7.0 Hz, 2H), 2.99 (d, J=6.6 Hz, 2H), 1.10 (t, J=7.0 Hz, 3H), 0.82 (s, 9H).

EXAMPLE 50

2-[2-(4-amidinophenylcarbamoyl)phenyl]-5-(2,2-dimethylpropylcarbamoyl)-3-furancarboxylic acid methanesulfonate

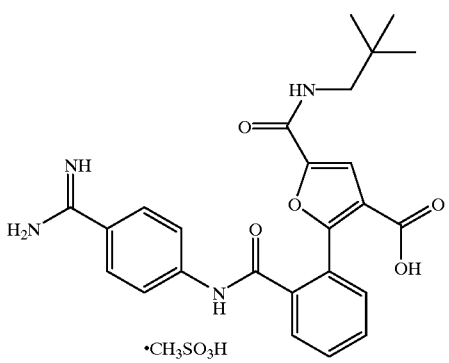

The title compound having the following physical data was obtained by the same procedure as a series of reaction of Example 11, using a compound prepared in Example 49.

TLC:Rf 0.31 (Chloroform:Methanol:Acetic acid=10:2:1); NMR ($d_6$-DMSO): δ 12.9–12.6 (br, 1H), 10.80 (s, 1H), 9.17 (s, 2H), 8.85 (s, 2H), 8.15 (t, J=6.6 Hz, 1H), 7.82 (d, J=9.0 Hz, 2H), 7.77 (d, J=9.0 Hz, 2H), 7.8–7.7 (m, 2H), 7.7–7.6 (m, 2H), 7.45 (s, 1H), 2.99 (d, J=6.6 Hz, 2H), 2.33 (s, 3H), 0.81 (s, 9H).

EXAMPLE 51

Benzyl 2-[2-(4-amidinophenylcarbamoyl)-6-methoxy-3-pyridyl]-5-[(3-amino-1(S)-t-butylpropyl)carbamoyl]benzoate dihydrochloride

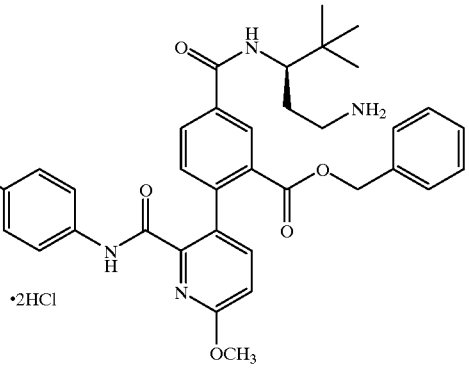

The title compound having the following physical data was obtained by the same procedure as a series of reaction of Example 1→Reference Example 8, using 304-(3-t-butylcarbonylamino-1(R)-t-butylpropylcarbamoyl)-2-benzyloxycarbonylphenyl]-6-methoxy-2-pyridinecarboxylic acid which was prepared by the same procedure as a series of reaction of Reference Example 1→Reference Example 2→Reference Example 3→Reference Example 4→Reference Example 5 using a corresponding compound.

TLC:Rf 0.10 (Chloroform:Methanol:Acetic acid= 10:2:1)).

EXAMPLE 52

2-[2-(4-amidinophenylcarbamoyl)-6-methoxy-3-pyridyl]-5-[(3-amino-1(S)-t-butylpropyl)carbamoyl]benzoic acid dimethanesulfonate

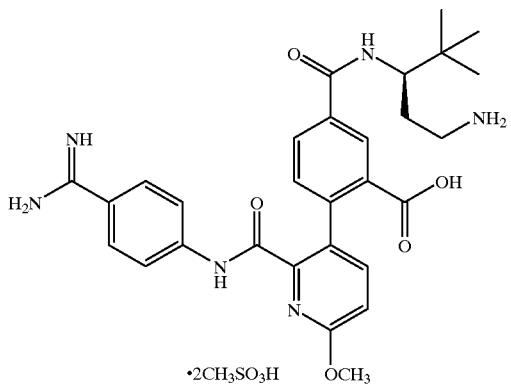

The title compound having the following physical data was obtained by the same procedure as a series of reaction of Example 2, using a compound prepared in Example 51.

TLC:Rf 0.60 (Ethyl acetate:Acetic acid:Water=3:1:1); NMR ($d_6$-DMSO): δ 12.75 (br, 1H), 10.63 (s, 1H), 9.19 (s, 2H), 8.84 (s, 2H), 8.41 (d, J=1.8 Hz, 1H), 8.28 (d, J=9.9 Hz, 1H), 8.04 (dd, J=8.1, 1.8 Hz, 1H), 7.92 (d, J=9.3 Hz, 2H), 7.79 (d, J=9.3 Hz, 2H), 7.71 (br, 2H), 7.64 (d, J=8.7 Hz, 1H), 7.33 (d, J=8.1 Hz, 1H), 7.15 (d, J=8.7 Hz, 1H), 4.11 (s, 3H), 3.96 (m, 1H), 2.85–2.70 (m, 2H), 2.32 (s, 6H), 1.91 (m, 1H), 1.77 (m, 1H), 0.96 (s, 9H).

EXAMPLE 53(1)–53(8)

The following compounds were obtained by the same procedure as a series of reaction of Reference Example 8→Example 52 (without a procedure of conversion to methanesulfoxide thereof, using a compound prepared in Example 40(51), or were obtained by the same procedure as a series of reaction of Example 51→Example 52 using a corresponding compound.

EXAMPLE 53(1)

2-[2-(4-amidinophenylcarbamoyl)-6-methoxy-3-pyridyl]-5-[(1,1-bishydroxy methyl-2-methylpropyl) carbamoyl]benzoic acid hydrochloride

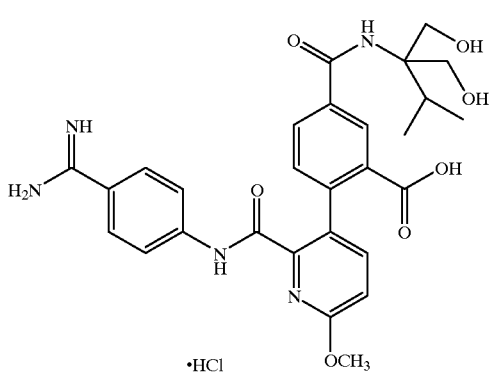

TLC:Rf 0.50 (Chloroform:Methanol:Acetic acid=10:2:1); NMR ($d_6$-DMSO): δ 12.0–11.4 (br, 1H), 9.23 (s, 2H), 9.11 (s, 2H), 8.18 (s, 1H), 7.84–7.71 (m, 6H), 7.61 (s, 1H), 7.53 (d, J=8.1 Hz, 1H), 7.17 (d, J=7.8 Hz, 1H), 7.03 (d, J=8.4 Hz, 1H), 4.94 (d, J=5.4 Hz, 1H), 4.92 (d, J=5.4 Hz, 1H), 3H), 3.74 (dd, J=11.4, 5.4 Hz, 2H), 3.65 (dd, J=11.4, 5.4 Hz, 2H), 2.41 (m, 1H), 0.93 (d, J=6.9 Hz, 6H).

EXAMPLE 53(2)

2-[2-(4-amidinophenylcarbamoyl)-6-methoxy-3-pyridyl]-5-[(2-amino- 2-hydroxymethyl-3-methylbutyl) carbamoyl]benzoic acid hydrochloride

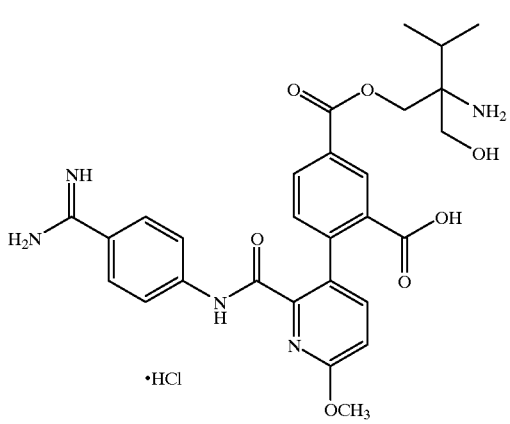

TLC:Rf 0.20 (Chloroform:Methanol:Acetic acid=10:2:1); NMR ($d_6$-DMSO): δ 12.9–12.5 (br, 1H), 9.36 (s, 2H), 9.26 (s, 2H), 8.60–7.90 (br, 2H), 8.28 (s, 1H), 8.07 (d, J=8.4 Hz, 1H), 7.77 (d, J=8,7 Hz, 2H), 7.68 (d, J=8.7 Hz, 2H), 7.49 (d, J=8.4 Hz, 1H), 7.17 (d, J=7.8 Hz, 1H), 6.99 (d, J=8.4 Hz, 1H), 5.55 (br, 1H), 4.37 (s, 2H), 3.97 (s, 3H), 3.64 (s, 2H), 2.18 (dd, J=7.2, 6.6 Hz, 1H), 0.98 (d, J=6.6 Hz, 3H), 0.96 (d, J=6.6 Hz, 3H).

EXAMPLE 53(3)

2-[2-(4-amidinophenylcarbamoyl)-6-methoxy-3-pyridyl]-5-[(4-(2-methylpropyl)-4-piperidino)carbamoyl] benzoic acid dimethanesulfonate

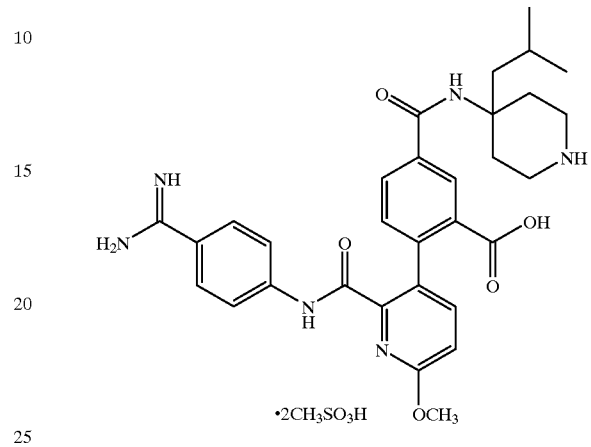

TLC:Rf 0.70 (Ethyl acetate:Acetic acid:Water=3:1:1); NMR ($d_6$-DMSO): δ 10.6 (s, 1H), 9.19 (br s, 2H), 8.89 (br s, 2H), 8.43 (br s, 2H), 8.36 (d, J=2.1 Hz, 1H), 8.06 (s, 1H), 8.02 (dd, J=8.1, 2.1 Hz, 1H), 7.90 (d, J=9.3 Hz, 2H), 7.79 (d, J=9.3 Hz, 1H), 7.63 (d, J=8.7 Hz, 1H), 7.30 (d, J=8.7 Hz, 1H), 7.13 (d, J=8.7 Hz, 1H), 4.10 (s, 3H), 3.20–3.16 (m, 2H), 3.06–3.02 (m, 2H), 2.64–2.59 (m, 2H), 2.33 (s, 6H), 1.80–1.55 (m, 1H), 1.74 (s, 2H), 1.66–1.59 (m, 2H), 0.90 (d, J=6.0 Hz, 6H).

EXAMPLE 53(4)

2-[2-(4-amidinophenylcarbamoyl)-6-methoxy-3-pyridyl]-5-[(2-amino-3-methyl butyl)carbamoyl]benzoic acid methanesulfonate trifluoroacetate

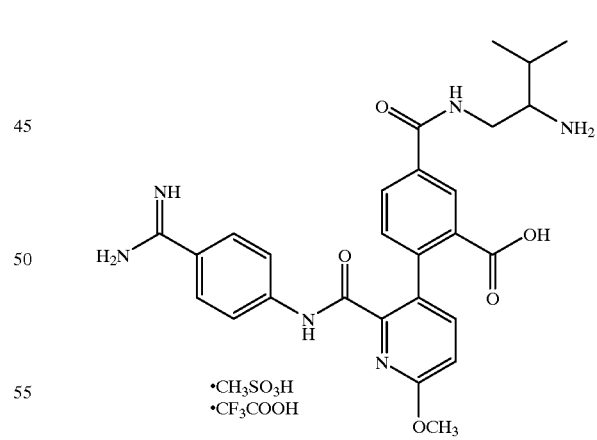

TLC:Rf 0.50 (Ethyl acetate:Acetic acid:Water=3:3:1); NMR ($d_6$-DMSO): δ 12.8–12.5 (br, 1H), 10.61 (s, 1H), 9.21 (s, 2H), 9.02 (s, 2H), 8.84 (t, J=5.7 Hz, 1H), 8.44 (d, J=1.8 Hz, 1H), 8.07 (dd, J=8.1, 1.8 Hz, 1H), 7.93 (brd, J=3.6 Hz, 2H), 7.91 (d, J=9.0 Hz, 2H), 7.79 (d, J=9.0 Hz, 2H), 7.64 (d, J=8.4 Hz, 1H), 7.33 (d, J=8.1 Hz, 1H), 7.12 (d, J=8.4 Hz, 1H), 4.10 (s, 3H), 3.5–3.3 (m, 3H), 3.08 (m, 1H), 2.34 (s, 3H), 1.96 (m, 1H), 1.01 (d, J=6.6 Hz, 3H), 0.99 (d J=6.6 Hz, 3H).

EXAMPLE 53(5)

2-[2-(4-amidinophenylcarbamoyl)-6-methoxy-3-pyridyl]-5-[(1(S)-(4-aminobutyl carbamoyl)-3-methylbutyl)carbamoyl]benzoic acid dimethanesulfonate

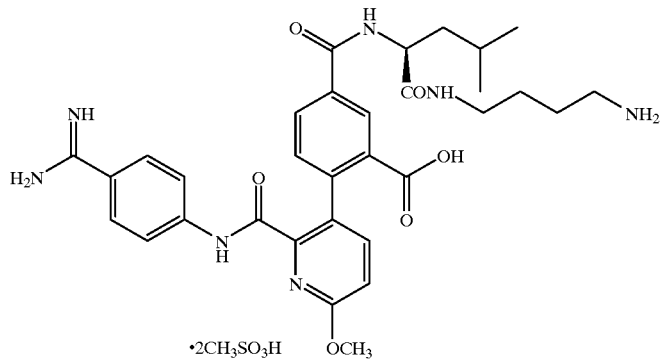

TLC:Rf 0.66 (Ethyl acetate:Acetic acid:Water=3:1:1); NMR (d$_6$-DMSO): δ 12.75 (br, 1H), 10.62 (s, 1H), 9.21 (s, 2H), 8.89 (s, 2H), 8.70 (d, J=8.4 Hz, 1H), 8.47 (d, J=1.8 Hz, 1H), 8.10 (dd, J=8.1, 1.8 Hz, 1H), 8.06 (t, J=5.7 Hz, 1H), 7.91 (d, J=9.3 Hz, 2H), 7.80 (d, J=9.3 Hz, 2H), 7.72 (br, 2H), 7.65 (d, J=8.4 Hz, 1H), 7.32 (d, J=8.1 Hz, 1H), 7.14 (d, J=8.4 Hz, 1H), 4.52 (m, 1H), 4.12 (s, 3H), 3.14–3.04 (m, 2H), 2.86–2.76 (m, 2H), 2.34 (s, 6H), 1.80–1.62 (m, 2H), 1.60–1.42 (m, 5H), 0.93 (d, J=6.3 Hz, 3H), 0.90 (d, J=6.3 Hz, 3H).

EXAMPLE 53(6)

2-[2-(4-amidinophenylcarbamoyl)-6-methoxy-3-pyridyl]-5-[(3-amino-2,2-dimethylpropyl)carbamoyl]benzoic acid dimethanesulfonate

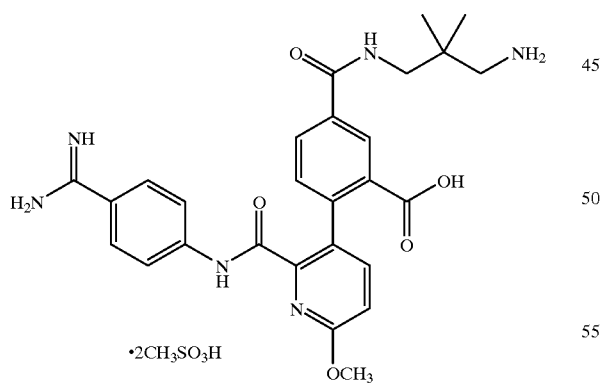

TLC:Rf 0.34 (Ethyl acetate:Acetic acid:Water=3:1:1); NMR (d$_6$-DMSO): δ 10.62 (s, 1H), 9.19 (s, 2H), 9.00 (t, J=6.3 Hz, 1H), 8.81 (s, 2H), 8.48 (d, J=1.5 Hz, 1H), 8.08 (dd, J=7.2, 1.5 Hz, 1H), 7.91 (d, J=9.0 Hz, 2H), 7.84–7.72 (m, 3H), 7.79 (d, J=9.0 Hz, 2H), 7.64 (d., J=8.4 Hz, 1H), 7.35 (d, J=7.2 Hz, 1H), 7.14 (d, J=8.4 Hz, 1H), 4.12 (s, 3H), 3.26 (d, J=6.3 Hz, 2H), 2.70–2.62 (m, 2H), 2.32 (s, 6H), 1.00 (s, 6H).

EXAMPLE 53(7)

2-[2-(4-amidinophenylcarbamoyl)-6-ethoxy-3-pyridyl]-5-[(3-amino-1(S)-t-butylpropyl)carbamoyl]benzoic acid dimethanesulfonate

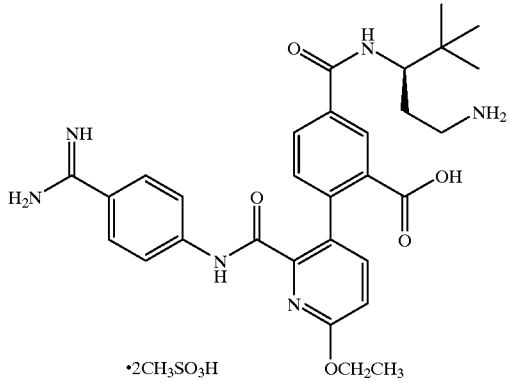

TLC:Rf 0.60 (Ethyl acetate:Acetic acid:Water=3:3:1); NMR (d$_6$-DMSO): δ 12.8–12.3 (brd, 1H), 10.58 (s, 1H), 9.20 (s, 2H), 8.90 (s, 2H), 8.39 (d, J=1.8 Hz, 1H), 8.27 (d, J=9.9 Hz, 1H), 8.02 (dd, J=8.1, 1.8 Hz, 1H), 7.88 (d, J=9.0 Hz, 2H), 7.78 (d, J=9.0 Hz, 2H), 7.77 (s, 2H), 7.62 (d, J=8.4 Hz, 1H), 7.31 (d, J=8.1 Hz, 1H), 7.10 (d, J=8.4 Hz, 1H), 4.56 (dd, J=12.9, 6.0 Hz, 2H), 3.94 (t, J=10.2 Hz, 1H), 2.78 (m, 2H), 2.32 (s, 6H), 1.90 (m, 1H), 1.76 (m, 1H), 1.41 (t, J=6.0 Hz, 3H), 0.95 (s, 9H).

EXAMPLE 53(8)

2-[2-(4-amidinophenylcarbamoyl)-6-ethoxy-3-pyridyl]-5-[(4-amino-1(S)-t-butylbutyl)carbamoyl]benzoic acid dimethanesulfonate

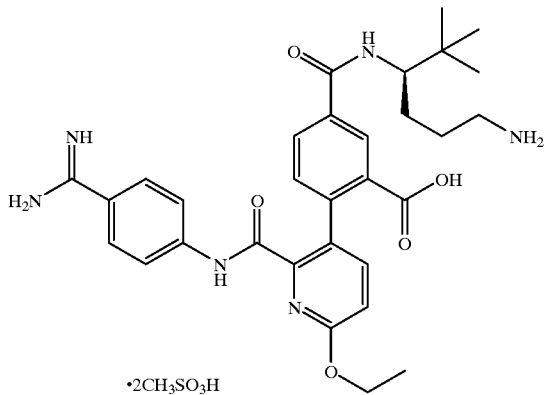

TLC:Rf 0.60 (Ethyl acetate:Acetic acid:Water=3:3:1); NMR (300 MHz, $d_6$-DMSO): δ 12.8–12.3 (brd, 1H), 10.58 (s, 1H), 9.20 (s, 2H), 8.88 (s, 2H), 8.41 (d, J=1.8 Hz, 1H), 8.16 (d, J=9.6 Hz, 1H), 8.04 (dd, J=7.8, 1.8 Hz, 1H), 7.88 (d, J=9.0 Hz, 2H), 7.79 (d, J=9.0 Hz, 2H), 7.68 (brd, 2H), 7.61 (d, J=8.4 Hz, 1H), 7.30 (d, J=8.4 Hz, 1H), 7.10 (d, J=7.8 Hz, 1H), 4.56 (m, 2H), 3.83 (m, 1H), 2.80–2.70 (m, 2H), 2.31 (s, 6H), 1.68–1.40 (m, 4H), 1.41 (t, J=6.9 Hz, 3H), 0.93 (s, 9H).

EXAMPLE 54

N-hydroxy-2'-(4-amidinophenylcarbamoyl)-4-[(1(R)2,2-trimethylpropyl) carbamoyl]-2-biphenylcarboxamide methanesulfonate

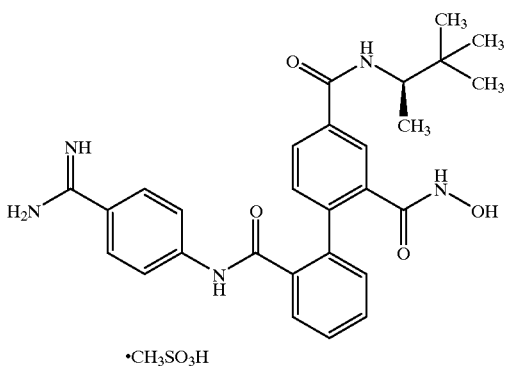

The title compound having the following physical data was obtained by the same procedure as a series of reaction of Example 21→Example 22, using a salt-free compound of a compound prepared in Example 41(12).

TLC:Rf 0.36 (Chloroform:Methanol:Water=7:3:0.3); NMR ($d_6$-DMSO): δ 11.52 (br, 1H), 11.22 (s, 1H), 9.15 (s, 2H), 8.91 (s, 2H), 8.11 (d, J=9.6 Hz, 1H), 8.02 (d, J=1.5 Hz, 1H), 7.89 (dd, J=7.8, 1.5 Hz, 1H), 7.73–7.68 (m, 3H), 7.60–7.54 (m, 4H), 7.22 (d, J=7.8 Hz, 1H), 7.12 (m, 1H), 3.96 (m, 1H), 2.38 (s, 3H), 1.07 (d, J=6.6 Hz, 3H), 0.89 (s, 9H).

REFERENCE EXAMPLE 28

Benzyl 2'-(4-nitrilebenzyloxy)-4'-methyl-4-[(1(S)-t-butyldimetylsilyloxymethyl-2,2-dimethylpropyl) carboxamide]-2-biphenylcarboxylate

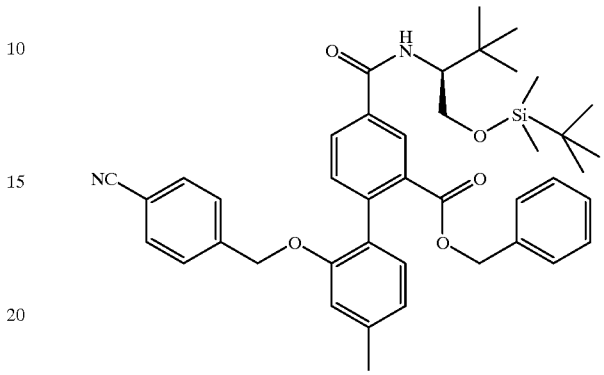

To a solution of a compound (1.10 g) prepared by the same procedure as a series of reaction of Reference Example 4 using 2-(4-formylbenzyloxy)-4-methylphenylboric acid and benzyl 2-trifluoromethylsulfonyloxy-5-((1(S)-t-butyidimethylsilyloxymethyl-2,2-dimethylpropyl) carbamoyl)benzoate, in pyridine (20 ml), hydroxylamine hydrochloride (220 mg) and anhydrous acetic acid (0.75 ml) was added. The mixture was stirred for 1.5 hour at 90° C. The reaction mixture was diluted with ethyl acetate. The solution was washed two times with a saturated aqueous solution of sodium chloride. The organic layer was dried over anhydrous sodium sulfate and concentrated. The residue was purified by column chromatography on silica gel (hexane:ethyl acetate=3:1) to give the title compound (1.05 g) having the following physical data.

TLC:Rf 0.69 (Hexane:Ethyl acetate=3:1); NMR (200 MHz, CDCl$_3$): δ 8.31 (d, J=1.8 Hz, 1H), 7.98 (dd, J=8.0, 1.8 Hz, 1H), 7.50 (d, J=8.4 Hz, 2H), 7.42 (d, J=8.0 Hz, 1H), 7.3–7.2 (m, 3H), 7.20 (d, J=8.4 Hz, 2H), 7.16 (d, J=8.0 Hz, 1H), 7.1–7.0 (m, 2H), 6.90 (br.d, J=8.0 Hz, 1H), 6.7–6.5 (m, 1H), 6.60 (br.s, 1H), 5.06 (s, 2H), 4.83 (s, 2H), 4.04 (m, 1H), 3.83 (dd, J=10.6, 3.4 Hz, 1H), 3.76 (dd, J=10.6, 4.0 Hz, 1H), 2.37 (s, 3H), 1.04 (s, 9H), 0.88 (s, 9H), 0.06 (s, 3H), 0.03 (s, 3H).

EXAMPLE 55(1)–55(3)

The following compounds were obtained by the same procedure as a series of reaction of Reference Example 20→Example 37→Example 45→Example 38 using a compound prepared in Reference Example 28, or were obtained by the same procedure as a series of reaction of Reference Example 4→Reference Example 28→Reference Example 20→Example 37→Example 38 using a corresponding compounds.

EXAMPLE 55(1)

2'-(4-amidinobenzyloxy)-4-(2-methylpropylcarbamoyl)-2-biphenylcarboxylic acid methanesulfonate

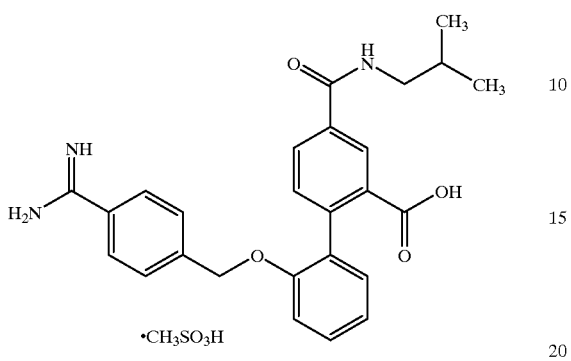

TLC:Rf 0.29 (Chloroform:Methanol:Acetic acid=10:2:1); NMR (d$_6$-DMSO): δ 12.70 (1H, br.s), 9.24 (2H, br.s), 8.81 (2H, br.s), 8.66 (1H, br.t, J=6.0 Hz), 8.29 (1H, br.s), 8.03 (1H, br.d, J=7.0 Hz), 7.72 (2H, d, J=8.1 Hz), 7.47 (2H, d, J=8.1 Hz), 7.40 (1H, d, J=7.8 Hz), 7.32 (1H, br.t, J=7.8 Hz), 7.21 (1H, br.d, J=7.8 Hz), 7.1–7.0 (2H, m), 5.15 (2H, s), 3.10 (2H, t, J=6.0 Hz), 2.30 (3H, s), 1.85 (1H, like septet, J=6.0 Hz), 0.89 (6H, d, J=6.0 Hz).

EXAMPLE 55(2)

2'-(4-amidinobenzyloxy)-4-(1(S)-hydroxymethyl-2,2-dimethylpropylcarbamoyl)-2-biphenylcarboxylic acid methanesulfonate

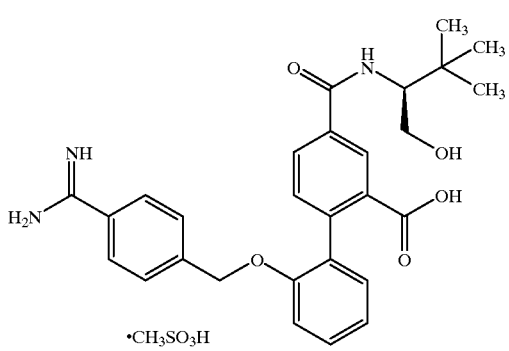

TLC:Rf 0.29 (Chloroform:Methanol:Acetic acid=10:2:1); NMR (d$_6$-DMSO): δ 9.27 (s, 2H), 8.99 (s, 2H), 8.29 (d, J=1.5 Hz, 1H), 8.09 (d, J=9.3 Hz, 1H), 8.05 (dd, J=1.5, 8.1 Hz, 1H), 7.73 (d, J=8.0 Hz, 2H), 7.48 (d, J=8.0 Hz, 2H), 7.39 (d, J=8.1 Hz, 1H), 7.32 (dt, J=1.5, 7.5 Hz, 1H), 7.20 (dd, J=1.5, 7.5 Hz, 1H), 7.1–7.0 (m, 2H), 5.16 (s, 2H), 4.1–3.6 (m, 2H), 3.92 (dt, J=3.3, 9.3 Hz, 1H), 3.67 (dd, J=3.3, 11.4 Hz, 1H), 3.49 (dd, J=9.3, 11.4 Hz, 1H), 2.34 (3H, s), 0.92 (s, 9H).

EXAMPLE 55(3)

2'-(4-amidinobenzyloxy)-4'-methyl-4-(1(S)-hydroxymethyl-2,2-dimethylpropyl carbamoyl)-2-biphenylcarboxylic acid methanesulfonate

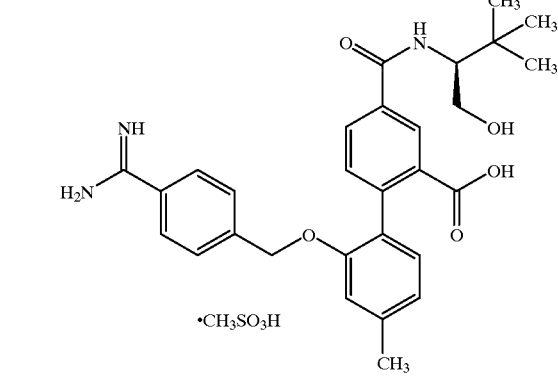

TLC:Rf 0.70 (Chloroform:Methanol:Acetic acid=10:2:1); NMR (d$_6$-DMSO): δ 9.27 (s, 2H), 8.96 (s, 2H), 8.27 (d, J=1.8 Hz, 1H), 8.07 (d, J=9.3 Hz, 1H), 8.03 (dd, J=8.1, 1.8 Hz, 11H), 7.73 (d, J=8.4 Hz, 2H), 7.48 (d, J=8.4 Hz, 2H), 7.36 (d, J=8.1 Hz, 1H), 7.08 (d, J=7.5 Hz, 1H), 6.93 (s, 1H), 6.86 (d, J=7.5 Hz, 1H), 5.14 (s, 2H), 3.91 (m, 1H), 4.0–3.6 (br, 2H), 3.67 (dd, J=11.4, 3.6 Hz, 1H), 3.48 (dd, J=11.4, 9.0 Hz, 1H), 2.33 (s, 3H), 2.33 (s, 3H), 0.91 (s, 9H).

EXAMPLE 56

2'-(4-amidinophenylaminomethyl)-4-(1(S)-hydroxymnethyl-2,2-dimethylpropyl carbamoyl)-2-biphenylcarboxylic acid methanesulfonate

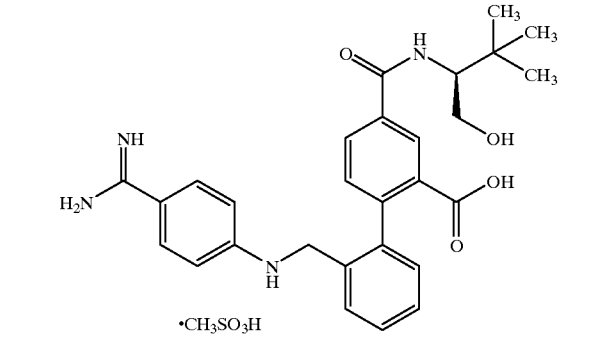

The title compound having the following physical data was obtained by the same procedure as a series of reaction of Reference Example 15→Reference Example 16→Example 16→Example 45→Example 2, using benzyl 2'-formyl-4-(1(R)-t-butyldimethylsilyloxymethyl-2,2-dimethylpropyl carbamoyl)-2-biphenylcarboxylate which was obtained by the same procedure as a series of reaction of Reference Example 4 using a corresponding compound.

TLC:Rf 0.54 (Ethyl acetate:Acetic acid:Water=3:1:1); NMR (d$_6$-DMSO): δ 8.74 (2H, br s), 8.36 (1H, d, J=1.4 Hz), 8.31 (2H, br s), 8.12 (1H, d, J=9.2 Hz), 8.07–8.04 (1H, m), 7.52 (2H, d, J=8.8 Hz), 7.44 (1H, d, J=8.0 Hz), 7.30–7.26 (4H, m), 7.12–7.06 (1H, m), 6.55 (2H, d, J=8.8 Hz), 4.07 (2H, br s), 3.98–3.86 (1H, m), 3.67 (1H, dd, J=4.0,11.2 Hz), 3.55–3.30 (2H, m), 2.30 (3H, s), 0.91 (9H, s).

REFERENCE EXAMPLE 29

Benzyl 2-[2-(4-cyanophenylaminomethyl)-3-pyridyl]-5-(2-methylpropyl carbamoyl)benzoate

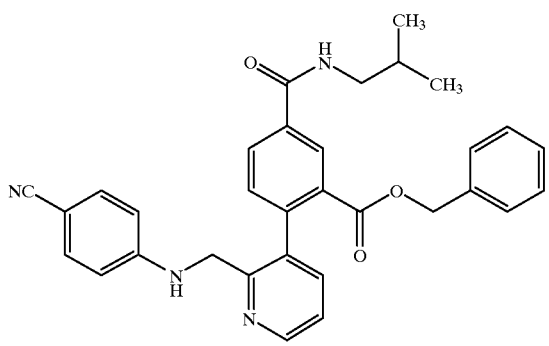

Benzyl 2-(2-formyl-3-pyridyl)-5-(2-methylpropylcarbamoyl)benzoate (674 mg) which was obtained by the same procedure as a series of reaction of Reference Example 4 using a corresponding compound, and 4-cyanoaniline (382 mg) were dissolved into ethanol (3 ml) and acetic acid (3 ml). Sodium cyanoborohydride (153 mg) was slowly added to the mixture at 0° C. The mixture was stirred for 30 minutes, and was made to more pH 8 by adding 1N aqueous solution of sodium hydroxide. A saturated aqueous solution of sodium bicarbonate was added to the solution. The solution was extracted with ethyl acetate. The organic layer was washed with a saturated aqueous solution of sodium bicarbonate and a saturated aqueous solution of sodium chloride, successively, dried over anhydrous magnesium sulfate and concentrated. The residue was purified by column chromatography on silica gel (hexane:ethyl acetate=2:1→1:1) to give the title compound (692 mg) having the following physical data.

TLC:Rf 0.21 (Hexane:Ethyl acetate=1:1); NMR (CDCl$_3$): δ 8.55 (d, J=1.8 Hz, 1H), 8.44 (d, J=1.8 Hz, 1H), 8.05 (dd, J=8.1, 1.8 Hz, 1H), 7.40 (dd, J=7.8, 1.8 Hz, 1H), 7.4–7.3 (m, 3H), 7.3–7.2 (m, 4H), 7.1–7.0 (m, 2H), 6.43 (d, J=8.7 Hz, 2H), 6.30 (br.t, J=6.6 Hz, 1H), 5.80 (br.t, J=4.5 Hz, 1H), 5.03 (s, 2H), 4.04 (dd, J=15.6, 4.5 Hz, 1H), 3.95 (dd, J=15.6, 3.9 Hz, 1H), 3.35 (t, J=6.6 Hz, 2H), 1.95 (like septet, J=6.6 Hz, 1H), 1.02 (d, J=6.6 Hz, 3H), 1.02 (d, J=6.6 Hz, 3H).

REFERENCE EXAMPLE 30

Benzyl 2-[2-(4-(imino-ethoxymethyl)phenylaminomethyl)-3-pyridyl]-5-(2-methyl propylcarbamoyl)benzoate hydrochloride

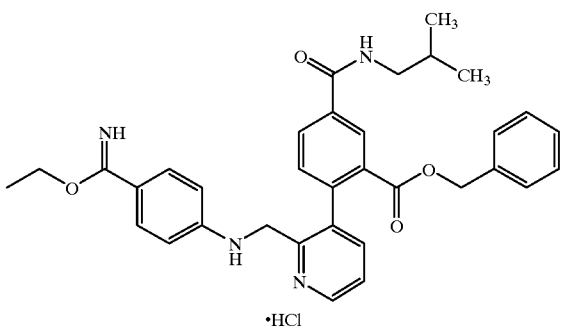

The compound prepared in Reference Example 29 (681 mg) was dissolved into ethanol (7 ml) and methylene chloride (7 ml), and the mixture was stirred at −20° C. Chloride gas was blown into the mixture slowly for 1 hour to be the solution was under 18° C. The solution was sealed up, and allowed to stand for 27 hours at 5° C. The reaction mixture was concentrated to give the title compound (643 mg) having the following physical data.

TLC:Rf 0.61 (Chloroform:Methanol:Water=9:1:0.1).

EXAMPLE 57

Benzyl 2-[2-(4-amidinophenylaminomethyl)-3-pyridyl]-5-(2-methylpropyl carbamoyl)benzoate

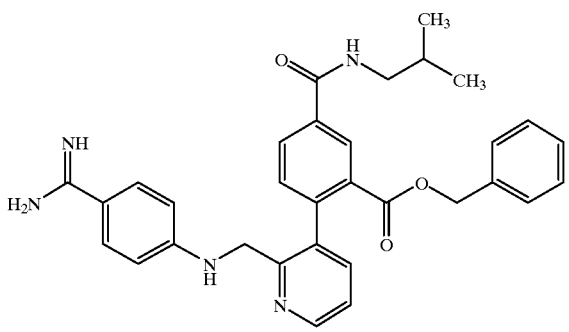

The compound prepared in Reference Example 30 (643 mg) was dissolved into ethanol (25 ml), and the solution was stirred at 0° C. An ammonium gas was blown into the mixture slowly for 15 minutes to be the solution was under 20° C. The solution was sealed up, and allowed to stand for 28 hours at room temperature. The reaction mixture was concentrated. The residue was purified by column chromatography on silica gel (Chloroform:Methanol=10:1→Chloroform:Methanol:Water=10:2:0.1) to give the title compound (307 mg) having the following physical data.

TLC:Rf 0.68 (Chloroform:Methanol:Acetic acid=10:2:1); NMR (d$_6$-DMSO): δ 8.77 (t, J=6.0 Hz, 1H), 8.9–8.4 (br, 3H), 8.52 (dd, J=4.8, 1.5 Hz, 1H), 8.47 (d, J=1.8 Hz, 1H), 8.13 (dd, J=7.8, 1.8 Hz, 1H), 7.53 (d, J=9.0 Hz, 2H), 7.6–7.45 (m, 1H), 7.46 (d, J=7.8 Hz, 1H), 7.35–7.25 (m, 4H), 7.2–7.1 (m, 2H), 6.98 (t, J=5.4 Hz, 1H), 6.53 (d, J=9.0 Hz, 2H), 5.07 (d, J=14.4 Hz, 1H), 5.04 (d, J=14.4 Hz, 1H), 4.2–4.0 (m, 2H), 3.11 (t, J=6.0 Hz, 2H), 1.87 (like septet, J=6.6 Hz, 1H), 0.90 (d, J=6.6 Hz, 3H), 0.90 (d, J=6.6 Hz, 3H).

EXAMPLE 58

2-[2-(4-amidinophenylaminomethyl)-3-pyridyl]-5-(2-methylpropylcarbamoyl) benzoic acid methanesulfonate

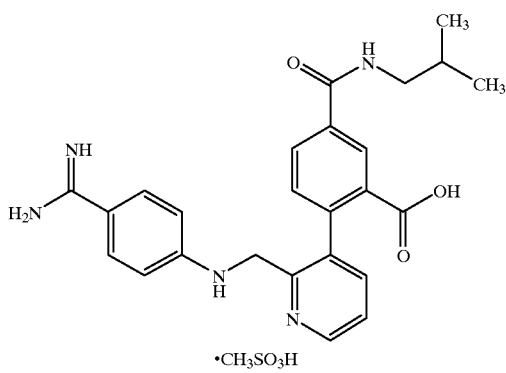

•CH₃SO₃H

The title compound was obtained by the same procedure as a series of reaction of Example 2, using a compound prepared in Example 57.

TLC:Rf 0.26 (Chloroform:Methanol:Acetic acid=10:2:1); NMR (d₆-DMSO): δ 8.81 (br.s, 2H), 8.77 (t, J=6.0 Hz, 1H), 8.64 (dd, J=5.1, 1.2 Hz, 1H), 8.51 (d, J=1.8 Hz, 1H), 8.49 (br.s, 2H), 8.13 (dd, J=8.0, 1.8 Hz, 1H), 7.87 (br.d, 1H), 7.62 (br.t, 1H), 7.55 (d, J=9.0 Hz, 2H), 7.51 (d, J=8.0 Hz, 1H), 6.58 (d, J=9.0 Hz, 2H), 4.32 (d, J=16.5 Hz, 1H), 4.22 (d, J=16.5 Hz, 1H), 4.4–3.5 (br, 2H), 3.12 (t, J=6.6 Hz, 2H), 2.33 (s, 3H), 1.87 (like septet, J=6.6 Hz 1H), 0.90 (d, J=6.6 Hz, 3H), 0.90 (d, J=6.6 Hz, 3H).

EXAMPLE 59 (1)–59 (2)

The following compounds were obtained by the same procedure as a series of reaction of Reference Example 29→Reference Example 30→Example 57→Example 58, using a corresponding compound.

EXAMPLE 59(1)

2-[2-(4-amidinophenylaminomethyl)-6-methyl-3-pyridyl]-5-(2-methylpropyl carbamoyl)benzoic acid methanesulfonate

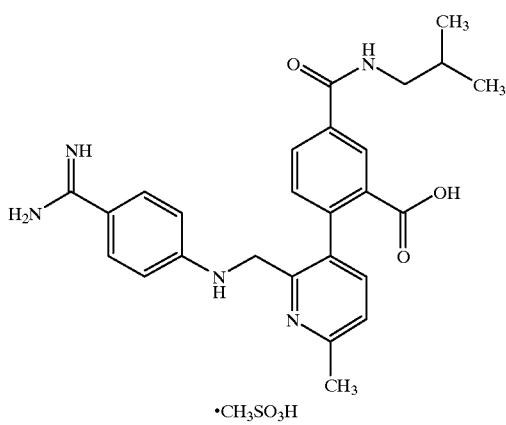

•CH₃SO₃H

TLC:Rf 0.58 (Chloroform:Methanol:Water=7:3:0.3); NMR (d₆DMSO): δ 8.81 (brs, 2H), 8.56 (brt, J=6.0 Hz, 1H), 8.54 (brs, 2H), 8.50 (d, J=1.5 Hz, 1H), 8.10 (dd, J=8.0, 1.5 Hz, 1H), 7.96 (brd, J=7.5 Hz, 1H), 7.64 (brd, J=7.5 Hz, 1H), 7.54 (d, J=9.0 Hz, 2H), 7.45 (d, J=8.0 Hz, 1H), 6.51 (d, J=9.0 Hz, 2H), 4.34 (brs, 2H), 3.11 (brt, J=6.0 Hz, 2H), 2.72 (s, 3H), 2.35 (s, 3H), 1.93–1.79 (m, 1H), 0.89 (d, J=6.6 Hz, 6H).

EXAMPLE 59(2)

2-[4-(4-amidinophenylaminomethyl)-3-pyridyl]-5-(2-methylpropylcarbamoyl) benzoic acid methanesulfonate

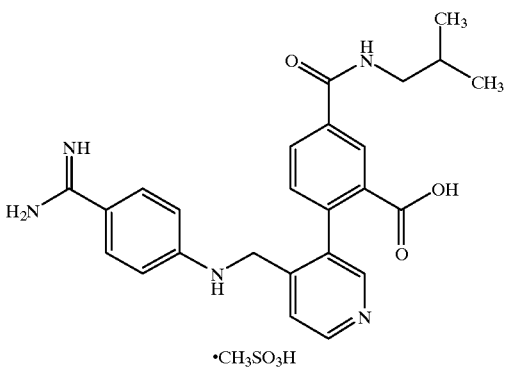

•CH₃SO₃H

TLC:Rf 0.36 (Chloroform:Methanol:Water=7:3:0.3); NMR (d₆-DMSO): δ 8.88 (brs, 2H), 8.83 (brt, J=6.0 Hz, 1H), 8.78 (d, J=5.7 Hz, 1H), 8.71 (s, 1H), 8.63 (brs, 2H), 8.59 (d, J=1.8 Hz, 1H), 8.22 (dd, J=8.0, 1.8 Hz, 1H), 7.72 (d, J=5.7 Hz, 1H), 7.63 (d, J=8.0 Hz, 1H), 7.59 (d, J=9.0 Hz, 2H), 6.58 (d, J=9.0 Hz, 2H), 4.32 (brd, J=18 Hz, 1H), 4.14 (brd, J=18 Hz, 1H), 3.13 (brt, J=6.0 Hz, 2H), 2.35 (s, 3H), 1.95–1.81 (m, 1H), 0.90 (d, J=6.6 Hz, 6H).

FORMULATION EXAMPLE 1

The following components were admixed in conventional method and punched out to obtain 100 tablets each containing 100 mg of active ingredient.

| | |
|---|---|
| 2-[2-(4-amidinophenylcarbamoyl)-6-methoxy-3-pyridyl]-5-[(1(S)-hydroxy methyl-2, 2-dimethylpropyl)carbamoyl]benzoic acid methanesulfonate | 10.0 g |
| Carboxymethyl Cellulose calcium (disintegrating agent) | 0.2 g |
| Magnesium stearate (lubricating agent) | 0.1 g |
| Microcrystalline cellulose | 9.7 g |

FORMULATION EXAMPLE 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| 2-[2-(4-amidinophenylcarbamoyl)-6-methoxy-3-pyridyl]-5-[(1(S)-hydroxy methyl-2, 2-dimethylpropyl)carbamoyl]benzoic acid methanesulfonate | 2.0 g |
| mannitol | 5.0 g |
| distilled water | 1000 ml |

What is claimed is:
1. An amidino compound of the formula (I):

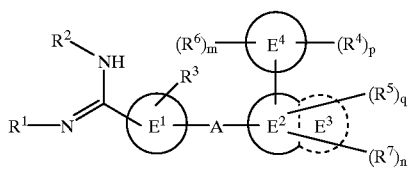

wherein $R^1$ and $R^2$ each independently, is
1) hydrogen,
2) hydroxy,
3) C1–4 alkoxycarbonyl,
4) C2–4 alkenyloxycarbonyl,
5) C1–4 alkoxycarbonyloxy or
6) —COO—(C1–4 alkyl)-phenyl,
with the proviso that when $R^1$ is group excepting hydrogen, $R^2$ is hydrogen, or when $R^2$ is group excepting hydrogen, $R^1$ is hydrogen $R^3$ is
1) hydrogen,
2) C1–4 alkyl,
3) hydroxy,
4) —O—(C1–4 alkyl)-phenyl, or
5) halogen atom, $E^1$ ring is
1) 5–7 membered unsaturated carbocyclic ring or
2) 5–7 membered unsaturated heterocyclic ring $E^2$ ring is
1) 5–7 membered unsaturated carbocyclic ring or
2) 5–7 membered unsaturated heterocyclic ring;

$E^3$ ring is
1) absent,
2) 5–7 membered unsaturated or saturated carbocyclic ring or
3) 5–7 membered unsaturated or saturated heterocyclic ring;

$E^4$ ring is
1) 5–6 membered unsaturated carbocyclic ring or
2) 5–6 membered unsaturated heterocyclic ring;

R4 and R5 each independently, is
1) —COOR$^8$, in which R$^8$ is hydrogen, C1–8 alkyl, —(C1–4 alkyl)-phenyl or —(C1–4 alkyl)—O—(C1–4 alkyl);
2) —(C1–4 alkyl)—COOR$^9$, in which R$^9$ is hydrogen, C1–8 alkyl—(C1–4 alkyl)-phenyl or —(C1–4 alkyl)—O—(C1–4 alkyl);
3) —(C2–4 alkenyl)—COOR$^{10}$, in which R$^{10}$ is hydrogen, C1–8 alkyl—(C1–4 alkyl)-phenyl or —(C1–4 alkyl)—O—(C1–4 alkyl); 4) —O—(C1–4 alkyl)—COOR$^{11}$, in which R$^{11}$ is hydrogen, C1–8 alkyl—(C1–4 alkyl)-phenyl or —(C1–4 alkyl)—O—(C1–4 alkyl);
5) —CONR$^{12}$R$^{13}$, in which R$^{12}$ is hydrogen, C1–4 alkyl, R$^{13}$ is hydroxy, —O—(C1–4 alkyl)-phenyl or cyano;
6) —P(O)(OR$^{14}$)$_2$, in which R$^{14}$ is hydrogen, C1–4 alkyl or —(C1–4 alkyl)-phenyl; or
7) tetrazol -5-yl which is optionally substituted by C1–8 alkyl; p and q each independently, is 0 or 1–2, with the proviso that p+q is 1 or 2;

$R^6$ and $R^7$ each independently, is
1) hydrogen,
2) C1–8 alkyl,
3) nitro,
4) cyano,
5) halogen atom,
6) —(C1–4 alkyl)—O—(C1–4 alkyl)-phenyl,
7) —NR$^{15}$R$^{16}$, in which R$^{15}$ and R$^{16}$ each independently, is hydrogen or C1–8 alkyl;
8) —OR$^{17}$, in which R$^{17}$ is hydrogen, C1–8 alkyl, CF$_3$, C2–5 acyl, —(C1–4 alkyl)-phenyl, —(C1–4 alkyl)—OH, —(C1–4 alkyl)—O—(C1–4 alkyl), or —(C1–4 alkyl)—O—(C1–4 alkyl)—O—(C1–4 alkyl);
9) —(C1–4 alkyl)—OR$^{17}$, in which R$^{17}$ is as hereinbefore defined;
10) —J$^1$–J$^2$, in which J$^1$ is
  (1) —CONR$^{18}$—, in which R$^{18}$ is hydrogen or C1–4 alkyl;
  (2) —NR$^{19}$CO—, in which R$^{19}$ is hydrogen or C1–4 alkyl;
  (3) —SO$_2$NR$^{20}$—, in which R$^{20}$ is hydrogen or C1–4 alkyl;
  (4) —NR$^{21}$SO$_2$—, in which R$^{21}$ is hydrogen or C1–4 alkyl;
  (5) —(C1–4 alkyl)—NR$^{22}$—, in which R$^{22}$ is hydrogen or C1–4 alkyl;
  (6) —CO—,
  (7) —(C1–4 alkyl)—NR$^{23}$CO—, in which R$^{23}$ is hydrogen or C1–4 alkyl; J$^2$ is
  (1) C1–15 alkyl optionally substituted by 1–3 of following groups (i)–(x):
    (i) C3–7 cycloalkyl optionally substituted by —(C1–4 alkyl)—OR$^{24}$;
    (ii) phenyl,
    (iii) 5–7 membered saturated heterocyclic ring optionally substituted by carboxyl or C1–4 alkoxycarbonyl;
    (iv) OR$^{24}$, in which R$^{24}$ is hydrogen, C1–4 alkyl, —COO—(C1–4 alkyl)-phenyl, C2–5 acyl, or —(C1–4 alkyl)-phenyl;
    (v) NR$^{25}$R$^{26}$, in which R$^{25}$ is hydrogen or C1–4 alkyl, R$^{26}$ is hydrogen, C1–4 alkyl, —COO (C1–4 alkyl)-phenyl, imino(C1–4 alkyl) or C1–4 alkoxycarbonyl;
    (vi) —S(O)$_r$—(C1–4 alkyl), in which r is 0–2;
    (vii) —COOR$^{27}$, in which R$^{27}$ is hydrogen, C1–4 alkyl or —(C1–4 alkyl)-phenyl;
    (viii) —CONR$^{28}$R$^{29}$, in which R$^{28}$ and R$^{29}$ each independently, is
      (i) hydrogen, (ii) C1–4 alkyl, (iii) hydroxy, or (iv) C1–4 alkyl substituted by one of hydroxy, phenyl or NR$^{25}$R$^{26}$, or R$^{28}$ and R$^{29}$ taken together with the nitrogen atom to which they are attached form 5–6 membered saturated heterocyclic ring containing nitrogen atom
    (ix) halogen atom,
    (x) trihalomethyl;
  (2) C2–8 alkenyl,
  (3) C5–7 cycloalkyl optionally substituted by 1–3 of C1–4 alkyl, —COOR$^{27}$, in which R$^{27}$ is as hereinbefore defined; —(C1–4 alkyl)—OR$^{24}$, in which R$^{24}$ is as hereinbefore defined;
  (4) —NR$^{25}$R$^{26}$, in which R$^{25}$ and R$^{26}$ is as hereinbefore defined;
  (5) 5–6 membered saturated heterocyclic ring optionally substituted by 1–3 of C1–4 alkyl, oxo, imino(C1–4 alkyl); or R$^{18}$ and J$^2$ taken together with the nitrogen atom to which they are attached form saturated heterocyclic ring optionally substituted by 1–3 of C1–8 alkyl, C2–8 alkenyl or —COOR$^{27}$, in which R$^{27}$ is as hereinbefore defined;

m is 1–3;

n is 1–3;

two R$^6$ taken together with the neighboring two carbon of E$^4$ ring to which they are attached form 5–6 membered unsaturated carbocyclic ring or 5–6 membered saturated heterocyclic ring, that rings may be substituted by 1–3 of R$^4$ or R$^6$;

A is
1) ethylene,
2) vinylene,
3) ethynylene,
4) —O—CH$_2$—,
5) —CH$_2$—O—,
6) —NR$^{30}$CO—, in which R$^{30}$ is hydrogen or C1–4 alkyl
7) —NR$^{31}$CHR$^{32}$—, in which R$^{31}$ is hydrogen or C1–4 alkyl, R$^{32}$ is hydrogen, cyano, COOR$^{36}$, in which R$^{36}$ is hydrogen or C1–4 alkyl; or CONR$^{37}$R$^{38}$, in which R$^{37}$ and R$^{38}$ each independently, is hydrogen or C1–4 alkyl;
8) —CH$_2$—NR$^{33}$—, in which R$^{33}$ is hydrogen or C1–4 alkyl;
9) —S—CH$_2$—,
10) —CH$_2$—S—,
11) —SO$_2$NR$^{34}$—, in which R$^{34}$ is hydrogen or C1–4 alkyl;
12) —NR$^{35}$SO$_2$—, in which R$^{35}$ is hydrogen or C1–4 alkyl; non-toxic salts thereof, or hydrates thereof.

2. A compound according to claim 1, wherein in E$^3$ ring is absent in the formula:

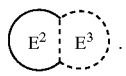

3. A compound according to claim 1, wherein E$^3$ ring is 5–7 membered unsaturated or saturated carbocyclic ring or 5–7 membered unsaturated or saturated heterocyclic ring in the formula:

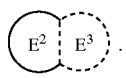

4. A compound according claim 1, wherein A is —CH$_2$—O—, —NR$^{30}$CO— or —NR$^{31}$CHR$^{32}$—.

5. An amidino compound according to claim 1 of the formula (I-1):

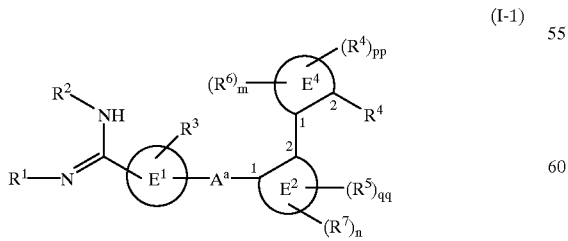

(I-1)

wherein R$^1$ and R$^2$ each independently, is
1) hydrogen,
2) hydroxy,
3) C1–4 alkoxycarbonyl,
4) C2–4 alkenyloxycarbonyl,
5) C1–4 alkoxycarbonyloxy or
6) —COO—(C1–4 alkyl)-phenyl, with the proviso that when R$^1$ is group excepting hydrogen, R$^2$ is hydrogen, or when R$^2$ is group excepting hydrogen, R$^1$ is hydrogen;

R$^3$ is
1) hydrogen,
2) C1–4 alkyl,
3) hydroxy,
4) —O—(C1–4 alkyl)-phenyl, or
5) halogen atom;

E$^1$ ring is
1) 5–7 membered unsaturated carbocyclic ring or
2) 5–7 membered unsaturated heterocyclic ring;

E$^2$ ring is
1) 5–7 membered unsaturated carbocyclic ring or
2) 5–7 membered unsaturated heterocyclic ring;

E$^4$ ring is
1) 5–6 membered unsaturated carbocyclic ring or
2) 5–6 membered unsaturated heterocyclic ring;

R$^4$ and R$^5$ each independently, is
1) —COOR$^8$, in which R$^8$ is hydrogen, C1–8 alkyl, —(C1–4 alkyl)-phenyl or —(C1–4 alkyl)—O—(C1–4 alkyl);
2) —(C1–4 alkyl)—COOR$^9$, in which R$^9$ is hydrogen, C1–8 alkyl, —(C1–4 alkyl)-phenyl or —(C1–4 alkyl)—O—(C1–4 alkyl);
3) —(C2–4 alkenyl)—COOR$^{10}$, in which R$^{10}$ is hydrogen, —C1–8 alkyl, (C1–4 alkyl)-phenyl or —(C1–4 alkyl)—O—(C1–4 alkyl);
4) —O—(C1–4 alkyl)—COOR$^{11}$, in which R$^{11}$ is hydrogen, C1–8 alkyl, —(C1–4 alkyl)-phenyl or —(C1–4 alkyl)—O—(C1–4 alkyl);
5) —CONR$^{12}$R$^{13}$, in which R$^{12}$ is hydrogen, C1–4 alkyl, R$^{13}$ is hydroxy, —O—(C1–4 alkyl)-phenyl or cyano;
6) —P(O)(OR$^{14}$)$_2$, in which R$^{14}$ is hydrogen, C1–4 alkyl or —(C1–4 alkyl)-phenyl; or
7) tetrazol -5-yl which is optionally substituted by C1–8 alkyl; pp and qq each independently, is 0 or 1, with the proviso that pp+qq is 0 or 1;

R$^6$ and R$^7$ each independently, is
1) hydrogen,
2) C1–8 alkyl,
3) nitro,
4) cyano,
5) halogen atom,
6) —(C1–4 alkyl)—O—(C1–4 alkyl)-phenyl,
7) —NR$^{15}$R$^{16}$, in which R$^{15}$ and R$^{16}$ each independently, is hydrogen or C1–8alkyl;
8) —OR$^{17}$, in which R$^{17}$ is hydrogen, C1–8 alkyl, CF$_3$, C2–5 acyl, —(C1–4 alkyl)-phenyl, —(C1–4 alkyl)—OH, —(C1–4 alkyl)—O—(C1–4 alkyl), or —(C1–4 alkyl)—O—(C1–4 alkyl)—O—(C1–4 alkyl);
9) —(C1–4 alkyl)—OR$^{17}$, in which R$^{17}$ is as hereinbefore defined;
10) —J$^1$–J$^2$, in which J$^1$ is
(1) —CONR$^{18}$—, in which R$^{18}$ is hydrogen or C1–4 alkyl;
(2) —NR$^{19}$CO—, in which R$^{19}$ is hydrogen or C1–4 alkyl;
(3) —SO$_2$NR$^{20}$—, in which R$^{20}$ is hydrogen or C1–4 alkyl;

(4) —NR²¹SO₂—, in which R²¹ is hydrogen or C1–4 alkyl;
(5) —(C1–4 alkyl)—NR²²—, in which R²² is hydrogen or C1–4 alkyl;
(6) —CO—,
(7) —(C1–4 alkyl)—NR²³CO—, in which R²³ is hydrogen or C1–4 alkyl; J² is
(1) C1–15 alkyl optionally substituted by 1–3 of following groups (i)–(x):
   (i) C3–7 cycloalkyl optionally substituted by —(C1–4 alkyl)—OR²⁴;
   (ii) phenyl,
   (iii) 5–7 saturated heterocyclic ring optionally substituted by carboxyl or C1–4 alkoxycarbonyl;
   (iv) OR²⁴, in which R²⁴ is hydrogen, C1–4 alkyl, —COO—(C1–4 alkyl)-phenyl, C2–5 acyl, or —(C1–4 alkyl)-phenyl;
   (v) NR²⁵R²⁶, in which R²⁵ is hydrogen or C1–4 alkyl, R²⁶ is hydrogen, C1–4 alkyl, —COO (C1–4 alkyl)-phenyl, imino(C1–4 alkyl) or C1–4 alkoxycarbonyl
   (vi) —S(O)ᵣ—(C1–4 alkyl), in which r is 0–2;
   (vii) —COOR²⁷, in which R²⁷ is hydrogen, C1–4 alkyl or —(C1–4 alkyl)-phenyl;
   (viii) —CONR²⁸R²⁹, in which R²⁹ and R²⁹ each independently, is
      (i) hydrogen, (ii) C1–4 alkyl, (iii) hydroxy, or (iv) C1–4 alkyl substituted by one of hydroxy, phenyl or NR²⁵R²⁶, or R²⁸ and R²⁹ taken together with the nitrogen atom to which they are attached form 5–6 membered saturated heterocyclic ring containing nitrogen atom;
   (ix) halogen atom,
   (x) trihalomethyl;
(2) C2–8 alkenyl,
(3) C5–7 cycloalkyl optionally substituted by 1–3 of C1–4 alkyl, —COOR²⁷, in which R²⁷ is as hereinbefore defined; —(C1–4 alkyl)—OR²⁴, in which R²⁴ is as hereinbefore defined;
(4) —NR²⁵R²⁶, in which R₂₅ and R²⁶ is as hereinbefore defined;
(5) 5–6 membered saturated heterocyclic ring optionally substituted by 1–3 of C1–4 alkyl, oxo, imino(C1–4 alkyl); or R¹⁸ and J² taken together with the nitrogen atom to which they are attached form saturated heterocyclic ring optionally substituted by 1–3 of C1–8 alkyl, C2–8 alkenyl or —COOR²⁷, in which R²⁷ is as hereinbefore defined;

m is 1–3;
n is 1–3;
two R⁶ taken together with the neighboring two carbon of E⁴ ring to which they are attached form 5–6 membered unsaturated carbocyclic ring or 5–6 membered saturated heterocyclic ring, that rings may be substituted by 1–3 of R⁴ or R⁶;
Aᵃ is
   1) —CH₂—O—,
   6) —NR³⁰CO—,
   7) —NR³¹CHR³²; with the proviso that Aᵃ and E⁴ ring attach to E² ring at ortho position, E² ring and essential one R⁴ attach to E⁴ ring at ortho position; non-toxic salts thereof, or hydrates thereof.

6. A compound according to claim 1, wherein at least one of R⁶ is —J¹–J².

7. A compound according to claim 1, which is selected from
(1) 2'-(4-amidinophenylcarbamoyl)-4-((2,2-dimethylpropyl)carbamoyl)-2-biphenylcarboxylic acid,
(2) 2'-(4-amidinophenylcarbamoyl)-4-dimethylcarbamoyl-2-biphenylcarboxylic acid,
(3) 2'-(4-amidinophenylcarbamoyl)-4-methylcarbamoyl-2-biphenylcarboxylic acid,
(4) 2'-(4-amidinophenylcarbamoyl)-4-((carboxymethyl)carbamoyl)-2-biphenylcarboxylic acid,
(5) 2'-(4-amidinophenylcarbamoyl)-4-((1-carboxy-2-phenylethyl)carbamoyl)-2-biphenylcarboxylic acid,
(6) 2'-(4-amidinophenylcarbamoyl)-4-benzylcarbamoyl-2-biphenylcarboxylic acid,
(7) 2'-(4-amidinophenylcarbamoyl)-4-phenylethylcarbamoyl-2-biphenylcarboxylic acid,
(8) 2'-(4-amidinophenylcarbamoyl)-4-((2-methylpropyl)carbamoyl)-2-biphenylcarboxylic acid,
(9) 2'-(4-amidinophenylcarbamoyl)-4'-methoxy-4-((1-methoxycarbonyl-2-methylpropyl)carbamoyl)-2-biphenylcarboxylic acid,
(10) 2'-(4-amidinophenylcarbamoyl)-4'-methoxy-4-((2-methylpropyl)carbamoyl)-2-biphenylcarboxylic acid,
(11) 2'-(4-amidinophenylcarbamoyl)-4-isopropylcarbamoyl-2-biphenylcarboxylic acid,
(12) 2'-(4-amidinophenylcarbamoyl)-4-((3-methylbutyi)carbamoyl)-2-biphenylcarboxylic acid,
(13) 2'-(4-amidinophenylcarbamoyl)-4-ethylcarbamoyl-2-biphenylcarboxylic acid,
(14) 2'-(4-amidinophenylcarbam oyl)-4-butylcarbamoyl-2-biphenylcarboxylic acid,
(15) 2'-(4-amidinophenylcarbamoyl)-4'-methyl-4-((2-methylpropyl)carbamoyl)-2-biphenylcarboxylic acid,
(16) 2'-(4-amidinophenylcarbamoyl)-4-((cyclohexylmethyl)carbamoyl)-2-biphenylcarboxylic acid,
(17) 2'-(4-amidinophenylcarbamoyl)-4-((5-(t-butoxycarbonylamino)pentyi)carbamoyl)-2-biphenylcarboxylic acid,
(18) 2'-(4-amidinophenylcarbamoyl)-4-((1-methylpropyl)carbamoyl)- 2-biphenylcarboxylic acid,
(19) 2'-(4-amidinophenylcarbamoyl)-4-((tetrahydropyran-4-ylmethyl)carbamoyl)-2-biphenylcarboxylic acid,
(20) 2'-(4-amidinophenylcarbamoyl)-4-((2-hydroxypropyl)carbamoyl)-2-biphenylcarboxylic acid,
(21) 2'-(4-amidino-2-hydroxyphenylcarbamoyl)-4-((2-methylpropyl)carbamoyl)-2-biphenylcarboxylic acid,
(22) 2'-(4-amidinophenylcarbamoyl)-4-(N-methyl-N-(2-methylpropyl)carbamoyl)-2-biphenylcarboxylic acid,
(23) 2'-(4-amidinophenylcarbamoyl)-4-((2-methyl-1-(methylaminomethyl) propyl)carbamoyl)-2-biphenylcarboxylic acid,
(24) 2'-(4-amidinophenylcarbamoyl)-4-((2-hydroxy-2-methylpropyl)carbamoyl)-2-biph enylcarboxylic acid,
(25) 2'-(4-amid ino-2-mrethyiphenylcarbamoyl)-4-((2-methylpropyl)carbamoyl)-2-biphenylcarboxylic acid,
(26) 2'-(4-amidinophenylcarbamoyl)-4-((cyclopropylmethyl)carbamcyl)-2-biphenylcarboxylic acid,
(27) 2'-(4-amidinophenylcarbamoyl)-4-((1-methylcarbamoyl-2-methylpropyl)carbamoyl)-2-biphenylcarboxylic acid,
(28) 2'-(4-amidinophenylcarbamoyl)-4-((cyclopentylmethyl)carbamoyl)-2-biphenylcarboxylic acid,
(29) 2'-(4-amidinophenylcarbamoyl)-4-((cyclobutylmethyl)carbamoyl)-2-biphenylcarboxylic acid,
(30) 2'-(4-amidinophenylcarbamoyl)-4-((1-methoxycarbonyl-2-methylpropyl)carbamoyl)-2-biphenylcarboxylic acid,

(31) 2'-(4-amidinophenylcarbamoyl)-4-((2-methoxycarbonylethyl)carbamoyl)-2-biphenylcarboxylic acid,
(32) 2'-(4-amidinophenylcarbamoyl)-4-((3-ethoxycarbonylpropyl)carbamoyl)-2-biphenylcarboxylic acid,
(33) 2'-(4-amidinophenylcarbamoyl)-4-((1-t-butoxycarbonylpiperidin- 4-ylmethyl)carbamoyl)-2-biphenylcarboxylic acid,
(34) 2'-(4-amidinophenylcarbamoyl)-4-((2-methyithioethyl)carbamoyl)-2-biphenylcarboxylic acid,
(35) 2'-(4-amidinophenylcarbamoyl)-4-((2-methylsulfinylethyl)carbamoyl)-2-biphenylcarboxylic acid,
(36) 2'-(4-amidinophenylcarbamoyl)-4-((1-dimethylaminomethyl-2-methylpropyl)carbamoyl)-2-biphenylcarboxylic acid,
(37) 2'-(4-amidinophenylcarbamoyl)-4-((1-(pyrrolidin-1-ylmethyl)-2-methylpropyl)carbamoyl)-2-biphenylcarboxylic acid,
(38) 2'-(4-amidinophenylcarbamoyl)-4-((1-hydroxymethyl-2-methylpropyl)carbamoyl)-2-biphenylcarboxylic acid,
(39) 2'-(4-amidinophenylaminomethyl)-4-((2,2-dimethylpropyl)carbamoyl)-2-biphenylcarboxylic acid,
(40) 2'-(4-amidinophenylaminomethyl)-4'-methoxy-4-((2-methylpropyl)carbamoyl)-2-biphenylcarboxylic acid,
(41) 2'-(4-amidinophenylaminomethyl)-4-((2-methylpropyl)carbamoyl)-2-biphenylcarboxylic acid,
(42) 2'-(4-amidinophenylaminomethyl)-4-((2-methylpropyl)carbamoyl)-2-biphenylcarboxylic acid,
(43) 2'-(4-($N^2$-hydroxyamidino)phenylaminomethyl)-4-((2-methylpropyl)carbamoyl)-2-biphenylcarboxylic acid,
(44) 2'-(4-($N^2$-hydroxyamidino)phenylcarbamoyl)-4-((2-methylpropyl)carbamoyl)-2-biphenylcarboxylic acid,
(45) 2-(4-(4-amidinophenylcarbamoyl)pyridin-3-yl)-5-((2-methylpropyl)carbamoyl)benzoic acid,
(46) 2'-(4-amidinophenylcarbamoyl)-4-propylcarbamoyl-2-biphenylcarboxylic acid,
(47) 2'-(4-amidinophenylcarbamoyl)-4-((3-hydroxy-2,2-dimethylpropyl)carbamoyl)-2-biphenylcarboxylic acid,
(48) 2'-amidinophenylcarbamoyl)-4-((1,2,2-trimethylpropyl)carbamoyl)- 2-biphenylcarboxylic acid,
(49) 2'-(4-amidinophenylcarbamoyl)-4-pentylcarbamoyl-2-biphenylcarboxylic acid,
(50) 2'-(4-amidinophenylcarbamoyl)-4-hexylcarbamoyl-2-biphenylcarboxylic acid,
(51) 2'-(4-amidinophenylcarbamoyl)-4-((1,2-dimethylpropyl)carbamoyl)-2-biphenylcarboxylic acid,
(52) 2'-(4-amidinophenylcarbamoyl)-4-(((1S)-1-hydroxymethyl-2-methylpropyl)carbamoyl)-2-biphenylcarboxylic acid,
(53) 2'-(4-amidinophenylcarbamoyl)-4-((3,3-dimethylbutyl)carbamoyl)-2-biphenylcarboxylic acid,
(54) 2'-(4-amidinophenylcarbamoyl)-4-(((1R)-1-hydroxymethyl-2-methylpropyl)carbamoyl)-2-biphenylcarboxylic acid,
(55) 2'-(4-amidinophenylcarbamoyl)-4-(((1S)-1-methoxycarbonyl-2-methylpropyl)carbamoyl)-2-biphenylcarboxylic acid,
(56) 2'-(4-amidinophenylcarbamoyl)-4-(((1R)-1-methoxycarbonyl-2-methylpropyl)carbamoyl)-2-biphenylcarboxylic acid,
(57) 2-(3-(4-amidinophenylcarbamoyl)pyridin-4-yl)-5-((2-methylpropyl)carbamoyl)benzoic acid,
(58) 2'-(6-amidinopyridin-3-yl)-4-((2-methylpropyl)carbamoyl)-2-biphenylcarboxylic acid,
(59) 2'-(4-amidinophenylcarbamoyl)-4'-methoxy-4-((1,2,2-trimethyipropyl)carbamoyl)-2-biphenylcarboxylic acid,
(60) 2'-(4-amidinophenylcarbamoyl)-4-(((1S)-1-hydroxymethyl-2,2-dimethylpropyi)carbamoyl)-biphenylcarboxylic acid,
(61) 2'-(6-amidinopyridin-3-ylcarbamoyl)-2-((1,2,2-trimethylpropyl)carbamoyl)-2-biphenylcarboxylic acid,
(62) 2'-(4-amidinophenylcarbamoyl)-4-((1-carboxy-2-methylpropyl)carbamoyl)-2-biphenylcarboxylic acid,
(63) 2'-(4-amidinophenylcarbamoyl)-4-((2-carboxyethyl)carbamoyl)- 2-biphenylcarboxylic acid,
(64) 2'-(4-amidinophenylcarbamoyl)-4-((3-carboxypropyl)carbamoyl)-2-biphenylcarboxylic acid,
(65) 2'-(4-amidinophenylcarbamoyl)-4-((5-aminopentyl)carbamoyl)-2-biphenylcarboxylic acid,
(66) 2'-(4-aridinophenylcarbamoyl)-4-((piperidin-4-ylmethyl)carbamoyl)-2-biphenylcarboxylic acid,
(67) 2'-(6-amidinopyridin-3-ylcarbamoyl)-4-((2-methylpropyl)carbamoyl)-2-biphenylcarboxylic acid,
(68) 2'-(6-amidinopyridin-3-ylcarbamoyl)-4'-methoxy-4-((1,2,2-trimethylpropyl)carbamoyl)-2-biphenylcarboxylic acid,
(69) N-hydroxy-2'-(4-amidinophenylcarbamoyl)-4-((2-methylpropyl)carbamoyl)-2-biphenylcarboxamide,
(70) N-hydroxy-2'-(4-amidinophenylcarbamoyl)-4'-methoxy-4-((2-methylpropyl)carbamoyl)-2-biphenylcarboxamide,
(71) 2-[4-(4-amidinophenylcarbamoyl)-3-pyridyl]-5-[(1,2,2-trimethylpropyl)carbamoyl]benzoic acid,
(72) 2-[2-(4-amidinophenylcarbamoyl)-6-methyl-3-pyridyl]-5-[(2-methylpropyl)carbamoyl]benzoic acid,
(73) 2-[2-(4-amidinophenylcarbamoyl)-6-methyl-3-pyridyl]-5-[(1,2,2-trimethylpropyl)carbamoyl]benzoic acid,
(74) 2'-(4-amidinophenylcarbamoyl)-4-(1,1-dimethylpropylcarbamoyl)-2-biphenylcarboxylic acid,
(75) 2'-(4-amidinophenylcarbamoyl)-4-[(1(S)-t-butyl-2-methoxycarbonylethyl)carbamoyl]-2-biphenylcarboxylic acid,
(76) 2'-(4-amidinophenylcarbamoyl)-4-(2,2-dimethylcyclohexylcarbamoyl)-2-biphenylcarboxylic acid,
(77) 2'-(4-amidinophenylcarbamoyl)-4-(1-isopropyl-2-methylpropylcarbamoyl)-2-biphenylcarboxylic acid,
(78) 2'-(4-amidinophenylcarbamoyl)-4-[(4,4-dimethyloxolan- 3(S)-yl)carbamoyl]-2-biphenylcarboxylic acid,
(79) 2-[2-(4-amidinophenylcarbamoyl)-3-pyridyl]-5-[(2-methylpropyl)carbamoyl]benzoic acid,
(80) 2-[2-(4-amidinophenylcarbamoyl)-6-methyl-3-pyridyl]-5-[(3-hydroxymethyl-2,2-dimethylpropyl)carbamoyl]benzoic acid,
(81) 2-[2-(4-amidinophenylcarbamoyl)-3-pyridyl]-5-[(1,2,2-trimethylpropyl)carbamoyl]benzoic acid,
(82) 2'-(4-amidinophenylcarbamoyl)-4-[(1(R), 2,2-trimethylpropyi)carbamoyl]-2-biphenylcarboxylic acid,
(83) 2'-(4-amidinophenylcarbamoyl)-4-[(1(S), 2,2-trimethylpropyl)carbamoyl]-2-biphenylcarboxylic acid,
(84) 2-[2-(4-amidinophenylcarbamoyl)-6-methyl-3-pyridyl]-5-[(2,2-dimethylpropyl)carbamoyl]benzoic acid,
(85) 2-[2-(4-amidinophenylcarbamoyl)-6-methoxy-3-pyridyl]-5-[(2-methylpropyl)carbamoyl]benzoic acid,
(86) 2'-(4-amidinophenylcarbamoyl)-4-(1-methoxycarbonylcyclopentylcarbamoyl)-2-biphenylcarboxylic acid,
(87) 2~14-(4-amidinophenylcarbamoyl)-3-pyridyl]-5-[(1(S)-hydroxymethyl-2-methylpropyl)carbamoyl]benzoic acid,
(88) 2-[2-(4-amidinophenylcarbamoyl)-6-methyl-3-pyridyl]-5-[(1(S)-hydroxymethyl-2-methylpropyl)carbamoyl]benzoic acid,

(89) 2-[2-(4-amidinophenylcarbamoyl)-3-pyridyl]-5-[(1(S)-hydroxymethyl-2-methylpropyl)carbamoyl]benzoic acid,

(90) 2'-(4-amidinophenylcarbamoyl)-4-[(2-methoxycarbonyl-2,2-dimethylethyl)carbamoyl]-2-biphenylcarboxylic acid,

(91) 2-[2-(4-amidinophenylcarbamoyl)-6-methyl-3-pyridyl]-5-[(1(S)-methoxycarbonyl-2-methylpropyl)carbamoyl]benzoic acid,

(92) 2-[4-(4-amidinophenylcarbamoyl)-3-pyridyl]-5-[(1(S)-methoxycarbonyl-2-methylp ropyl)carbam oyl]benzoic acid,

(93) 2'-(4-amidino-3-hydroxyphenylcarbamoyl)-4-(2-methylpropylcarbamoyl)- 2-biphenylcarboxylic acid,

(94) 2'-(4-amidino-3-hydroxyphenylcarbamoyl)-4-(1,2,2-trimethylpropylcarbamoyl)-2-biphenylcarboxylic acid,

(95) 2'-(4-amidinophenylcarbamoyl)-4-(1,3-dimethylbutylcarbamoyl)-2-biphenylcarboxylic acid,

(96) 2'-(4-amidinophenylcarbamoyl)-4-(2,2-dimethyl-1(R)-cyclopentylcarbamoyl)-2-biphenylcarboxylic acid,

(97) 2-[2-(4-amidinophenylcarbamoyl)-3-pyridyl]-5-[(1(S)-carboxy-2-methylpropyl)carbamoyl]benzoic acid,

(98) 2-[3-(4-amidinophenylcarbamoyl)-2-furyl]-5-(2-methylpropylcarbamoyl)benzoic acid,

(99) 2-[2-(4-amidinophenylcarbamoyl)-3-thienyl]-5-(2-methylpropylcarbamoyl)benzoic acid, (100) 2'-(4-amidinophenylcarbamoyl)-4-[(1-methoxycarbonyl-1-methylethyl)carbamoyl]-2-biphenylcarboxylic acid, (101) 2'-(4-amidinophenylcarbamoyl)-4-(1(S)-carboxy-3-methylbutylcarbamoyl)-2-biphenylcarboxylic acid, (102) 2-[2-(4-amidinophenylcarbamoyl)-3-pyridyl]-5-(2,2-dimethylpropylcarbamoyl)benzoic acid, (103) 2-[2-(4-amidinophenylcarbamoyl)-6-methoxy-3-pyridyl]-5-(2,2-dimethylpropylcarbamoyl)benzoic acid, (104) 2'-(4-amidinophenylcarbamoyl)-4-(2,2-dimethyl-1(S)-cyclopentylcarbamoyl)-2-biphenylcarboxylic acid, (105) 2-[3-(4-amidinophenylcarbamoyl)-2-thienyl]-5-(2,2-dimethylpropylcarbamoyl)benzoic acid, (106) 2-[2-(4-amidinophenylcarbamoyl)-3-thienyl]-5-(2,2-dimethylpropylcarbamoyl)benzoic acid, (107) 2-[4-(4-amidinophenylcarbamoyl)-3-pyridyl]-5-(2,2-dimethylpropylcarbamoyl)benzoic acid, (108) 2-[2-(4-amidinophenylcarbamoyl)-5-methyl-3-thienyl]-5-( 2,2-dimethylpropylcarbamoyl)benzoic acid, (109) 2'-(4-amidinophenylcarbamoyl)-4'-amino-4-(2,2-dimethylpropylcarbamoyl)-2-biphenylcarboxylic acid, (110) 2-[2-(4-amidinophenylcarbamoyl)-5-methyl-3-furyl]-5-(2,2-dimethylpropylcarbamoyl)benzoic acid, (111) 2-[4-(4-amidinophenylcarbamoyl)-2-methyl-pyrimidin-5-yl]-5-(2,2-dimethylpropylcarbamoyl)benzoic acid, (112) 2-[2-(4-amidinophenylcarbamoyl)-6-methyl-3-pyridyl]-5-(1(S)-morpholinocarbonyl-3-methylbutylcarbamoyl)benzoic acid, (113) 2-[2-(4-amidinophenylcarbamoyl)-6-methyl-3-pyridyl]-5-(1(S)-methoxymethyl-2,2-dimethylpropylcarbamoyl)benzoic acid, (114) 2-[2-(4-amidinophenylcarbamoyl)-6-methoxy-3-pyridyl]-5-(1(S)-methoxymethyl-2,2-dimethylpropylcarbamoyl)benzoic acid, (115) 2-[2-(4-amidino-3-fluorophenylcarbamoyl)-6-methyl-3-pyridyl]-5-(2,2-dimethylpropylcarbamoyl)benzoic acid, (116) 2'-(4-amidinophenylcarbamoyl)-5'-amino-4-(2,2-dimethylpropylcarbamoyl)-2-biphenylcarboxylic acid, (117) 2-[2-(4-amidinophenylcarbamoyl)-6-methyl-3-pyridyl]-5-(1,1,3,3-tetramethylbutylcarbamoyl)benzoic acid, (118) 2-[2-(4-amidinophenylcarbamoyl)-5-methyl-3-pyridyl]-5-(2,2-dimethylpropylcarbamoyl)benzoic acid, (119) 2-[2-(4-amidinophenylcarbamoyl)-6-methoxy-3-pyridyl]-5-[[5-(1-methylethyl)-2,2-dimethyidioxan-5-yl]carbamoyl]benzoic acid, (120) 2-[2-(4-amidinophenylcarbamoyl)-6-methoxy-3-pyridyl]-5-[1(S)-(4-ethoxycarbonyloxazol-2-yl)-3-methylbutyl)carbamoyl]benzoic acid, (121) 2-[2-(4-amidinophenylcarbamoyl)-6-methoxy-3-pyridyl]-5-[(1(S)-N-hydroxycarbamoyl)-3-methylbutylcarbamoyl]benzoic acid, (122) 2-[2-(4-amidinophenylcarbamoyl)-6-methoxy-3-pyridyl]-5-(2,2-dimethylpropylcarbamoyl)-4-methylbenzoic acid, (123) 2-[2-(4-amidinophenylcarbamoyl)-6-methoxy-3-pyridyl]-5-( 1(S)-hydroxymethyl-3-methylbutytcarbamoyl)-4-methylbenzoic acid, (124) 2-[2-(4-amidinophenylcarbamoyl)-6-methoxy-3-pyridyl]-5-[(4,4-dimethyioxolan-3(S)-yl)carbamoyl]-4-methylbenzoic acid, (125) 2-[2-(4-amidinophenylcarbamoyl)-6-methoxy-3-pyridyl]-5-(1(R), 2,2-trimethylpropylcarbamoyl)benzoic acid, (126) 2-[2-(4-amidinophenylcarbamoyl)-6-methoxy-3-pyridyl[3-5-[(1(R)-2,2-dimethylcyclopentyl)carbamoyl]benzoic acid, (127) 2-[2-(4-amidinophenylcarbamoyl)-6-methoxy-3-pyridyl]-5-[(1(S)-methylaminomethyl-3-methylbutyl)carbamoyl]benzoic acid, (128) 2-[2-(4-amidinophenylcarbamoyl)-6-methoxy-3-pyridyl)-5-[(4,4-dimethyl-2-oxooxolan-3(S)-yl)carbamoyl]benzoic acid, (129) 2-[2-(4-amidinophenylcarbamoyl)-3-thienyl]-5-[(1(S)-acetyloxymethyl-2,2-dimethylpropyl)carbamoyl]benzoic acid, (130) 2-[2-(4-amidinophenylcarbamoyl)-6-methoxy-3-pyridyl]-5-[[4-carboxy-4-(2-methyl-2-propenyl)piperidinyl]carbonyl]benzoic acid, (131) 2-[2-(4-amidinophenylcarbamoyl)-6-methoxy-3-pyridyl]-5-[1(S)-[N-methyl-N-(1-iminoethyl)aminomethyl]3-methylbutylbenzoic acid, (132) 2'-(4-amidinophenylcarbamoyl)-4'-amino-4-(1(R),2,2-trimethylpropylcarbamoyl)-2-biphenylcarboxylic acid, (133) 2-[2-(4-amidinophenylcarbamoyl)-6-methoxy-3-pyridyl]-5-[[1-(1-iminoethyl)-4-(2-methylpropyl)piperidin-4-yl]carbamoyl]benzoic acid, (134) 3-[2-(4-amidinophenylcarbamoyl)-6-methoxy-3-pyridyl]-6-[(1(R), 2,2-trimethylpropyl)carbamoyl]-2-pyridinecarboxylic acid, (135) 2-[2-(4-amidinophenylcarbamoyl)-6-methoxy-3-pyridyl]-5-(t-butylcarbamoyl)benzoic acid, (136) 2-[2-(4-amidinophenylcarbamoyl)-6-methoxy-3-pyridyl]-5-(2,2,2-trichloroethylcarbamoyl)benzoic acid, (137) 2-[3-(4-amidinophenylcarbamoyl)-2-thienyl]-6-(t-butylcarbamoyl)-2-pyridinecarboxylic acid, (138) 2-[2-(4-amidinophenylcarbamoyl)-6-methoxy-3-pyridyl]-5-( 2,2,2-trifluoroethylcarbamoyl)benzoic acid, (139) 2-[2-[(2-amidinopyrimidin-5-yl)carbamoyl]-6-methoxy-3-pyridyl]-5-(2,2-dimethylpropylcarbamoyl)benzoic acid, (140) 2-[2-(4-amidinophenylcarbamoyl)-6-methoxy-3-pyridyl]-5-[[1(S)-(2-aminoethyl)-3-mathylbutyl]carbamoyl]benzoic acid, (141) 2-[2-(4-amidinophenylcarbamoyl)-6-methoxy-3-pyridyl]-5-[(2,2-dimethyl-3-hydroxypropyl)carbamoyl]benzoic acid, (142) 2-[2-(4-amidinophenylcarbamoyl)-6-methoxy-3-pyridyl]-5-[(2,2-diethylbutyl)carbamoyl]benzoic acid,
(143) 2-[2-(4-amidinophenylcarbamoyl)-6-methoxy-3-pyridyl]-5-[((1-hydroxymethyl)cyclobutylmethyl)carbamoyl]benzoic acid,
(144) 2-[2-(4-amidinophenylcarbamoyl)-6-methoxy-3-pyridyl]-5-[(2-ethyl-2-hydroxymethylbutyl)carbamoyf]benzoic acid,
(145) 2-[2-(4-amidinophenylcarbamoyl)-6-methoxy-3-pyridyl]-5-[((1-hydroxymethyl)cyclopentylmethyl)carbamoyl]benzoic acid,
(146) 2-[2-(4-amidinophenylcarbamoyl)-6-methoxy-3-pyridyl]-5-[(2-propyl-2-hydroxymethylpentyl)carbamoyl]benzoic acid,
(147) 2-[2-(4-amidinophenylcarbamoyl)-6-methoxy-3-pyridyl]-5-[(2-(2-methylpropyl)-2-hydroxymethyl-4-methylpentyl)carbamoyl]benzoic acid,
(148) 2-[2-(4-amidinophenylcarbamoyl)-6-methoxy-3-pyridyl]-5-[(1-hydroxymethylcyclopentyl)carbamoyl]benzoic acid,
(149) 2-[2-(4-amidinophenylcarbamoyl)-6-methoxy-3-pyridyl]-5-[(1-(2-methylpropyl)-1-hydroxymethyl-3-methylbutyl)carbamoyl]benzoic acid,
(150) 2-[2-(4-amidinophenylcarbamoyl)-6-methoxy-3-pyridyl]-5-[(1(S)-(hydroxymethyl)-2(S)-methylbutyl)carbamoyl]benzoic acid,
(151) 2-[2-(4-amidinophenylcarbamoyl)-6-ethoxy-3-pyridyl]-5-[(1(S)-isopropyl-3-aminopropyl)carbamoyl]benzoic acid,
(152) 2-[2-(4-amidinophenylcarbamoyl)-6-ethoxy-3-pyridyl]-5-[(1(S)-(2-aminoethyl)-3-methylbutyl)carbamoyl]benzoic acid,
(153) 2-[2-(4-amidinophenylcarbamoyl)-6-ethoxy-3-pyridyl]-5-[(1(S)-( 2-aminoethyl)-2(S)-methylbutyl)carbamoyl]benzoic acid,
(154) 2'-(4-amidinophenylcarbamoyl)-4-[(1(S)-carboxymethyl-2,2-dimethylpropyl)carbamoyl]-2-biphenylcarboxylic acid,
(155) 2'-(4-amidinophenylcarbamoyl)-4-(1-carboxycyclopentylcarbamoyl)-2-biphenylcarboxylic acid,
(156) 2'-(4-amidinophenylcarbamoyl)-4-[(2-carboxy-2,2-dimethylethyl)carbamoyl]-2-biphenylcarboxylic acid,
(157) 2-[2-(4-amidinophenylcarbamoyl)-6-methyl-3-pyridyl]-5-[(1(S)-carboxy-2-methylpropyl)carbamoyl]benzoic acid,
(158) 2-[4-(4-amidinophenylcarbamoyl)-3-pyridyl]-5-[(1(S)-carboxy-2-methylpropyl)carbamoyl]benzoic acid,
(159) 2'-(4-amidinophenylcarbamoyl)-4-[(1-carboxy-1-methylethyl)carbamoyl]-2-biphenylcarboxylic acid,
(160) 2-[2-(4-amidinophenylcarbamoyl)-6-methoxy-3-pyridyl]-5-[1(S)-(4-carboxyoxazol-2-yl)-3-methylbutyl)carbamoyl]benzoic acid,
(161) 2'-(4-amidinophenylcarbamoyl)-4-(2,2-dimethylcyclopentylcarbamoyl)-2-biphenylcarboxylic acid,
(162) 2'-(4-amidinophenylcarbamoyl)-4-[(N-methyl-N-t-butylamino)carbamoyl]-2-biphenylcarboxylic acid,
(163) 2-[2-(4-amidinophenylcarbamoyl)-6-methyl-3-pyridyl]-5-[(3-methyl-2-butenyl)carbamoyl]benzoic acid,
(164) 2'-(4-amidinophenylcarbamoyl)-5'-nitro-4-(2,2-dimethylpropylcarbamoyl)-2-biphenylcarboxyiic acid,
(165) 3-[2-(4-amidinophenylcarbamoyl)-6-methoxy-3-pyridyl]-6-[(1-isopropyl-2-methylpropyl)carbamoyl]-2-pyridinecarboxylic acid,
(166) 2-[2-(4-amidinophenylcarbamoyl)-6-methoxy-3-pyridyl]-5-[(1(S)-hydroxymethyl-2,2-dimethylpropyl)carbamoyl]benzoic acid,
(167) 2'-[(2-amidino-5-pyridyl)carbamoyl]-4'-methoxy-4-[(1(S)-hydroxymethyl-2,2-dimethylpropyl)carbamoyl]-2-biphenylcarboxylic acid,
(168) 2'-[(2-amidino-5-pyridyl)carbamoyl]-4-[(1(S)-hydroxymethyl- 2,2-dimethylpropyl)carbamoyl]-2-biphenylcarboxylic acid,
(169) 2-[4-(4-amidinophenylcarbamoyl)-3-pyridyl]-5-[(1(S)-hydroxymethyl-2,2-dimethylpropyl)carbamoyl]benzoic acid,
(170) 2-[4-[(2-amidino-5-pyridyl)carbamoyl]-3-pyridyl]-5-[(1(S)-hydroxymethyl-2,2-dimethylpropyl)carbamoyl]benzoic acid,
(171) 2-[2-(4-amidinophenylcarbamoyl)-3-pyridyl]-5-[(1(S)-hydroxymethyl-2,2-dimethyipropyl)carbamoyl]benzoic acid,
(172) 2-[2-[(2-amidino-5-pyridyl)carbamoyl]-3-pyridyl]-5-[(1(S)-hydroxymethyl-2,2-dimethyipropyl)carbamoyl]benzoic acid,
(173) 2-[2-(4-amidinophenylcarbamoyl)-6-methyl-3-pyridyl]-5-[(1(S)-hydroxymethyl-2,2-dimethylpropyl)carbamoyl]benzoic acid,
(174) 2-[2-(4-amidinophenylcarbamoyl)-6-methyl-3-pyridyl]-5-[(1(S)-hydroxymethyl-3-methylbutyl)carbamoyl]benzoic acid,
(175) 2-[2-(4-amidinophenylcarbamoyl)-6-methoxy-3-pyridyl]-4-methyl-5-[(1(S)-hydroxymethyl-2,2-dimethylpropyl)carbamoyl]benzoic acid,
(176) 2-[3-(4-amidinophenylcarbamoyl)-2-thienyl]-5-[(1(S)-hydroxymethyl-2,2-dimethyipropyl)carbamoyl]benzoic acid,
(177) 2-[2-(4-amidinophenylcarbamoyl)-3-thienyl]-5-[(1(S)-hydroxymethyl-2,2-dimethylpropyl)carbamoyl]benzoic acid,
(178) 2-[2-(4-amidinophenylcarbamoyl)-6-methoxy-3-pyridyl]-5-[(1-hydroxymethyl-1-methoxycarbonyl-3-methylbutyl)carbamoyl]benzoic acid,
(179) 2-[2-[N-(4-amidinophenyl)-N-methylcarbamoyl]-6-methoxy-3-pyridyl]-5-[(1(S)-hydroxymethyl-2,2-dimethylpropyi)carbamoyl]benzoic acid,
(180) 2-[2-(4-amidinophenylcarbamoyl)-6-ethoxy-3-pyridyl]-5-[(1(S)-hydroxymethyl-2,2-dimethylpropyl)carbamoyl]benzoic acid,
(181) 2-[2-(4-amidinophenylcarbamoyl)-6-isopropyloxy-3-pyridyl]-5-[(1(S)-hydroxymethyl-2,2-dimethylpropyl)carbamoyl]benzoic acid,
(182) 2-[2-(4-amidinophenylcarbamoyl)-6-chloro-3-pyridyl]-5-[(1(S)-hydroxymethyl-2,2-dimethylpropyl)carbamoyl]benzoic acid,
(183) 2-[2-(4-amidinophenylcarbamoyl)-6-methoxy-3-pyridyl]-5-[( 1(S)-(2-hydroxyethyl)-2,2-dimethylpropyl)carbamoyl]benzoic acid,
(184) 3-[3-(4-amidinophenylcarbamoyl)-2-thienyl]-6-[(1(S)-hydroxymethyl-2,2-dimethylpropyl)carbamoyl]-2-pyridinecarboxylic acid,
(185) 3-[2-(4-amidinophenylcarbamoyl)-6-methoxy-3-pyridyl]-6-[(1(S)-hydroxymethyl-2,2-dimethylpropyl)carbamoyl]-2-pyridinecarboxylic acid,
(186) 2-[2-(4-amidinophenylcarbamoyl)-6-methoxy-3-pyridyl]-5-[[1(S)-(2-hydroxyethyicarbamoyl)-3-methylbutyl]carbamoyl]benzoic acid,
(187) 3-[2-(2-amidino-5-pyridylcarbamoyl)-6-methoxy-3-pyridyl]-6-[(1(S)-hydroxymethyl-2,2-dimethylpropyl)carbamoyl]-2-pyridinecarboxylic acid,
(188) 2-[2-(4-amidinophenylcarbamoyl)-6-dimethylamino-3-pyridyl]-5-[(1(S)-hydroxymethyl-2,2-dimethylpropyl)carbamoyl]benzoic acid,
(189) 2-[2-(4-amidinophenylcarbamoyl)-6-butoxy-3-pyridyl]-5-[(1(S)-hydroxymethyl-2,2-dimethylpropyl)carbamoyl]benzoic acid, (190) 2-[2-(2-amidinopyrimidin-5-yl)carbamoyl-6-methoxy-3-pyridyl]-5-[(1(S)-hydroxymethyl-2,2-dimethylpropyl)carbamoyl]benzoic acid,
(191) 2-[2-(4-amidinophenylcarbamoyl)-6-propoxy-3-pyridyl]-5-[(1(S)-hydroxymethyl-2,2-dimethylpropyl)carbamoyl]benzoic acid,
(192) 2-[2-(4-amidinophenylcarbamoyl)-6-methoxy-3-pyridyl]-5-[(1(S), 2-bishydroxymethyl-2-methylpropyl)carbamoyl]benzoic acid,
(193) 2-[2-(4-amidinophenylcarbamoyl)-6-ethoxy-3-pyridyl]-5-[(1(S), 2-bishydroxymethyl-2-methylpropyl)carbamoyl]benzoic acid,
(194) 5-[2-(4-amidinophenylcarbamoyl)-6-methoxy-3-pyridyl]-2-[(1(S)-hydroxymethyl-2,2-dimethylpropyl)carbamoyl]-4-pyridinecarboxyfic acid,
(195) 2-[2-(4-amidinophenylcarbamoyl)-6-methoxy-3-pyridyl]-5-[(1(S)-hydroxymethyl-2-methylpropyl)carbamoyl]benzoic acid,
(196) 2-[2-(4-amidinophenylcarbamoyl)-6-ethoxy-3-pyridyl]-5-[(1(S)-hydroxymethyl-3,3-dimethylbutyl)carbamoyl]benzoic acid,
(197) 2-[2-(4-amidinophenylcarbamoyl)-6-methoxy-3-pyridyl]-5-[(1(S)-hydroxymethyl-3,3-dimethylbutyl)carbamoyl]benzoic acid,
(198) 2'-(4-amidinophenylcarbamoyl)-4'-hydroxymethyl-4-( 2-methylpropylcarbamoyl)-2-biphenylcarboxylic acid,
(199) 2'-(4-amidinophenylcarbamoyl)-4'-hydroxymethyl-4-(1,2,2-trimethylpropylcarbamoyl)-2-biphenylcarboxylic acid,
(200) 3-[2-(4-amidinophenylcarbamoyl)-4-methoxyphenyl]-6-[(1(S)-hydroxymethyl-2,2-dimethylpropyl)carbamoyl]-2-pyridinecarboxylic acid,
(201) 2-[2-(4-amidinophenylcarbamoyl)phenyl]-5-(2,2-dimethylpropylcarbamoyl)-3-furancarboxylic acid,
(202) 2-[2-(4-amidinophenylcarbamoyl)-6-methoxy-3-pyridyl]-5-[(3-amino-1(S)-t-butylpropyl)carbamoyl]benzoic acid,
(203) 2-[2-(4-amidinophenylcarbamoyl)-6-methoxy-3-pyridyl]-5-[(1,1-bishydroxymethyl-2-methylpropyl)carbamoyl]benzoic acid,
(204) 2-[2-(4-amidinophenylcarbamoyl)-6-methoxy-3-pyridyl]-5-[(4-(2-methylpropyl)-4-piperidino)carbamoyl]benzoic acid,
(205) 2-[2-(4-amidinophenylcarbamoyl)-6-methoxy-3-pyridyl]-5-[(2-amino-3-methylbutyl)carbamoyl]benzoic acid,
(206) 2-[2-(4-amidinophenylcarbamoyl)-6-methoxy-3-pyridyl]-5-[(1(S)-(4-aminobutylcarbamoyl)-3-methylbutyl)carbamoyl]benzoic acid,
(207) 2-[2-(4-am idin ophenylcarbamoyl)-6-methoxy-3-pyridyl]-5-[(3-amino-2,2-dimethylpropyl)carbamoyl]benzoic acid,
(208) 2-[2-(4-amidinophenylcarbamoyl)-6-ethoxy-3-pyridyl]-5-[(3-amino-1(S)-t-butylpropyl)carbamoyl]benzoic acid,
(209) 2-[2-(4-amidinophenylcarbamoyl)-6-ethoxy-3-pyridyl]-5-[(4-amino-1(S)-t-butylbutyl)carbamoyl]benzoic acid,
(210) N-hydroxy-2'-(4-amidinophenylcarbamoyl)-4-[(1(R),2,2-trimethylpropyl)carbamoyl]-2-biphenylcarboxamide,
(211) 2'-(4-amidinobenzyloxy)-4-(2-methylpropylcarbamoyl)-2-biphenylcarboxylic acid,
(212) 2'-(4-amidinobenzyloxy)-4-(1(S)-hydroxymethyl-2,2-dimethylpropylcarbamoyl)-2-biphenylcarboxylic acid,
(213) 2'-(4-amidinobenzyioxy)-4'-methyl-4-(1(S)-hydroxymethyl- 2,2-dimethylpropylcarbamoyl)-2-biphenylcarboxylic acid,
(214) 2'-(4-amidinophenylaminomethyl)-4-(1(S)-hydroxymethyl-2,2-dimethylpropyicarbamoyl)-2-biphenylcarboxylic acid,
(215) 2-[2-(4-amidinophenylaminomethyl)-3-pyridyl]-5-(2-methylpropylcarbamoyl)benzoic acid,
(216) 2-[2-(4-amidinophenylaminomethyl)-6-methyl-3-pyridyl]-5-(2-methylpropylcarbamoyl)benzoic acid,
(217) 2-[4-(4-amidinophenylaminomethyl)-3-pyridyl]-5-(2-methylpropylcarbamoyl)benzoic acid, methyl ester, ethyl ester, benzyl ester thereof, non-toxic salts thereof or hydroxide thereof.

8. A compound according to claim 1, which is selected from
(1) 2'-(4-amidinophenylcarbamoyl)-4'-methyl-2-biphenylcarboxylic acid,
(2) 2'-(4-amidinophenylcarbamoyl)-4'-((1-carboxy-2-methylpropyl)carbamoyl)-2-biphenylcarboxylic acid,
(3) 2'-(4-amidinophenylcarbamoyl)-2-biphenylcarboxylic acid,
(4) 2,3-dihydro-2,2-dimethyl-5-(2-(4-amidinophenylcarbamoyl)phenyl)-6-benzofurancarboxylic acid,
(5) 2'-(4-amidinophenylcarbamoyl)-2,3-biphenyldicarboxylic acid,
(6) 2'-(4-amidinophenylcarbamoyl)-6-methyl-2-biphenylcarboxylic acid,
(7) 2'-(4-amidinophenylcarbamoyl)-5-methoxy-2-biphenylcarboxylic acid,
(8) 2'-(4-amidinophenylcarbamoyl)-4-methoxy-2-biphenylcarboxylic acid,
(9) 2'-(4-amidinophenylcarbamoyl)-6-methoxy-2-biphenylcarboxylic acid,
(10) 2'-(4-amidinophenylcarbamoyl)-4-hydroxy-2-biphenylcarboxylic acid,
(11) 2'-(4-amidinophenylcarbamoyl)-5-hydroxy-2-biphenylcarboxylic acid,
(12) 2'-(4-amidinophenylcarbamoyl)-5-methyl-2-biphenylcarboxylic acid,
(13) 2'-(4-amidinophenylcarbamoyl)-4-methyl-2-biphenylcarboxylic acid,
(14) 2'-(4-amidinophenylcarbamoyl)-3-hydroxy-2-biphenylcarboxylic acid,
(15) 2'-(4-amidinophenylcarbamoyl)-4'-methyl-5-chloro-2-biphenylcarboxylic acid,
(16) 2'-(4-amidinophenylcarbamoyl)-3-methoxy-2-biphenylcarboxylic acid,
(17) 2'-(4-amidinophenylcarbamoyl)-4'-methyl-4-methoxy-2-biphenylcarboxyic acid,
(18) 2-(2-(4-amidinophenylcarbamoyl)phenyl)-1-naphthalenecarboxylic acid,
(19) 2'-(4-amidinophenylcarbamoyl)-3-methyl-2-biphenylcarboxylic acid,
(20) 3-(2-(4-amidinophenylcarbamoyl)phenyl)-7-methoxy-2-naphthalenecarboxylic acid,
(21) 3-(2-(4-amidinophenylcarbamoyl)phenyl)-5-methoxy-2-naphthalenecarboxylic acid,
(22) 2'-(4-amidinophenylcarbamoyl)-2,4-biphenyldicarboxylic acid,
(23) 3-(2-(4-amidinophenylcarbamoyl)phenyl)-6-methoxy-2-naphthalenecarboxylic acid,
(24) 3-(2-(4-amidinophenylcarbamoyl)phenyl)-8-methoxy-2-naphthalenecarboxylic acid,
(25) 2'-(4-amidinophenylcarbamoyl)-3,4-dimethoxy-2-biphenylcarboxylic acid,
(26) 6-(2-(4-amidinophenylcarbamoyl)phenyl)-1,2-methylenedioxybenzen-5-carboxylic acid,
(27) 2'-(4-amidinophenylcarbamoyl)-4'-nitro-2-biphenylcarboxylic acid,

(28) 2'-(4-amidinophenylcarbamoyl)-2-biphenylphosphoric acid,
(29) 2'-(4-amidinophenylcarbamoyl)-4-fluoro-2-biphenylcarboxyiic acid,
(30) 2'-(4-amidinophenylcarbamroy)-4-(2-methoxycarbonylethyl)-2-biphenylcarboxylic acid,
(31) 2'-(4-amidinophenylcarbamoyl)-4-(2-methoxyethoxy)-2-biphenylcarboxylic acid,
(32) 2'-(4-amidinophenylcarbamoyl)-4-trifluoromethoxy-2-biphanylcarboxylic acid,
(33) 3-(2-(4-amidinophenylcarbamoyl)phenyl)-8-(2-methoxyethoxy)-2-naphthalenecarboxylic acid,
(34) 2'-(4-amidinophenylcarbamoyl)-4-((isopropyicarbonyl)aminomethyl)-2-biphenylcarboxylic acid,
(35) 2'-(4-amidinophenylcarbamoyl)-4-((2-methylpropyi)sulfamoyl)-2-biphenylcarboxylic acid,
(36) 2'-(4-amidinophenylcarbamoyl)-5-chloro-2-biphenylcarboxylic acid,
(37) 3-(2-(4-amidinophenylcarbamoyl)phenyl)-2-naphthalenecarboxylic acid,
(38) 2'-(3-amidinophenylcarbamoyl)-2-biphenyl(carboxylic acid,
(39) 2-(2-(4-amidinophenylcarbamoyl)phenyl)cinnamic acid,
(40) 2'-(4-amidinophenylcarbamoyl)biphenyl-2-yloxyacetic acid,
(41) 3-(2-(4-amidinophenylcarbamoyl)-4-methyiphenyl)-2-naphthalenecarboxylic acid,
(42) 1(2-(4-amidinophenylcarbamocyl)phanyl)-2-naphthalenecarboxylic acid,
(43) 3-(2-(4-amidinophenylcarbamoyl)-4-methoxyphenyl)-2-naphthalenecarboxylic acid,
(44) 3-(2-(4-amidinophenylcarbamoyl)-4-propoxyphenyl)-2-naphthalenecarboxylic acid,
(45) 2'-(4-amidinophenylcarbamoyl)-4-nitro-2-biphenylcarboxylic acid,
(46) 2'-(4-amidinophenylcarbamoyl)-4-methylsulfonylamino-2-biphenylcarboxyiic iacid,
(47) 2'-(4-amidinophenylcarbamoyl)-4-chloro-2-biphenylcarboxylic acid,
(48) 2'-(4-amidinophenylcarbamoyl)biphenyl-2-yiacetic acid,
(49) 2'-(4-amidinophenylcarbamoyl)-5-nitro-2-biphenylcarboxylic acid,
(50) 2'-(4-amidinophenylcarbamoyl)-4-mathylaminomethyl-2-biphenylcarboxylic acid,
(51) 2'-(4-amidinophenylcarbamnoyl)-4-ethoxycarbonylmethoxy-2-biphanylcarboxylic acid,
(52) 2'-(4-amidin ophenylcarbamoyl)-4-(2-(methoxymethoxy)ethoxy)-biphenylcarboxylic acid,
(53) 3-(2-(4-amidinophenylcarbamoyl)phenyl)-5-methoxymethoxcy- 2-naphthalenecarboxylic acid,
(54) 3-(2-(4-amidinophenylcarbamoyl)phenyl)-8-methoxymethoxy-2-naphthaienecarboxylic acid,
(55) 2'-(4-amidinophenylcarbamoyl)-4'-amino-2-biphenyl carboxylic acid,
(56) 2'-(4-amidinophenylcarbamoyl)-4'-chloro-2-biphenylcarboxylic acid,
(57) 2'-(4-amidinophenylcarbamoyl)-4'-(2-methoxycarbonylethyl)-2-biphenylcarboxylic acid,
(58) 2'-(4-amidinophenylcarbamoyl)-3'-benzyloxy-2-biphenylcarboxylic acid,
(59) 2'-(4-amidinophenylcarbamoyl)-6'-methyl-2-biphenylcarboxylic acid,
(60) 2'-(4-amidinophenylcarbamoyl)-5'-methyi-2-biphenylcarboxylic acid,
(61) 2'-(4-amidinophenylcarbamoyl)-4'-isopropyl-2-biphenylcarboxylic acid,
(62) 2'-(4-amidinophenylcarbamoyl)-4'-t-butyl-2-biphenylcarboxylic acid,
(63) 2'-(4-amidinophenylcarbamoyl)-4'-ethyl-2-biphenylcarboxylic acid,
(64) 2'-(4-amidinophenylcarbamoyl)-4'-methoxy-2-biphenylcarboxyiic acid,
(65) 2'-(4-amidinophenylcarbamoyl)-4'-ciano-2-biphenylcarboxylic acid,
(66) 2'-(4-amidinophenylcarbamoyl)-5'-methoxy-2-biphenylcarboxylic acid,
(67) 2'-(4-amidinophenylcarbamoyl)-6'-methoxy-2-biphenylcarboxylic acid,
(68) 2'-(4-amidinophenylcarbamoyl)-5'-chloro-4-methyl-2-biphenylcarboxylic acid,
(69) 2'-(4-amidinophenylcarbamoyl)-4'-methoxy-4-methyl-2-biphenylcarboxylic acid,
(70) 2'-(4-amidinophenylcarbamoyl)-4'-dimethylcarbamoyl-2-biphenylcarboxylic acid,
(71) 2'-(4-amidinophenylcarbamoyl)-2,4'-biphenyldicarboxylic acid,
(72) 2'-(4-amidinophenylcarbamoyl)-4'-methylcarbamoyl-2-biphenylcarboxylic acid,
(73) 2'-(4-amidinophenylcarbamoyl)-4'-methyiaminomethyl-2-biphenylcarboxylic acid,
(74) 2'-(4-amidinophenylcarbamoyl)-4'-(2-hydroxyethoxy)-2-biphenylcarboxylic acid,
(75) 2'-(4-amidinophenylcarbamoyl)-4'-fluoro-2-biphenylcarboxylic acid,
(76) 2'-(4-amidinophenylcarbamoyl)-4'-(2-methoxyethoxy)-2-biphenylcarboxylic acid,
(77) 2'-(4-amidinophenylcarbamoyl)-4'-trifluoromethoxy-2-biphenylcarboxylic acid,
(78) 2'-(4-amidinophenylcarbamoyl)-4'-((methoxycarbonylmethyl)carbamoyl)-2-biphenylcarboxyiic acid,
(79) 2'-(4-amidinophenylcarbamoyl)-4'-((1-methoxycarbonyl-2-phenylethyl)carbamoyl)-2-biphenylcarboxytic acid,
(80) 2'-(4-amidinophenylcarbamoyl)-4'-ethoxycarbonylmethoxy-biphenylcarboxylic acid,
(81) 2'-(4-amidinophenylcarbamoyl)-4'-hydroxy-2-biphenylcarboxylic acid,
(82) 2'-(4-amidinophenylcarbamoyl)-5'-hydroxy-2-biphenylcarboxylic acid,
(83) 2'-(4-amidinophenylcarbamoyl)-4'-bromo-2-biphenylcarboxylic acid,
(84) 2'-(4-amidinophenylcarbamoyl)-4-bromo-2-biphenylcarboxylic acid,
(85) 2'-(4-amidinophenylcarbamoyl)-3'-methoxy-2-biphenylcarboxylic acid,
(86) 2'-(4-amidinophenylaminomethyl)-2-biphenylcarboxylic acid,
(87) 2'-(4-amidinophenylaminomethyl)-4'-methoxy-2-biphenylcarboxylic acid,
(88) 2'-(4-($N^2$-t-butoxycarbonyloxyamidino)phenylcarbamoyl)-2-biphenylcarboxylic acid,
(89) 2'-(4-($N^2$-ethoxycarbonylamidino)phenylcarbamoyl)-2-biphenylcarboxylic acid,
(90) 2-(2-(4-amidinophenylcarbamoyl)pyridin-3-yl)benzoic acid,
(91) 2'-(4-amidinophenylcarbamoyl)-4-(3-methylbutoxy)-2-biphenylcarboxylic acid,
(92) 2'-(4-amidinophenylcarbamoyl)-4-methylaminomethyl-2-biphenylcarboxylic acid,
(93) 2'-(4-amidinophenylcarbamoyl)-4-carboxymethoxy-2-biphenylcarboxylic acid,

(94) 2'-(4-amidinophenylcarbamoyl)-4-(2-hydroxyethoxy)-2-biphenylcarboxylic acid,
(95) 3-(2-(4-amidinophenylcarbamoyl)phenyl)-5-hydroxy-2-naphthalenecarboxylic acid,
(96) 3-(2-(4-amidinophenylcarbamoyl)phenyl)-8-hydroxy-2-naphthalenecarboxylic acid,
(97) 2'-(4-amidinophenylcarbamoyl)-4-((2-methylpropyl)aminomethyl)-2-biphenylcarboxylic acid,
(98) 2'-(4-amidinophenylcarbamoyl)-3'-hydroxy-2-biphenylcarboxylic acid,
(99) 2'-(4-amidinophenylcarbamoyl)-4'-((carboxymethyl)carbamoyl)-2-biphenylcarboxylic acid,
(100) 2'-(4-amidinophenylcarbamoyl)-4'-((1-carboxy-2-phenylethyl)carbamoyl)-2-biphenylcarboxylic acid,
(101) 2'-(4-amidinophenylcarbamoyl)-4'-carboxymethoxy-2-biphenylcarboxylic acid,
(102) 2'-(4-($N^2$-hydroxyamidino)phenylcarbamoyl)-2-biphenylcarboxylic acid,
(103) N-hydroxy-2'-(4-amidinophenylcarbamoyl)-2-biphenylcarboxamide,
(104) N-hydroxy-N-methyl-2'-(4-amidinophenylcarbamoyl)-2-biphenylcarboxamide,
(105) N-hydroxy-2'-(4-amidinophenylcarbamoyl)-4'-methyl-2-biphenylcarboxamide,
(106) N-hydroxy-2'-(4-amidinophenylcarbamoyl)-4'-methoxy-2-biphenylcarboxamide,
(107) N-hydroxy-2'-(4-($N^2$-ethoxycarbonylamidino)phenylcarbamoyl)-2-biphenylcarboxamide,
(108) 2'-(4-amidinophenylcarbamoyl)-4-amino-2-biphenylcarboxylic acid,
(109) 3-(2'-(4-amidinophenylcarbamoyl)biphenyl-2-yl)propanoic acid,
(110) 2'-(4-amidinophenylcarbamoyl)-4-methylcarbonylamino-2-biphenylcarboxylic acid,
(111) 2'-(4-amidinophenylcarbamoyl)-4'-methyicarbonylamino-2-biphenylcarboxylic acid,
(112) 2'-(4-amidinophenylcarbamoyl)-4-((2-methyipropylcarbonyl)amino)-2-biphenylcarboxylic acid,
(113) N-hydroxy-2'-(4-($N^2$-hydroxyamidino)phenylcarbamoyl)-2-biphenylcarboxamide,
(114) 2'-(4-($N^2$-propenyl)oxycarbonylamidino)phenylearbamoyl)-2-biphenylcarboxylic acid,
(115) 2'-(1-(4-amidinophenylamino)-1-methoxycarbonylmethyl)-2-biphenylcarboxylic acid,
(116) 2'-(1-(4-amidinophenylamino)-1-methylcarbamoylmethyl)-2-biphenylcarboxylic acid,
(117) 2'-(1-(4-amidinophenylamino)-1-cianomethyl)-2-biphenylcarboxylic acid,
(118) 2'-(1-(4-amidinophenylamino)-1-carboxymethyl)-2-biphenylcarboxylic acid,
(119) 2'-(4-amidinobenzyloxy)-2-biphenylcarboxylic acid,
(120) 2'-(4-amidinophenylcarbamoyl)-2-(tetrazol-5-yl)biphenyl,
(121) 2-[2-(4-amidinophenylcarbamoyl)-6-methyl-3-pyridyl]-5-(2,2-dimethylpropyloxycarbonyl)benzoic acid,
(122) 4-[2-(4-amidinophenylcarbamoyl)-6-methyl-3-pyridyl]isophthalic acid,
(123) 4-[2-(4-amidinophenylcarbamoyl)-6-methoxy-3-pyridyl]isophthalic acid,
(124) 2-[2-(4-amidinophenylcarbamoyl)-6-methoxy-3-pyridyl]-5-[1-(2,2-dimethylpropyl)tetrazol-5-yl]benzoic acid,
(125) 2-[2-(4-amidinophenylcarbamoyl)-6-methoxy-3-pyridyl]-5[(2,2-diethylbutyloxy)carbamoyl]benzoic acid,
(126) 2'-(4-amidinophenylcarbamoyl)-4-(3-methylbutylcarbonyl)-2-biphenylcarboxylic acid,
(127) 2-[2-(4-amidinophenylcarbamoyl)-6-methoxy-3-pyridyl]-5-[(2-amino-2-hydroxymethyl-3-methylbutyl)carbamoyl]benzoic acid, methyl ester, ethyl ester, benzyl ester thereof, non-toxic salts thereof or hydroxide thereof.

9. A compound according to claim 1, which is selected from
(1) 3-(4-amidinophenylcarbamoyl)-4-biphenycarboxylic acid,
(2) 4-(4-amidinophenylcarbamoyl)-3-biphenylcarboxylic acid,
(3) 3'-(4-amidinophenylcarbamoyl)-2-biphenylcarboxylic acid,
(4) 2'-(4-amidinophenylcarbamoyl)-3-biphenylcarboxylic acid,
(5) 2'-(4-amidinophenylcarbamoyl)-4-biphenylcarboxylic acid,
(6) 2'-(4-amidinophenoxymethyl)-4-((2-methylpropyl)carbamoyl)-2-biphenylcarboxylic acid,
(7) 2'-(4-amidinophenylthiomethyl)-4-((2-methylpropyl)carbamoyl)-2-biphenylcarboxylic acid,
(8) 2'-(4-amidinophenylethynyl)-4-((2-methylpropyl)carbamoyl)-2-biphenylcarboxylic acid,
(9) 2'-(4-amidinophenylethynyl)-2-biphenylcarboxylic acid,
(10) 2'-((1E)-2-(4-amidinophenyl)ethenyl)-4-((2-methylpropyl)carbamoyl)-2-biphenylcarboxylic acid,
(11) 2'-((1E)-2-(4-amidinophenyl)ethenyl)-2-biphenylcarboxylic acid,
(12) 2'-(2-(4-amidinophenyl)ethyl)-4-((2-methyipropyl)carbamoyl)-2-biphenylcarboxylic acid,
(13) 2'-(2-(4-amidinophenyl)ethyl)-2-biphenylcarboxylic acid,
(14) 2-[2-(4-amidinophenoxycarbonyl)-6-methoxy-3-pyridyl]-5-[(1(S)-hydroxymethyl-2,2-dimethylpropyl)carbamoyl]benzoic acid, methyl ester, ethyl ester, benzyi ester thereof, non-toxic salts thereof or hydroxide thereof.

10. A compound according to claim 1, which is selected from
(1) 2-(3-(4-amidinophenylcarbamoyl(napthalen-2-yl)benzoic acid),
(2) 2-(3-(4-amidinophenylcarbamoyl)naphthalen-2-yl)-5-((1-methoxycarbonyl-2-methylpropyl)carbamoyl)benzoic acid,
(3) 2-(3-(4-amidinophenylcarbamoyl)naphthalen-2-yl)-5-((2-methylpropyl)carbamoyl)benzoic acid,
(4) 2-(3-(4-amidinophenylcarbamoyl)-6-methoxynaphthalen-2-yl)benzoic acid,
(5) 2-(3-(4-amidinophenylcarbamoyl)-7-methoxynaphthalen-2-yl)benzoic acid,
(6) 2-(3-(4-amidinophenylcarbamoyl)-5-methoxynaphthalen-2-yl)benzoic acid,
(7) 2-(3-(4-amidinophenylcarbamoyl)naphthalen-2-yl)-5-methylbenzoic acid,
(8) 2-(2-(4-amidinophenylcarbamoyl)naphthalen-1-yl) benzoic acid,
(9) 2-(3-(4-amidinophenylcarbamoyl)naphthalen-2-yl)-5-methoxybenzoic acid,
(10) 2-(3-(4-amidinophenylcarbamoyl)naphthalen-2-yl)-5-propoxybenzoic acid,
(11) 2-(2,3-dihydro-2,2-dimethyl-6-(4-amidinophenylcarbamoyl)benzofuran-5-yl)benzoic acid,
(12) 2-(5,6,7,8-tetrahydro-3-(4-amidinophenylcarbamoyl)naphthalen-2-yl)benzoic acid,
(13) 2-(6-(4-amidinophenylcarbamoyl)indan-5-yl)benzoic acid,
(14) 2-(3-(4-amidinophenylcarbamoyl)-8-methoxynaphthalen-2-yl)benzoic acid,
(15) 2-(6-(4-amidinophenylcarbamoyl)-1,2-methylenedioxybenzen-5-yl)benzoic acid,

(16) 2-(3-(4-amidinophenylcarbamoyl)-8-hydroxynaphthalen-2-yl)benzoic acid,
(17) 2-(3-(4-amidinophenylcarbamoyl)-5-(2-methoxyethoxy)naphthalen-2-yl)benzoic acid,
(18) 2-(3-(4-amidinophenylcarbamoyl)-5-hydroxynaphthalen-2-yl)benzoic acid,
(19) 2-(6-(4-amidinophenylcarbamoyl)-1-benzyfoxymethylbenzimidazol-5-yl)benzoic acid,
(20) 2-(5-(4-amidinophenylcarbamoyl)-1-benzyloxymethylbenzimidazol- 6-yl)benzoic acid,
(21) 2-(6-(4-amidinophenylcarbamoyl)benzofuran-5-yl)benzoic acid,
(22) 2-(5-(4-amidinophenylcarbamoyl)benzofuran-6-yl)benzoic acid,
(23) 2-(3-(4-amidinophenylaminomethyl)naphthalen-2-yl)benzoic acid,
(24) 2-(3-(4-amidinophenylaminomethyl)naphthalen-2-yl)-5-((2-methylpropyl)carbamoyl)benzoic acid,
(25) 2-(2-(4-amidinophenylcarbamoyl)benzothiophene-3-yl)benzoic acid,
(26) 2-(3-(4-amidinophenylcarbamoyl)-5-methoxybenzofuran-2-yl)benzoic acid,
(27) 2-(6-(4-amidinophenylcarbamoyl)benzimidazol-5-yl)benzoic acid,
(28) N-hydroxy-2-(3-(4-amidinophenylcarbamoyl)naphthalen-2-yl)-5-((2-methylpropyl)carbamoyl)benzcarboxamide,
(29) N-hydroxy-2-(3-(4-amidinophenylcarbamoyl)naphthalen-2-yl)benzcarboxamide,
(30) N-hydroxy-2-(3-(4-amidinophenylcarbamoyl)naphthalen-2-yl)-5-methoxybenzcarboxamide,
(31) 2-(6-(4-amidinophenylcarbamoyl)isoquinolin-7-yl)benzoic acid, methyl ester, ethyl ester, benzyl ester thereof, non-toxic salts thereof or hydroxide thereof.

11. A blood coagulation factor VIIa inhibitor composition comprising a compound according to claim 1, as active ingredient.

12. A method for the prevention and/or treatment of angiopathy in a patient said method comprising administering to said patient an effective amount of an amidino compound of the formula (I) as defined in claim 1, non-toxic salts thereof or hydrates thereof as active ingredient.

13. The method according to claim 12 wherein said angiopathy is selected from the group consisting of disseminated intravascular coagulation, coronory thrombosis, cerebral infarction, cerebral embolism, deep venous thrombosis, peripheral arterial obstruction, thrombosis after artificial vascular transplantation and artificial valve transplantation, post-operative thrombosis, re-obstruction and restonsis after coronary artery bypass operation, re-obstruction and restonsis after PTCA (percutaneous transluminal coronary angioplasty) or TRCP (percutaneous transluminal coronary angioplasty), thrombosis by extracorporeal circulation and procoagulative diseases.

14. The method according to claim 12, wherein the anigopathy is a pulmonary disease selected from the group consisting of pulmonary infarction and pulmonary embolism.

15. A method according to claim 13, wherein procoagulative disease is glomerlonephritis.

* * * * *